US012458647B2

(12) United States Patent
Zhang et al.

(10) Patent No.: US 12,458,647 B2
(45) Date of Patent: Nov. 4, 2025

(54) MACROCYCLIC DERIVATIVE AND USE THEREOF

(71) Applicant: Guangzhou Joyo Pharmatech Co., Ltd., Guangdong (CN)

(72) Inventors: Yang Zhang, Shanghai (CN); Kai Zhou, Shanghai (CN); Fen Jiang, Shanghai (CN); Li Zhang, Shanghai (CN); Xiao Liu, Shanghai (CN); Zheng Wang, Shanghai (CN); Kevin X. Chen, Shanghai (CN); Jian Li, Shanghai (CN); Shuhui Chen, Shanghai (CN)

(73) Assignee: Guangzhou Joyo Pharmatech Co., Ltd., Guangzhou (CN)

( * ) Notice: Subject to any disclaimer, the term of this patent is extended or adjusted under 35 U.S.C. 154(b) by 2 days.

(21) Appl. No.: 19/069,098

(22) Filed: Mar. 3, 2025

(65) Prior Publication Data

US 2025/0205245 A1 Jun. 26, 2025

Related U.S. Application Data

(63) Continuation of application No. PCT/CN2023/122877, filed on Sep. 28, 2023.

(30) Foreign Application Priority Data

| | | |
|---|---|---|
| Sep. 29, 2022 | (CN) | 202211213222.2 |
| Feb. 17, 2023 | (CN) | 202310132699.6 |
| Apr. 7, 2023 | (CN) | 202310371165.9 |
| Jun. 9, 2023 | (CN) | 202310685748.9 |
| Jul. 24, 2023 | (CN) | 202310911632.2 |

(51) Int. Cl.

| | |
|---|---|
| ***A61K 31/5383*** | (2006.01) |
| ***A61K 31/5025*** | (2006.01) |
| ***C07D 519/00*** | (2006.01) |

(52) U.S. Cl.

CPC ...... *A61K 31/5383* (2013.01); *A61K 31/5025* (2013.01); *C07D 519/00* (2013.01)

(58) Field of Classification Search

CPC ............ A61K 31/5383; A61K 31/5025; C07D 519/00

USPC .......................................................... 514/249

See application file for complete search history.

(56) References Cited

U.S. PATENT DOCUMENTS

2023/0374035 A1 11/2023 Koltun et al.

FOREIGN PATENT DOCUMENTS

| | | | |
|---|---|---|---|
| CN | 113498342 | A | 10/2021 |
| CN | 114786777 | A | 7/2022 |
| CN | 114867735 | A | 8/2022 |
| CN | 114901366 | A | 8/2022 |
| CN | 117534684 | A | 2/2024 |
| CN | 117534685 | A | 2/2024 |
| CN | 117534687 | A | 2/2024 |
| CN | 117720554 | A | 3/2024 |
| CN | 117720555 | A | 3/2024 |
| CN | 117903169 | A | 4/2024 |
| WO | WO-2020132597 | A1 | 6/2020 |
| WO | WO-2021091956 | A1 | 5/2021 |
| WO | WO-2021091967 | A1 | 5/2021 |
| WO | WO-2021091982 | A1 | 5/2021 |
| WO | WO-2021104454 | A1 | 6/2021 |
| WO | WO-2022060583 | A1 | 3/2022 |
| WO | WO-2022060836 | A1 | 3/2022 |
| WO | WO-2022109307 | A1 | 5/2022 |
| WO | WO-2022212894 | A1 | 10/2022 |
| WO | WO-2022217053 | A1 | 10/2022 |
| WO | WO-2022235864 | A1 | 11/2022 |
| WO | WO-2022235870 | A1 | 11/2022 |
| WO | WO-2022251292 | A1 | 12/2022 |
| WO | WO-2023004308 | A1 | 1/2023 |
| WO | WO-2023015559 | A1 | 2/2023 |
| WO | WO-2023025832 | A1 | 3/2023 |
| WO | WO-2023060253 | A1 | 4/2023 |
| WO | WO-2023086341 | A1 | 5/2023 |
| WO | WO-2023133543 | A1 | 7/2023 |
| WO | WO-2023172940 | A1 | 9/2023 |
| WO | WO-2023190748 | A1 | 10/2023 |
| WO | WO-2023208005 | A1 | 11/2023 |
| WO | WO-2023230577 | A1 | 11/2023 |
| WO | WO-2023232776 | A1 | 12/2023 |

(Continued)

OTHER PUBLICATIONS

Co-pending U.S. Appl. No. 19/198,758, inventors Zhang; Yang et al., filed May 5, 2025.

(Continued)

*Primary Examiner* — Kahsay Habte

(74) *Attorney, Agent, or Firm* — WILSON SONSINI GOODRICH & ROSATI

(57) ABSTRACT

The present disclosure discloses a class of macrocyclic derivatives, and specifically discloses a compound shown in formula (VI), a stereoisomer thereof, and a pharmaceutically acceptable salt thereof.

(VI)

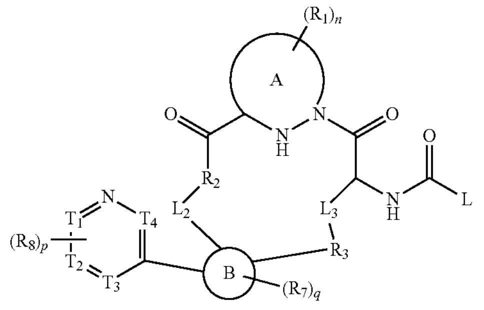

30 Claims, 5 Drawing Sheets

(56) References Cited

FOREIGN PATENT DOCUMENTS

| | | | |
|---|---|---|---|
| WO | WO-2023235356 | A1 | 12/2023 |
| WO | WO-2023240263 | A1 | 12/2023 |
| WO | WO-2024008610 | A1 | 1/2024 |
| WO | WO-2024008834 | A1 | 1/2024 |
| WO | WO-2024017859 | A1 | 1/2024 |
| WO | WO-2024050297 | A1 | 3/2024 |
| WO | WO-2024060966 | A1 | 3/2024 |
| WO | WO-2024067631 | A1 | 4/2024 |
| WO | WO-2024067857 | A1 | 4/2024 |
| WO | WO-2024081363 | A1 | 4/2024 |
| WO | WO-2024081674 | A1 | 4/2024 |
| WO | WO-2024082724 | A1 | 4/2024 |
| WO | WO-2024104364 | A1 | 5/2024 |
| WO | WO-2024111609 | A1 | 5/2024 |
| WO | WO-2024149819 | A1 | 7/2024 |
| WO | WO-2024153208 | A1 | 7/2024 |
| WO | WO-2024167880 | A1 | 8/2024 |
| WO | WO-2024169914 | A1 | 8/2024 |
| WO | WO-2024173761 | A1 | 8/2024 |
| WO | WO-2024176131 | A1 | 8/2024 |
| WO | WO-2024187174 | A2 | 9/2024 |
| WO | WO-2024189481 | A1 | 9/2024 |
| WO | WO-2024191972 | A2 | 9/2024 |
| WO | WO-2024206858 | A1 | 10/2024 |
| WO | WO-2024208934 | A1 | 10/2024 |
| WO | WO-2024211663 | A1 | 10/2024 |
| WO | WO-2024211712 | A1 | 10/2024 |
| WO | WO-2024216008 | A1 | 10/2024 |
| WO | WO-2024216016 | A1 | 10/2024 |
| WO | WO-2024216017 | A2 | 10/2024 |
| WO | WO-2024216048 | A1 | 10/2024 |
| WO | WO-2024220421 | A1 | 10/2024 |
| WO | WO-2024222864 | A1 | 10/2024 |
| WO | WO-2024229406 | A1 | 11/2024 |
| WO | WO-2024249299 | A2 | 12/2024 |
| WO | WO-2024249551 | A1 | 12/2024 |
| WO | WO-2024263833 | A2 | 12/2024 |
| WO | WO-2025019318 | A2 | 1/2025 |
| WO | WO-2025034702 | A1 | 2/2025 |
| WO | WO-2025045233 | A1 | 3/2025 |
| WO | WO-2025087431 | A1 | 5/2025 |

OTHER PUBLICATIONS

Kallen, Joerg et al. Structure of human cyclophilin A in complex with the novel immunosuppressant sanglifehrin A at 1.6 A resolution. J Biol Chem 280(23):21965-71 (2005).

Flores-Gómez, Alejandra A. et al. HRS-4642: The next piece of the puzzle to keep KRAS in check. Cancer Cell 42(7):1157-1159 (2024).

Holderfield, Matthew et al. Concurrent inhibition of oncogenic and wild-type RAS-GTP for cancer therapy. Nature 629(8013):919-926 (2024).

Parry, Charles et al. Reversible Small Molecule pan-Ras Inhibitors Display Tunable Affinity for the Active and Inactive forms of Ras. ChemRxiv doi:10.26434/chemrxiv-2024-nsd7r-v2 (2024).

PCT/CN2023/122877 International Search Report and Written Opinion dated Dec. 20, 2023, and a partial English translation.

PCT/CN2023/122877 Third Party Observation dated Jan. 30, 2025.

Poongavanam, Vasanthanathan et al. Beware of extreme calculated lipophilicity when designing cyclic peptides. Nat Med Chem 20(10):1242-1245 (2024).

PubChem 164885345. N-[21-ethyl-20-[2-(1-methoxyethyl)-5-(4-methylpiperazin-1-yl)pyridin-3-yl]-17,17-dimethyl-8,14-dioxo-15-oxa-4-thia-9,21,27,28-tetrazapentacyclo[17.5.2.12,5.19,13.022,26]octacosa-1(25),2,5(28),19,22(26),23-hexaen-7-yl]-2-methylcyclopropane-1-carboxamide. Created Aug. 30, 2022/ Modified Mar. 1, 2025 (pp. 1-10).

Revolution Medicines Corporate Presentation, Jan. 11, 2022, JP Morgan (San Francisco, CA) (pp. 1-33).

Revolution Medicines Corporate Presentation, Jan. 12, 2021, JP Morgan (San Francisco, CA) (pp. 1-34).

Senft, Daniela. Right ON target: a new RAS-GTP inhibitor Nat Rev Cancer 24(6):361 (2024).

Shay, Shay. Patent Crash: WuXi vs. Revolution Who Covers Whose Patents? Erasca in danger? People are on the way to medicine. Dec. 8, 2024 (pp. 1-17) (w/English Translation).

Song, Ying-Qi et al. RMC-7977, a highly selective inhibitor of the active RAS-GTP to treat pancreatic cancer. Acta Pharm Sin B. 14(10):4622-4624 (2024).

MACROCYCLIC DERIVATIVE AND USE THEREOF

CROSS REFERENCE TO RELATED APPLICATIONS

This application is a continuation of International Application No. PCT/CN2023/122877, filed Sep. 28, 2023, which claims priority to Chinese Application No. 202211213222.2, filed Sep. 29, 2022; Chinese Application No. 202310132699.6, filed Feb. 17, 2023; Chinese Application No. 202310371165.9, filed Apr. 7, 2023; Chinese Application No. 202310685748.9, filed Jun. 9, 2023; and Chinese Application No. 202310911632.2, filed Jul. 24, 2023.

TECHNICAL FIELD

The present disclosure relates to a class of macrocyclic derivatives and the applications thereof particularly to a compound shown in formula (VI), a stereoisomer thereof, and a pharmaceutically acceptable salt thereof.

BACKGROUND ART

RAS (including KRAS, NRAS and HRAS) is downstream of growth factor receptors such as EGFR, and is a small GTPase of molecular switch. It is a key node of the RAS-RAF-MEK-ERK signaling pathway and PI3K-AKT-mTOR signaling pathway, which regulate events such as cell proliferation and survival. Mutations in RAS leads to functional activation of proteins by disrupting the GTP hydrolysis process. Under normal physiological conditions, RAS typically exists in the form of non-activated RAS (OFF) that binds to GDP; while in RAS-mutated tumor cells, RAS mainly exists in the form of activated RAS (ON) that binds to GTP. RAS-mutant cancer patients account for 30% of all cancer patients (US data), wherein KRAS. NRAS, and HRAS mutations account for 85%, 11%, and 4%, respectively, and there are nearly 20 types of mutations in each RAS, such as $KRAS^{G12C}$, $KRAS^{G12D}$, $KRAS^{G12V}$, $KRAS^{G12R}$, $KRAS^{G13C}$. Since RAS mutation is an important factor in the development of cancer, mutant RAS has become an important cancer treatment target. Although the targeted covalent inhibitors of $KRAS^{G12C}$, namely sotorasib and adagrasib, have achieved great success in non-small cell lung cancer with $KRAS^{G12C}$ mutation, there are still no effective targeted therapeutic drugs for cancer with other types of KRAS mutation such as $^{G12D}$, $KRAS^{G12V}$, $KRAS^{G13}$ and other types of RAS mutation such as NRAS. Therefore, the development of broad-spectrum RAS inhibitors is of great clinical significance.

Revolution Medicines, Inc. The company announced a class of macrocyclic compounds (WO2020132597, WO2021091982, WO2021091967, WO2021091956), which are capable of forming ternary complexes with chaperons CypA and RAS(ON) in the body. The formation of ternary complexes blocks the binding of RAF downstream of RAS, thereby inhibiting the RAS-RAF-MEK-ERK signaling pathway and achieving anti-tumor effects. Such RAS inhibitors have great inhibitory effects on different RAS-mutant and RAS-dependent tumors. Broad-spectrum RAS inhibitors with excellent druggability that are designed and synthesized based on such macrocyclic compounds have significant clinical application value.

SUMMARY OF THE INVENTION

The present disclosure provides a compound shown in formula (VI), a stereoisomer thereof, or a pharmaceutically acceptable salt thereof, (VI)

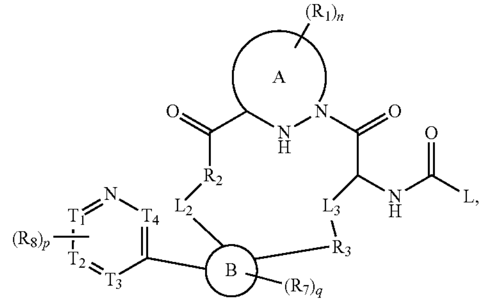

L is R6 or

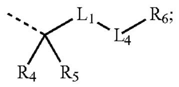

L1 is selected from —N(R9)C(═O)—;

L2 is selected from C1-6 alkyl, which is optionally substituted with 1, 2 or 3 Ra;

L3 is selected from —CH2- and C3-6 cycloalkyl;

L4 is selected from a single bond and —C1-4 alkyl-N(R10)C(═O)—;

ring A is selected from tetrahydropyridazinyl, 3,4-diazabicyclo[4.1.0]heptyl, 2,3-diazabicyclo[3.1.0]hexyl, 5,6-diazaspiro[2.5]octyl, 3,4-diazabicyclo[4.2.0]octyl, and 2,3-diazabicyclo[3.1.1]heptyl;

ring B is selected from 5-membered heteroaryl and 5-membered heteroaryl, indolyl, and

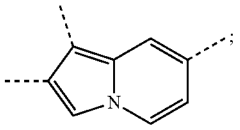

T1, T2, T3, and T2 are each independently selected from CH and N;

R1 is selected from H, F, Cl, Br, I, OH, C1-4 alkyl, and C1-4 alkoxy, and the C1-4 alkyl and C1-4 alkoxy are each independently optionally substituted with 1, 2, or 3 Rh;

R2 is selected from —O— and —NH—;

R3 is selected from phenyl and 5-6-membered heteroaryl, which are each independently optionally substituted with 1, 2, or 3 Rb;

R4 and R5 are each independently selected from H, C1-4 alkyl, C3-6 cycloalkyl, and 3-6-membered heterocycloalkyl, and the C1-4 alkyl, C3-6 cycloalkyl, and 3-6-membered heterocycloalkyl are each independently optionally substituted with 1, 2, or 3 Rc;

R6 is selected from C3-6 cycloalkyl and 3-6-membered heterocycloalkyl, which are each independently optionally substituted with 1, 2, or 3 Rd;

each R7 is independently selected from H, halogen, C1-4 alkyl and C1-4 alkoxy, and the C1-4 alkyl and C1-4 alkoxy are each independently optionally substituted with 1, 2 or 3 Re;

each R8 is independently selected from H, C1-4 alkyl, C1-4 alkoxy, C3-6 cycloalkyl, and 3-10-membered heterocycloalkyl, and the C1-4 alkyl, C1-4 alkoxy, C3-6 cycloalkyl, and 3-10-membered heterocycloalkyl are each independently optionally substituted with 1, 2, or 3 Rf;

R9 and R10 are selected from H and C1-4 alkyl, and the C1-4 alkyl is optionally substituted with 1, 2 or 3 Rg;

each Ra, each Rb, each Rc, each Re, each Rf, each Rg and each Rh are independently selected from H, D, F, Cl, Br, I, OH, C1-3 alkyl and C1-3 alkoxy, and the C1-3 alkyl and C1-3 alkoxy are each independently optionally substituted with 1, 2 or 3 R;

each Rd is independently selected from C1-4 alkyl, C3-6 cycloalkyl, 3-6-membered heterocycloalkyl, phenyl, 5-6-membered heteroaryl, and —C(═O)—C2-4 alkenyl, and the C1-4 alkyl, C3-6 cycloalkyl, 3-6-membered heterocycloalkyl, phenyl, 5-6-membered heteroaryl, and —C(═O)—C2-4 alkenyl are each independently optionally substituted with 1, 2, or 3 R;

each R is independently selected from D, F, Cl, Br, I, OH, CH3, CF3, OCH3, and OCF3;

n, p, and q are each independently selected from 0, 1, 2, and 3;

the "3-6-membered heterocycloalkyl", "3-10-membered heterocycloalkyl", and "5-6-membered heteroaryl" each independently contains 1 or 2 heteroatoms or heteroatom groups independently selected from —NH—, —O—, —S—, and N.

The present disclosure further provides a compound shown in formula (III), a stereoisomer thereof, or a pharmaceutically acceptable salt thereof, (III)

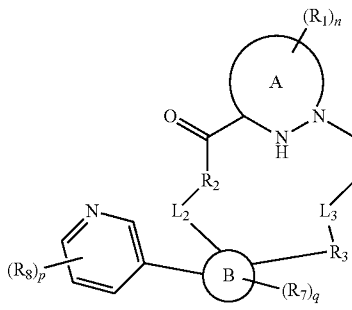

L is $R_6$ or

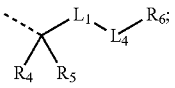

$L_1$ is selected from —N($R_9$)C(═O)—;

L2 is selected from C1-6 alkyl, which is optionally substituted with 1, 2 or 3 Ra;

L3 is selected from —CH2- and C3-6 cycloalkyl;

L4 is selected from a single bond and —C1-4 alkyl-N(R10)C(═O)—;

ring A is selected from tetrahydropyridazinyl, 3,4-diazabicyclo[4.1.0]heptyl, 2,3-diazabicyclo[3.1.0]hexyl, 5,6-diazaspiro[2.5]octyl, 3,4-diazabicyclo[4.2.0]octyl, and 2,3-diazabicyclo[3.1.1]heptyl;

ring B is selected from 5-membered heteroaryl and 5-membered heteroaryl, indolyl, and

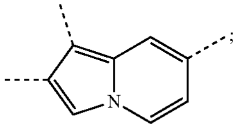

R1 is selected from H, F, Cl, Br, I, OH, C1-4 alkyl, and C1-4 alkoxy, and the C1-4 alkyl and C1-4 alkoxy are each independently optionally substituted with 1, 2, or 3 Rh;

R2 is selected from —O— and —NH—;

R3 is selected from phenyl and 5-6-membered heteroaryl, which are each independently optionally substituted with 1, 2, or 3 Rb;

R4 and R5 are each independently selected from H, C1-4 alkyl, C3-6 cycloalkyl, and 3-6-membered heterocycloalkyl, and the C1-4 alkyl, C3-6 cycloalkyl, and 3-6-membered heterocycloalkyl are each independently optionally substituted with 1, 2, or 3 Rc;

R6 is selected from C3-6 cycloalkyl and 3-6-membered heterocycloalkyl, which are each independently optionally substituted with 1, 2, or 3 Rd;

each R7 is independently selected from H, halogen, C1-4 alkyl and C1-4 alkoxy, and the C1-4 alkyl and C1-4 alkoxy are each independently optionally substituted with 1, 2 or 3 Re;

each R8 is independently selected from H, C1-4 alkyl, C1-4 alkoxy, C3-6 cycloalkyl, and 3-7-membered heterocycloalkyl, and the C1-4 alkyl, C1-4 alkoxy, C3-6 cycloalkyl, and 3-7-membered heterocycloalkyl are each independently optionally substituted with 1, 2, or 3 Rf;

R9 and R10 are selected from H and C1-4 alkyl, and the C1-4 alkyl is optionally substituted with 1, 2 or 3 Rg;

each Ra, each Rb, each Rc, each Re, each Rf, each Rg, and each Rh are each independently selected from F, Cl, Br, I, OH, CH3, CF3, OCH3, and OCF3;

each Rd is independently selected from C1-4 alkyl, C3-6 cycloalkyl, 3-6-membered heterocycloalkyl, phenyl, 5-6-membered heteroaryl, and —C(═O)—C2-4 alkenyl, and the C1-4 alkyl, C3-6 cycloalkyl, 3-6-membered heterocycloalkyl, phenyl, 5-6-membered heteroaryl, and —C(═O)—C2-4 alkenyl are each independently optionally substituted with 1, 2, or 3 R;

each R is independently selected from F, Cl, Br, I, OH, CH3, CF3, OCH3, and OCF3;

n, p, and q are each independently selected from 0, 1, 2, and 3;

the "3-6-membered heterocycloalkyl," "3-7-membered heterocycloalkyl," and "5-6-membered heteroaryl" each independently contains 1 or 2 heteroatoms or heteroatom groups independently selected from —NH—, —O—, —S—, and N.

The present disclosure further provides a compound shown in formula (I), a stereoisomer thereof, or a pharmaceutically acceptable salt thereof, (I)

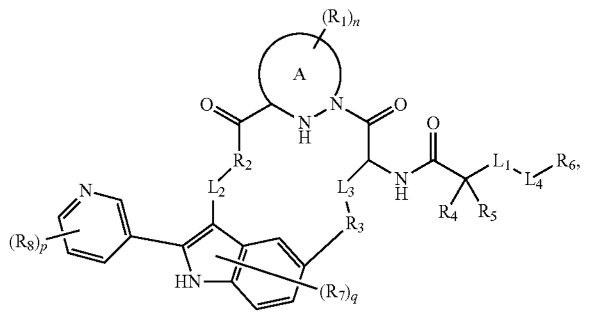

$L_1$ is selected from —$N(R_9)C(=O)$—;

$L_2$ is selected from $C_{1-6}$ alkyl, which is optionally substituted with 1, 2 or 3 $R_a$;

L3 is selected from —CH2—;

L4 is selected from a single bond and —C1-4 alkyl-N(R10)C(=O)—;

ring A is selected from tetrahydropyridazinyl, 3,4-diazabicyclo[4.1.0]heptyl, 2,3-diazabicyclo[3.1.0]hexane, and 5,6-diazaspiro[2.5]octane;

R1 is selected from H, F, Cl, Br, I, OH, C1-4 alkyl, and C1-4 alkoxy, and the C1-4 alkyl and C1-4 alkoxy are each independently optionally substituted with 1, 2, or 3 Rh;

R2 is selected from —O— and —NH—;

R3 is selected from phenyl and 5-6-membered heteroaryl, which are each independently optionally substituted with 1, 2, or 3 Rb;

R4 and R5 are each independently selected from H, C1-4 alkyl, C3-6 cycloalkyl, and 3-6-membered heterocycloalkyl, and the C1-4 alkyl, C3-6 cycloalkyl, and 3-6-membered heterocycloalkyl are each independently optionally substituted with 1, 2, or 3 Rc;

R6 is selected from C3-6 cycloalkyl and 3-6-membered heterocycloalkyl, which are each independently optionally substituted with 1, 2, or 3 Rd;

R7 is selected from H, C1-4 alkyl and C1-4 alkoxy, the C1-4 alkyl and C1-4 alkoxy are each independently optionally substituted with 1, 2 or 3 Re;

R8 is selected from H, C1-4 alkyl, C1-4 alkoxy, C3-6 cycloalkyl, and 3-7-membered heterocycloalkyl, and the C1-4 alkyl, C1-4 alkoxy, C3-6 cycloalkyl, and 3-7-membered heterocycloalkyl are each independently optionally substituted with 1, 2, or 3 Rf;

R9 and R10 are selected from H and C1-4 alkyl, and the C1-4 alkyl is optionally substituted with 1, 2 or 3 Rg;

each Ra, Rb, Rc, Re, Rf, Rg, and Rh are each independently selected from F, Cl, Br, I, OH, CH3, CF3, OCH3, and OCF3;

each Rd is independently selected from C1-4 alkyl, C3-6 cycloalkyl, 3-6-membered heterocycloalkyl, phenyl, 5-6-membered heteroaryl, and —C(=O)—C2-4 alkenyl, and the C1-4 alkyl, C3-6 cycloalkyl, 3-6-membered heterocycloalkyl, phenyl, 5-6-membered heteroaryl, and —C(=O)—C2-4 alkenyl are each independently optionally substituted with 1, 2, or 3 R;

each R is independently selected from F, Cl, Br, I, OH, CH3, CF3, OCH3, and OCF3;

n, p, and q are each independently selected from 0, 1, 2, and 3;

the "3-6-membered heterocycloalkyl," "3-7-membered heterocycloalkyl," and "5-6-membered heteroaryl" each independently contains 1 or 2 heteroatoms or heteroatom groups independently selected from —NH—, —O—, —S—, and N.

In some embodiments of the present disclosure, each R above is independently selected from D and F, and other variables are as defined herein.

In some embodiments of the present disclosure, each R above is independently selected from F, and other variables are as defined herein.

In some embodiments of the present disclosure, each Ra above is independently selected f-om H, D, F, Cl and CH3, and other variables are as defined herein.

In some embodiments of the present disclosure, each Rb above is independently selected from H, D, F, Cl, OH and CH3, and other variables are as defined herein.

In some embodiments of the present disclosure, each Rc above is independently selected from H, D, F and Cl, and other variables are as defined herein.

In some embodiments of the present disclosure, each Rd above is independently selected from $CH_3$, $CH_2CH_3$, phenyl, cyclopropyl, cyclobutyl, oxetanyl, azetidinyl, and

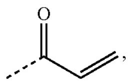, which are each independently optionally substituted with 1, 2 or 3 R, and other variables are as defined herein.

In some embodiments of the present disclosure, each $R_d$ above is independently selected from $CH_3$,

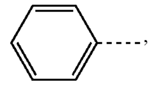, 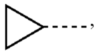, and 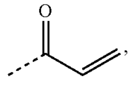, and other variables are as defined herein.

In some embodiments of the present disclosure, each Rd above is independently selected from C1-3 alkyl, which is optionally substituted with 1, 2 or 3 R, and other variables areas defined herein.

In some embodiments of the present disclosure, each Rd above is independently selected from CH3 and CH2CH3, which are each independently optionally substituted with 1, 2 or 3 F, and other variables are as defined herein.

In some embodiments of the present disclosure, each Rd above is independently selected from CH3, which is optionally substituted with 1, 2 or 3 F, and other variables are as defined herein.

In some embodiments of the present disclosure, each Rd above is independently selected from CH3, and other variables are as defined herein.

In some embodiments of the present disclosure, each Rd above is independently selected from CH3, and other variables are as defined herein.

In some embodiments of the present disclosure, each Re above is independently selected from H, D, F and Cl, and other variables are as defined herein.

In some embodiments of the present disclosure, each Re above is independently selected from D and F, and other variables are as defined herein.

In some embodiments of the present disclosure, each Rf above is independently selected from H, D, F, Cl, CH3 and OCH3, and the CH3 and OCH3 are each independently optionally substituted with 1, 2 or 3 R, and other variables are as defined herein.

In some embodiments of the present disclosure, each Rf above is independently selected from H, D, F, Cl, CH3, CD3, CF3 and OCH3, and other variables are as defined herein.

In some embodiments of the present disclosure, each Rg above is independently selected from H, D, F and Cl, and other variables are as defined herein.

In some embodiments of the present disclosure, each Rh above is independently selected from H, D, F and Cl, and other variables are as defined herein.

In some embodiments of the present disclosure, each R1 above is independently selected from H, F, OH and CH3, and other variables are as defined herein.

In some embodiments of the present disclosure, each R1 above is independently selected from H, F and CH3, and other variables are as defined herein.

In some embodiments of the present disclosure, the above structural unit

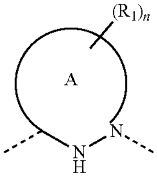

is selected from

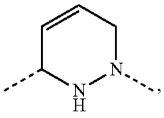, 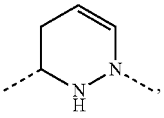, 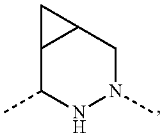, 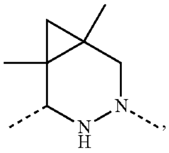, 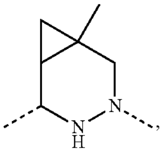, 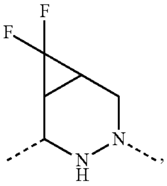, 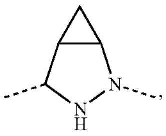, 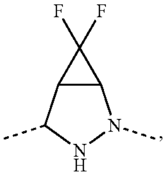, 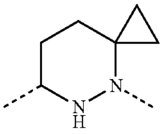 and 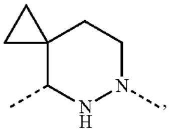, and other variables are as defined herein.

In some embodiments of the present disclosure, the above structural unit

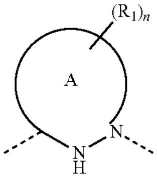

is selected from

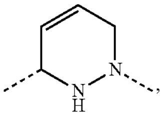, 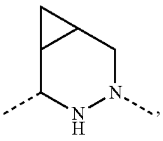, 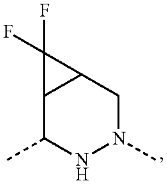, 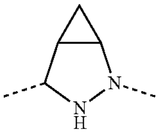 and 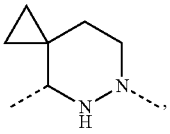, and other variables are as defined herein.

In some embodiments of the present disclosure, the above structural unit

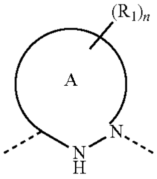

is selected from

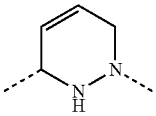, 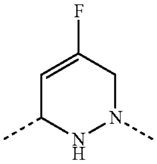, 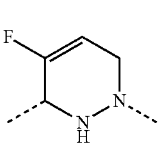, 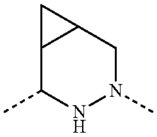, 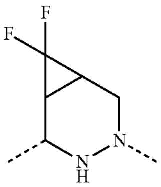, 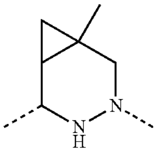, 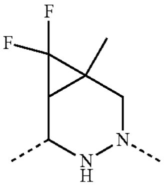, 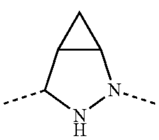, 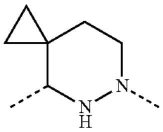, -continued

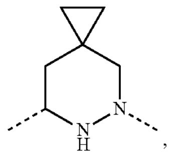

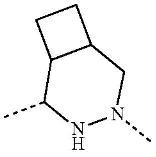

and

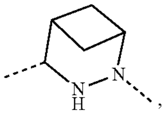

and other variables are as defined herein.

In some embodiments of the present disclosure, the above structural unit

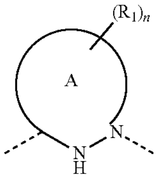

is selected from

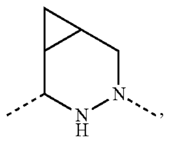

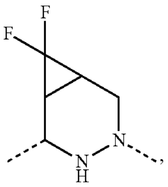

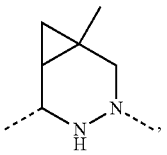

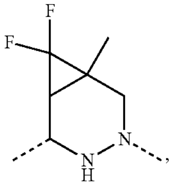

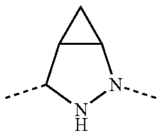

and

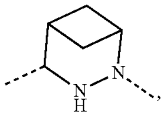

and other variables are as defined herein.

In some embodiments of the present disclosure, the above ring A is selected from 3,4-diazabicyclo[4.1.0]heptyl and 2,3-diazabicyclo[3.1.1]heptyl, and other variables areas defined herein.

In some embodiments of the present disclosure, the above ring A is selected from

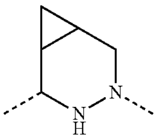

and

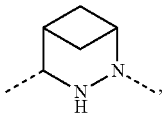

and other variables are as defined herein.

In some embodiments of the present disclosure, the above ring A is

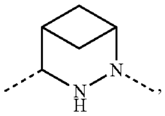

and other variables are as defined herein.

In some embodiments of the present disclosure, the above structural unit

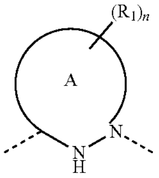

is selected from

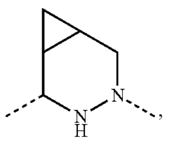

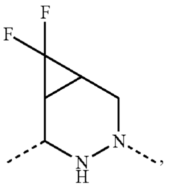

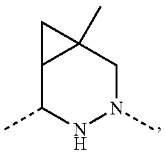

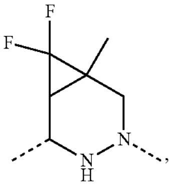

and

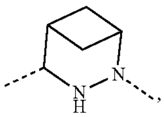

and other variables are as defined herein.

In some embodiments of the present disclosure, the above R2 is selected from —O—, and other variables are as defined herein.

In some embodiments of the present disclosure, the above R3 is selected from 5-6-membered heteroaryl, which is optionally substituted with 1, 2 or 3 Rb, and other variables are as defined herein.

In some embodiments of the present disclosure, the above R3 is selected from 5-membered heteroaryl, which is optionally substituted with 1, 2 or 3 Rb, and other variables are as defined herein.

In some embodiments of the present disclosure, the above R3 is selected from thiazolyl, thienyl, oxazolyl, pyrazolyl and imidazolyl, which are each independently optionally substituted with 1, 2 or 3 Rb, and other variables are as defined herein.

In some embodiments of the present disclosure, the above R3 is selected from thiazolyl and thienyl, and other variables are as defined herein.

In some embodiments of the present disclosure, the above R3 is selected from

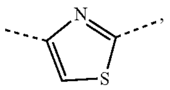

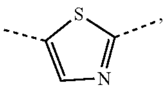

-continued

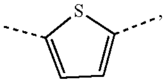

and

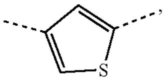

and other variables are as defined herein.

In some embodiments of the present disclosure, the above R3 is selected from

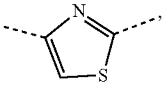

and other variables are as defined herein.

In some embodiments of the present disclosure, the above R3 is selected from phenyl, pyridinyl, pyrimidinyl, thiazolyl, thienyl, oxazolyl, pyrazolyl and imidazolyl, which are each independently optionally substituted with 1, 2 or 3 Rb, and other variables are as defined herein.

In some embodiments of the present disclosure, the above R3 is selected from phenyl, pyridinyl, pyrimidinyl, thiazolyl, oxazolyl, pyrazolyl and imidazolyl, which are each independently optionally substituted with 1, 2 or 3 Rb, and other variables are as defined herein In some embodiments of the present disclosure, the above R3 is selected from

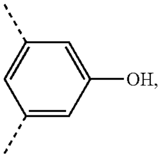

and

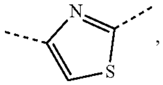

,

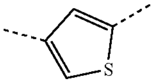

, and other variables are as defined herein.

In some embodiments of the present disclosure, the above R3 is selected from

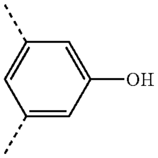

and

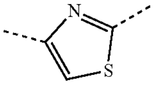

, and other variables are as defined herein.

In some embodiments of the present disclosure, the above R3 is selected from

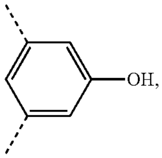

and other variables are as defined herein.

In some embodiments of the present disclosure, the above R4 is selected from H, CH3, CH2CH3, CH2CH2CH3, CH(CH3)2, cyclopropyl, cyclobutyl and cyclopentyl, the CH3, CH2CH3, CH2CH2CH3, CH(CH3)2, cyclopropyl, cyclobutyl and cyclopentyl are each independently optionally substituted with 1, 2 or 3 Rc, and other variables are as defined herein.

In some embodiments of the present disclosure, the above $R_5$ is selected from H, $CH_3$, $CH_2,CH_3$. $CH_2CH_2CH_3$, $CH(CH_3)_2$, cyclopropyl, cyclobutyl and cyclopentyl, the $CH_3$, $CH_2CH3$, $CH_2CH_2CH_3$, $CH(CH_3)_2$, cyclopropyl, cyclobutyl and cyclopentyl are each independently optionally substituted with 1, 2 or 3 $R_c$, and other variables are as defined herein In some embodiments of the present disclosure, the above R4 is selected from H, R5 is selected from H, CH(CH3)2 and

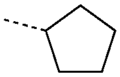

, and other variables are as defined herein.

In some embodiments of the present disclosure, the above R6 is selected from cyclopentyl, aziridinyl, azetidinyl, pyrrolidinyl, piperidinyl, piperazinyl, morpholinyl, oxetanyl, oxolanyl, and oxacyclohexyl, which are each independently optionally substituted with 1, 2, or 3 Rd, and other variables are as defined herein.

In some embodiments of the present disclosure, the above R6 is selected from cyclopropyl, cyclobutyl, cyclopentyl, aziridinyl, azetidinyl, pyrrolidinyl, piperidinyl, piperazinyl, morpholinyl, oxetanyl, oxolanyl, and oxacyclohexyl, which are each independently optionally substituted with 1, 2, or 3 Rd, and other variables are as defined herein.

In some embodiments of the present disclosure, the above R6 is selected from

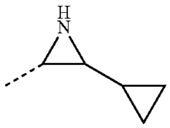

,

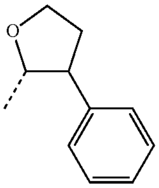

,

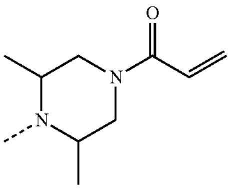

,

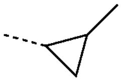

and

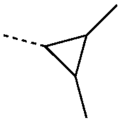

, and other variables are as defined herein.

In some embodiments of the present disclosure, the above R6 is selected from

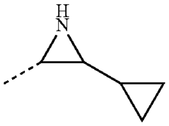

, and

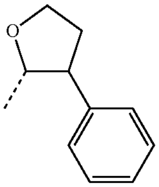

,

-continued

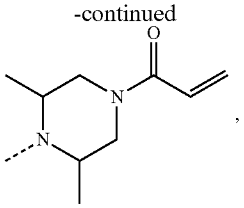

, and other variables are as defined herein.

In some embodiments of the present disclosure, the above R6 is selected from C3-6 cycloalkyl, which is optionally substituted with 1, 2 or 3 Rd, and other variables are as defined herein.

In some embodiments of the present disclosure, the above R6 is selected from cyclopropyl, which is optionally substituted with 1, 2 or 3 Rd, and other variables are as defined herein.

In some embodiments of the present disclosure, the above R6 is selected from

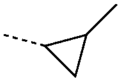

and

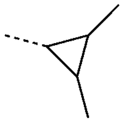

, and other variables are as defined herein.

In some embodiments of the present disclosure, the above R6 is selected from

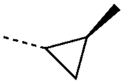

and

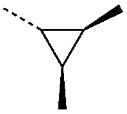

, and other variables are as defined herein.

In some embodiments of the present disclosure, each R7 above is independently selected from H, F, Cl, and C1-3 alkyl, the C1-3 alkyl is optionally substituted with 1, 2, or 3 Re, and other variables are as defined herein In some embodiments of the present disclosure, the above R7 is selected from H, F, Cl, CH3, and CH2CH3, the CH3 and C12CH3 are each independently optionally substituted with 1, 2, or 3 Re, and other variables are as defined herein In some embodiments of the present disclosure, the above R7 is selected from H, F, Cl, CH3, CH2CH3, CH2F, CHF2, CF3, CH2CF3 and CD3, and other variables are as defined herein In some embodiments of the present disclosure, the above R7 is selected from H, F, Cl, CH3 and CH2CH3, and other variables are as defined herein.

In some embodiments of the present disclosure, the above R7 is selected from H, CH3 and CH2CH3, and other variables are as defined herein.

In some embodiments of the present disclosure, each R8 above is independently selected from H, C1-3 alkyl, and 3-10-membered heterocycloalkyl, the C1-3 alkyl and 3-10-membered heterocycloalkyl are each independently optionally substituted with 1, 2, or 3 Rf, and other variables are as defined herein.

In some embodiments of the present disclosure, each R8 above is independently selected from H, C1-3 alkyl, and 5-10-membered heterocycloalkyl, the C1-3 alkyl and 5-10 membered heterocycloalkyl are each independently optionally substituted with 1, 2, or 3 Rf, and other variables are as defined herein In some embodiments of the present disclosure, each R8 above is independently selected from H, C1-3 alkyl, and 5-6-membered heterocycloalkyl, the C1-3 alkyl and 5-6-membered heterocycloalkyl are each independently optionally substituted with 1, 2, or 3 Rf, and other variables are as defined herein In some embodiments of the present disclosure, the above R8 is selected from H, CH3, CH2CH3, piperazinyl, homopiperazinyl, piperidinyl, tetrahydropyridinyl, piperidinyl, tetrahydropyridinyl, piperidinyl, morpholinyl,

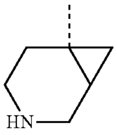

and

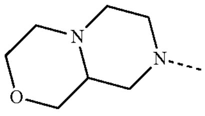

, the CH3, CH2CH3, piperazinyl, homopiperidinyl, piperidinyl, tetrahydropyridinyl, homopiperidinyl, morpholinyl,

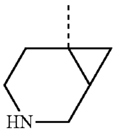

and

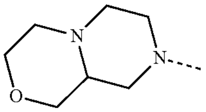

and are each independently optionally substituted with 1, 2 or 3 Rf, and other variables are as defined herein In some embodiments of the present disclosure, the above R8 is selected from H,

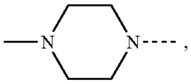

,

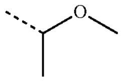

,

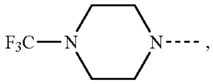

,

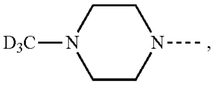

,

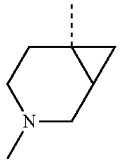

,

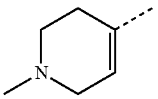

and

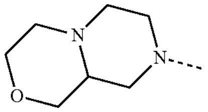

, and other variables are as defined herein

In some embodiments of the present disclosure, the above R8 is selected from H, CH3, CH2CH3, piperazinyl, homopiperazinyl, piperidinyl, homopiperidinyl, morpholinyl, and

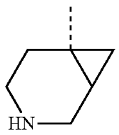

, the CH3, CH2CH3, piperazinyl, homopiperazinyl, piperidinyl, homopiperidinyl, morpholinyl, and

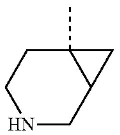

are each independently optionally substituted with 1, 2, or 3 Rf, and other variables are as defined herein In some embodiments of the present disclosure, the above R8 is selected from H, CH3, CH2CH3, piperazinyl, homopiperazinyl, piperidinyl, homopiperidinyl and morpholinyl, the CH3, CH2CH3, piperazinyl, homopiperazinyl, piperidinyl, homopiperidinyl and morpholinyl are each independently optionally substituted with 1, 2 or 3 Rf, and other variables are as defined herein In some embodiments of the present disclosure, the above R8 is selected from H,

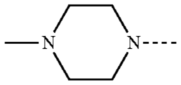, 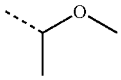, 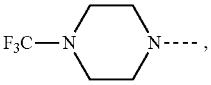, 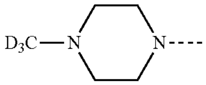, 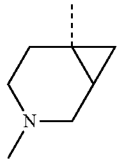, and other variables are as defined herein.

In some embodiments of the present disclosure, the above $R_8$ is selected from H, and

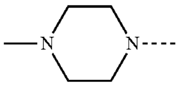, 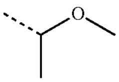, and other variables are as defined herein.

In some embodiments of the resent disclosure, the above structural unit

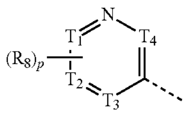

is selected from

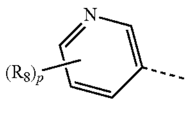, 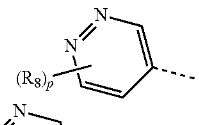, and 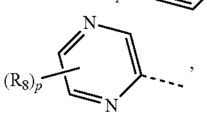, and other variables are as defined herein.

In some embodiments of the present disclosure, the above structural unit

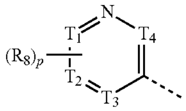

is selected from

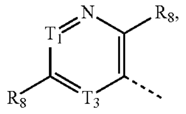

and other variables are as defined herein.

In some embodiments of the present disclosure, the above structural unit

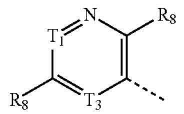

is selected from

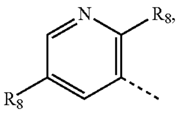 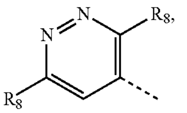 and 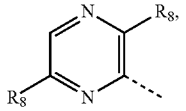

and other variables are as defined herein.

In some embodiments of the present disclosure, the above structural unit

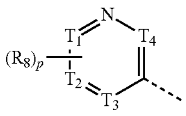

is selected from

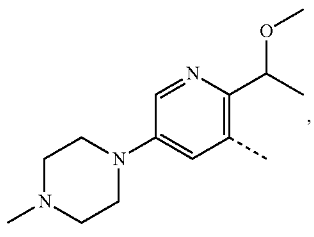, 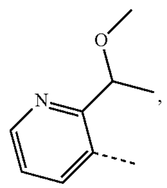,

-continued
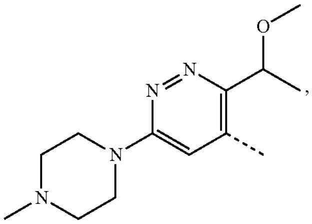
,
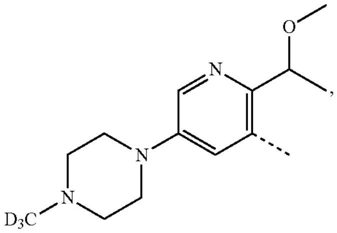
,
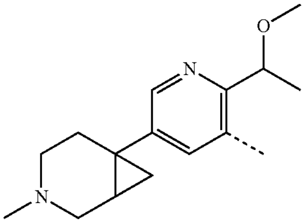
,
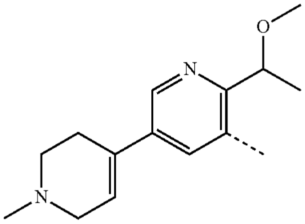
and
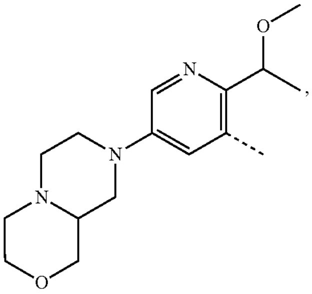
,
and other variables are as defined herein.
In some embodiments of the present disclosure, the above structural unit
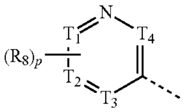
is selected from
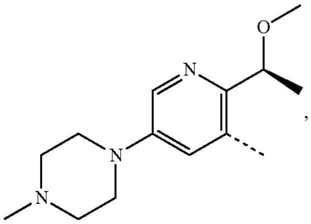
,
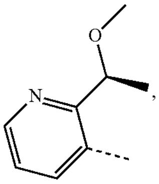
,
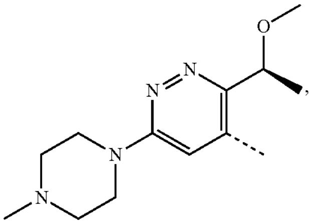
,
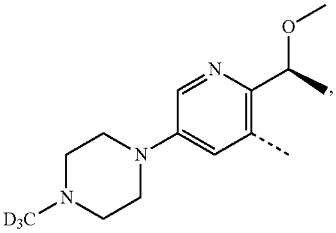
,
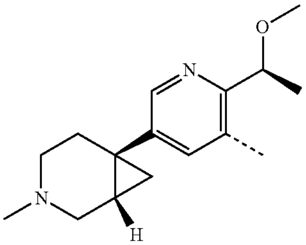
,
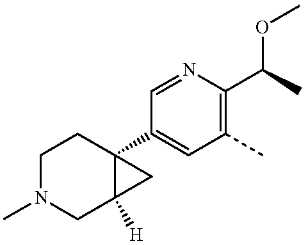
,
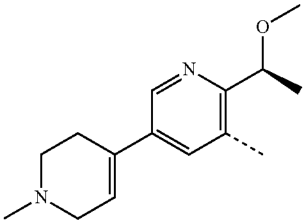
and -continued

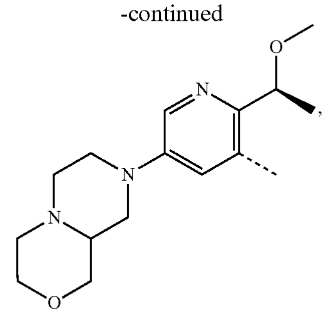

and other variables are as defined herein.

In some embodiments of the present disclosure, the above structural unit

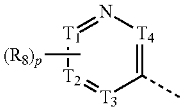

is selected from

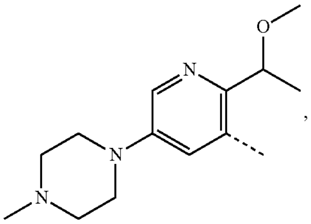
,
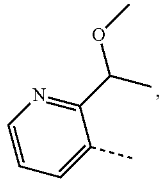
,
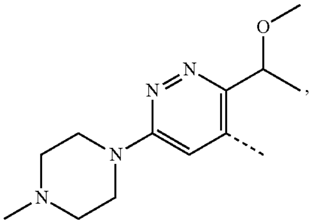
,
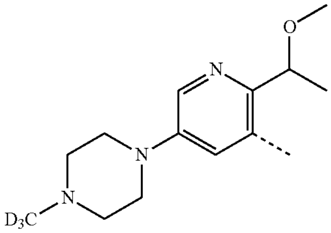
and
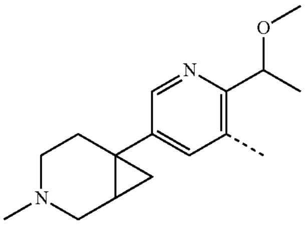
, and other variables are as defined herein.

In some embodiments of the present disclosure, the above structural unit

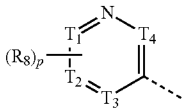

is selected from

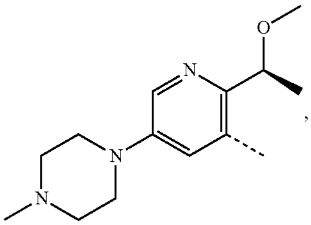
,
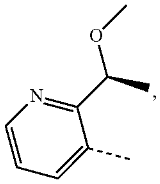
,
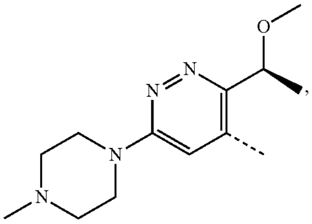
,
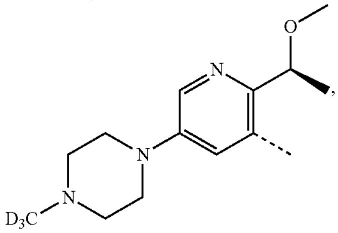
,
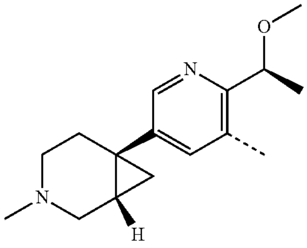
and
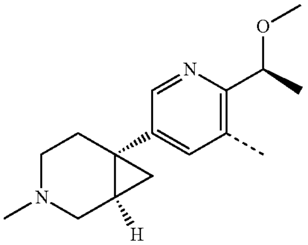
, and other variables are as defined herein.

In some embodiments of the present disclosure, the above structural unit

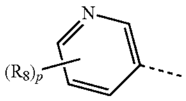

is selected from

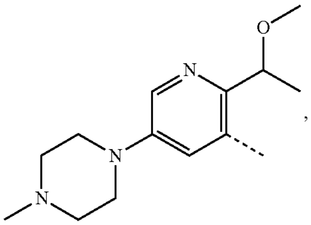

, and other variables are as defined herein.

In some embodiments of the present disclosure, the above structural unit

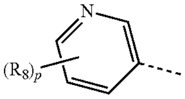

is selected from

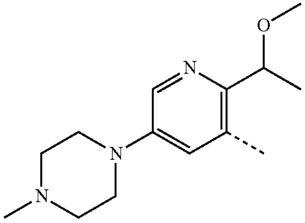

and

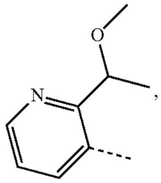

, and other variables are as defined herein.

In some embodiments of the present disclosure, the above structural unit

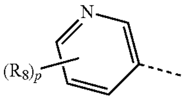

is selected from

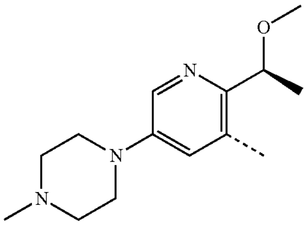

and

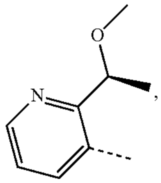

, and other variables are as defined herein.

In some embodiments of the present disclosure, the above ring B is selected from

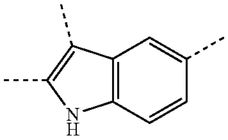

,

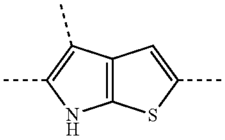

and

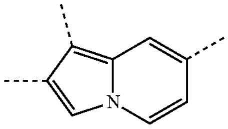

, and other variables are as defined herein.

In some embodiments of the present disclosure, the above ring B is selected from indolyl, and other variables are as defined herein.

In some embodiments of the present disclosure, the above ring B is selected from

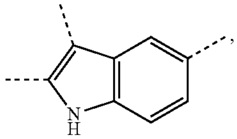

, and other variables are as defined herein.

In some embodiments of the present disclosure, the above 1 is selected from —N(CH3)C(=O)— and other variables are as defined herein In some embodiments of the present disclosure, the above L2 is selected from

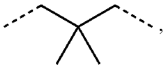

, and other variables are as defined herein.

In some embodiments of the present disclosure, the above L3 is selected from —CH2-, cyclopropyl, cyclobutyl, cyclopentyl and cyclohexyl, and other variables are as defined herein.

In some embodiments of the present disclosure, the above L3 is selected from —CH2-,

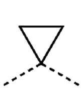

and

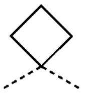

, and other variables are as defined herein.

In some embodiments of the present disclosure, the above L3 is selected from other variables are as defined herein.

In some embodiments of the present disclosure, the above L3 is selected from

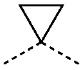

and

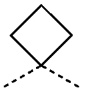

, and other variables are as defined herein. In some embodiments of the present disclosure, the above L4 is selected from a single bond and —CH2-N(CH3)C(═O)—, and other variables are as defined herein.

In some embodiments of the present disclosure, the above Lis selected from

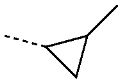
,
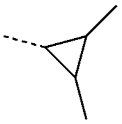
,
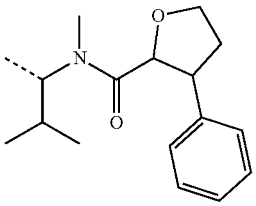
,
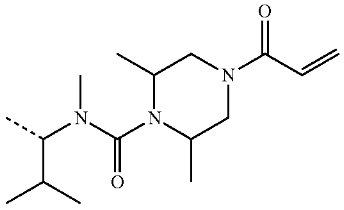
and
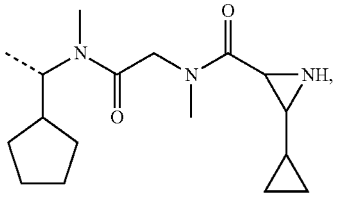

and other variables are as defined herein.

In some embodiments of the resent disclosure, the above L is selected from

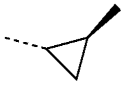
,
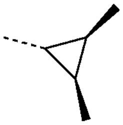
,
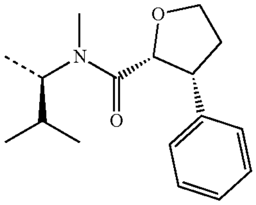
,
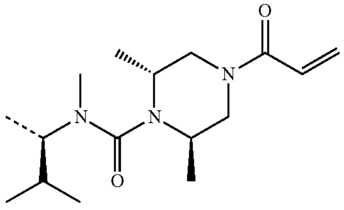
and

-continued

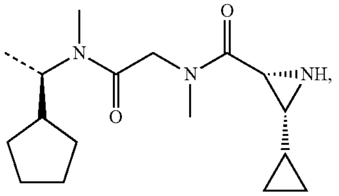

and other variables are as defined herein.

In some embodiments of the present disclosure, the above L is R6, and other variables areas defined herein.

In some embodiments of the present disclosure, the above L is selected from

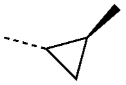
and
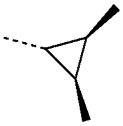
, and other variables are as defined herein.

In some embodiments of the present disclosure, the above compound, a stereoisomer thereof, or a pharmaceutically acceptable salt thereof, is selected from, (VI-1)

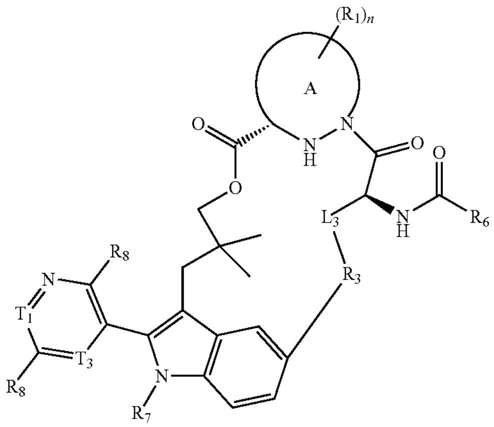

(VI-2)

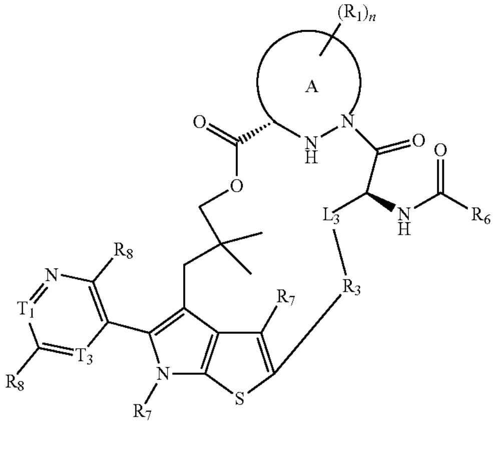
and

-continued
(VI-3)
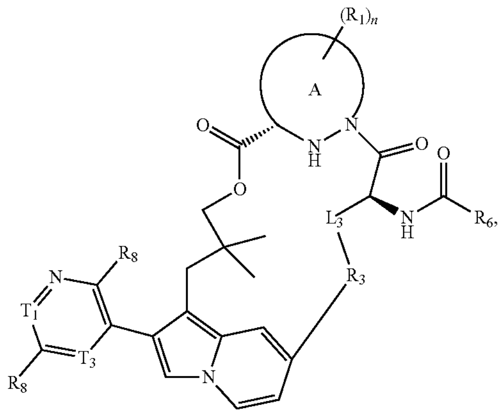
wherein, ring A, T1, T3, R1, R3, R6, R7, R8, L3, and n are as defined herein.
In some embodiments of the present disclosure, the above compound, a stereoisomer thereof, or a pharmaceutically acceptable salt thereof, is selected from,
(VI-1)
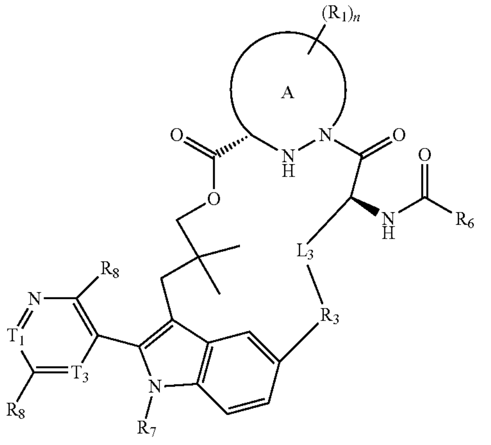
(VI-2)
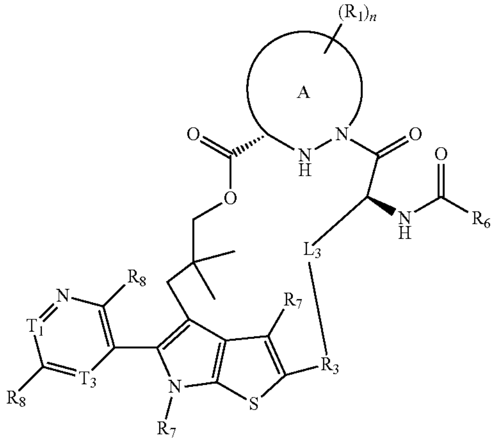
and
-continued
(VI-3)
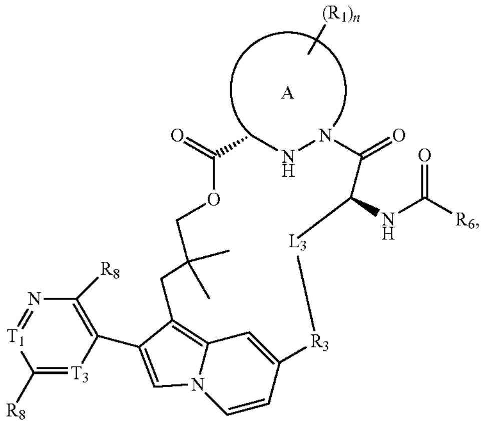
Wherein
the structural unit
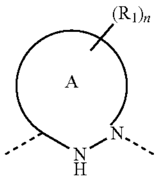
is selected from
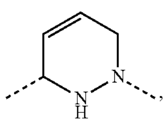,
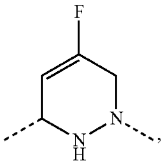,
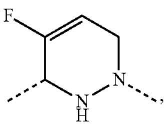,
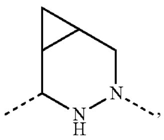,
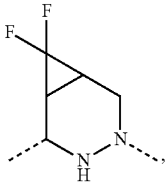,
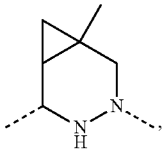,
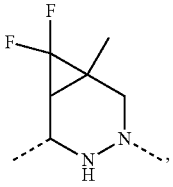,
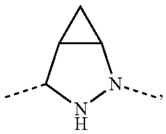,
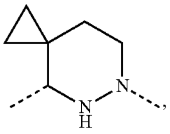,
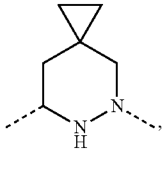,
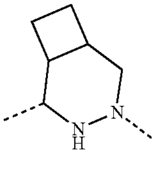
and
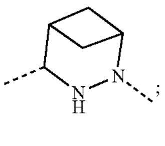;

the structural unit

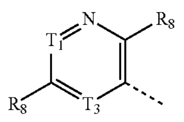

is selected from

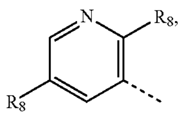

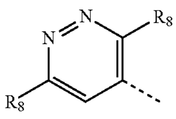

and

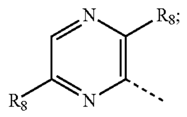

R6 is selected from C3-6 cycloalkyl, which is optionally substituted with 1, 2 or 3 Rd;

each Rd is independently selected from C1-4 alkyl, which is optionally substituted with 1, 2, or 3 R;

L3, R3, R7, each R8, and each R are as defined herein.

In some embodiments of the present disclosure, the above compound of formula (VI-1), formula (VI-2) or formula (VI-3), a stereoisomer thereof, or a pharmaceutically acceptable salt thereof wherein the structural unit

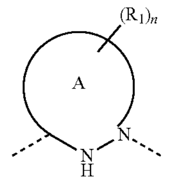

is selected from

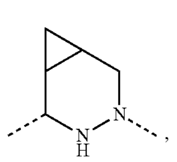

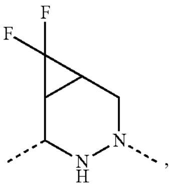

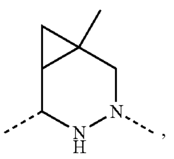

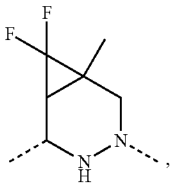

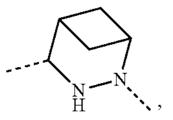

and other variables are as defined herein

In some embodiments of the present disclosure, the above compound of formula (VI-1), a stereoisomer thereof, or a pharmaceutically acceptable salt thereof, is selected from, (P-1)

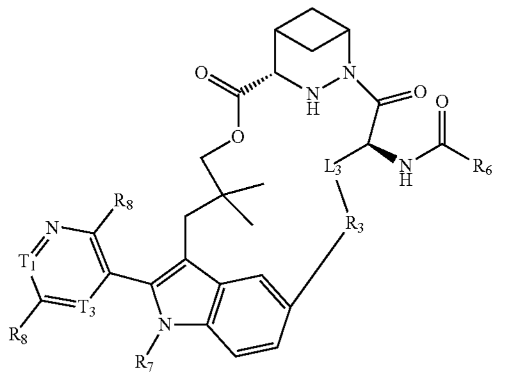

and (P-2)

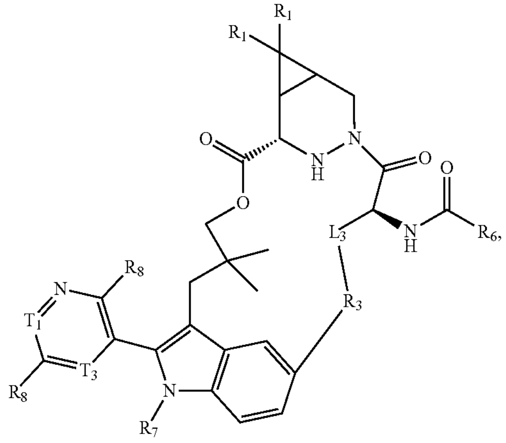

Wherein

T1 and T3 are each independently selected from CH and N;

each R1 is independently selected from H, F, OH and CH3;

R3 is selected from phenyl and 5-6-membered heteroaryl, which are each independently optionally substituted with 1, 2, or 3 Rb;

R6 is selected from C3-6 cycloalkyl, which is optionally substituted with 1, 2 or 3 Rd;

R7 is selected from H and C1-3 alkyl, the C1-3 alkyl is optionally substituted with 1, 2 or 3 Re;

each R8 is independently selected from H, C1-3 alkyl, and 5-10 membered heterocycloalkyl, and the C1-3 alkyl and 5-10-membered heterocycloalkyl are each independently optionally substituted with 1, 2, or 3 Rf, respectively;

L3 is selected from —CH2-, cyclopropyl, cyclobutyl, cyclopentyl, and cyclohexyl;

each Rd is independently selected from C1-3 alkyl, which is optionally substituted with 1, 2, or 3 R;

each Rb is independently selected from H, D, F, Cl, OH, and CH3;

each Re is independently selected from H, D, F and Cl;

each Rf is independently selected from H, D, F, Cl, CH3 and OCH3, and the CH3 and OCH3 are each independently optionally substituted with 1, 2 or 3 R;

each R is independently selected from D and F.

In some embodiments of the present disclosure, the above compound of formula (P-1) or (P-2), a stereoisomer thereof, or a pharmaceutically acceptable salt thereof, wherein each R1, R3, R6, R7, each R8, T1, T3, and L3 are as defined by formula (VI), formula (III), or formula (I) herein.

In some embodiments of the present disclosure, the above compound of formula (P-1) or (P-2), a stereoisomer thereof, or a pharmaceutically acceptable salt thereof, wherein R3 is 5-6-membered heteroaryl, and other variables are as defined herein.

In some embodiments of the present disclosure, the above compound of formula (P-1) or (P-2), a stereoisomer thereof, or a pharmaceutically acceptable salt thereof, wherein R3 is thienyl and thiazolyl, and other variables are as defined herein.

In some embodiments of the present disclosure, the above compound of formula (P-1) or (P-2), a stereoisomer thereof, or a pharmaceutically acceptable salt thereof, wherein, each R8 is independently selected from H, C1-3 alkyl, and 5-6-membered heterocycloalkyl, the C1-3 alkyl and 5-6-membered heterocycloalkyl are each independently optionally substituted with 1, 2, or 3 RE and other variables are as defined herein.

In some embodiments of the present disclosure, the above compound of formula (P-1) or (P-2), a stereoisomer thereof, or a pharmaceutically acceptable salt thereof, wherein T1 is CH, T3 is CH, and other variables are as defined herein.

In some embodiments of the present disclosure, the compound of formula (P-1) or (P-2) above, a stereoisomer thereof, or a pharmaceutically acceptable salt thereof, wherein, L3 is selected from —CH2-.

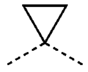 and 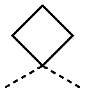, and other variables are as defined herein.

In some embodiments of the present disclosure, the above compound of formula (P-1) or (P-2), a stereoisomer thereof, or a pharmaceutically acceptable salt thereof, is selected from, (P-1a)

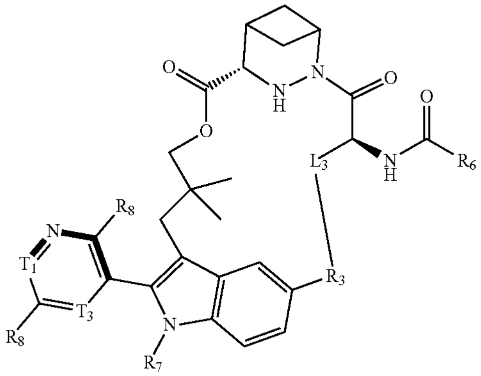

-continued (P-1b)

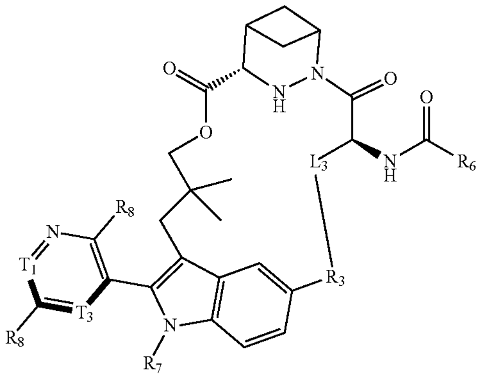

(P-2a)

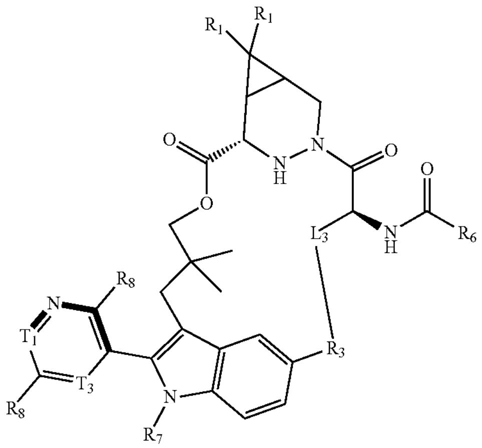

(P-2b)

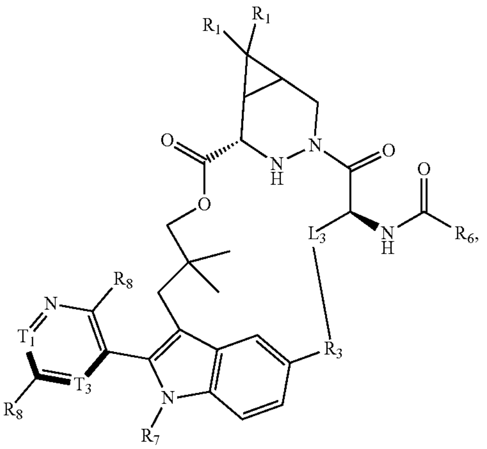

wherein each R1, R3, R6, R7, each R8, T1, T3, and L3 are as defined by formula (P-1) or (P-2) herein.

In some embodiments of the present disclosure, the above compound, a stereoisomer thereof or a pharmaceutically acceptable salt thereof, is selected from, (III-1)

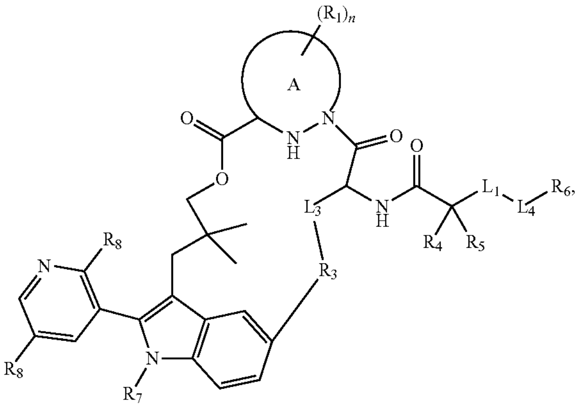

(III-2)

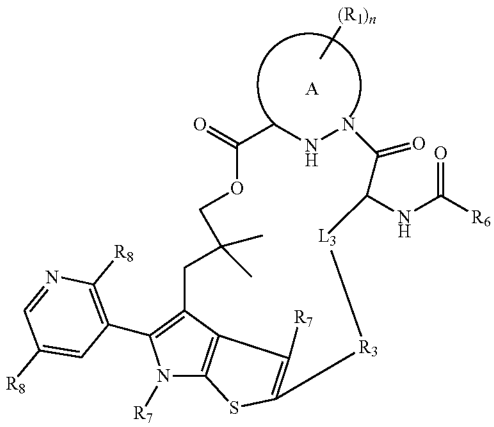

and (III-3)

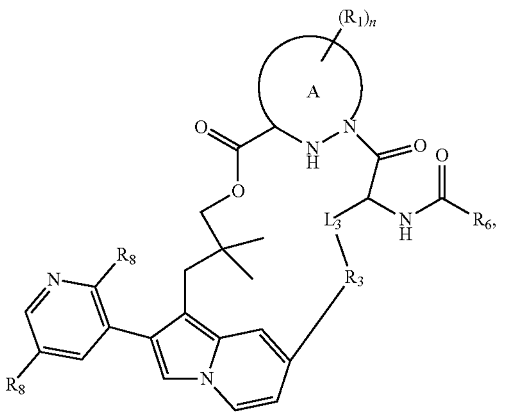

wherein, R1, R3, R4, R5, R6, R7, R8, L1, L3, L4, and n are as defined herein.

In some embodiments of the present disclosure, the above compound, a stereoisomer thereof or a pharmaceutically acceptable salt thereof, is selected from, (IV)

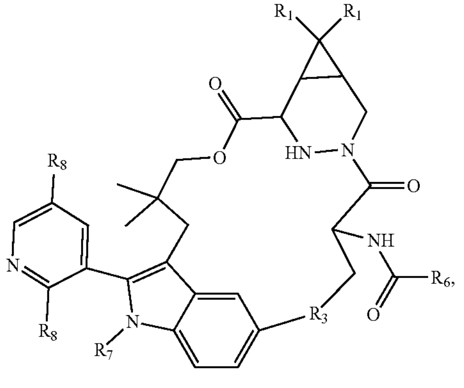

wherein, R1, R3, R6, R7, and R8 are as defined herein.

In some embodiments of the present disclosure, the above compound of formula (IV), a stereoisomer thereof, or a pharmaceutically acceptable salt thereof, is selected from, (IV-1a)

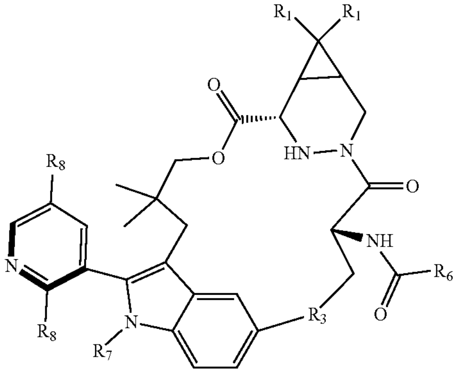

(IV-1b)

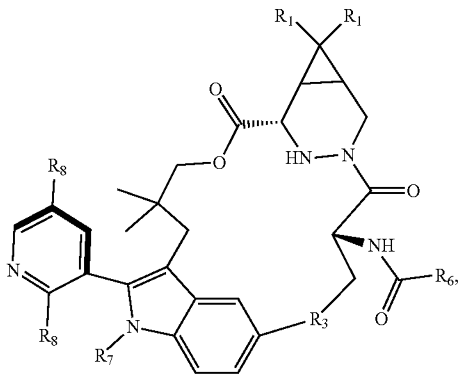

wherein, R1, R3, R6, R7, and R8 are as defined herein.

In some embodiments of the present disclosure, the above compound of formula (IV-1a) or formula (IV-1b), a stereoisomer thereof, or a pharmaceutically acceptable salt thereof, is selected from, (IV-1a-1)

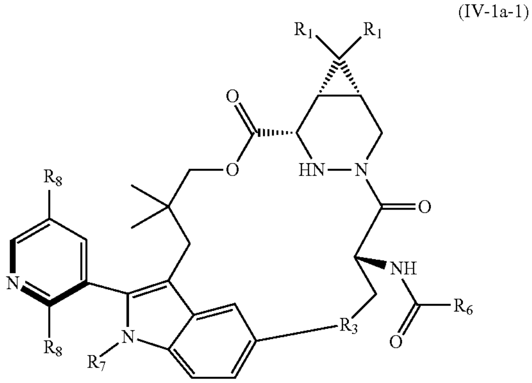

(IV-1a-2)

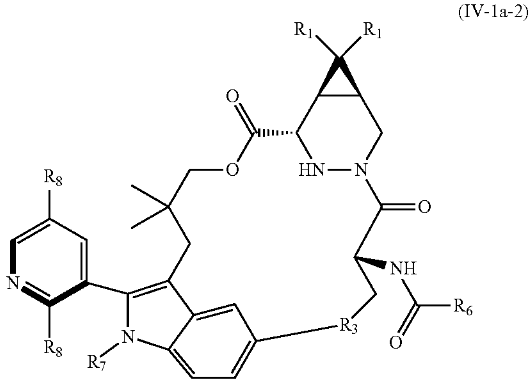

(IV-1b-1)

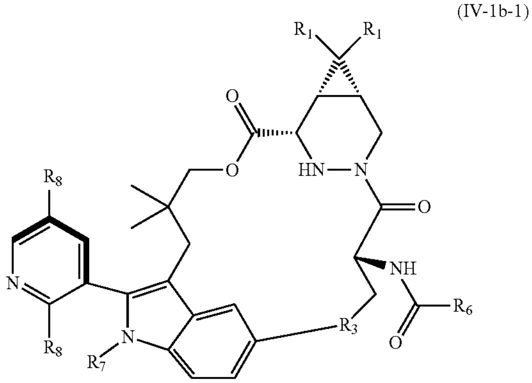

-continued (IV-1b-2)

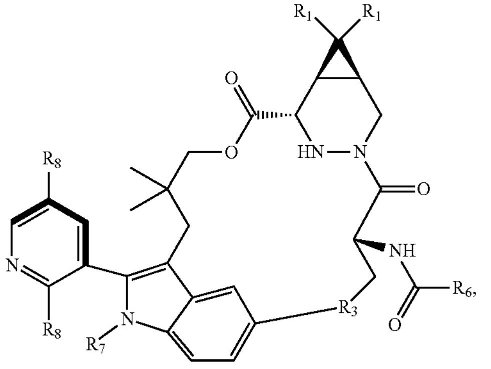

wherein, R1, R3, R6, R7, and R8 are as defined herein.

In some embodiments of the present disclosure, the above compound of formula (IV), (IV-1a), (IV-1b), (IV-1a-1), (IV-1a-2), (IV-1b-1), (IV-1b-2), a stereoisomer thereof, or a pharmaceutically acceptable salt thereof, wherein R1 is selected from H, F, OH and CH3; R3 is selected from phenyl aid thiazolyl, which are each independently optionally substituted with 1, 2, or 3 Rb; R6 is selected from cyclopropyl, which is optionally substituted with 1, 2, or 3 Rd; R7 is selected from H, F, Cl, CH3, and CH2CH3; R8 is selected from H,

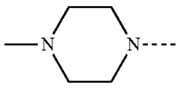 and 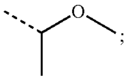;

each Rb is independently selected from F, Cl, Br, I, OH, CH3, CF3, OCH3, and OCF3; each Rd is independently selected from CH3,

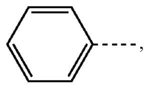, 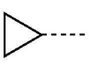 and 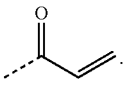.

Some embodiments of the present disclosure are derived from any combination of the above variables.

The present disclosure further provides the following compounds, a stereoisomer thereof, or a pharmaceutically acceptable salt thereof.

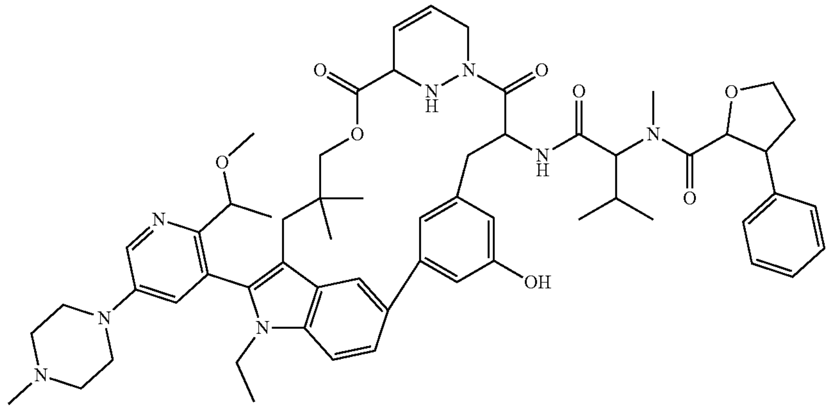
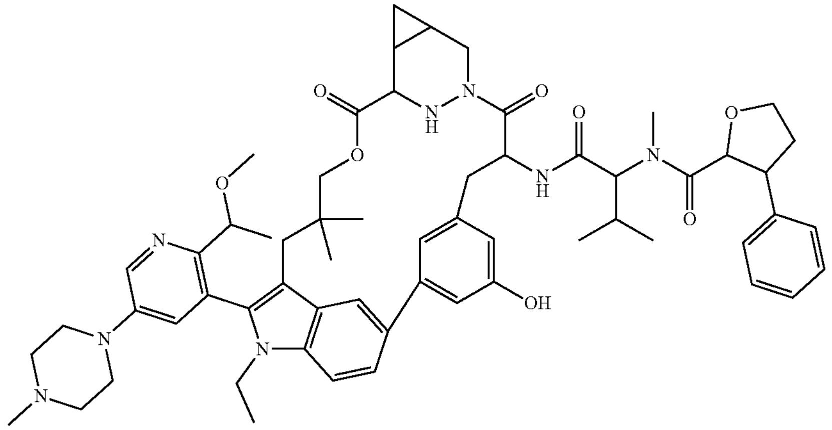
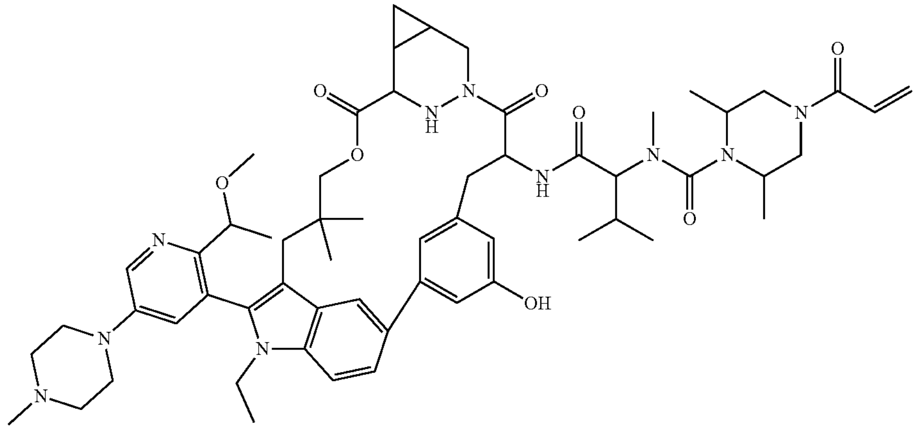
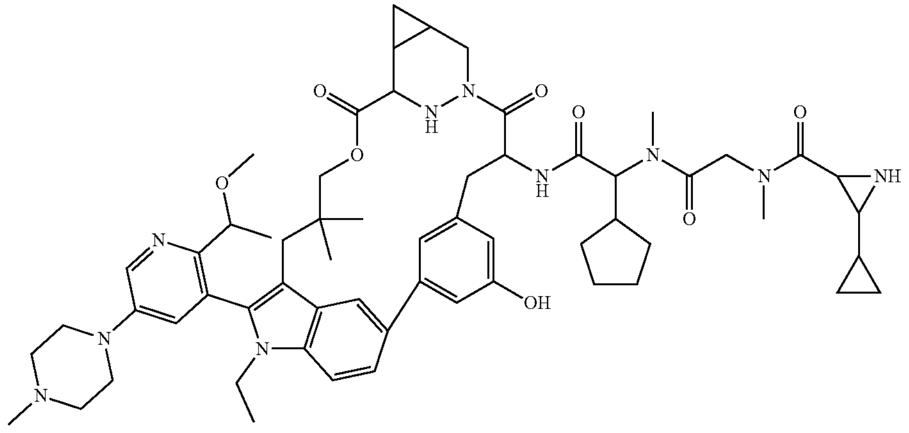

-continued
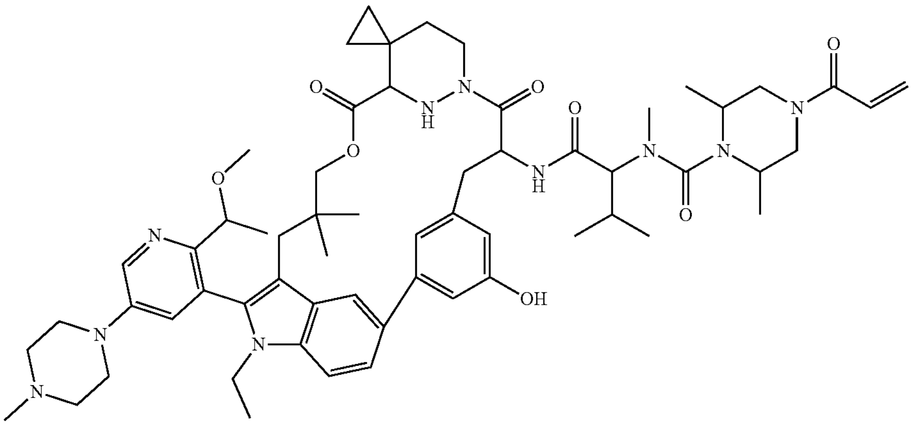
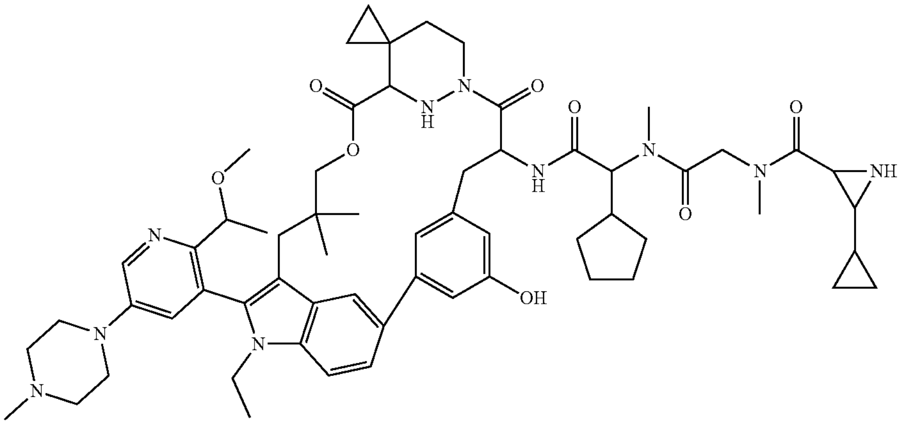
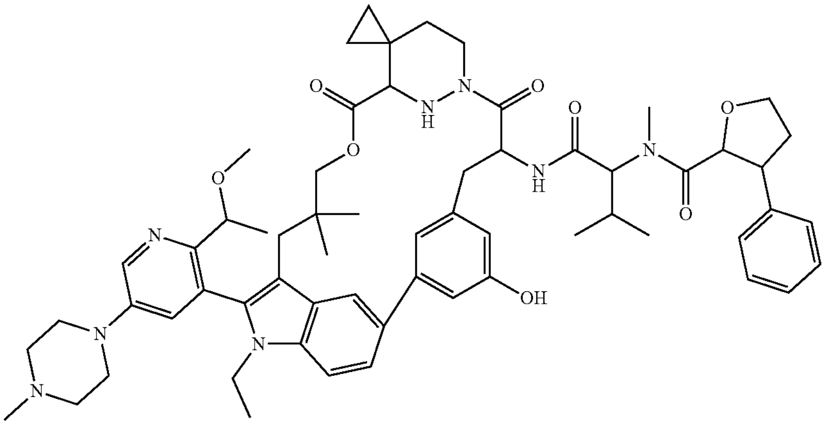
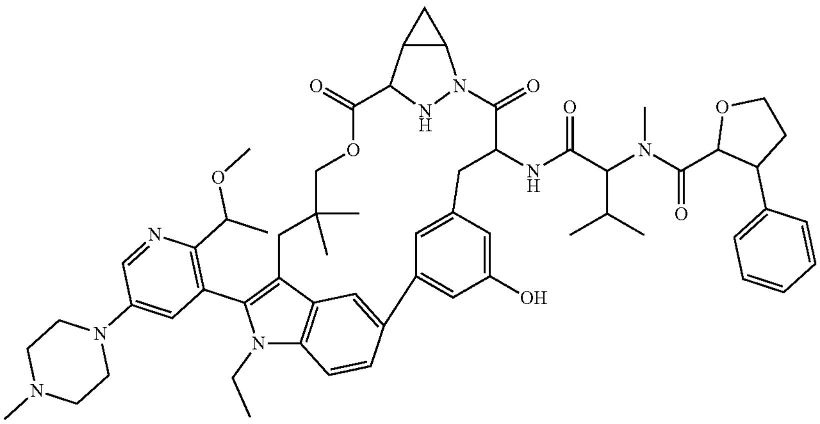

-continued
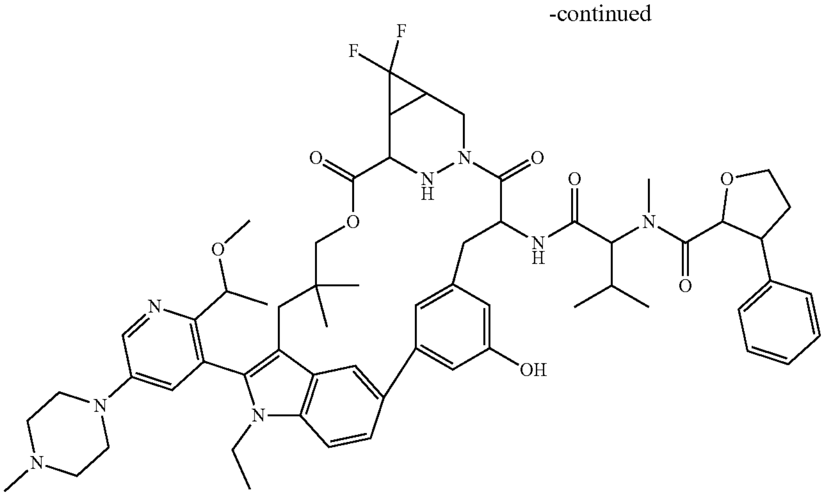
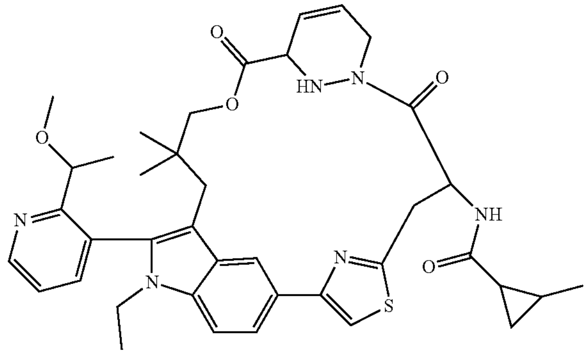
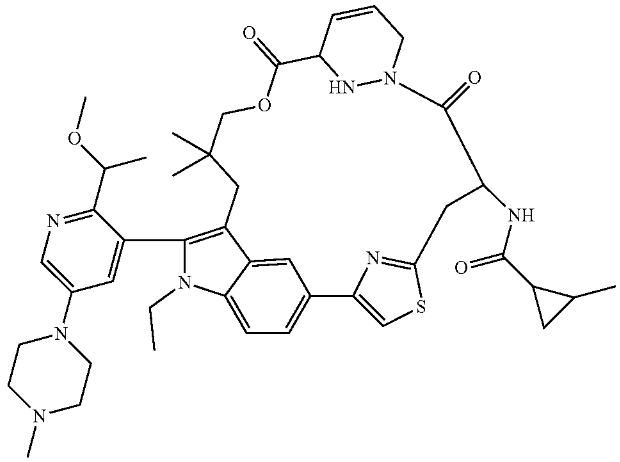
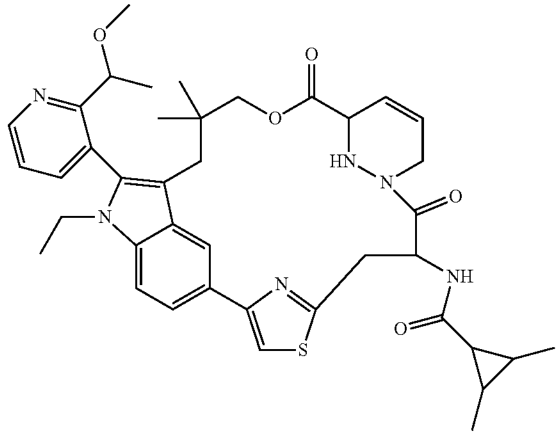

-continued
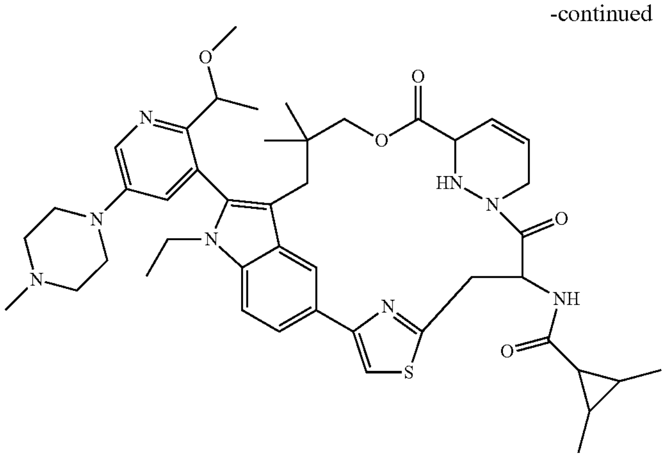
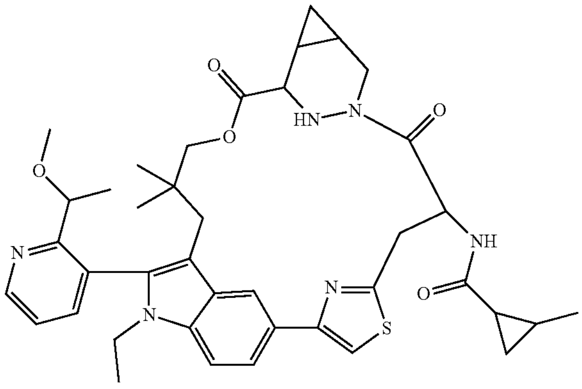
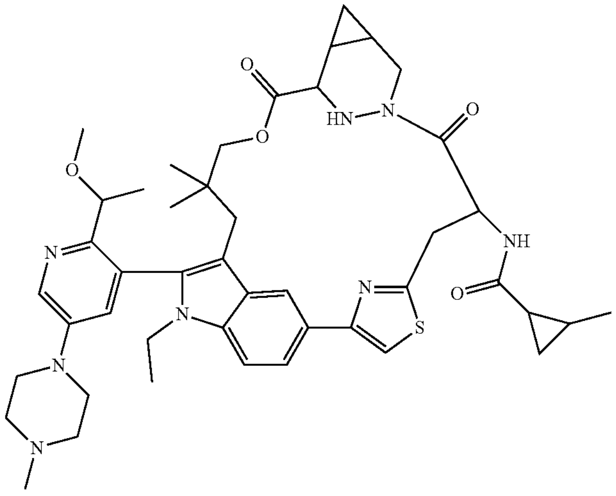
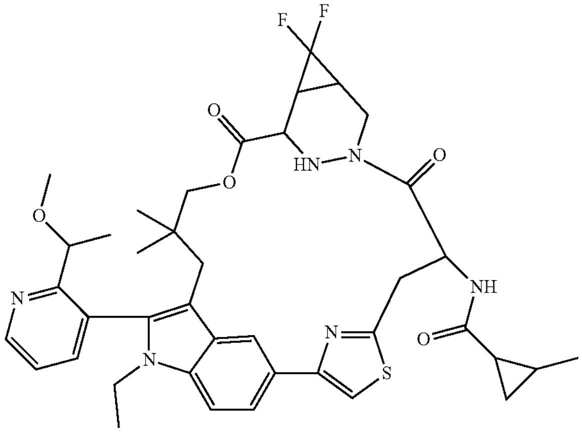
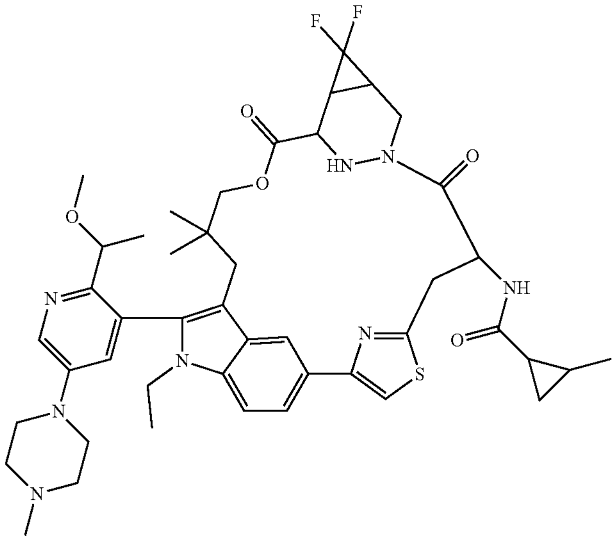

-continued
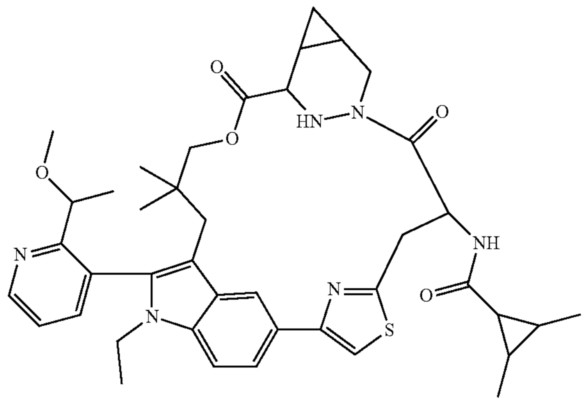
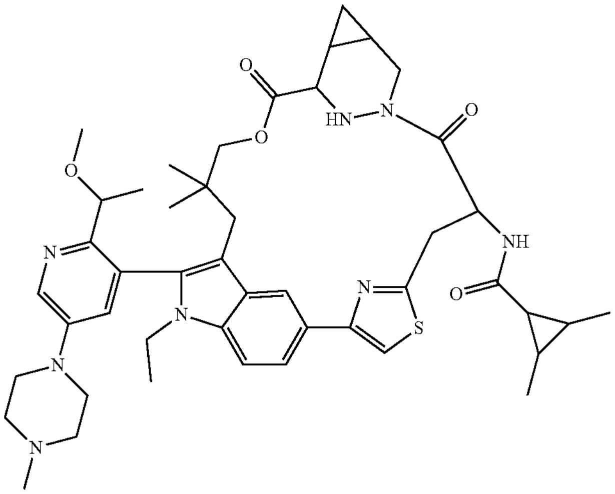
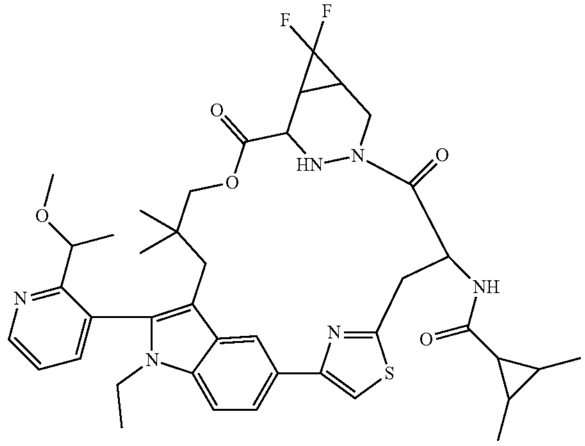
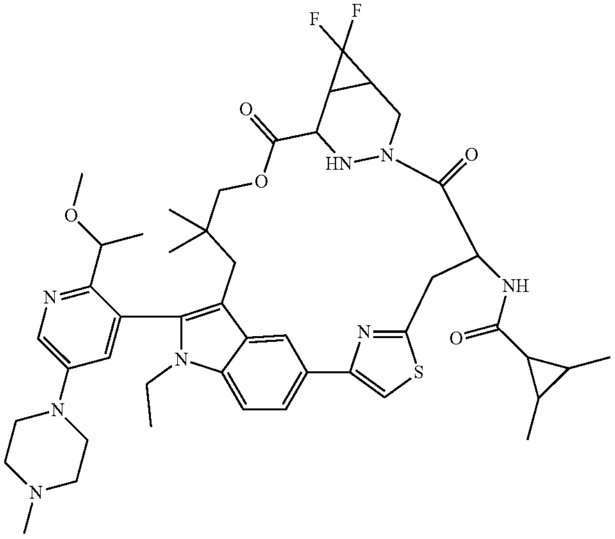
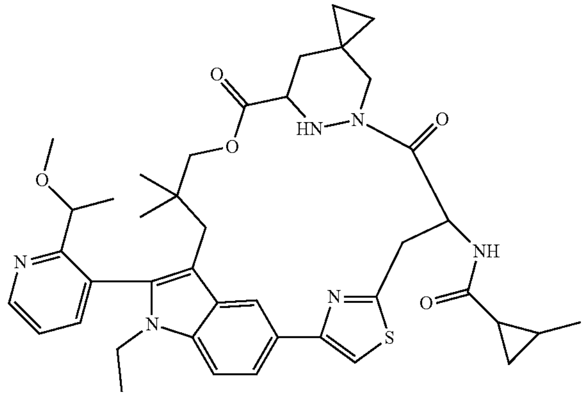
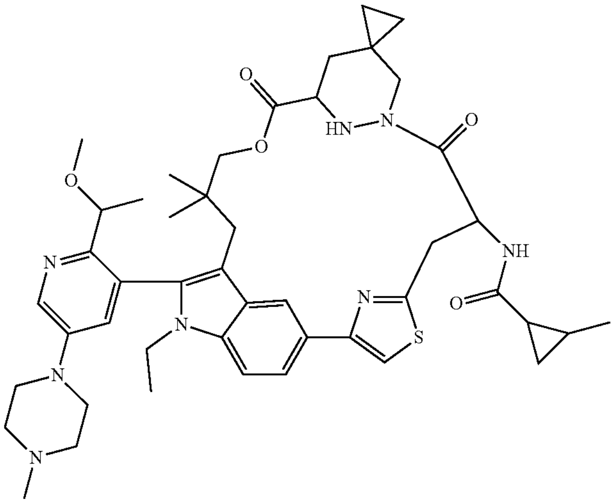

-continued
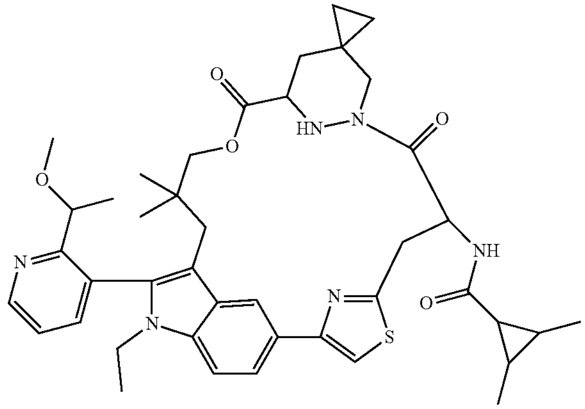
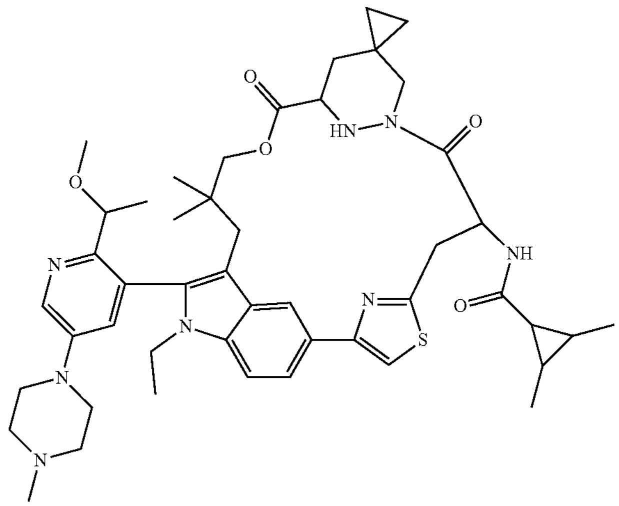
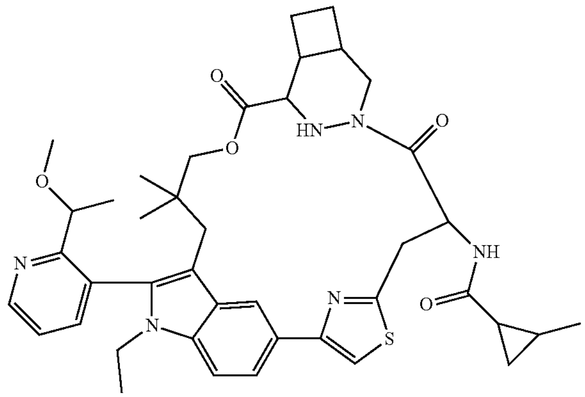
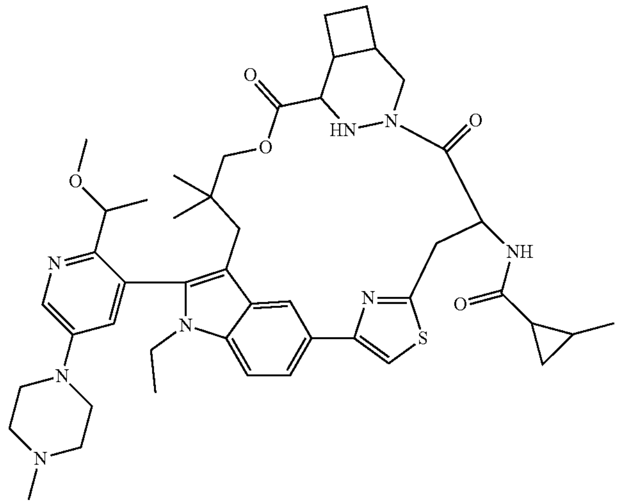
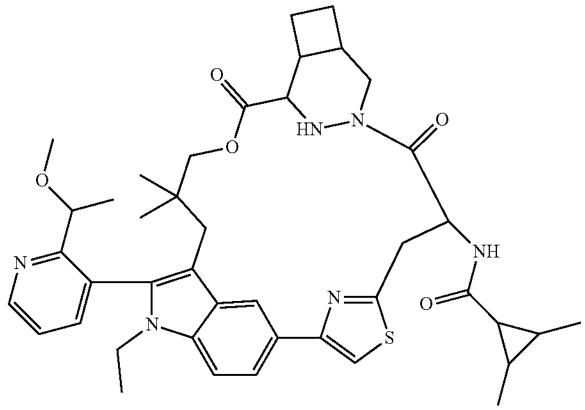
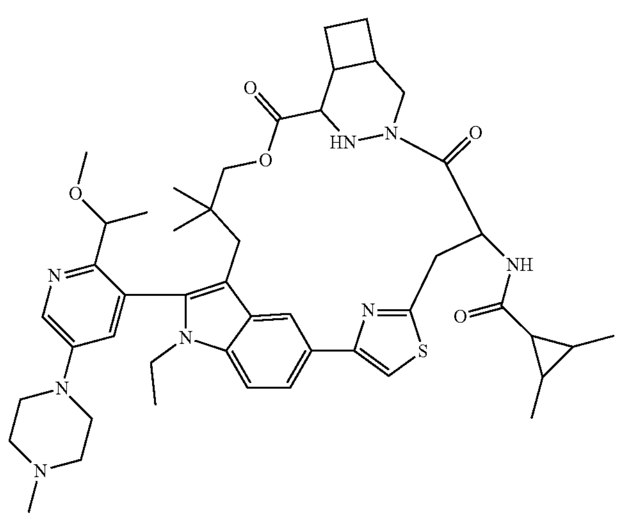

-continued
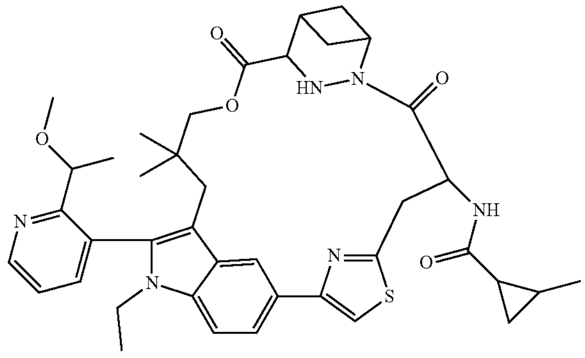
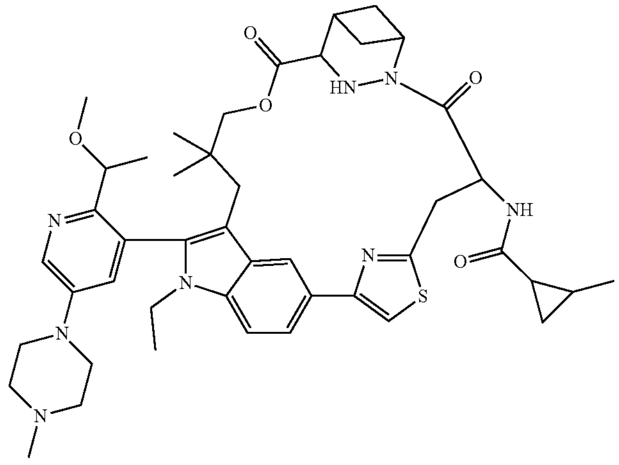
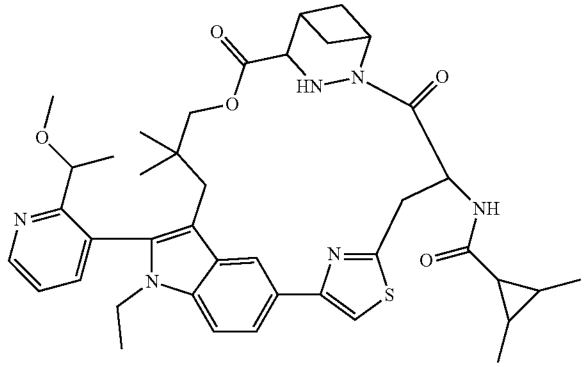
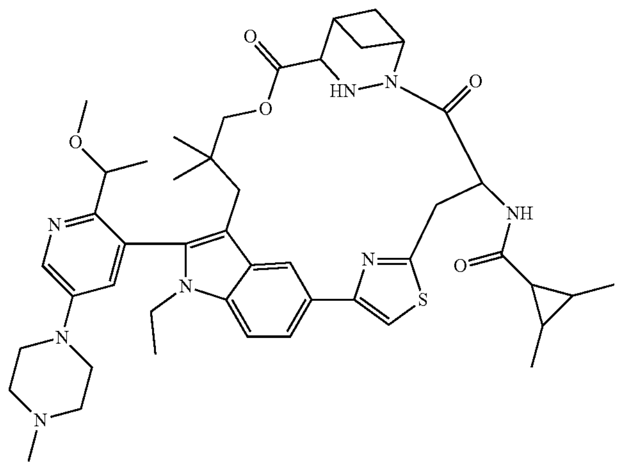
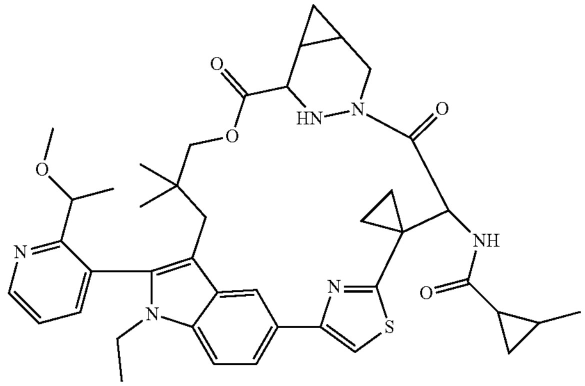
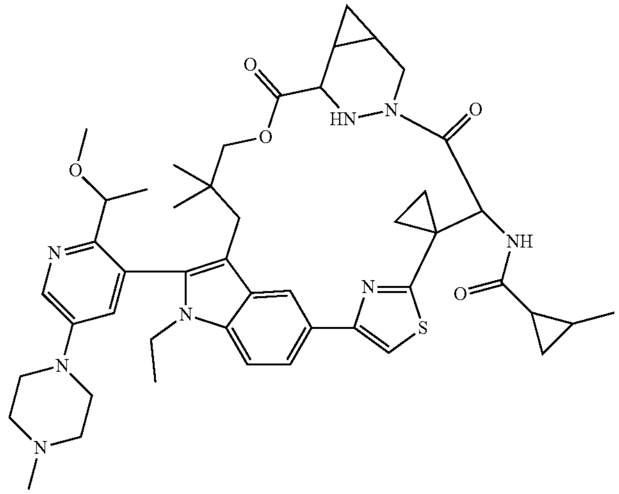

-continued
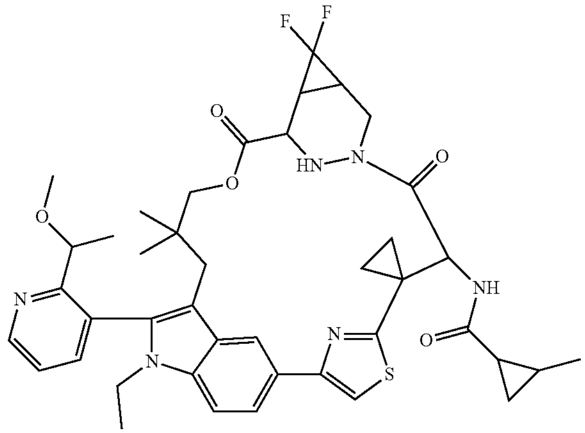
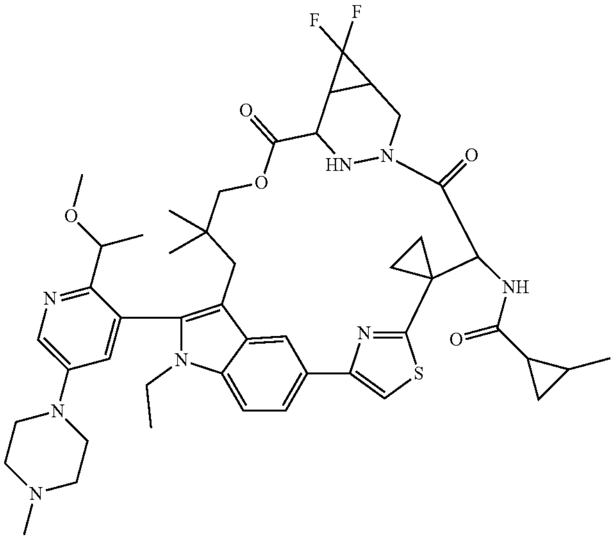
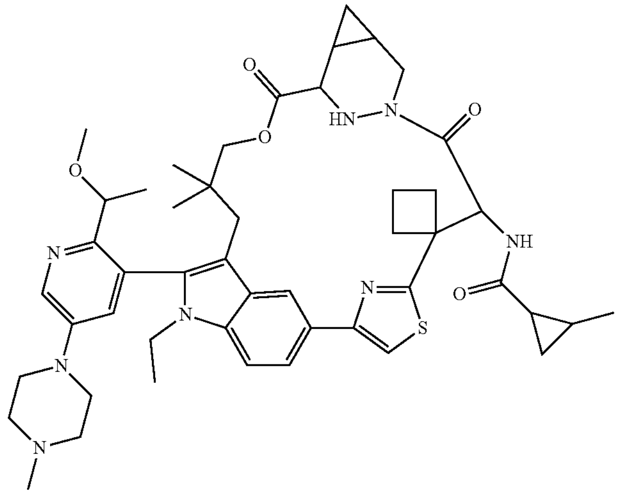
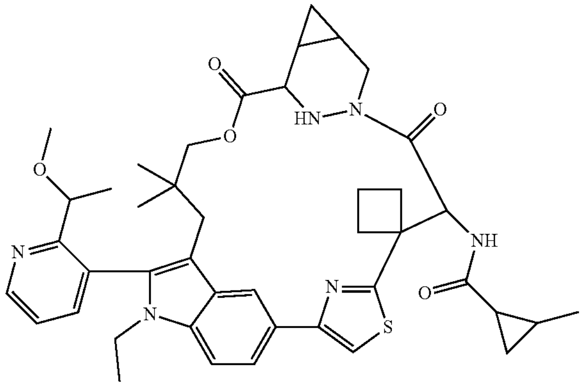
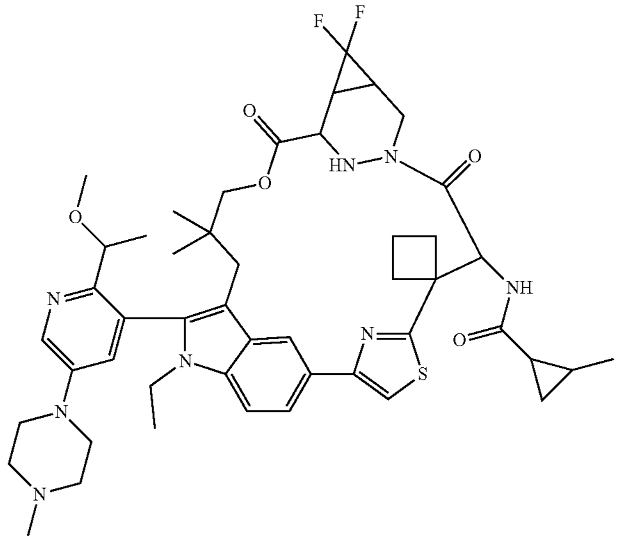
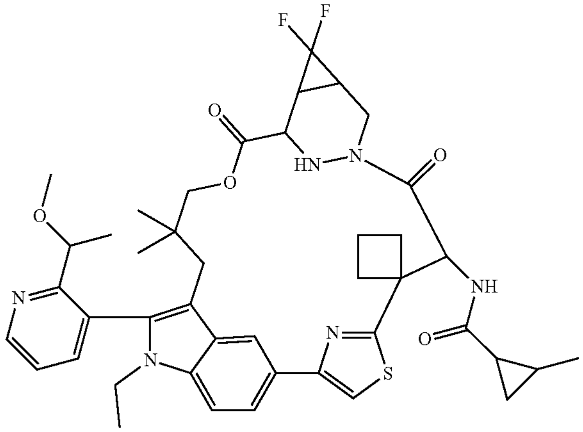

-continued
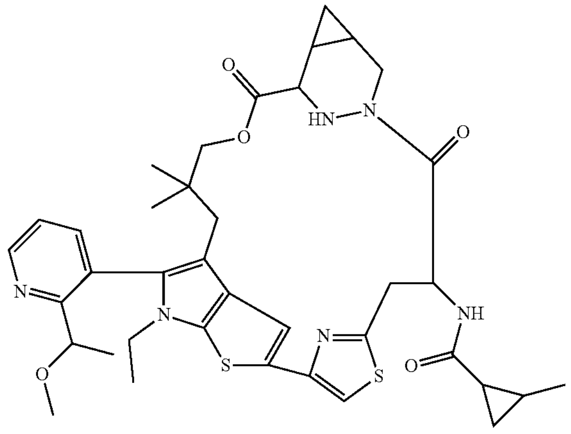
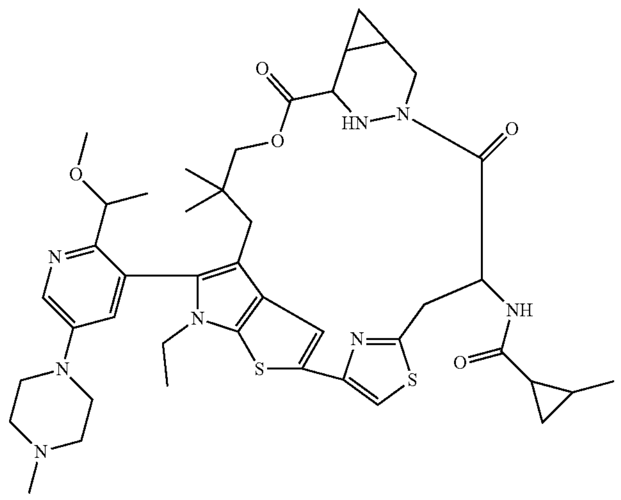
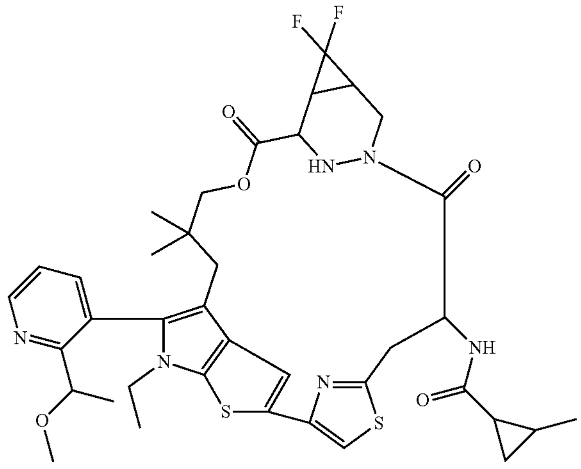
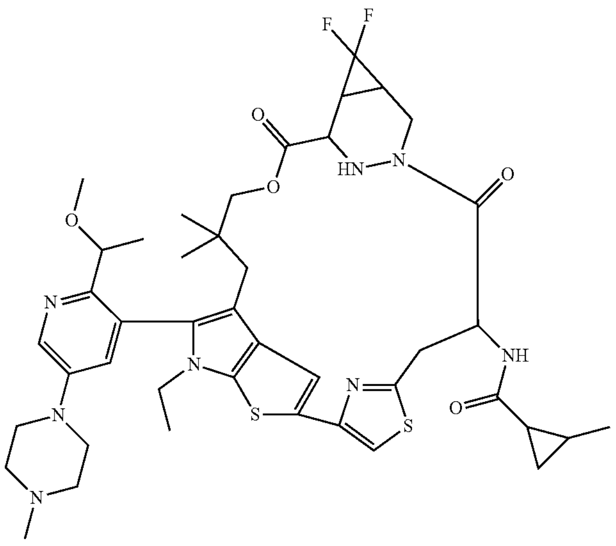
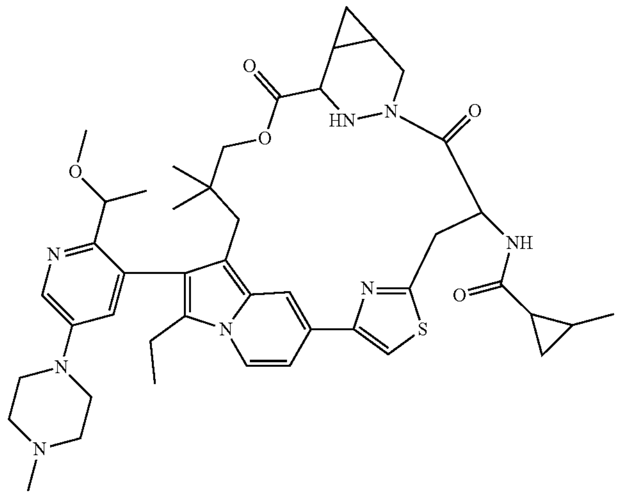
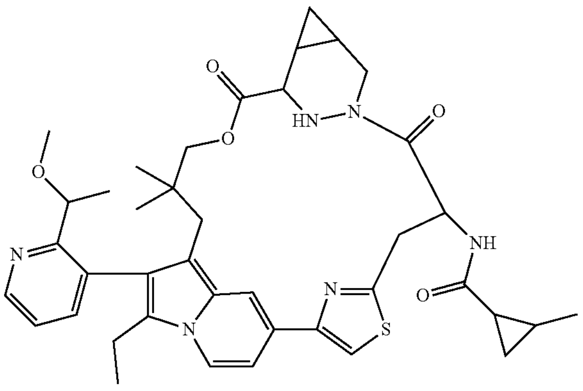

-continued
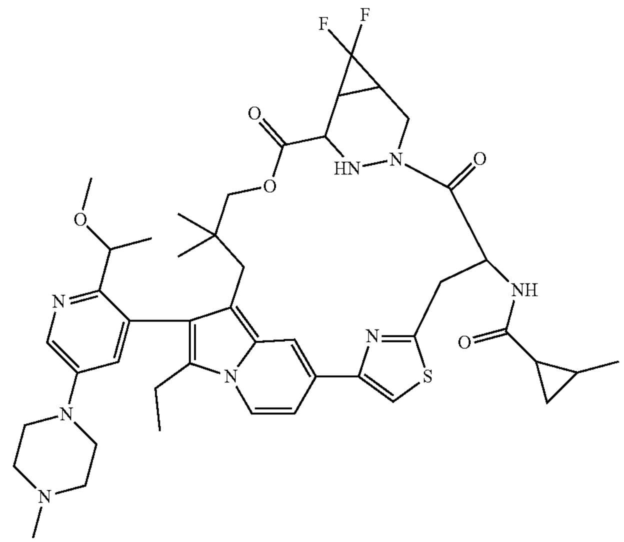
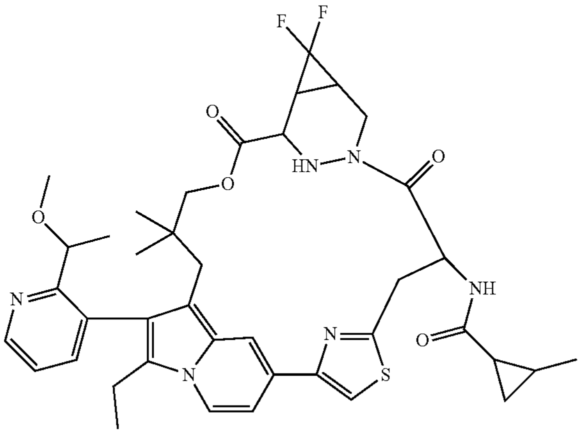
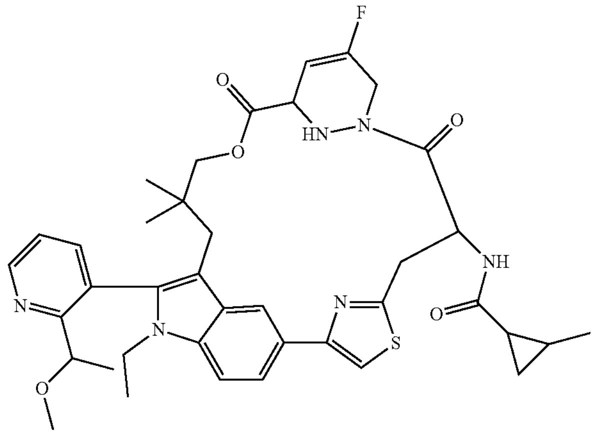
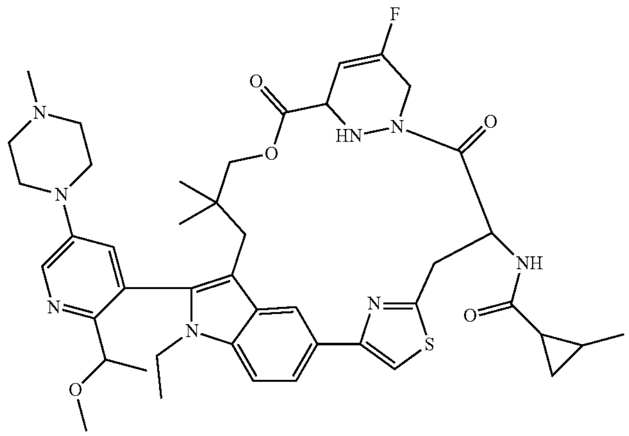

-continued
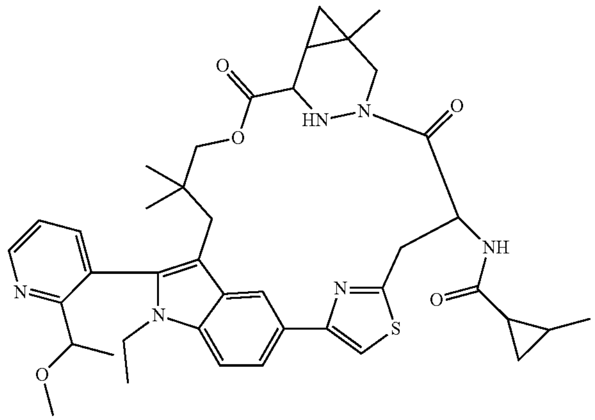
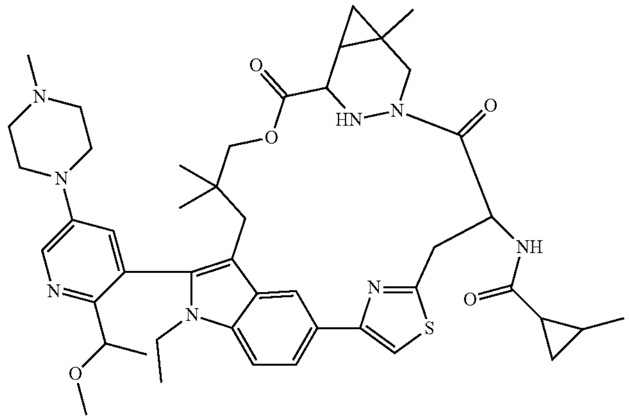
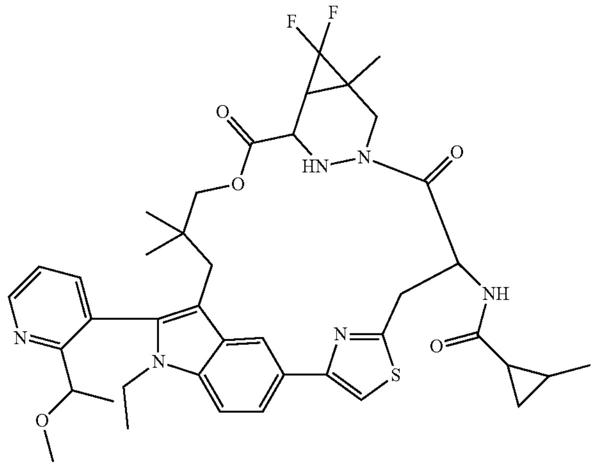

-continued
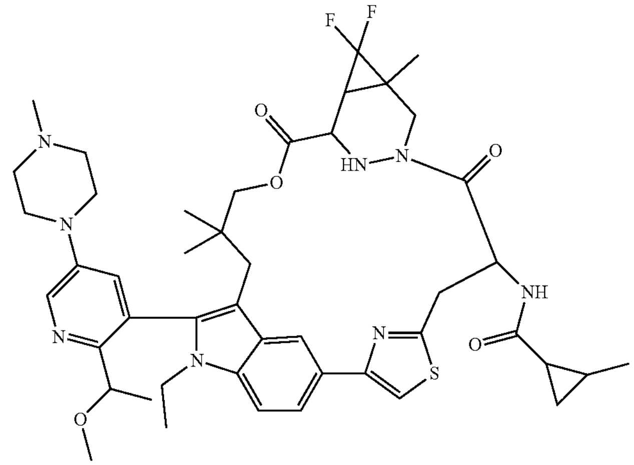
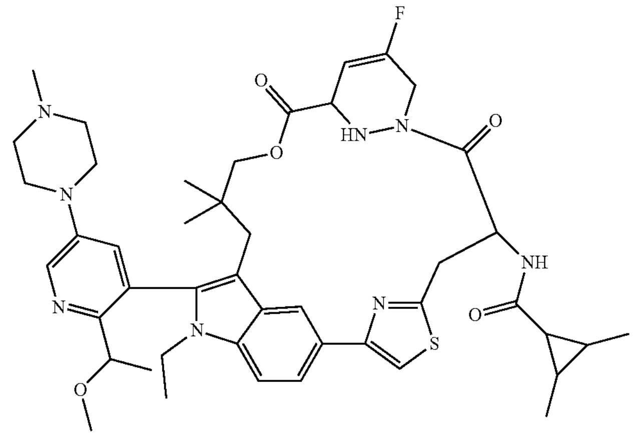
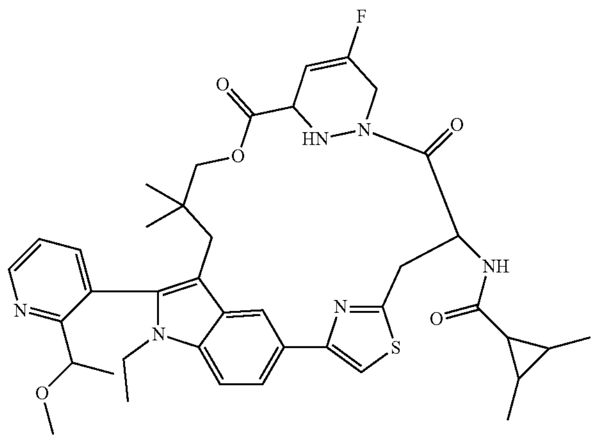
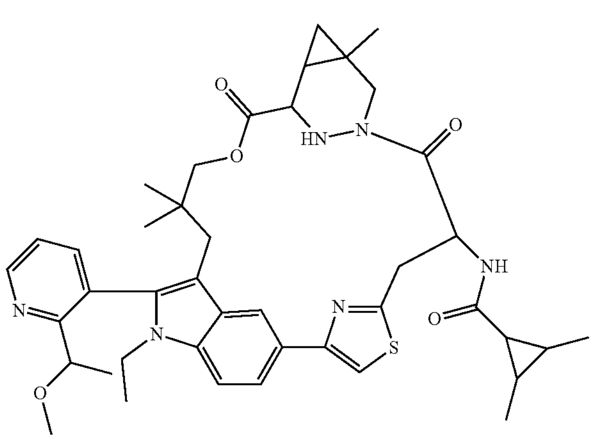

-continued
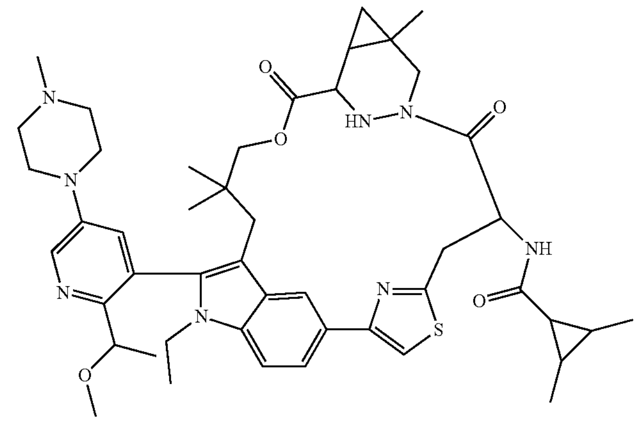
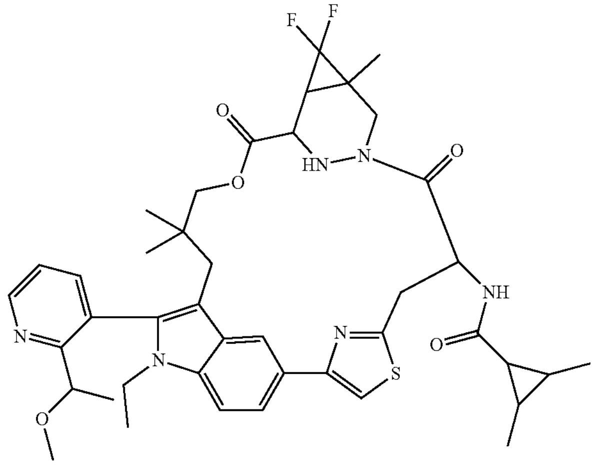
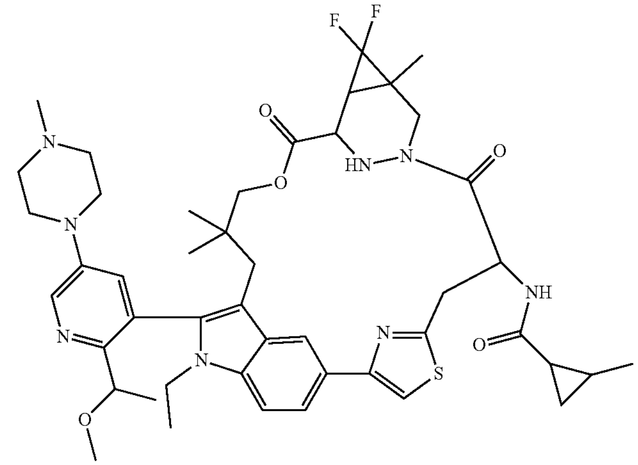

-continued
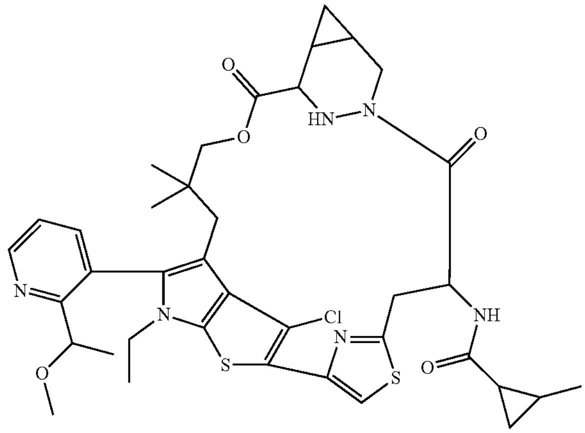
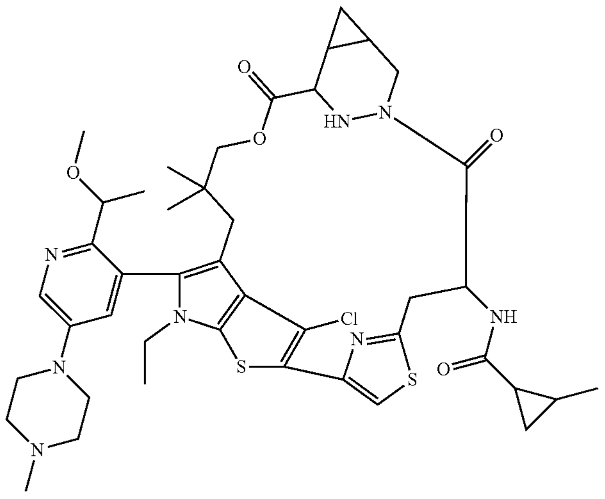
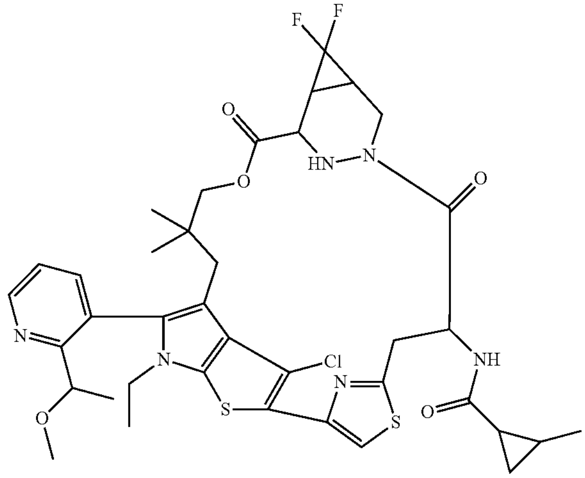
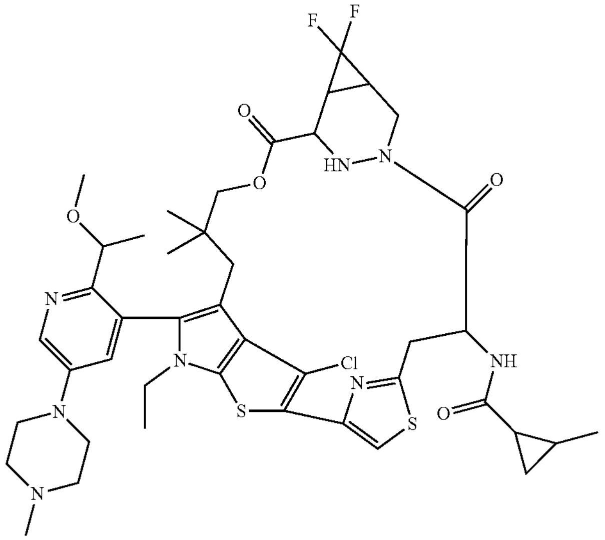
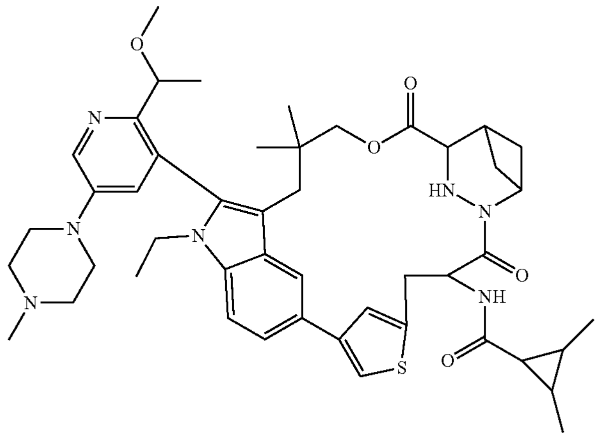
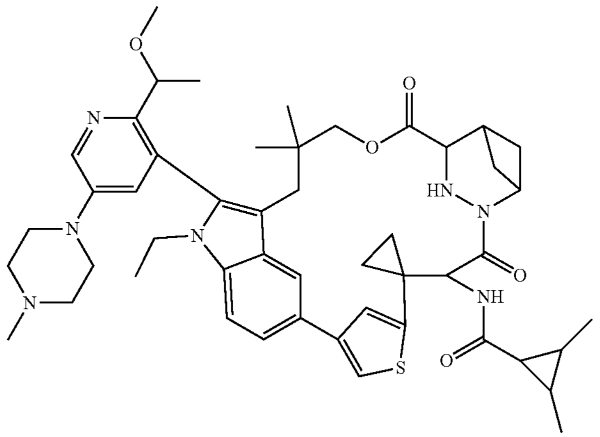

-continued
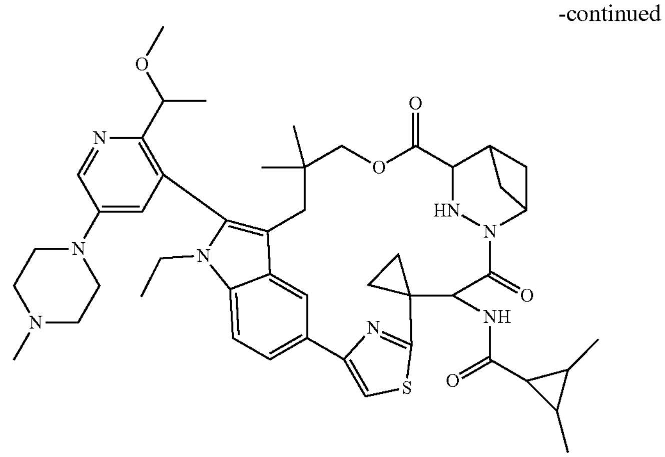
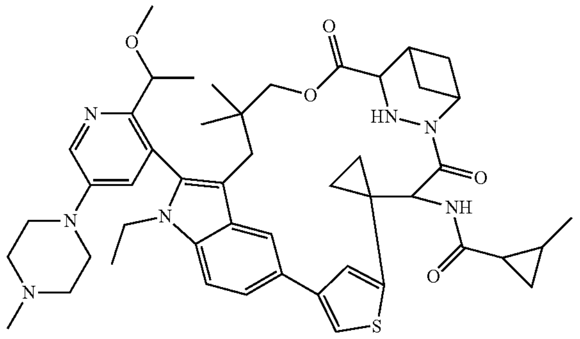
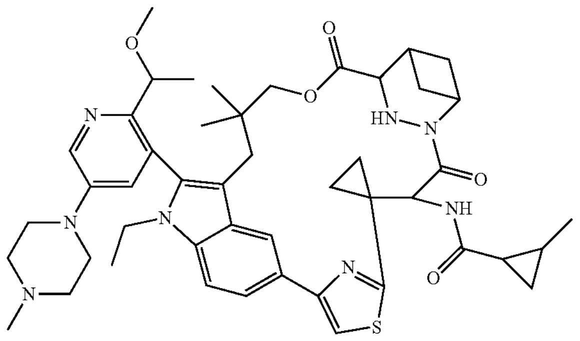
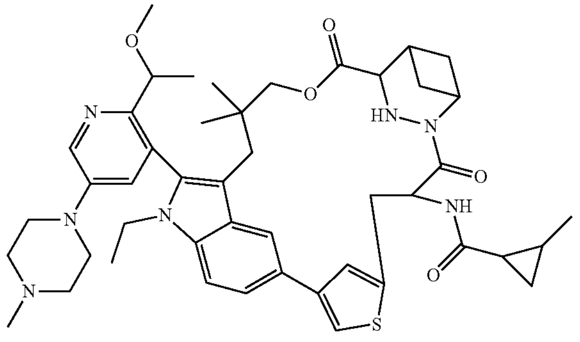
-continued
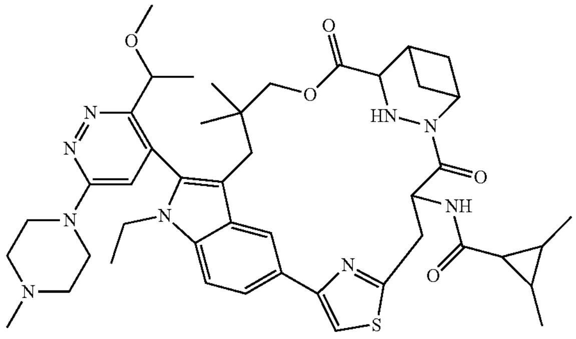
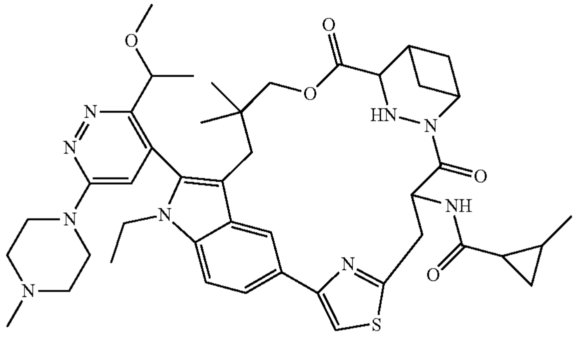
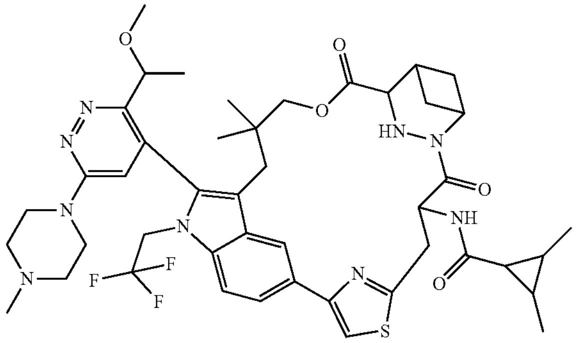

-continued
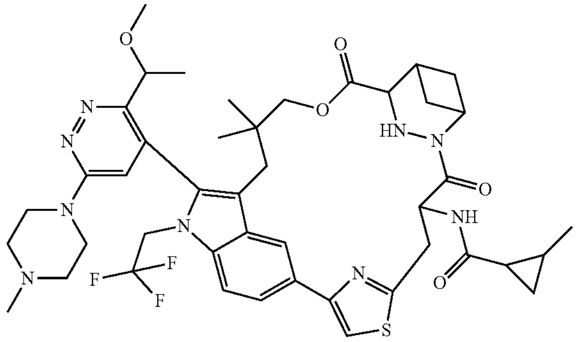
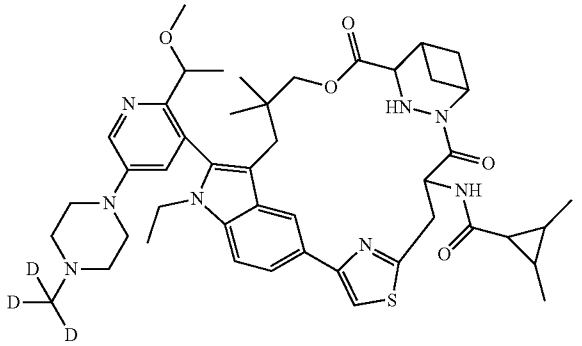
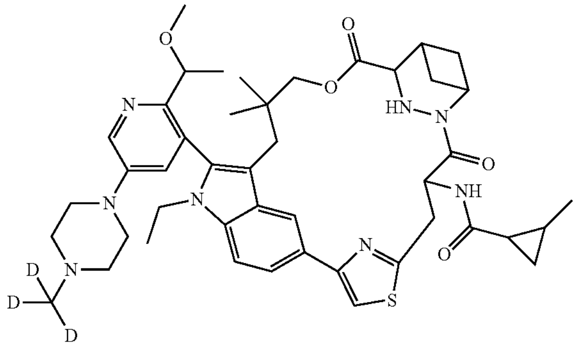
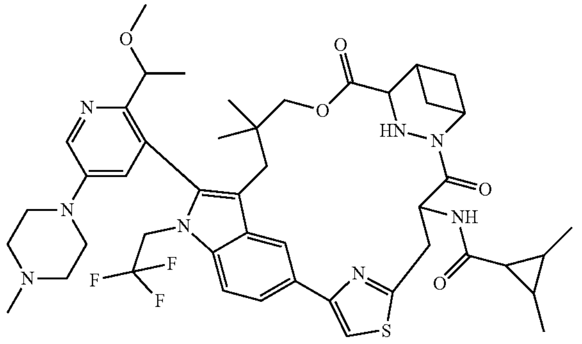
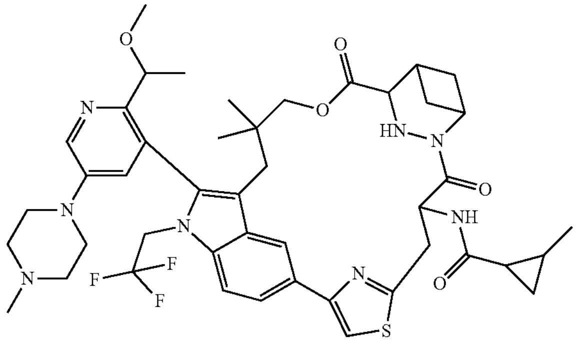
-continued
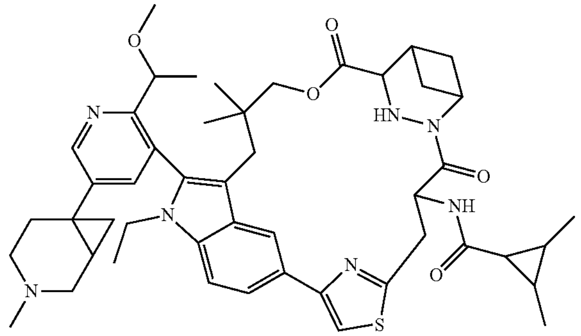
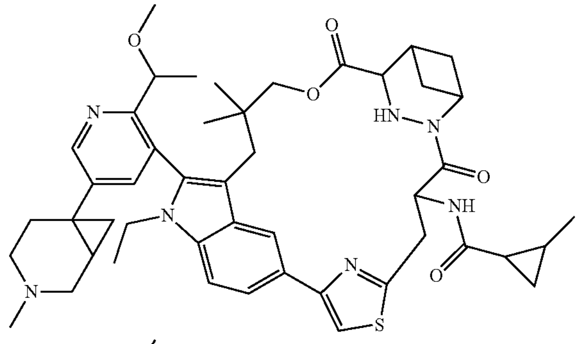
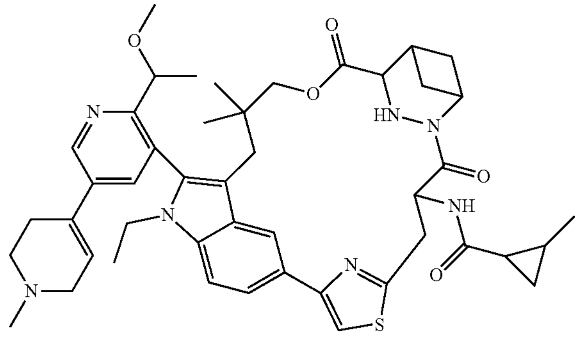
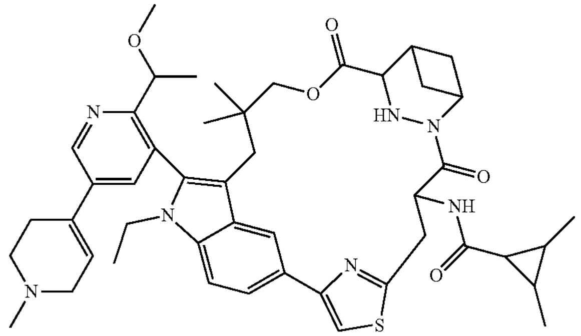
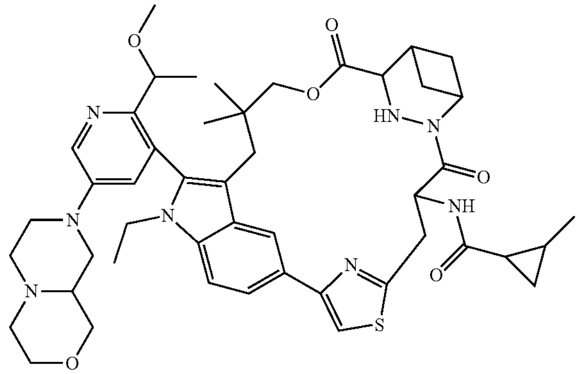

-continued
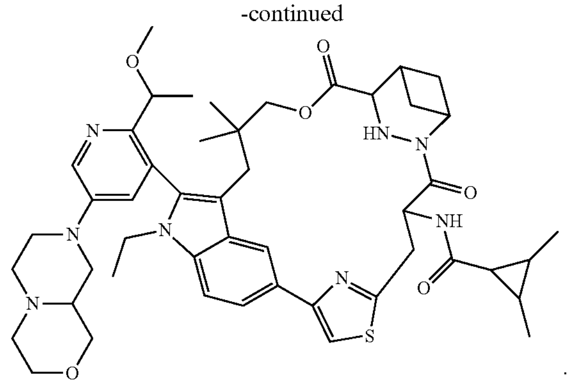
.
In some embodiments of the present disclosure, the above compound, a stereoisomer thereof, or a pharmaceutically acceptable salt thereof, is selected from,
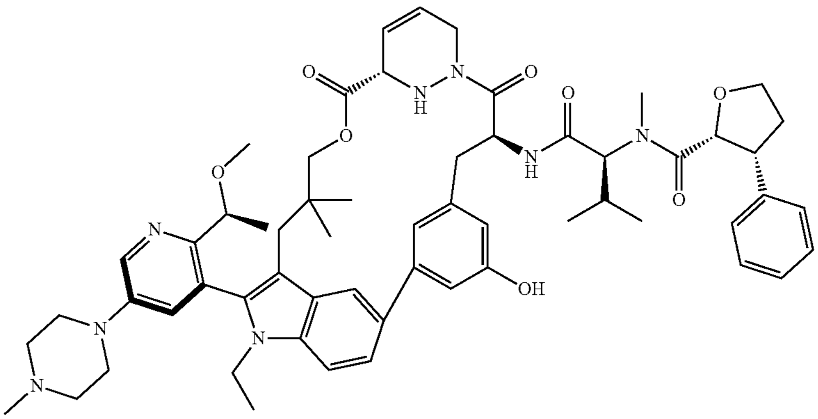
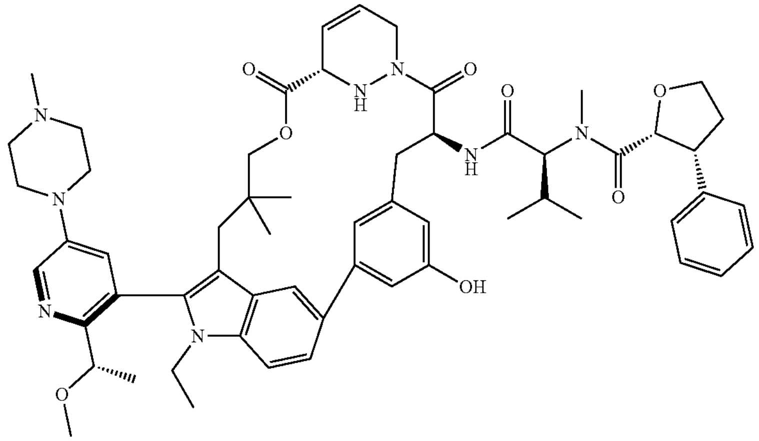

-continued
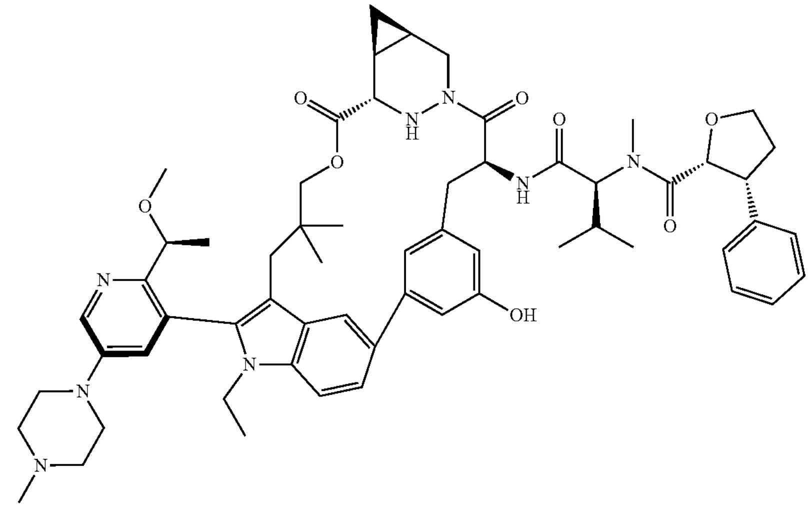
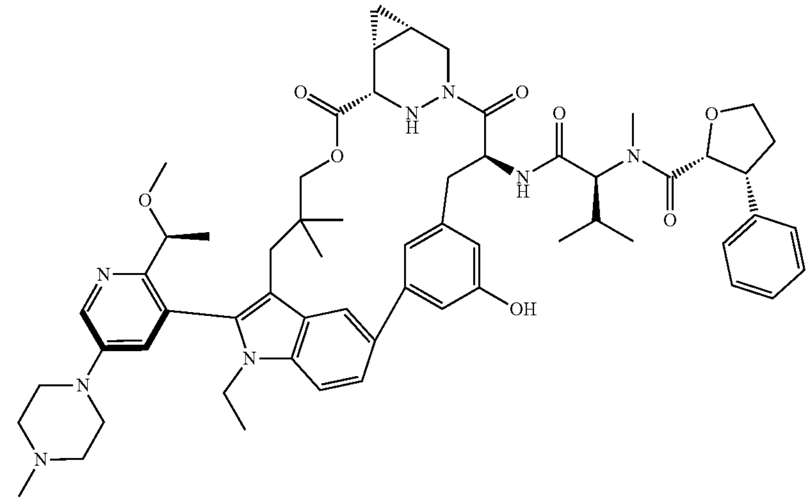
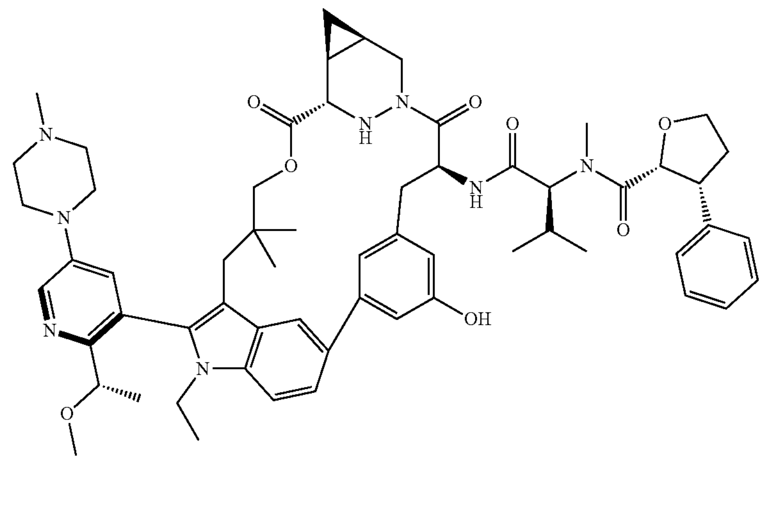

-continued
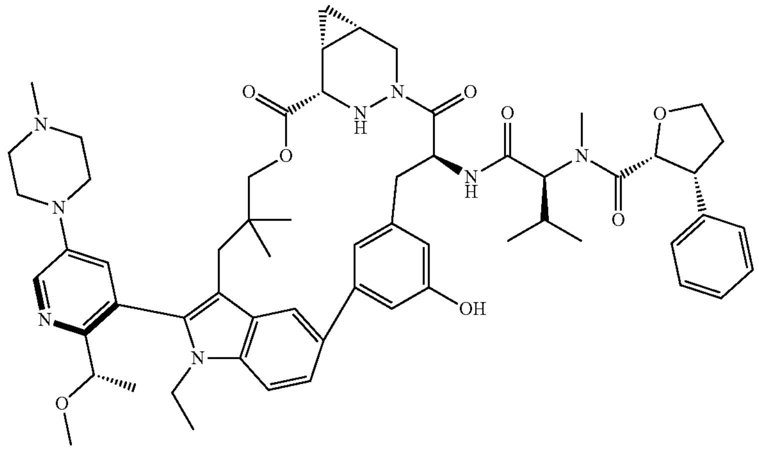
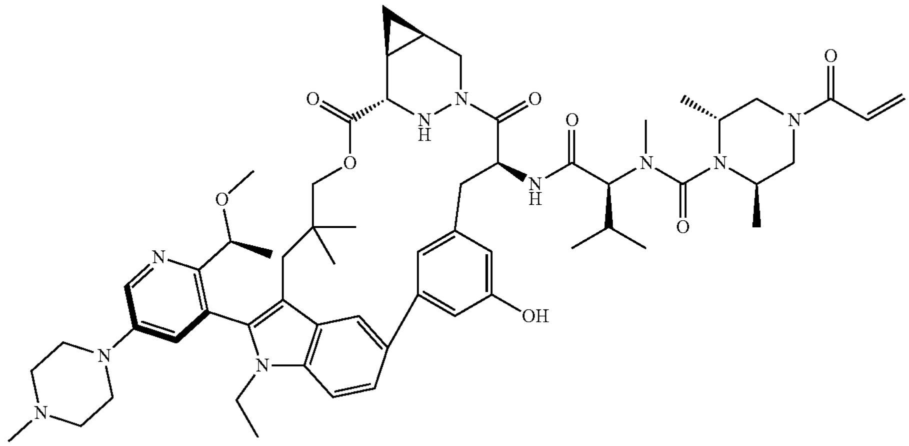
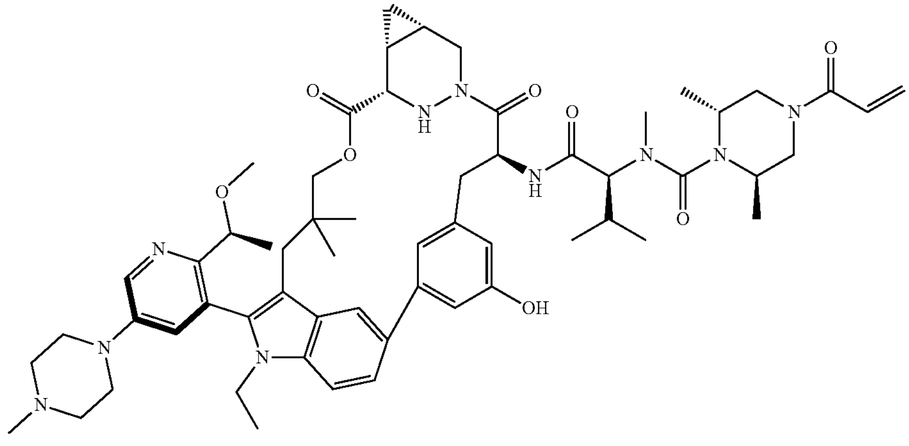

-continued
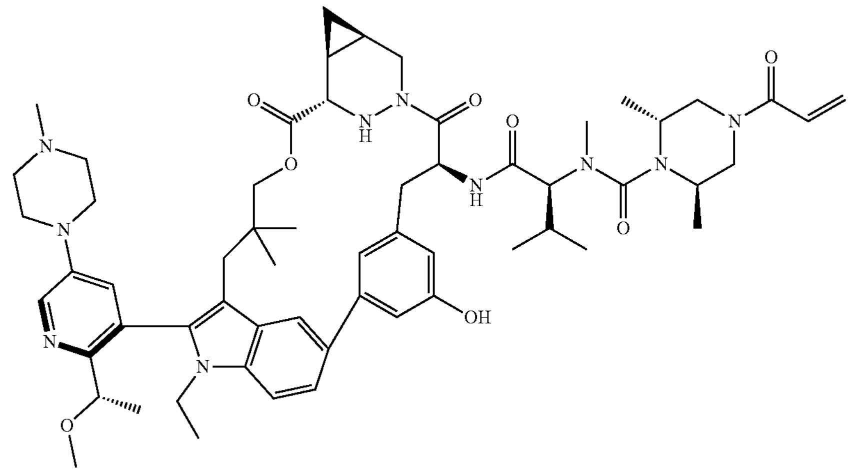
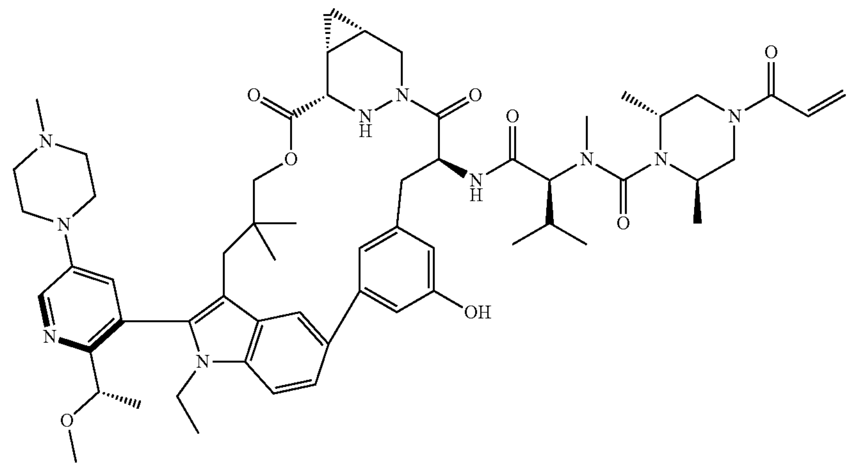
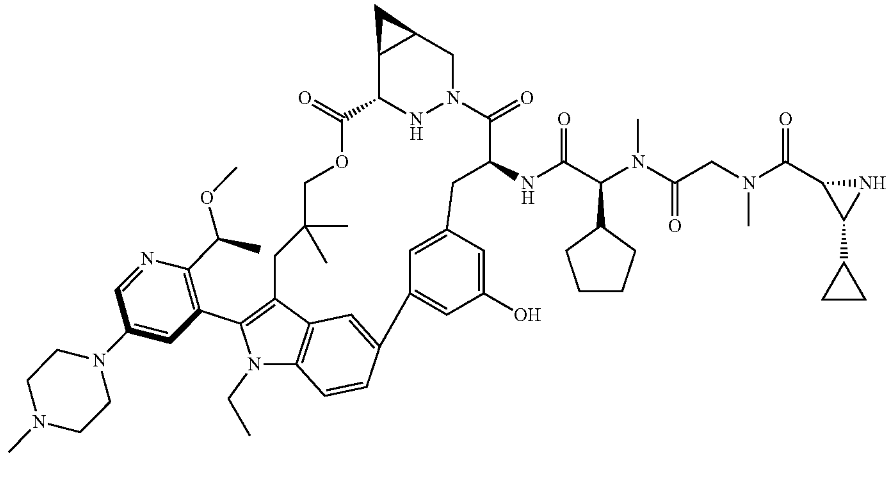

-continued
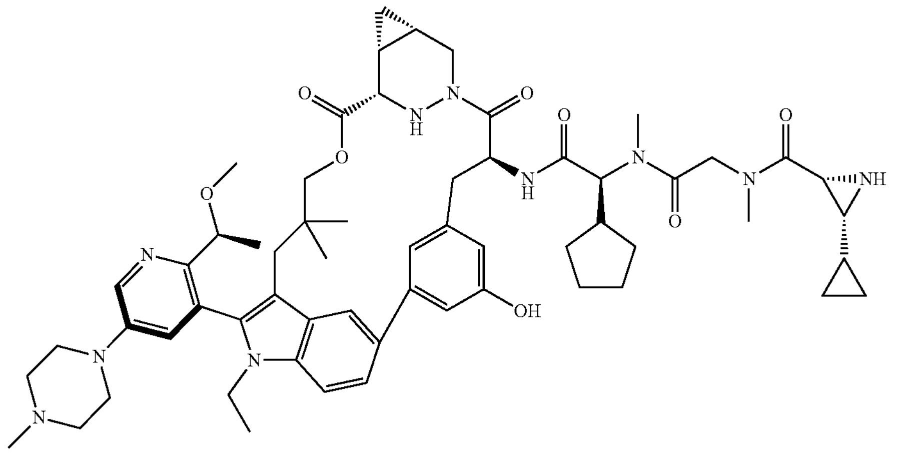
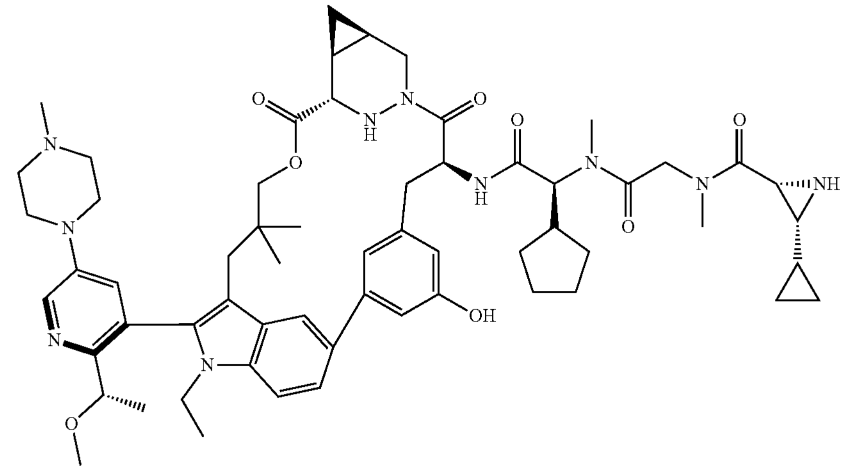
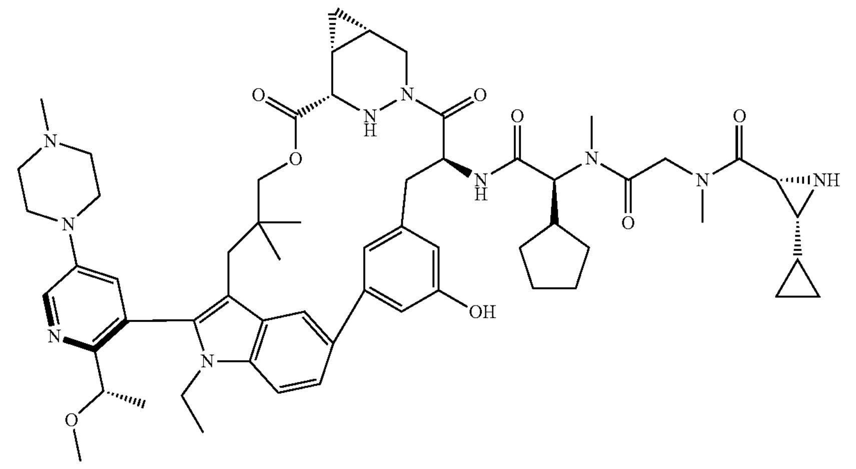

-continued
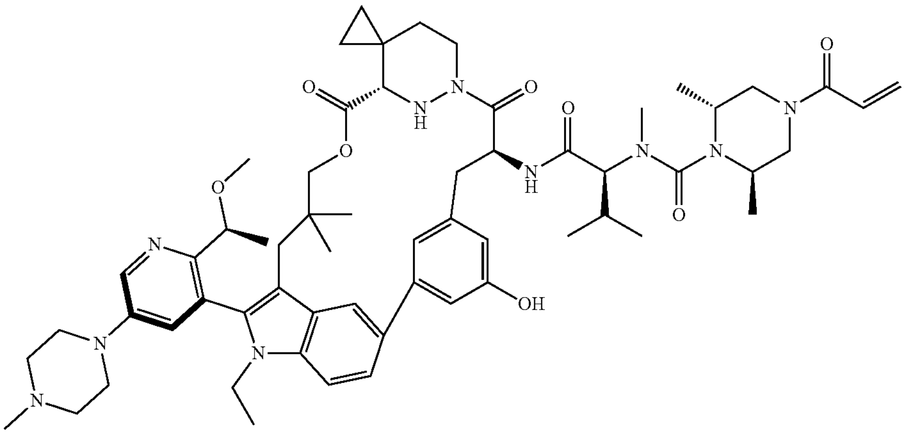
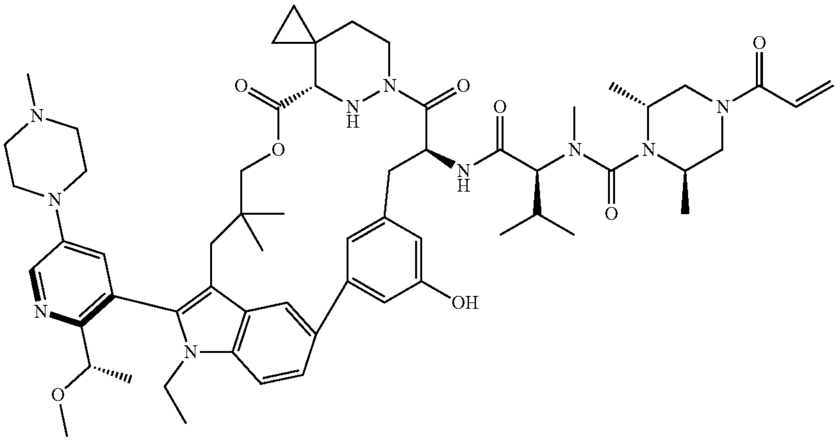
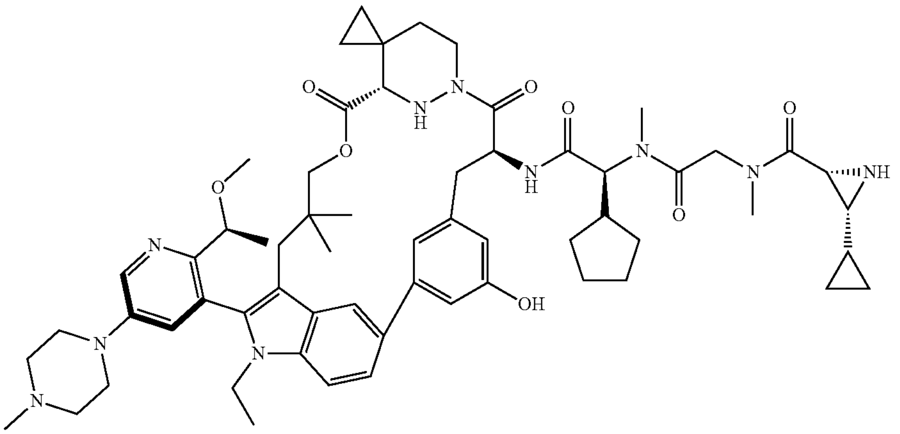

-continued
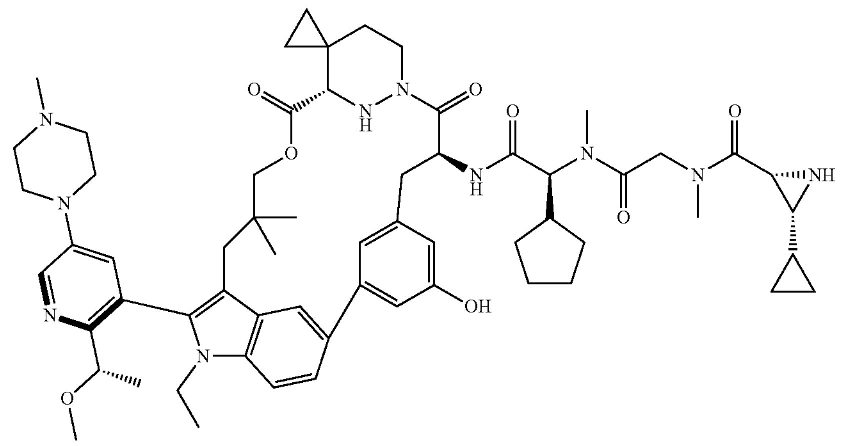
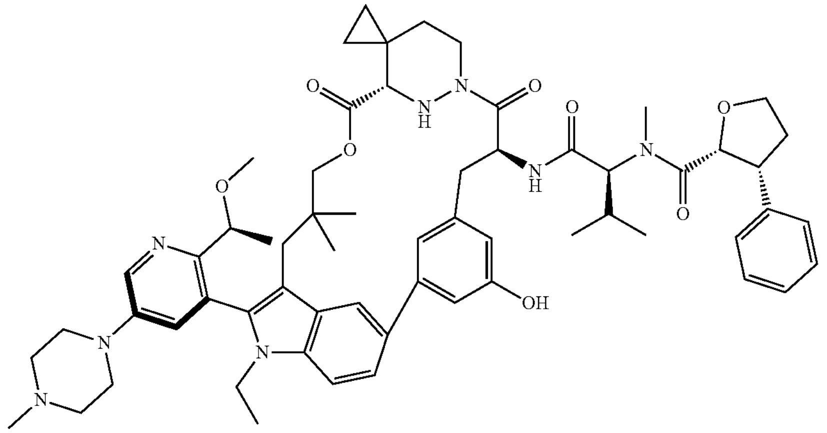
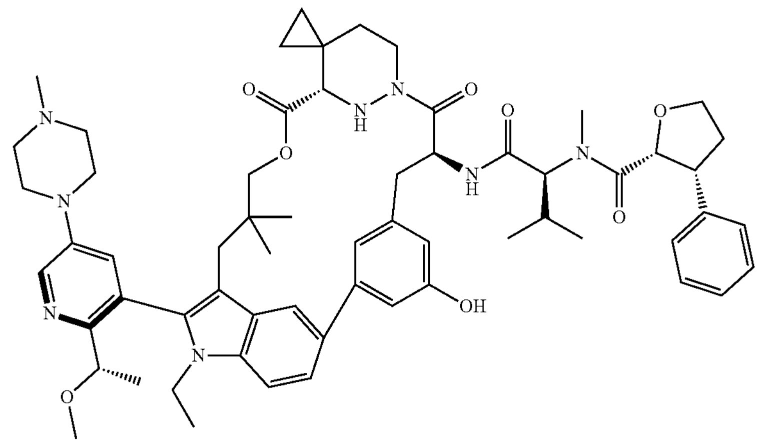

-continued
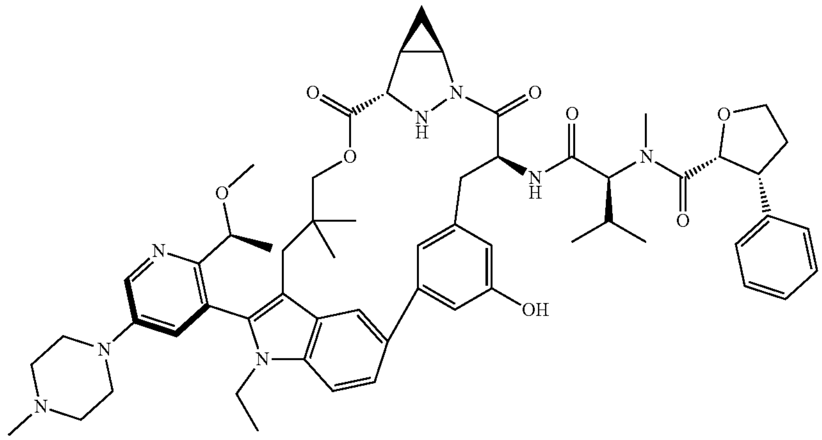
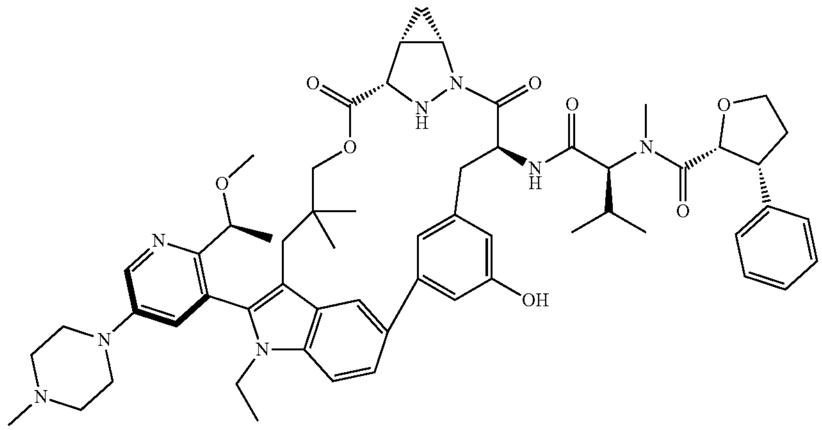
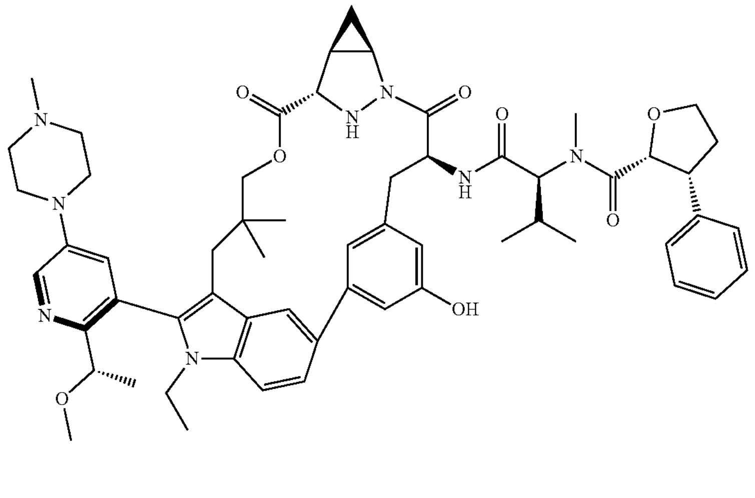

-continued
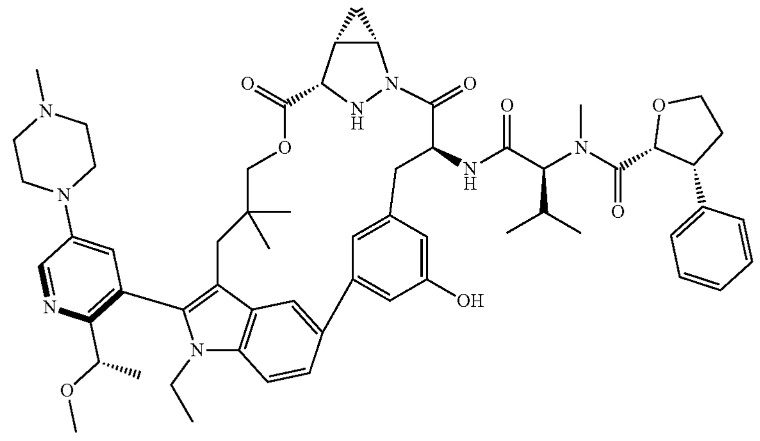
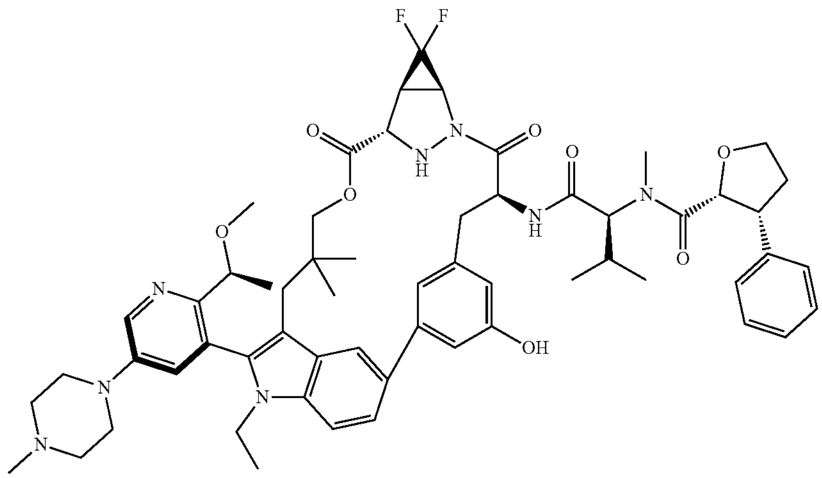
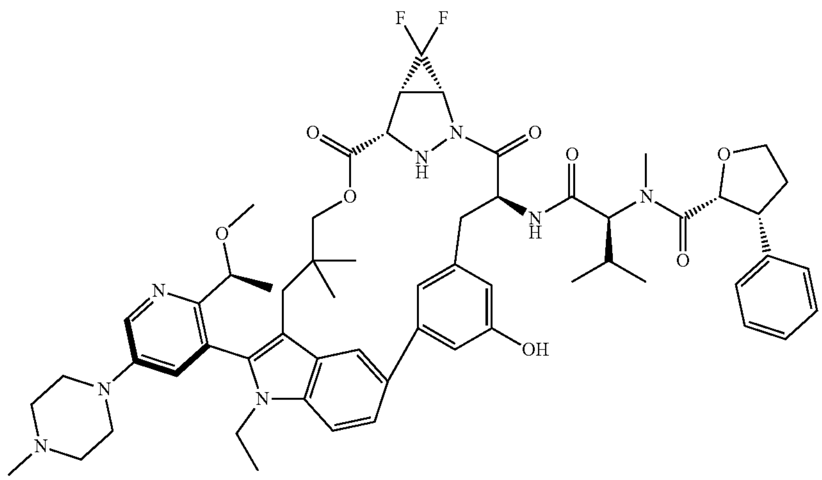

-continued
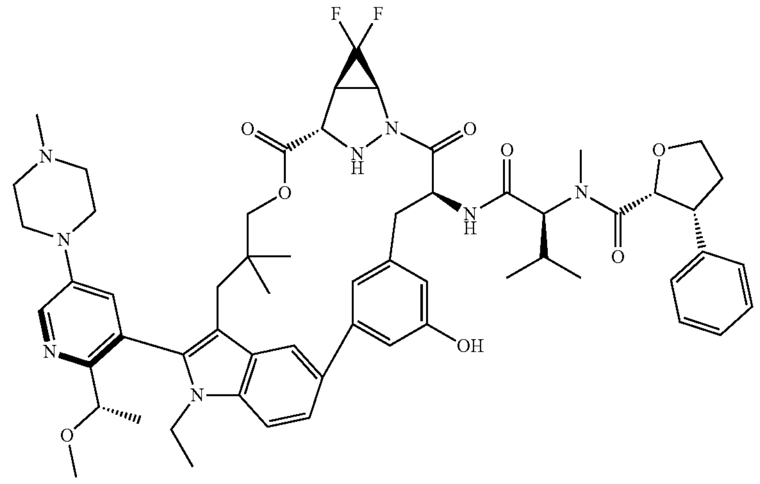
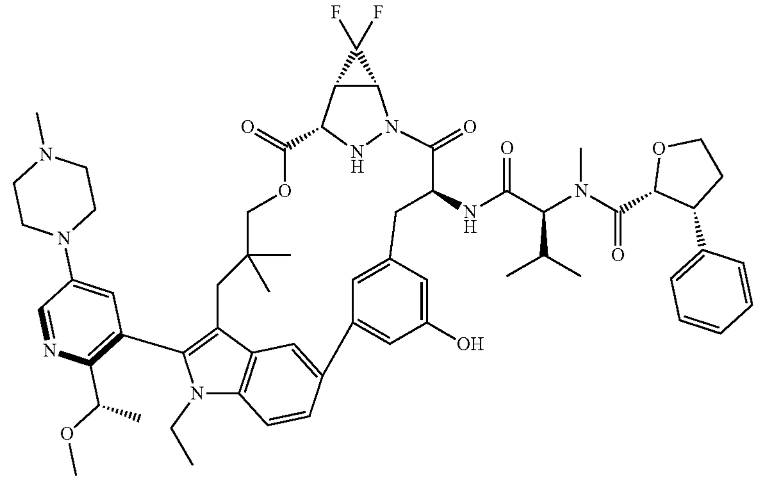
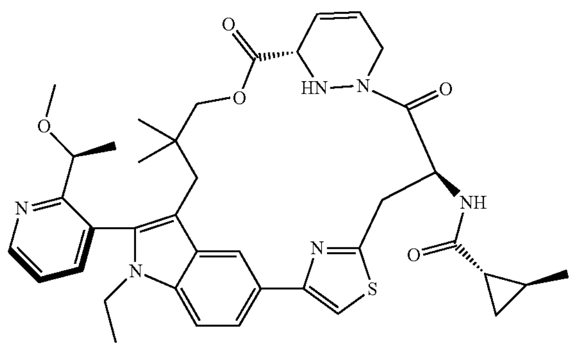
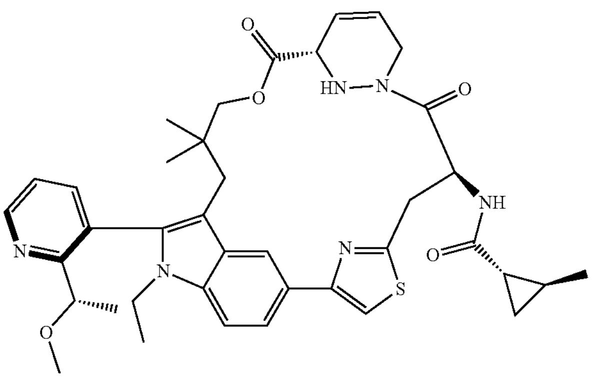

-continued
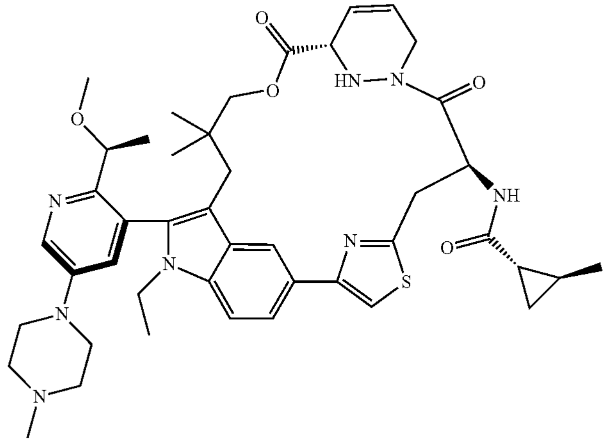
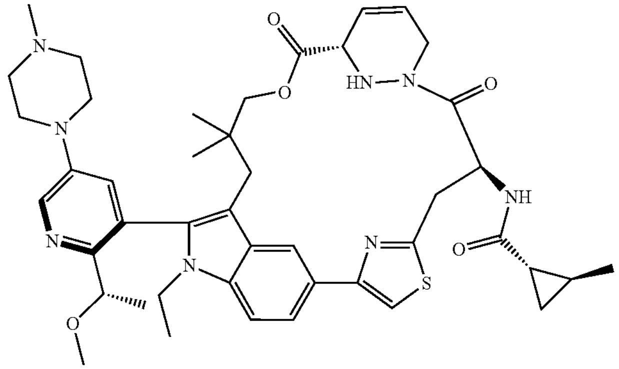
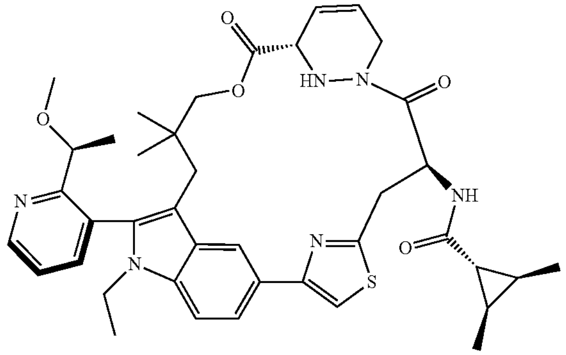
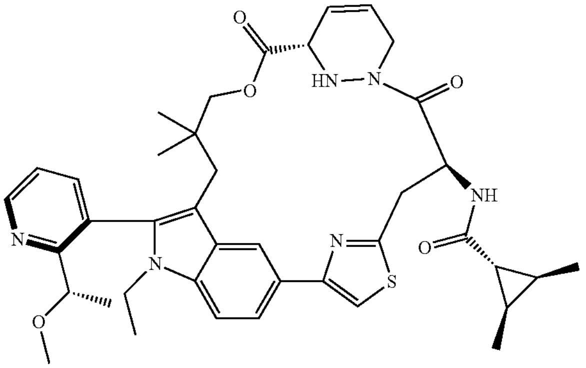
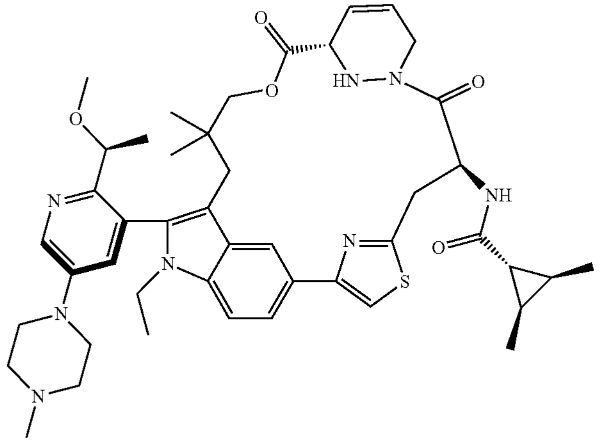
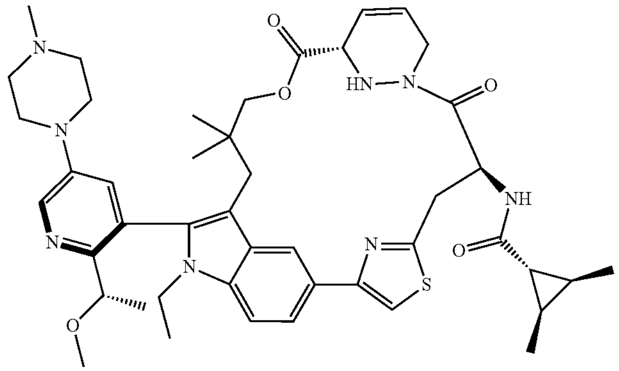
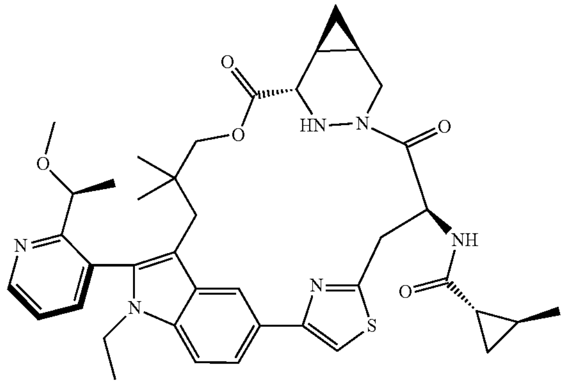

-continued
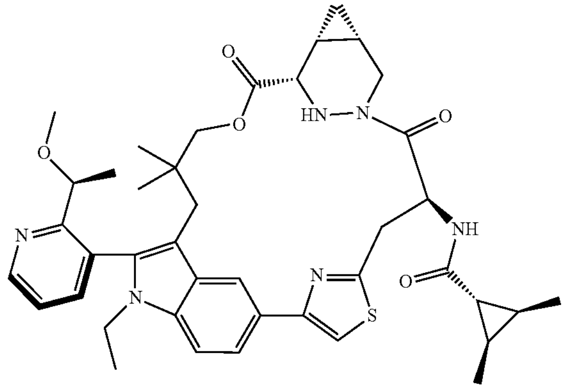
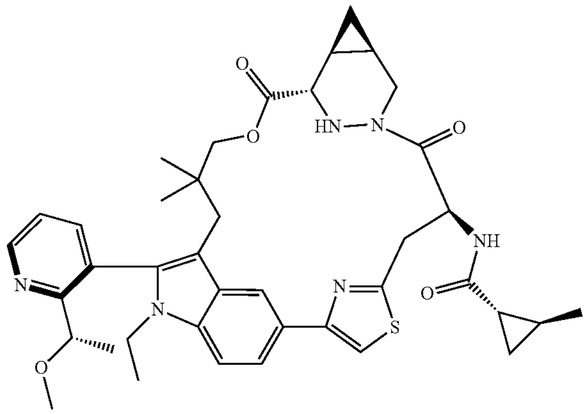
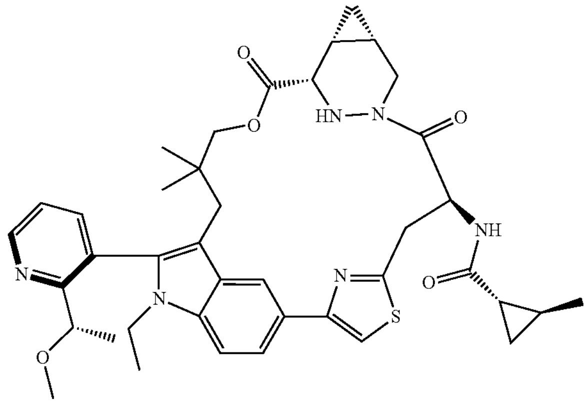
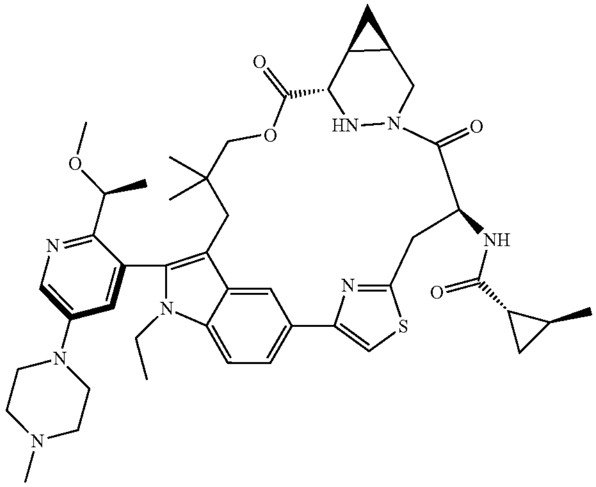
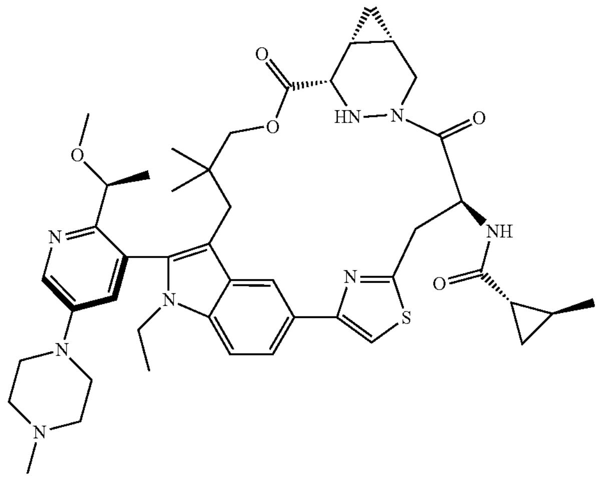

-continued
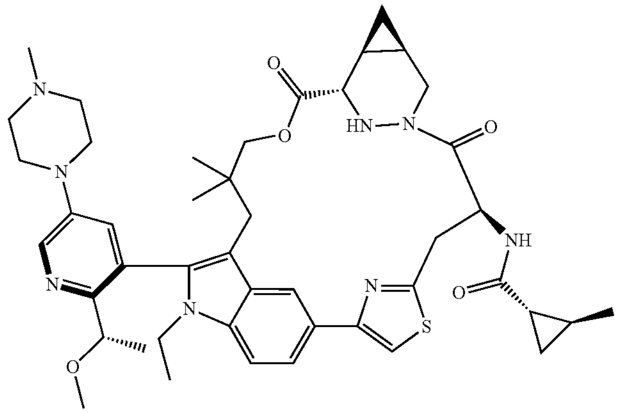
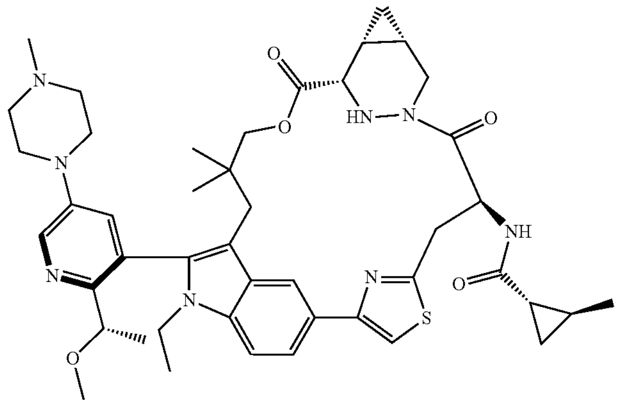
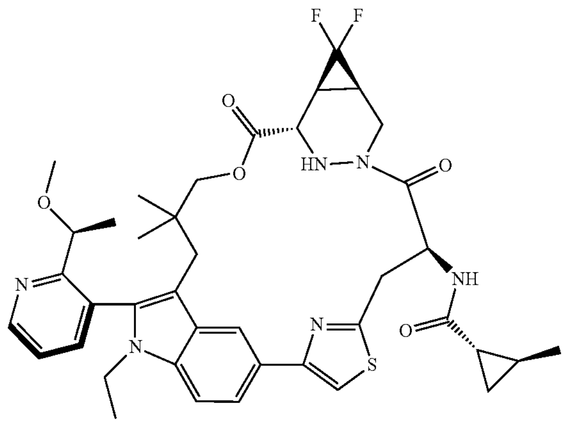
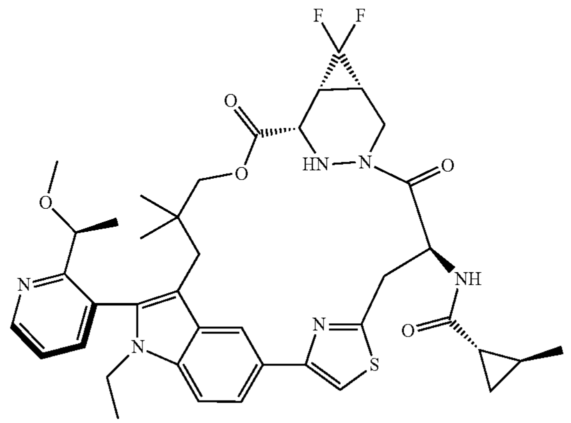
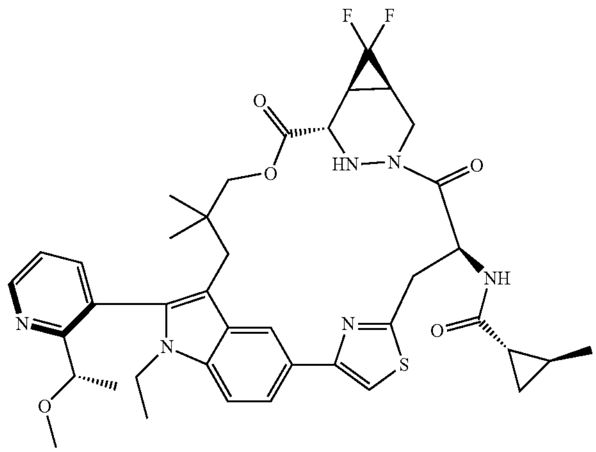
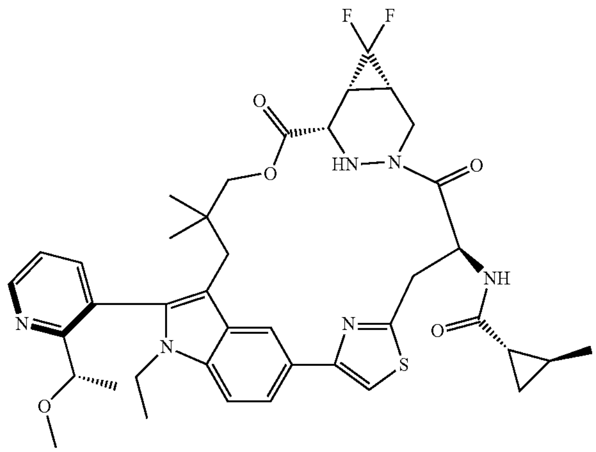

-continued
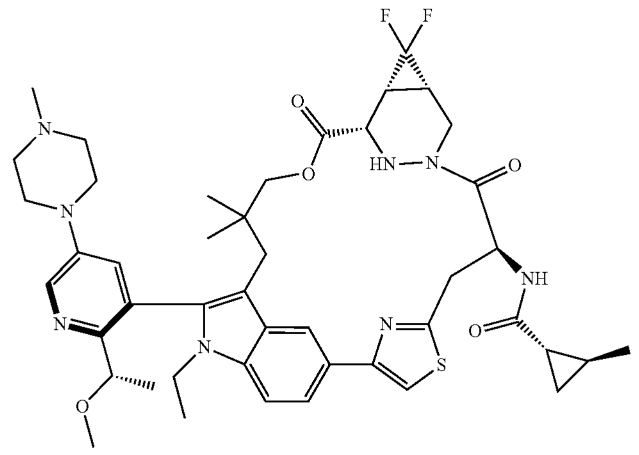
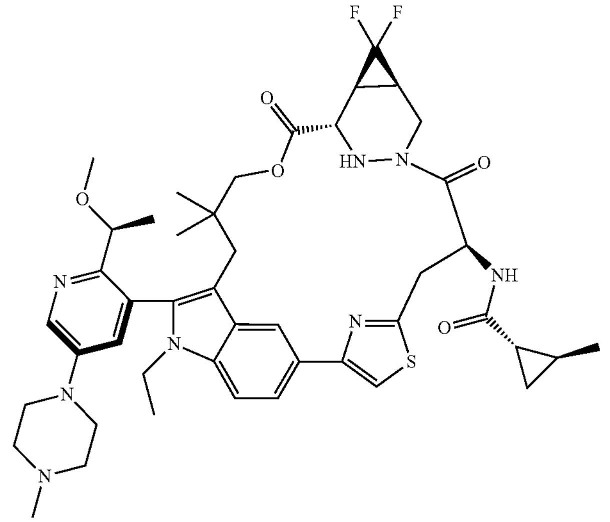
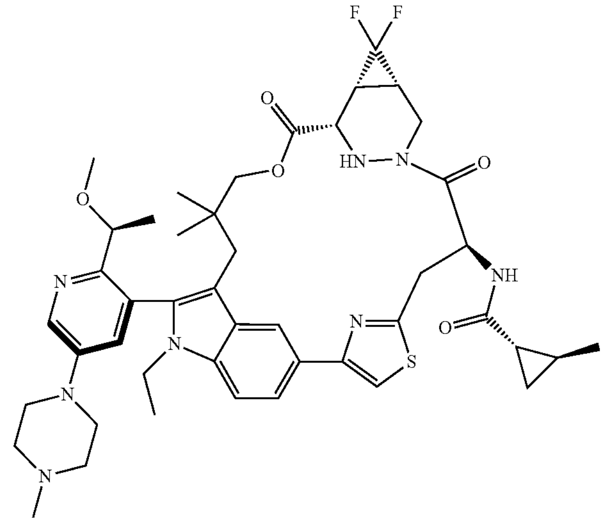
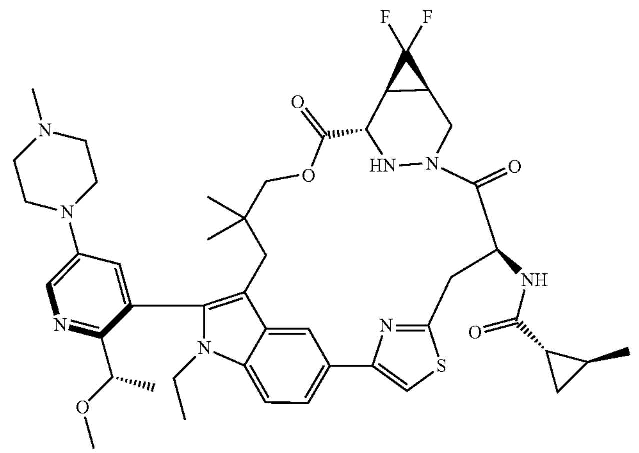
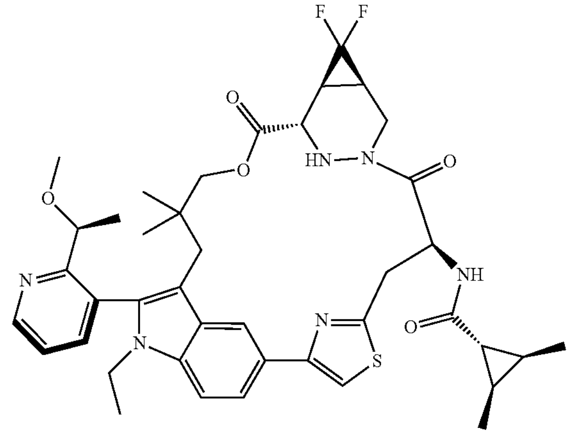

-continued
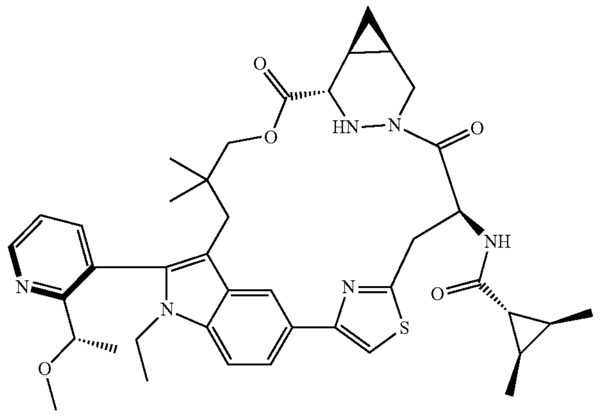
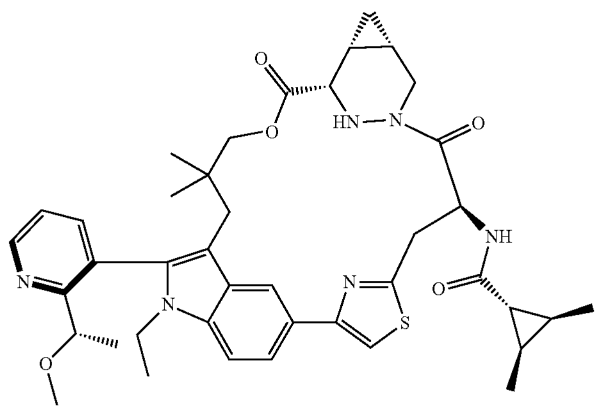
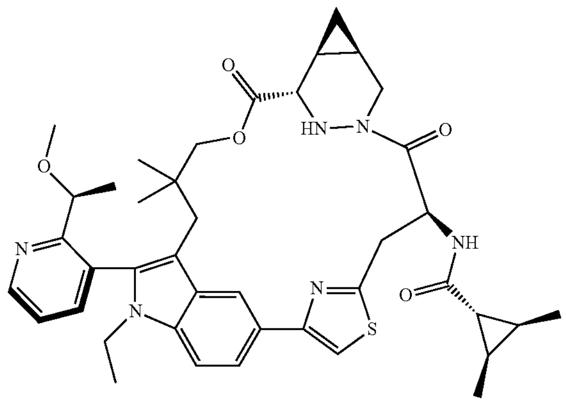
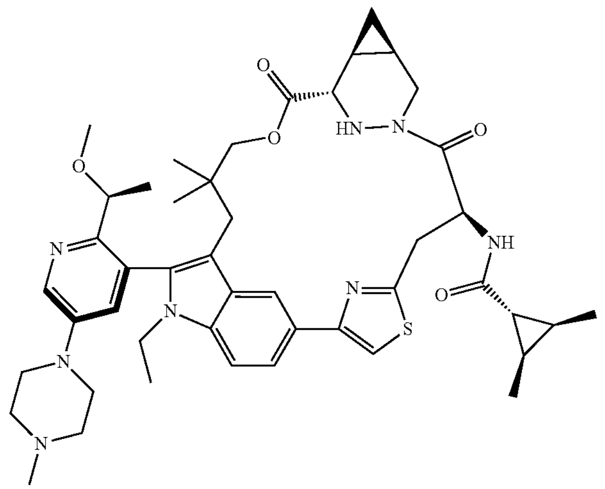
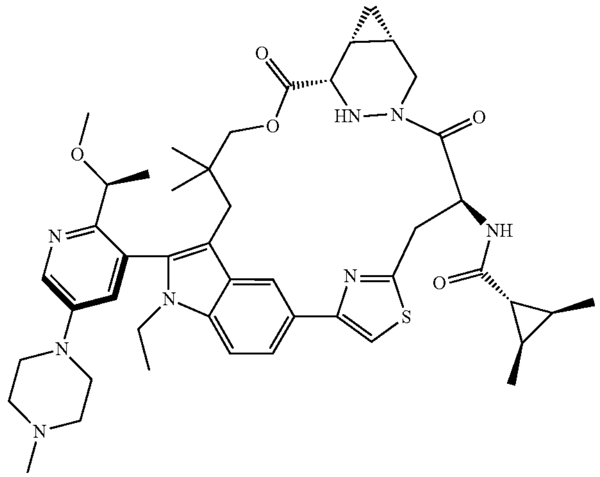

-continued
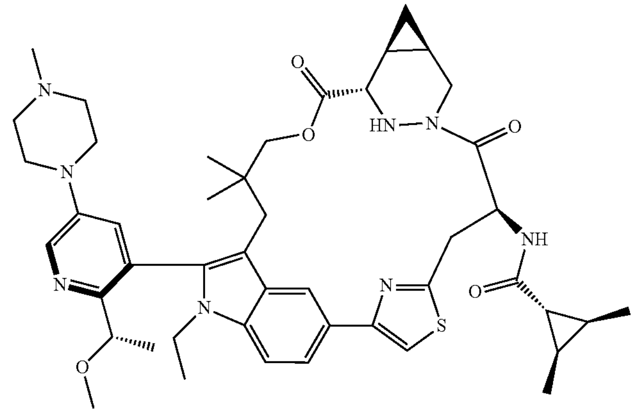
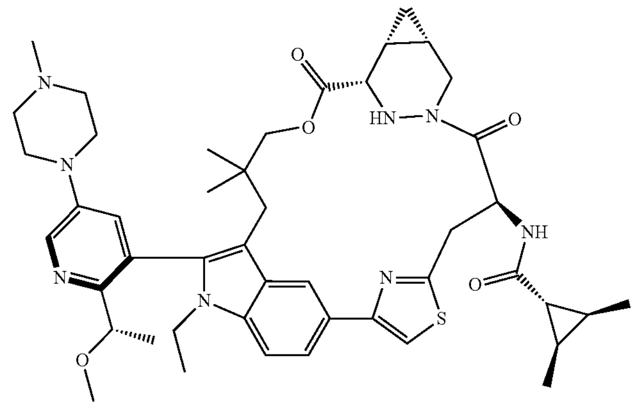
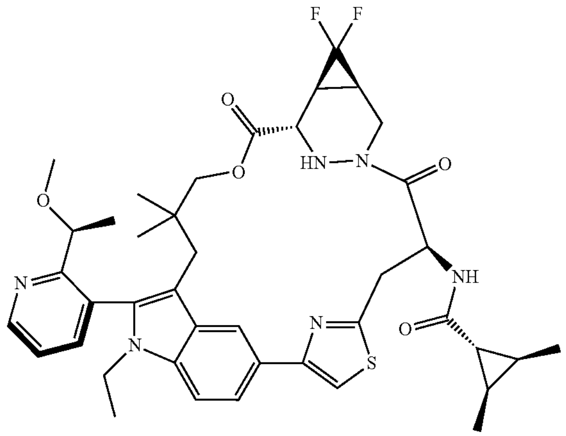
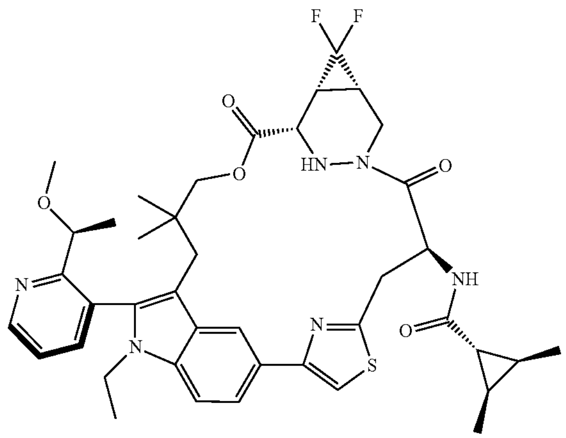
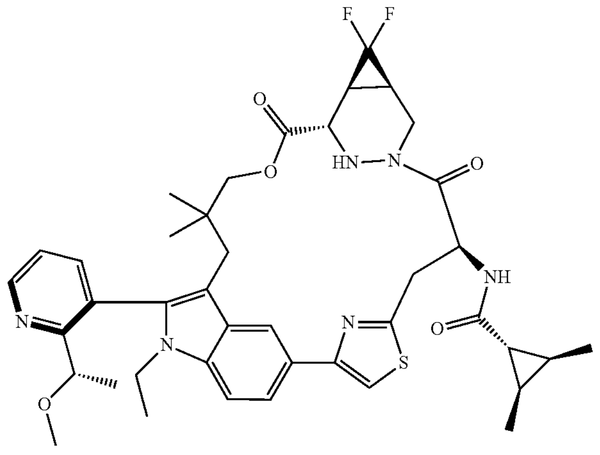

-continued
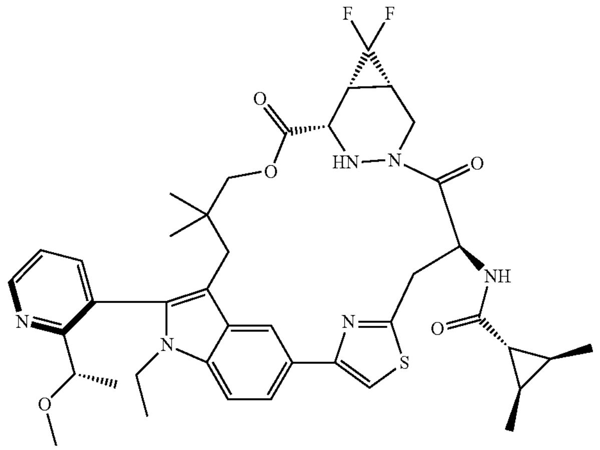
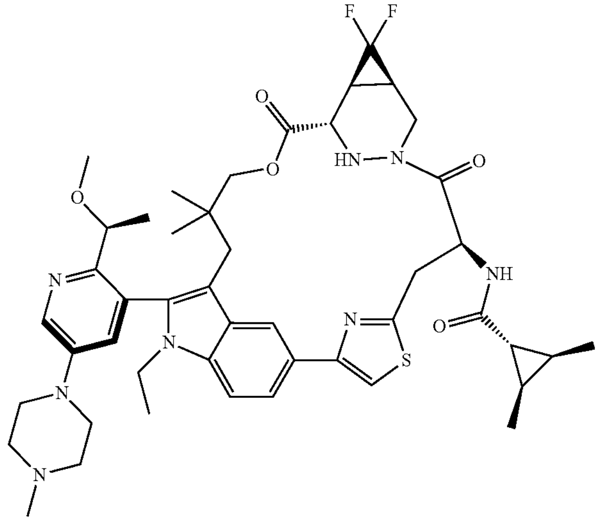
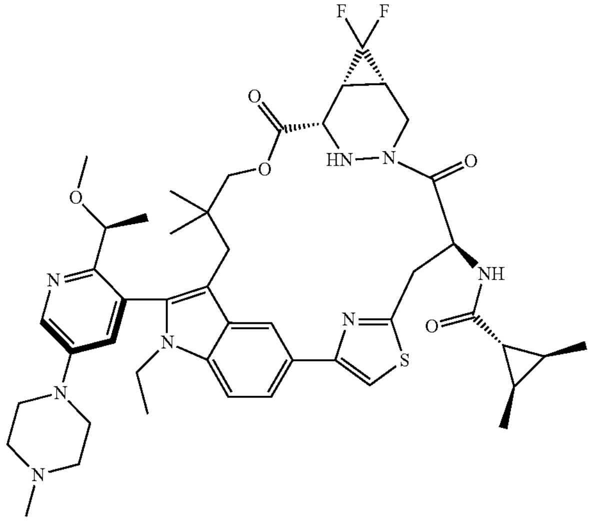
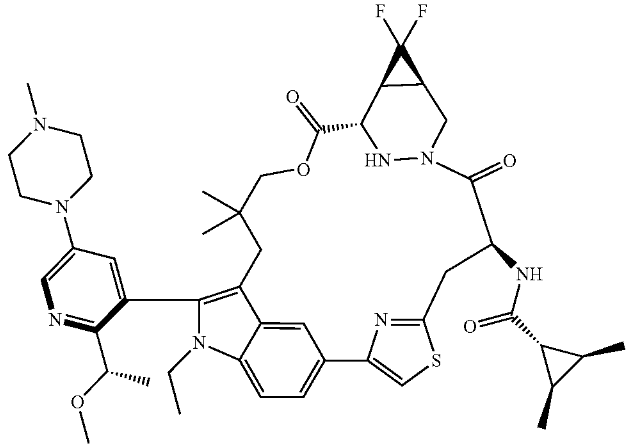

-continued
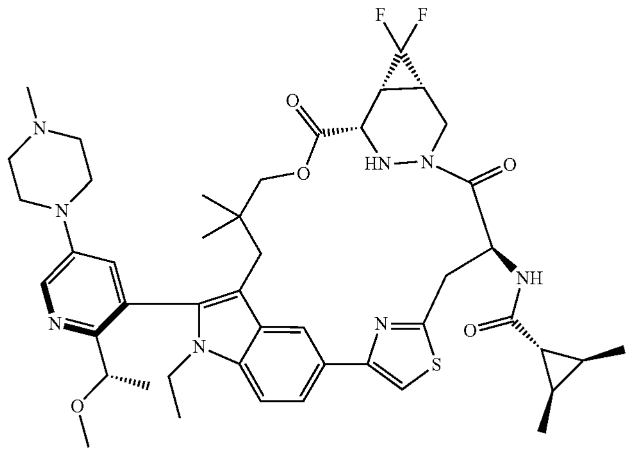
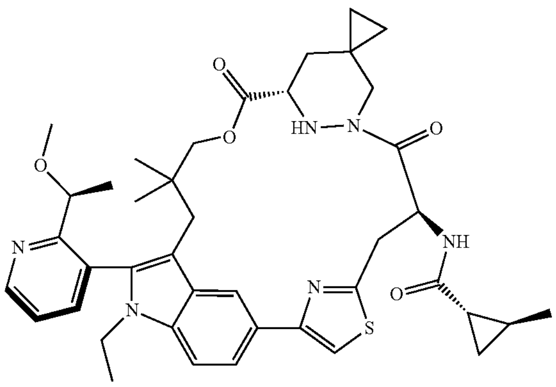
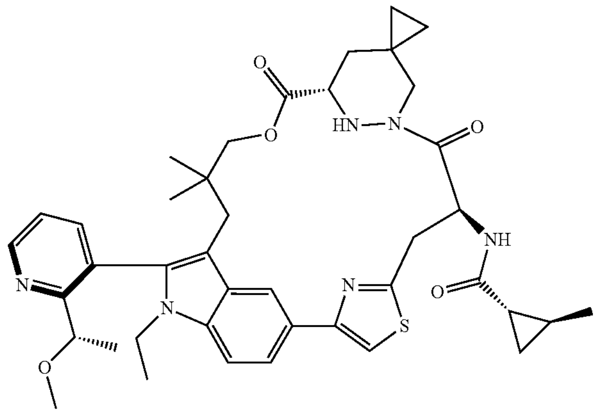
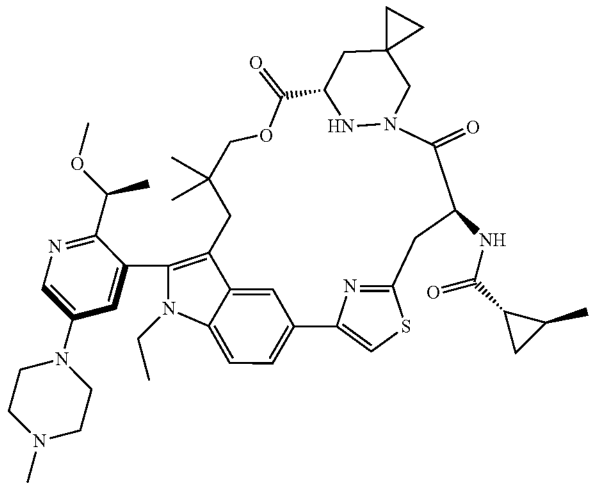

-continued
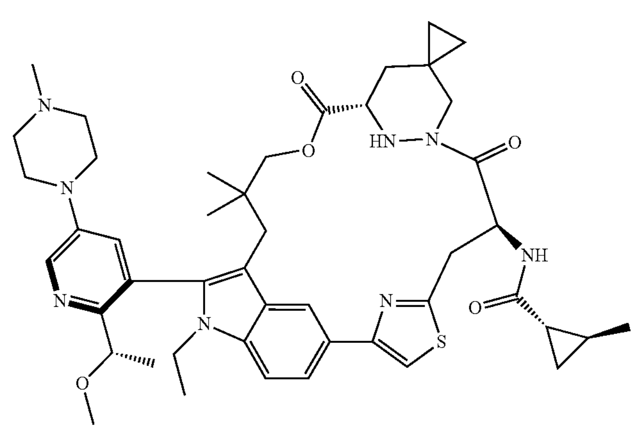
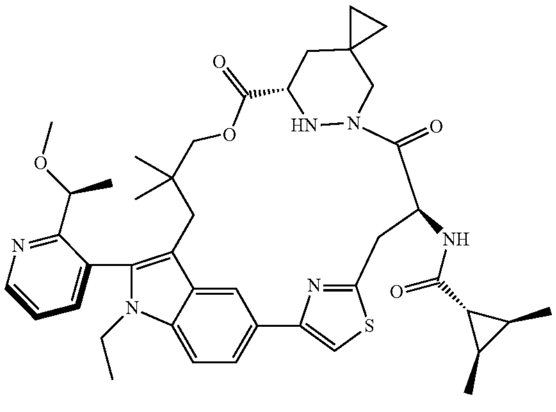
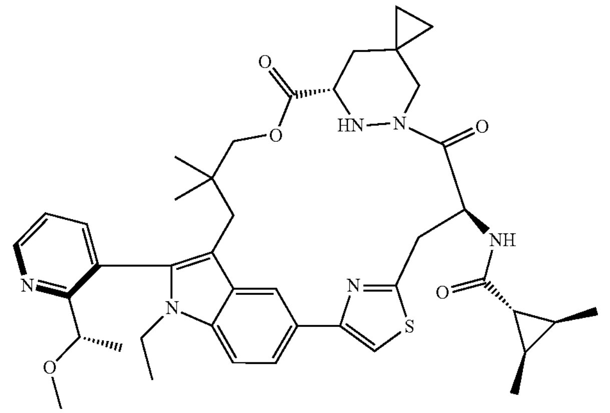
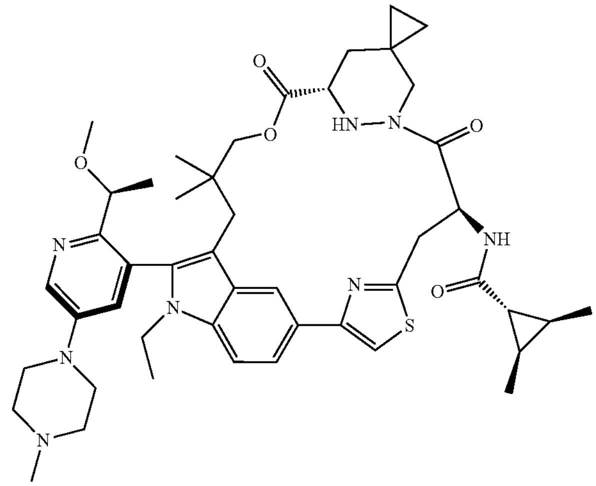
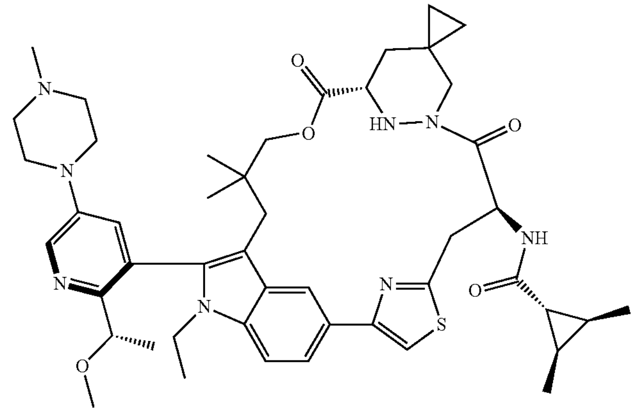
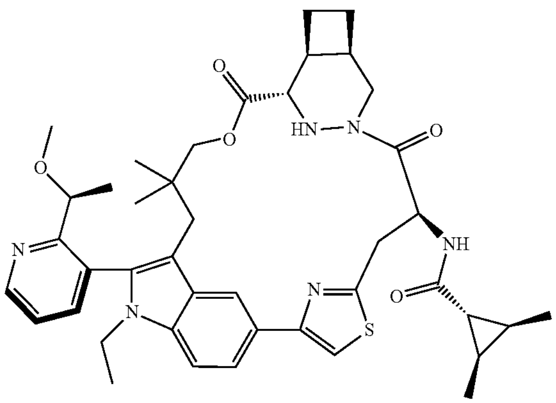

-continued
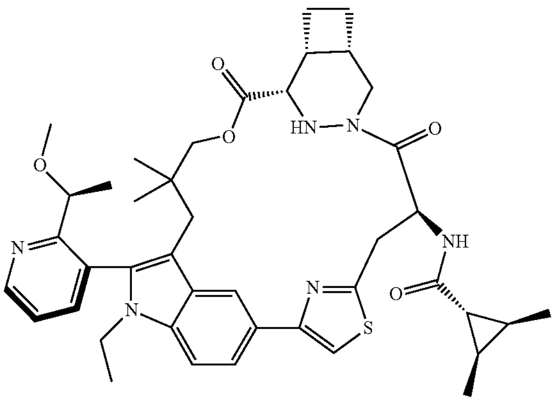
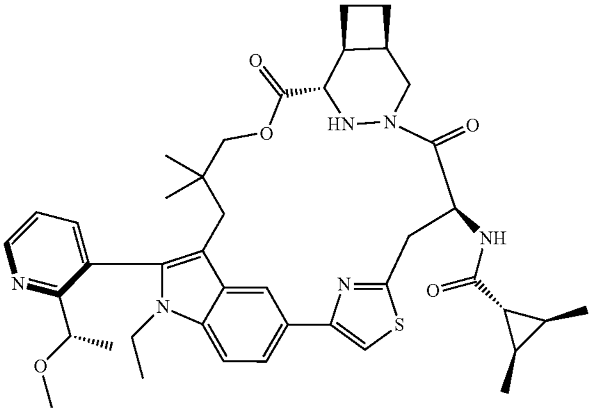
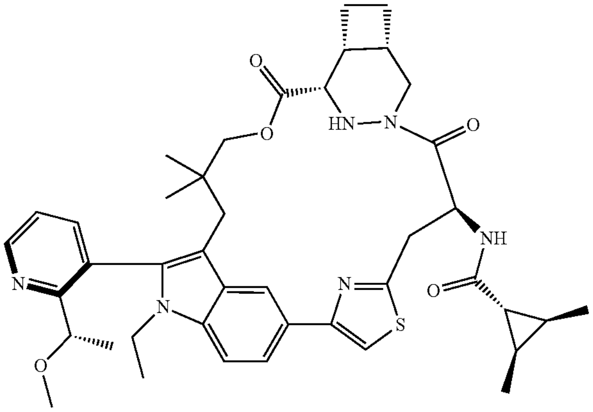
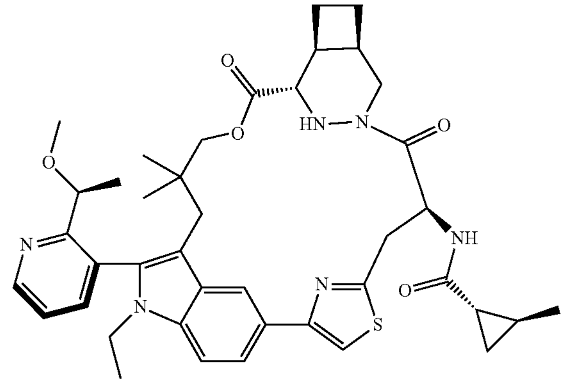
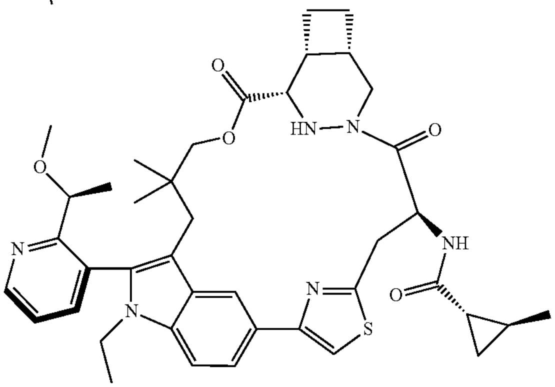
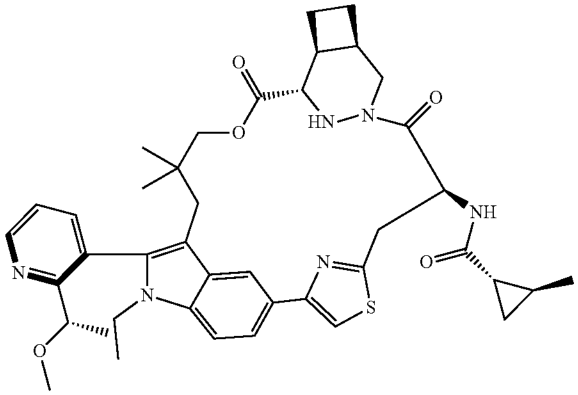
-continued
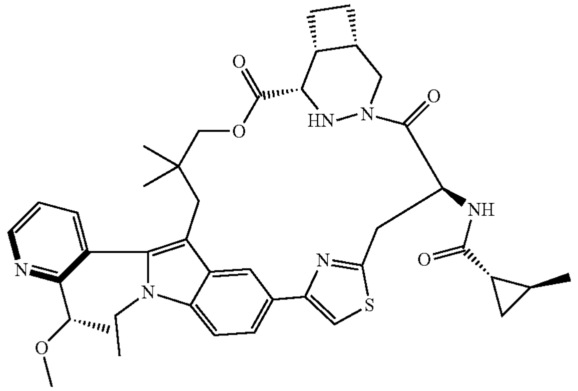

-continued
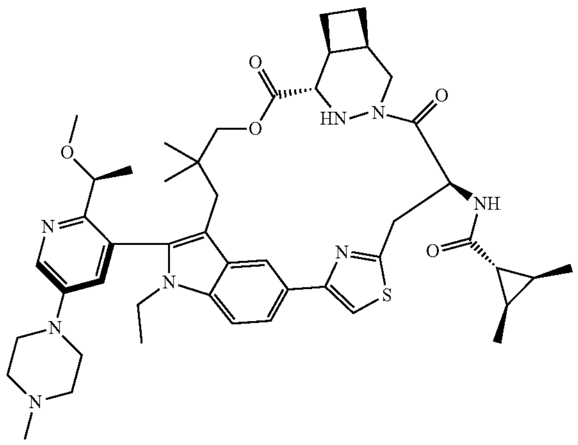
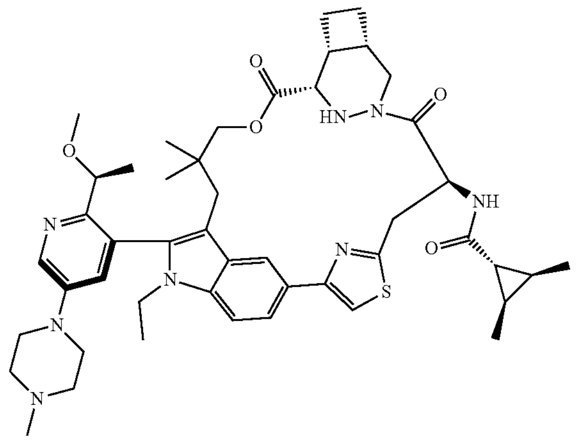
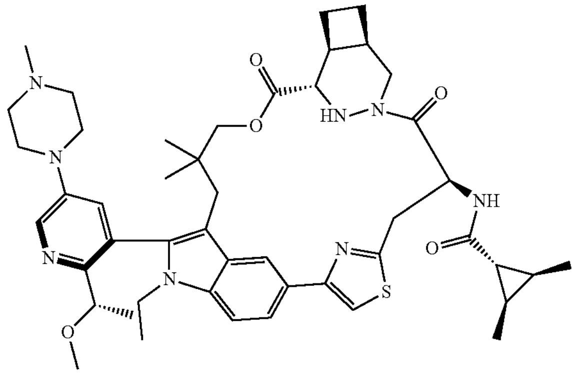
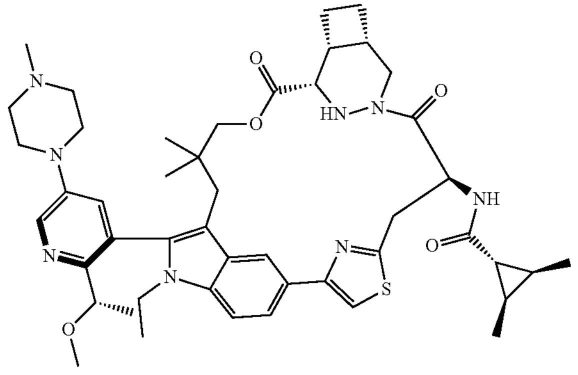
-continued
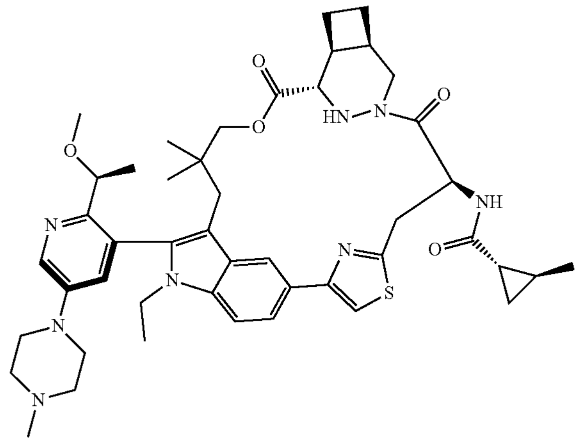
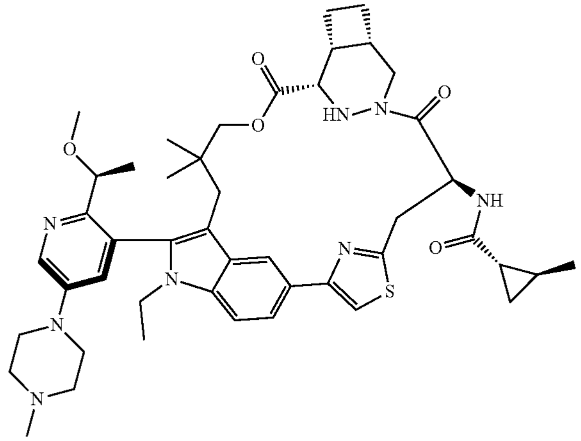
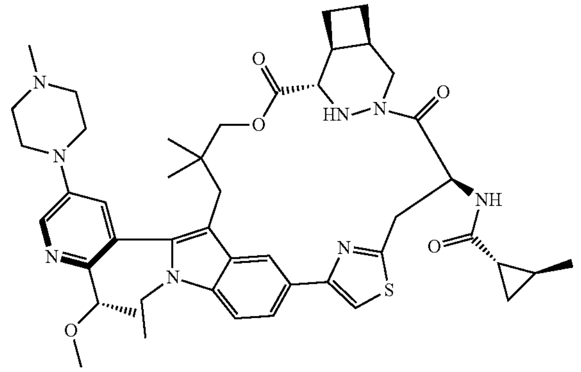
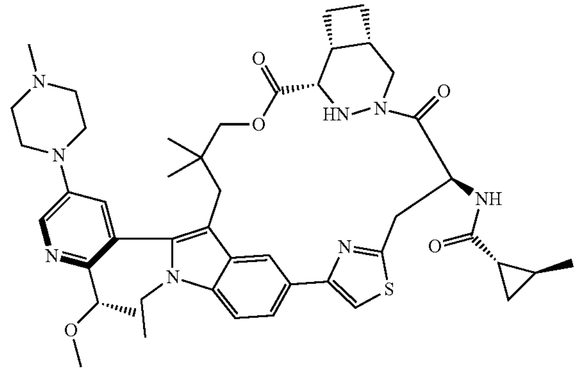

-continued
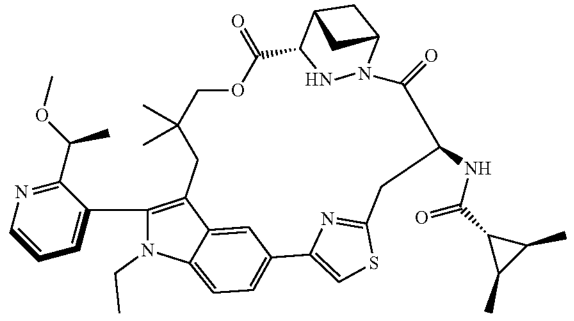
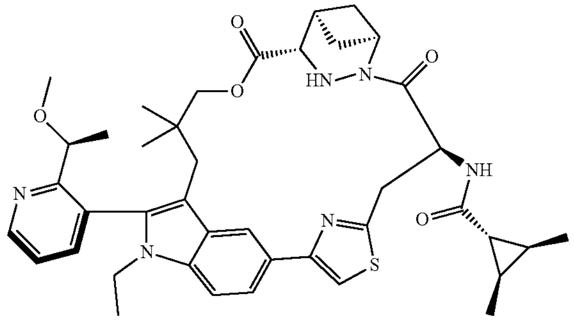
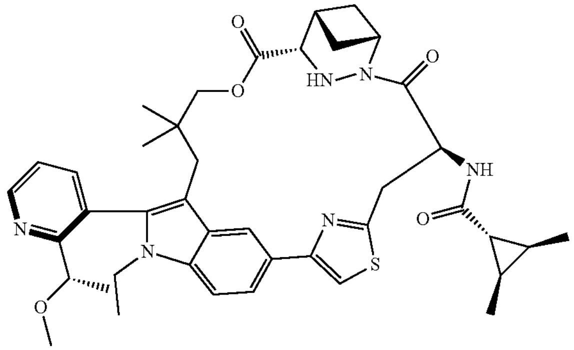
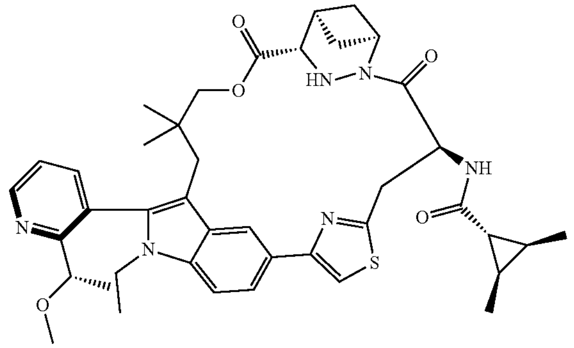
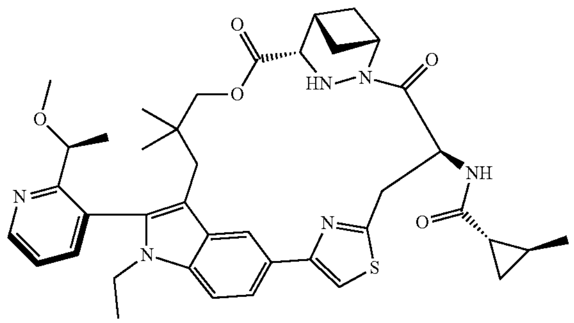
-continued
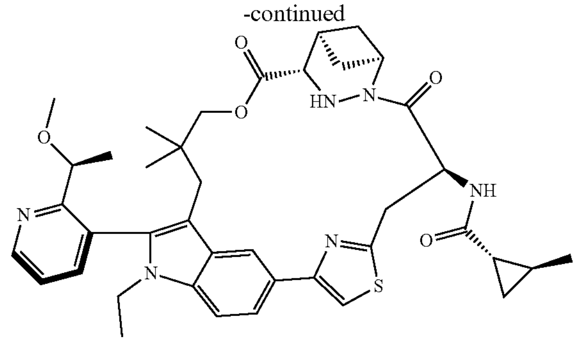
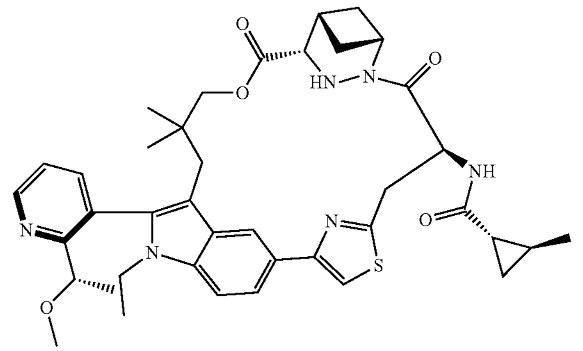
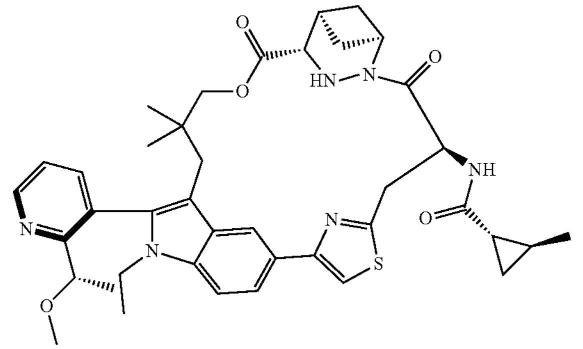
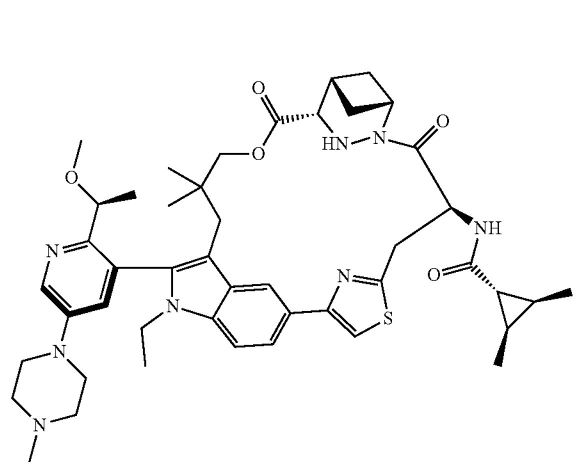

-continued
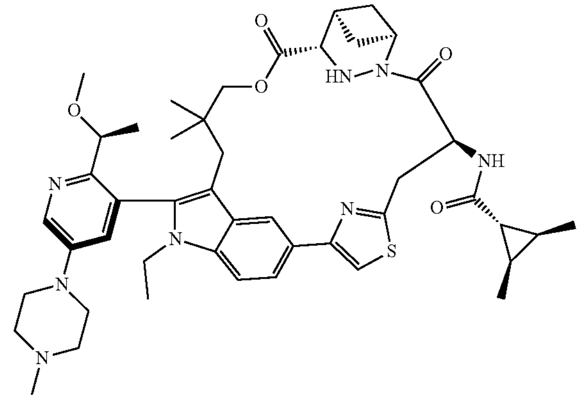
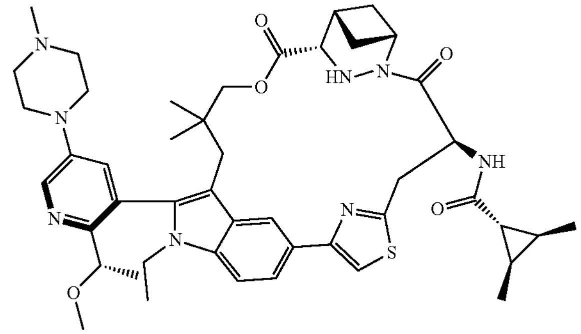
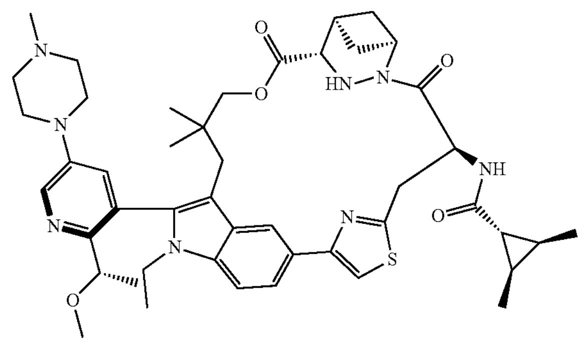
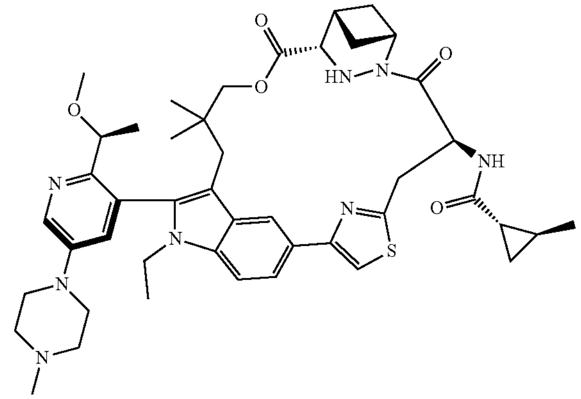
-continued
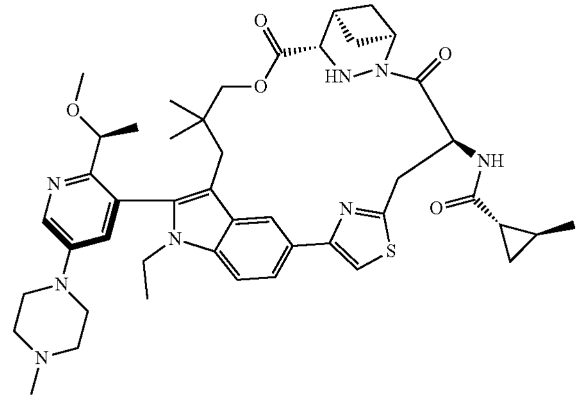
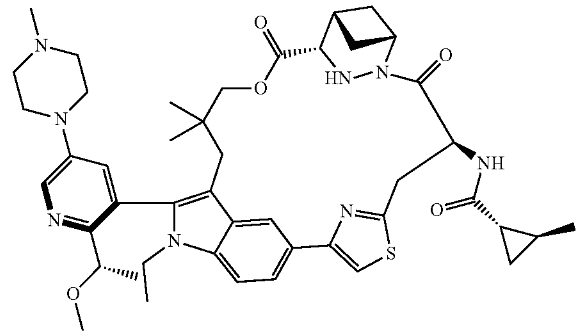
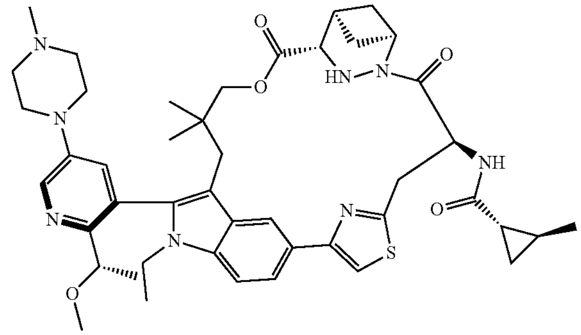
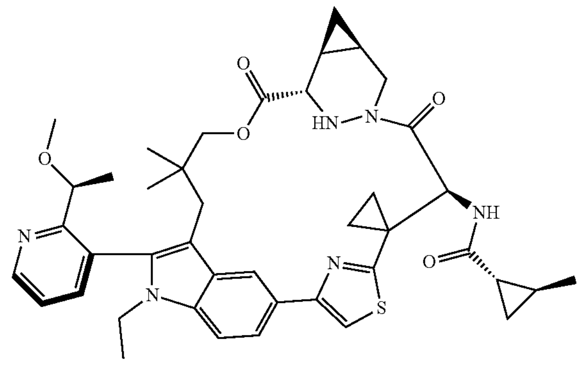

-continued
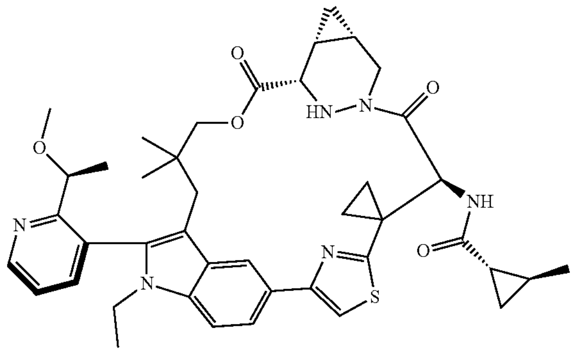
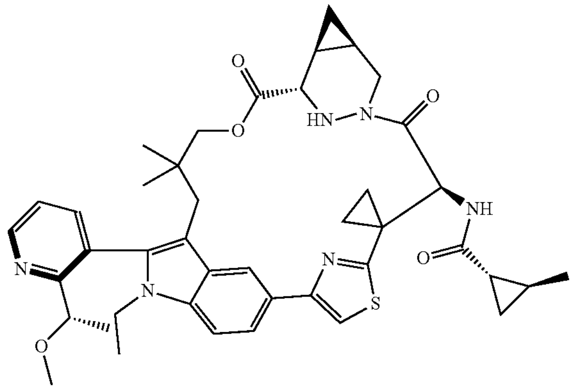
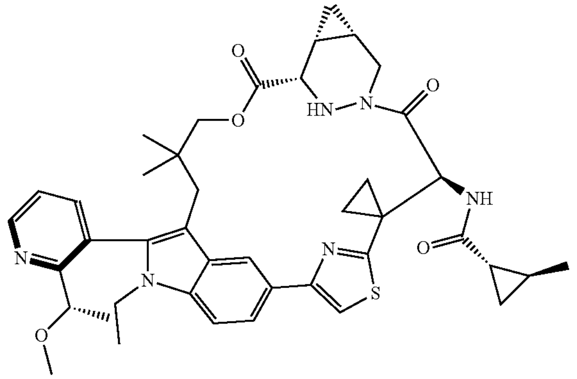
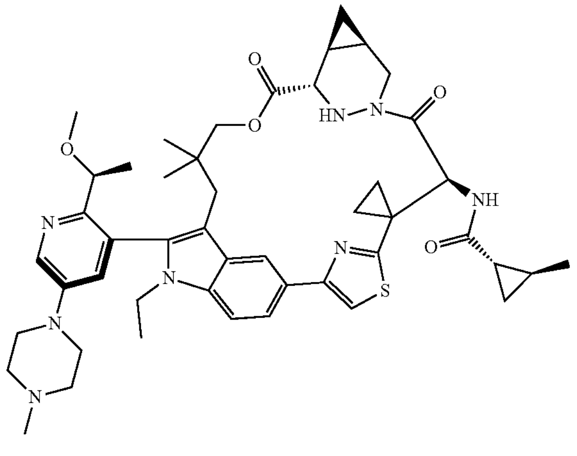
-continued
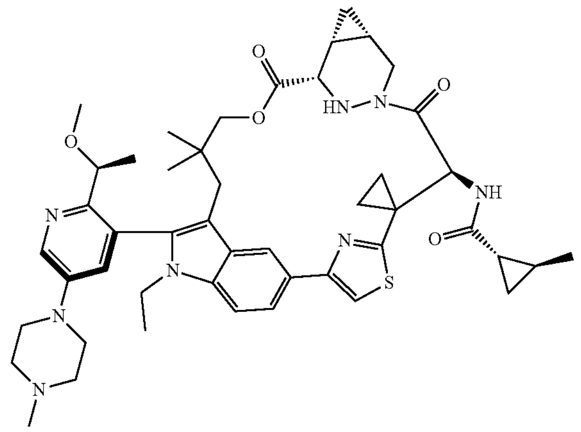
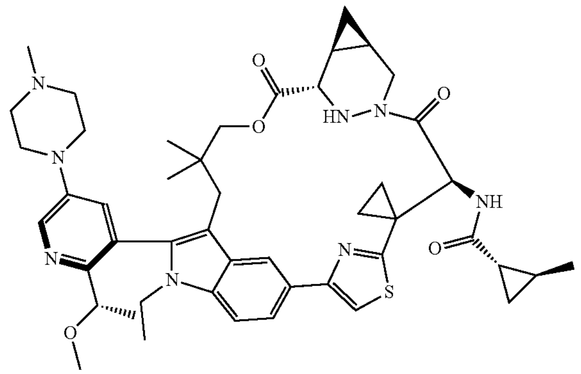
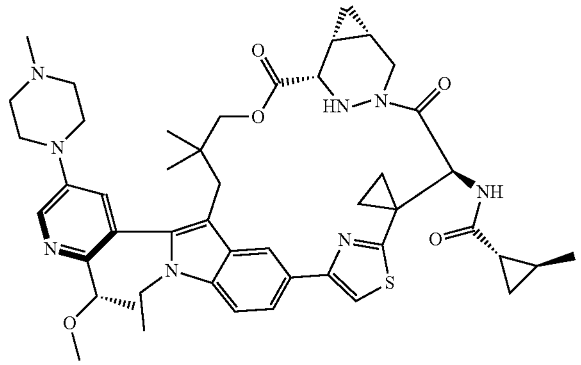
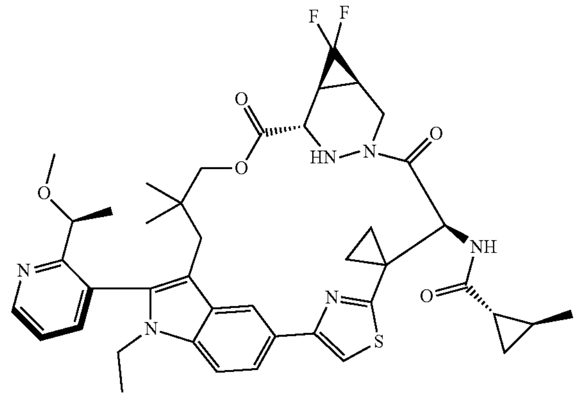

-continued
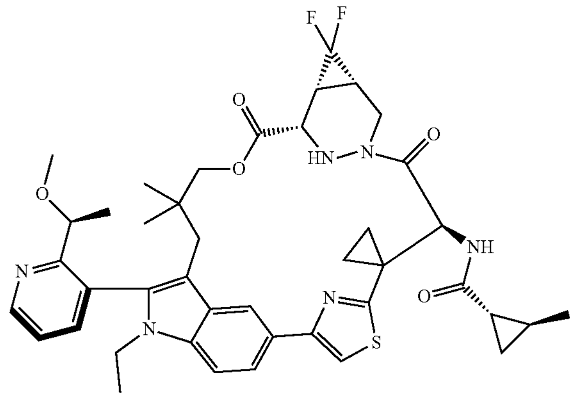
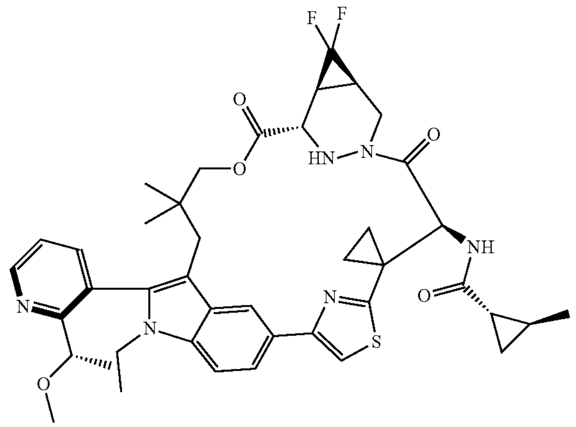
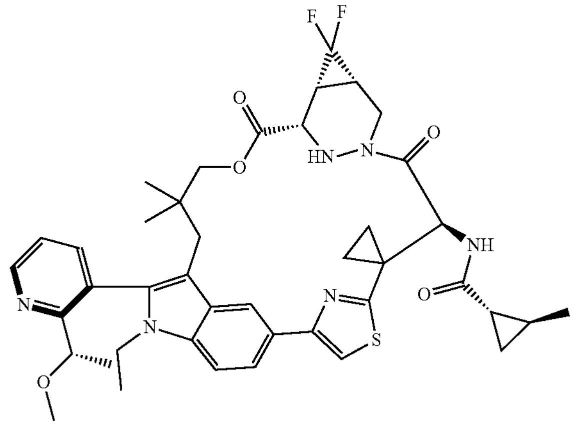
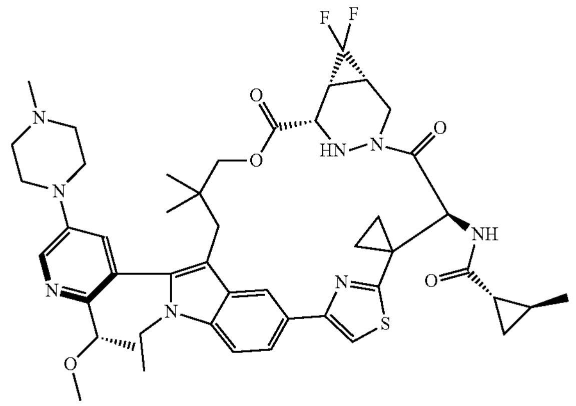
-continued
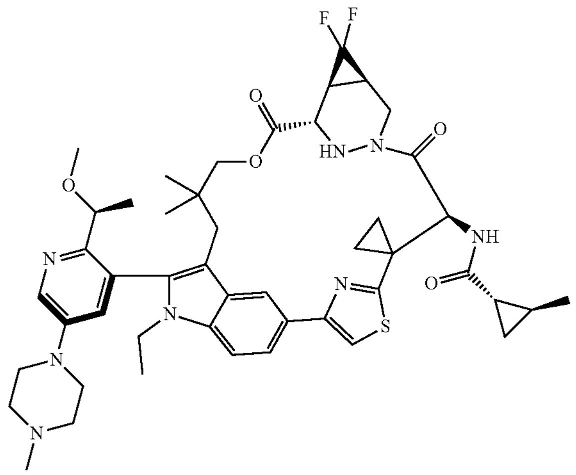
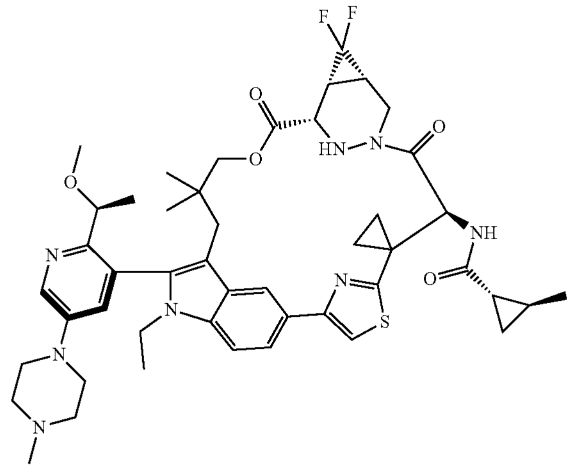
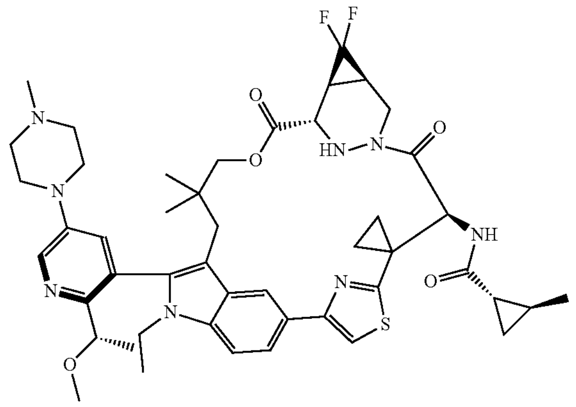
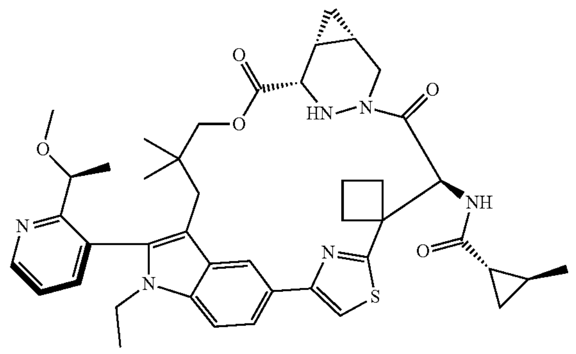

-continued
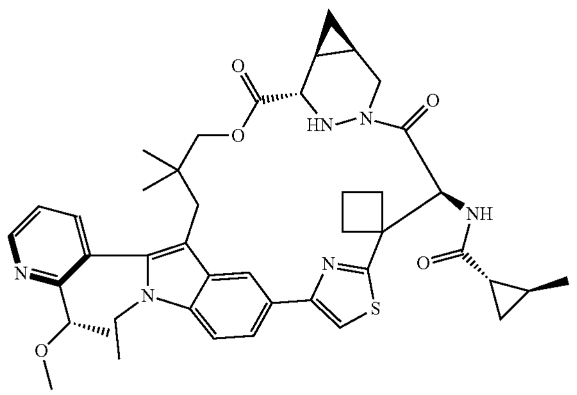
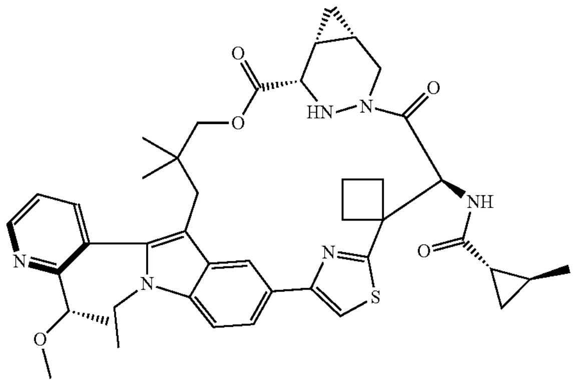
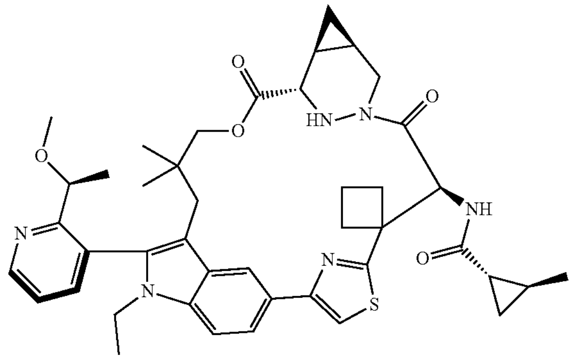
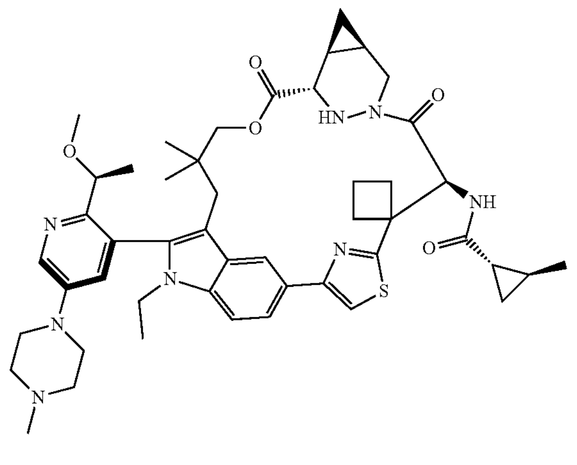
-continued
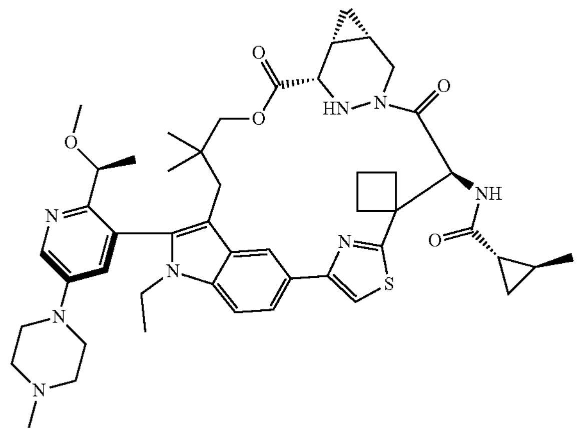
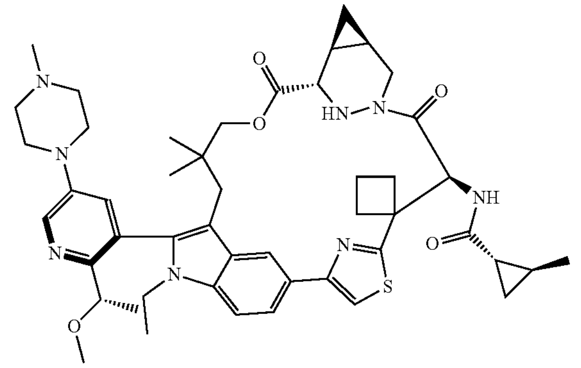
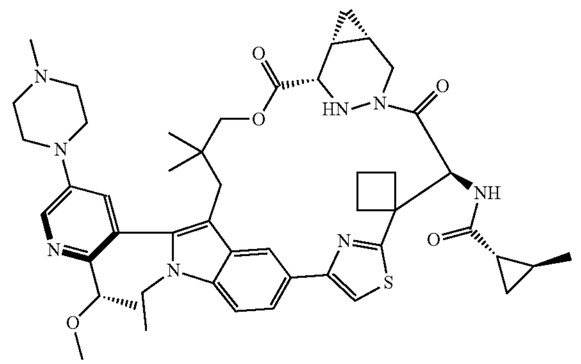
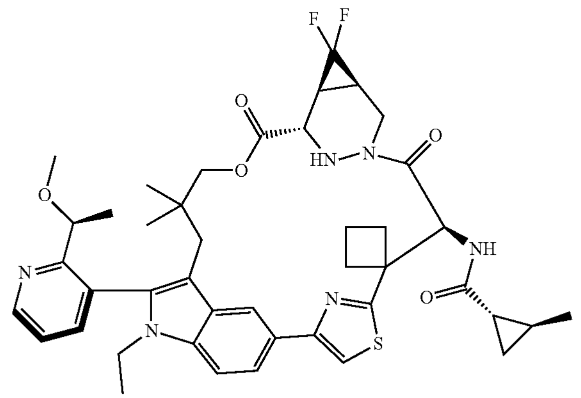

-continued
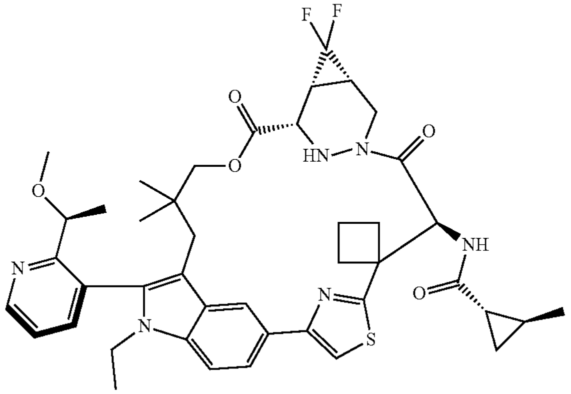
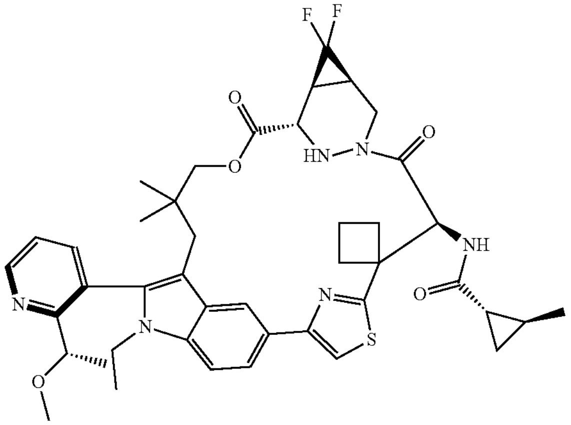
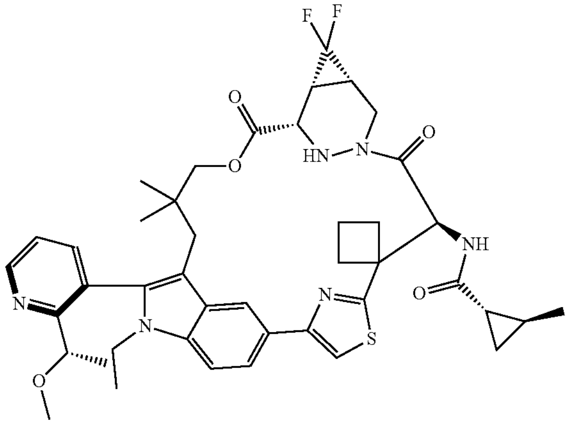
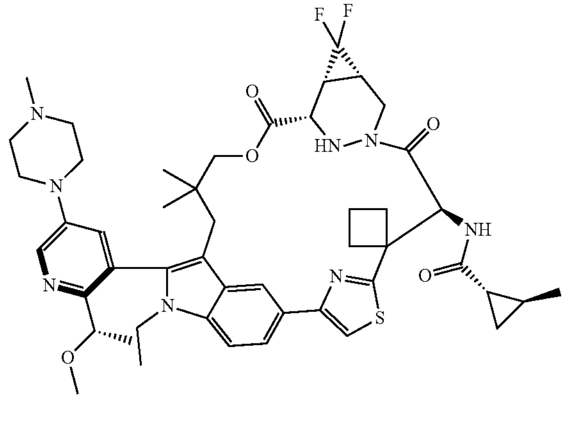
-continued
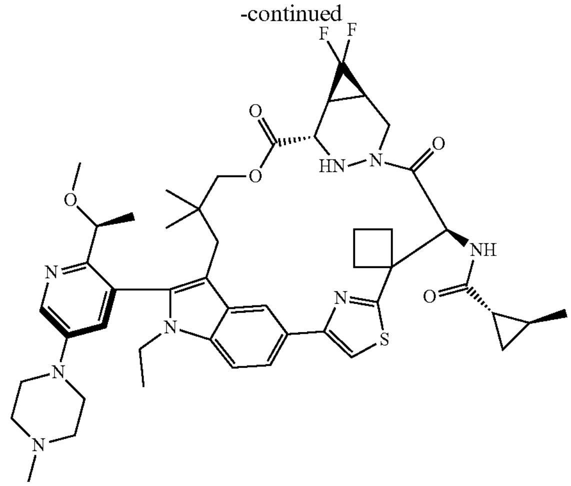
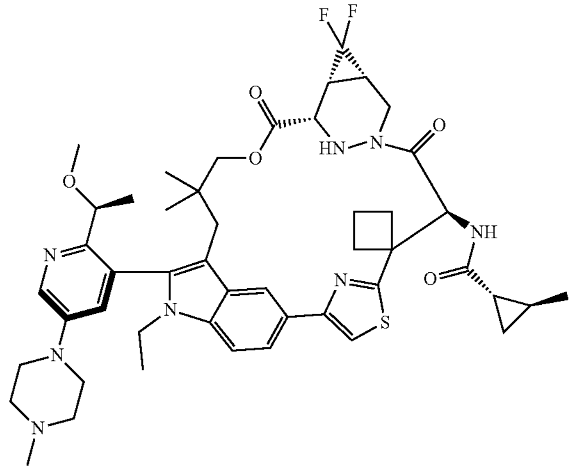
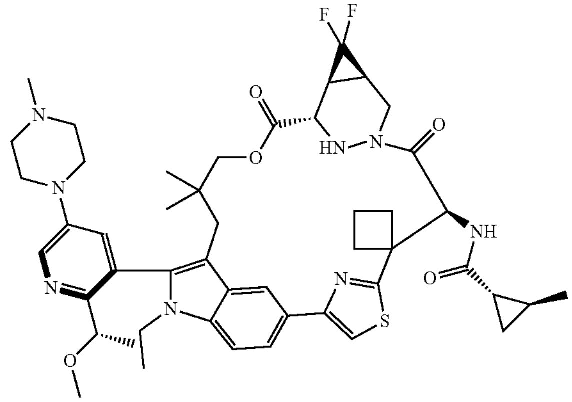
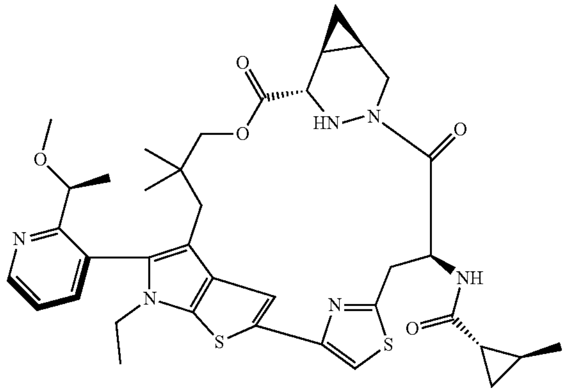

-continued
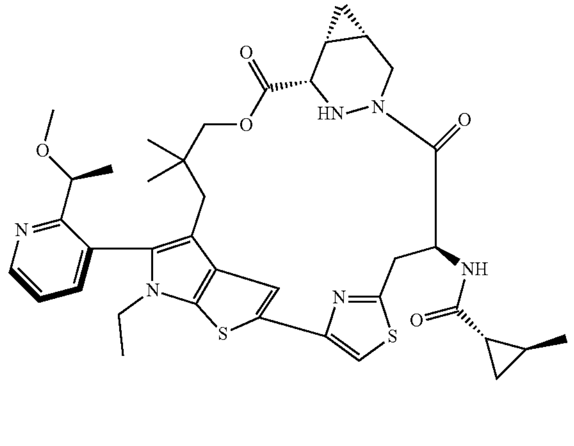
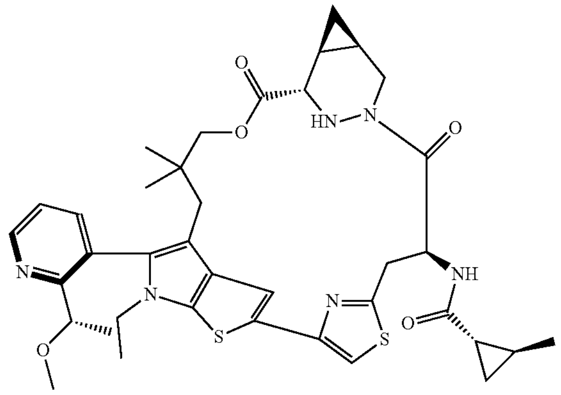
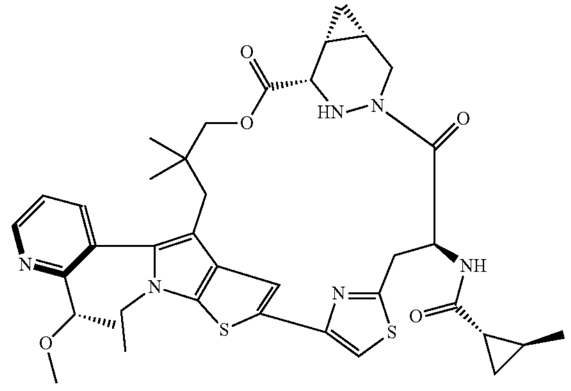
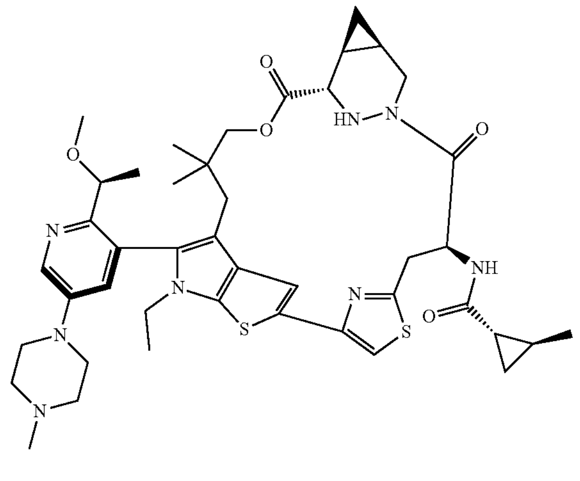
-continued
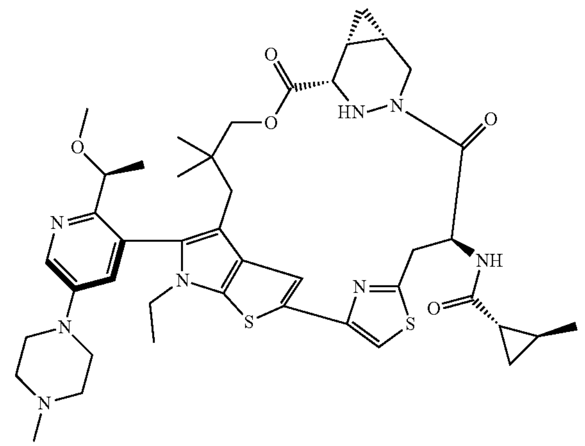
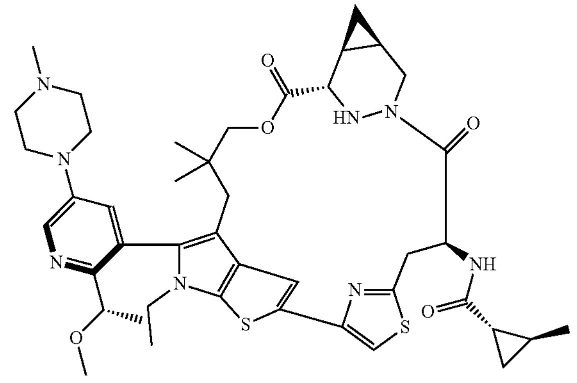
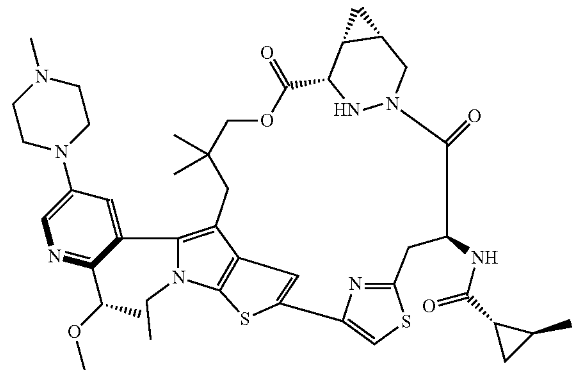
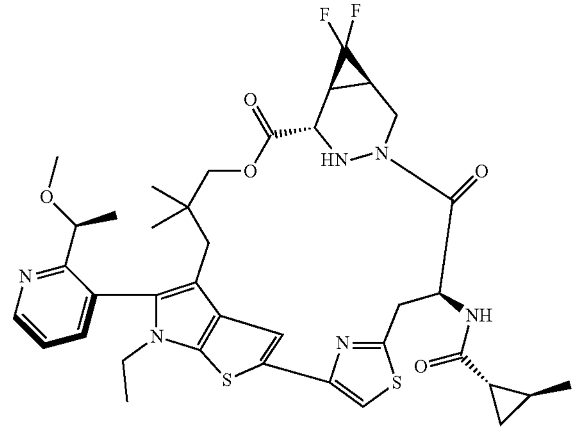

-continued
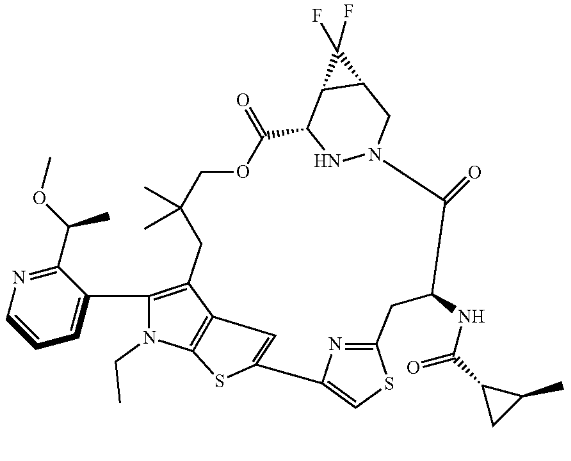
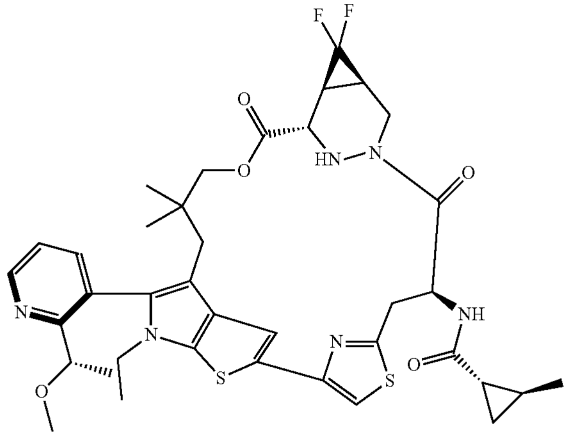
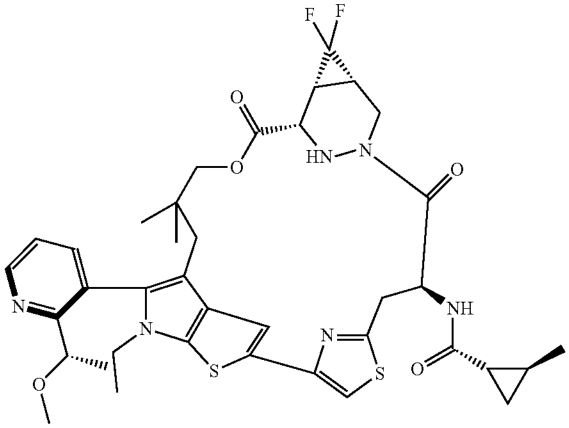
-continued
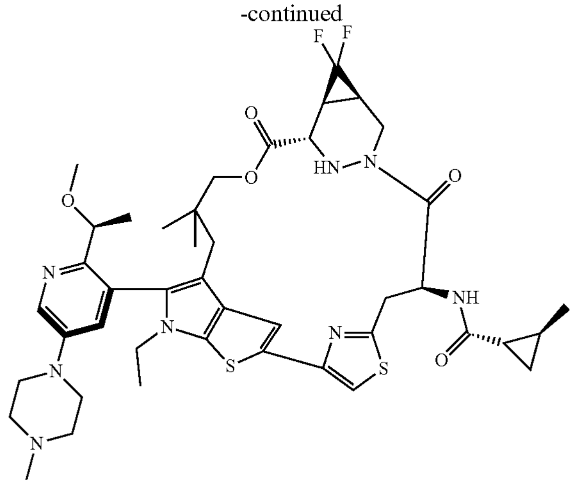
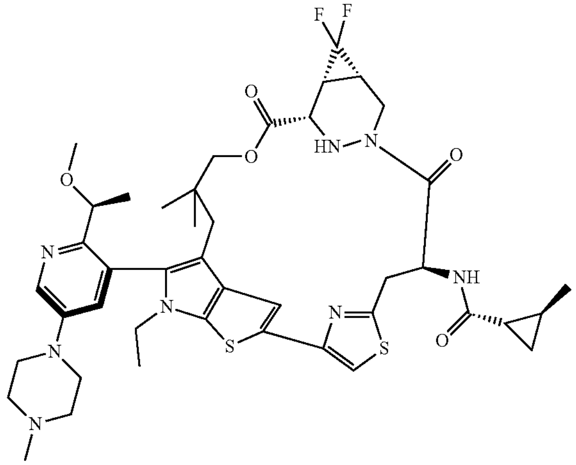
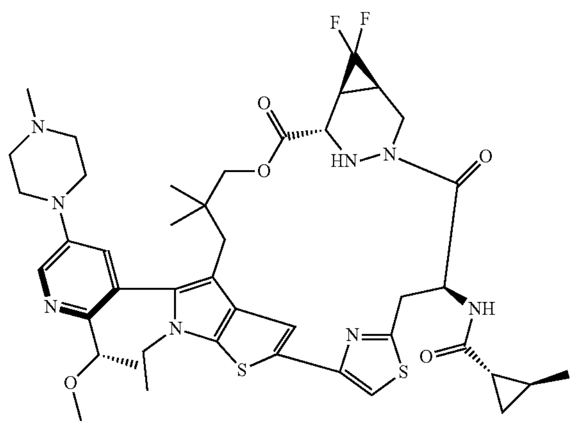

-continued
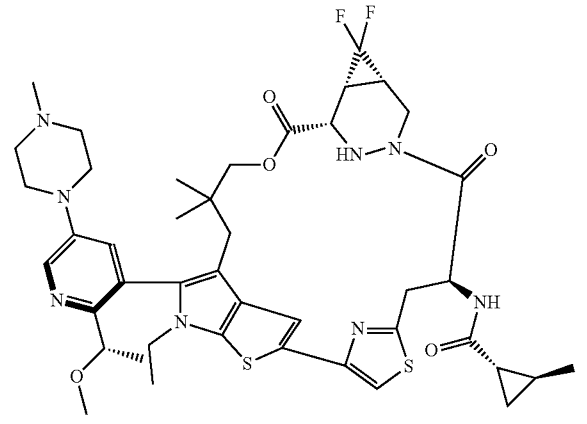
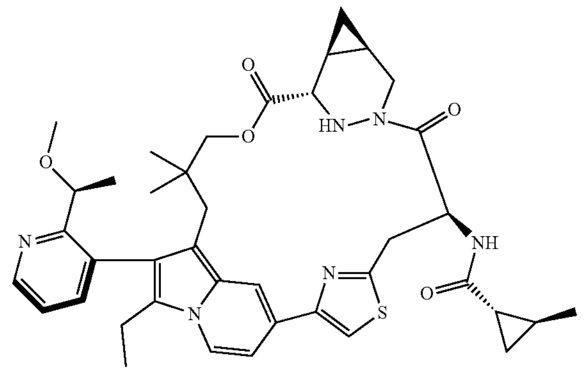
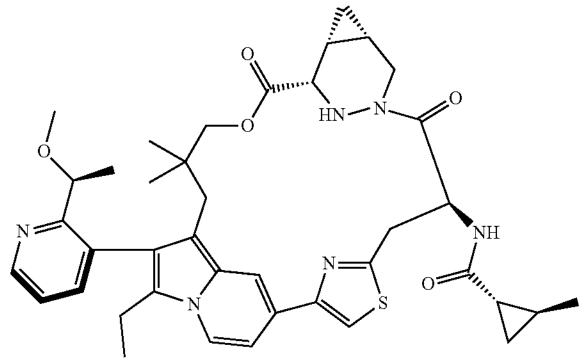
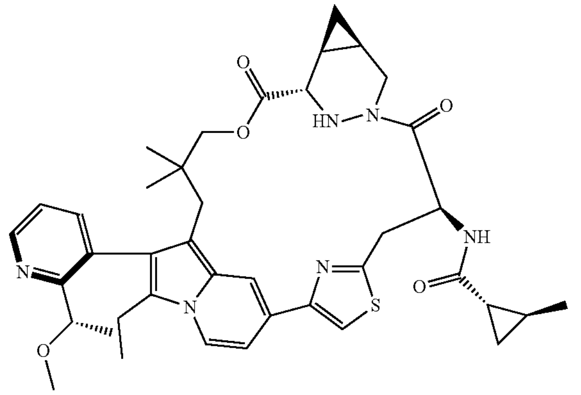
-continued
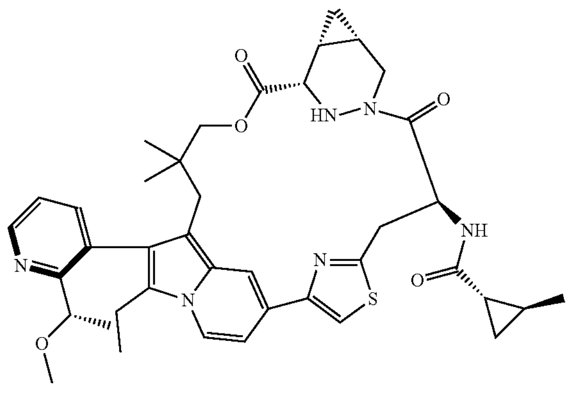
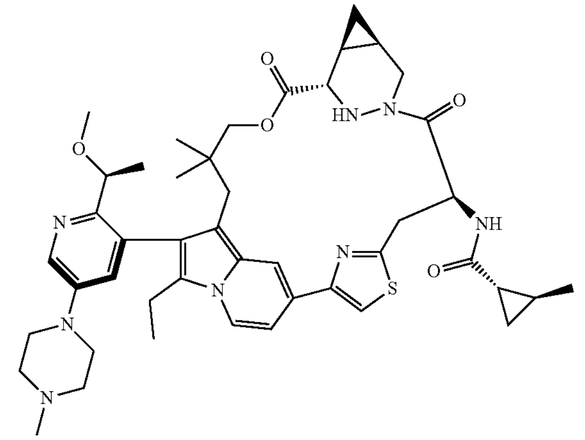
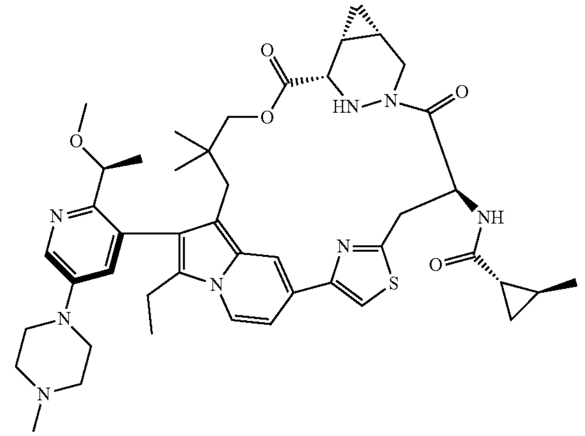
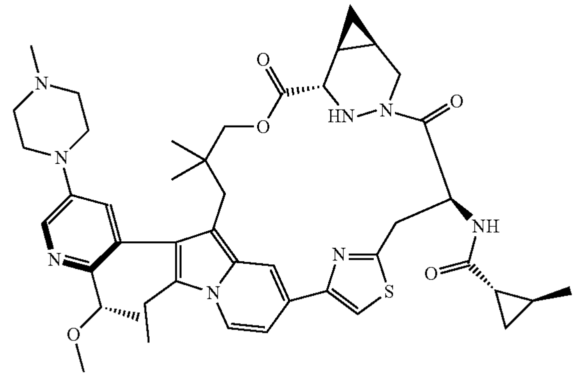

-continued
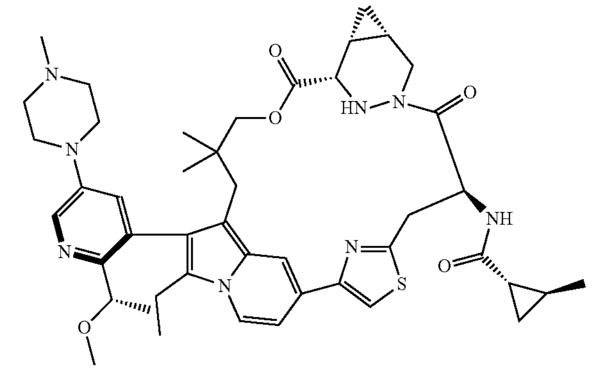
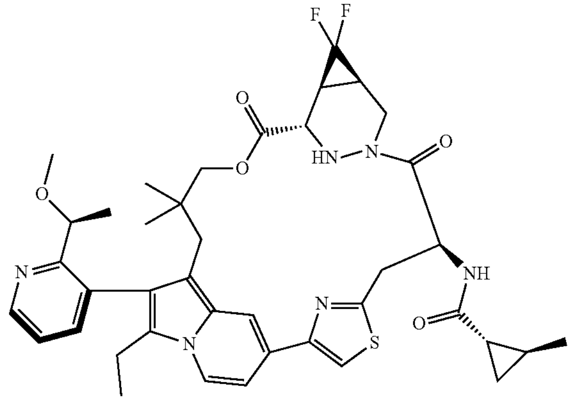
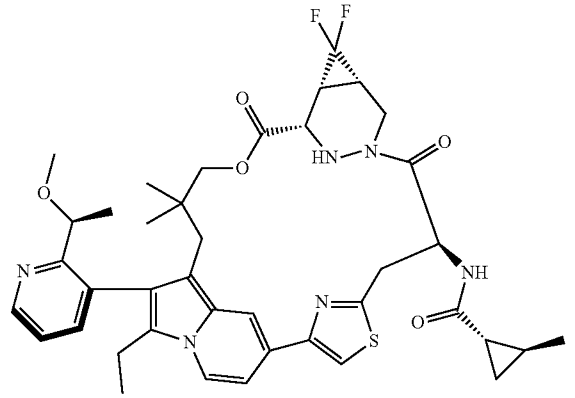
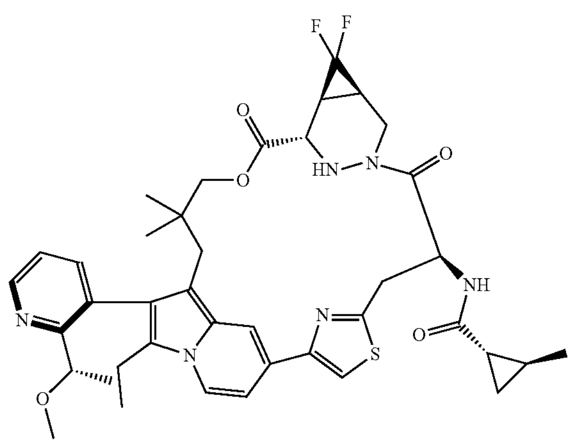
-continued
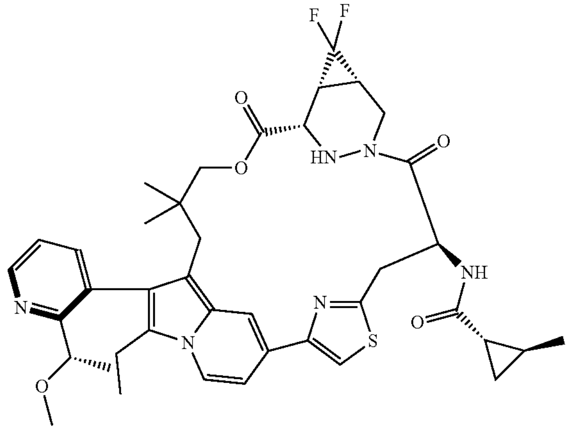
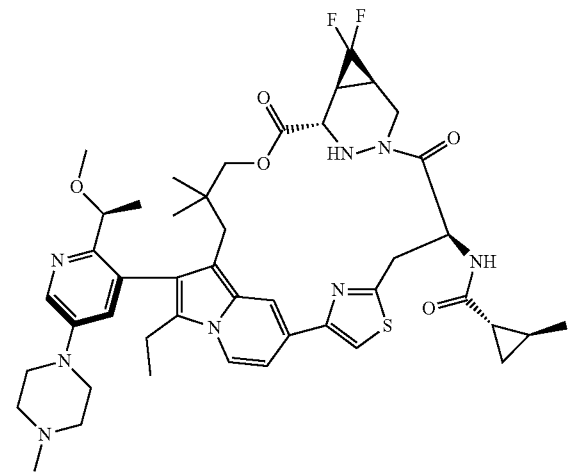
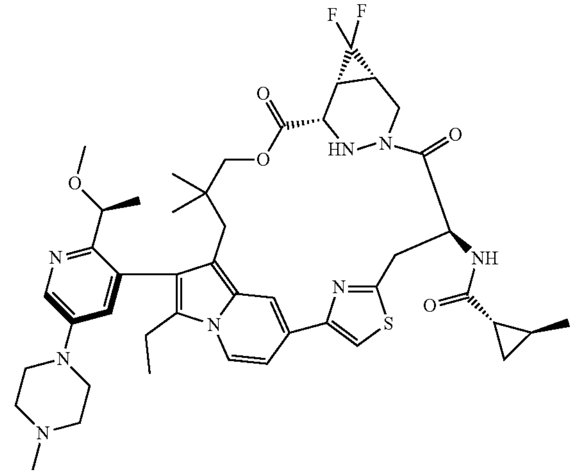

-continued
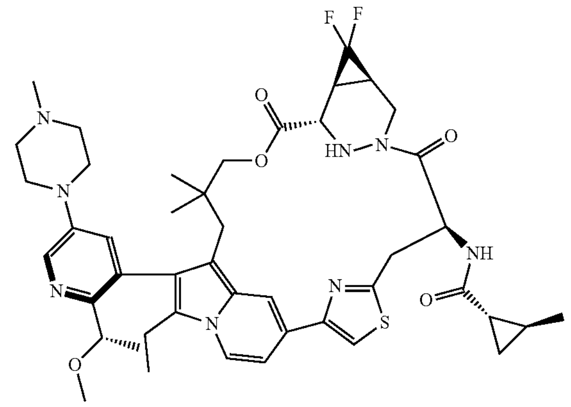
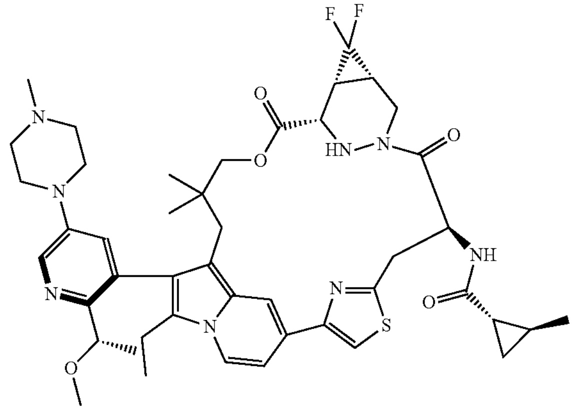
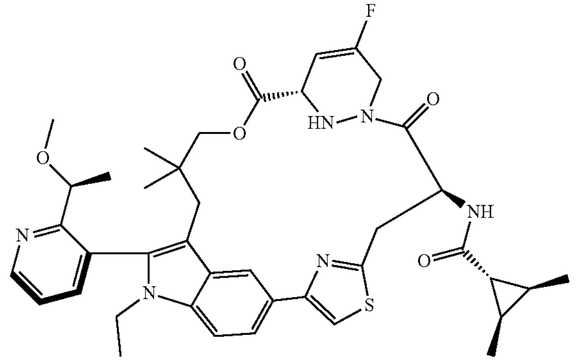
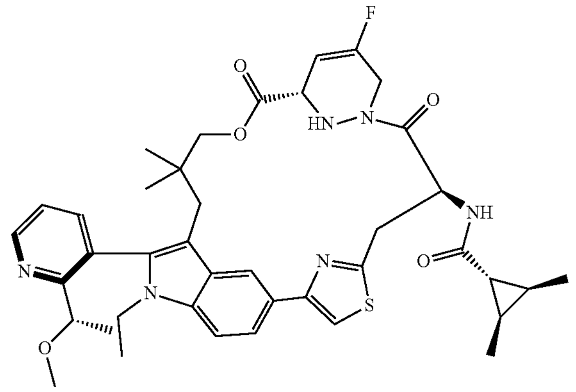
-continued
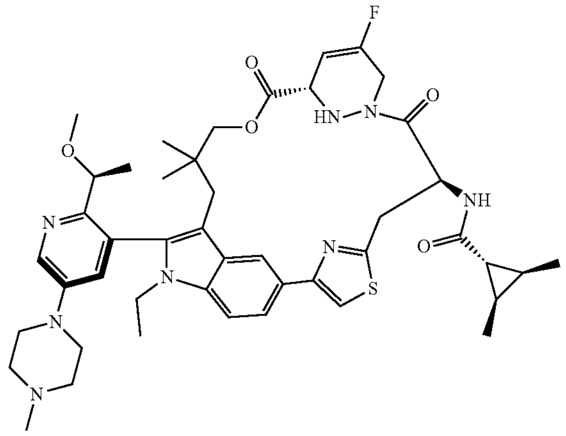
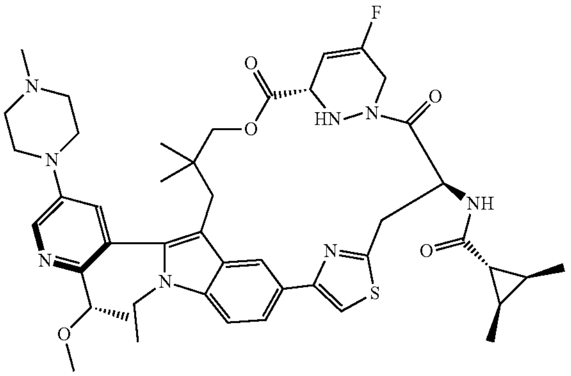
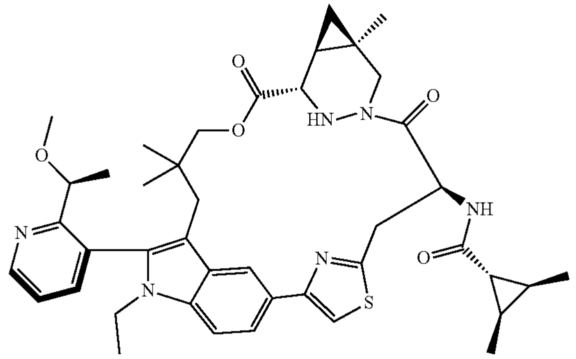
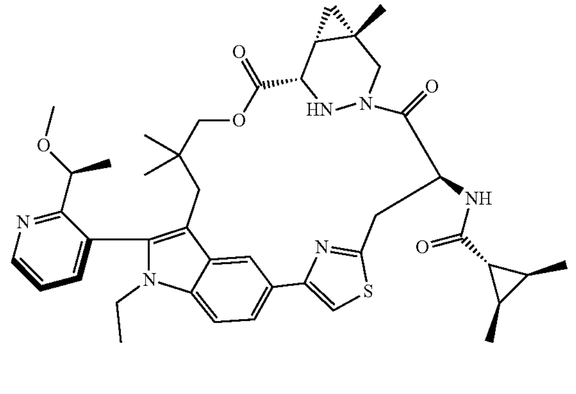

-continued
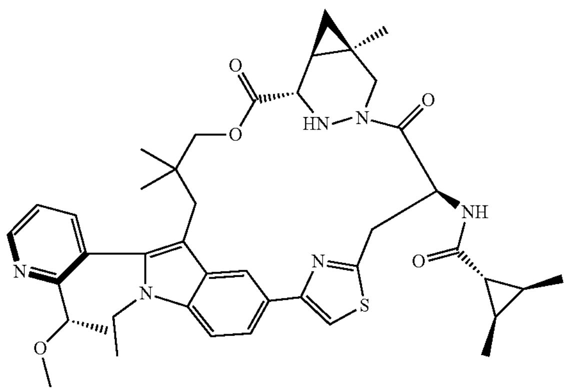
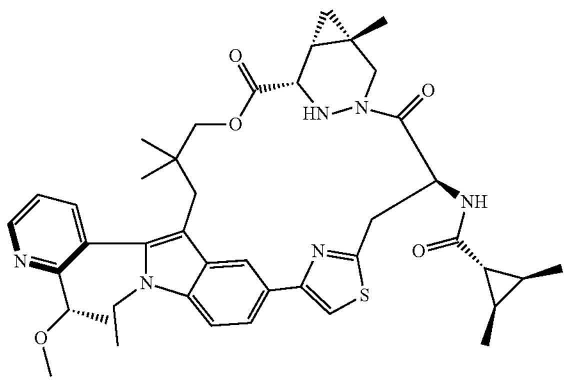
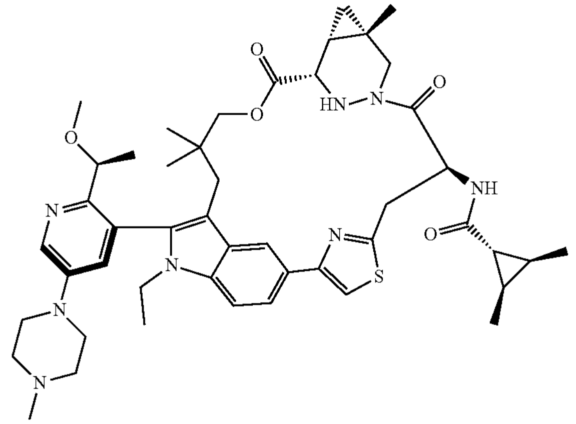
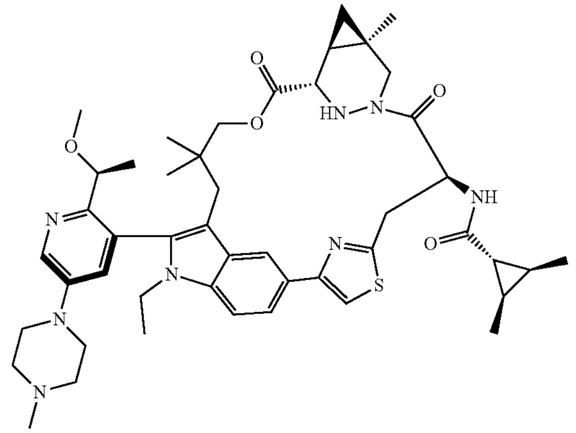
-continued
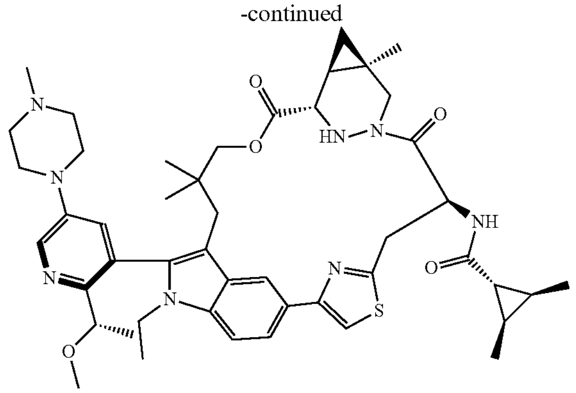
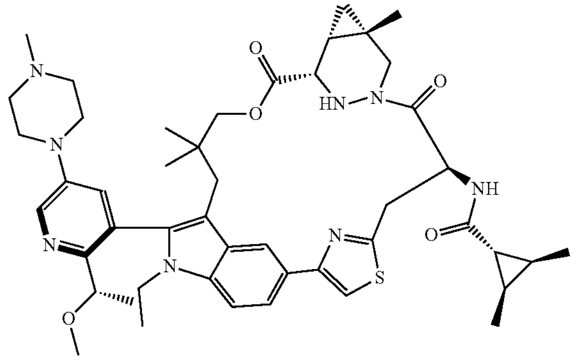
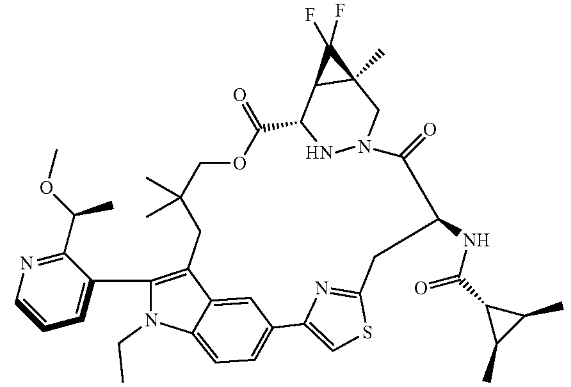
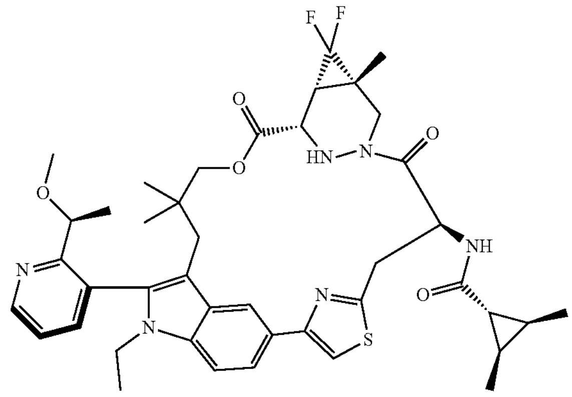

-continued
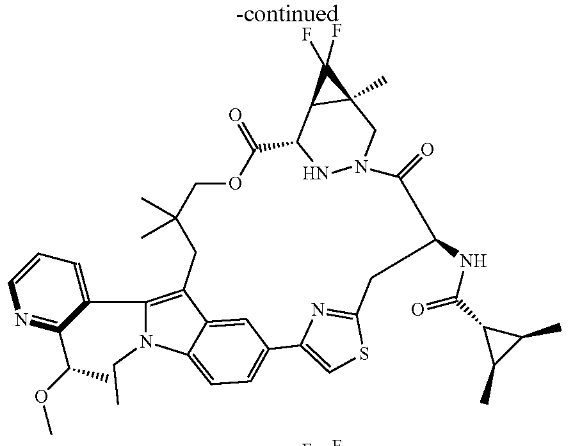
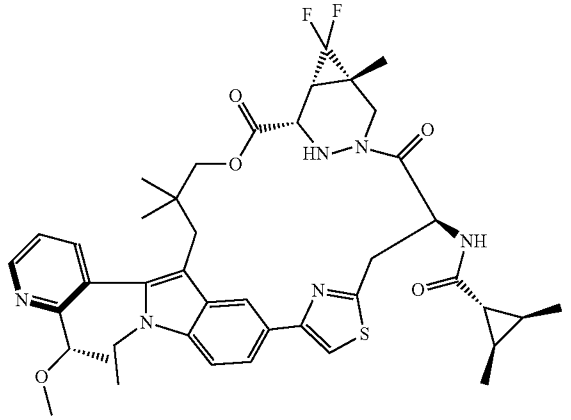
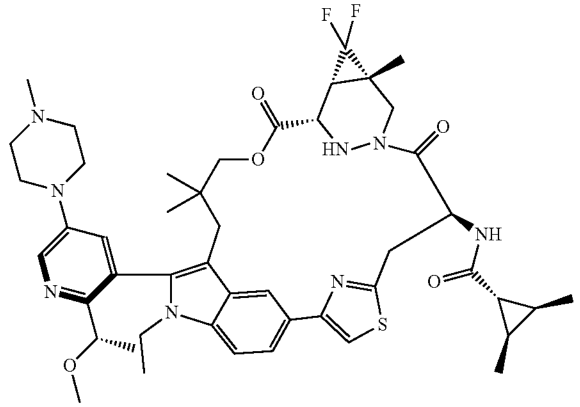
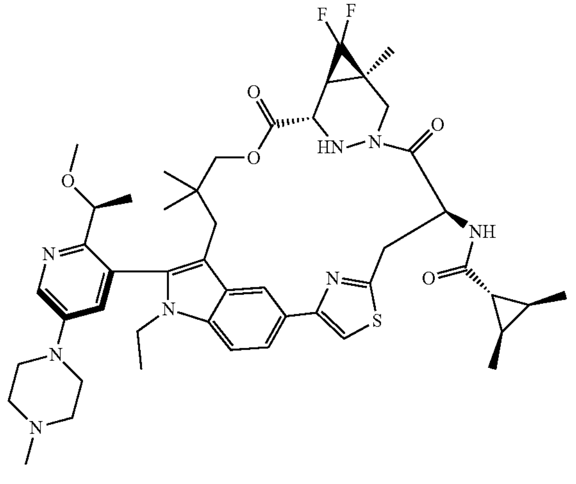
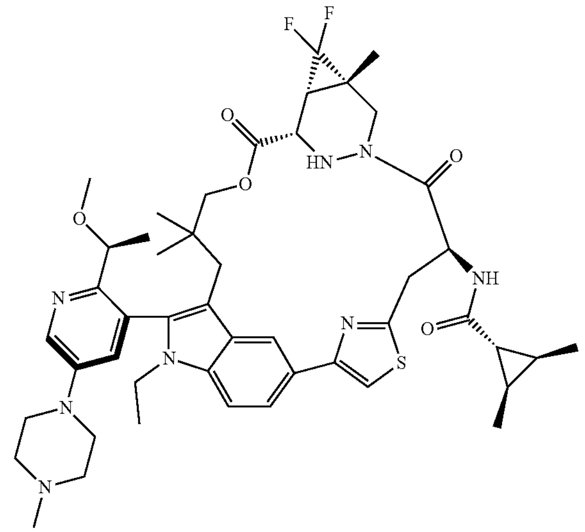
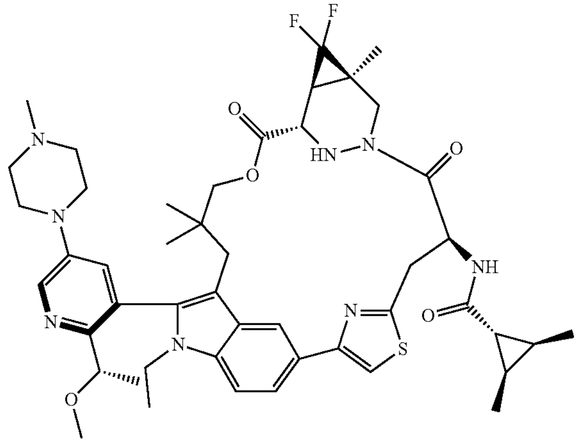
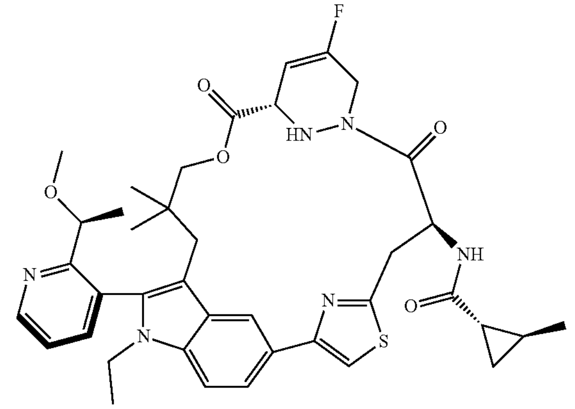

-continued
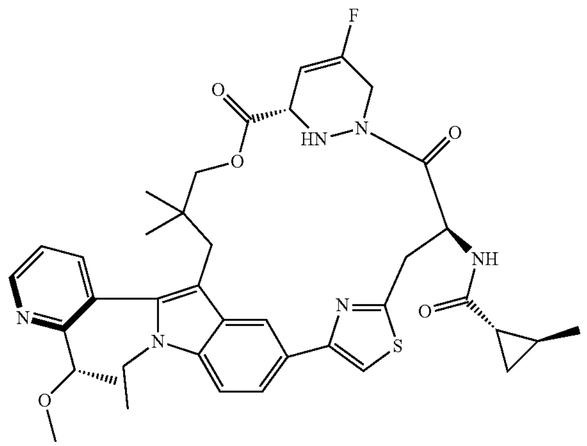
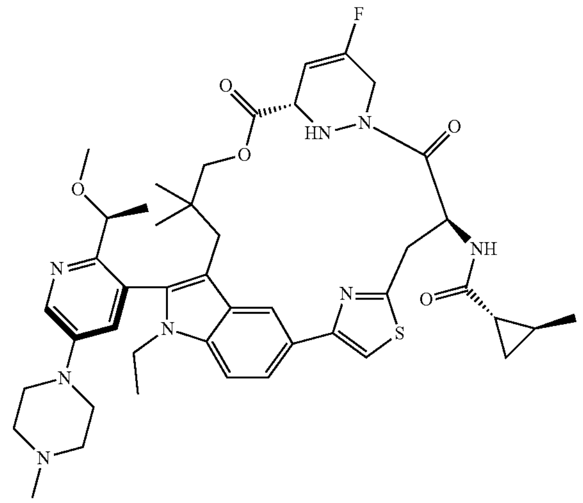
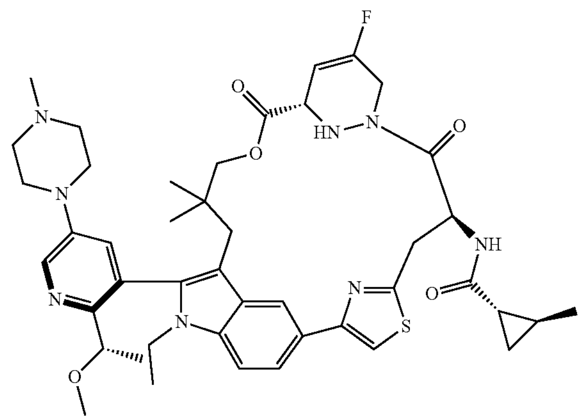
-continued
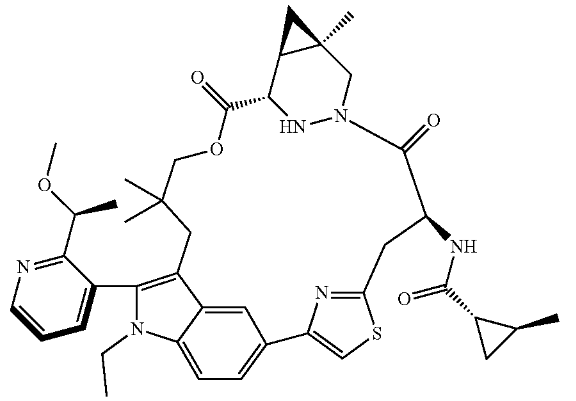
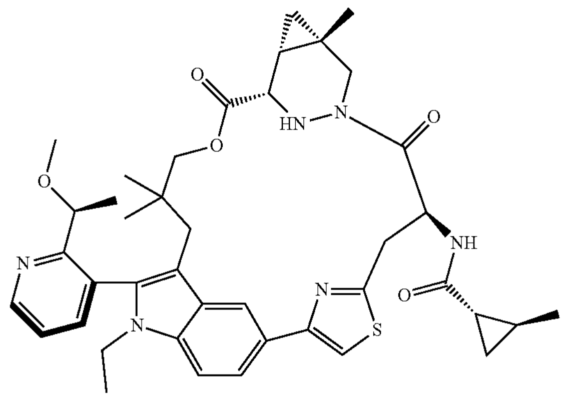
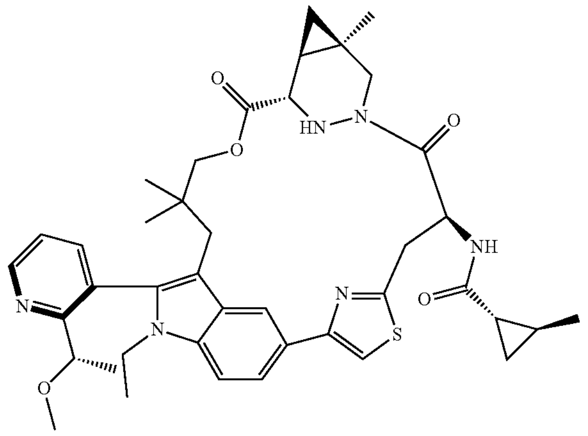
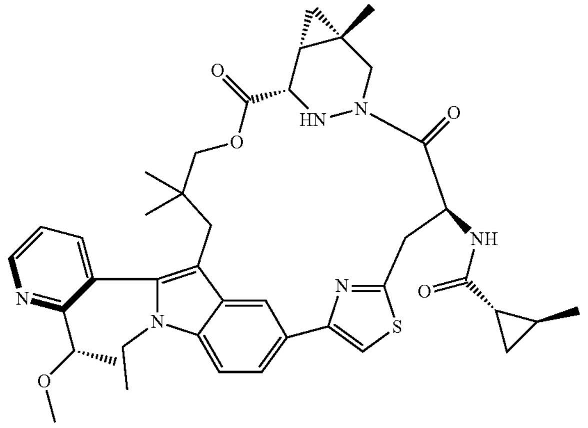

-continued
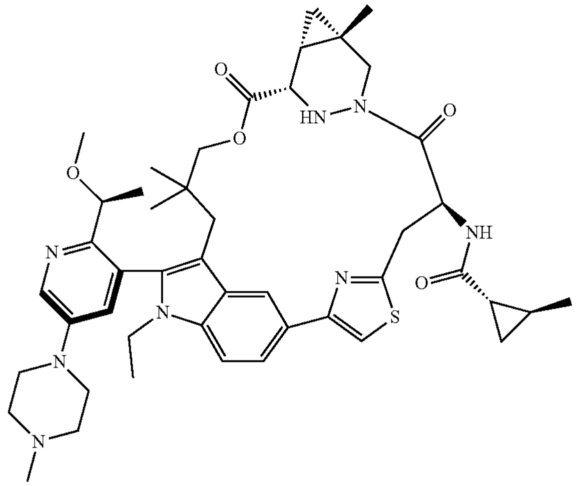
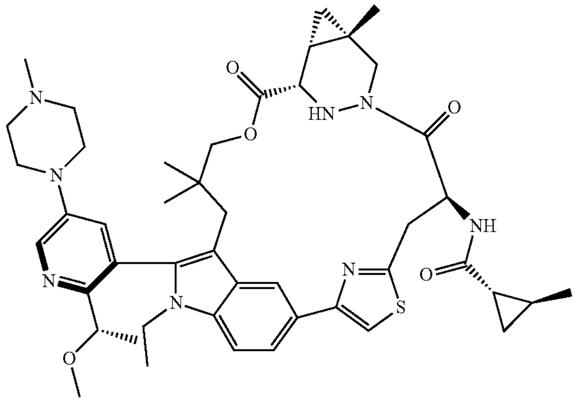
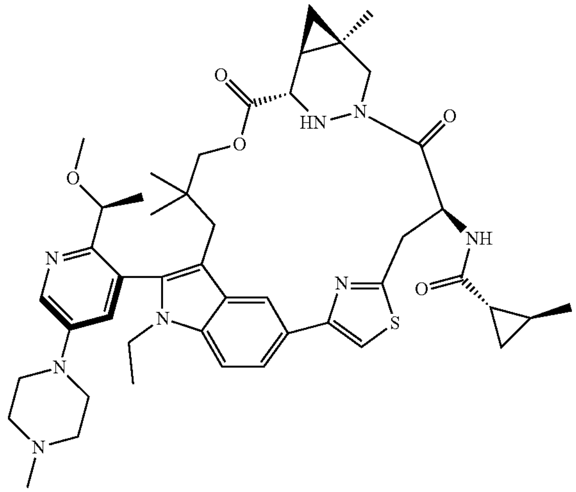
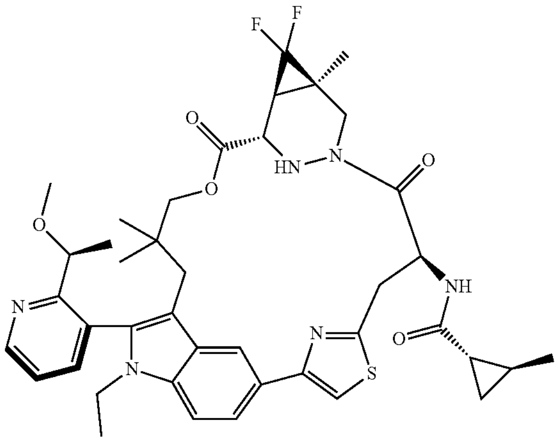
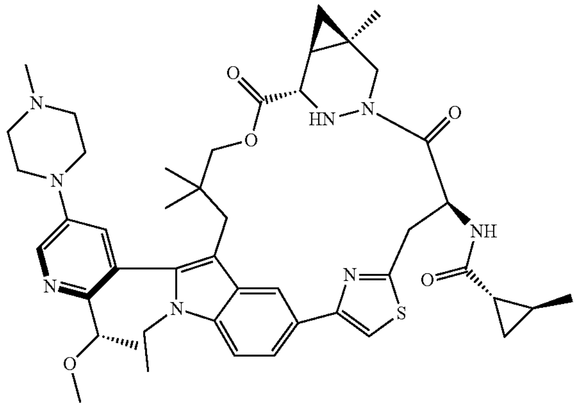
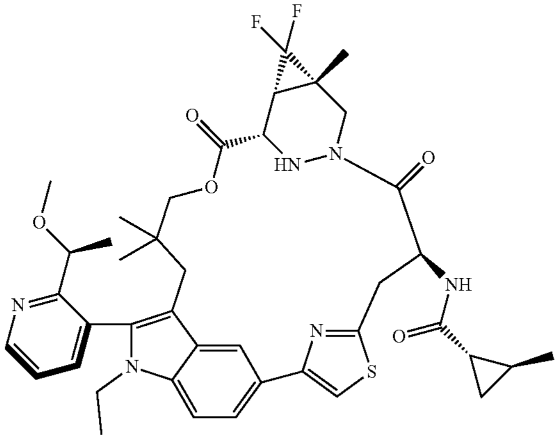

-continued
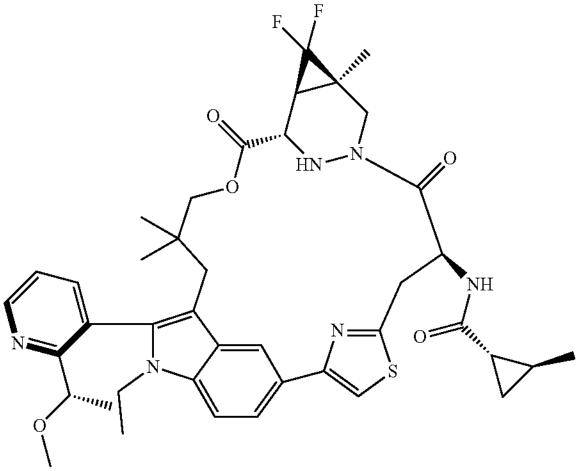
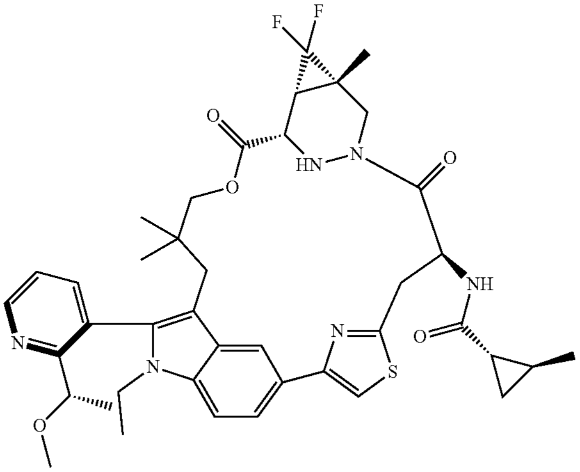
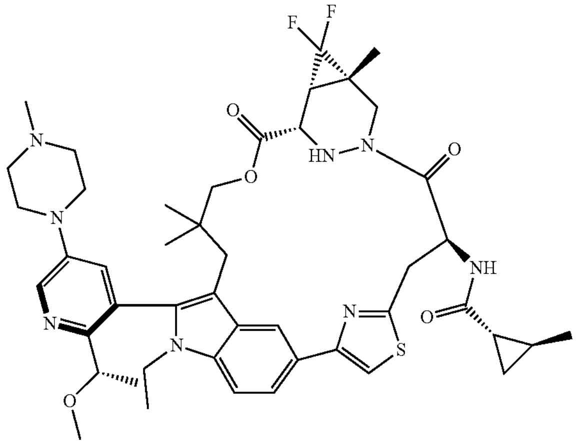
-continued
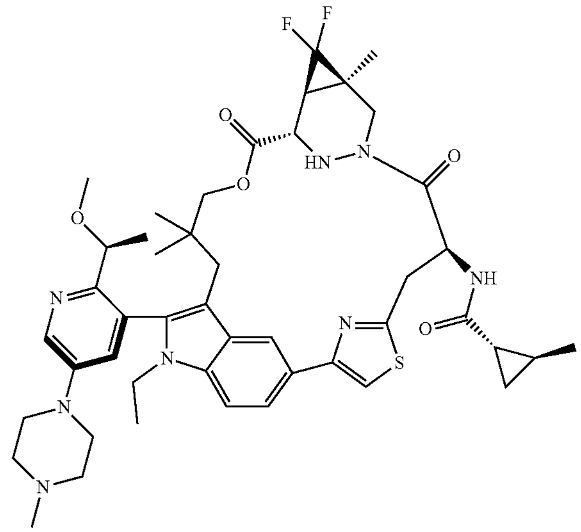
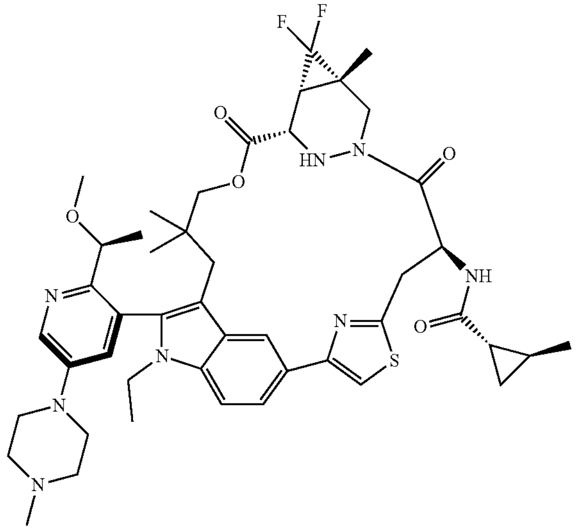
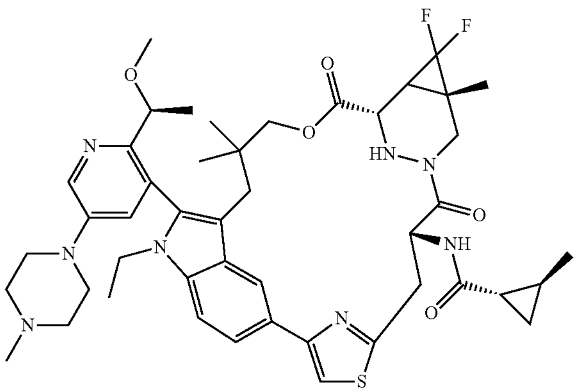

-continued
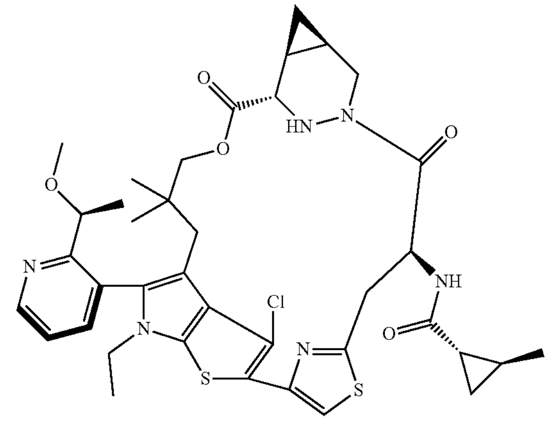
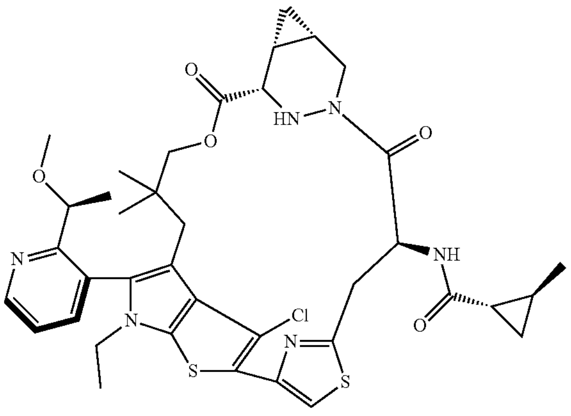
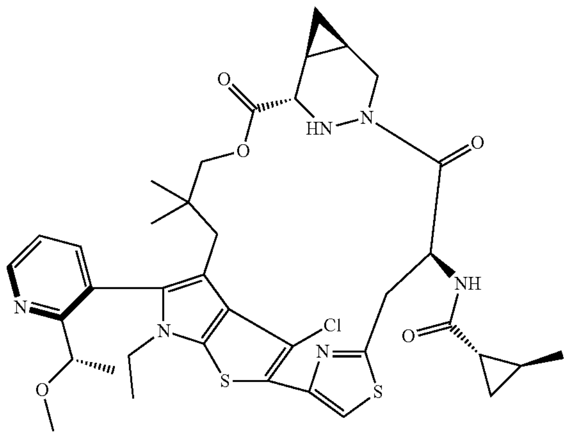
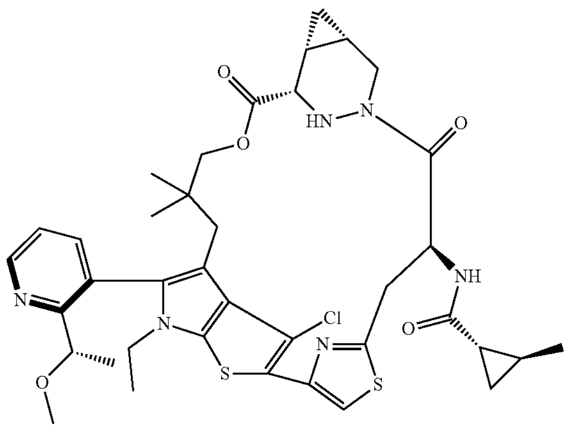
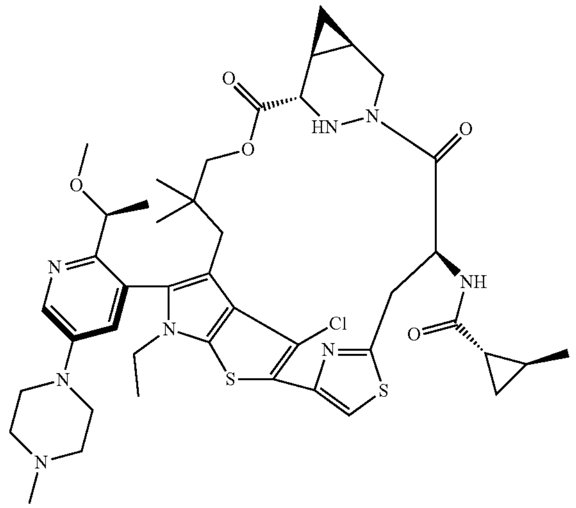
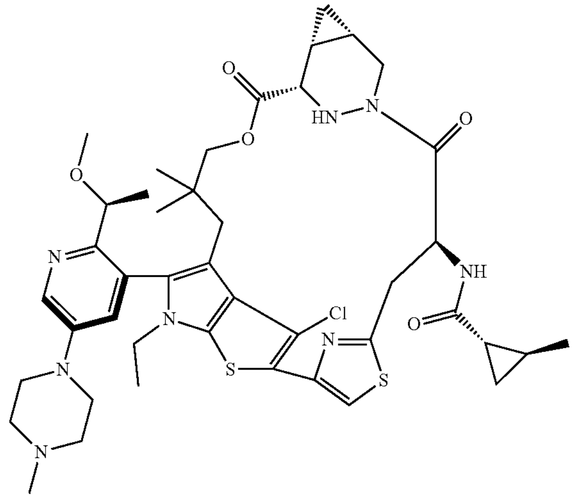
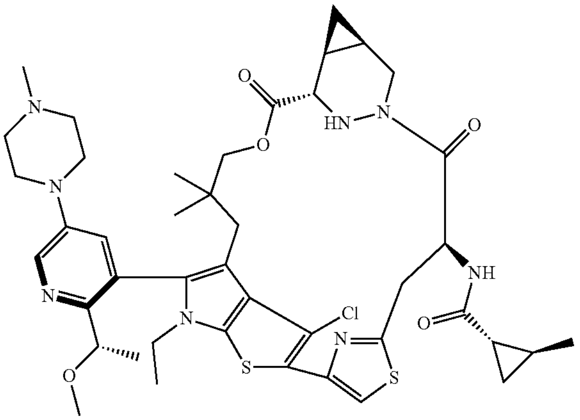
-continued -continued
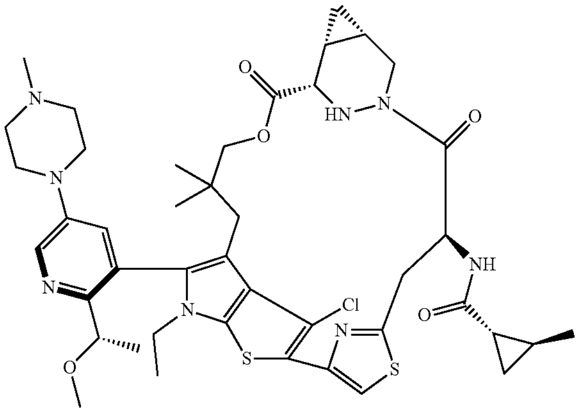
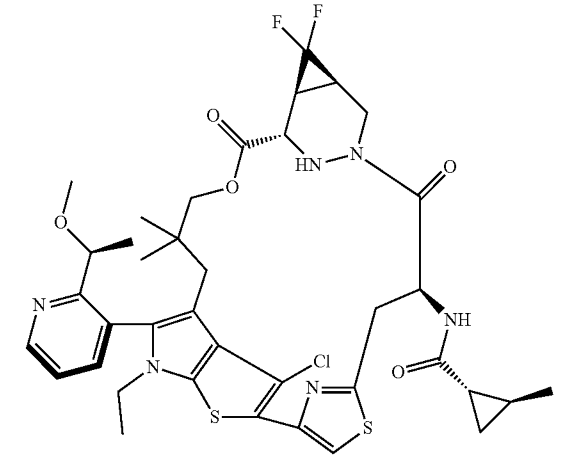
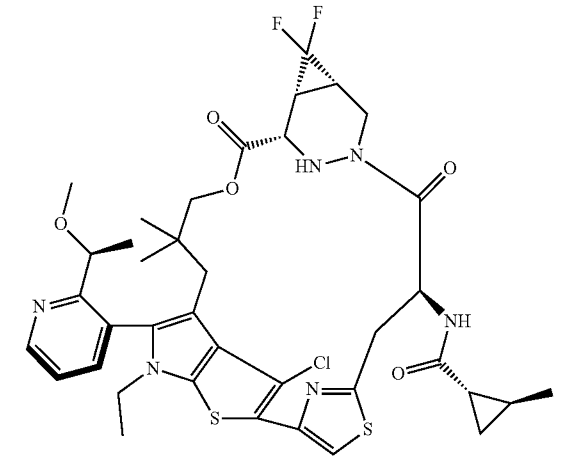
-continued
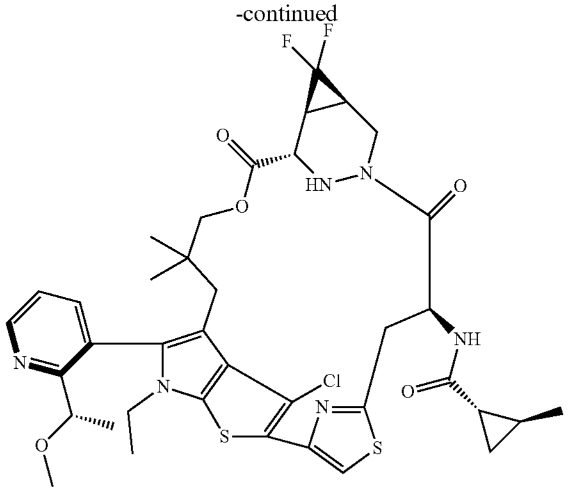
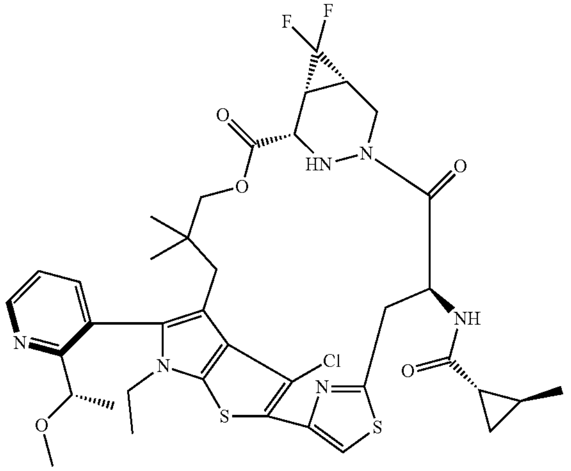
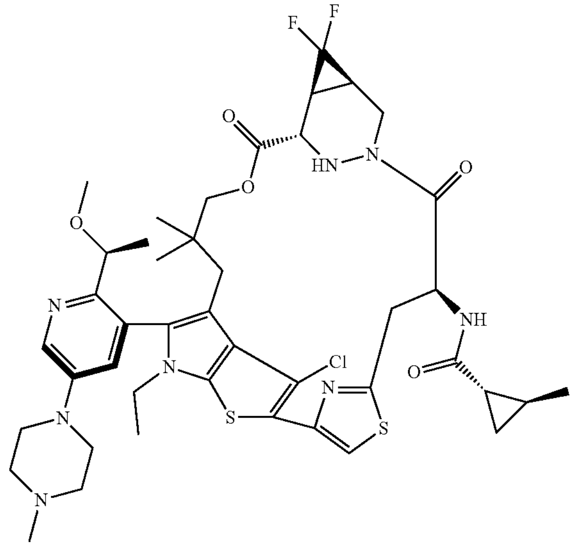

-continued
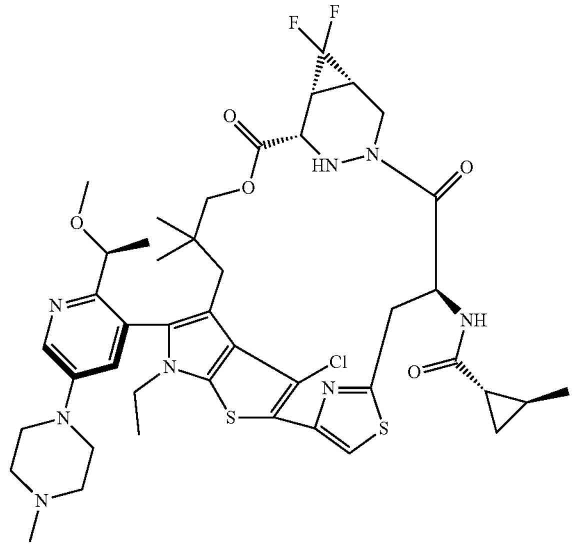
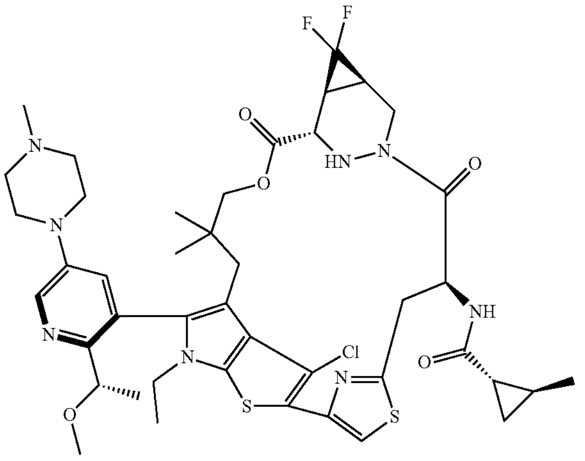
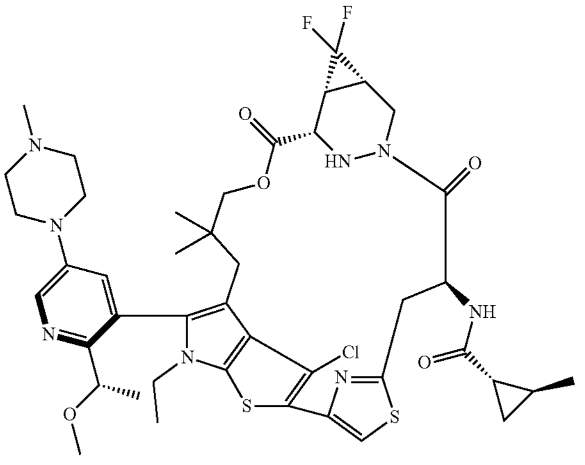
-continued
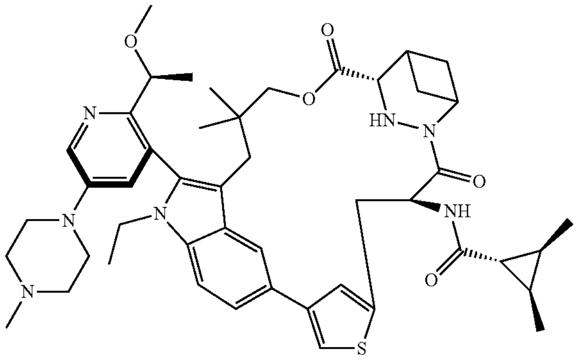
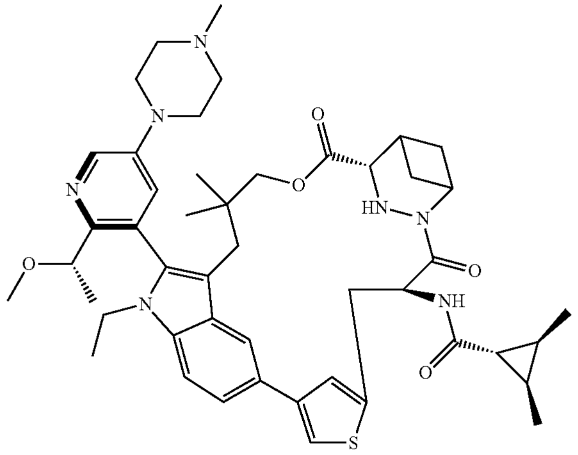
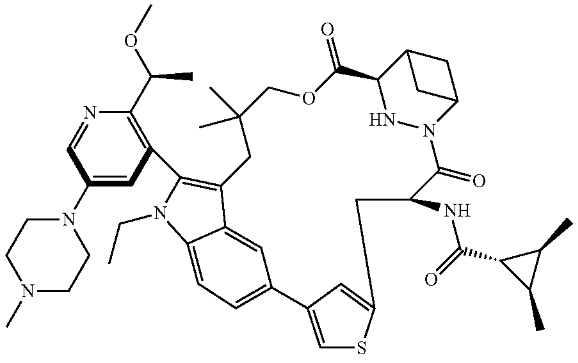
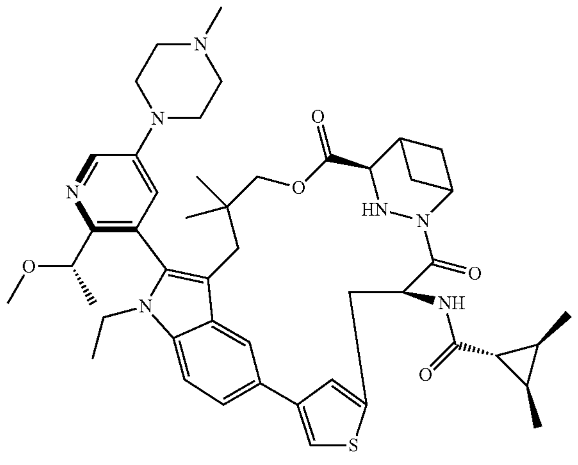

-continued
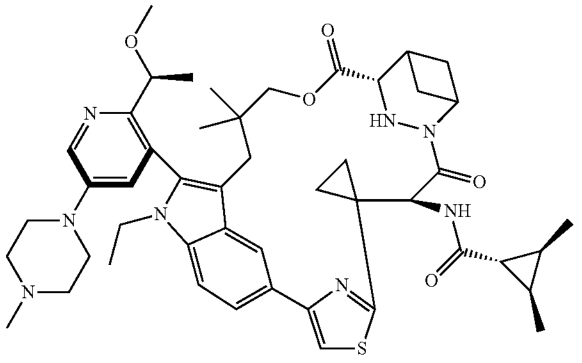
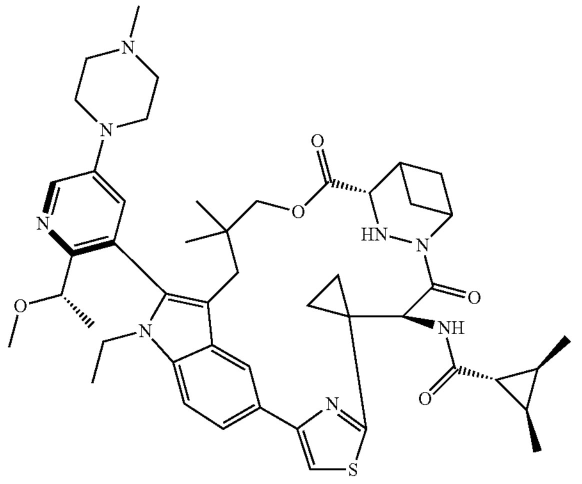
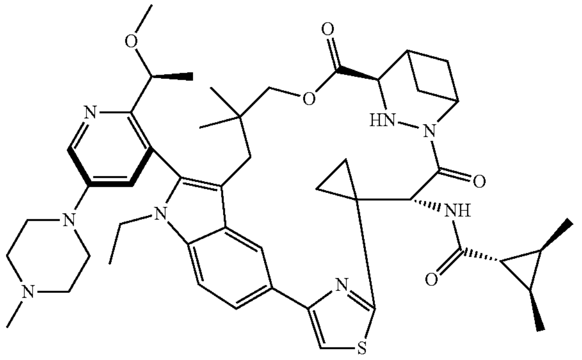
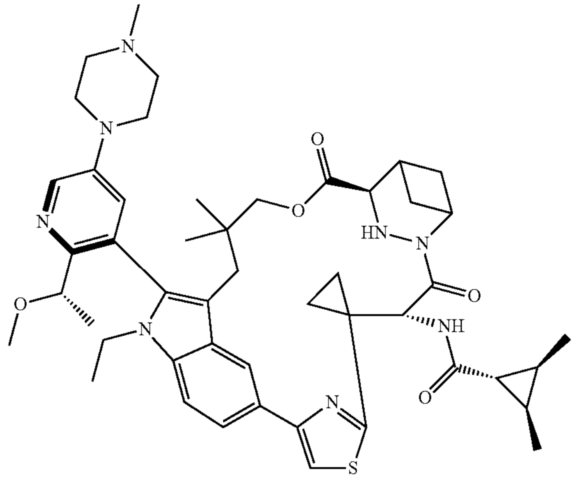
-continued
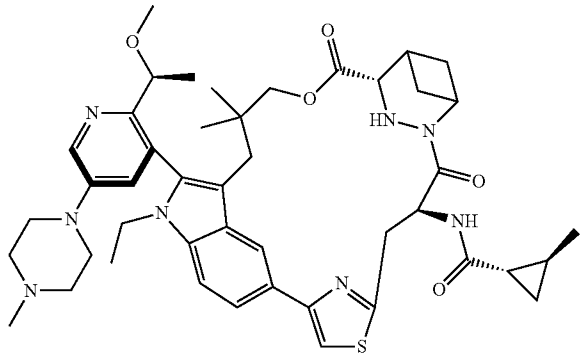
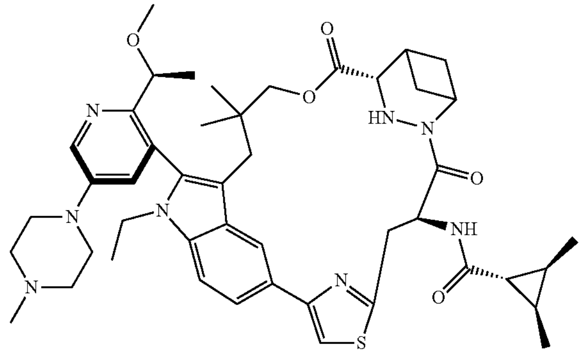
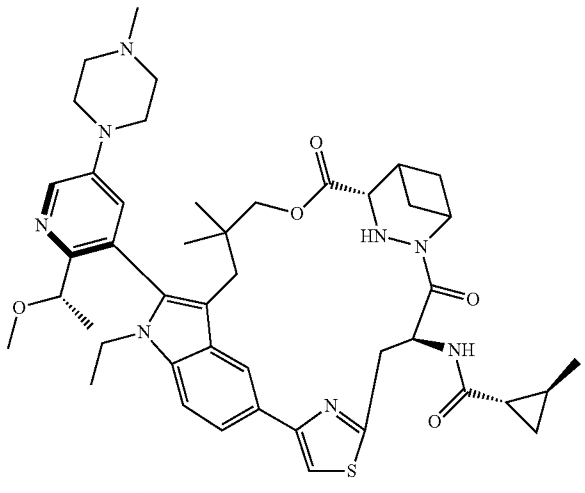
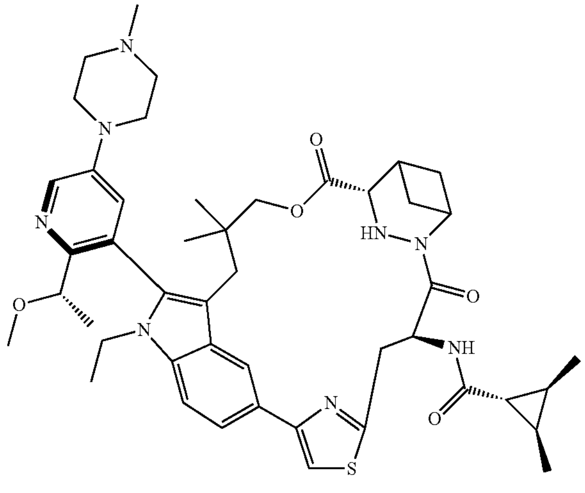

-continued
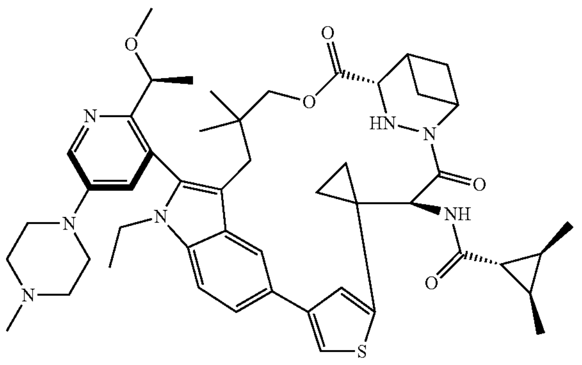
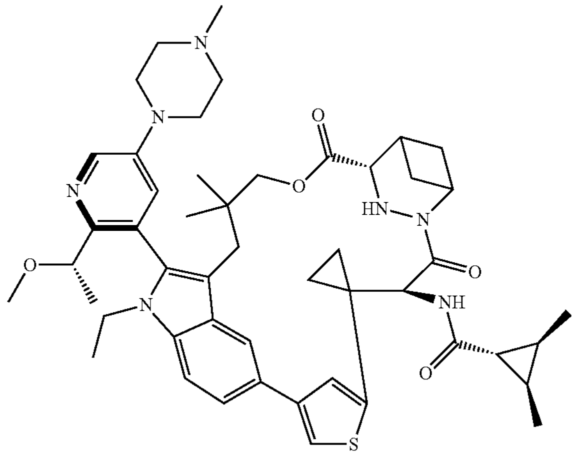
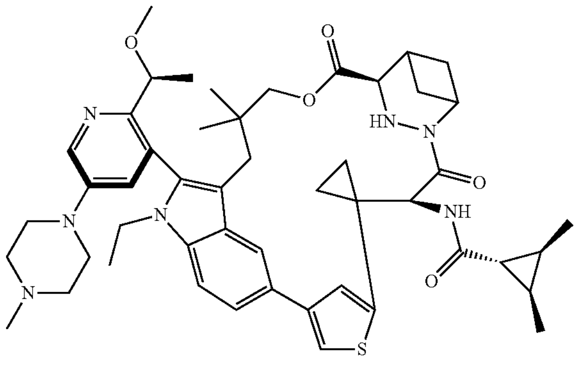
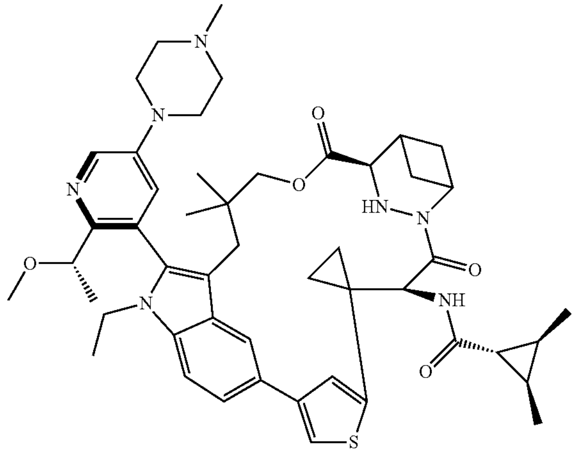
-continued
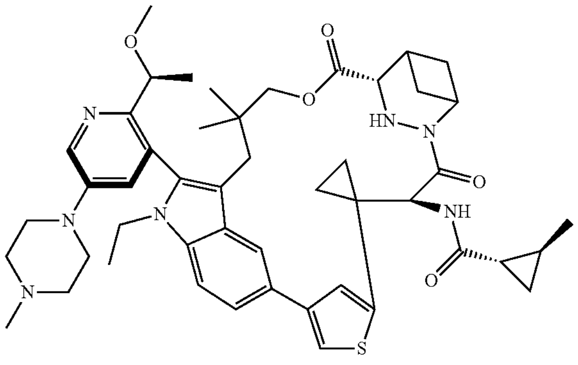
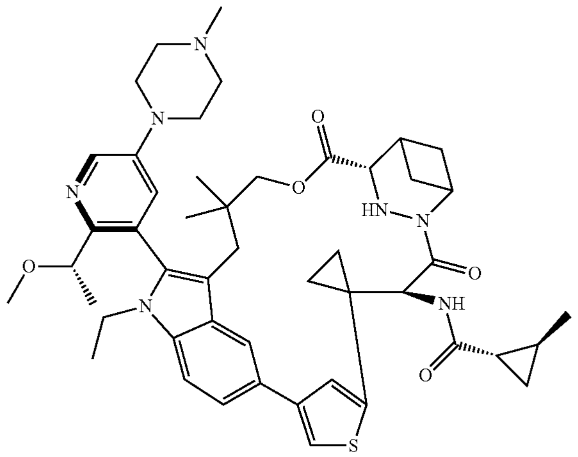
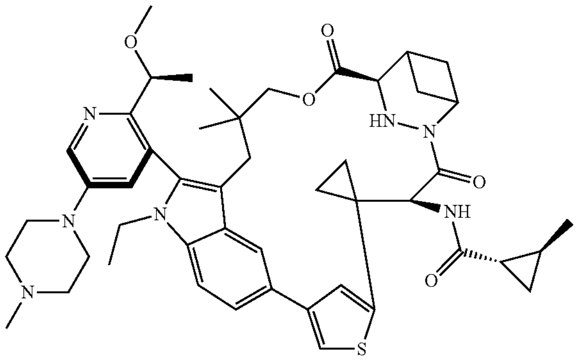
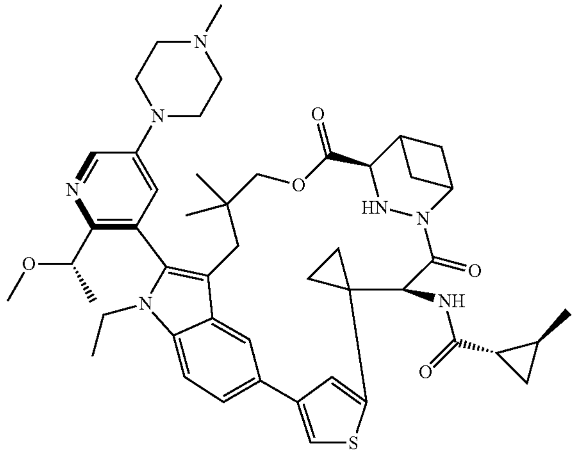

-continued
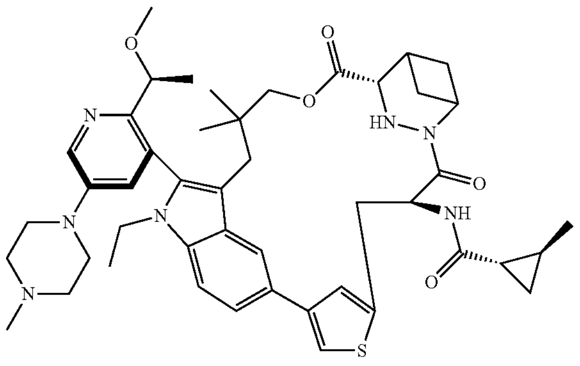
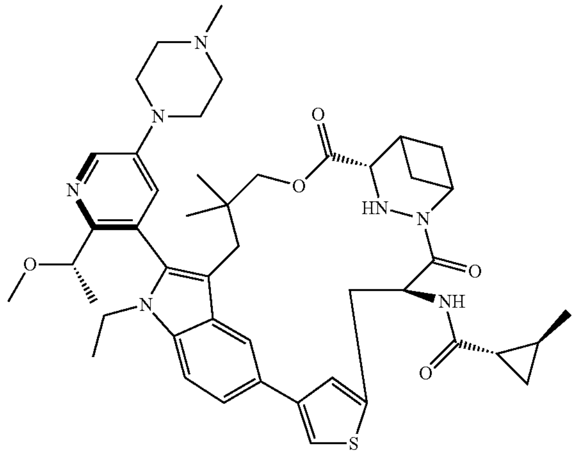
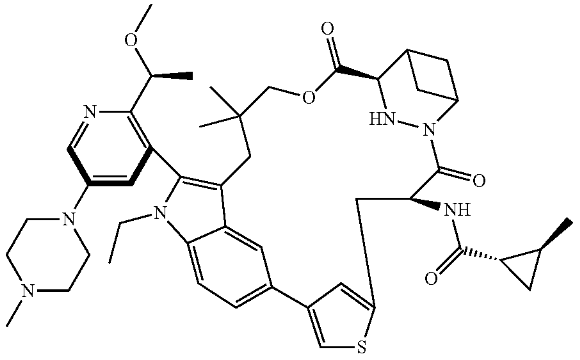
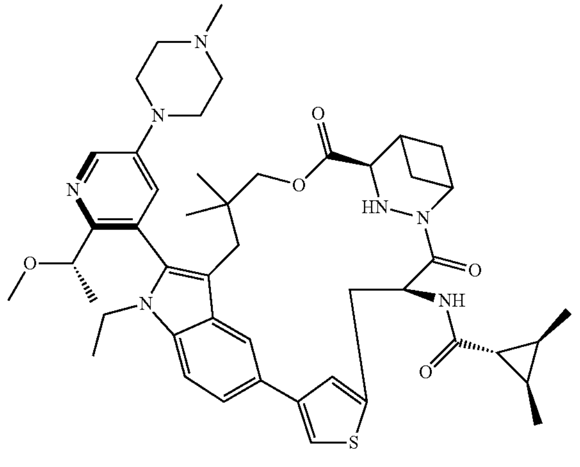
-continued
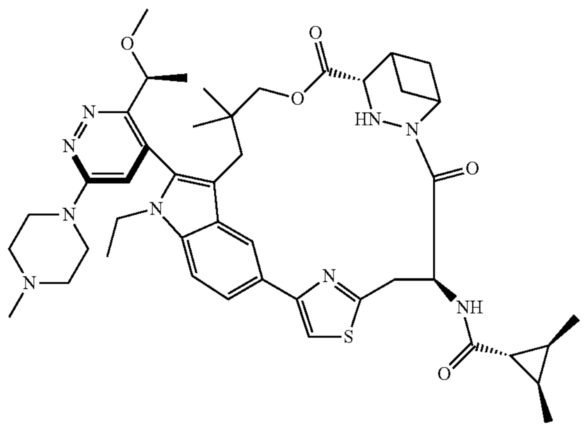
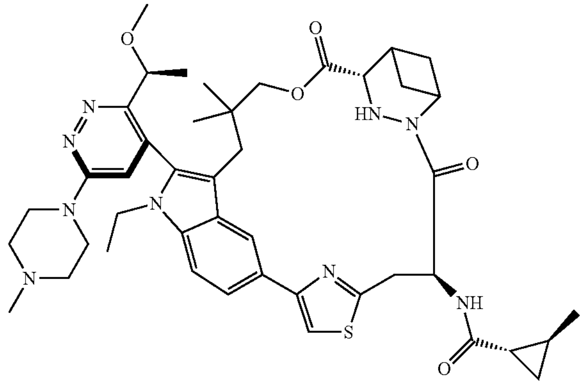
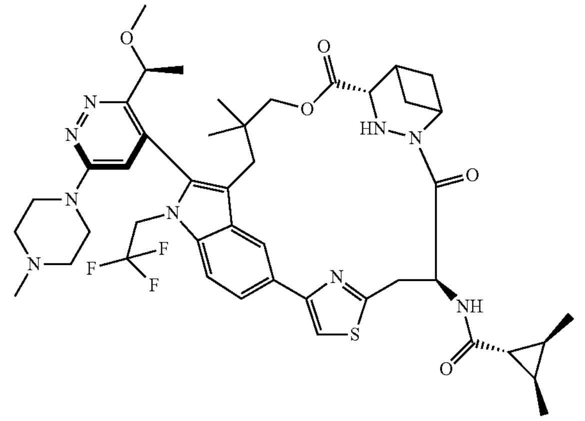
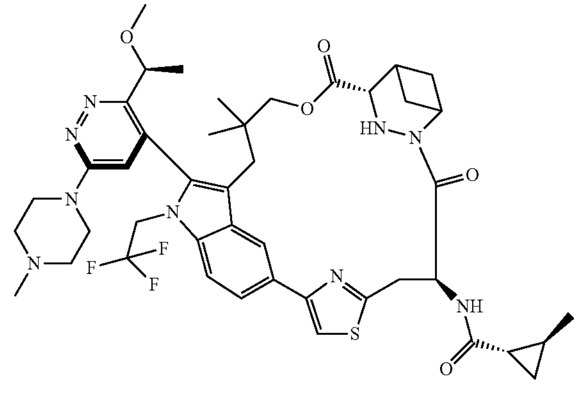

-continued
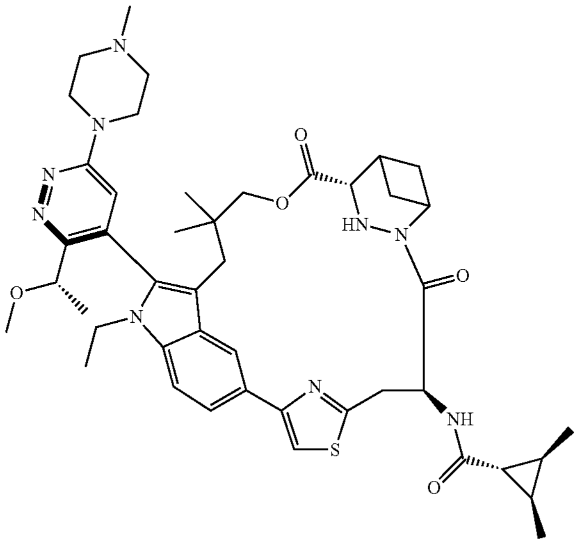
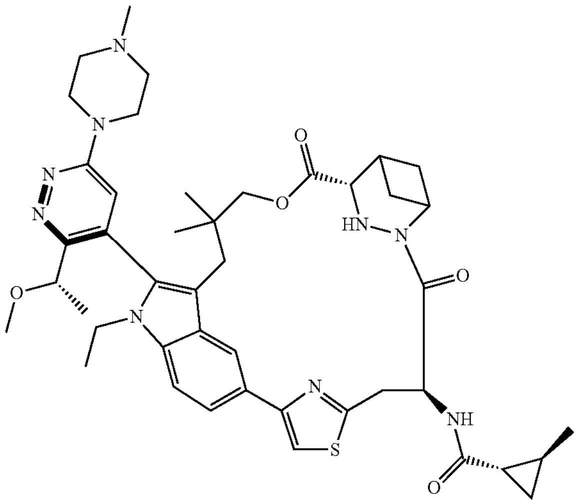
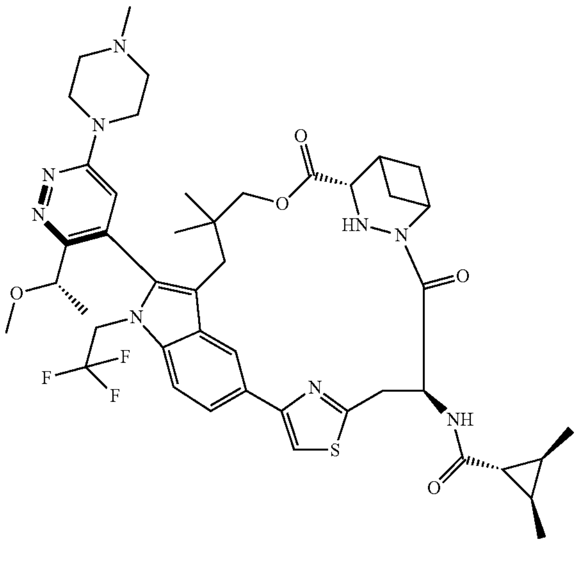
-continued
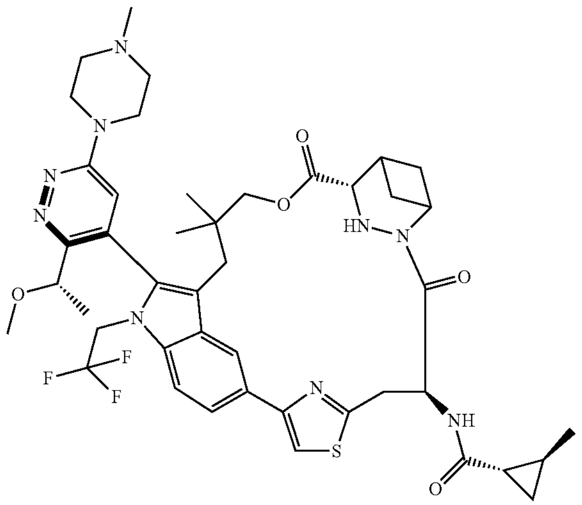
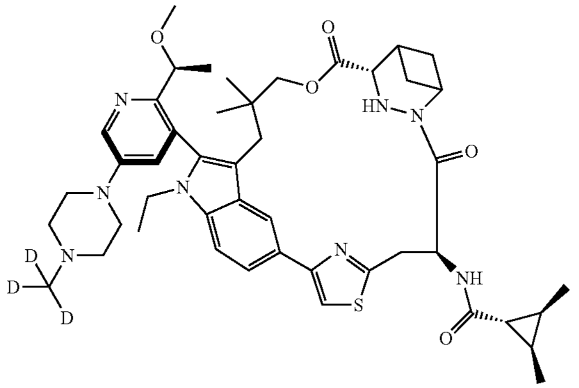
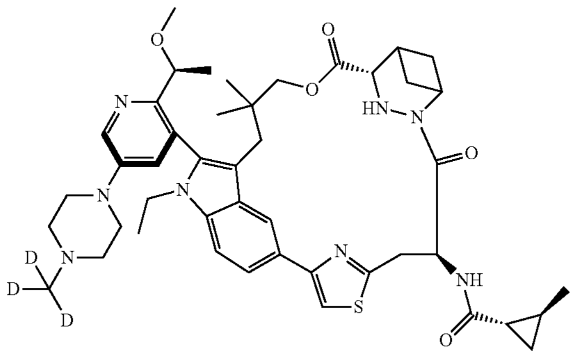
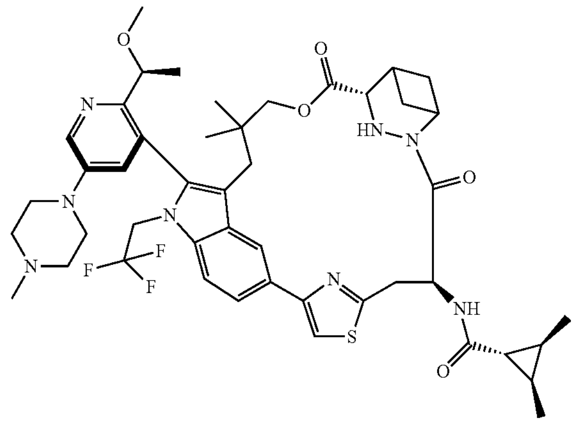

-continued
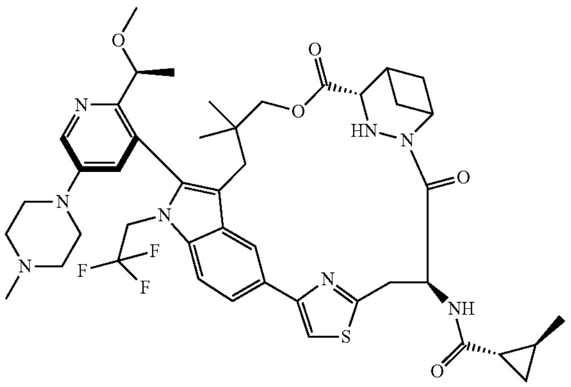
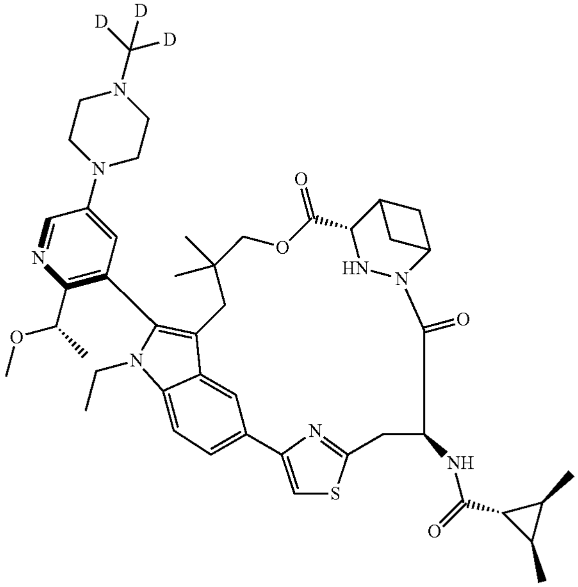
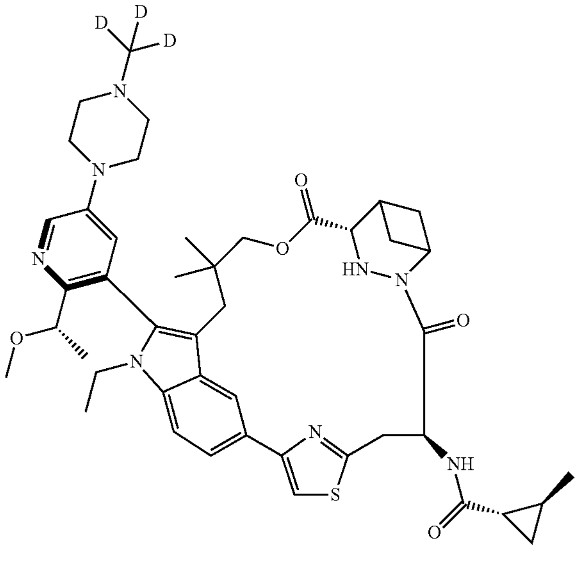
-continued
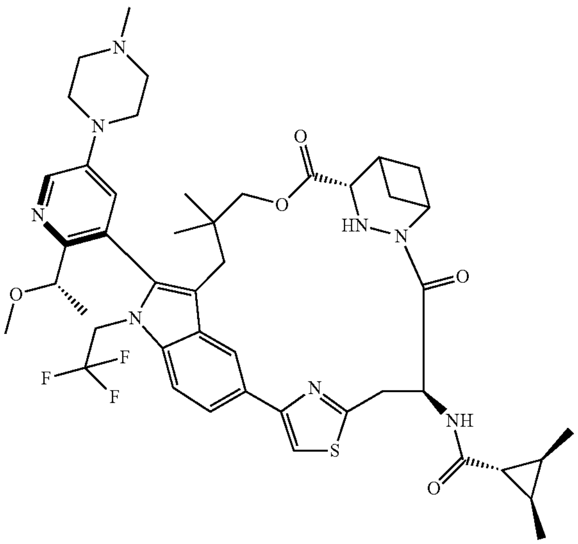
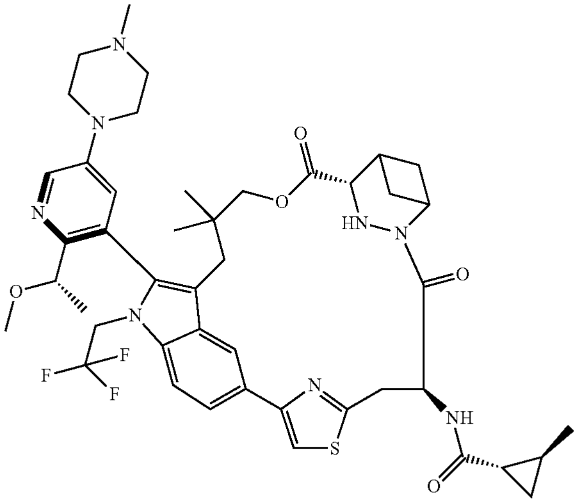
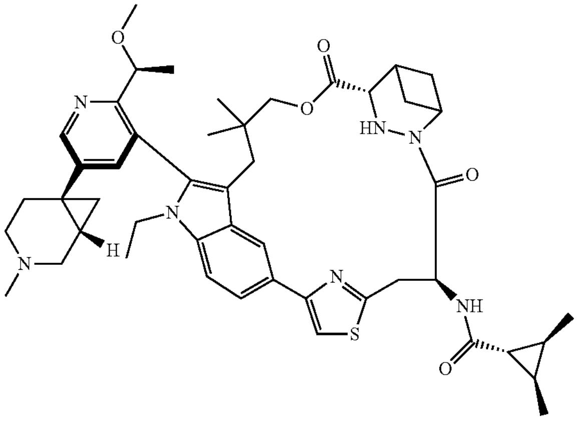

-continued
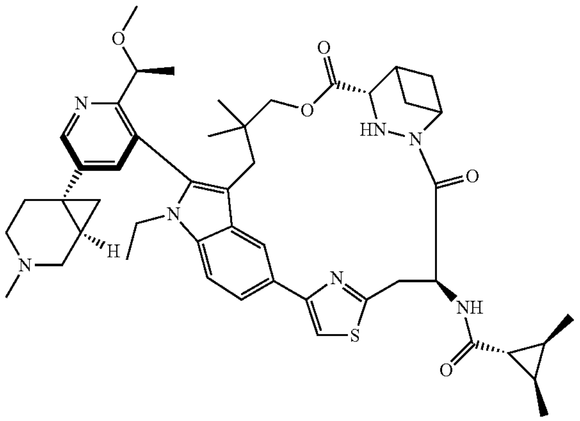
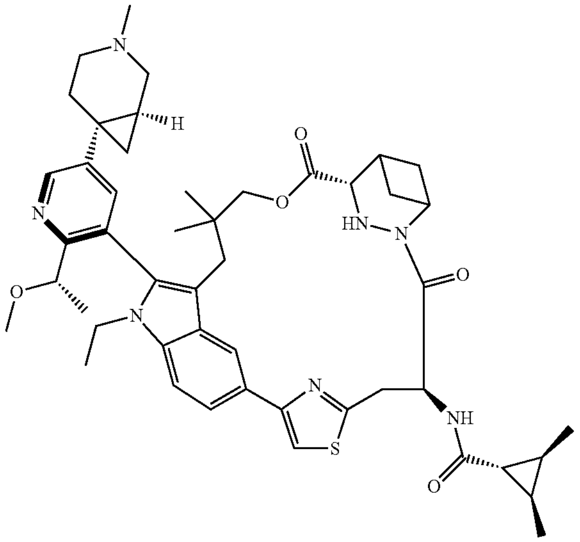
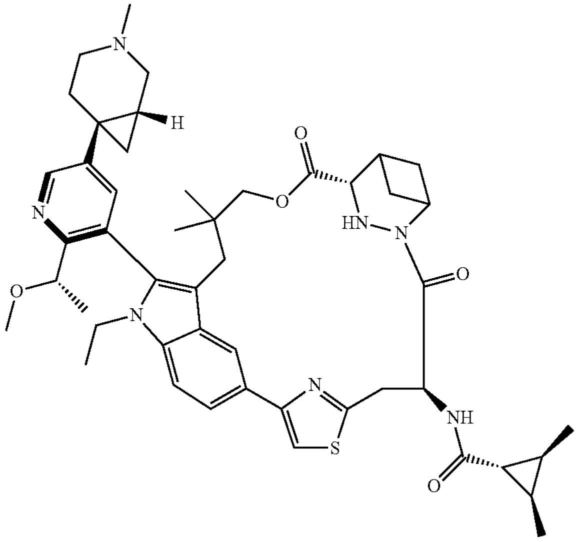
-continued
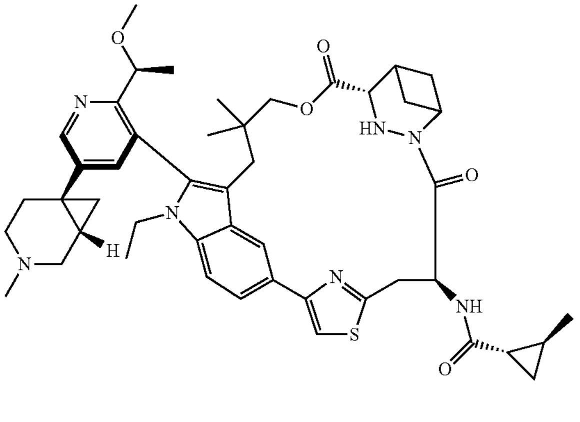
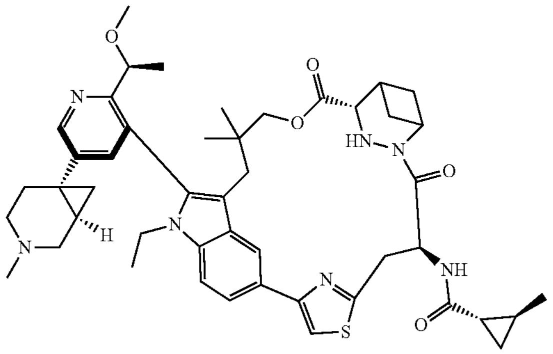
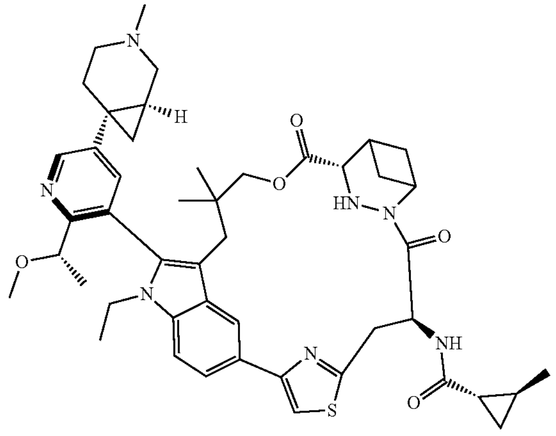
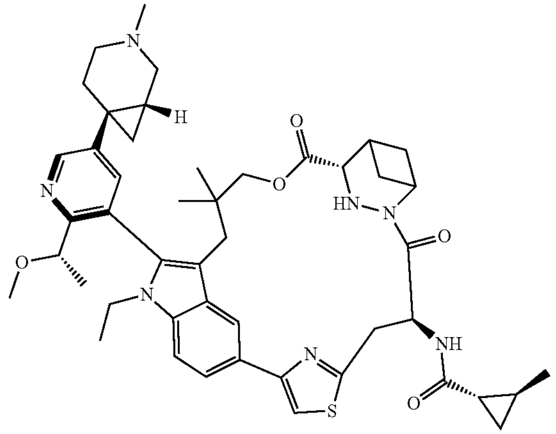

-continued
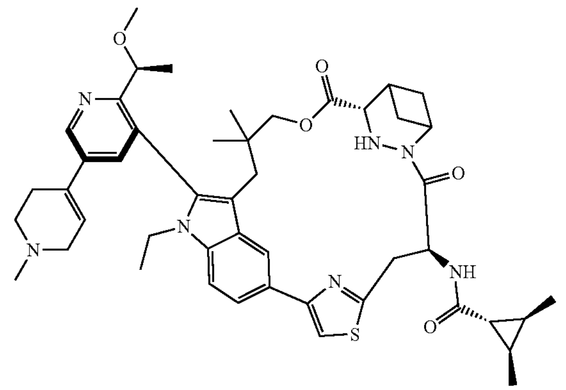
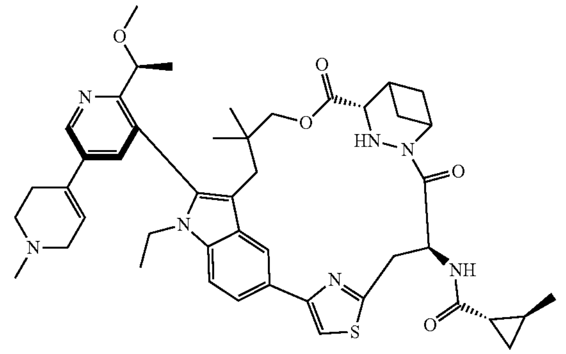
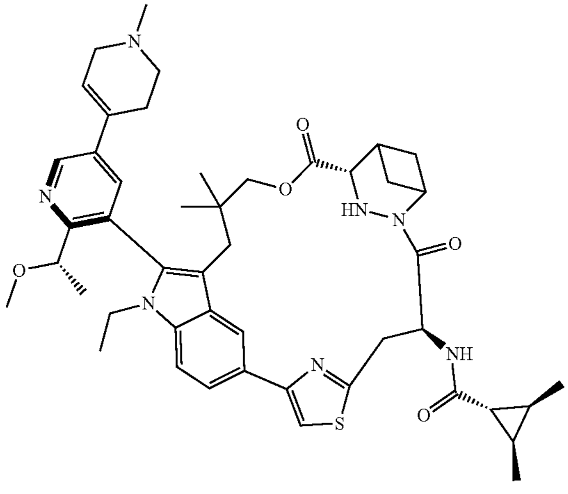
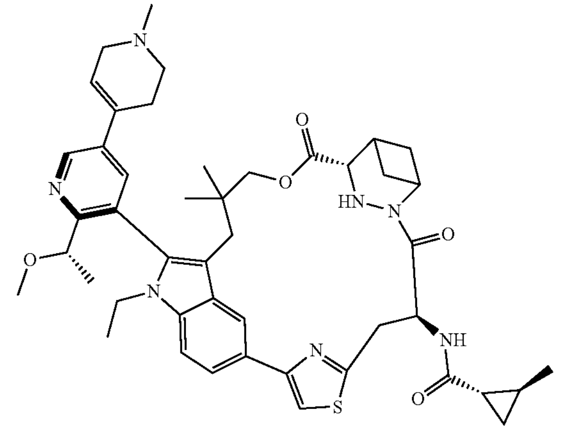
-continued
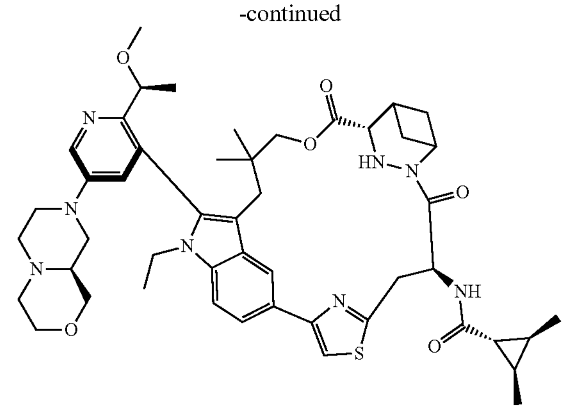
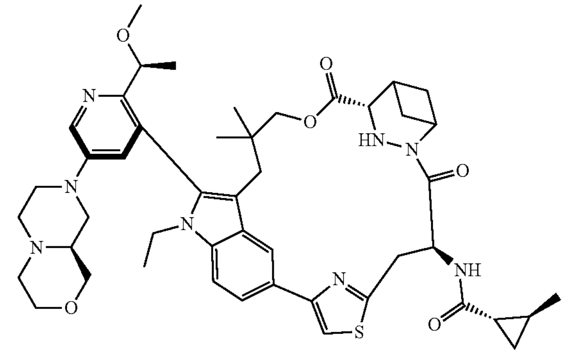
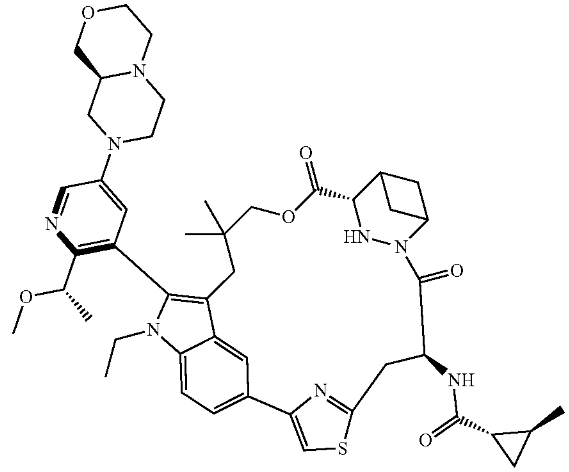
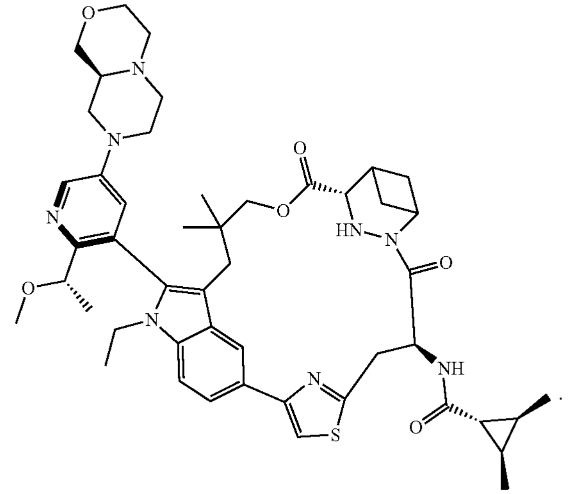

The present disclosure further provides the application of the above compounds, a stereoisomer thereof, or a pharmaceutically acceptable salt thereof, in the preparation of RAS inhibitor drugs.

The RAS inhibitor drugs of the present disclosure are used to treat RAS-mutant and RAS-dependent tumors, such as solid tumors; further, the solid tumors are pancreatic cancer, lung cancer or colorectal cancer.

The present disclosure further provides the following synthesis methods:

Method 1—Intermediate

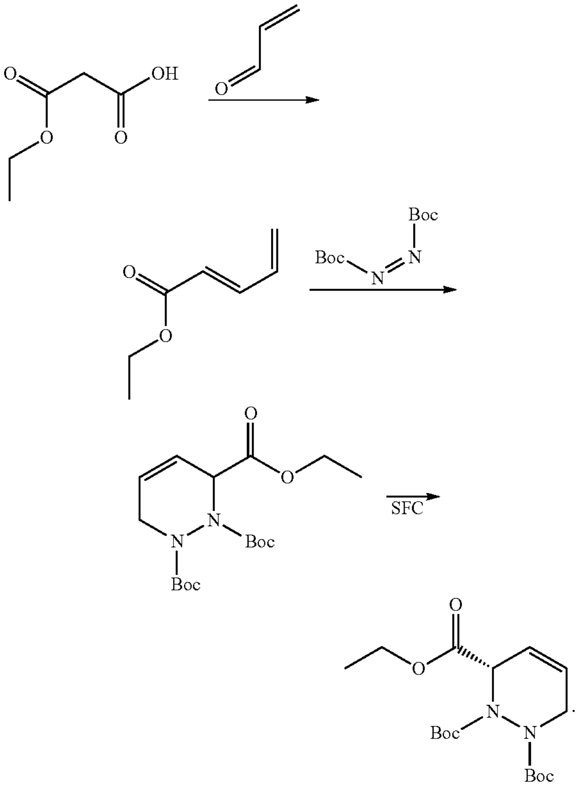

Method 2—Intermediate

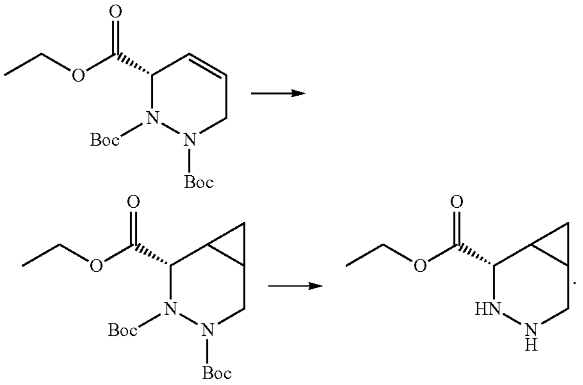

Method 3—Intermediate

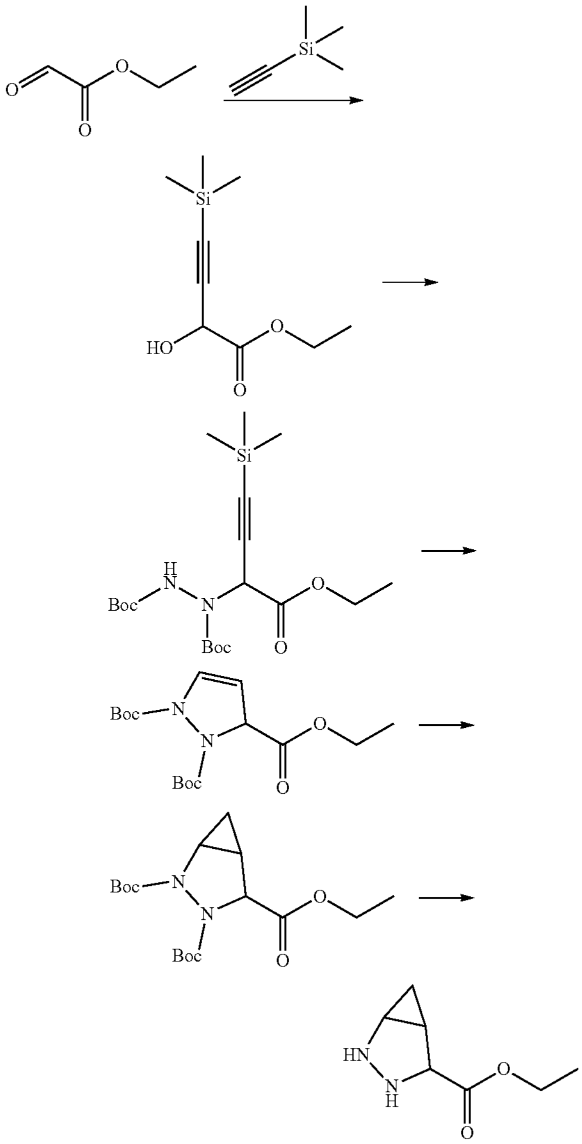

Method 4—Intermediate

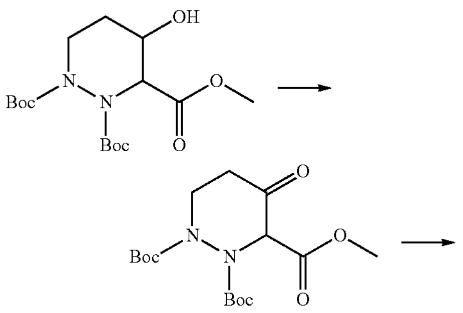

-continued
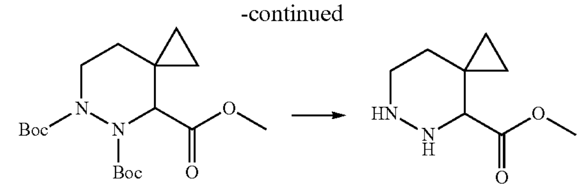
Method 5—Intermediate
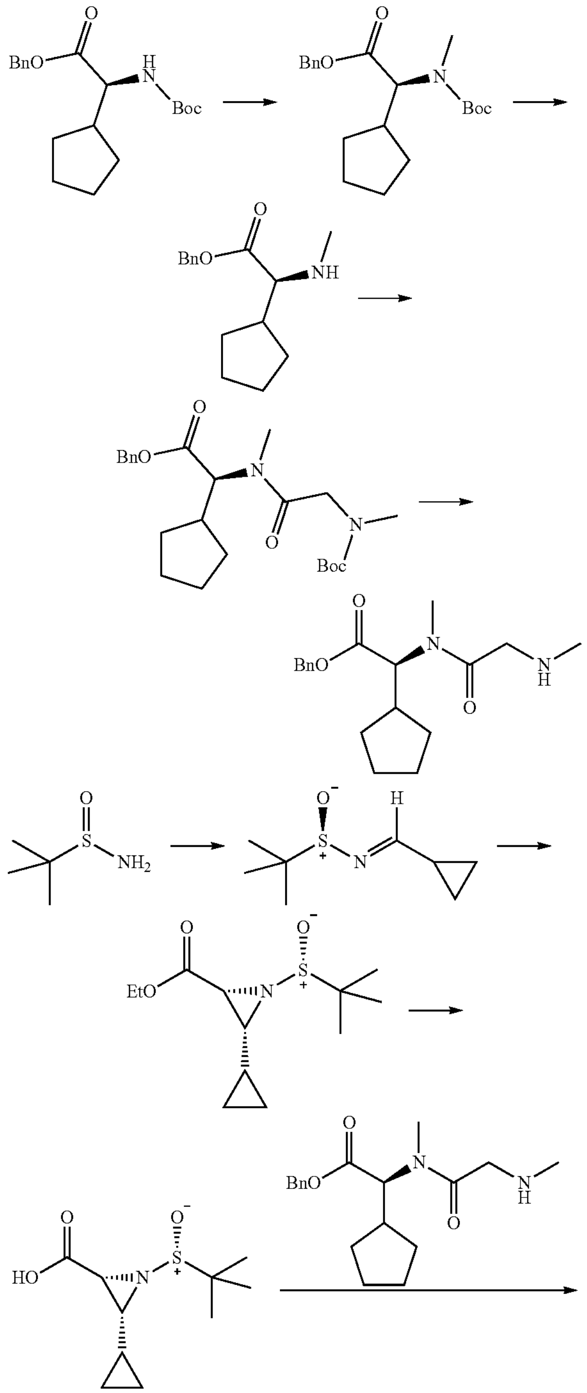
-continued
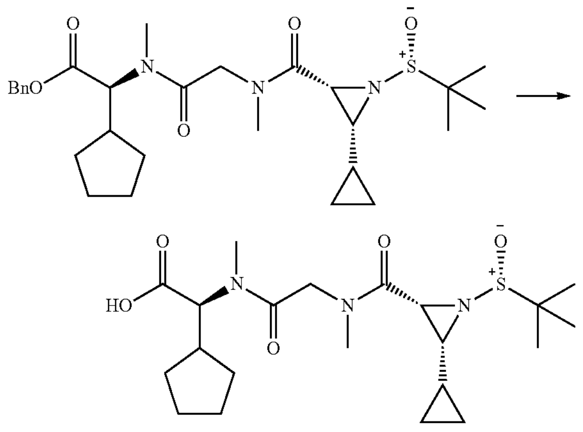
Method 6—Intermediate
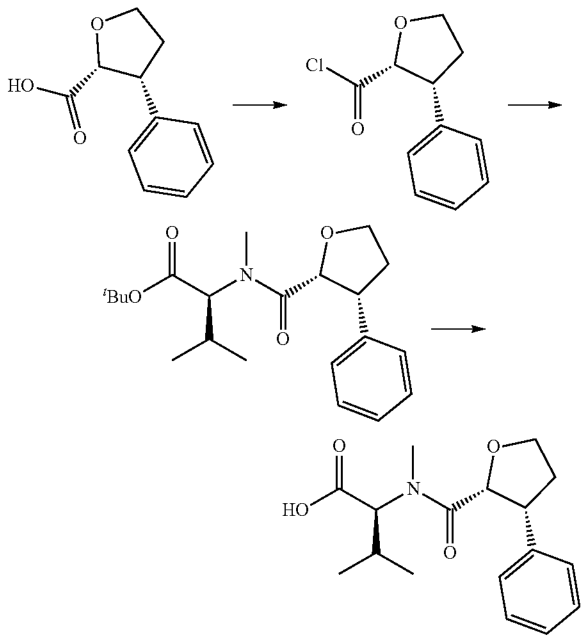
Method 7—Intermediate
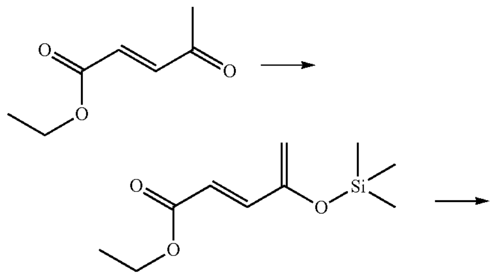

-continued
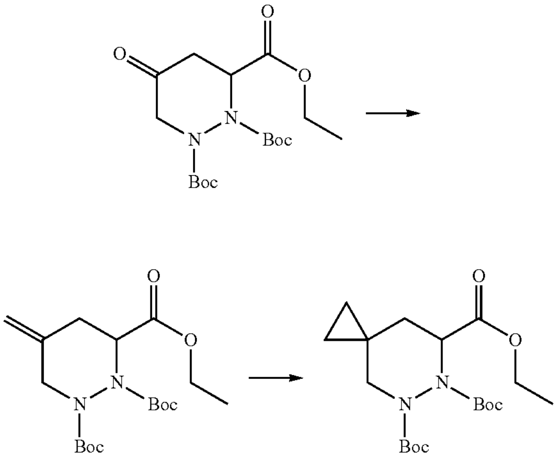
Method 8—Intermediate
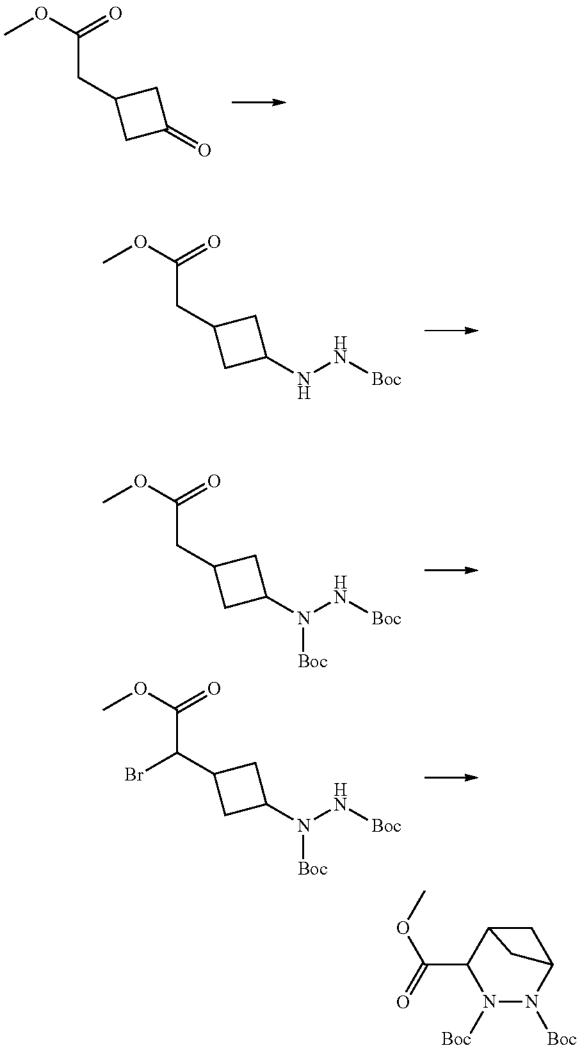
Method 9—Intermediate
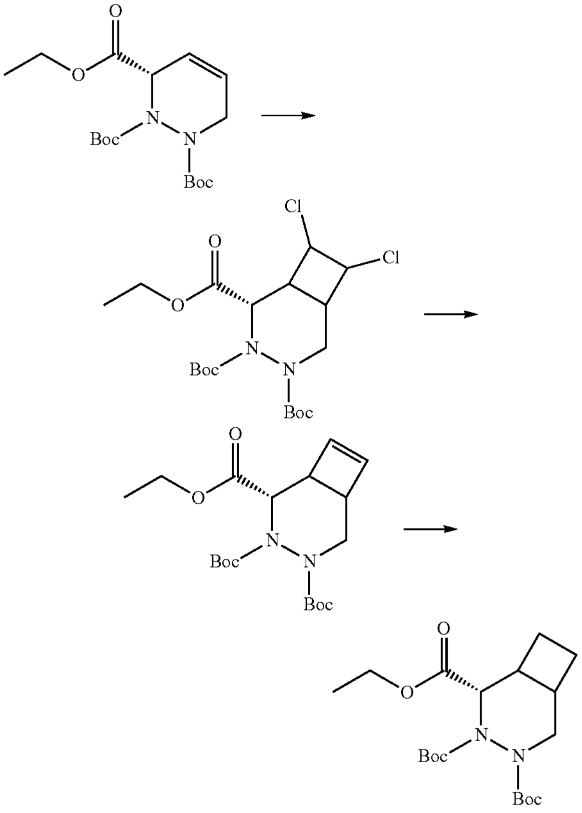
Method 10—Intermediate
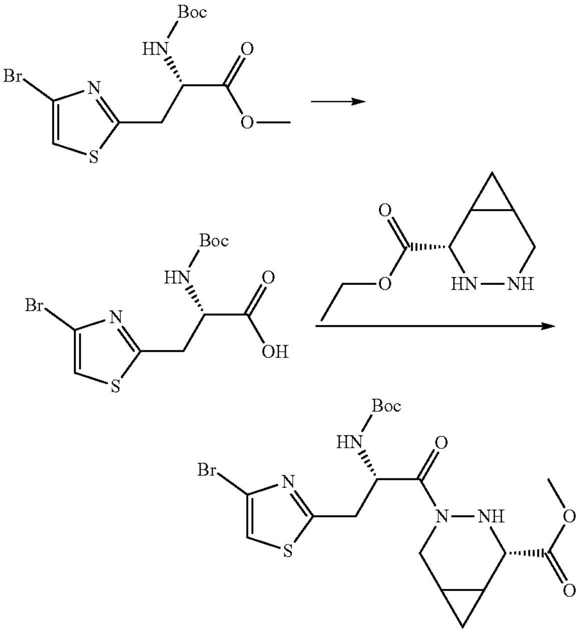

Method 11
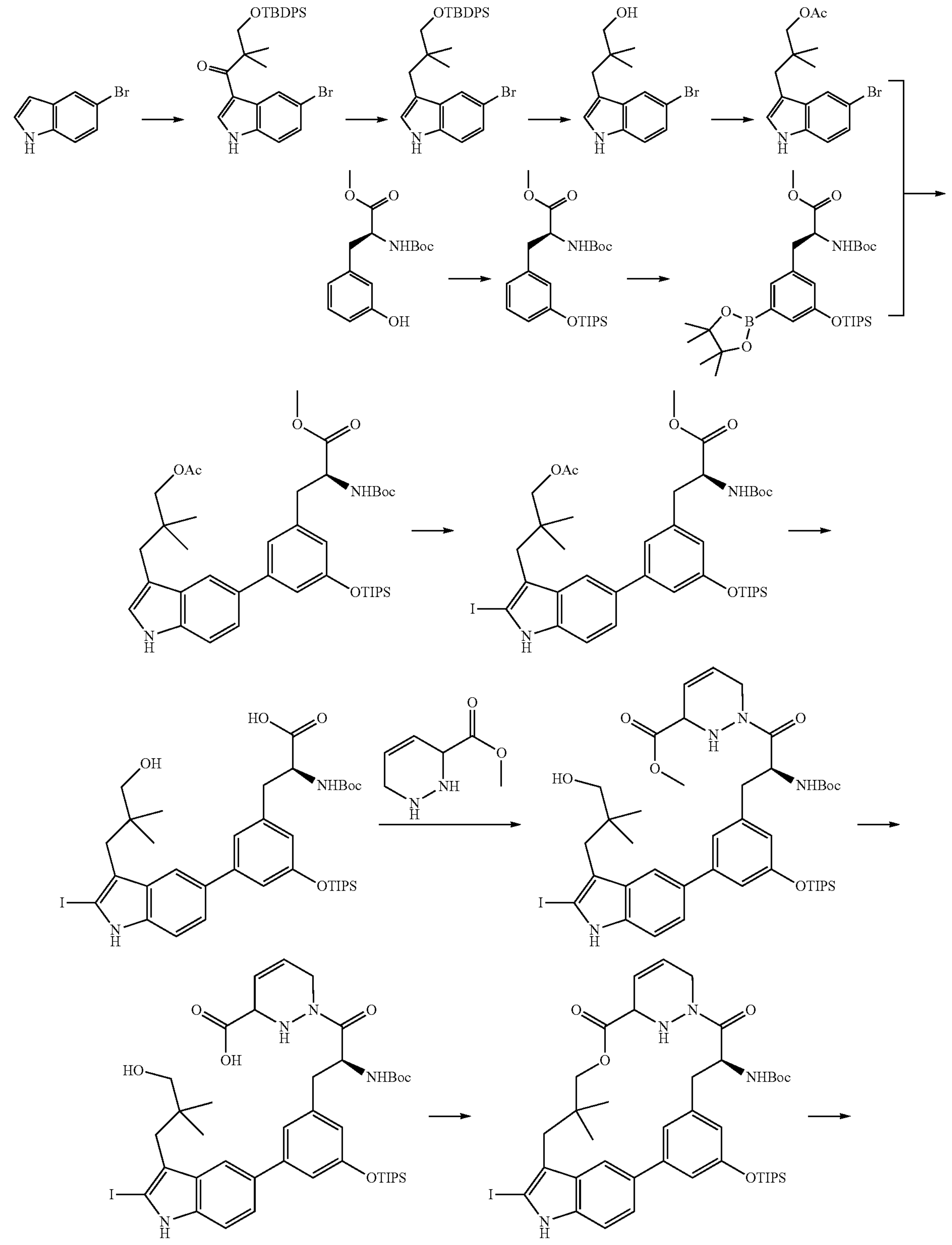

-continued
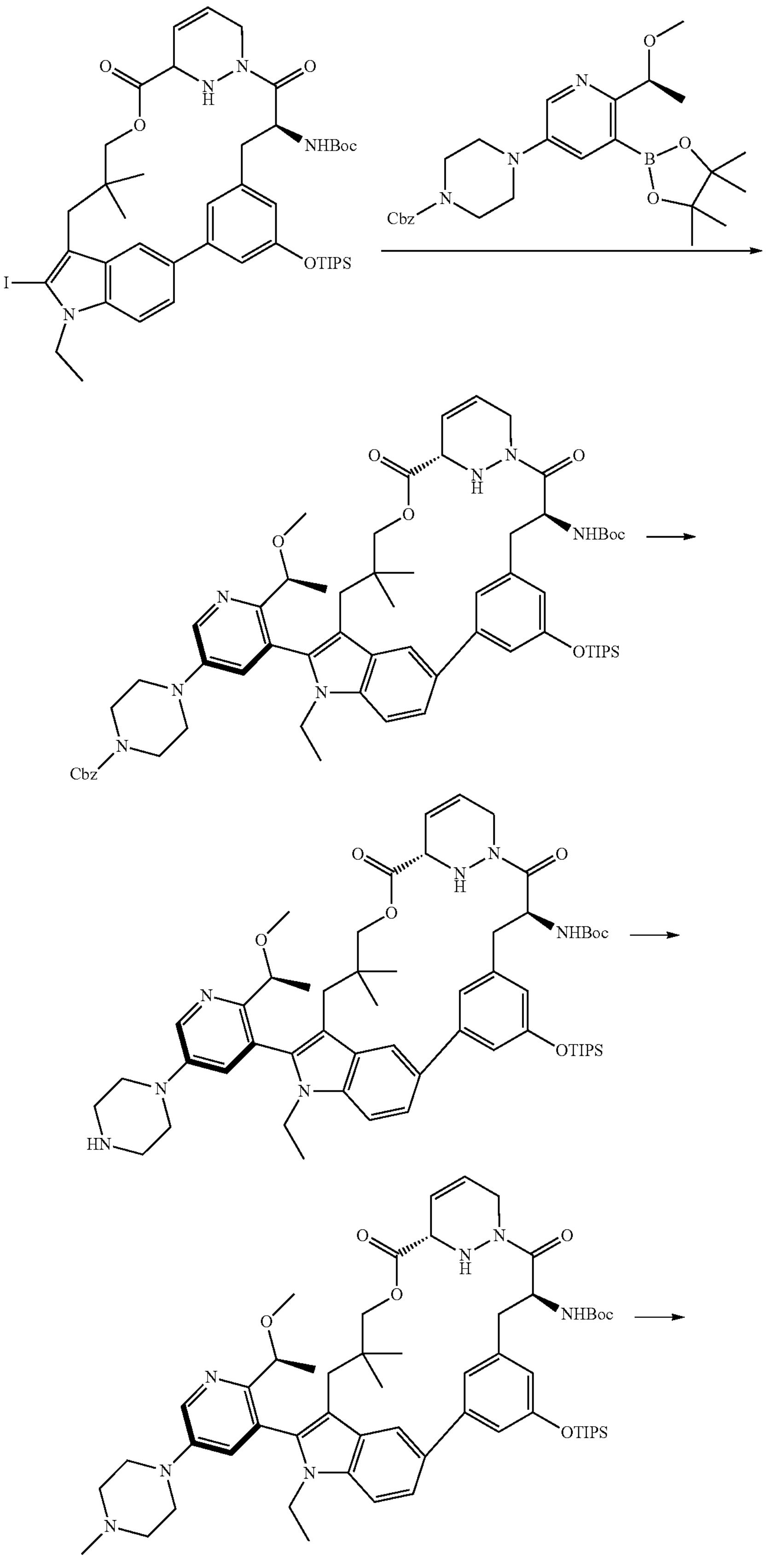

-continued
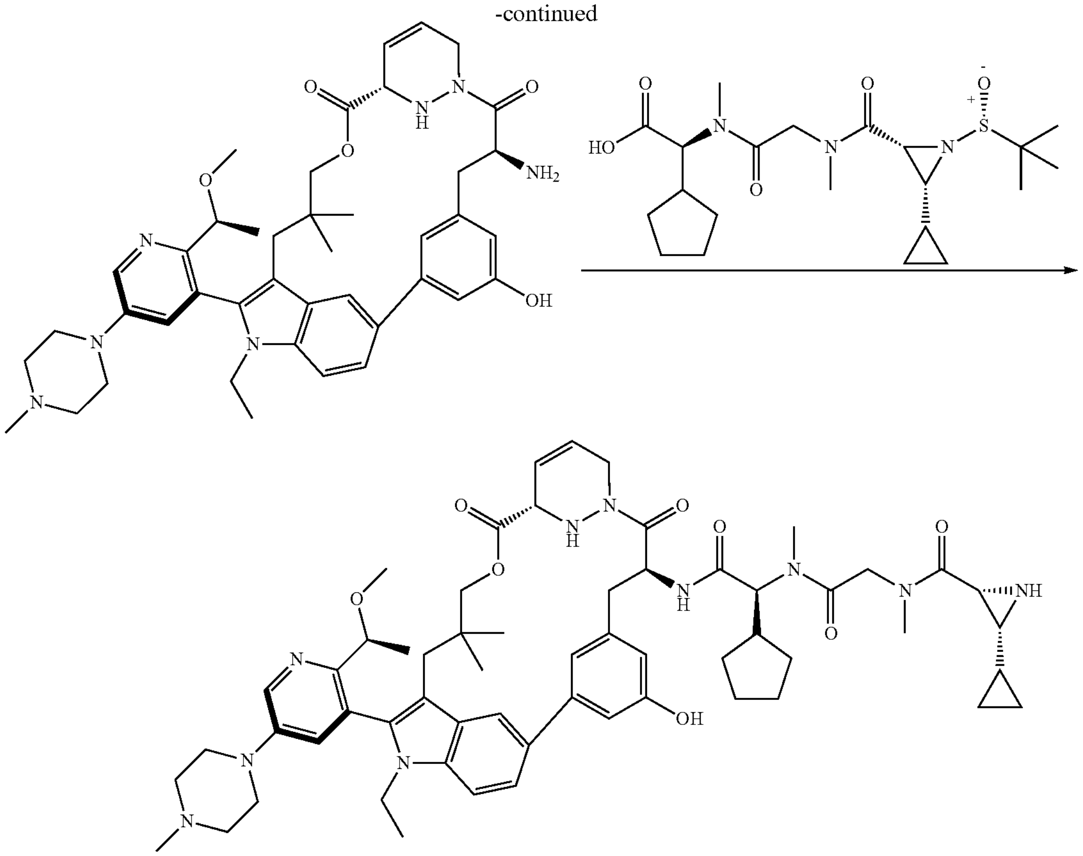
Method 12
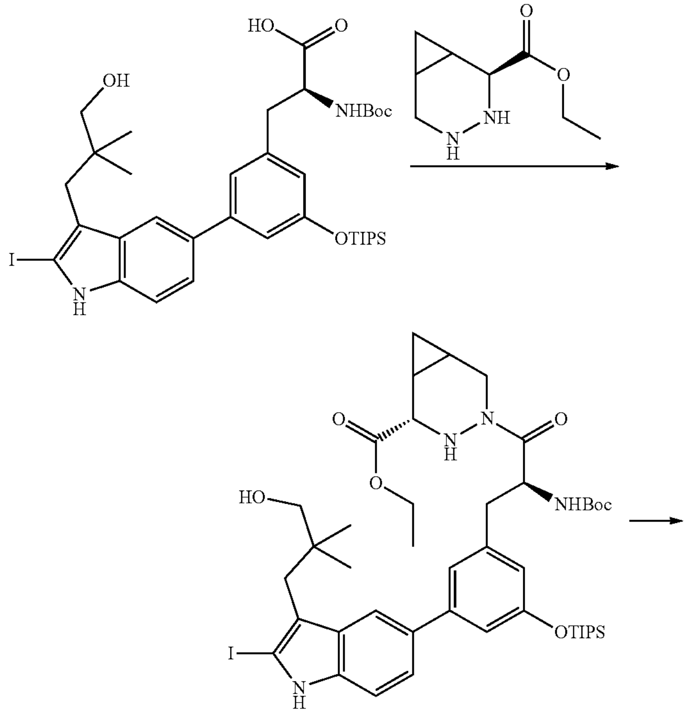

-continued
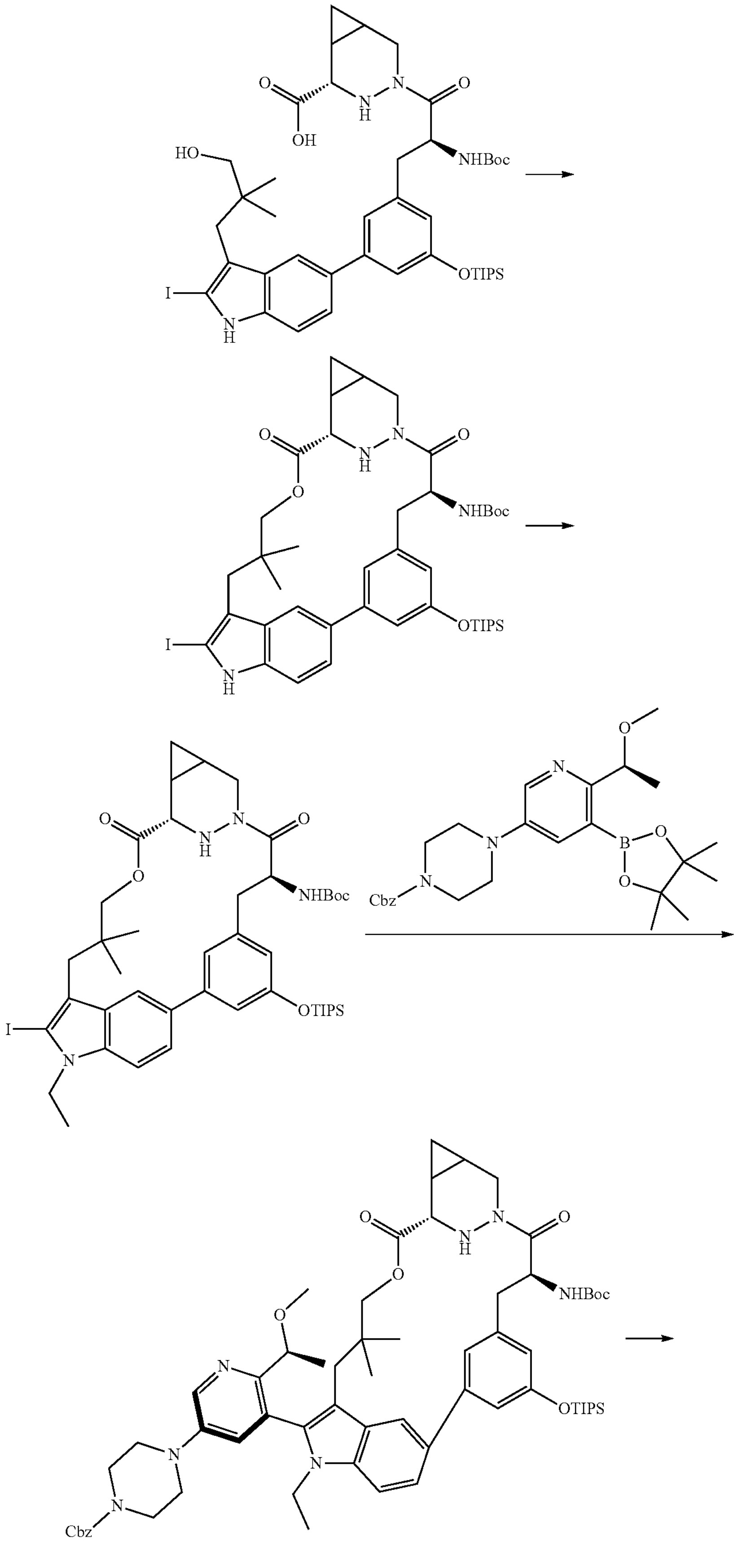

-continued
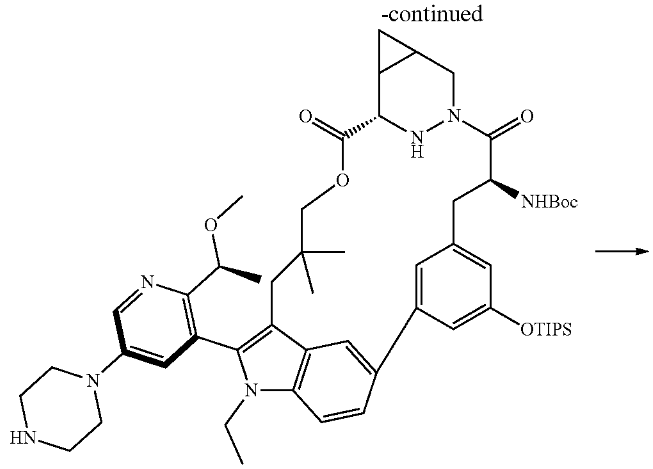
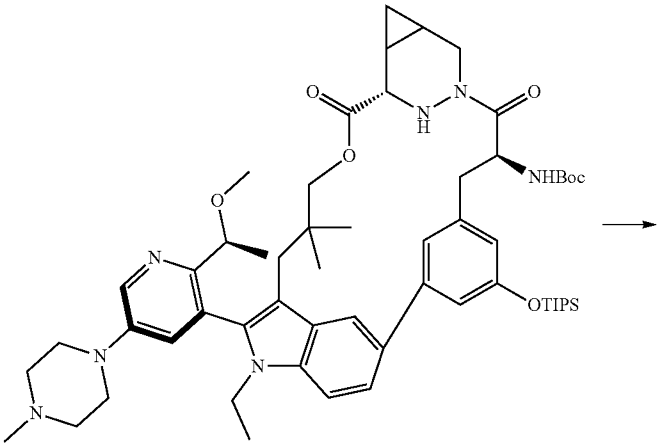
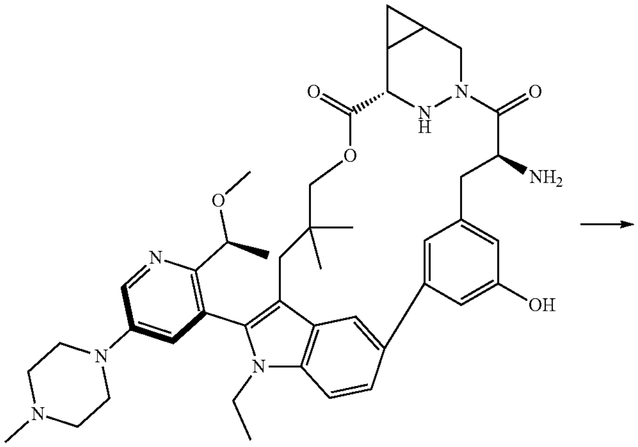

-continued
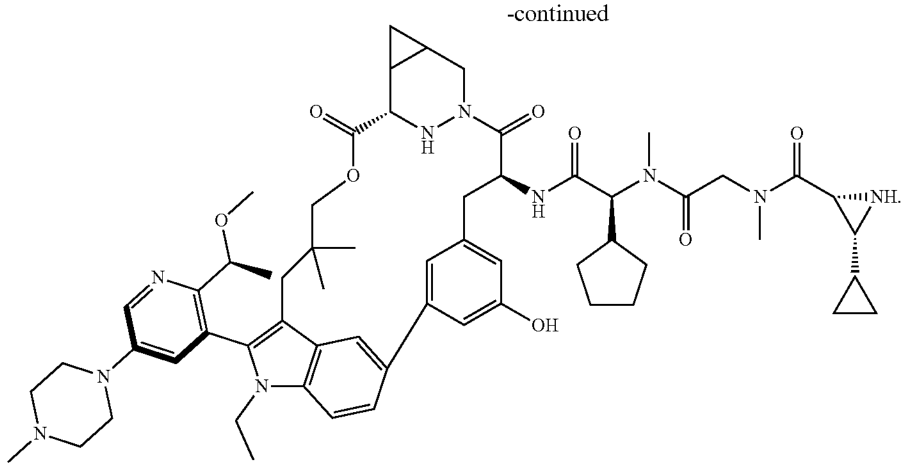
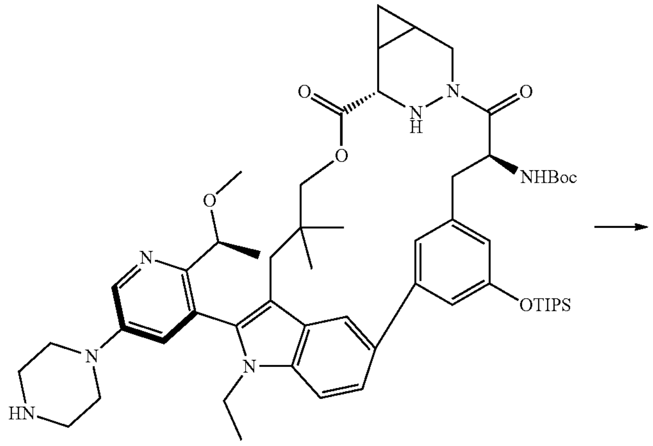
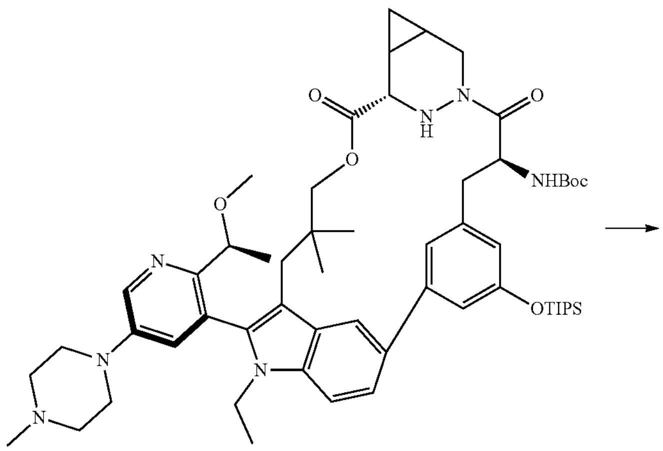

-continued
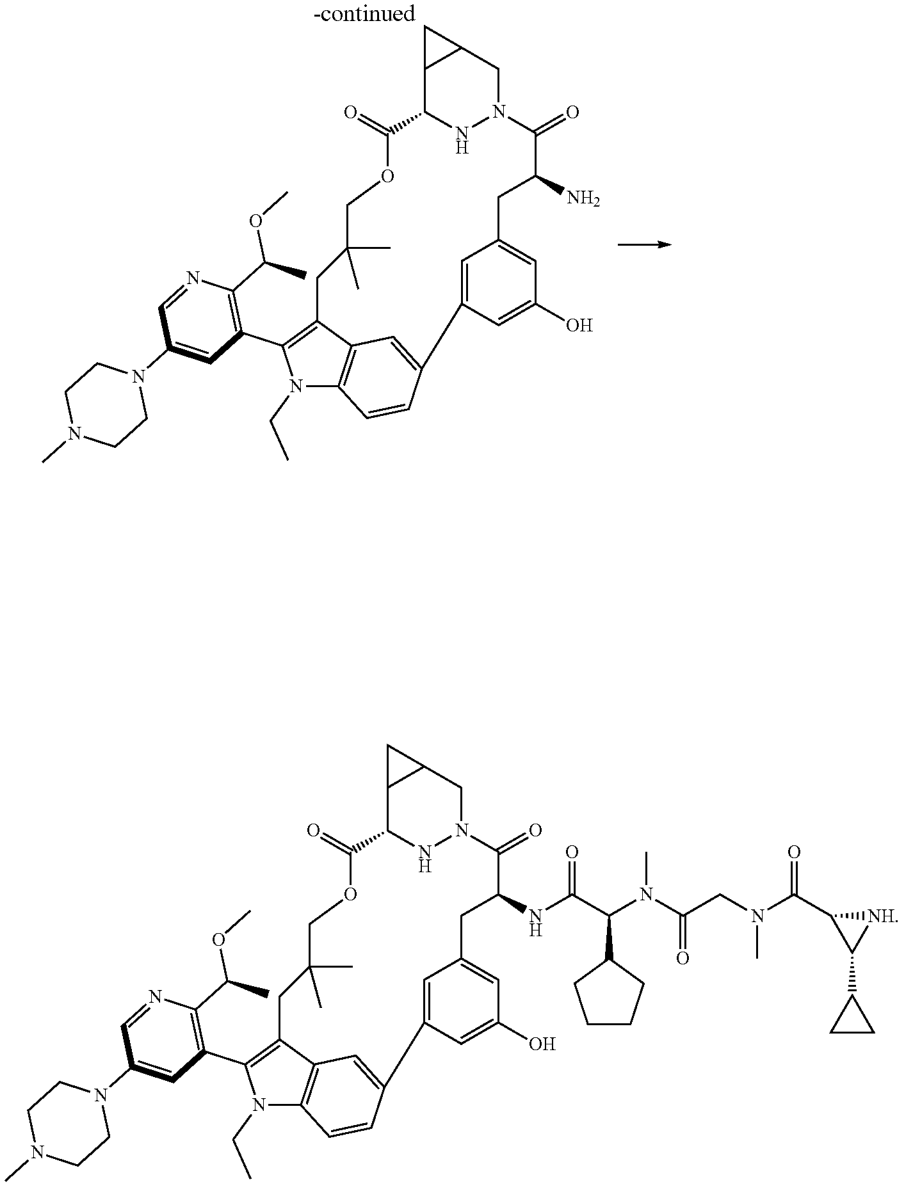
Method 13
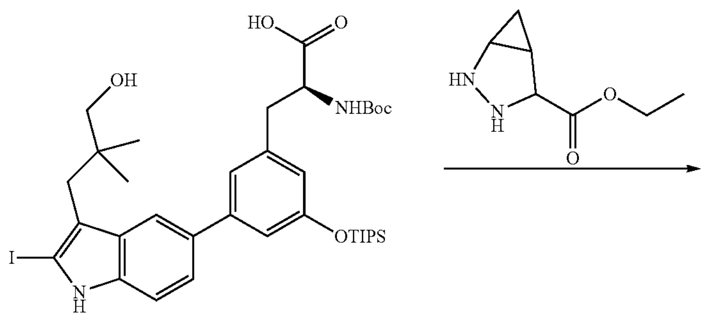

-continued
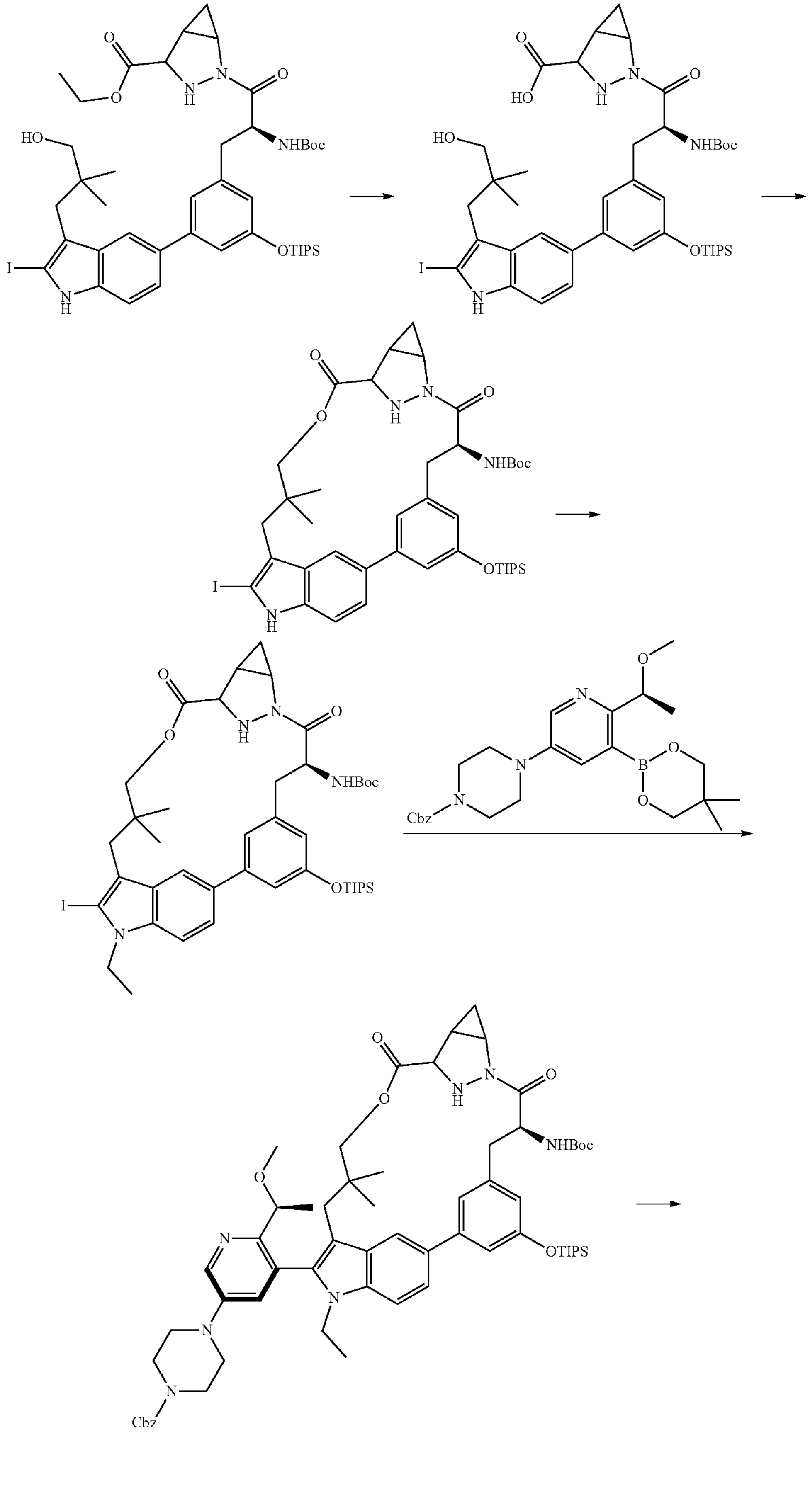

-continued
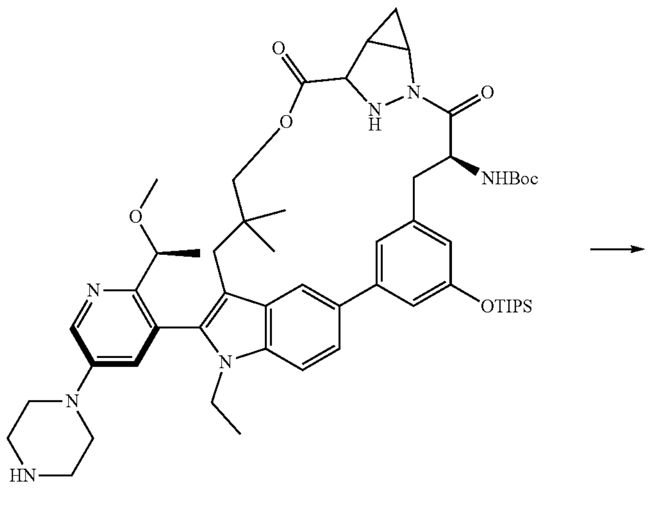
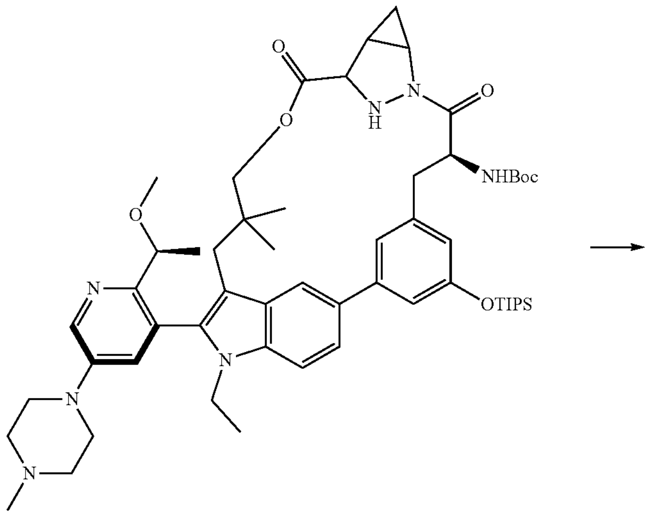
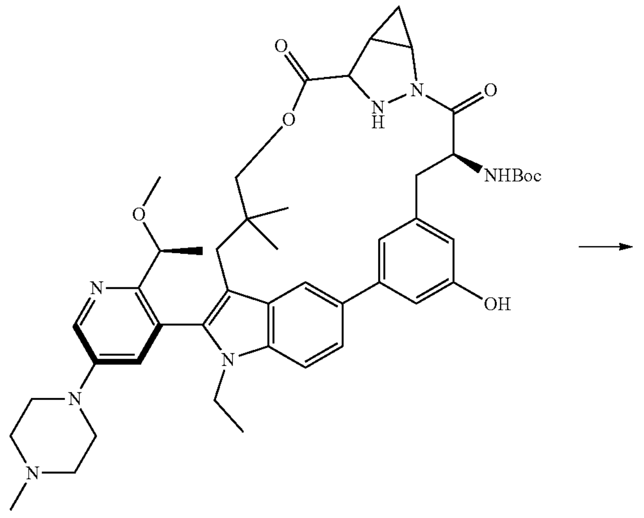

-continued
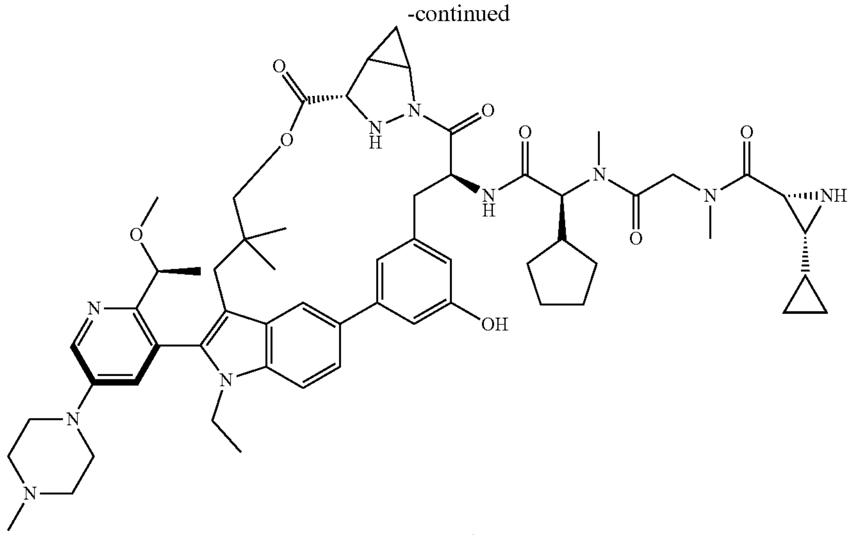
+
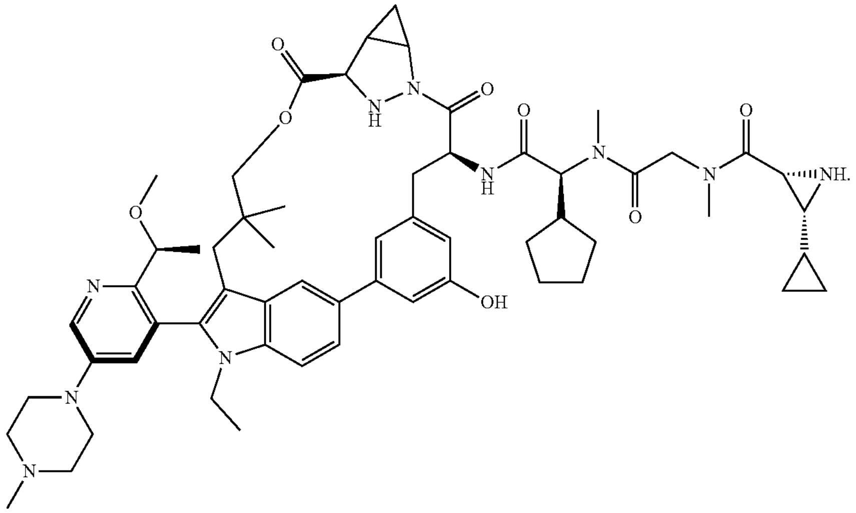
Method 15
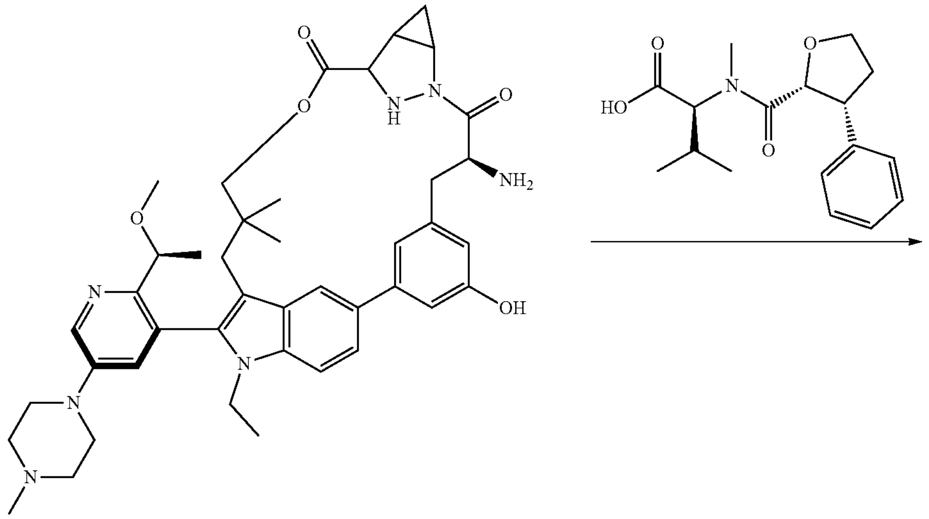

-continued
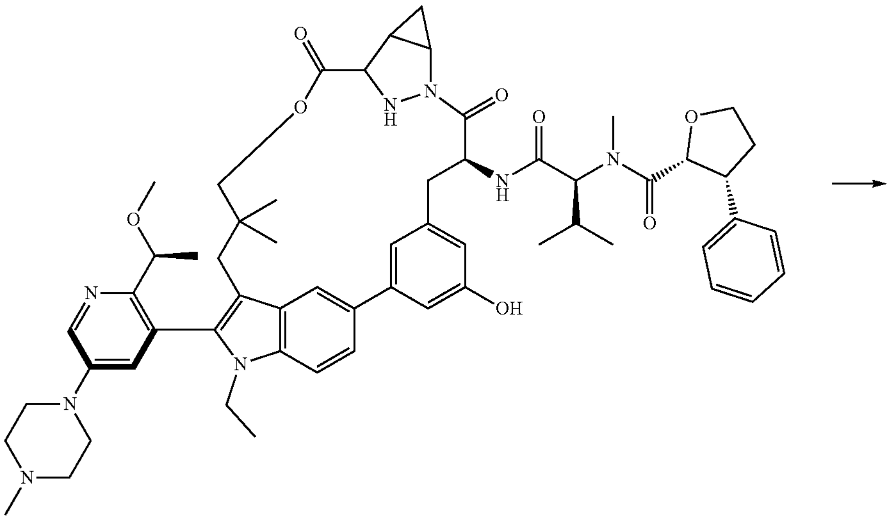
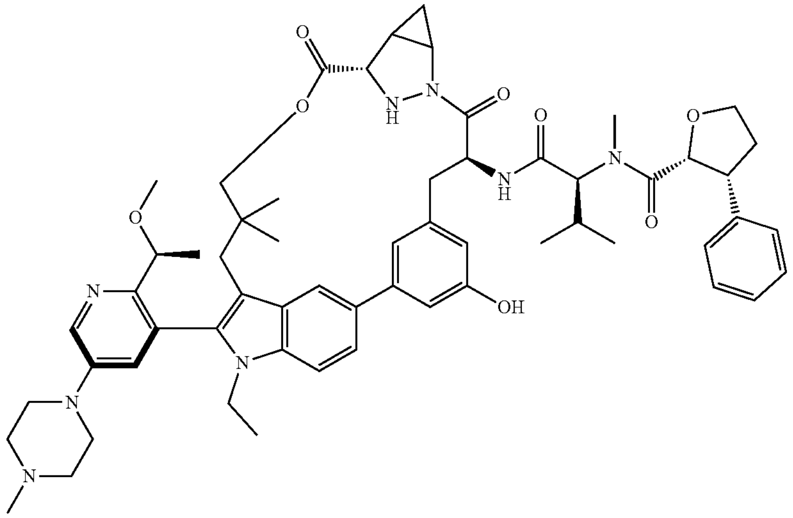
+
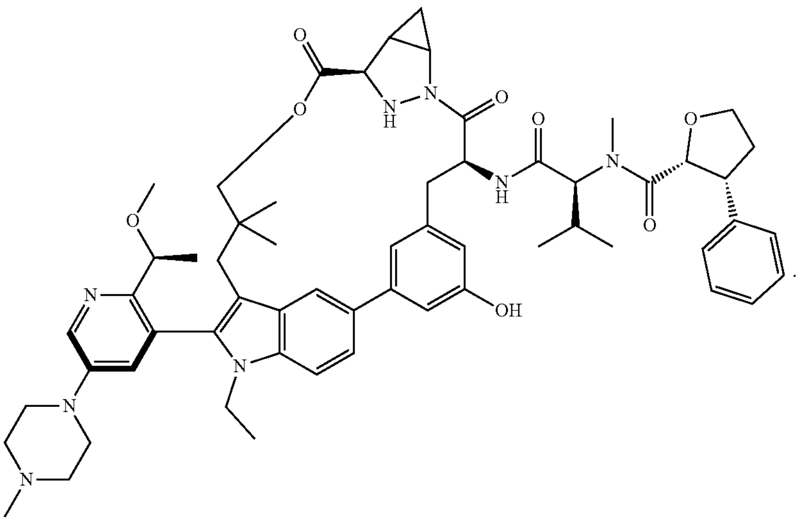
.

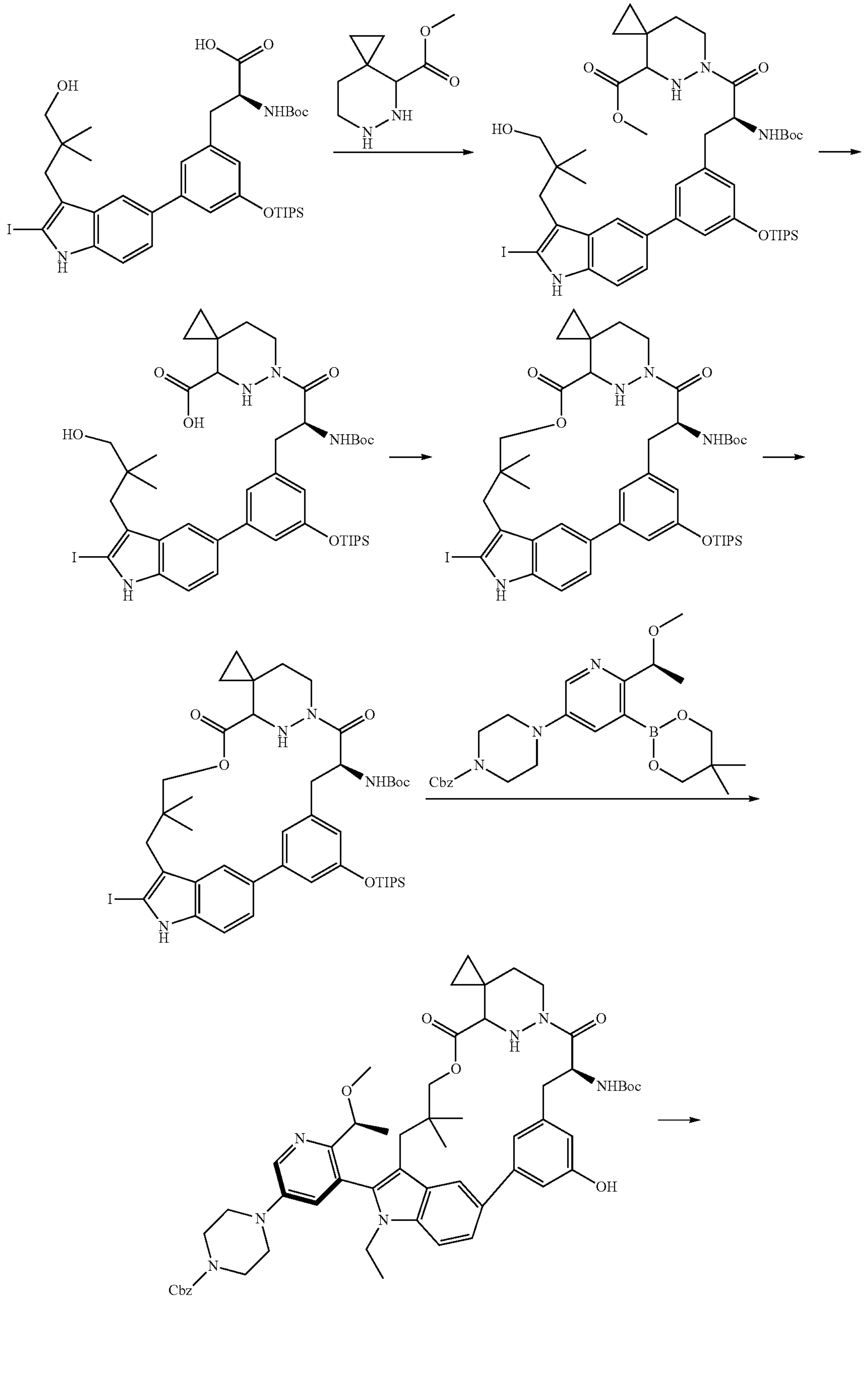

-continued
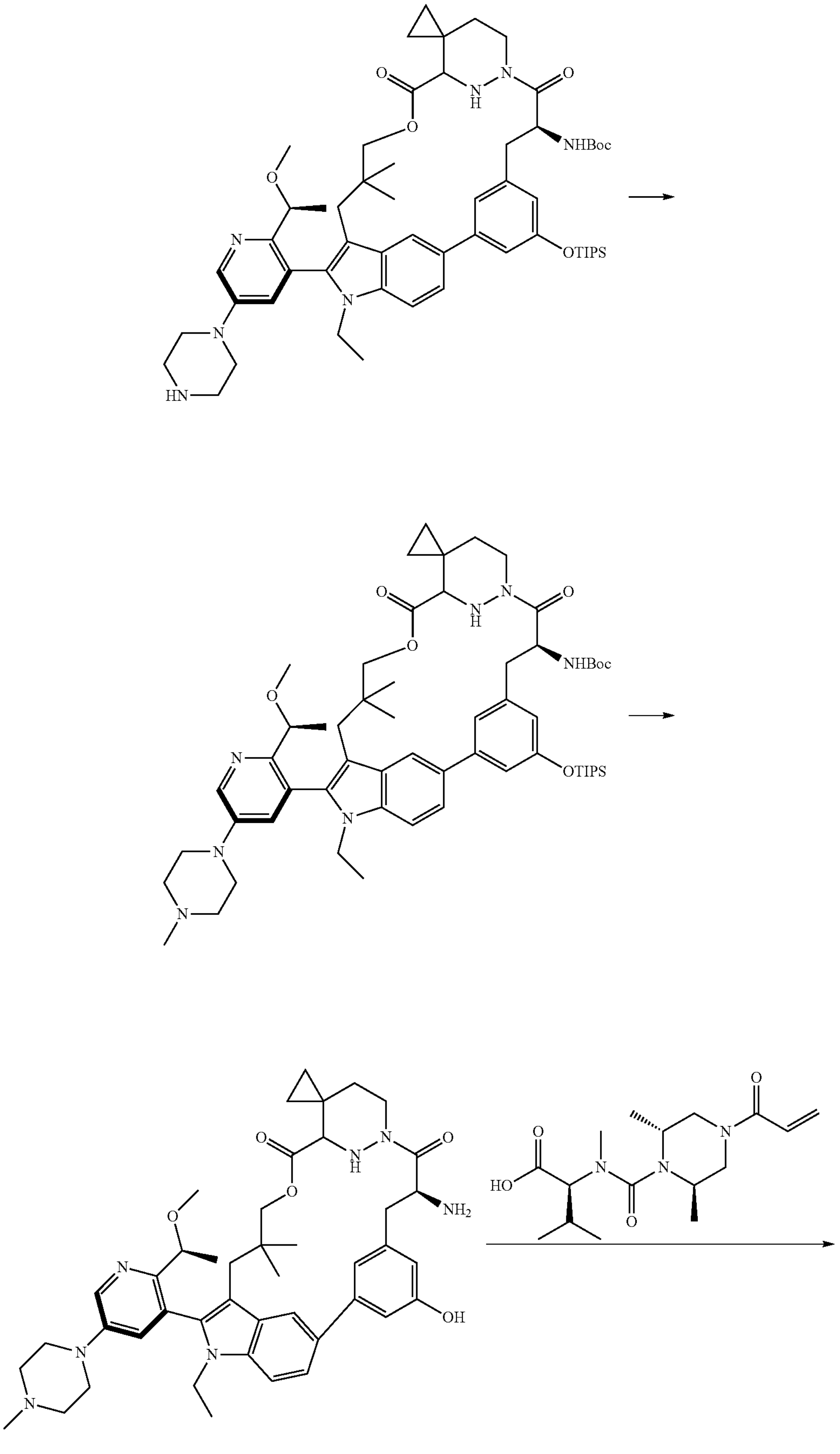

-continued
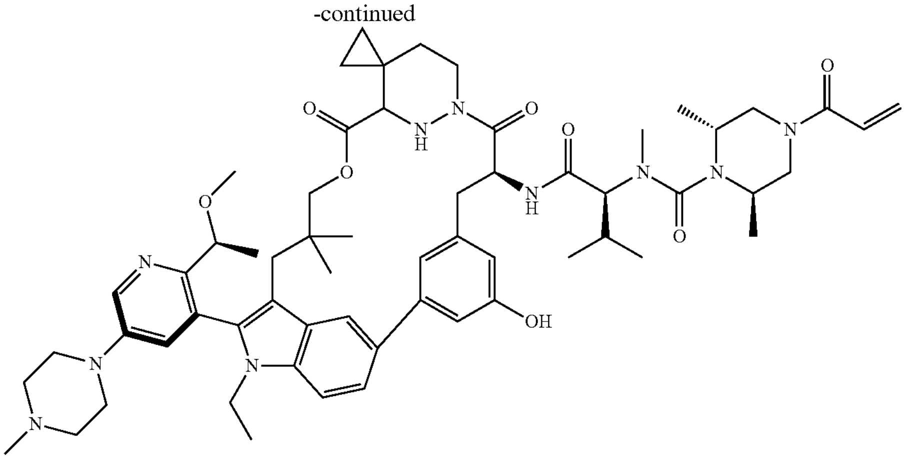
Method 16
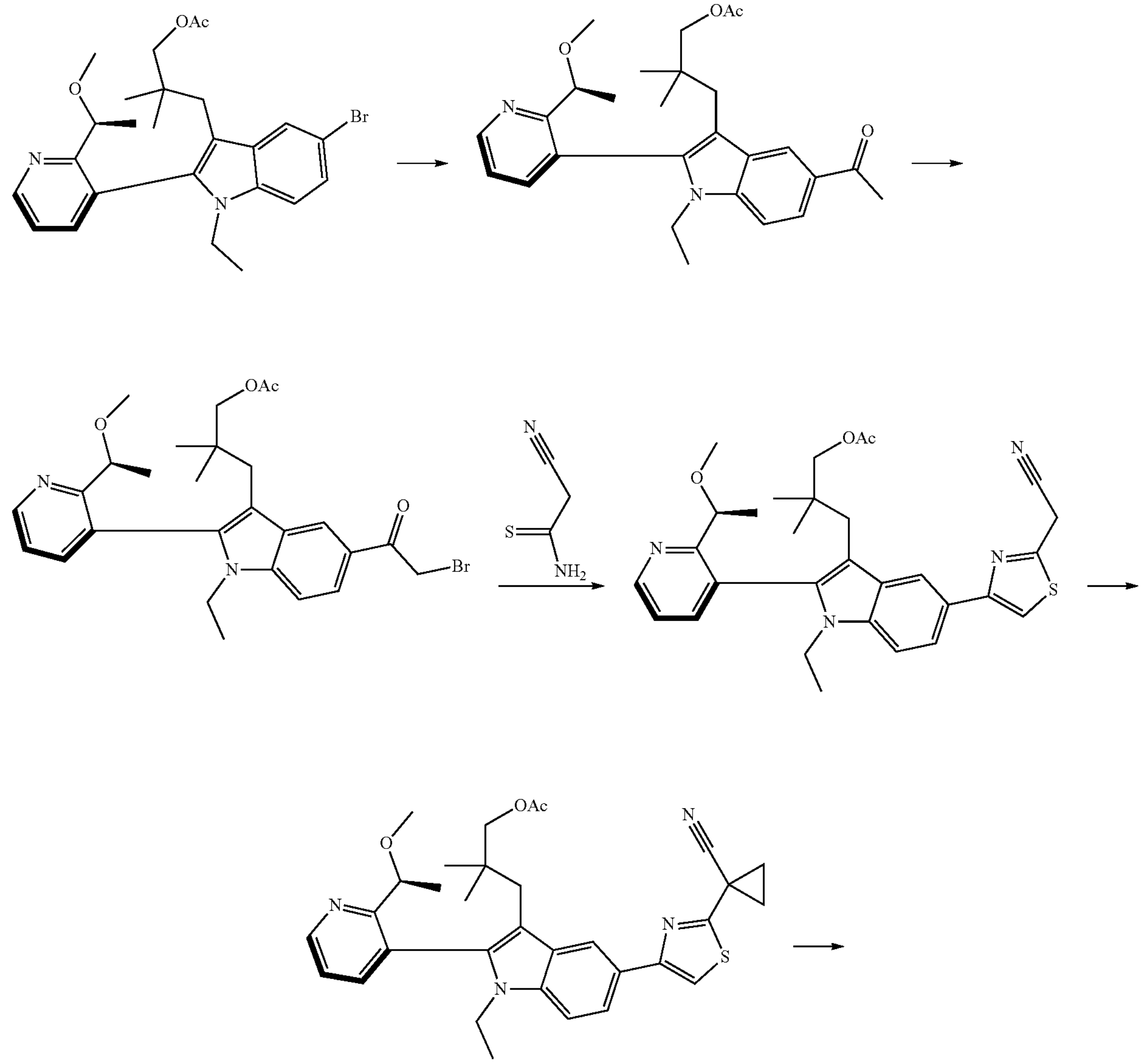

-continued
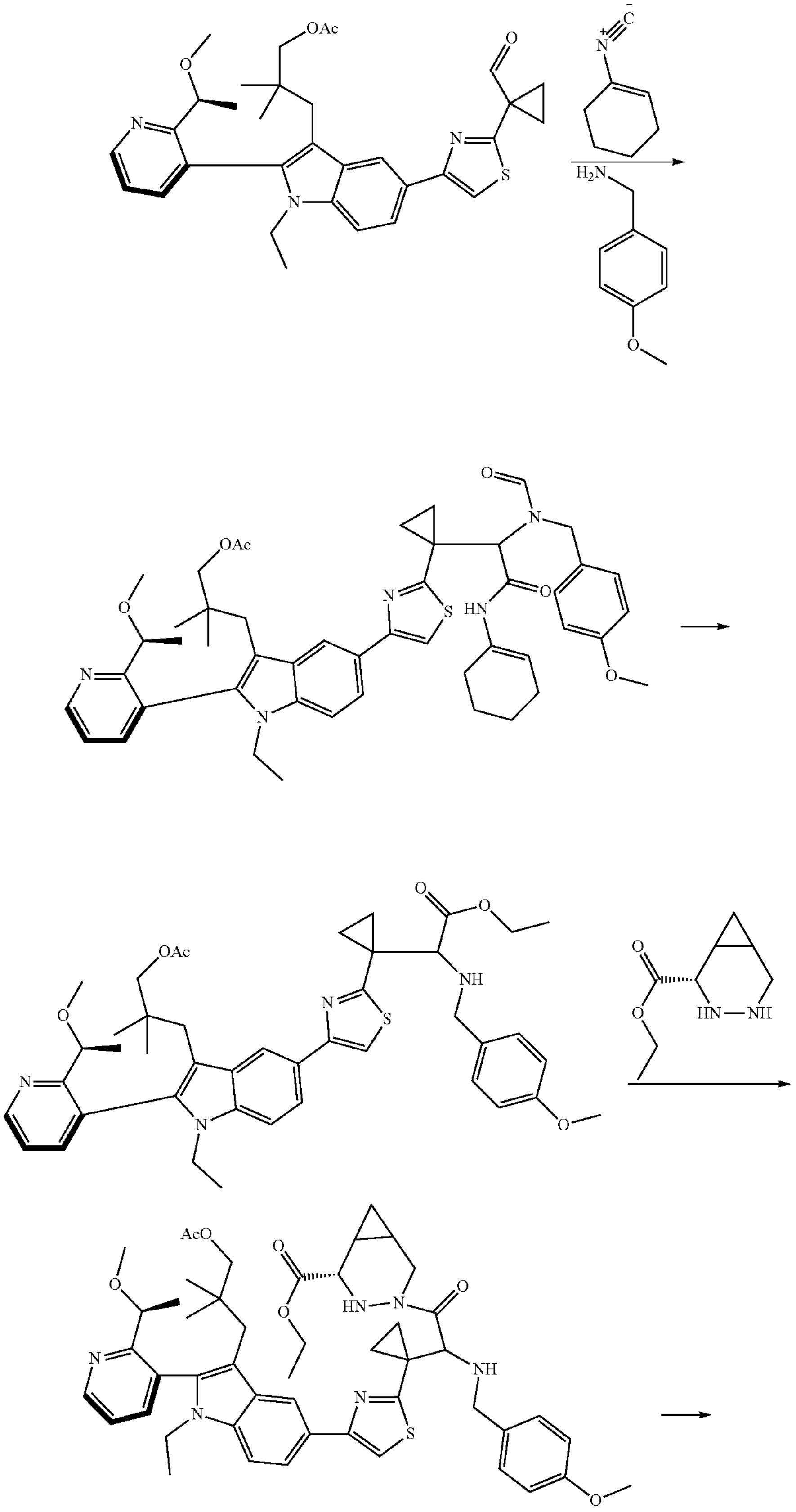

-continued
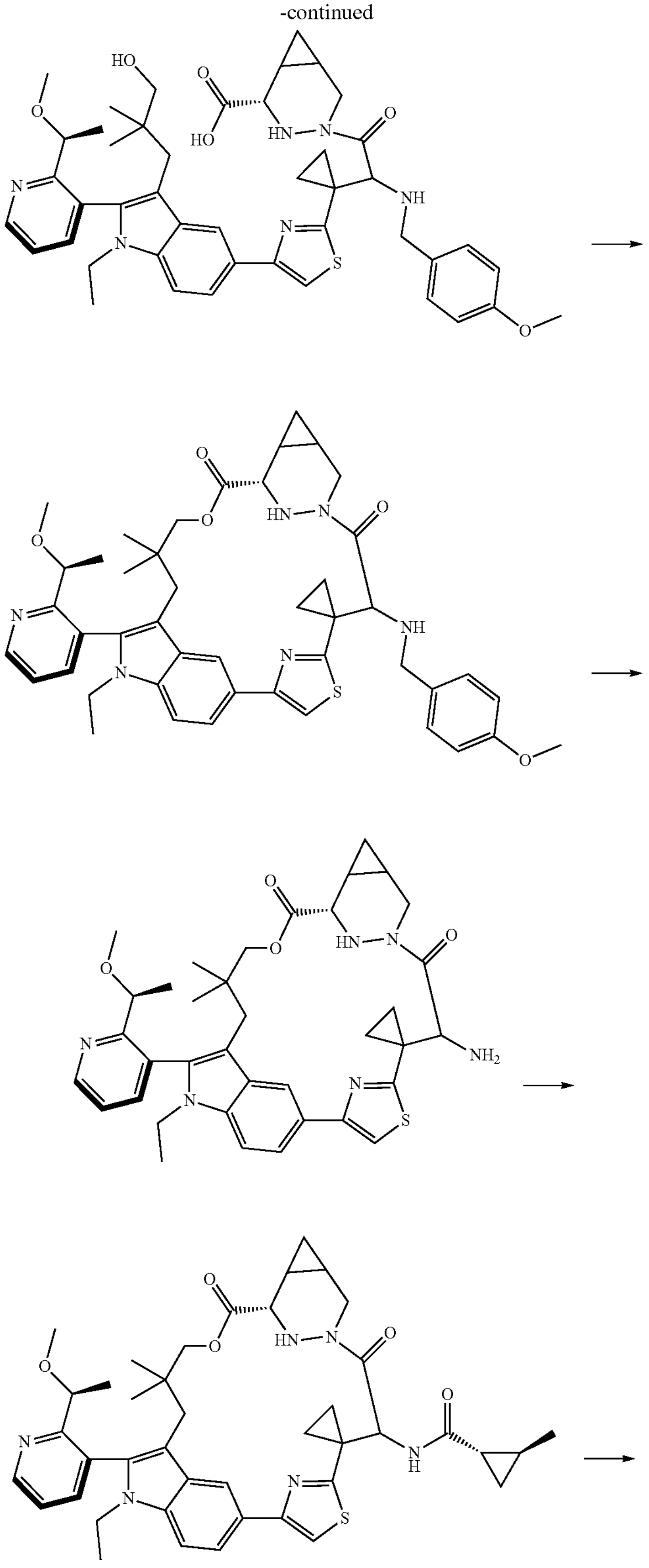

-continued
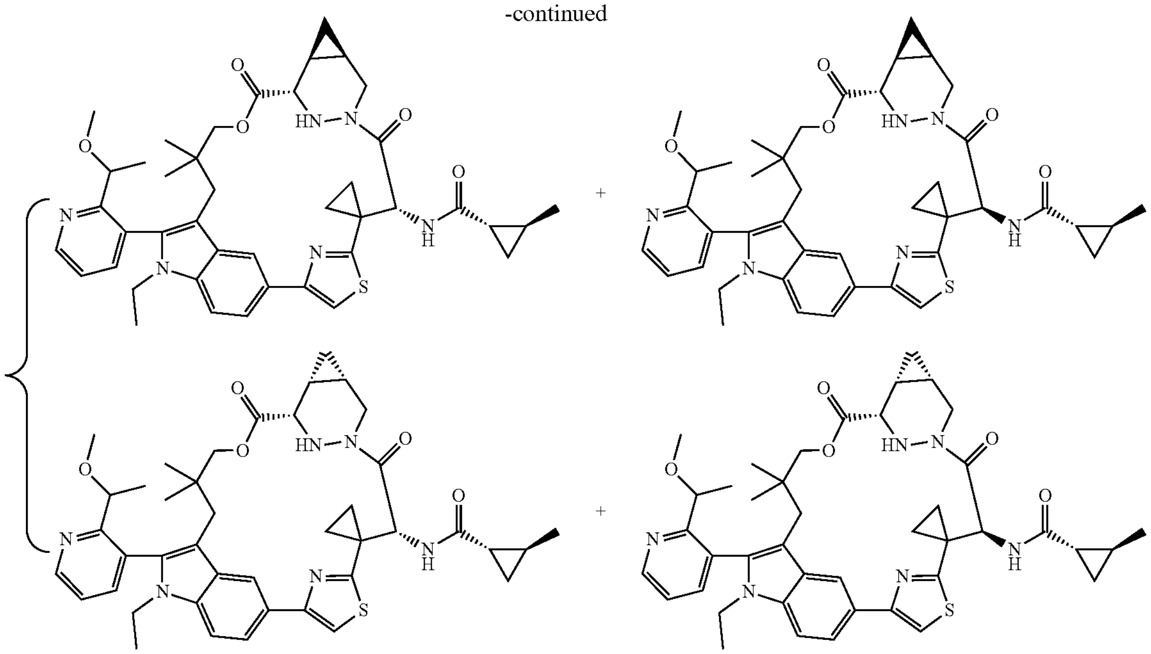
Method 17
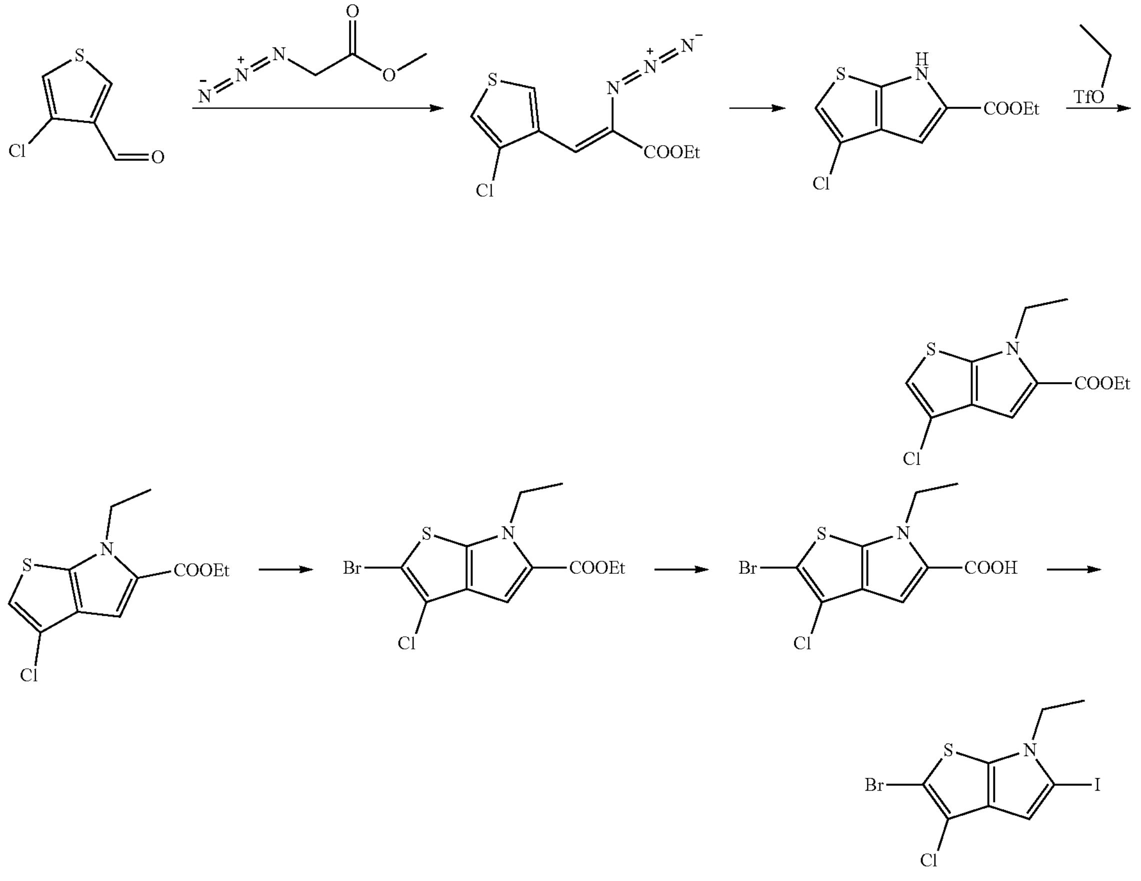

-continued
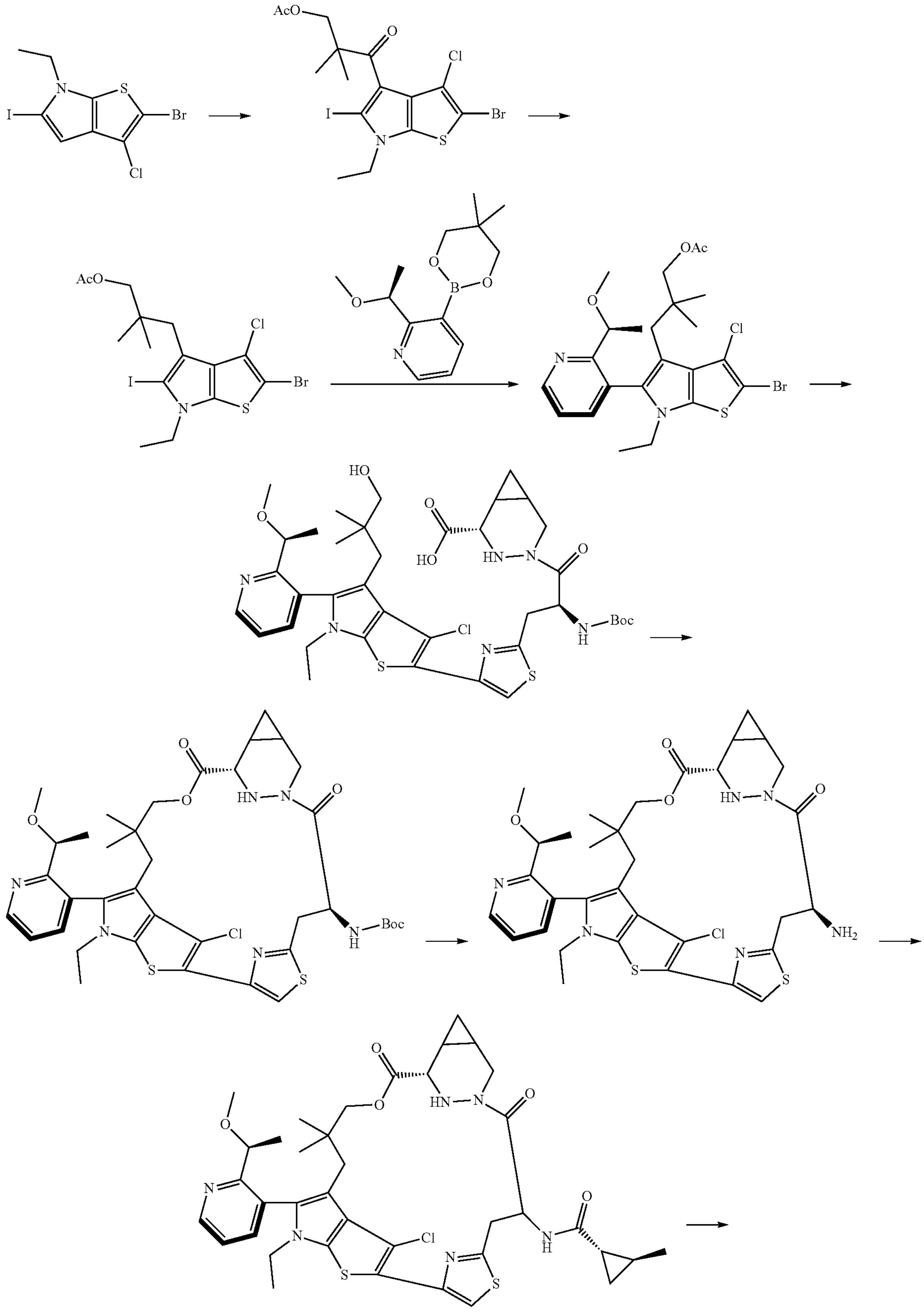

-continued
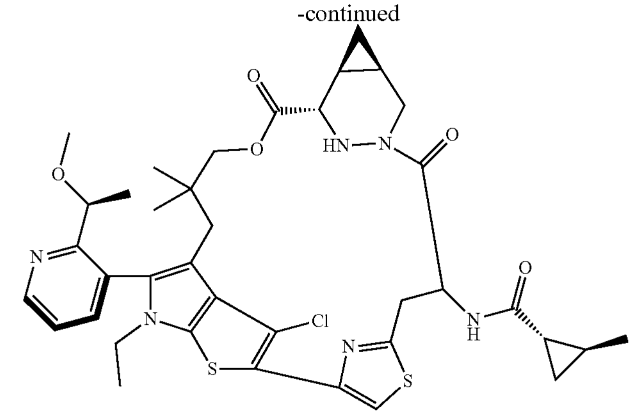
+
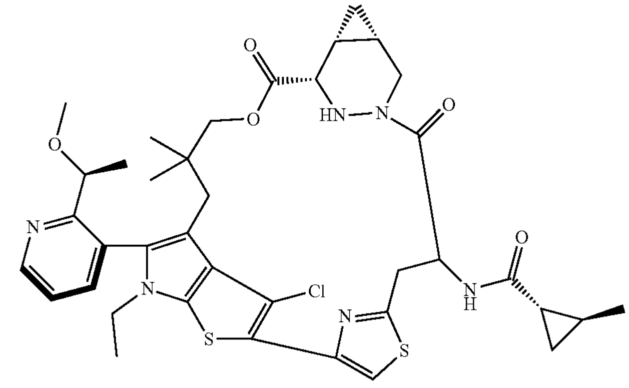
Method 18
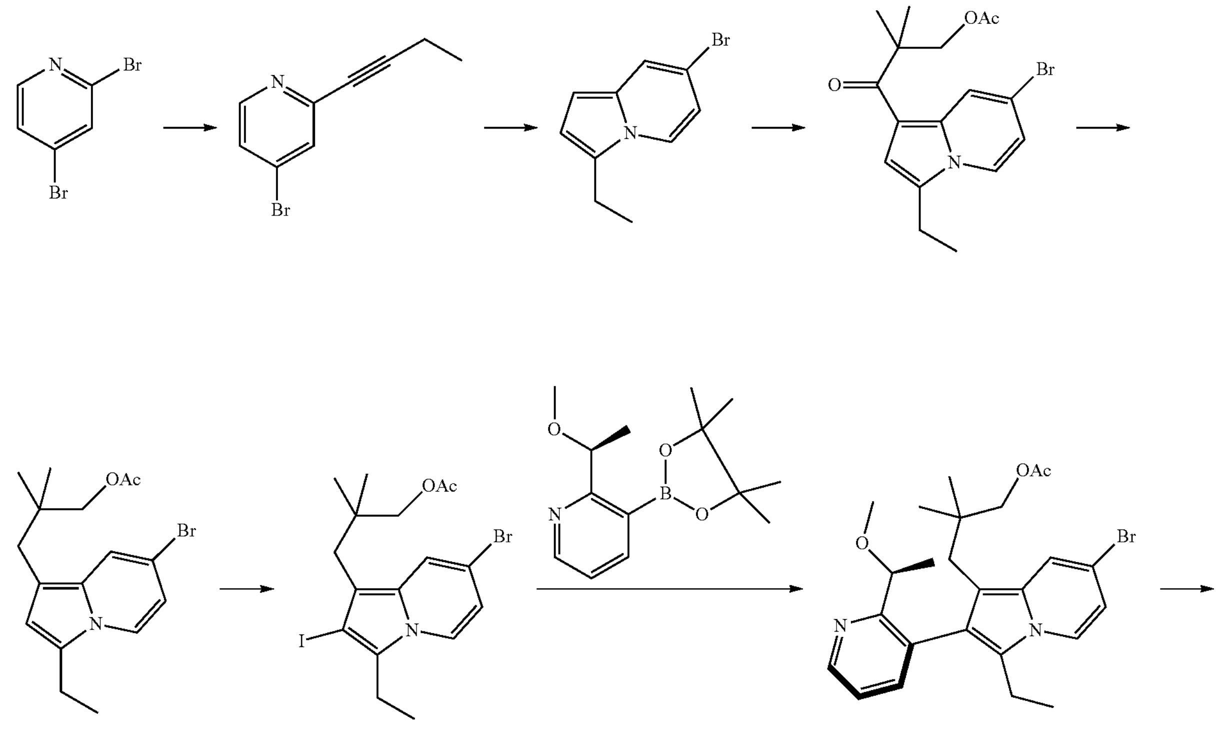

-continued
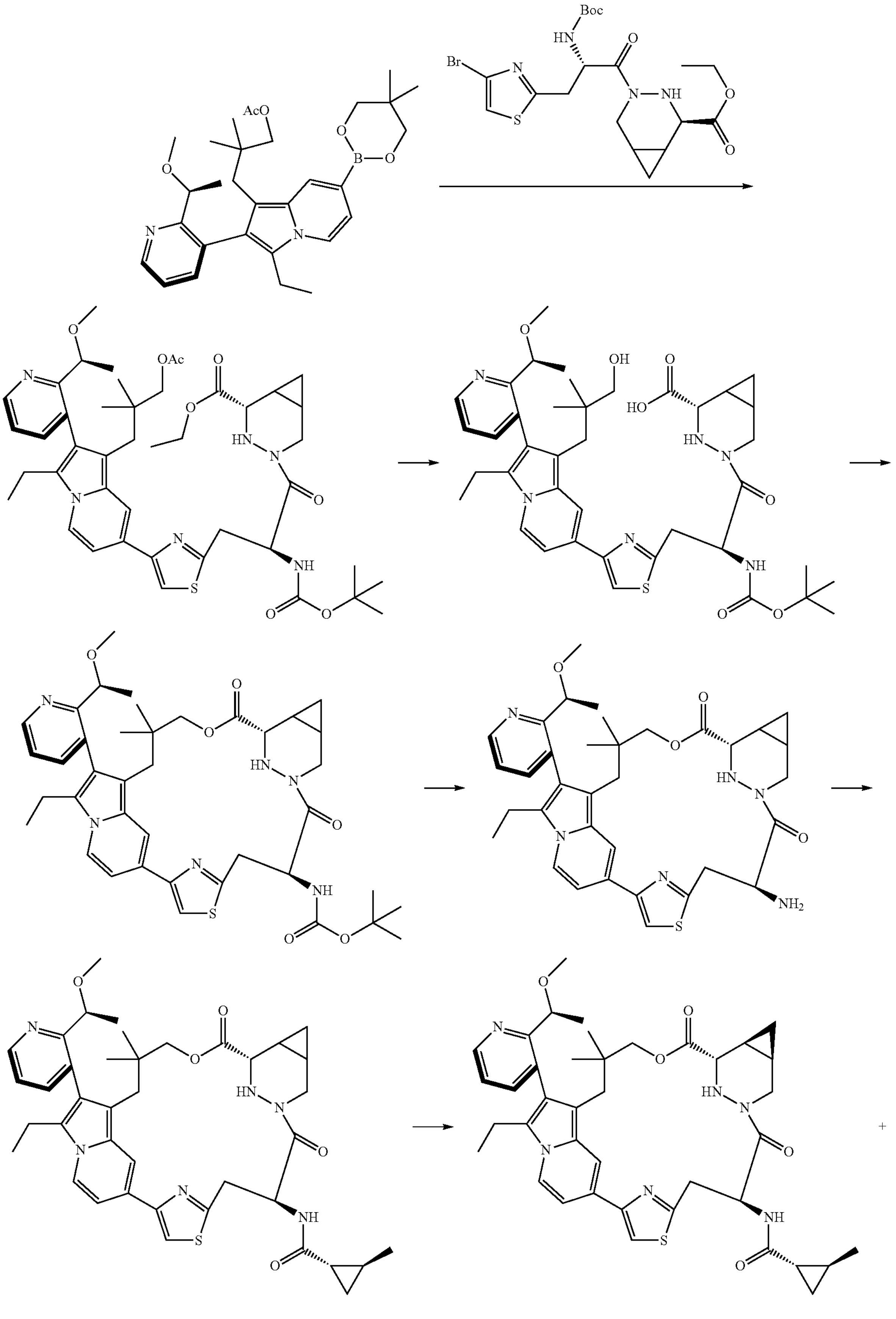
+

-continued

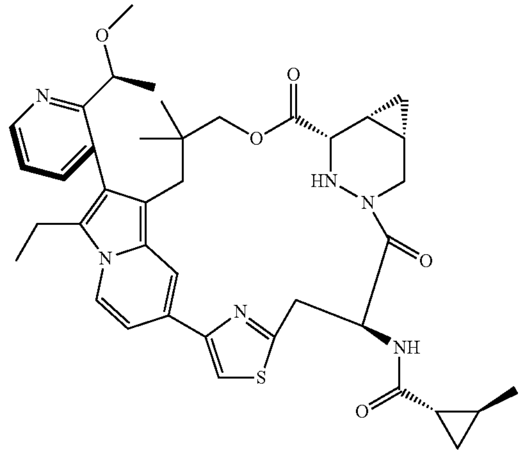

Technical Effect

The compound of the present disclosure binds to the chaperon CypA relatively well, and binding to CypA blocks the binding of RAS downstream RAF to RAS, thereby inhibiting the RAS-RAF-MEK-ERK signaling pathway to achieve an anti-tumor effect. The compound of the present disclosure has significant inhibitory activity on the cell proliferation of RAS mutant cell lines (such as GP2D, PK-59, AsPC-1, PSN-1, RKN, Capan-1, SW620, HCT116, LOVO, A549, H441, H727, LU99 and A427), but it does not demonstrate significant inhibitory effect on wild-type independent cell lines (such as A375), and it also has great selectivity. It also has significant inhibitory activity on AsPC-1 and GP2D cell pERK levels. In pharmacokinetic experiments in various species, the compound of the present disclosure has demonstrated good pharmacokinetic properties (such as high exposure and long half-life). The compound of the present disclosure has relatively high distribution in whole blood and red blood cells as compared to human and mouse plasma. In in vivo pharmacodynamic experiments, the compound of the present disclosure has demonstrated excellent anti-tumor effects, requiring a low dose, and is safe and has broad application prospects.

Definitions and Descriptions

Unless otherwise specified, the following terms and phrases used herein are intended to have the following meanings. A particular term or phrase should not be considered uncertain or unclear without a particular definition, but rather understood in the ordinary sense. When a trade name is used herein, it is meant to refer to its corresponding commodity or its active ingredient.

The term "pharmaceutically acceptable" as used herein is directed to those compounds materials, compositions, and/or dosage forms that are within the scope of sound medical judgment suitable for use in contact with the tissues of humans and animals without undue toxicity, irritation, allergic response, or other problems or complications, commensurate with a reasonable benefit/risk proportion.

The term "pharmaceutically acceptable salt" refers to a salt of a compound of the present disclosure that is prepared from a compound found by the present disclosure having a particular substituent and a relatively non-toxic acid or base. When the compound of the present disclosure contains a relatively acidic functional groups, a base addition salt may be obtained by contacting such compound with a sufficient amount of base in a pure solution or a suitable inert solvent. When the compound of the present disclosure contains a relatively basic functional group, an acid addition salt may be obtained by contacting such a compound with a sufficient amount of acid in a pure solution or a suitable inert solvent. Certain particular compounds of the present disclosure contain both basic and acidic functional groups and may be converted to any base or acid addition salt.

The pharmaceutically acceptable salt of the present disclosure may be synthesized by conventional chemical methods from parent compounds containing acid radicals or bases. In general, such salts are prepared by: the free acid or base form of the compound reacting with a stoichiometric amount of the appropriate base or acid in water or an organic solvent or a mixture thereof.

The compound of the present disclosure may exist in particular geometric or stereoisomeric forms. All such compounds are contemplated herein, including cis and trans isomers. (−)- and (+)-enantiomers, (R)- and (S)-enantiomers, diastereisomers, (D)-isomers, (L)-isomers, and racemic mixtures and other mixtures thereof, such as enantiomer or diastereoisomer enriched mixtures, all of which are encompassed within the scope of the present disclosure. Substituents such as alkyl may have an additional asymmetric carbon atom. All these isomers and mixtures thereof are encompassed within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" results from the inability of a single bond of a ring carbon atom or a double bond to rotate freely.

Unless otherwise specified, the term "diastereoisomer" refers to stereoisomers in which molecules each have two or more chiral centers and are not mirror images of each other.

Unless otherwise specified, "+" stands for dextrorotation, "(−)" stands for levorotation, and "±" stands for racemization.

Unless otherwise specified, the absolute configuration of one stereocenter is represented by a solid wedged bond ( ) and a dashed wedged bond ( ), the relative configuration of the stereocenter is represented by a straight solid bond ( ) and a straight dashed bond ( ), the solid wedged bond ( ) and/or a dashed wedged bond ( ) is represented by a wavy line ( ), or the straight solid bond ( ) and/or a straight dashed bond ( ) is represented with a wavy line ( ).

Certain compounds of the present disclosure may exist as an atropisomer, which is a conformational isomer that arises when the rotation around a single bond in a molecule is prevented or greatly slowed by steric interaction with other parts of the molecule. The compound disclosed herein includes all atropisomers, which may be pure individual atropisomers, rich in one of the atropisomers, or a nonspecific mixture of the respective. If the rotational potential around a single bond is high enough, and the interconversion between conformations is slow enough, it may allow for isomer separation.

Unless otherwise specified, the terms “rich in one isomer”, “isomer enriched”, “rich in one enantiomer” and “enantiomer enriched” refer to one of the isomers or enantiomers containing less than 100%, and the content of the isomers or enantiomers is greater than or equal to 60%, greater than or equal to 70%, greater than or equal to 80%, greater than or equal to 90%, greater than or equal to 95%, greater than or equal to 96%, greater than or equal to 97%, greater than or equal to 98%, greater than or equal to 99%, greater than or equal to 99.5%, greater than or equal to 99.6%, greater than or equal to 99.7%, greater than or equal to 99.8%, or greater than or equal to 99.9%.

Unless otherwise specified, the term “isomeric excess” or “enantiomeric excess” refers to the difference between the relative percentages of two isomers or enantiomers. For example, if the content of one isomer or enantiomer is 90% and the content of the other isomer or enantiomer is 10%, the isomeric or enantiomeric excess (ee value) is 80%.

Optically active (R)- and (S)-isomers and D and L isomers may be prepared by chiral synthesis or chiral reagents or other conventional techniques. If one kind of enantiomer of certain compound disclosed herein is to be obtained, the desired pure enantiomer may be prepared by asymmetric synthesis or derivatization using a chiral auxiliary, wherein the resulting diastereoisomeric mixture is separated and the auxiliary group is cleaved. Alternatively, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods in the art to get the pure enantiomer. Furthermore, the enantiomer and the diastereoisomer are typically separated through chromatography using a chiral stationary phase, optionally in combination with chemical derivatization (e.g., carbamate generated from amine). The compound disclosed herein may contain an unnatural proportion of atomic isotope at one or more of the atoms that constitute the compound. For example, the compound may be labelled with a radioisotope, such as tritium (3H), iodine-125 (125I), or C-14 (14C). Citing another example, hydrogen may be substituted by deuterium to form a deuterated drug, and the bond formed by deuterium and carbon is firmer than that formed by common hydrogen and carbon. Compared with an un-deuterated drug, the deuterated drug has the advantages of reduced toxic side effect, increased stability, enhanced efficacy, prolonged biological half-life and the like. All isotopic variations of the compound described herein, whether radioactive or not, are encompassed within the scope of the present disclosure.

The term “substituted” means that one or more hydrogen atoms on a specific atom are substituted by substituent(s) which may include deuterium and hydrogen variants, as long as the valence of the specific atom is normal and the substituted compound is stable. When the substituent is an oxygen (i.e., =O), it means that two hydrogen atoms are substituted. The term “optionally substituted” means that an atom may or may not be substituted. Unless otherwise specified, the type and number of the substituents may be arbitrary as long as being chemically achievable.

When any variable (e.g., R) occurs more than once in the constitution or structure of a compound, the definition of the variable in each case is independent. Thus, for example, if a group is substituted by 0-2 R, the group may be optionally substituted by two R at most, and the definition of R in each case is independent. Furthermore, a combination of a substituent and/or a variant thereof is permissible only if the combination can result in a stable compound.

When the number of a linking group is 0, such as —(CRR)0-, it means that the linking group is a single bond.

When the number of a substituent is 0, it means that the substituent is absent, for example, -A-(R)0 means that the structure is actually -A.

When a substituent is vacant, it means that the substituent does not exist. For example, when X is vacant in A-X, it means that the structure is actually A.

When one of the variables is selected from a single bond, it means that the two groups to which it is connected are directly connected. For example, when L represents a single bond in A-L-Z, it means that the structure is actually A-Z.

When the linking direction of the listed linking group is not indicated, the linking direction thereof is arbitrary. For example, the linking group L in

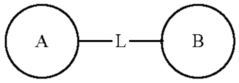

is -M-W—, and at this time, -M-W— may be constructed as

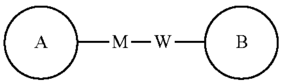

by linking ring A and ring B in the same direction as the reading order from left to right, or as

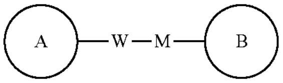

by connecting ring A and ring B in the direction opposite to the reading order from left to right. A combination of the linking group, substituent and/or variant thereof is permissible only if such combination can result in a stable compound.

Unless otherwise specified, when a group has one or more linking sites, any one or more sites of the group may be linked to other groups through a chemical bond. When the chemical bond is formed in a non-localized manner, and H atoms are present at the linking site, when the chemical bond is formed, the number of H atoms at the site is reduced according to the number of formed chemical bonds and become a group of corresponding valency. The chemical bond linking the site to the other groups may be represented by a straight solid bond (  ), a straight dashed bond (  ), or a wavy line

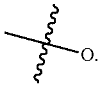

For example, a straight solid bond in —OCH3 indicates that it is linked to other groups through the oxygen, atom in the group; a straight dashed bond in

indicates that it is linked to other groups through both ends of the nitrogen atom in the group; a wavy line in

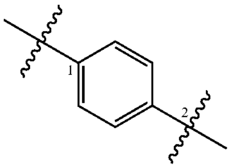 [SMILES: *c1ccc(*)cc1]

indicates that it is linked to other groups through carbon atoms at positions 1 and 2 in the phenyl group;

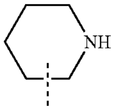

indicates that any linking site on the piperidinyl group may be linked to other groups through a chemical bond, including at least 4 linking methods, namely

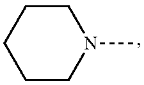, 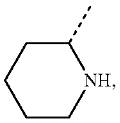, 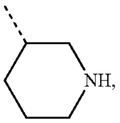, and 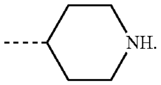.

Even if an H atom is drawn on —N—,

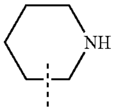

still includes a group of such a linking method as

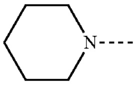

and only when a chemical bond is formed, the H at this site is reduced by 1 and becomes a corresponding monovalent piperidinyl group.

Unless otherwise specified, the number of atoms on a ring is typically defined as the number of members of the ring, e.g., a "5-7-membered ring" refers to a "ring" that is arranged around 5-7 atoms.

Unless otherwise specified, the term "C1-6 alkyl" is used by itself or in conjunction with other terms to represent a straight or branched, saturated hydrocarbon group consisting of 1 to 6 carbon atoms, respectively. The C1-6 alkyl includes C1-5, C1-4, C1-3, C1-2, C2-6, C2-4, C6, C5 alkyl, and the like; it may be monovalent (e.g., methyl), divalent (e.g., methylene), or multivalent (e.g., methine). Examples of C1-6 alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, and the like. Unless otherwise specified, the tan "C1-4 alkyl" is used by itself or in conjunction with other terms to represent a straight or branched, saturated hydrocarbon group consisting of 1 to 4 carbon atoms, respectively. The C1-4 alkyl includes C1-2, C1-3, C2-3 alkyl, and the like, and may be monovalent (e.g., methyl), divalent (e.g. methylene), or polyvalent (e.g., methenyl). Examples of C1-4 alkyl include, but are not limited to, methyl (Me), ethyl (Et), propyl (including n-propyl and isopropyl), butyl (including n-butyl, isobutyl, s-butyl, and t-butyl), and the like.

Unless otherwise specified, the term "C1-4 alkoxy" is used by itself or in conjunction with other terms to represent an alkyl group containing 1 to 4 carbon atoms linked to the rest of the molecule through one oxygen atom, respectively. The C1-4 alkoxy includes C1-3. C1-2, C2-4, C4, C3 alkoxy, and the like, and may be monovalent, divalent, or multivalent. Examples of C1-4 alkoxy include, but are not limited to, methoxy, ethoxy, propoxy (including n-propoxy and isopropoxy), butoxy (including n-butoxy, isobutoxy, s-butoxy, and t-butoxy), and the like.

Unless otherwise specified, "C3-6 cycloalkyl" is used by itself or in conjunction with other terms to represent a saturated cyclic hydrocarbon group consisting of 3 to 6 carbon atoms, respectively. The C3-6 cycloalkyl contains a monocyclic ring and a polycyclic ring, wherein the polycyclic ring contains a spiro ring, a parallel ring, and a bridged ring. The C3-6 cycloalkyl includes C3-5, C4-5, C5-6 cycloalkyl, and the like, and may be monovalent, divalent, or multivalent. Examples of C3-6 cycloalkyl include, but are not limited to, cyclopropyl, cyclobutyl, cyclopentyl, cyclohexyl, bicyclo[1.1.1]pentanyl, and the like.

Unless otherwise specified, the term "3-10-membered heterocycloalkyl" is used by itself or in conjunction with other terms to represent a saturated or partially unsaturated cyclic group consisting of 3 to 10 ring atoms, respectively, wherein 1, 2, 3 or 4 ring atoms are heteroatoms independently selected from O, S and N, and the rest are carbon atoms, wherein the carbon atoms are optionally substituted with oxygen (i.e., form C═O), the nitrogen atoms are optionally quaternized, and the nitrogen and sulfur heteroatoms may optionally be oxidized (i.e., NO and S(O)p, p is 1 or 2). The 3-10-membered heterocycloalkyl contains a monocyclic ring and a polycyclic ring, wherein the polycyclic ring contains a spiro ring, a parallel ring, and a bridged ring. Furthermore, in the case of this "3-10-membered heterocycloalkyl", a heteroatom may occupy the position of the heterocycloalkyl linking to the rest of the molecule. The 3-10-membered heterocycloalkyl includes 3-6-membered, 4-6-membered, 5-6-membered, 4-7-membered, 5-7-membered, 5-8-membered, 6-8-membered, 6-9-membered, 6-10-membered, 4-membered, 5-membered, 6-membered, 7-membered, 8-membered, 9-membered, and 10-membered heterocycloalkyl, and the like, and may be monovalent divalent, or multivalent. Examples of 3-10-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl, tetrahydrothiophen-3-yl and the like), tetrahydrofuranyl (including tetrahydrofuran-2-yl and the like), tetrahydropyranyl, piperidinyl(including 1-piperidinyl, 2-piperidinyl, 3-piperidinyl, and the like), piperazinyl (including 1-piperazinyl, 2-piperazinyl, and the like), morpholinyl (including 3-morpholinyl, 4-morpholinyl, and the like), dioxanyl, dithianyl, isoxazolidinyl, isothiazolidinyl, 1, 2-oxazinyl, 1,2-thiazinyl or hexahydropyridazinyl, homopiperazinyl, homopiperidinyl, tetrahydropyridinyl,

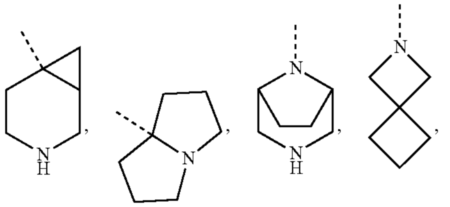

and the like.

Unless otherwise specified, the term "3-7-membered heterocycloalkyl" is used by itself or in conjunction with other terms to represent a saturated or partially unsaturated cyclic group consisting of 3 to 7 ring atoms, respectively, wherein 1, 2, 3 or 4 ring atoms are heteroatoms independently selected from O, S and N, and the rest are carbon atoms, wherein the carbon atoms are optionally substituted with oxygen (i.e., form C═O), the nitrogen atoms are optionally quaternized, and the nitrogen and sulfur heteroatoms may optionally be oxidized (i.e., NO and S(O)p, p is 1 or 2). The 3-7-membered heterocycloalkyl contains a monocyclic ring and a polycyclic ring, wherein the polycyclic ring contains a spiro ring, a parallel ring, and a bridged ring. Furthermore, in the case of this "3-7-membered heterocycloalkyl", a heteroatom may occupy the position of the heterocycloalkyl linking to the rest of the molecule. The 3-7-membered heterocycloalkyl includes 3-6-membered, 4-6-membered, 5-6-membered, 4-7-membered, 5-7-membered, 4-membered, 5-membered, 6-membered, and 7-membered heterocycloalkyl, and the like, and may be monovalent, divalent, or multivalent. Examples of 3-7-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl, tetrahydrothiophen-3-yl and the like), tetrahydrofuranyl (including tetrahydrofuran-2-yl and the like), tetrahydropyranyl, piperidinyl (including 1-piperidinyl, 2-piperidinyl, 3-piperidinyl, and the like), piperazinyl (including 1-piperazinyl, 2-piperazinyl, and the like), morpholinyl (including 3-morpholinyl, 4-morpholinyl, and the like), dioxanyl, dithianyl, isoxazolidinyl, isothiazolidinyl, 1, 2-oxazinyl, 1,2-thiazinyl or hexahydropyridazinyl, homopiperazinyl, homopiperidinyl, tetrahydropyridinyl, and the like.

Unless otherwise specified, the term "3-6-membered heterocycloalkyl" is used by itself or in conjunction with other terms to represent a saturated or partially unsaturated cyclic group consisting of 3 to 6 ring atoms, respectively, wherein 1, 2, 3 or 4 ring atoms are heteroatoms independently selected from O, S and N, and the rest are carbon atoms, wherein the carbon atoms are optionally substituted with oxygen (i.e., form C═O), the nitrogen atoms are optionally quaternized, and the nitrogen and sulfur heteroatoms may optionally be oxidized (i.e., NO and S(O)p, p is 1 or 2). The 3-6-membered heterocycloalkyl contains a monocyclic ring and a polycyclic ring, wherein the polycyclic ring contains a spiro ring, a parallel ring, and a bridged ring. Furthermore, in the case of this "3-6-membered heterocycloalkyl", a heteroatom may occupy the position of the heterocycloalkyl linking to the rest of the molecule. The 3-6-membered heterocycloalkyl includes 4-6-membered, 5-6-membered, 4-membered, 5-membered, and 6-membered heterocycloalkyl, and the like, and may be monovalent, divalent, or multivalent. Examples of 3-6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl, tetrahydrothiophen-3-yl and the like), tetrahydrofuranyl (including tetrahydrofuran-2-yl and the like), tetrahydropyranyl, piperidinyl (including 1-piperidinyl, 2-piperidinyl, 3-piperidinyl, and the like), piperazinyl (including 1-piperazinyl, 2-piperazinyl, and the like), morpholinyl (including 3-morpholinyl, 4-morpholinyl, and the like), dioxanyl, dithianyl, isoxazolidinyl, isothiazolidinyl, 1, 2-oxazinyl, 1,2-thiazinyl or hexahydropyridazinyl, piperidenyl, and the like.

Unless otherwise specified, the terms "5-6-membered heteroaryl ring" and "5-6-membered heteroaryl" herein are used interchangeably, and the term "5-6-membered heteroaryl" represents a monocyclic group consisting of 5 to 6 ring atoms having a conjugated π-electron system, wherein 1, 2, 3, or 4 ring atoms are heteroatoms independently selected from O, S, and N, and the rest are carbon atoms. Wherein carbon atoms are optionally substituted with oxygen (i.e. form C═O), nitrogen atoms are optionally quaternized, and nitrogen and sulfur heteroatoms may optionally be oxidized (i.e. NO and S(O)p, p is 1 or 2). The 5-6-membered heteroaryl may be linked to the rest of the molecule through a heteroatom or a carbon atom. The 5-6-membered heteroaryl includes 5- and 6-membered heteroaryl, and may be monovalent, divalent, or multivalent. Examples of the 5-6-membered heteroaryl include, but are not limited to, pyrrolyl (including N-pyrrolyl, 2-pyrrolyl, 3-pyrrolyl, and the like), pyrazolyl (including 2-pyrazolyl, 3-pyrazolyl, and the like), imidazolyl (including N-imidazolyl, 2-imidazolyl, 4-imidazolyl, 5-imidazolyl, and the like), oxazolyl (including 2-oxazolyl, 4-oxazolyl, 5-oxazolyl, and the like), triazolyl(1H-1, 2, 3-triazolyl, 2H-1, 2, 3-triazolyl, 1H-1, 2, 4-triazolyl, 4H-1, 2, 4-triazolyl, and the like), tetrazolyl, isoxazolyl(3-isoxazolyl, 4-isoxazolyl, 5-isoxazolyl, and the like), thiazolyl (including 2-thiazolyl, 4-thiazolyl, 5-thiazolyl, and the like), furanyl (including 2-furanyl, 3-furanyl, and the like), thienyl (including 2-thienyl, 3-thienyl, and the like), pyridinyl (including 2-pyridinyl, 3-pyridinyl, 4-pyridinyl, and the like), pyrazinyl or pyrimidinyl (including 2-pyrimidinyl, 4-pyrimidinyl, and the like), Unless otherwise specified, the terms "5-membered heteroaryl and 5-membered heteroaryl" herein represents one 5-membered heteroaryl condensed together with another 5-membered heteroaryl through two adjacent atoms. Examples of "5-membered heteroaryl and 5-membered heteroaryl" include, but are not limited to

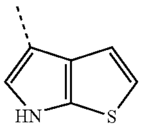
and
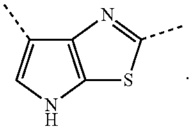
.

Unless otherwise specified, Cn–n+m or Cn–Cn+m includes any one of the specific cases of n–n+m carbon atoms. For example, C1-12 includes C1, C2, C3, C4, C5, C6, C7, C8, C9, C10, C11 and C12. Also, any range within n–n+m may be included. For example, C1-12 includes C1-3, C1-6, C1-9, C3-6, C3-9, C3-12, C6-9, C6-12, C9-12, and the like. Similarly, n-n+m means that the number of atoms on the ring is n-n+m. For example, 3-12-membered ring includes 3-membered ring, 4-membered ring, 5-membered ring, 6-membered ring, 7-membered ring, 8-membered ring, 9-membered ring, 10-membered ring, 11-membered ring and 12-membered ring n-n+m also represents any range within n–n+m. For example, 3-12-membered ring includes 3-6-membered ring, 3-9-membered ring, 5-6-membered ring, 5-7-membered ring, 6-7-membered ring, 6-8-membered ring, 6-10-membered ring, and the like.

The term "leaving group" refers to a functional group or atom that may be substituted by another functional group or atom by a substitution reaction (e.g., a nucleophilic substitution reaction). For example, representative leaving groups include triflate; chlorine, bromine and iodine; sulfonate esters, such as mesylate, N,N'-dioctadecyloxacarbocyanine p-toluenesulfonate, p-bromobenzenesulfonate, p-toluenesulfonate and the like; acyloxy, such as acetoxy, trifluoroacetoxy and the like.

The term "protecting group" includes, but is not limited to, "amino protecting group," "hydroxy protecting group," and "mercapto protecting group." The term "amino protecting group" refers to a protecting group suitable for blocking the side reaction on the nitrogen of an amino. Representative amino protecting groups include, but are not limited to: formyl; acyl such as alkanoyl (such as acetyl, trichloroacetyl, and trifluoroacetyl); alkoxycarbonyl, such as tert-butoxycarbonyl(Boc); arylmethoxycarbonyl, such as benzyloxycarbonyl (Cbz) and 9-fluorenylmethyloxycarbonyl (Fmoc); arylmethyl, such as benzyl (Bn), trityl(Tr), 1,1-bis-(4'-methoxyphenyl)methyl; silyl, such as trimethylsilyl (TMS) and tert-butyldimethylsilyl (TBS) and the like. The term "hydroxy protecting group" refers to a protecting group suitable for blocking the side reaction on hydroxy. Representative hydroxyl protecting groups include, but are not limited to: alkyl, such as methyl, ethyl and tert-butyl; acyl, such as alkanoyl (e.g. acetyl); arylmethyl, such as benzyl (Bn), p-methoxybenzyl (PMB), 9-fluorenylmethyl(Fm), and diphenylmethyl(benzhydryl, DPM); silyl, such as trimethylsilyl (TMS) and tert-butyldimethylsilyl (TBS) and the like.

The structure of the compound of the present disclosure may be confirmed by conventional methods well known to those skilled in the art, and if the present disclosure relates to the absolute configuration of the compound, the absolute configuration may be confirmed by conventional technical means in the art. For example, single crystal X-ray diffraction (SXRD) may be used, wherein a cultured single crystal is analyzed by a Bruker D8 Venture diffractometer to collect diffraction intensity data, and the light source is CuKα radiation, and the scanning mode is φ/ω scanning, and after relevant data are collected, the crystal structure is further analyzed by using a direct method (Shelxs97), so that the absolute configuration can be confirmed.

The solvents used in the present disclosure are commercially available. Compounds are named according to conventional nomenclature in the art or using ChemDraw® software, and supplier's catalogue names are adopted for commercially available compounds.

DESCRIPTION OF THE ATTACHED DRAWINGS

DETAILED DESCRIPTION OF EMBODIMENTS

The present disclosure is described in detail below by way of examples. However, this is by no means disadvantageously limiting the scope of the present disclosure. The present disclosure has been described in detail herein, in which specific examples thereof are also disclosed. It will be apparent to those skilled in the art that various changes and modifications may be made to the specific embodiments of the present disclosure without departing from the spirit and scope of the present disclosure.

Calculation Example 1
Compound A
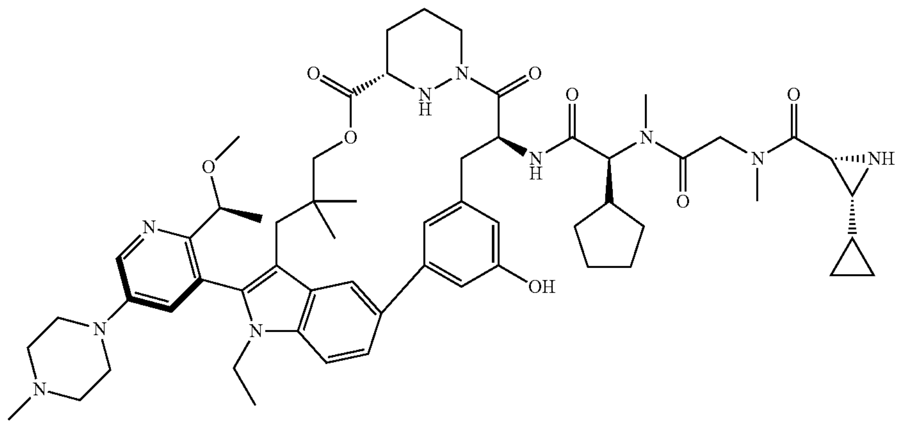
Compound B
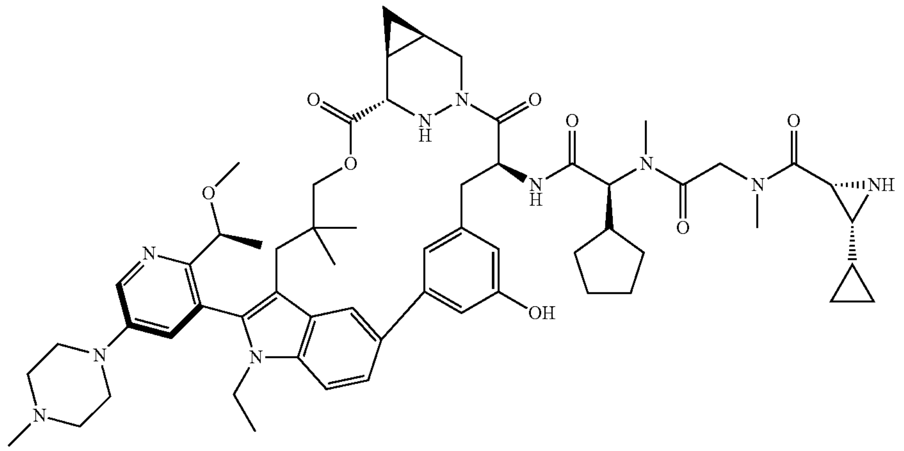
Compound C
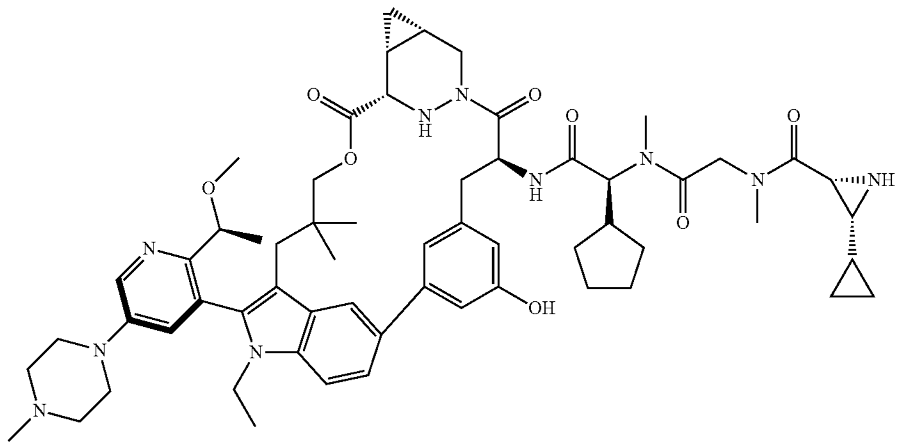

-continued
Compound D
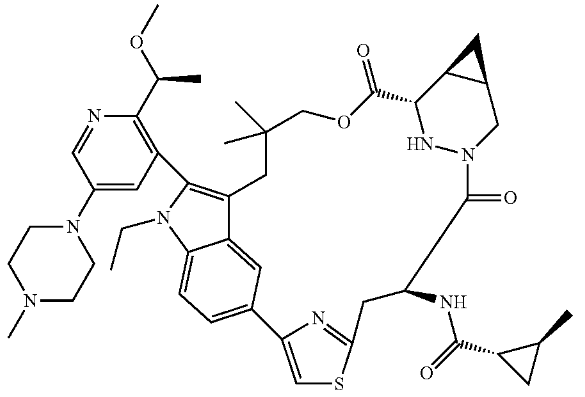
Compound E
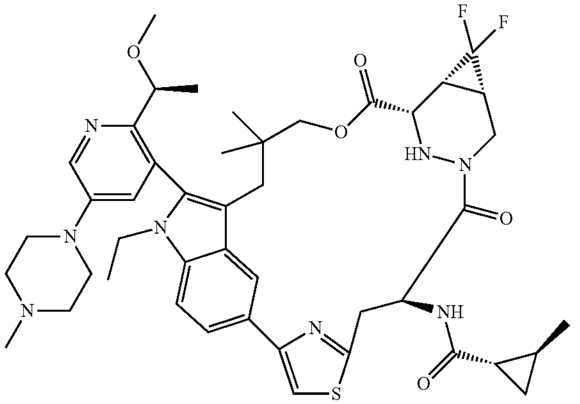
Compound F
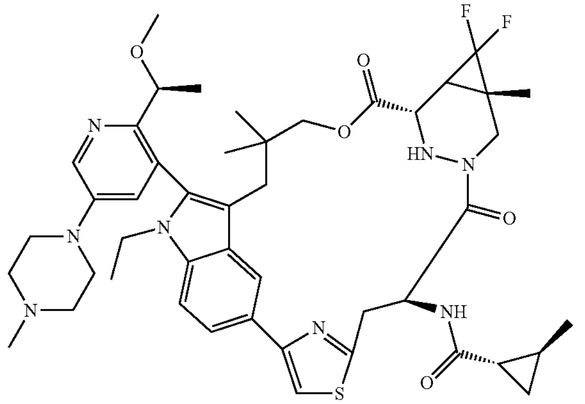
Compound G
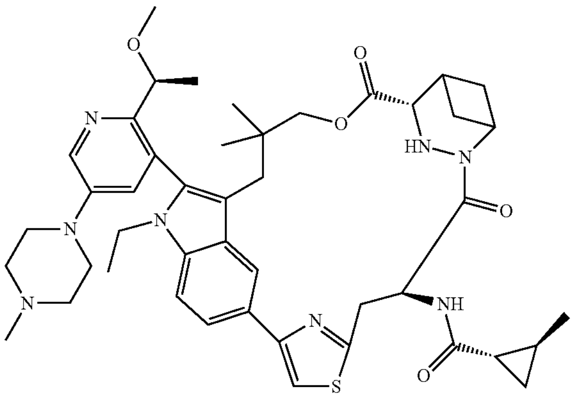
Compound H
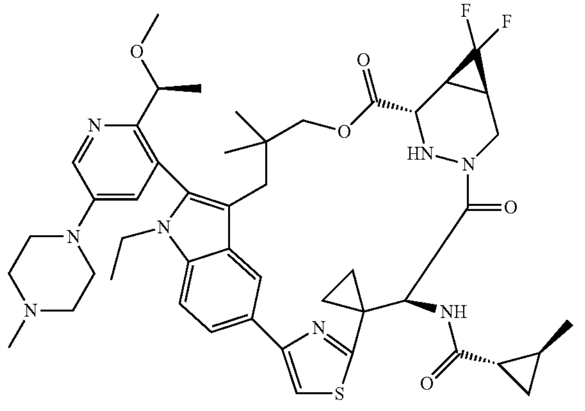
Compound I
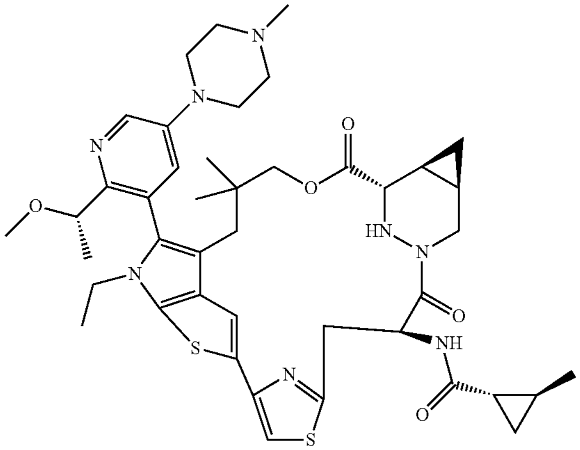

-continued

Compound J

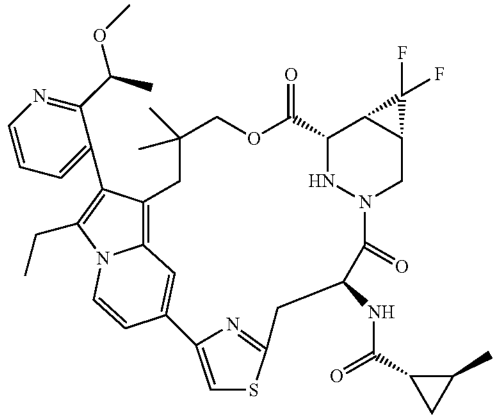

Figure 1:
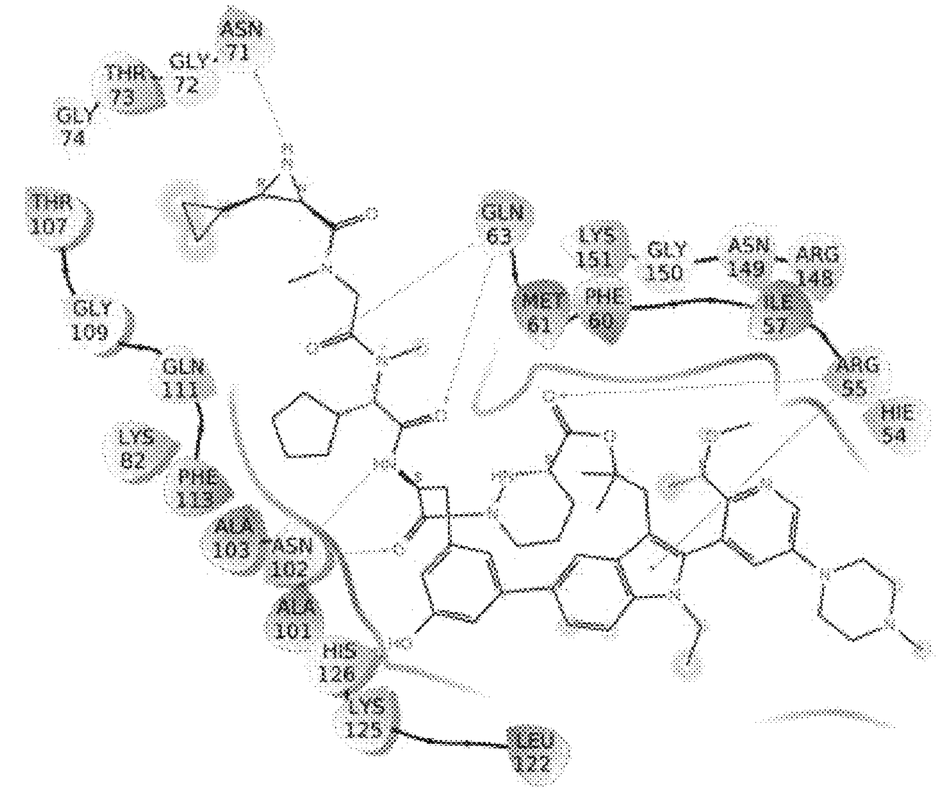
FIG. 1 shows the binding mode diagram of Compound A to CypA protein.
Figure 2:
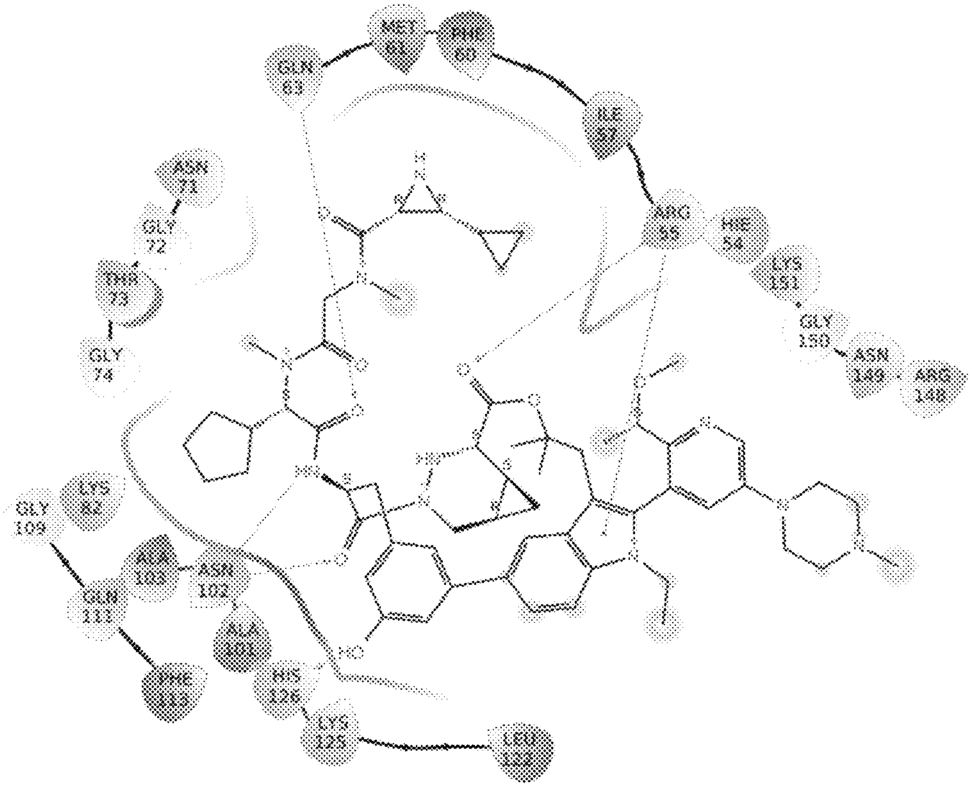
FIG. 2 shows the binding mode diagram of Compound B to CypA protein.
Figure 3:
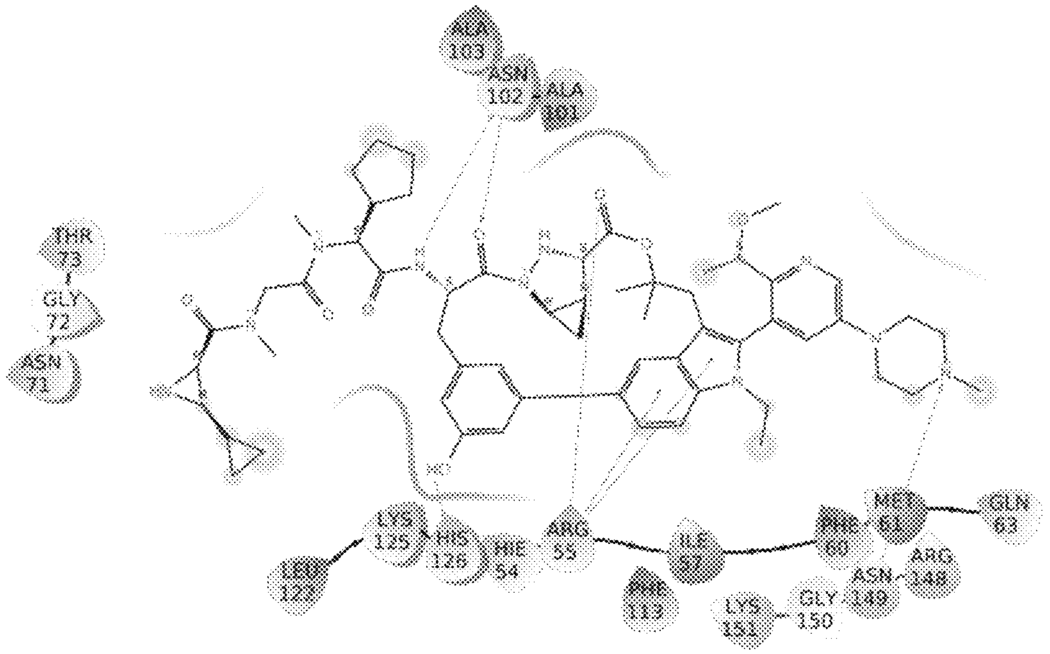
FIG. 3 shows the binding mode diagram of Compound C to CypA protein.
Figure 4:
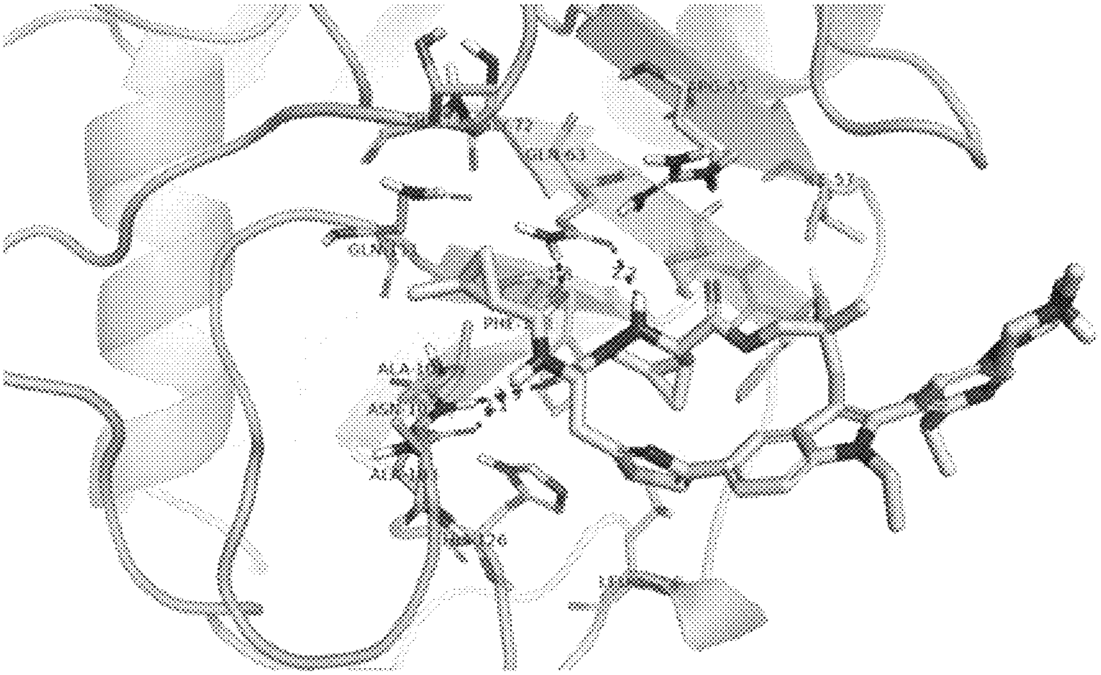
FIG. 4 shows the binding mode diagram of Compound D to CypA protein.
Figure 5:
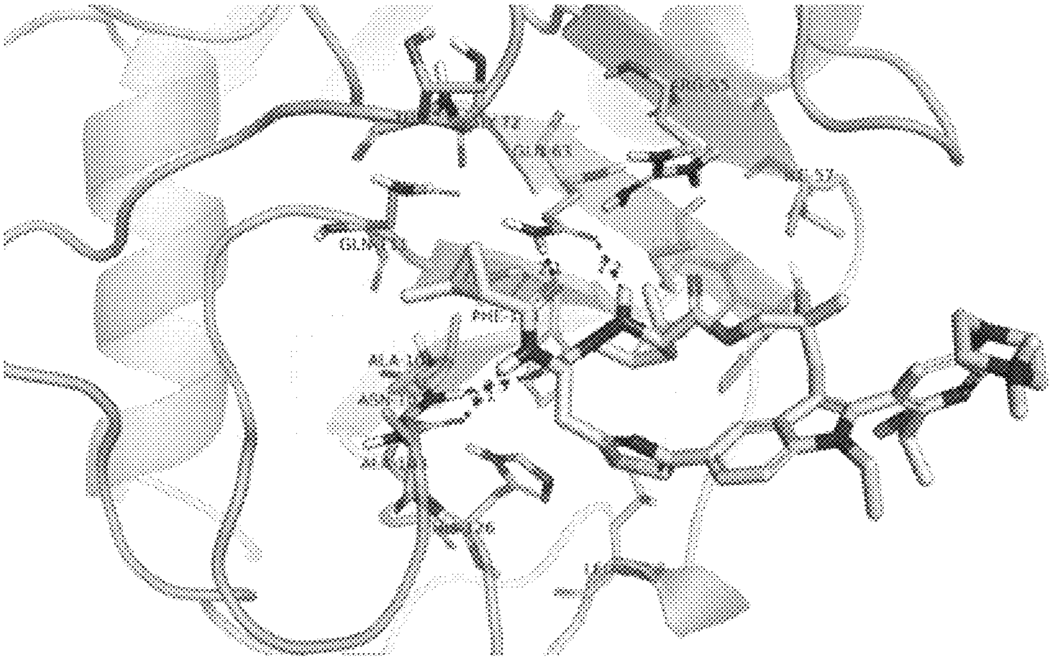
FIG. 5 shows the binding mode diagram of Compound E to CypA protein.
Figure 6:
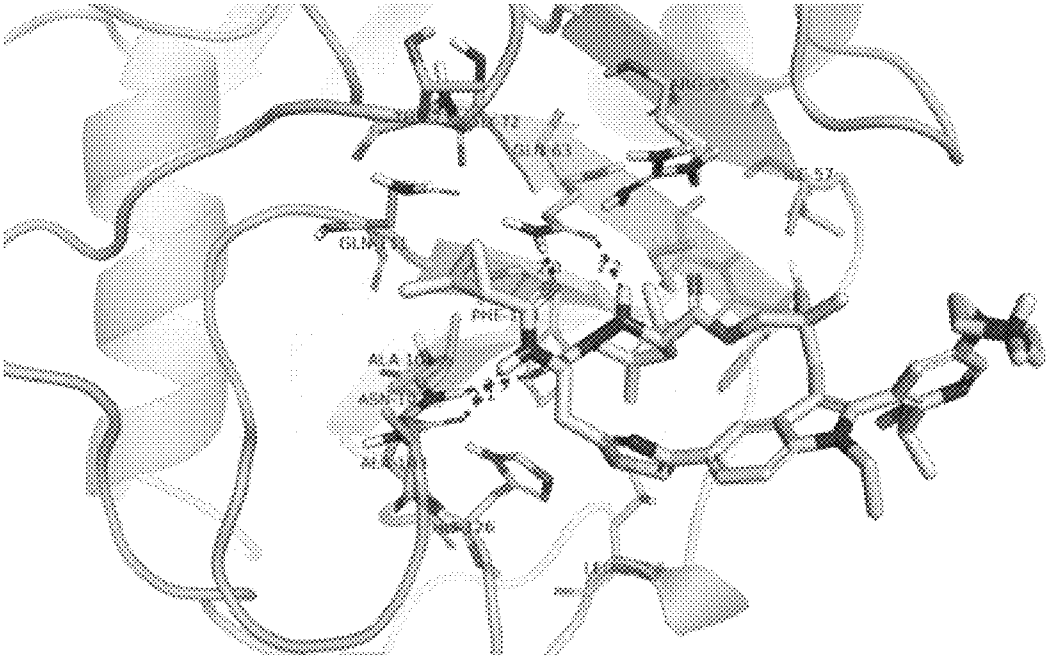
FIG. 6 shows the binding mode diagram of Compound F to CypA protein.
Figure 7:
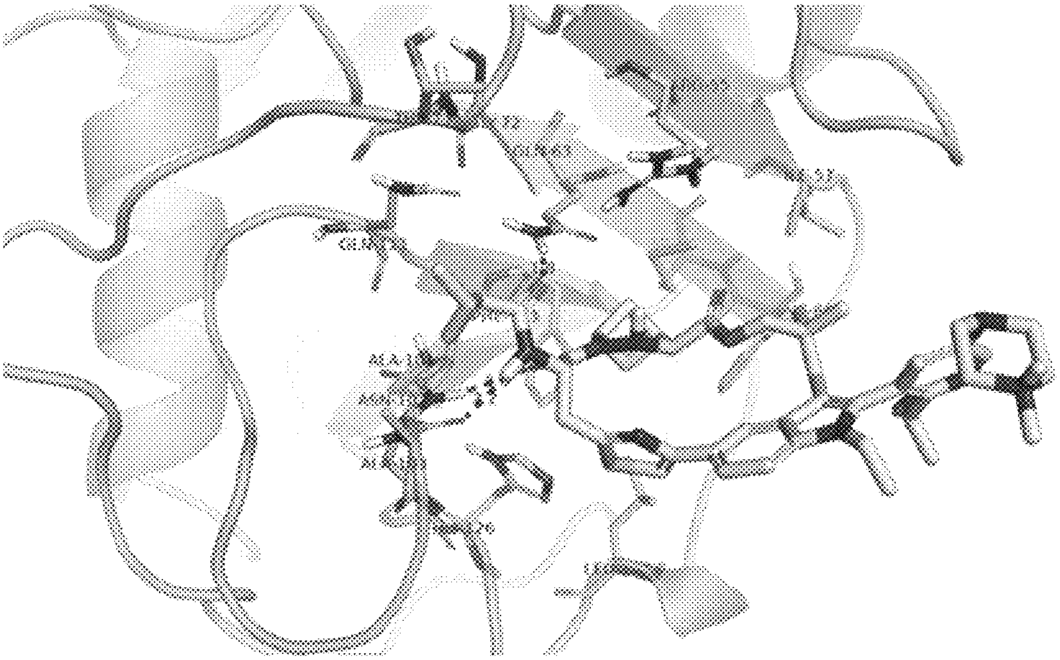
FIG. 7 shows the binding mode diagram of Compound G to CypA protein.
Figure 8:
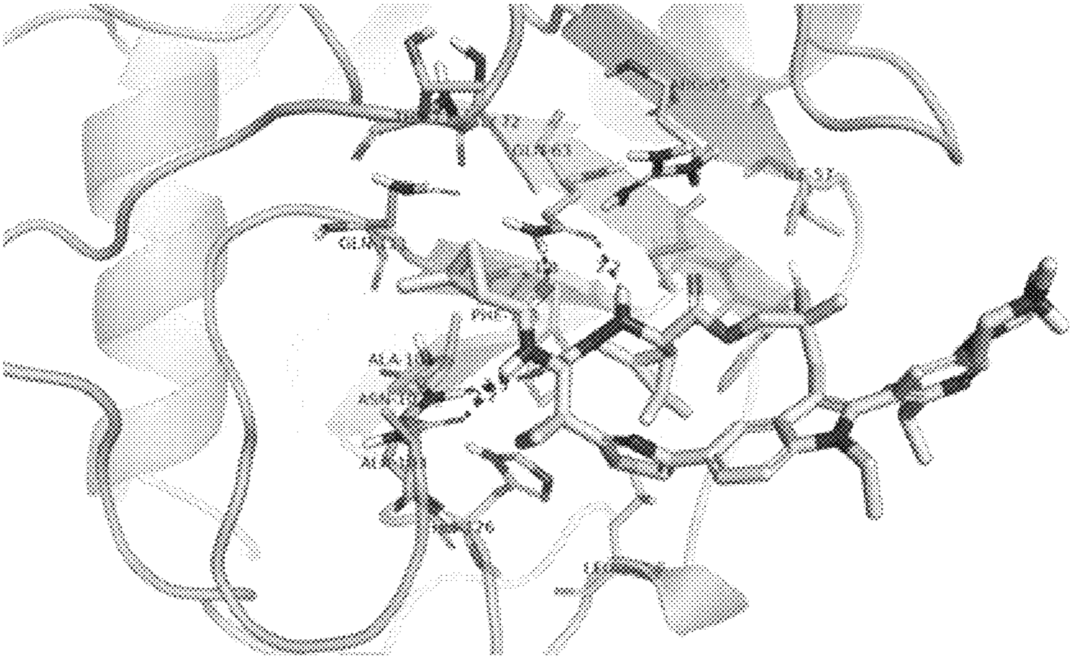
FIG. 8 shows the binding mode diagram of Compound H to CypA protein.
Figure 9:
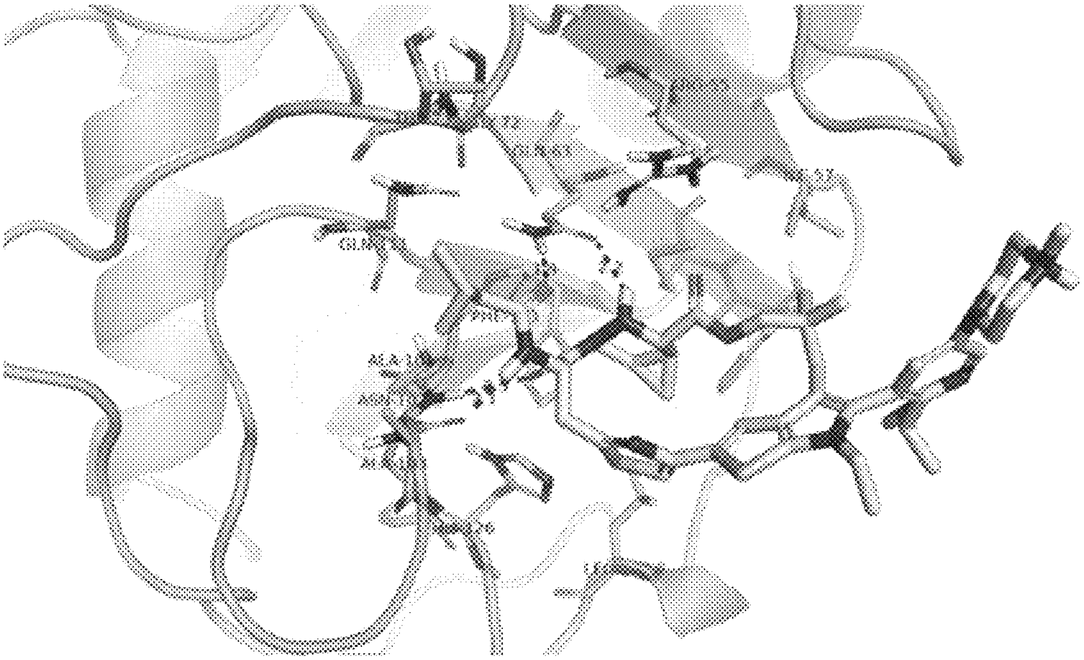
FIG. 9 shows the binding mode diagram of Compound I to CypA protein.
Figure 10:
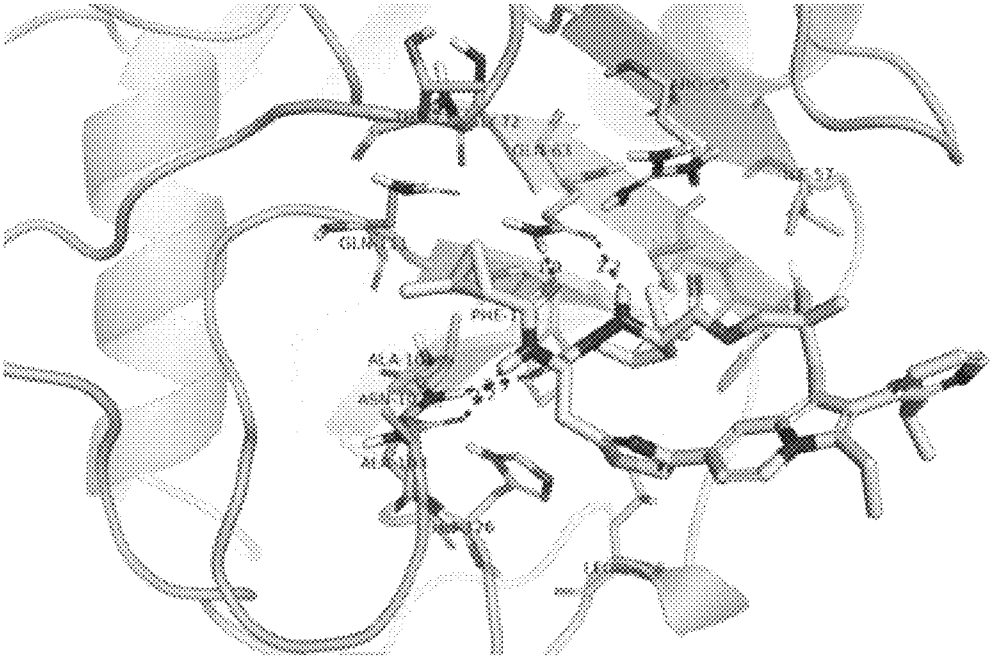
FIG. 10 shows the binding mode diagram of Compound J to CypA Protein.

The binding mode was predicted by using a eutectic complex of human CypA protein with natural product Sanglifehrin A (PDB ID code: 1YND) as the docking template. To prepare the proteins hydrogen atoms were added using the protein preparation guide module of Maestro[1] and hydrogen bonding was optimized for the eutectic structure using the OPLS4 force field to remove water molecules other than the ligand Sanglifehrin A3 Å in the eutectic complex, and energy was optimized on the whole. For ligand preparation: The molecules to be docked were generated into 3D structures and energy minimization was performed using LigPrep.[2] Induced Fit Docking[3] in Maestro (Schrödinger version 2021-2) and Protocol: Extended Sampling option were used, and Compound A was connected to the 1YND protein structure to be completed. The best binding model was selected, see FIG. 1. The selected model maintained the major hydrogen bonding of the ligand Sanglifehrin A to the protein in the original eutectic complex. A 30 Å docking grid was generated with the centroid of Compound Ain this binding mode, and a docking model was generated with the Glide[4] Receptor Grid Generation module. Based on this docking model, the SP docking mode in Glide[3] was used for docking of Compounds B-J, and the binding mode of Compounds B-J is shown in FIG. 2-FIG. 10.

[1] Maestro, Schrödinger, LLC, New York, NY, 2021.
[2] LigPrep, Schrödinger, LLC, New York, NY, 2021.
[3] Induced Fit Docking protocol; Glide, Schrödinger, LLC, New York, NY, 2021; Prime, Schröding; LLC, New York, NY, 2021.
[4] Glide, Schrödinger, LLC. New York, NY, 2021.

Conclusion: The compounds of the present disclosure bind relatively well to human Cyp A protein. The compounds of the present disclosure form hydrogen bonds with Arg55, G1n63, Asn102, and His126. Additionally, Arg55 forms a cation a bond with the indole ring. As the compounds of the present disclosure act on the surface of proteins, the hydrogen bonds listed as anchor points not only replicate the binding mode of natural product Sanglifehrin Ain the eutectic complex, but also tightly fix the compounds of the present disclosure on the surface of proteins. The binding of the compounds of the present disclosure to CypA blocks the binding of RAS downstream RAF to RAS, thereby inhibiting the RAS-RAF-MEK-ERK signaling pathway to achieve an anti-tumor effect.

Reference Example 1: Compound M1

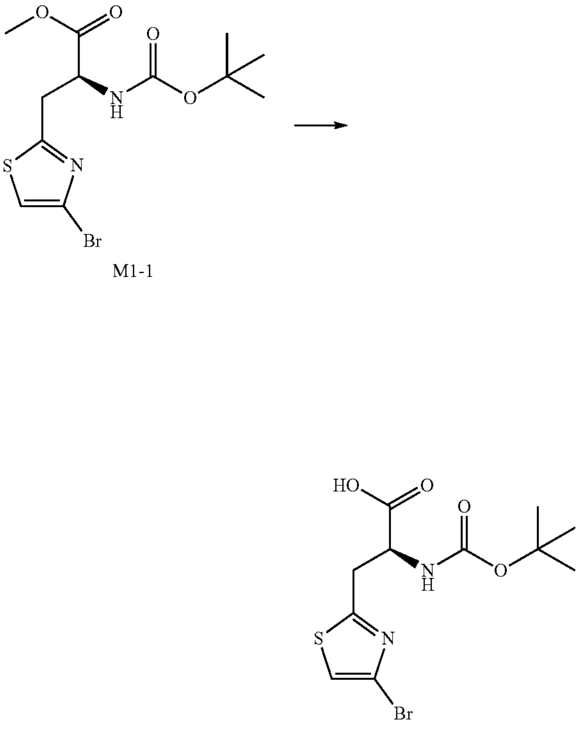

M1-1

M1

Compound M1-1 (39 g, 106.78 mmol) was dissolved in water (100 mL) and tetrahydrofuran (200 mL), lithium hydroxide monohydrate (13.44 g, 320.33 mmol) was added, and the reaction solution was stirred and reacted at 25° C. for 1.5 hours. After the reaction was completed, the pH of the reaction solution was adjusted to 5-6 with 2 M dilute hydrochloric acid, and then the reaction solution was extracted with ethyl acetate (200 mL*3). The organic phases were washed with saturated brine, dried with anhydrous sodium sulfate, and distilled under reduced pressure to remove the organic solvent to obtain Compound M1. LCMS: m/z=372.8, 374.8 [M+23]+.

Reference Example 2: Compound M2

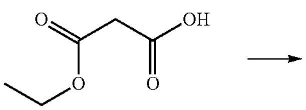

M2-1

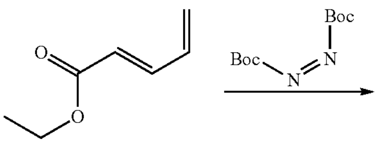

M2-2

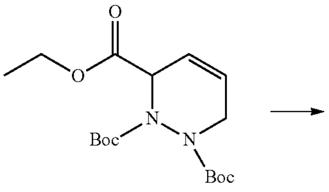

M2-3

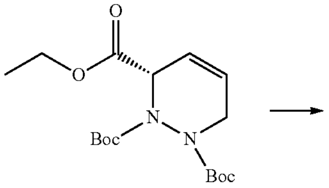

M2-3A

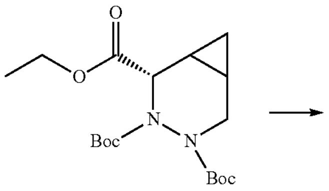

M2-5

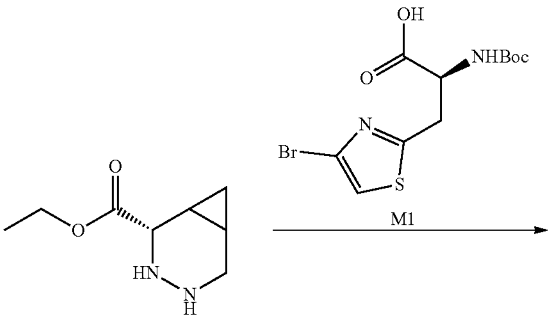

M1

M2-6

-continued

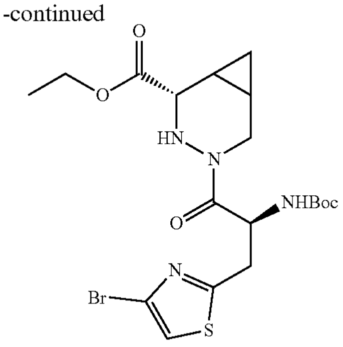

M2

Step 1

Compound M2-1 (150 g, 1.14 mol) was dissolved in pyridine (200 mL), then 4-dimethylaminopyridine (7.4 g, 60.57 mmol) and acrolein (38.58 g, 688.11 mmol) were added. The reaction solution was stirred at 50° C. for 48 hours. The reaction solution was cooled to room temperature then poured into 2,000 mL of water, and extracted with ethyl acetate (300 mL*3). The organic phases were combined, washed with diluted hydrochloric acid (2 M, 300 mL*3), then washed once with water (500 mL), washed once with saturated brine (200 mL), dried with anhydrous sodium sulfate, filtered, and the filtrate was concentrated to obtain the crude product. Then, the crude product was distilled under reduced pressure at about −0.1 MPa, 90-95° C. to obtain Compound M2-2.

Step 2

Compound M2-2 (17 g, 134.76 mmol) and di-tert-butyl azodicarboxylate (31.03 g, 134.76 mmol) were dissolved in toluene (170 mL), and the reaction solution was stirred at 80° C. for 16 hours. The reaction solution was concentrated and the crude product was purified with a flash chromatography column (silica gel, eluent: ethyl acetate/petroleum ether, ethyl acetate proportion: 0-15%) to obtain Compound M2-3. $^1$H NMR (400 MHz, $CDCl_3$) δ ppm 5.93 (s, 2H) 5.06-5.37 (m, 1H) 4.13-4.24 (m, 3H) 3.57-3.79 (m, 1H) 1.48 (s, 18H), 1.27-1.30 (m, 3H).

Step 3

Chiral separation was performed on Compound M2-3 by SFC (column: DAICEL CHIRALPAK IC (250 mm*50 mm, 10 um); mobile phases: phase A supercritical carbon dioxide phase B: [0.1% ammonia solution in isopropanol]; B %: 20%-20%) to obtain Compound M2-3A. SFC analysis method (column: Cellulose 2 (150 mm*4.6 mm, I.D., 5 um; mobile phases: phase A supercritical carbon dioxide, phase B: [0.05% diethylamine in isopropanol], gradient elution B %: 5%-5%, column temperature: 35° C. column pressure: 1,500 psi), ee=100%, the peak time of Compound M2-3A was 2.798 min, and the peak time of the enantiomer was 2.133 min. LCMS: m/z=379.0 $[M+23]^+$.

Step 4

Under nitrogen protection, trimethylsulfoxonium iodide (3.09 g, 14.03 mmol) was dissolved in dimethyl sulfoxide (10 mL), then potassium tert-butoxide (1.26 g, 11.22 mmol) was added, and the mixture was stirred at 50° C. for 2 hours. Then, Compound M2-3A (1 g, 2.81 mmol) was added and the reaction solution was stirred at 70° C. for 12 hours. The reaction solution was diluted with water (100 mL), and the solution was extracted with ethyl acetate (50 mL*3). The organic phases were combined and washed once with saturated brine (50 mL), dried with anhydrous sodium sulfate, filtered, the filtrate was concentrated, and the crude product was purified with a flash chromatography column (silica gel, eluent: ethyl acetate/petroleum ether, ethyl acetate proportion: 0-15%) to obtain Compound M2-5. LCMS: m/z=371.2 $[M+1]^+$, $^1H$ NMR (400 MHz, $CDCl_3$) δ ppm 4.22-4.33 (m, 1H), 4.07-4.20 (m, 2H), 2.56-2.73 (m, 1H), 2.11-2.24 (m, 1H), 1.84-1.95 (m, 2H), 1.71-1.82 (m, 1H), 1.45-1.53 (m, 18H), 1.23-1.31 (m, 3H), 0.97-1.07 (m, 1H).

Step 5

Compound M2-5 (630.00 mg, 1.70 mmol) was dissolved in dichloromethane (2 mL), then trifluoroacetic acid (3.07 g, 26.93 mmol, 2 mL) was added. The reaction solution was stirred at 20° C. for 2 hours. The reaction solution was concentrated to obtain the crude trifluoroacetate of M2-6, which was directly used in the next step.

Step 6

The crude trifluoroacetate of Compound M2-6 obtained in step 5 was dissolved in dichloromethane (10 mL), then N-methylmorpholine (959.97 mg, 9.49 mmol), Compound M1 (0.4 g, 1.14 mmol), 1-ethyl-3-(3-dimethylaminopropyl) carbodiimide hydrochloride (364 mg, 1.90 mmol), 1-hydroxybenzotriazole (39 mg, 284.8 μmol) were added. The reaction solution was stirred at 25° C. for 12 hours. The reaction solution was diluted with water (50 mL), and the solution was extracted with dichloromethane (50 mL*3). The organic phases were combined and washed once with saturated brine (50 mL), dried with anhydrous sodium sulfate, filtered, and the filtrate was concentrated. The crude product was purified with a flash chromatography column (silica gel, eluent: ethyl acetate/petroleum ether, ethyl acetate proportion: 0-60%) to obtain Compound M2. LCMS: m/z=503.1, 505.1 $[M+1]^+$.

Reference Example 3: Compound M3

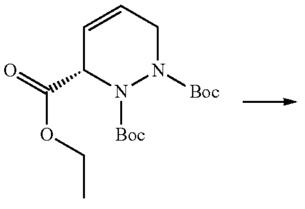

M2-3A

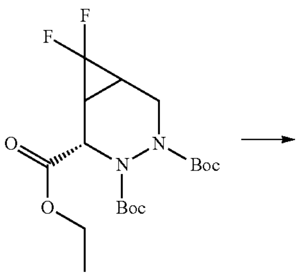

M3-1

-continued

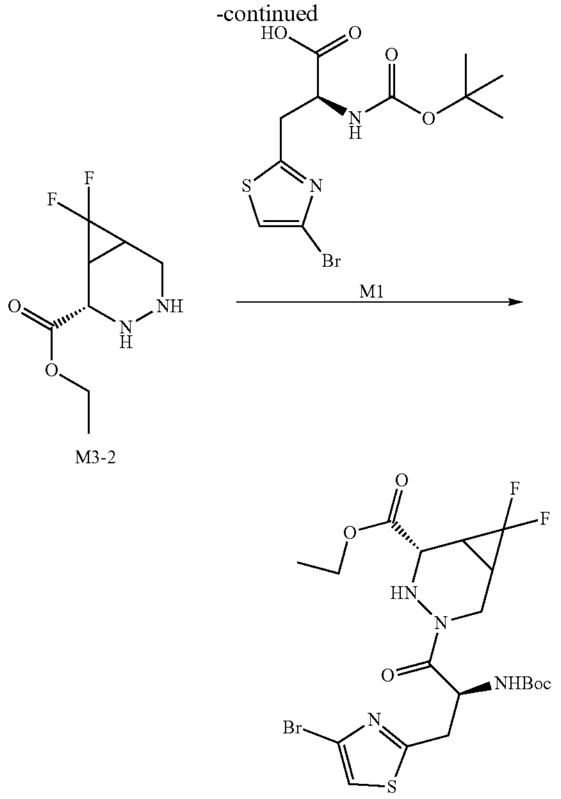

M3-2

M3

Step 1

Tetrabutylammonium bromide (116.14 mg, 360.26 μmol) and difluorobromomethyhltrimethylsilane (3.66 g, 18.01 mmol) were added to a solution of Compound M2-3A (4.28 g, 12.01 mmol) in toluene (24 mL). The mixture was stirred at 110° C. for 4 hours. More difluorobromomethyltrimethylsilane (3.66 g, 18.01 mmol) was added and stirred at 110° C. for 16 hours. More difluorobromomethyltrimethylsilane (3.66 g, 18.01 mmol) continued to be added and stirred at 110° C. for 4 hours. More difluorobromomethyltrimethylsilane (3.66 g, 18.01 mmol) was added again and stirred at 110° C. for 16 hours. The solution was concentrated under reduced pressure to remove toluene, 20 mL of water was added to the residue, and extracted with ethyl acetate (20 mL*3). The organic phases were combined, washed with saturated brine (10 mL*1), dried with anhydrous sodium sulfate, filtered, and the filtrate was concentrated under reduced pressure. The residue was purified by flash silica gel column chromatography (0-10% ethyl acetate/petroleum ether) to obtain Compound M3-1. LCMS: m/z=206.9 $[M-2Boc+1]^+$; $^1H$ NMR (400 MHz, $CDCl_3$) δ 4.96-5.25 (m, 1H) 4.17-4.51 (m, 3H) 3.19 (br s, 1H) 2.18 (br d, J=10.54 Hz, 1H) 2.00-2.11 (m, 1H) 1.40-1.55 (m, 18H) 1.30-1.38 (m, 3H).

Step 2

Compound M3-1 (1 g, 2.46 mmol) was dissolved in dichloromethane (10 mL), trifluoroacetic acid (7.68 g, 67.31 mmol, 5 mL) was added, and the reaction solution was stirred and reacted at 25° C. for 3 hours. After the reaction, the reaction solution was distilled under reduced pressure to remove the organic solvent to obtain the crude trifluoroacetate of Compound M3-2, which was used in the next step. LCMS: m/z=206.8 $[M+1]^+$.

Step 3

Compound M1 (1.04 g, 2.95 mmol) and Compound M3-2 (507 mg, crude trifluoroacetate) were dissolved in dichloromethane (10 mL) at 0° C., N-methylmorphine (2.49 g, 24.59 mmol), 1-(3-dimethylaminopropyl)-3-ethylcarbodiimide (1.41 g, 7.38 mmol), and 1-hydroxybenzotriazole (66.45 mg, 491.78 μmol) were added sequentially, and the reaction solution was stirred and reacted at 25° C. for 3 hours. The reaction solution was concentrated under reduced pressure to obtain the crude product. The crude product was purified by silica gel column chromatography (20-60% ethyl acetate/petroleum ether) to obtain Compound M3. LCMS: m/z=539.1, 541.1 $[M+1]^+$.

Reference Example 4: Compound M4

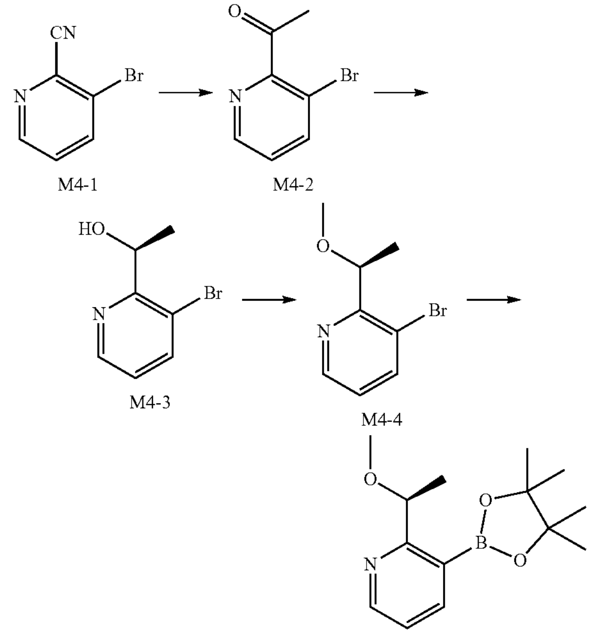

M4-1 M4-2 M4-3 M4-4 M4

Step 1

Under nitrogen protection, a solution of Compound M4-1 (25 g, 136.61 mmol) in tetrahydrofuran was added to a solution of methylmagnesium bromide in tetrahydrofuran (3 M, 91.07 mL) at 0° C. and the mixture was stirred at 0° C. for 2 hours. The reaction solution was slowly poured into ice water, and concentrated hydrochloric acid was added to adjust the pH to 6-7. Ethyl acetate was added for extraction (500 mL*2). The organic phases were combined, then dried with anhydrous sodium sulfate, filtered, and the filtrate was concentrated under reduced pressure. The residue was purified by flash silica gel column chromatography (ethyl acetate/petroleum ether 0-30%) to obtain M4-2. LCMS: m/z=200.0, 202.0 $[M+1]^+$; $^1H$ NMR (400 MHz, $CDCl_3$) δ 8.58 (d, J=3.2 Hz, 1H) 8.00 (d, J=8.4 Hz, 1H) 7.29 (dd, J=8.4, 4.8 Hz, 1H) 2.69 (s, 3H).

Step 2

Under nitrogen protection, Compound [(η-6-Cymene)[(S,S)-1,2-diphenyl-N-tosyl-1,2-ethanediaminato]ruthenium] chloride (700.83 mg, 1.10 mmol) was added to a mixed solvent of formic acid (12.68 g, 263.96 mmol) and triethylamine (133.55 g, 1.32 mol, 183.70 mL) at 0° C. Then, it was stirred at 40° C. for 15 minutes, then cooled to 25° C., M4-2 (22 g, 109.98 mmol) was added, then stirred at 40° C. for 2 hours. The reaction solution was concentrated under reduced pressure, and the residue was diluted with 100 mL, and extracted with ethyl acetate (50 mL*2). The organic phases were combined, then dried with anhydrous sodium sulfate, filtered, and concentrated under reduced pressure to obtain the crude product. The crude product was subjected to flash silica gel column chromatography (ethyl acetate/petroleum ether 0-40%) to obtain Compound M4-3. LCMS: m/z=202.0, 204.0 $[M+1]^+$; $^1H$ NMR (400 MHz, $CDCl_3$) δ 8.50 (d, J=4.8 Hz, 1H) 7.84 (d, J=8.0 Hz, 1H) 7.13 (dd, J=8.0, 4.8 Hz, 1H) 5.11 (br s, 1H) 4.44 (br s, 1H) 1.44 (d, J=4.8 Hz, 3H).

Step 3

Under nitrogen protection, sodium hydrogen (5.23 g, 130.66 mmol, 60% purity) was added to a solution of Compound M4-3 (22 g, 108.88 mmol) in tetrahydrofuran (200 mL) in batches at 0° C. The solution was stirred at 0° C. for 1 hour and iodomethane (217.77 mmol, 13.56 mL) was added. After addition, the mixture was slowly warmed from 0° C. to 25° C. and stirred at this temperature for 2 hours. The mixture was quenched by adding saturated ammonium chloride aqueous solution (100 mL) at (PC and water (200 mL) was added, then the solution was extracted with ethyl acetate (100 mL*2). The combined organic phases were collected, dried with anhydrous sodium sulfate, filtered, and the filtrate was concentrated under reduced pressure. The crude product was separated and purified with a silica gel column (ethyl acetate:petroleum ether 0-20%) to obtain Compound M4-4. LCMS: m/z=216.0, 218.0$[M+1]^+$; $^1H$ NMR (400 MHz, $CDCl_3$) δ 8.59 (d, J=3.2 Hz, 1H) 7.82 (dd, J=8.4, 3.2 Hz, 1H) 7.08 (dd, J=8.0, 4.4 Hz, 1H) 4.91 (dd, J=13.2, 6.4 Hz, 1H) 3.29 (s, 3H) 1.44 (d, J=4.8 Hz, 3H).

Step 4

Bis(pinacolato)diboron (7.05 g, 27.77 mmol), Pd(dppf)$Cl_2$ (1.69 g, 2.31 mmol) and potassium acetate (4.54 g, 46.28 mmd) were added to a solution of Compound M4-4 (5 g, 23.14 mmol) in toluene (50 mL). After the addition, nitrogen was replaced three times. The solution was stirred at 100° C. for 3 hours. It was cooled to room temperature, water (100 mL) was added, and then extracted with ethyl acetate (50 mL*2). The combined organic phases were collected, dried with anhydrous sodium sulfate, filtered, the filtrate was concentrated under reduced pressure, and the crude product was separated and purified with a silica gel column (ethyl acetate:petroleum ether 0-25%) to obtain Compound M4 LCMS: m/z=182.0 [boric acid M+1]+; $^1H$ NMR (400 MHz, $CDCl_3$) δ 8.59 (dd, J=4.8, 1.6 Hz, 1H) 7.90 (dd, J=7.6, 2.0 Hz, 1H) 7.16 (dd, J=8.4, 4.8 Hz, 1H) 4.77 (dd, J=13.2, 6.4 Hz, 1H) 3.61 (s, 3H) 3.26 (s, 3H) 1.37 (s, 12H).

Reference Example 5: Compound M5

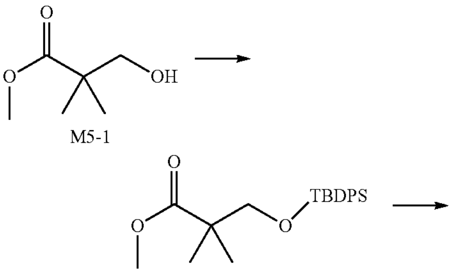

M5-1 M5-2

-continued

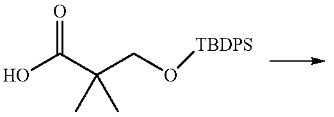

M5-3

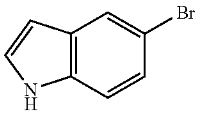

M5-5

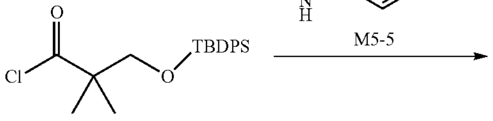

M5-4

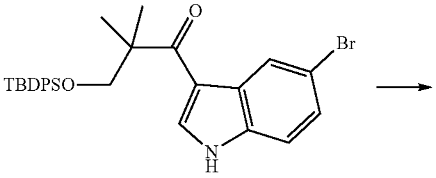

M5-6

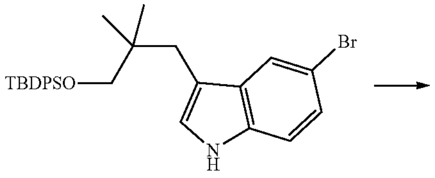

M5-7

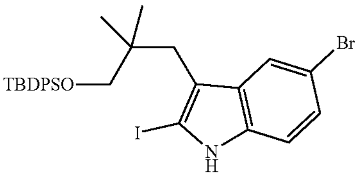

M5

Step 1

Compound M5-1 (18.3 g, 138.47 mmol), tert-butyldiphenylchlorosilane (40 g, 145.53 mmol) and imidazole (12.3 g, 180.68 mmol) were dissolved in 300 mL of anhydrous and the mixture was stirred at 15° C. for 20 hours. The mixture was concentrated, the crude product was diluted with 200 mL of water, and extracted with ethyl acetate (3*200 mL). The organic phases were dried with anhydrous sodium sulfate, filtered, and concentrated under reduced pressure. The residue was purified with a flash chromatography column (silica gel, eluent: ethyl acetate/petroleum ether, ethyl acetate proportion: 0-10%) to obtain Compound M5-2. $^1$H NMR (400 MHz, $CDCl_3$) δ=7.67 (dd, J=1.6, 8.0 Hz, 4H) 7.49-7.36 (m, 6H) 3.70 (s, 3H) 3.66 (s, 2H) 1.22 (s, 6H) 1.05 (s, 9H).

Step 2

Compound M5-2 (51 g, 137.63 mmol) and potassium hydroxide (16.51 g, 294.35 mmol) were dissolved in 200 mL of water and 200 mL of ethanol, and the mixture was stirred at 90° C. for 3 hours. The reaction solution was concentrated until about 250 mL was remaining, 500 mL of ethyl acetate w added for dilution, the pH was adjusted to 3-4 with concentrated hydrochloric acid, and the solution was separated. The aqueous phase was extracted with ethyl acetate (2*500 mL). The organic phases were combined, dried with anhydrous sodium sulfate, filtered, and concentrated to obtain Compound M5-3. $^1$H NMR (400 MHz, $CDCl_3$) δ=7.58 (dd, J=1.6, 8.0 Hz, 4H) 7.39-7.27 (m, 6H) 3.58 (s, 2H) 1.15 (s, 6H) 0.97 (s, 9H).

Step 3

Oxalyl chloride (233.64 mmol, 20.45 mL) was slowly added drop wise to Compound M5-3 (49 g, 137.44 mmol) and DMF (13.74 mmol, 1.06 mL) in 500 mL of anhydrous dichloromethane at 0° C., and the mixture was stirred at 20° C. for 15 hours. The reaction solution was concentrated, 300 mL of anhydrous toluene was added, and concentrated under reduced pressure to obtain Compound MS-4.

Step 4

Tin tetrachloride (136.00 mmol, 15.92 mL) was slowly added to a solution of Compound MS-4 (51.00 g, 136.00 mmol) in 200 mL of anhydrous dichloromethane at 0° C., and the mixture was stirred under nitrogen atmosphere for half an hour. Compound M5-5 (26.66 g, 136 mmol) in 200 mL of anhydrous dichloromethane was slowly added dropwise to the above reaction mixture at 0° C., and the reaction system was stirred at 0° C. for 1 hour under nitrogen atmosphere. 500 mL of water was added for quenching, the mixture was filtered, and the filtrate was left to stand to separate. The aqueous phase was extracted with dichloromethane (3*500 mL). The organic phases were combined, dried with anhydrous sodium sulfate, filtered, and the filtrate was concentrated. The residue was purified with a flash chromatography column (silicagel, eluent: ethyl acetate/petroleum ether, ethyl acetate proportion: 0-30%) to obtain Compound M5-6. LCMS: m/z=534.1, 536.1 $[M+1]^+$; $^1$H NMR (400 MHz, $CDCl_3$) δ=8.70 (d, J=1.6 Hz, 1H) 8.62 (brs, 1H) 7.69 (d, J=3.2 Hz, 1H) 7.57-7.51 (m, 4H) 7.44-7.39 (m, 2H) 7.38-7.27 (m, 6H) 3.96-3.88 (m, 2H) 1.44 (s, 6H) 0.98 (s, 9H).

Step 5

Lithium borohydride-tetrahydrofuran solution (1 M, 123.47 mL) was slowly added dropwise to Compound M5-6 (22 g, 41.16 mmol) in 220 mL of anhydrous tetrahydrofuran at 0° C. under a nitrogen atmosphere. After dropwise addition, the temperature was increased to 60° C., and the mixture was stirred for 15 hours. It was cooled to room temperature, 10 mL of saturated ammonium chloride aqueous solution was added dropwise sequentially, then 100 mL of ethyl acetate was added, and it was washed with 50 mL of saturated brine. The organic phases were collected, dried with anhydrous sodium sulfate, filtered, and the filtrate was concentrated. The residue was purified with a flash chromatography column (silica gel, eluent: ethyl acetate/petroleum ether, ethyl acetate proportion: 0-20%) to obtain Compound MS-7. LCMS: m/z=520.1, 522.1 $[M+1]^+$.

Step 6

Compound M5-7 (18.5 g, 35.54 mmol), elemental iodine (9.02 g, 35.54 mmol) and silver triflate (10.04 g, 39.09 mmol) were sequentially added to 185 mL of anhydrous tetrahydrofuran and the mixture was stirred at 20° C. for 2 hours. 50 mL of saturated sodium sulfite aqueous solution was added for quenching, 200 mL of ethyl acetate was added for dilution, filtered, and the filtrate was left to stand to separate. The organic phases were combined, dried with anhydrous sodium sulfate, filtered, and the filtrate was concentrated to obtain Compound M5. $^1$H NMR (400 MHz, $CDCl_3$) δ=8.07 (s, 1H) 7.78-7.69 (m, 5H) 7.49-7.40 (m, 6H) 7.24-7.20 (m, 1H) 7.19-7.16 (m, 1H) 3.50 (s, 2H) 2.71 (s, 2H) 1.17 (s, 9H) 0.95 (s, 6H).

Reference Example 6: Compound M6

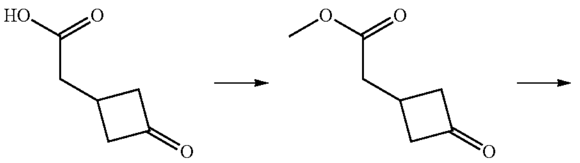

M6-1 M6-2

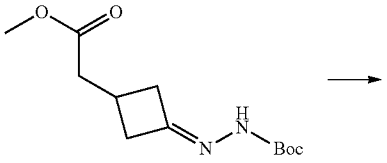

M6-3

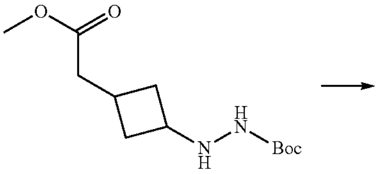

M6-4

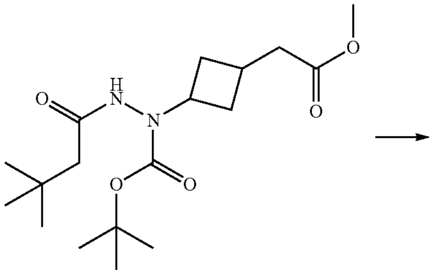

M6-5

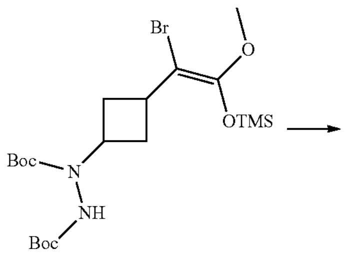

M6-6

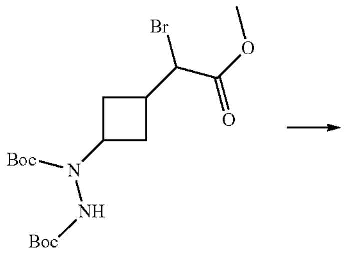

M6-7

-continued

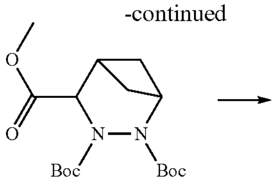

M6-8

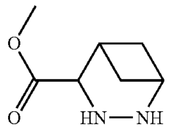

M6

Step 1

Compound M6-1 (10 g, 78.05 mmol) was dissolved in DCM (100 mL) and MeOH (20 mL) and a solution of trimethylsilyldiazomethane in n-hexane (2 M, 78.05 mL) was added dropwise at (PC. Stirring was continued at 0° C. for 10 minutes. The mixture was concentrated to obtain Compound M6-2, which was directly used in the next step.

Step 2

Compound M6-2 (10 g, 70.35 mmol) was dissolved in n-heptane (200 mL), tert-butyl carbazate (11.69 g, 70.35 mmol) was added, then the mixture was warmed to 70° C. and stirred for 12 hours. Stirring was stopped, water (100 mL) and ethyl acetate (1(0) mL) were added when the system cooled to room temperature, and the separated organic phases were dried with anhydrous sodium sulfate, filtered, and the filtrate was concentrated to obtain Compound M6-3, which was directly used in the next step. LCMS: m/z=201 [M+1-56].

Step 3

Under nitrogen protection, a solution of Compound M6-3 (7 g, 27.31 mmol) in tetrahydrofuran (10 mL) was slowly added dropwise to borane dimethylsulfide (10 M, 273.12 mL) g 0° C., stirred at 0° C. for half an hour, then warmed to room temperature and stirring was continued for 1 hour. Methanol (250 mL) was slowly added dropwise at 0° C. to quench the reaction. After the quenched reaction solution was concentrated under reduced pressure, the crude product obtained was purified by column chromatography (eluent: ethyl acetate/petroleum ether 3% to 7%) to obtain Compound M6-4. LCMS: m/z=203 $[M+1-56]^+$.

Step 4

Compound M6-4 (1.7 g, 6.58 mmol) was dissolved in tetrahydrofuran (30 mL), di-tert-butyl dicarbonate (2.15 g, 9.87 mmol), triethylamine (2.0) g, 19.74 mmol) and 4-dimethylaminopyridine (80.40 mg, 658.12 μmol) were added sequentially at 25° C. and stirred at 25° C. for 1 hour Water (50 mL) and ethyl acetate (30 mL) were added to the reaction system. The extracted organic phases were dried with anhydrous sodium sulfate, and the filtrate was concentrated. The obtained crude product was purified by column chromatography (eluent: ethyl acetate/petroleum ether 3% to 7%) to obtain Compound M6-5. LCMS: m/z=359 $[M+1]^+$.

Step 5

Compound M6-5 (585 mg, 1.63 mmol) was dissolved in tetrahydrofuran (20 mL). Under nitrogen protection, lithium bis(trimethylsilyl)amide (1 M, 4.90 mL) was added dropwise at −70° C., stirred at −70° C. for half an hour and then trimethylsilyl chloride (531.94 mg, 4.90 mmol) was added dropwise. After stirring was continued at −70° C. for 1 hour, N-bromosuccinimide (1.16 g, 6.53 mml) was added dropwise, slowly warmed to 25° C. and stirring continued for 1 hour. Saturated brine (30 mL) was added and the solution was extracted with ethyl acetate (30 mL). The organic phases were dried with anhydrous sodium sulfate, filtered, and the filtrate was concentrated to obtain Compound M6-6, which was directly used in the next step. LCMS: m/z=353, 355 $[M+1-100-56]^+$.

Step 6

A solution of citric acid (618.66 mg, 2.94 mmol) in water (5 mL) was added to Compound M6-6 (500 mg, 981.34 μmol) in tetrahydrofuran (20 mL) and stirred at 25° C. for 1 hour. After the reaction was completed, saturated brine (30 mL) was added and the solution was extracted with ethyl acetate (30 mL). The organic phases were dried with anhydrous sodium sulfate, filtered, the filtrate was concentrated and purified by column chromatography (eluent: ethyl acetate/petroleum ether 3% to 7%) to obtain Compound M6-7. LCMS: m/z=281, 283 $[M+1-100-56]^+$.

Step 7

Compound M6-7 (150 mg, 342.99 μmol) was dissolved in acetonitrile (20 mL), cesium carbonate (447.02 mg, 1.37 mmol) was added, heated to 60° C. and stirred for 12 hours. The mixture was filtered, the filtrate was concentrated and purified by column chromatography (eluent: ethyl acetate/petroleum ether 3% to 7%) to obtain Compound M6-8. LCMS: m/z=201$[M+1-100-56]^+$. $^1$H NMR (400 MHz, $CDCl_3$) 5.24-4.93 (m, 1H) 4.45 (br d, J=4.6 Hz, 1H) 3.77-3.71 (m, 3H) 2.89 (qd, J=5.8, 11.6 Hz, 1H) 2.39 (td, J=4.9, 10.0 Hz, 1H) 2.13 (td, J=5.0, 10.0 Hz, 1H) 1.62 (s, 2H) 1.52-1.48 (m, 18H).

Step 8

Compound M6-8 (50 mg, 140.29 μmol) was dissolved in methanol (5 mL) and ethyl acetate (5 mL), hydrogen chloride ethyl acetate solution (5 mL, 4M) was added, and stirred at 40° C. for 1 hour. The reaction solution was concentrated to obtain the hydrochloride salt of Compound M6. LCMS: m/z=157 $[M+1]^+$.

Reference Example 7; Compound M8

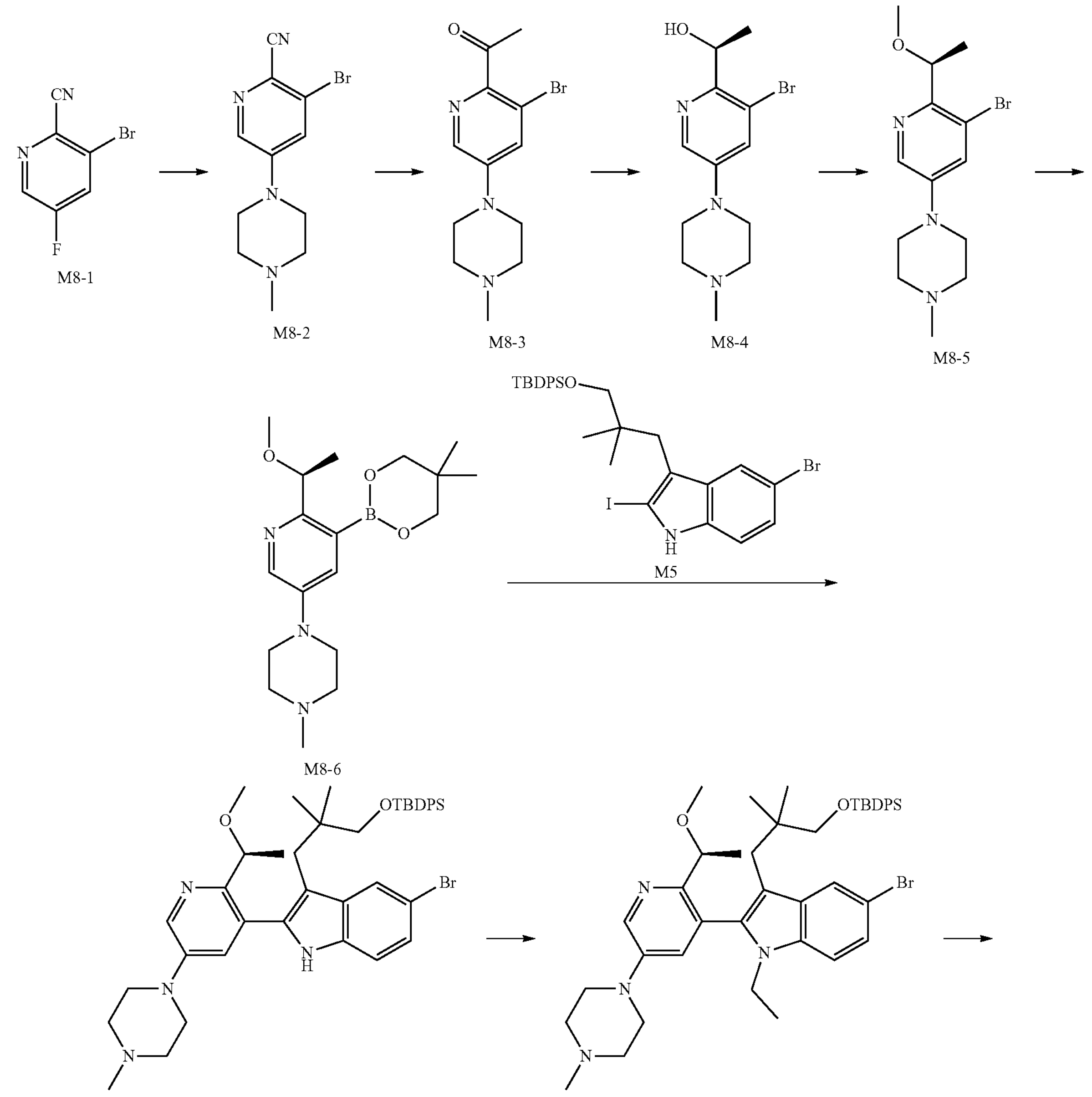

M8-1 M8-2 M8-3 M8-4 M8-5

M8-6 M5

M8-7 M8-8

-continued

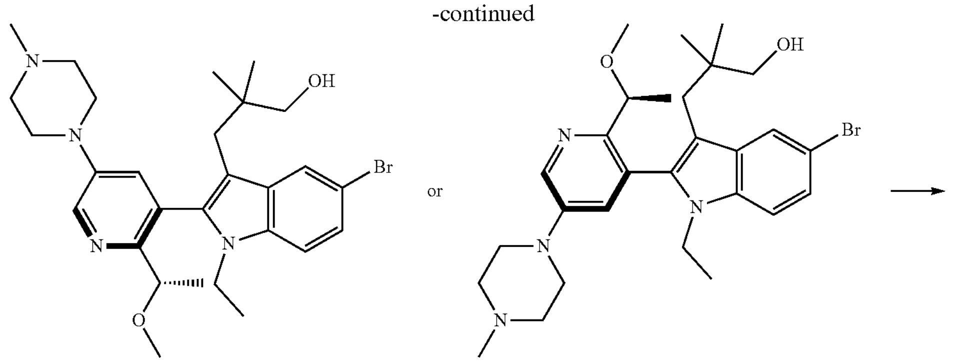

M8-9A

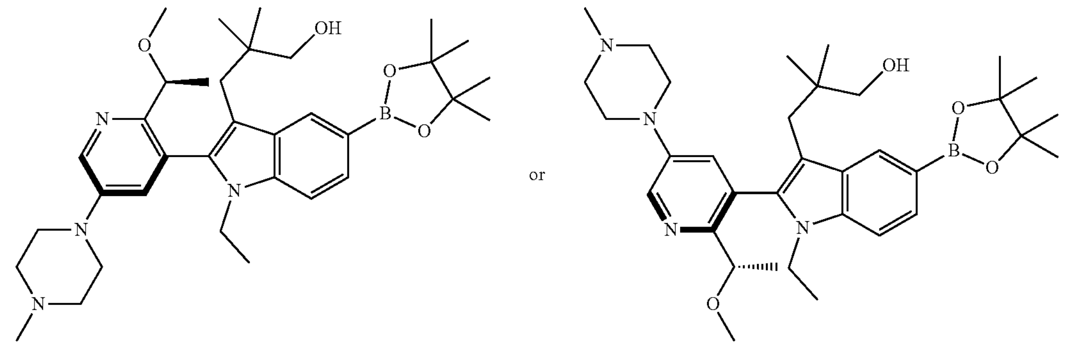

M8

Step 1

Triethylamine (111.94 mmol, 15.58 mL) and 1-methylpiperazine (16.82 g, 167.91 mmol 18.63 mL) were added to a solution of M8-1 (22.5 g, 111.94 mmol) in tetrahydrofuran (250 mL, then the mixture was stirred at 60° C. for 16 hours. The reaction solution was diluted with water (200) mL), and the solution was extracted with ethyl acetate (00 mL*3). The organic phases were combined and washed once with saturated brine (100 mL), dried with anhydrous sodium sulfate, filtered, and the filtrate was directly concentrated. The crude product obtained was added with petroleum ether (100 mL), filtered, and the filter cake was dried to obtain Compound M8-2. $^1H$ NMR (400 MHz, DMSO-$d_6$) δ ppm 8.40 (d, J=2.4 Hz, 1H) 7.65 (d, J=2.4 Hz, 1H) 3.42-3.48 (m, 4H) 2.36-2.44 (m, 4H) 2.21 (s, 3H).

Step 2

Compound M8-2 (10 g, 35.57 mmol) was dissolved in tetrahydrofuran (150 mL). Under nitrogen protection, methylmagnesium chloride (3 M tetrahydrofuran solution, 23.7 mL) was added at 0° C. The reaction solution was stirred at 0° C. for 2 hours. Saturated ammonium chloride (100 mL) w poured into the reaction solution for quenching, and the solution was extracted with ethyl acetate (100 mL*3). The organic phases were combined and washed once with saturated brine (100 mL), dried with anhydrous sodium sulfate, filtered, and the filtrate was directly concentrated. The obtained crude product was purified with a flash chromatography column (silicagel, eluent: methanol/dichloromethane, methanol proportion: 0-10%) to obtain Compound M8-3. LCMS: m/z=298.1, 300.1 $[M+1]^+$. $^1H$ NMR (400 MHz, DMSO-$d_6$) δ ppm 8.38 (d, J=2.4 Hz, 1H) 7.53 (d, J=2.4 Hz, 1H) 3.39-3.47 (m, 4H) 2.54 (s, 3H) 2.40-2.45 (m, 4H) 2.22 (s, 3H).

Step 3

Under nitrogen protection, triethylamine (57.1 g, 563.9 mmd) was added dropwise to formic acid (5.27 g, 109.67 mmol) at 0° C., then [(η-6-Cymene)[(S,S)-1,2-diphenyl-N-tosyl-1,2-ethanediaminato]ruthenium] chloride (140 mg, 220 μmol) was added. The mixture was stirred at 40° C. for 15 minutes. It was then cooled to room temperature and Compound M8-3 (6.54 g, 21.93 mmol) was added in batches. The reaction solution was heated to 50° C. and stirred for 12 hours. The reaction solution was concentrated directly, and the obtained crude product was purified with a flash chromatography column (silica gel, eluent: methanol/dichloromethane, methanol proportion: 0-10%) to obtain Compound M8-4. LCMS: m/z=300.0, 302.0$[M+1]^+$.

Step 4

Under nitrogen protection, Compound MS-4 (1 g, 3.33 mmol) was dissolved in N,N-dimethylformamide (DMF) (10 mL), cooled to 0° C., and then sodium hydrogen (160 mg, 4.00 mmol, purity 60%) was added in batches. The solution was stirred at 0° C. for 1 hour, then iodomethane (520 mg, 3.68 mmol) was added dropwise, and the reaction solution continued to react at 0° C. for 2 hours Saturated ammonium chloride (50 mL) was added dropwise to the reaction solution for quenching, and the solution was extracted with ethyl acetate (50 mL*3). The organic phases were combined and washed once with saturated brine (50 mL), dried with anhydrous sodium sulfate, filtered, and the filtrate was directly concentrated to obtain the crude product, which was purified with a flash chromatography, column (silica gel, eluent: methanol/dichloromethane, methanol proportion: 0-10%) to obtain Compound M8-5. LCMS: m/z=313.9, 316.0 $[M+1]^+$.

Step 5

Compound M8-5 (0.72 g, 2.29 mmol) and bis(neopentyl glycolato)diboron (777 mg, 3.5 mmol) were dissolved in toluene (20 mL), potassium acetate (563 mg, 5.75 mmol) and 1,1-bis(diphenylphosphino)ferrocene]palladium(II) dichloride (168 mg, 230 μmol) were successively added, nitrogen was replaced three times, and the solution was heated to 70° C. and reacted for 12 hours. The reaction solution was filtered, the filtrate was directly concentrated, and the obtained M8-6 crude product was directly used in the next step. LCMS: m/z=348.1$[M+1]^+$.

Step 6

Compound M8-6 (11.05 g, 31.82 mmol) and Compound M5 (24.69 g, 38.18 mmol) were dissolved in dioxane (100 mL) and water (20 mL), potassium carbonate (13.19 g, 95.46 mmol) was added, nitrogen was replaced three times, 1,1-bis(diphenylphosphino)ferrocene]palladium(II) dichloride (22.07 mg, 33.86 μmol) was added, and the reaction solution was stirred and reacted under nitrogen at 70° C. for 12 hours. The reaction solution was filtered, and the filtrate was concentrated under reduced pressure to obtain the crude product, which was purified by column chromatography (0-15% methanol/dichloromethane) to obtain Compound M8-7. LCMS: m/z=753.2, 755.2 $[M+1]^+$.

Step 7

Compound M8-7 (15 g, 19.90 mmol) was dissolved in tetrahydrofuran (150 mL), sodium hydrogen (4 g, 100.00 mmol, purity 60%) was added in batches at 0° C., stirred under nitrogen protection for 30 min, and then ethyl iodide (30.01 mmol, 2.4 mL) was added dropwise. The reaction solution was stirred at 0° C. for 1 hour, and ethyl iodide (25.01 mmol, 2 mL) was added again. The reaction solution was stirred and reacted at 20° C. for 30 min. The reaction solution was quenched in ice water (100 mL) in batches and extracted with dichloromethane (50 mL*3). The organic phases were washed with saturated brine (50 mL*3), dried with anhydrous sodium sulfate, and the filtrate was concentrated to obtain the Compound M8-8 crude product. LCMS: m/z=781.3, 783.3 $[M+1]^+$.

Step 8

Compound M8-8 (13.7 g, 17.52 mmol) was dissolved in tetrahydrofuran (150 mL), tetrabutylammonium fluoride in tetrahydrofuran solution (1 M, 175.21 mL) was added, and the reaction solution was stirred and reacted under nitrogen at 50° C. for 12 hours. The reaction solution was quenched with water (20 mL) and extracted with ethyl acetate (50 mL*3). The aqueous phase was extracted with dichloromethane (50 mL*3). The organic phases were washed with saturated brine, dried with anhydrous sodium sulfate, and concentrated. The remaining product was purified by column chromatography (0-15% methanol/dichloromethane) to obtain the crude product. The crude product was then added with acetonitrile (10 mL) and stirred for 10 nm, filtered, and the filter cake was then prepared by prep-HPLC (column: C18 100×40 mm; mobile phase: [water (trifluoroacetic acid)-acetonitrile]; gradient:mobile phase acetonitrile proportion was increased from 13% to 43% within 8 minutes) and purified to obtain the trifluoroacetate of Compound M8-9A (HPLC analysis method Column ChromCore 120 C18 3 μm 3.0*30 mm; phase A was a 4 L aqueous solution containing 1.5 mL trifluoroacetic acid, and phase B was a 4 L acetonitrile solution containing 0.75 mL trifluoroacetic acid; elution gradient: phase B was increased from 10% to 80% in 6 minutes, held at 80% for 0.5 minutes, and then held at 10% for 0.5 minutes; the retention time of Compound M8-9A was 3.205 min. and the retention time of the isomer thereof was 3.146 min). LCMS: m/z=543.5, 545.5 $[M+1]^+$.

Step 9

Compound M8-9A (0.6 g, 1.10 mmol) and bis(pinacolato) diboron (420.47 mg, 1.66 mmol) were dissolved in toluene (6 mL) and dioxane (2 mL), and potassium acetate (216.67 mg, 2.21 mmol), [1,1]-bis(diphenylphosphino)ferrocene]dichloropalladium(II)(80.77 mg, 110.39 μmol) were added. The reaction solution was stirred and reacted under nitrogen at 90° C. for 5 hours. The reaction solution was filtered, the filtrate was concentrated under reduced pressure, and the crude product was purified by column chromatography (0-15% methanol/dichloromethane) to obtain Compound M8. LCMS: m/z=591.4 $[M+1]^+$.

Reference Example 8: Compound M9

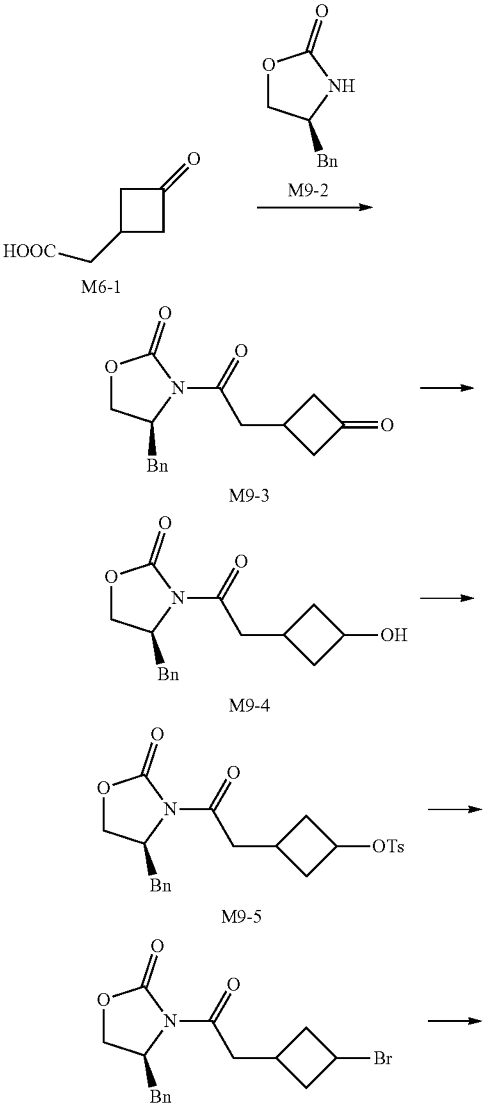

M9-2

M6-1

M9-3

M9-4

M9-5

M9-6

-continued

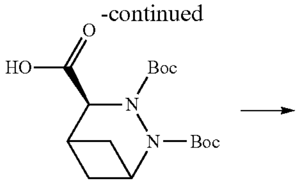

M9-7

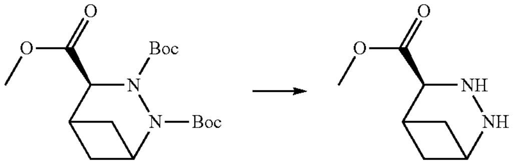

M9-8 M9

Step 1

Compound M6-1 (78.5 g, 612.68 mmol), Compound M9-2 (119.42 g, 673.95 mmol), 4-dimethylaminopyridine (7.49 g, 61.27 mmol), and triethylamine (185.99 g, 1.84 mol) were sequentially added to 1.5 L of anhydrous dichloromethane, then 2-chloro-1-methylpyridinium iodide (266.10 g, 1.04 mol) was added in batches, and the mixture was stirred at 25° C. for 1 hour. After the reaction was completed, the organic phases were washed with water (2*1 L). The organic phases were dried with sodium sulfate, filtered, and concentrated under reduced pressure to obtain Compound M9-3. $^{1}H$ NMR (400 MHz, $CDCl_3$) δ=7.40-7.31 (m, 3H) 7.25-7.19 (m, 2H) 4.79-4.66 (m, 1H) 4.29-4.20 (m, 2H) 3.43-3.26 (m, 5H) 3.01-2.79 (m, 4H).

Step 2

Compound M9-3 (220 g, 765.72 mmol) and acetic acid (91.97 g, 1.53 mol) were added sequentially to 2 L of anhydrous tetrahydrofuran and sodium borohydride (23.18 g, 612.58 mmol) was slowly added to the above solution in batches at 0° C. After the addition was completed, stirring of the mixture was continued at 0° C. for 2 hours. After the reaction was completed, 500 mL of saturated ammonium chloride aqueous solution was slowly added dropwise, concentrated under reduced pressure until about 1 L of residue was left, and the solution was extracted with ethyl acetate (3*500 mL). The organic phases were washed with saturated sodium bicarbonate to pH-8, and the organic phases were combined, dried with anhydrous sodium sulfate, filtered, and concentrated to obtain Compound M9-4. LCMS: m/z=290.1 $[M+1]^{+}$.

Step 3

4-dimethylaminopyridine (74.32 g, 608.31 mmol), Compound M9-4 (220 g, 760.39 mmol) and N,N-diisopropylethylamine (147.41 g, 1.14 mol) were sequentially added to 2 L of anhydrous dichloromethane at 0° C., and then tosyl chloride (159.46 g, 836.43 mmol) was added to the above solution in batches. After the addition was completed, the mixture was stirred at 25° C. for 3 hours. After the reaction was completed, the mixture was washed with water (1.5 L). The aqueous phase was extracted with dichloromethane (2*500 mL). The organic phases were combined, dried with anhydrous sodium sulfate, filtered, concentrated, and the residue was purified with a flash chromatography column (silicagel, eluent: ethyl acetate/petroleum ether, ethyl acetate proportion: 0-30%) to obtain Compound M9-5. $^{1}H$ NMR (400 MHz, $CDCl_3$) δ=7.81 (br d, J=8.0 Hz, 2H) 7.41-7.28 (m, 5H) 7.19 (br d, J=7.2 Hz, 2H) 4.84-4.70 (m, 1H) 4.65 (br s, 1H) 4.29-4.18 (m, 2H) 3.26 (br d, J=13.6 Hz, 1H) 3.17-2.96 (m, 2H) 2.85-2.71 (m, 1H), 2.60-2.49 (m, 2H), 2.47 (s, 3H), 2.37-2.20 (m, 1H), 1.90 (br s, 2H).

Step 4

Compound M9-5 (90 g, 202.93 mmol) and lithium bromide (35.25 g, 405.85 mmol) were sequentially added to 90 mL of 1-methyl-2-pyrrolidinone, and the mixture was stirred at 90° C. for 13 hours. After the reaction was completed, 2 L of saturated brine was added for dilution, and the solution was extracted with ethyl acetate (3*1 L). The organic phases were washed again with saturated brine (2*1 L), the organic phases were dried with anhydrous sodium sulfate, filtered, concentrated, and the residue was purified with a flash chromatography column (silica gel, eluent: ethyl acetate/petroleum ether, ethyl acetate proportion: 0-20%) to obtain Compound M9-6. LCMS: m/z=352.0, 354.0$[M+1]^{+}$.

Step 5

Compound M9-6 (9.5 g, 23.80 mmol) was dissolved in 95 mL of anhydrous tetrahydrofuran at −78° C., and then lithium diisopropylamide in 2M tetrahydrofuran n-heptane mixed solution (15.47 mL, 30.94 mmol) was slowly added dropwise and the mixture was stirred under nitrogen atmosphere for half an hour. Di-tert-butyl azodicarboxylate (6.58 g, 28.56 mmol) in 20 mL of anhydrous dichloromethane solution was added to the above solution in one portion, and the stirring was continued for half an hour. 1,3-dimethyl-3,4,5,6-tetrahydro-2(1H)-pyrimidinone (91.50 g, 713.89 mmol) was slowly added to the above reaction solution, naturally raised to room temperature, and stirring was continued for 13 hours. After the reaction was completed, 100 mL of water was slowly added for quenching, lithium hydroxide monohydrate (3.00 g, 71.39 mmol) was added, and the mixture was stirred at room temperature for 1 hour. The mixture was concentrated, the residue was diluted with 200 mL of saturated brine, washed with ethyl acetate (3*200 mL), the organic phases were discarded, the pH of the aqueous phase was adjusted to 5 with 1 N hydrochloric acid, then the solution was extracted with ethyl acetate (3*200 mL). The organic phases were washed with saturated brine (2*200 mL), dried with anhydrous sodium sulfate, filtered, concentrated, and the residue was purified with a flash chromatography column (silica gel, eluent: ethyl acetate/petroleum ether, ethyl acetate proportion: 0-30%) to obtain Compound M9-7. LCMS: m/z=365.1 $[M+23]^{+}$.

Step 6

Trimethylsilyldiazomethane in 2 M n-hexane (11.68 mL, 23.36 mmol) was slowly added dropwise to a solution of Compound M9-7 (1.6 g, 4.67 mmol) in 32 mL of anhydrous methanol at 25° C. and the mixture was stirred at 25° C. for 10 minutes. After the reaction was completed, 0.1 mL of acetic acid was added to quench the reaction. The reaction solution was concentrated to obtain Compound M9-8. LCMS: m/z=379.1 [M+23]. SFC analysis method was used for detection (column: Cellulose-4 (100 mm*4.6 mm, 3 μm; mobile phase: phase A supercritical carbon dioxide, phase B: 0.05% diethylamine in isopropanol]; B %: increased from 5% to 40% in 4 minutes, then held at 40% for 0.5 minutes, then held at 5% for 1.5 minutes) The retention time of Compound M9-8 was 1.342 min, and the chiral purity was 93.38%; the retention time of the enantiomer thereof was 1.431 min, and the chiral purity was 6.62%.

Step 7

Compound M9-8 (1.6 g, 4.49 mmol) was dissolved in 5 mL of trifluoroacetic acid and 15 mL of dichloromethane, and the mixture was stirred at 25° C. for 12 hours. After the reaction was completed, the mixture was concentrated, and 20 mL of methyl tert-butyl ether was added to the residue and stirred at room temperature for 10 min, filtered, and the filter cake was dried to obtain the trifluoroacetate of Compound M9. $^1$H NMR (400 MHz, $D_2O$) δ=4.30 (d, J=3.8 Hz, 1H) 3.97 (q, J=4.9 Hz, 1H) 3.73 (s, 3H) 2.93-2.83 (m, 1H) 2.54 (ddd, J=4.5, 6.5, 11.5 Hz, 1H) 2.39 (td, J=5.7, 11.7 Hz, 1H) 2.04 (dd, J=9.4, 11.7 Hz, 1H) 1.76 (dd, J=9.5, 12.0 Hz, 1H).

Reference Example 9: Compound M10

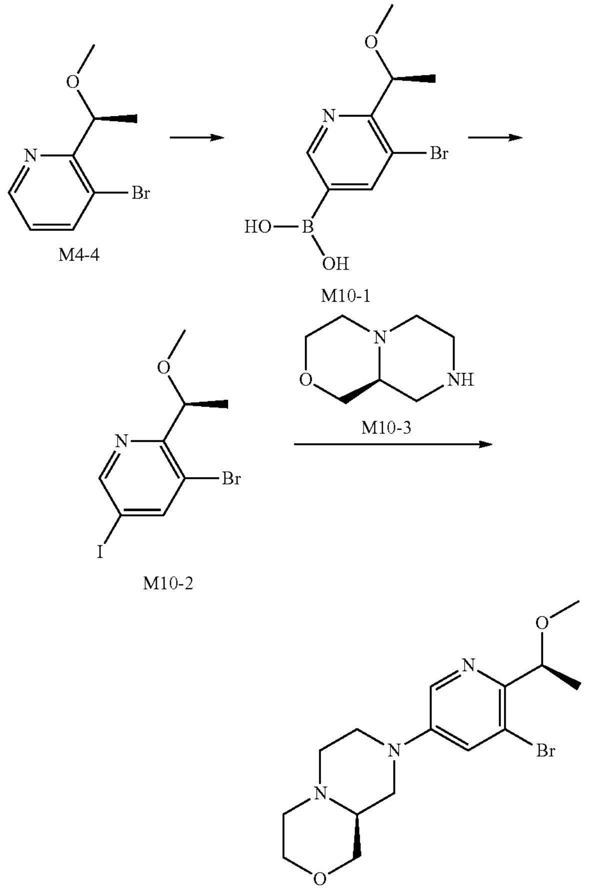

M4-4

M10-1

M10-3

M10-2

M10

Step 1

Compound M4-4 (9.2 g, 42.58 mmol), bis(pinacolato) diboron (16.22 g, 63.87 mmol), 1,5-cyclooctadiene iridium chloride dimer (858 mg, 1.28 mmol), 4,4'-di-tert-butyl-2,2'-dipyridyl (1.71 g, 6.39 mmol) was dissolved in tetrahydrofuran (200 mL), nitrogen was replaced three times, and the reaction solution was stirred at 70° C. for 16 hours. After the reaction was completed, the reaction solution was concentrated, and then diluted with 150 mL of water and 150 mL of ethyl acetate, and the alkaline water (7.5 g of sodium hydroxide and 30 g of sodium carbonate in 400 mL of aqueous solution) was added to adjust the pH to 10, and separated. The organic phases were discarded. The aqueous phase was adjusted to pH 6 with concentrated hydrochloric acid, then extracted with ethyl acetate (100 mL×3). The organic phases were combined, dried with anhydrous sodium sulfate, filtered, and the filtrate was concentrated to obtain Compound M10-1.

Step 2

Compound M10-1 (5 g, 19.24 mmol) was dissolved in acetonitrile (50 mL), and copper(I) iodide (733 mg, 3.85 mmol), potassium iodide (6.39 g, 38.48 mmol), potassium carbonate (5.32 g, 38.48 mmol), and 1,10-phenanthroline (694 mg, 3.85 mmol) were added sequentially. The reaction solution was stirred at 60° C. for 2 hours. After the reaction was completed, the reaction solution was filtered and the filtrate was directly concentrated. The crude product was purified using a flash chromatography column (silica gel, eluent: ethyl acetate/petroleum ether, ethyl acetate proportion: 0-10%) to obtain Compound M10-2. LCMS: m/z=341.8, 343.8 [M+1]$^+$.

Step 3

Compound M10-2 (0.27 g, 789.54 μmol) and Compound M10-3 (170 mg, 790.54 μmol, 2 HCl) were dissolved in toluene (5 mL), cooled to 0° C., then cesium carbonate (1.29 g, 3.95 mmol), (R)-(+)-2,2-bis(diphenylphosphino)-1,1-binaphthalene (50 mg, 80.95 μmol) and palladium (II) acetate (36 mg, 158.91 μmol) were added. Nitrogen was replaced three times, and the reaction solution was stirred at 90° C. for 12 hours. After the reaction was completed, the reaction solution was directly concentrated, and the obtained crude product was purified using a flash chromatography column (silica gel, eluent: methanol/dichloromethane, methanol proportion-0-10%) to obtain Compound M10. LCMS: m/z=356.0, 358.0 [M+1]$^+$.

Reference Example 10: Compound M11

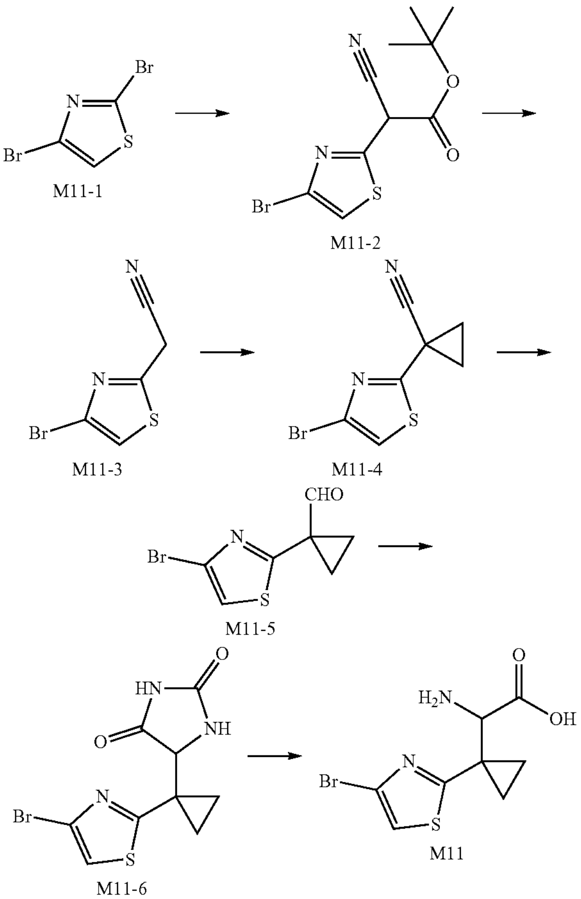

M11-1

M11-2

M11-3

M11-4

M11-5

M11-6

M11

Step 1

Compound M11-1 (5 g, 20.58 mmol) and potassium carbonate (8.53 g, 61.75 mmol) were dissolved in methyl-2-pyrrolidone (25 mL), and then tert-butyl cyanoacetate (4.65 g, 32.93 mmol) was added. The reaction solution was stirred at 85° C. for 12 hours. After the reaction was completed, water (25 mL) was added to cool to room temperature, pH was adjusted to =2 with 3 M hydrochloric acid, solids were precipitated, filtered, and the filter cake was dried to obtain Compound M11-2. $^1H$ NMR (400 MHz, $CD_3OD$) δ ppm 1.53 (s, 9H) 4.85 (s, 1H) 6.93 (s, 1H).

Step 2

Compound M11-2 (6.2 g, 20.45 mmol) was dissolved in hydrochloric acid (4 M, 24 mL), then acetic acid (439.68 mmol, 25.17 mL) was added, and it was stirred at 80° C. for 15 minutes. After the reaction was completed, water (100 mL) was added, and the solution was extracted with ethyl acetate (150 mL*3). The organic phases were dried with anhydrous sodium sulfate, and then concentrated under reduced pressure to obtain the crude product, which was purified by column chromatography (petroleum ether:ethyl acetate=10:1 to 3:1) to obtain Compound M11-3. $^1H$ NMR (400 MHz, $CD_3OD$) δ ppm 4.90 (s, 2H) 7.61 (s, 1H).

Step 3

Compound M11-3 (3 g, 14.77 mmol) was dissolved in tetrahydrofuran (30 mL), sodium hydrogen (1.48 g, 36.93 mmol, purity 60%) was added at 0° C., stirred at 0° C. for 20 minutes under nitrogen protection, and then 1,2-dibromoethane (22.16 mmol, 1.67 mL) was added and stirred at 25° C. for 12 hours under nitrogen protection. After the reaction was completed, water (100 mL) was added for quenching, and the solution was extracted with ethyl acetate (150 mL*3). The organic phases were dried with anhydrous sodium sulfate, and then concentrated under reduced pressure to obtain the crude product, which was purified by column chromatography (petroleum ether:ethyl acetate=10:1 to 3:1) to obtain Compound M11-4. $^1H$ NMR (400 MHz, $CD_3OD$) δ ppm 1.78-1.83 (m, 2H) 1.84-1.89 (m, 2H) 7.07 (s, 1H).

Step 4

Compound M11-4 (1 g, 4.36 mmol) was dissolved in tetrahydrofuran (10 mL), and then a solution of diisobutylaluminium hydride in toluene (1 M, 10.91 mL) was added at 0° C. and stirred at 0° C. for 1 hour under nitrogen protection. After the reaction was completed, it was quenched with water (120 mL), the solution was extracted with ethyl acetate (50 mL*3). The organic phases were dried with anhydrous sodium sulfate, and then concentrated under reduced pressure to obtain the crude product, which was purified by column chromatography (petroleum ether:ethyl acetate=10:1 to 3:1) to obtain Compound M11-5. $^1H$ NMR (400 MHz, DMSO-d6) δ ppm 1.97-2.01 (m, 2H) 2.07-2.11 (m, 2H) 7.79 (s, 1H) 8.90 (s, 1H).

Step 5

Compound M11-5 (0.2 g, 861.71 μmol) and ammonium carbonate (248.39 mg, 2.59 mmol) were dissolved in ethanol (5 mL) and water (5 mL), and potassium cyanide (84.17 mg, 1.29 mmol) was added and stirred at 80° C. for 6 hours. After the reaction was completed, water (150 mL) was added for quenching and the solution was extracted with ethyl acetate (150 mL*3). The organic phases were dried with anhydrous sodium sulfate, and concentrated under reduced pressure to obtain the crude product to obtain Compound M11-6. LCMS: m/z=302.1, 304.1 $[M+1]^+$. $^1H$ NMR (400 MHz, $CD_3OD$) δ ppm 1.20-1.32 (m, 2H) 1.37-1.50 (m, 2H) 4.06 (s, 1H) 7.39 (s, 1H).

Step 6

Compound M11-6 (0.17 g, 562.64 μmol) was dissolved in dioxane (1 mL) and water (1 mL), barium hydroxide (385.61 mg, 2.25 mmol) was added, and the reaction system was microwaved at 130° C. for 30 minutes. Water (50 mL) was added to the reaction system, washed with ethyl acetate (50 mL*3), and the aqueous phase was collected to obtain an aqueous solution of Compound M11. LCMS: m/z=277.1, 279.1 $[M+1]^+$.

Reference Example 11: Compound M12

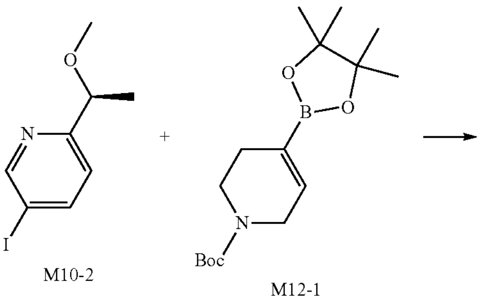

M10-2 M12-1

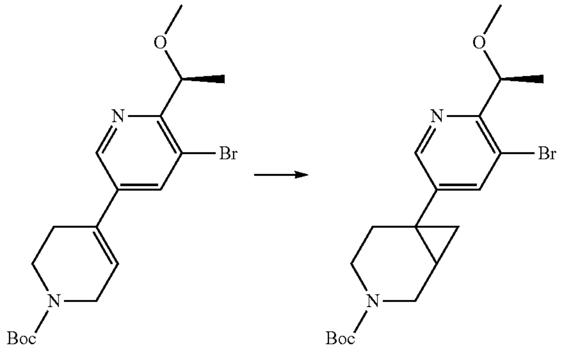

M12-2 M12

Step 1

Compound M10-2 (0.1 g, 292.42 μmol), Compound M12-1 (108 mg, 350.91 μmol), potassium carbonate (101 mg, 731.06 μmol), 1,1-bis(diphenylphosphino)ferrocene-palladium(II) (21 mg, 29.24 μmol) were dissolved in dioxane (5 mL) and water (1 mL), and nitrogen was replaced three times. The reaction solution was stirred at 60° C. for 3 hours. After the reaction was completed, the reaction solution was directly concentrated and the crude product was purified with a flash chromatography column (silica gel, eluent: ethyl acetate/petroleum ether, ethyl acetate proportion: 0-40%) to obtain Compound M12-2. LCMS: m/z=397, 1, 399.0 $[M+1]^+$.

Step 2

Trimethylsulfoxonium iodide (139 mg, 629.24 μmol) and potassium tert-butoxide (71 mg, 629.24 μmol) were added to dimethyl sulfoxide (3 mL) and stirred at 50° C. for 2 hours. Then, the mixture was cooled to 25° C. and Compound M12-2 (0.05 g, 125.85 μmol) in dimethyl sulfoxide (1 mL) was added dropwise. The reaction solution was stirred at 80° C. for 12 hours. After the reaction was completed, the reaction was diluted with water (50 mL), and the solution was extracted with ethyl acetate (50 mL*3). The organic phases were combined and washed once with saturated brine (50 mL), dried with anhydrous sodium sulfate, filtered, the filtrate was directly concentrated, and the crude product was purified with a flash chromatography column (silica gel, eluent: ethyl acetate/petroleum ether, ethyl acetate proportion: 0-50%) to obtain Compound M12. LCMS: m/z=410.9, 412.9$[M+1]^+$.

Example 1
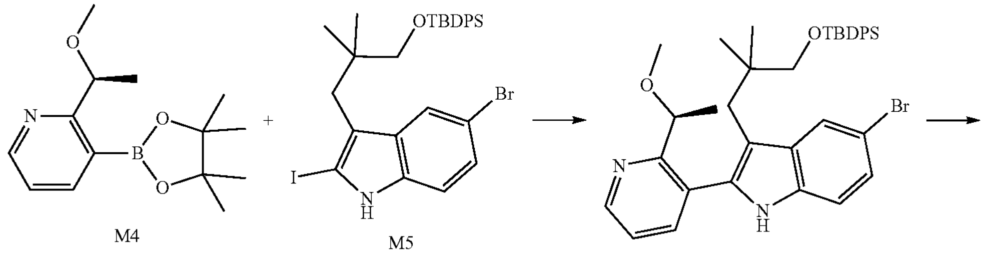
M4 M5 1-1
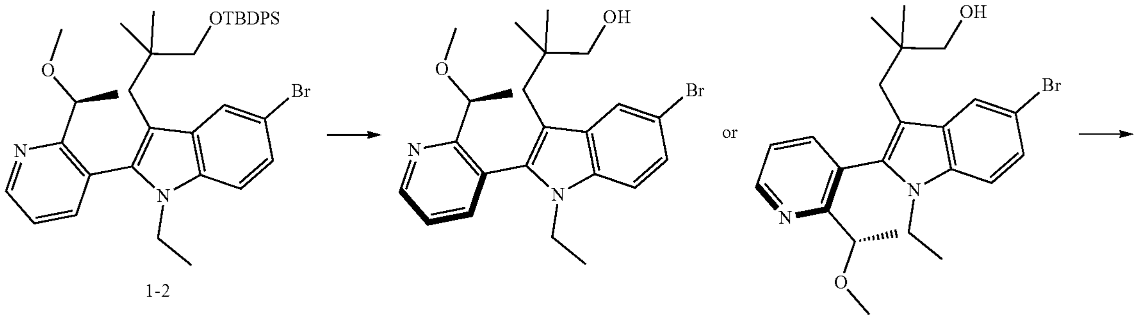
1-2 or 1-3A
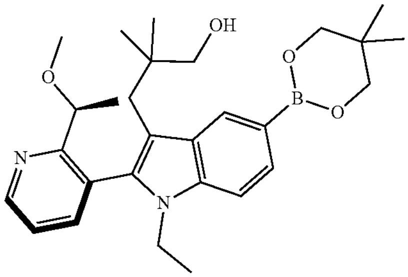
or
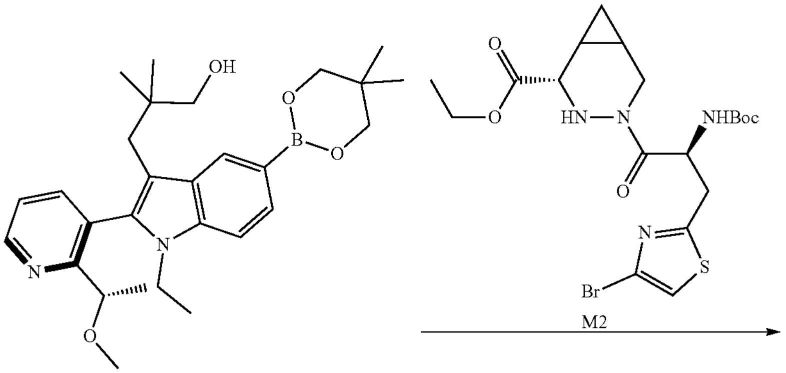
M2
1-4A
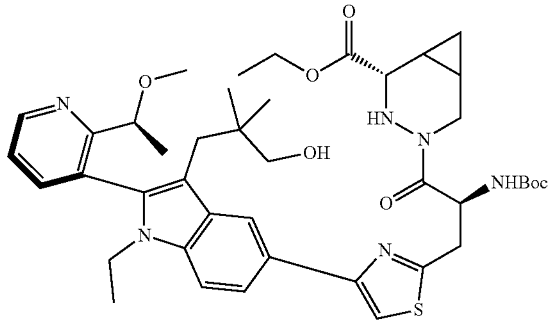
or -continued
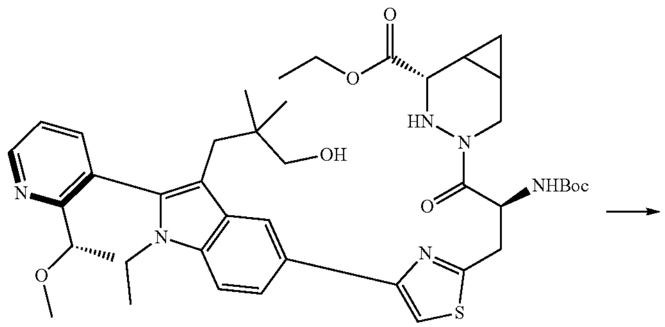
1-5A
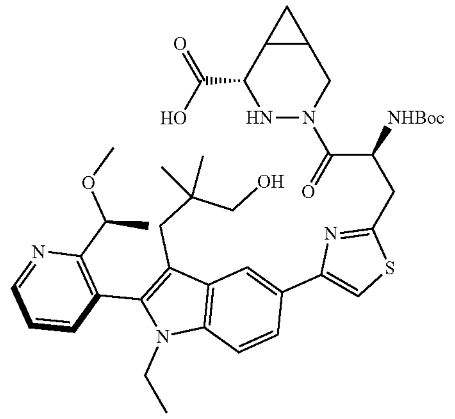
or
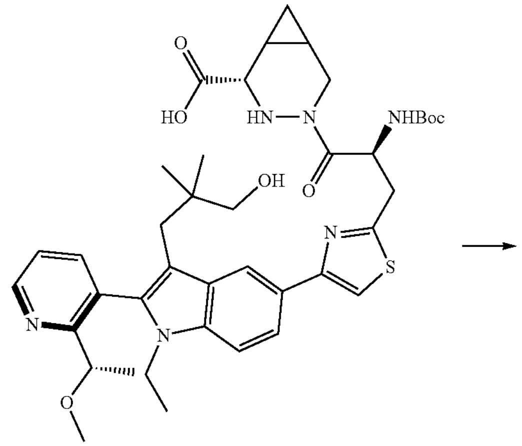
1-7A
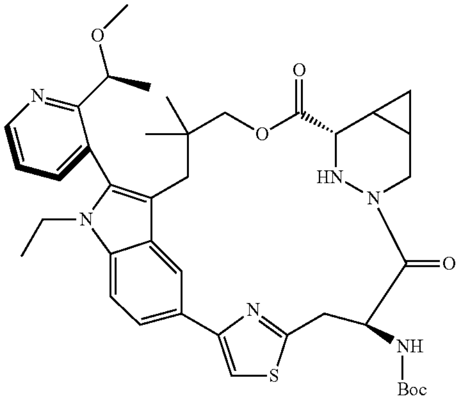
or
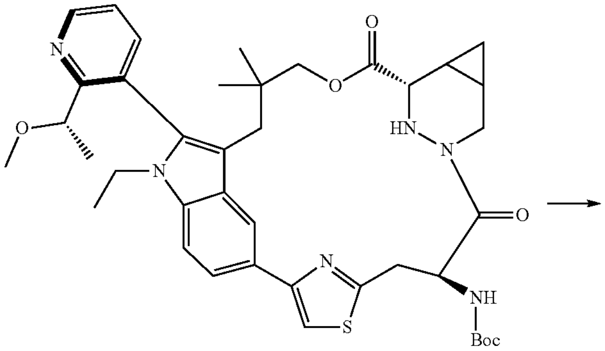
1-8A
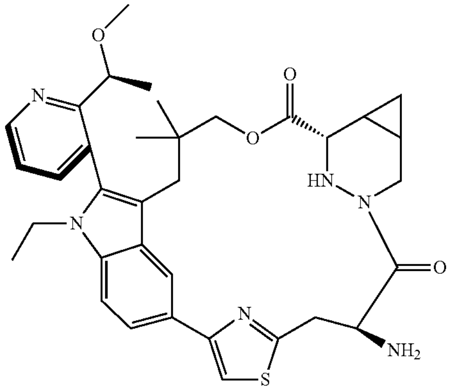
or
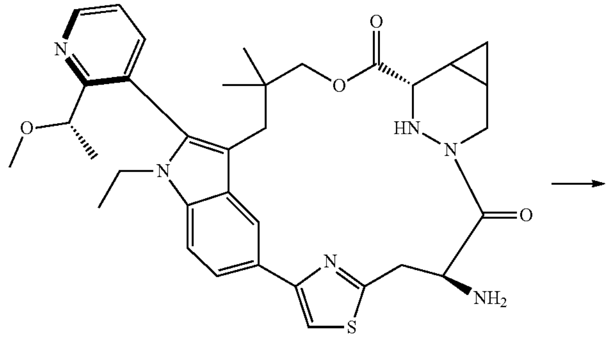
1A
1-9A -continued

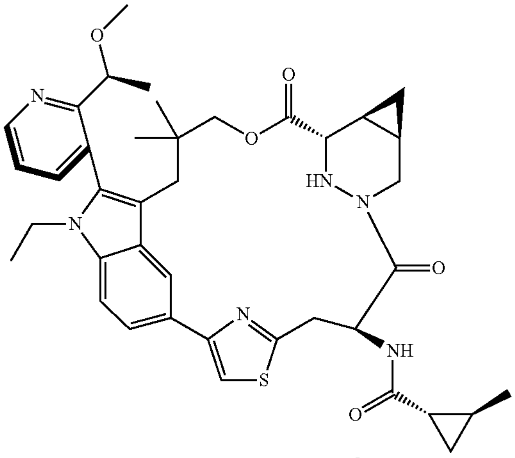

or

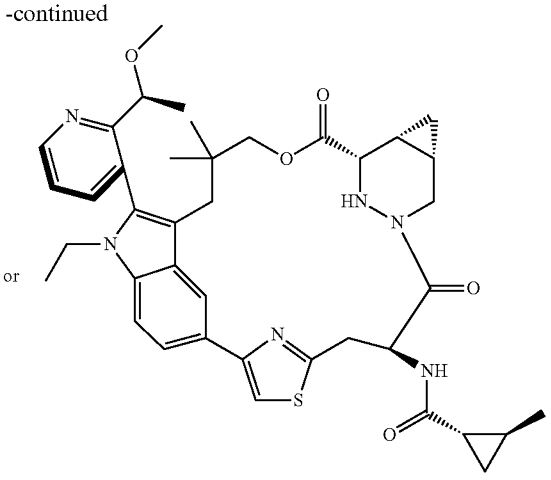

or

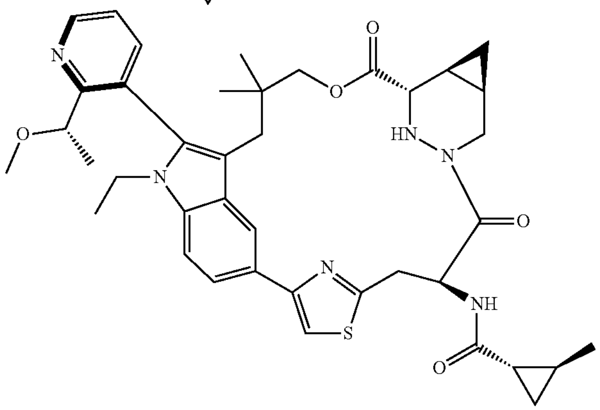

or

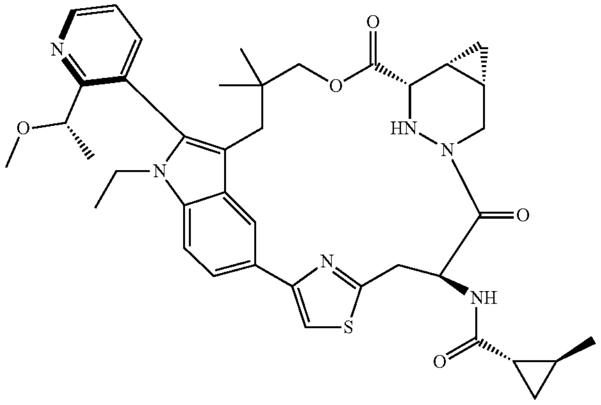

1A

Step 1

$K_2CO_3$ (3.75 g, 27.14 mmol) and 1,1-bis(diphenylphosphino)ferrocene]palladium(II) dichloride (794.48 mg, 1.09 mmol) were added to a mixed solution of Compound M4 (5 g, 19.00 mmol) and Compound M5 (7.02 g, 10.86 mmol) in 70 mL of dioxane and 15 mL of water, nitrogen was replaced three times, and the mixture was stirred at 85° C. for 4 hours. The reaction solution was concentrated. The residue was diluted with 100 mL of water and extracted with ethyl acetate (3*50 mL). The organic phases were dried with anhydrous sodium sulfate, filtered, and the filtrate was concentrated under reduced pressure. The residue was purified with a flash chromatography column (silica gel, eluent: ethyl acetate/petroleum ether, ethyl acetate proportion: 0-100%) to obtain Compound 1-1. LCMS: m/z=655.1, 657.1 $[M+1]^+$.

Step 2

Ethyl iodide (2.14 g, 13.73 mmol) and cesium carbonate (4.47 g, 13.73 mmol) were added sequentially to a solution of Compound 1-1 (4.5 g, 6.86 mmol) in DMF (50 mL) at 0° C. After the addition, the temperature was increased to 25° C. and the solution was stirred at 25° C. for 16 hours. The reaction solution was diluted with 100 mL of water and extracted with ethyl acetate (2*50 mL). The organic phases were dried with anhydrous sodium sulfate, filtered, and the filtrate was concentrated under reduced pressure to obtain Compound 1-2. LCMS: m/z=683.2, 685.2 $[M+1]^+$.

Step 3

Compound 1-2 (3.4 g) and tetrabutylammonium fluoride in tetrahydrofuran solution (1 M 34.81 mL) were sequentially added to 35 mL of anhydrous tetrahydrofuran, and the mixture was stirred at 50° C. for 16 hours. The reaction solution was diluted with 100 mL of water and extracted with ethyl acetate (2*50 mL). The organic phases were dried with anhydrous sodium sulfate, filtered, and the filtrate was concentrated under reduced pressure. The residue was purified with a flash chromatography column (silica gel, eluent: ethyl acetate/petroleum ether, ethyl acetate proportion: 0-80%) to obtain Compound 1-3A (TLC developing solvent: ethyl acetate, Rr of Compound 1-3A=0.38, $R_f$ of the isomer thereof=0.17). LCMS: m/z=445.1, 447.1[M+1]$^+$; $^1$H NMR (400 MHz, $CDC_3$) δ 8.85 (dd, J=1.76, 4.77 Hz, 1H) 7.92 (d, J=1.76 Hz, 1H) 7.71 (dd, J=1.76, 7.78 Hz, 1H) 7.33-7.41 (m, 2H) 7.24-7.28 (m, 1H) 4.08-4.14 (m, 1H) 3.96-4.08 (m, 1H) 3.83-3.96 (m, 1H), 3.19-3.33 (m, 2H), 3.09 (s, 3H), 2.74 (d, J=14.05 Hz, 1H), 2.27 (d, J=14.05 Hz, 1H), 1.50 (d, J=6.27 Hz, 3H), 1.16-1.24 (m, 4H), 0.80 (s, 6H).

Step 4

Compound 1-3A (0.4 g, 898.09 μmol) and bis(neopentyl glycolato)diboron (406 mg, 1.80 mmol) were dissolved in toluene (10 mL), 1,1-bis(diphenylphosphino)ferrocene]palladium(II) dichloride (131 mg, 179.62 μmol) and potassium acetate (264 mg, 2.69 mmol) were added successively, nitrogen was replaced three times, and the reaction solution was heated to 90° C. and stirred for 12 hours. The reaction solution was filtered, and the filtrate was concentrated to obtain Compound 1-4A. LCMS: m/z=411.2 [Mboric acid+1]$^+$.

Step 5

Compound 1-4A (300.00 mg, 627.05 μmol), Compound M2 (0.36 g, 715.12 μmol), 1,1-di(tert-butylphosphino)ferrocenepalladium chloride (47 mg, 71.51 μmol), and potassium phosphate (455 mg, 2.15 mmol) were dissolved in toluene (6 mL), dioxane (2 mL) and water (2 mL), and nitrogen was replaced three times. The reaction solution was stirred at 70° C. for 12 hours. The reaction solution was concentrated. The crude product was purified using a flash chromatography column (silica gel, eluent: ethyl acetate/petroleum ether, ethyl acetate proportion: 0-100%) to obtain Compound 1-5A LCMS: m/z=789.4 [M+1]$^+$.

Step 6

Compound 1-5A (100.00 mg, 126.74 μmol) was dissolved in tetrahydrofuran (2 mL) and water (0.2 mL), then lithium hydroxide monohydrate (16 mg, 380.23 μmol) was added. The reaction solution was stirred at 15° C. for 12 hours. 1 M HCl was added to the reaction solution to adjust the pH to ~5, and the solution was extracted with ethyl acetate (50 mL*3). The organic phases were combined and washed once with saturated brine (50 mL), dried with anhydrous sodium sulfate, filtered, and the filtrate was concentrated to obtain Compound 1-7A. LCMS: m/z=761.3 [M+1]$^+$.

Step 7

Compound 1-7A (50.00 mg, 65.71 μmol) was dissolved in dichloromethane (5 mL), then N,N-diisopropylethylamine (260 mg, 2.01 mmol, 0.35 mL), 1-hydroxybenzotriazole (0.044 g, 325.63 gmol), and 1-ethyl-3-(3-dimethylaminopropyl)carbodiimide hydrochloride (0.35 g, 1.83 mmol) were added. The reaction solution was stirred at 20° C. for 12 hours. The reaction solution was diluted with water (50 mL), and the solution was extracted with dichloromethane (20 mL*3). The organic phases were combined and washed once with saturated brine (20 mL), dried with anhydrous sodium sulfate, filtered, the filtrate was concentrated to obtain the crude product, which was purified with a flash chromatography column (silica gel, eluent: ethyl acetate/petroleum ether, ethyl acetate proportion: 0-80%) to obtain Compound 1-8A. LCMS: m/z=743.4 [M+1]$^+$.

Step 8

Compound 1-8A (20.00 mg, 26.92 μmol) was dissolved in dichloromethane (1 mL) at (PC and trifluoroacetic acid (1.54 g, 13.46 mmol, 1 mL) was added. The reaction solution was stirred at 15° C. for 12 hours. The reaction solution was concentrated to obtain the crude trifluoroacetate of Compound 1-9A. LCMS: m/z=643.3 [M+1]$^+$.

Step 9

Compound 1-9A (20.00 mg, crude trifluoroacetate) was dissolved in DMF (2 mL) and then N,N-diisopropylethylamine (311.13 μmol, 54 μL), (1S,2S)-2-methylcyclopropane-1-carboxylicacid (7 mg, 62.3 μmol) and O-(7-azabenzotriazol-1-YL)-N,N,N,N-tetramethyluronium hexafluorophosphonate (HATU) (36 mg, 93.4 μmol) were added. The reaction solution was stirred at 20° C. for 1.5 hours. The reaction solution was diluted with water (20 mL), and the solution was extracted with ethyl acetate (20 mL*3). The organic phases were combined and washed once with saturated brine (20 mL), dried with anhydrous sodium sulfate, filtered, the filtrate was concentrated to obtain the crude product, which was purified with a flash chromatography column (silica gel, eluent: ethyl acetate/petroleum ether, ethyl acetate proportion: 0-80%) to obtain Compound 1A. LCMS: m/z=725.3 [M+1]$^+$; $^1$H NMR (400 MHz, $CD_3OD$) δ ppm 8.64 (dd, J=4.8, 1.6 Hz, 1H) 8.12 (s) 1H) 7.79 (dd) J=7.6, 1.6 Hz, 1H) 7.54 (d) J=8.4 Hz, 1H) 7.44 (dd) J=7.6, 4.8 Hz, 1H) 7.34-7.39 (m, 2H) 6.02 (t) J=6.2 Hz, 1H) 4.03-4.13 (m, 2H) 3.71-3.86 (m, 3H) 3.43-3.56 (m, 2H) 3.03 (s, 3H) 2.64-2.72 (m, 1H) 2.37-2.44 (m, 1H) 2.06-2.13 (m, 1H) 1.89-1.97 (m, 2H) 1.70-1.80 (m, 1H) 1.48-1.60 (m, 3H) 1.32-1.37 (m, 2H) 1.18-1.23 (m, 6H) 0.90-0.97 (m, 2H) 0.76-0.83 (m, 2H) 0.57-0.66 (m, 6H) 0.45-0.51 (m, 1H).

Example 2

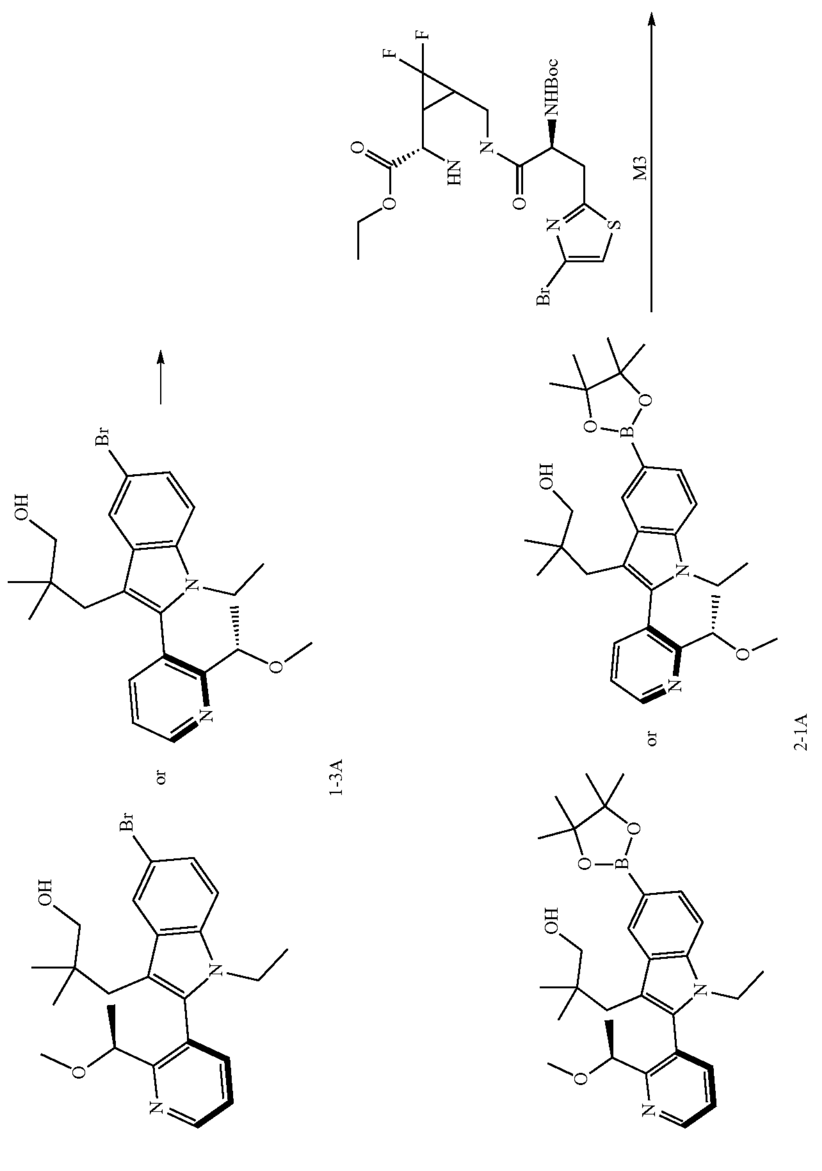
or
1-3A
or
2-1A

-continued
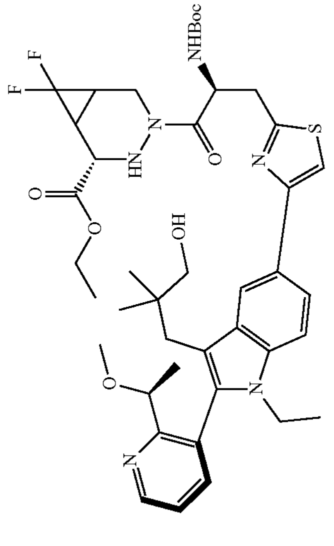
or
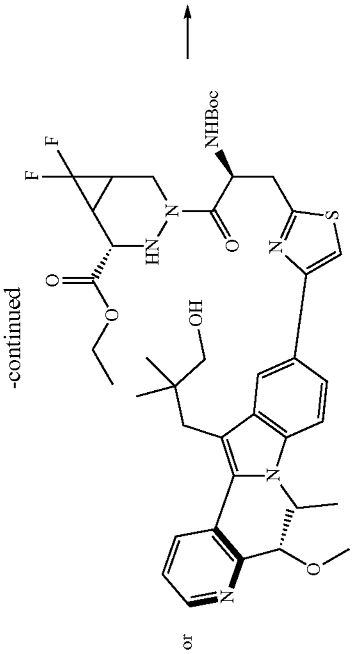
2-2A
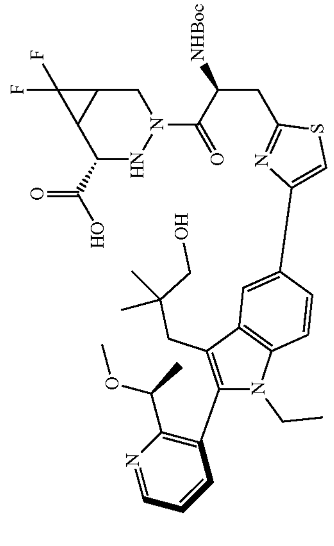
or
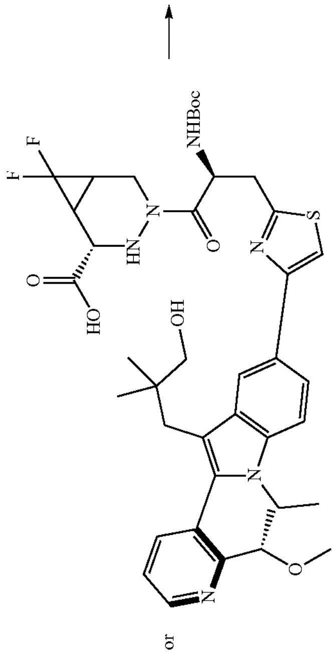
2-3A
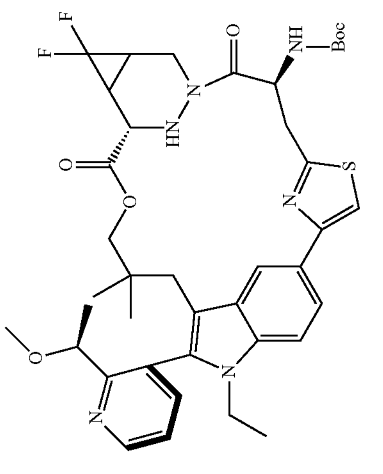
or
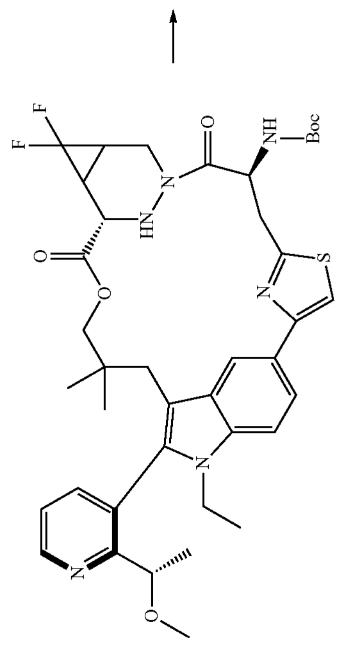
2-4A -continued
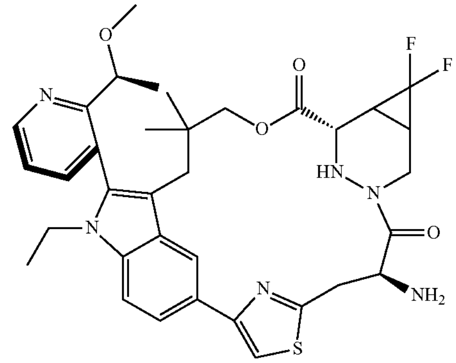
or
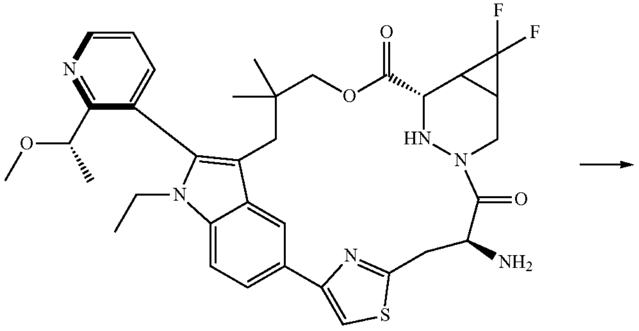
2-5A
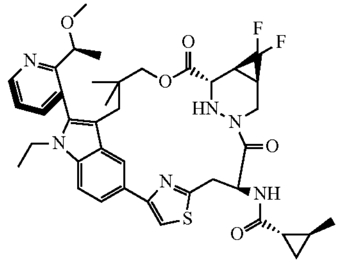
or
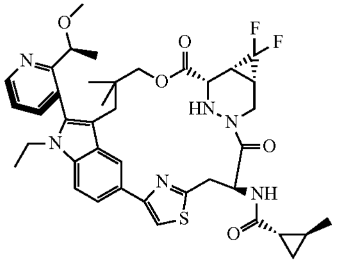
or
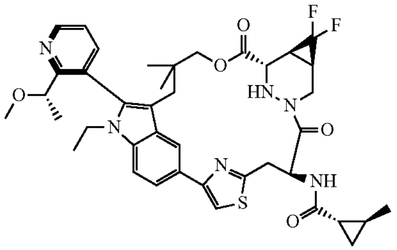
or
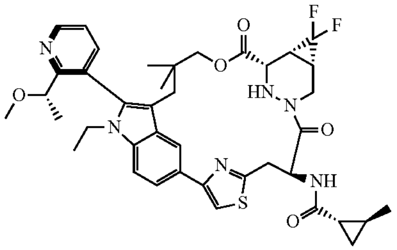
2A Step 1

Compound 2-3A (295 mg, 662.34 μmol) and bis(pinacolato)diboron (252.29 mg, 993.51 μmol) were dissolved in toluene (2 mL), and potassium acetate (130.01 mg, 1.32 mmol) and [1,1-bis(diphenylphosphino)ferrocene]dichloropalladium(II) (48.46 mg, 66.23 μmol) were added. The reaction solution was stirred and reacted at 110° C. under nitrogen atmosphere for 12 hours. The reaction solution was filtered, and the filtrate was concentrated under reduced pressure to obtain Compound 2-1A. LCMS: m/z=493.3 [M+1]$^+$.

Step 2

Compound 2-1A (300) mg, 609.19 μmol) and Compound M3 (492.89 mg, 913.79 μmol) were dissolved in a mixed solvent of 1,4-dioxane (3 mL), toluene (3 mL), and water (0.5 mL), potassium phosphate (387.94 mg, 1.83 mmol) was added, and 1,1-di(tert-butylphosphino)ferrocenepalladium chloride (39.70 mg, 60.92 μmol) was added. The reaction solution was stirred and reacted under nitrogen atmosphere and 70° C. for 12 hours. The reaction solution was filtered, and the filtrate was concentrated to obtain the crude product, which was purified by silica gel column chromatography (20-80% ethyl acetate/petroleum ether) to obtain Compound 2-2A. LCMS: m/z=825.1 [M+1]$^+$.

Step 3

Compound 2-2A (280 mg, 339.40 μmol) was dissolved in a mixed solution of tetrahydrofuran (3 mL) and water (1 mL), and lithium hydroxide monohydrate (71.21 mg, 1.70 mmol) was added. The reaction solution was stirred and reacted at 25° C. for 2 hours, then the reaction solution was adjusted to neutral with 1 M dilute hydrochloric acid, and then extracted with ethyl acetate (5 mL×3). The organic phases were combined and washed with saturated brine, dried with anhydrous sodium sulfate, and the filtrate was concentrated under reduced pressure to obtain Compound 2-3A. LCMS: m/z=797.21M+11'.

Step 4

Compound 2-3A (0.3 g, 376.45 μmol) was dissolved in dichloromethane (30 mL), and 1-hydroxybenzotriazole (508.67 mg, 3.76 mmol), N,N-diisopropylethylamine (11.29 mmol, 1.97 mL), and 1-(3-dimethylaminopropyl)-3-ethylcarbodiimide (2.16 g, 11.29 mmol) were added, and the reaction solution was stirred and reacted at 25° C. for 12 hours. The reaction solution was concentrated under reduced pressure to obtain the crude product, which was purified by silica gel column chromatography (0-30% ethyl acetate/petroleum ether), and then prepared and separated by high performance liquid chromatography (HPLC) (column: C18 100×40 mm; mobile phase: [water (trifluoroacetic acid)-acetonitrile]; gradient (acetonitrile %): 39%-69% to obtain Compound 2-4A. LCMS: m/z=779.3 [M+1]$^+$.

Step 5

Compound 2-4A (20 mg, 25.68 μmol) was dissolved in dichloromethane (1 mL), and trifluoroacetic acid (25.68 μmol, 1.91 IL) was added. The reaction solution was stirred and reacted at 25° C. for 5 hours, and concentrated under reduced pressure to obtain the crude trifluoroacetate of Compound 2-5A. LCMS: m/z=679.3 [M+1]$^+$.

Step 6

Compound 2-5A (17 mg, trifluoroacetate) and (1S,2S)-2-methylcyclopropane-1-carboxylic acid (3.76 mg, 37.57 μmol) were dissolved in DMF (1 mL), then N,N-diisopropylethylamine (9.71 mg 75.13 μmol, 13.09 μL) and HATU (19.05 mg, 50.09 μmol) were added while stirring. The reaction solution was stirred and reacted at 25° C. for 12 hours and extracted with ethyl acetate (5 mL×3). The organic phases were washed with saturated brine, dried with anhydrous sodium sulfate, and the residue was concentrated under reduced pressure and prepared by HPLC (column: C18 100×40 mm; mobile phase: [water (trifluoroacetic acid)-acetonitrile]; gradient (acetonitrile %): 27%-57%) to obtain the trifluoroacetate of Compound 2A LCMS: m/z=761.2 [M+1]1; $^1$H NMR ($CDCl_3$, 400 MHz) δ 9.1-9.2 (m, 1H), 8.3-8.4 (m, 1H) 8.0-8.2 (m, 1H) 7.7-7.8 (m, 1H) 7.6-7.7 (m, 1H), 7.3-7.5 (m, 1H), 6.6-6.7 (m, 1H), 5.7-5.8 (m, 1H), 4.4-4.5 (m, 1H), 4.17 (br d, J=5.8 Hz, 1H), 4.11 (br d, J=10.51 Hz, 1H), 4.0-4.1 (m, 1H), 3.88 (br d) J=10.3 Hz, 1H), 3.64 (br d, J=15.6 Hz, 1H), 3.1-3.3 (m, 6H), 21-2.2 (m, 1H), 1.9-2.0 (m, 2H), 1.6-1.7 (m, 1H), 1.52 (br d, 3H, J=5.8 Hz), 1.2-1.4 (m, 8H), 1.1-1.2 (m, 1H), 1.07 (br d, 3H, J=5.5 Hz), 0.92 (br s, 3H), 0.6-0.7 (m, 3H), 0.5-0.6 (m, 1H).

Example 3

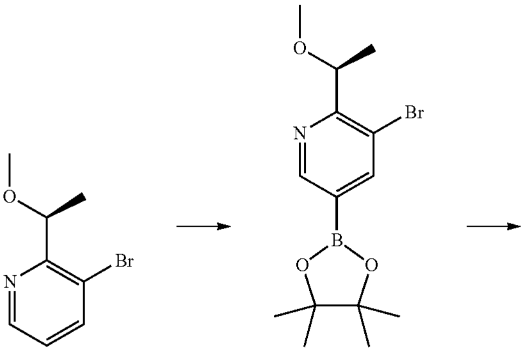

M4-4

3-1

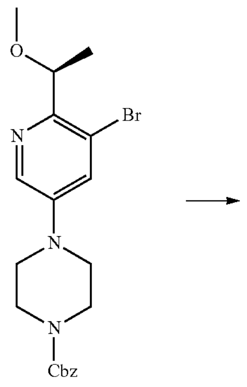

3-2

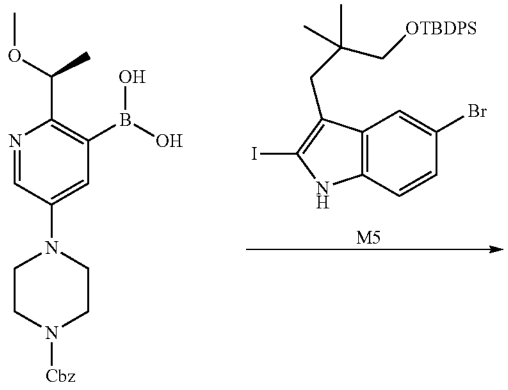

3-3

-continued
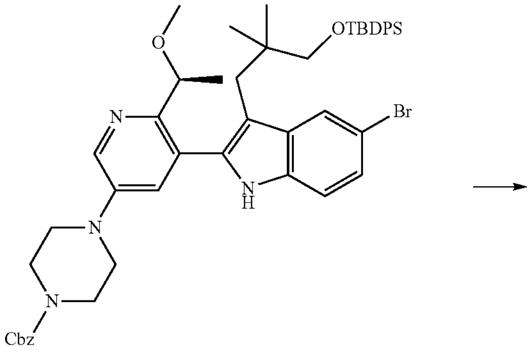
3-4
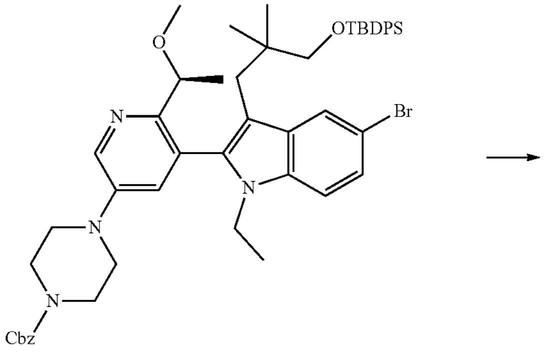
3-5
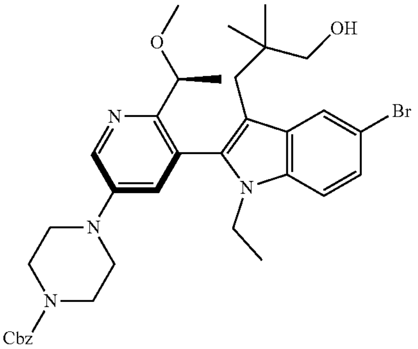
or
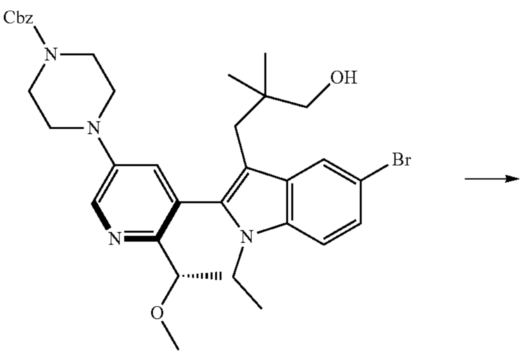
3-6A
-continued
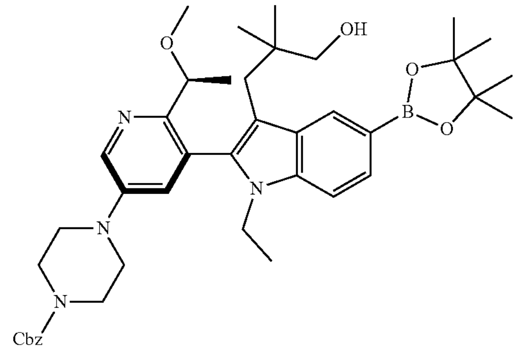
or
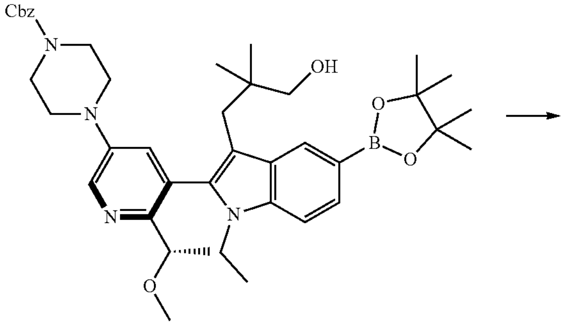
3-7A
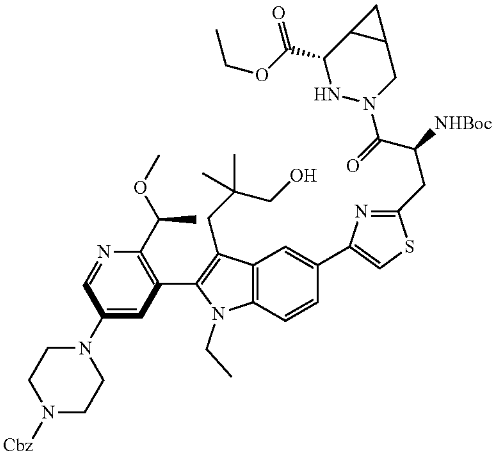
or
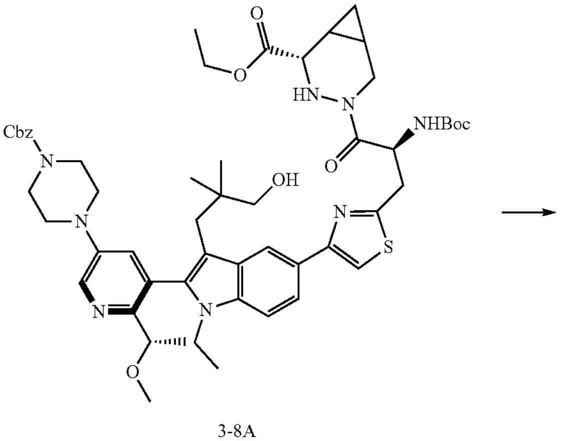
3-8A -continued
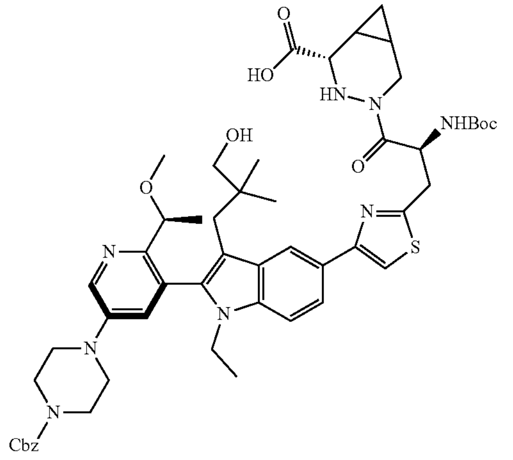
or
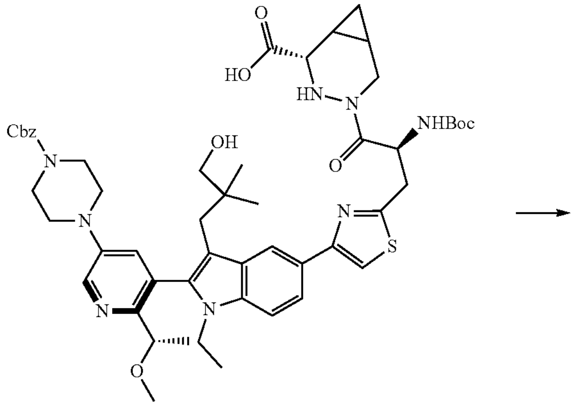
3-9A
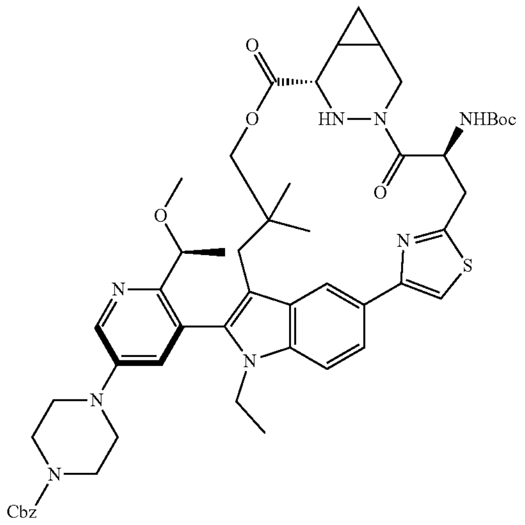
or
-continued
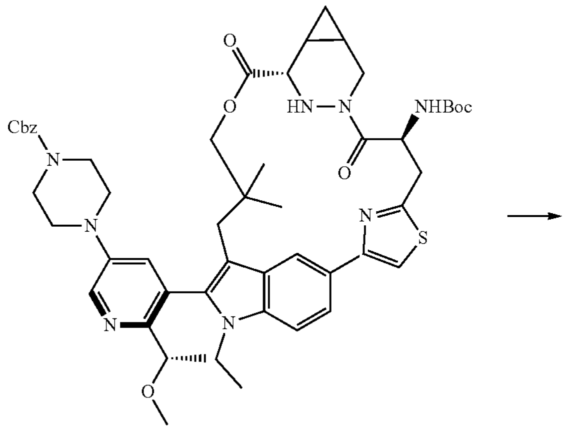
3-10A
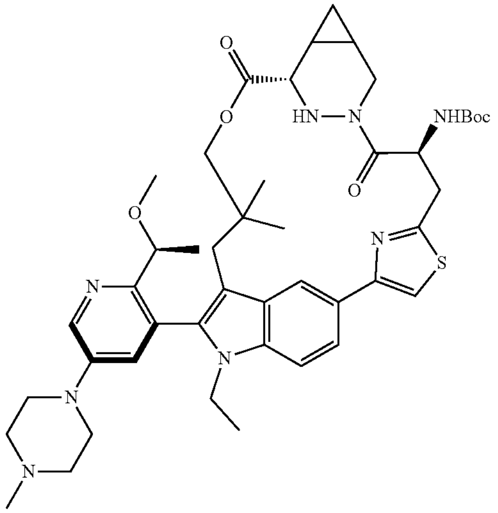
or
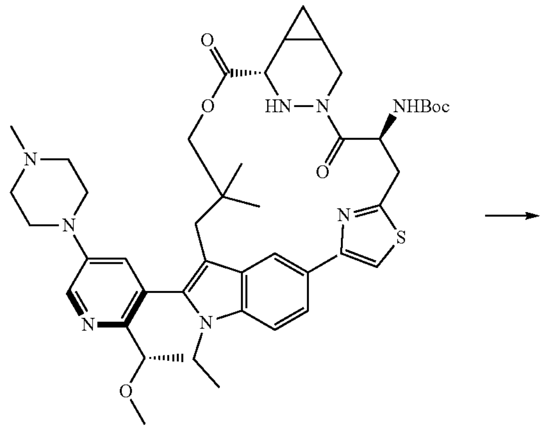
3-11A -continued

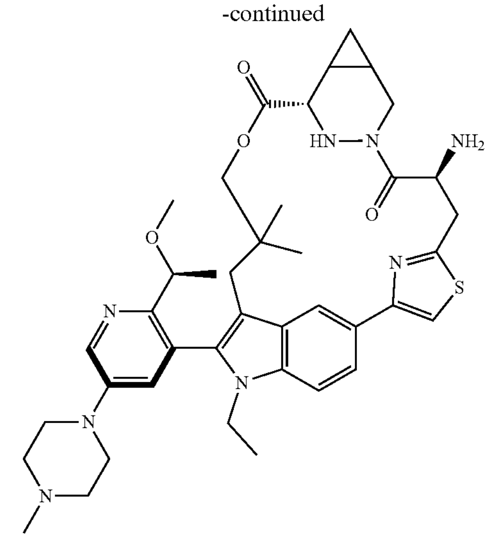

or

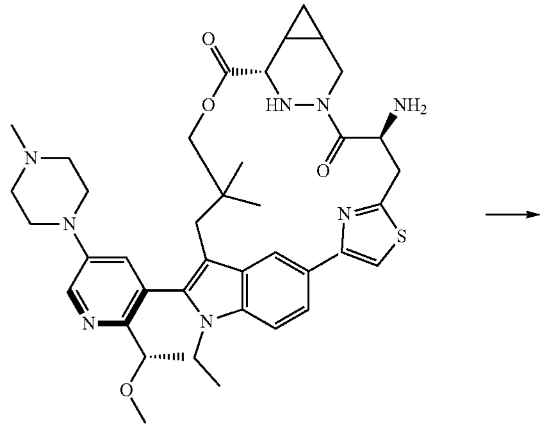

3-12A

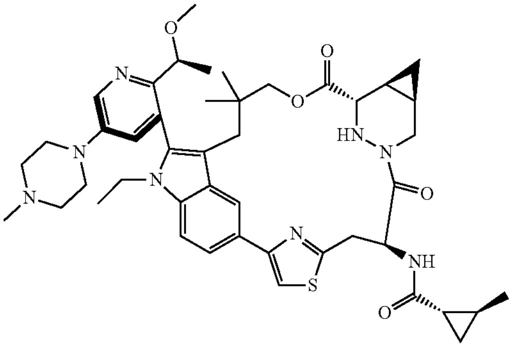

or

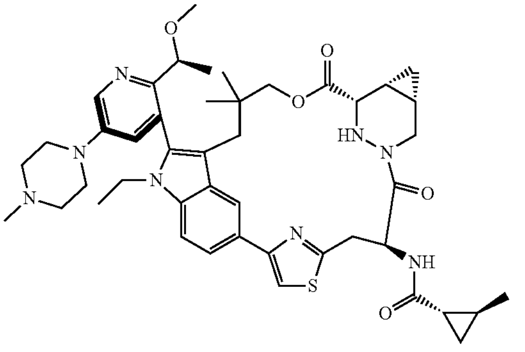

or

3A

-continued

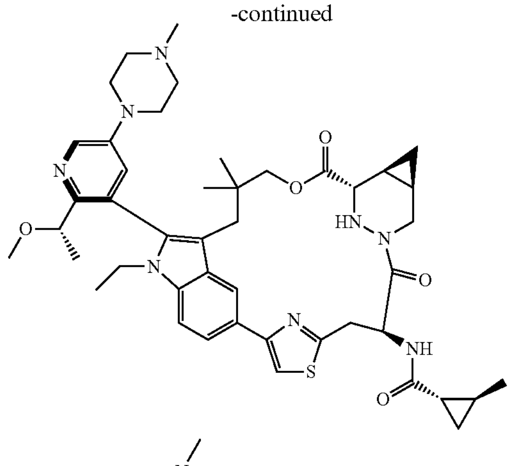

or

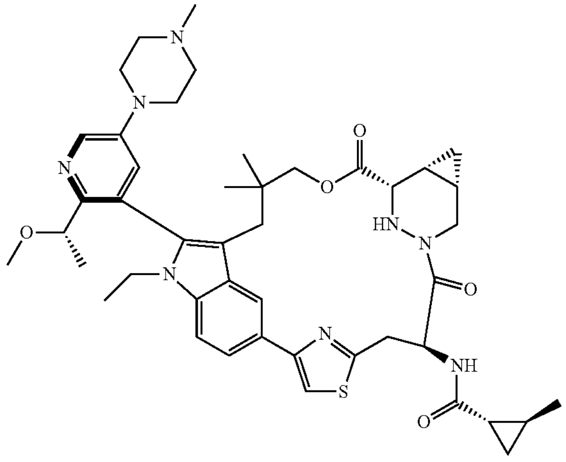

Step 1

Compound M4-4 (30 g, 138.84 mmol), bis(pinacolato) diboron (52.89 g, 208.26 mmol), 1,5-cyclooctadiene iridium chloride dimer (2.80 g, 4.17 mmol) and 4,4'-di-tert-butyl-2, 2'-dipyridyl (5.59 g, 20.83 mmol) were sequentially added to 600 mL of anhydrous tetrahydrofuran, nitrogen was replaced three times, and the mixture was stirred at 80° C. for 20 hours. The reaction solution was concentrated. The residue was diluted with 300 mL of water and 200 mL of ethyl acetate, and alkaline water (10 g of NaOH and 40 g of 400 mL of sodium carbonate aqueous solution) was added to adjust the pH to 10. The solution was separated, and the organic phases were discarded. The pH of the aqueous phase was adjusted with concentrated hydrochloric acid to 6. 500 mL of ethyl acetate was added for extraction three times. The organic phases were combined, dried with anhydrous sodium sulfate, filtered, and the filtrate was concentrated to obtain Compound 3-1. $^{1}H$ NMR (400 MHz, $CDCl_3$) δ=8.93 (d, J=1.6 Hz, 1H) 8.22 (d, J=1.6 Hz, 1H) 4.96 (q, J=6.4 Hz, 1H) 3.32 (s, 3H) 1.50 (d, J=6.4 Hz, 3H) 1.37 (s, 12H).

Step 2

Compound 3-1 (40 g, 116.95 mmol) was slowly added dropwise to a 1.5 L acetonitrile suspension of benzyl-1-piperazine carbonate (77.28 g, 350.84 mmol), copper acetate (21.24 g, 116.95 mmol), and triethylamine (116.95 mmol, 16.28 mL) at 80° C. The mixture was stirred at 80° C. for 1 hour. The reaction solution was concentrated under reduced pressure, and the residue was purified with a flash chromatography column (silicagel, eluent: ethyl acetate/petroleum ether, ethyl acetate proportion: 0-30%) to obtain Compound 3-2. MS-ESI calculated value $[M+1]^+$ 434.1, 436.1 measured value 434.3, 436.3; $^1$H NMR (400 MHz, $CDC_3$) δ=8.23 (d, J=2.4 Hz, 1H) 7.39-7.25 (m, 5H) 7.23 (d, J=2.4 Hz, 1H) 5.09 (s, 2H) 4.78 (q, J=6.4 Hz, 1H) 3.68-3.55 (m, 4H) 3.21 (s, 3H) 3.13 (br s, 4H), 1.39 (d, J=6.4 Hz, 3H).

Step 3

Compound 3-2 (7 g, 16.12 mmol), bis(neopentyl glycolato)diboron (5.46 g, 24.18 mmol), 1,1-bis(diphenylphosphino)ferrocene]palladium(II) dichloride (589.65 mg, 805.85 μmol) and potassium acetate (3.95 g, 40.29 mmol) were added to 140 mL of anhydrous dioxane, nitrogen was replaced the times, and the mixture was stirred at 80° C. for 20 hours. The reaction solution was concentrated. The residue was purified with a flash chromatography column (silicagel, eluent: methanol/dichloromethane, methanol proportion: 0-10/%) to obtain Compound 3-3. LCMS: m/z=400.1 $[M+1]^+$.

Step 4

Compound 3-3 (9 g, 22.54 mmol), Compound M5 (14.57 g, 22.54 mmol), 1,1-bis(diphenylphosphino)ferrocene]palladium(II) dichloride (824.72 mg, 1.13 mmol) and potassium phosphate (11.96 g, 56.36 mmol) were sequentially added to 250 mL of anhydrous dioxane and 80 mL of water, nitrogen was replaced three times, and the mixture was stirred at 70° C. for 12 hours. The reaction solution was concentrated. The residue was diluted with 200 mL of water and extracted with ethyl acetate (3*200 mL). The organic phases were dried with anhydrous sodium sulfate, filtered, and the filtrate was concentrated under reduced pressure. The residue was purified with a flash chromatography column (silica gel, eluent: ethyl acetate/petroleum ether, ethyl acetate proportion 0-80%) to obtain Compound 3-4. LCMS: m/z=873.3, 875.3 $[M+1]^+$.

Step 5

Compound 3-4 (6.2 g, 7.09 mmol), ethyl iodide (14.19 mmol, 1.13 mL) and cesium carbonate (4.62 g, 14.19 mmol) were sequentially added to 100 mL of anhydrous DMF and the mixture was stirred at 20° C. for 10 hours. The reaction solution was concentrated. The residue was diluted with 100 mL of water and extracted with ethyl acetate (3*150 mL). The organic phases were dried with anhydrous sodium sulfate, filtered, and the filtrate was concentrated under reduced pressure to obtain Compound 3-5. LCMS: m/z=901.4, 903.4 $[M+1]^+$.

Step 6

Compound 3-5 (6.2 g, 6.87 mmol) and tetrabutylammonium fluoride in tetrahydrofuran solution (1 M, 13.75 mL) were sequentially added to 100 mL of anhydrous tetrahydrofuran, and the mixture was stirred at 50° C. for 15 hours. The reaction solution was concentrated. The residue was purified with a flash chromatography column (silica gel, eluent: ethyl acetate/petroleum ether, ethyl acetate proportion: 0-100%) to obtain Compound 3-6A (TLC developing solvent:ethyl acetate, W of Compound 3-6A=0.43, and Rr of the isomer thereof=0.33). LCMS: m/z=663.2, 665.2 $[M+1]^+$.

Step 7

Compound 3-6A (1.70 g, 2.56 mmol), bis(pinacolato) diboron (975.74 mg, 3.84 mmol) 1, 1-bis(diphenylphosphino)ferrocene]palladium(II) dichloride (187.43 mg, 256.16 μmol) and potassium acetate (754.21 mg, 7.68 mmol) were successively added to 50 mL of anhydrous dioxane, nitrogen % w replaced three times, and the mixture was stirred at 90° C. for 20 hours. The reaction solution was concentrated. The residue was purified with a flash chromatography column (silica gel, eluent: ethyl acetate/petroleum ether, ethyl acetate proportion: 0-100%) to obtain Compound 3-7A. LCMS: m/z=711.1 $[M+1]^+$.

Step 8

Compound 3-7A (0.38 g, 534.68 μmol). Compound M2 (322.99 mg, 641.61 μmol), 1,1-di(tert-butylphosphino)ferrocenepalladium chloride (34.85 mg, 53.47 μmol) and potassium phosphate (283.74 mg, 1.34 mmol) were successively added to 15 mL of dioxane and 5 mL of water, nitrogen was replaced three times, and the mixture was stirred at 70° C. for 4 hours. The reaction solution was concentrated. The residue was purified with a flash chromatography column (silica gel, eluent: ethyl acetate/petroleum ether, ethyl acetate proportion: 0-100%) to obtain Compound 3-8A. LCMS: m/z=1007.4 $[M+1]^+$.

Step 9

Compound 3-8A (650 mg, 645.33 μmol) and lithium hydroxide monohydrate (54.16 mg, 1.29 mmol) were sequentially added to 20 mL of tetrahydrofuran and 20 mL of water, and the mixture was stirred at 15° C. for 20 hours. The reaction solution was concentrated. The residue was diluted with 5 mL of water, 1 N dilute hydrochloric acid was added dropwise to adjust the pH to 6-7, and the solution was extracted with ethyl acetate (3*30 mL). The organic phases were dried with anhydrous sodium sulfate, filtered, and the filtrate was concentrated under reduced pressure to obtain Compound 3-9A LCMS: m/z=979.4 $[M+1]^+$.

Step 10

Compound 3-9A (650 mg, 663.81 μmol), 1-(3-dimethylaminopropyl)-3-ethylcarbodiimide (3.82 g, 19.91 mmol), N-diisopropylethylamine (26.55 mmol, 4.62 mL), and 1-hydroxybenzotriazole (896.94 mg, 6.64 mmol) were sequentially added to 65 mL of acetonitrile, and the mixture was stirred at 25° C. for 40 hours. The reaction solution was concentrated. The residue was purified with a flash chromatography column (silica gel, eluent: ethyl acetate/petroleum ether, ethyl acetate proportion: 0-100% to obtain Compound 3-10A. LCMS: m/z=961.4 $[M+1]^+$.

Step 11

Compound 3-10A (150 mg, 156.06 μmol) and paraformaldehyde (23.45 mg, 780.30 μmol) and palladium hydroxide on carbon (100 mg, 10% w/w, 50% water content) were sequentially added to 10 mL of methanol, hydrogen was replaced three times, and the mixture was stirred at 20° C. for 2 hours under a hydrogen atmosphere (15 psi). It was filtered and the filtrate was concentrated. The residue was purified with a flash chromatography column (silica gel, eluent: methanol/dichloromethane, methanol proportion: 0-10%) to obtain Compound 3-11A. LCMS: m/z=841.4 $[M+1]^+$.

Step 12

1 mL of trifluoroacetic acid was slowly added dropwise to Compound 3-11A (56 mg, 58.26 μmol) in 5 mL of anhydrous dichloromethane at 0° C., and the mixture was stirred at 0° C. for 5 hours. The reaction was concentrated to obtain the trifluoroacetate of Compound 3-12A. LCMS: m/Z=741.3 $[M+1]^+$.

Step 13

Compound 3-12A (45 mg, trifluoroacetate), Compound (1S,2S)-2-methylcyclopropane-1-carboxylic acid (9.12 mg, 91.10 μmol of N, N-diisopropylethylamine (303.66 μmol, 52.89 μL), and HATU (69.28 mg, 182.20 μmol) were sequentially added to 5 mL of anhydrous DMF, and the mixture was stirred at 20° C. for 1 hour. The reaction solution was concentrated, and the crude product was separated by preparative HPLC (preparation method: column model: C18 100×40 mm; mobile phase:[water (trifluoroacetic acid)-acetonitrile]; gradient (acetonitrile %): increased from 14% to 44% in 8 minutes) to obtain the trifluoroacetate of Compound 3A. LCMS: m/z=823.4 $[M+1]^+$; $^1$H NMR (400 MHz, 1H NMR $CDCl_3$) δ=8.67 (br s, 1H), 8.38 (s, 1H), 7.57 (br d, J=8.4 Hz, 1H), 7.37 (d, J=8.4 Hz, 1H), 7.27 (s, 1H), 7.20 (s, 1H), 6.78 (br d, J=7.6 Hz, 1H), 5.91 (br s, 1H), 4.22 (br d, J=6.0 Hz, 1H), 4.14-4.06 (m, 2H), 3.99-3.91 (m, 2H), 3.67 (br s, 4H), 3.53 (br dd, J=5.6, 14.8 Hz, 4H), 3.27 (s, 3H), 3.26-2.99 (m, 3H), 2.92 (br s, 3H), 2.81 (br d, J=14.4 Hz, 1H), 2.52 (br d, J=14.2 Hz, 1H), 2.12-1.71 (m, 4H), 1.47 (br d, J=6.0 Hz, 3H), 1.43-1.14 (m, 6H), 1.14-1.06 (m, 6H), 0.79 (s, 3H), 0.66 (s, 3H), 0.63 (br s, 1H).

Example 4

3-12A
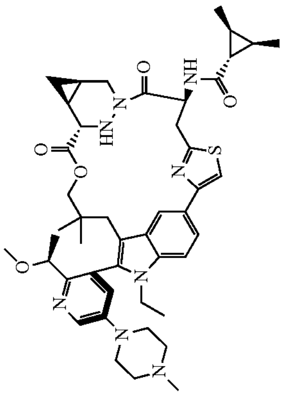
or
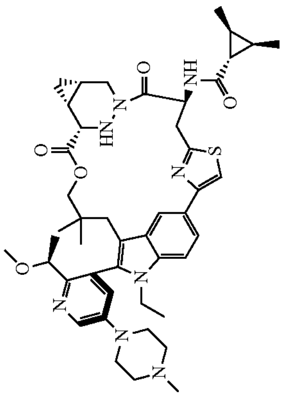
or
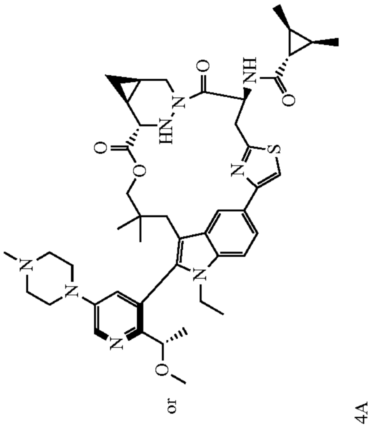
or
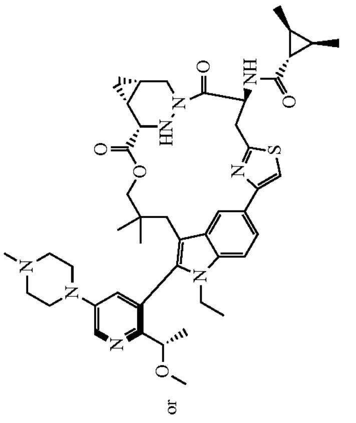
4A

Compound 3-12A (0.1 g, 134.96 μmol), (1r,2R,3S)-2,3-dimethylcyclopropyl-1-carboxylic acid (31 mg, 269.98 μmol) was dissolved in DMF (2 mL), then N,N-diisopropylethylamine (175 mg, 1.35 mmol) and HATU (154 mg, 404.9 μmol) were added. The reaction solution was stirred at 20° C. for 2 hours. The reaction solution was filtered, and the filtrate was directly prepared and purified by HPLC (purification method: column model: C18 100-40 mm; mobile phase: [water (trifluoroacetic acid)-acetonitrile]; gradient (acetonitrile %): increased from 16% to 46% in 8 minutes) to obtain the trifluoroacetate of Compound 4A. LCMS: m/z=837.4 $[M+1]^+$; $^1H$ NMR (400 MHz, $CD_3OD$) δ ppm 8.53 (s, 1H) 8.27 (s, 1H) 7.93 (s, 1H) 7.70 (d, J=8.8 Hz, 1H) 7.49-7.57 (m, 2H) 6.16 (t, J=6.0 Hz, 1H) 4.95-5.04 (m, 3H) 4.10-4.28 (m, 3H) 3.88-4.06 (m, 4H) 3.45-3.70 (m, 3H) 3.24 (s, 3H) 3.02 (s, 3H) 2.82-2.90 (m, 1H) 2.46-2.55 (m, 1H) 2.01-2.11 (m, 1H) 1.81-1.91 (m, 1H) 1.68-1.74 (m, 1H) 1.58-1.66 (m, 1H) 1.42-14.7 (m, 3H) 1.26-1.41 (m, 7H) 1.17-1.23 (m, 3H) 1.08-1.15 (m, 7H) 0.75-0.85 (m, 6H).

Example 5

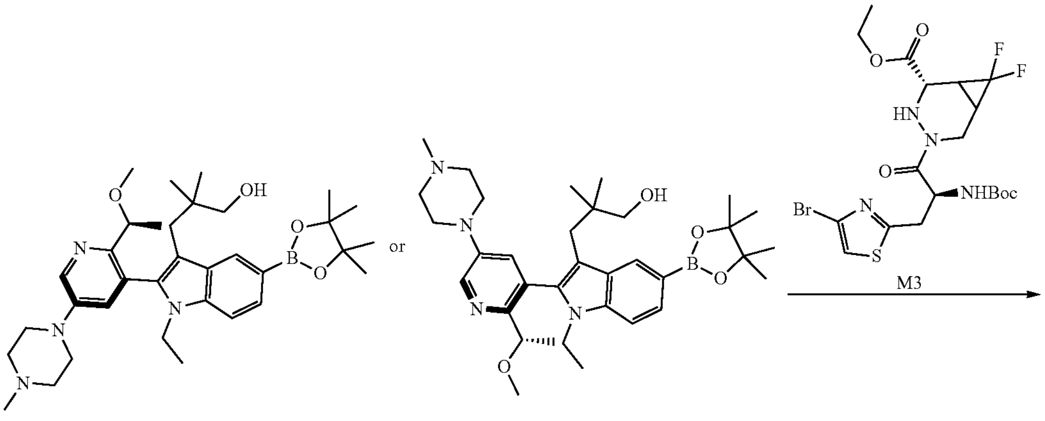

M8

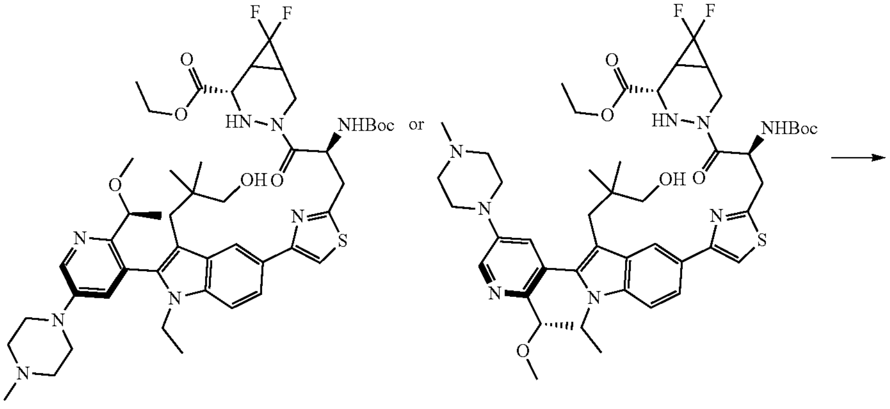

5-1A

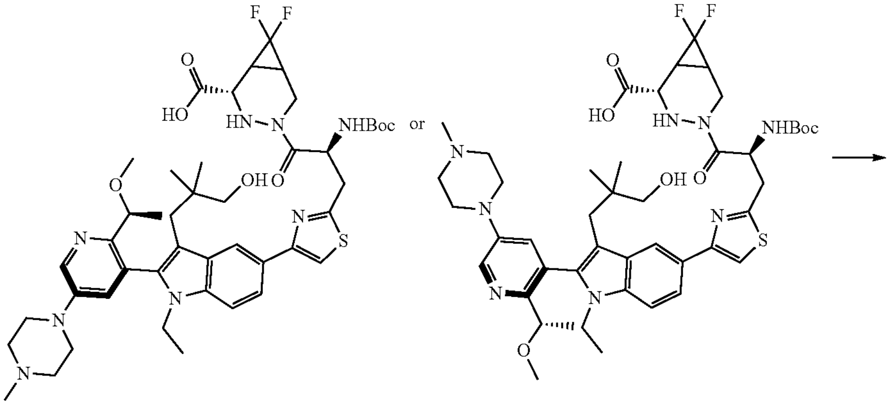

5-2A

-continued
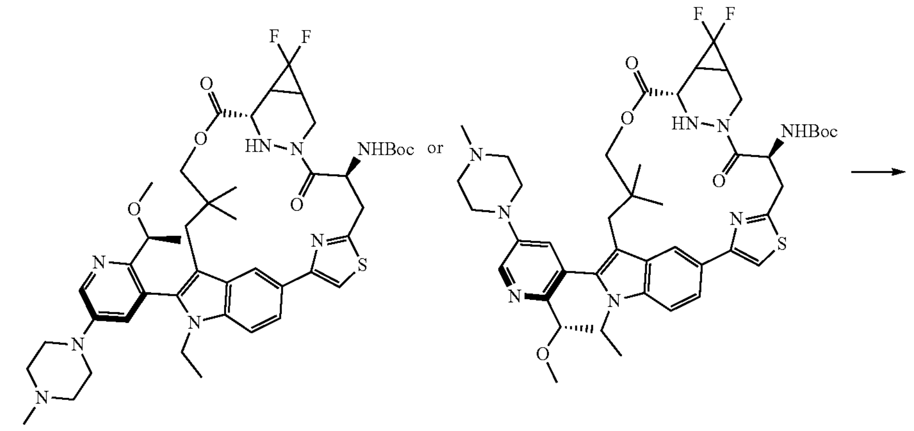
5-3A
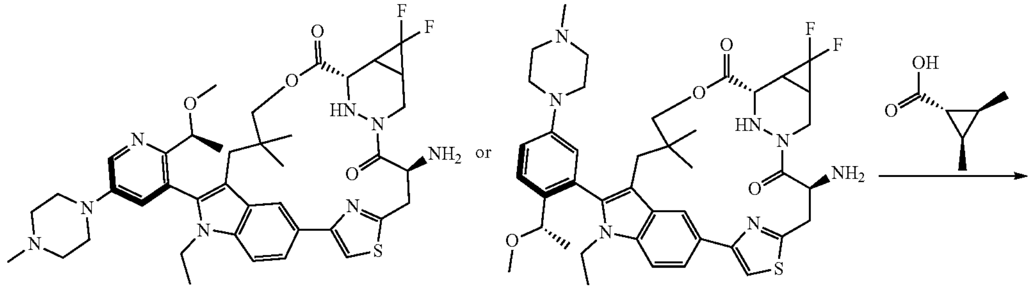
5-4A
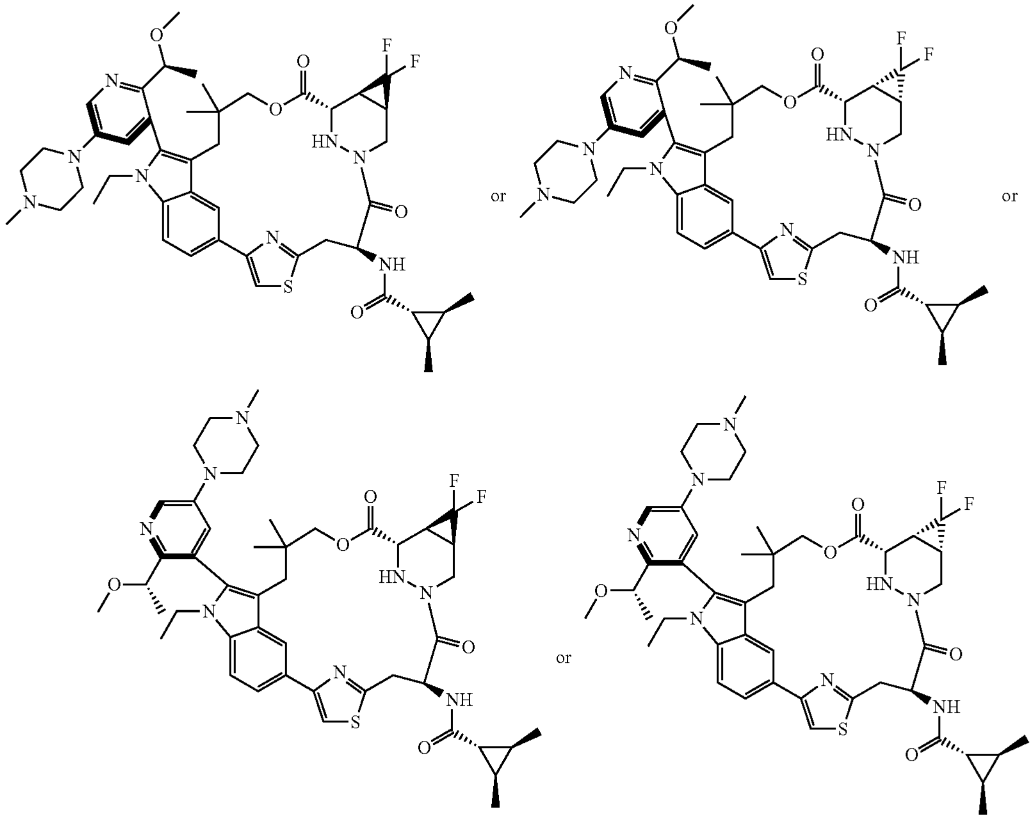
5A

Step 1

Compound M8 (200 mg, 338.64 μmol) and Compound M3 (274 mg, 507.98 μmol) were dissolved in dioxane (4 mL), toluene (1.3 mL) and water (1.3 mL), potassium phosphate (215.65 mg, 1.02 mmol) and 1,1-di(tert-butylphosphino)ferrocenepalladium chloride (22.07 mg, 33.86 μmol) were added, and the reaction solution was stirred and reacted at 70° C. for 12 hours under nitrogen atmosphere. The reaction solution was filtered, and the filtrate was concentrated under reduced pressure to obtain the crude product, which was purified by column chromatography (0-15% methanol/dichloromethane) to obtain Compound 5-1A. LCMS: m/z=923.5 $[M+1]^+$.

Step 2

Compound 5-A (205 mg, 222.07 μmol) was dissolved in a mixed solution of tetrahydrofuran (2 mL) and water (0.5 mL), lithium hydroxide monohydrate (46.59 mg, 1.11 mmol) was added, and the reaction solution was stirred and reacted at 25° C. for 1 hour. Then, the pH of the reaction solution was adjusted to 7-8 with 1 M dilute hydrochloric acid, then the solution was extracted with ethyl acetate (10 mL*5). The organic phases were washed with saturated brine (10 mL), dried with anhydrous sodium sulfate, and concentrated under reduced pressure to obtain Compound 5-2A, which was directly used in the next step. LCMS: m/z=895.3 $[M+1]^+$.

Step 3

Compound 5-2A (45 mg, 50.28 μmol) was dissolved in acetonitrile (4.5 mL), N,N,N',N'-tetramethylchloroformamidinium hexafluorophosphate (21.16 mg, 75.41 μmol) and N-methylimidazole (12.38 mg, 150.83 μmol) were added, and the reaction solution was stirred and reacted at 25° C. for 1 hour. The reaction solution was diluted with water (20 mL) and extracted with dichloromethane (5 mL*3). The organic phases were washed with saturated brine (5 mL), dried with anhydrous sodium sulfate, and concentrated to obtain Compound 5-3A. LCMS: m/z=877.4 $[M+1]^+$.

Step 4

Compound 5-3A (50 mg, 57.01 μmol) was dissolved in dichloromethane (0.5 mL), and trifluoroacetic acid (767.50 mg, 6.73 mmol, 0.5 mL) was added. The reaction solution was stirred and reacted at 25° C. for 1 hour, and concentrated under reduced pressure to obtain the crude trifluoroacetate of Compound 5-4A, which was directly used in the next step.

Step 5

The crude trifluoroacetate of Compound 5-4A obtained in Step 4 was dissolved in DMF (1 mL), (1r,2R,3S)-2,3-dimethylcyclopropyl-1-carboxylic acid (9.70 mg, 84.95 μmol) was added, then N,N-diisopropylethylamine (21.96 mg, 169.90 μmol) and HATU (43.07 mg, 113.27 μmol) were added while stirring. The reaction solution was stirred and reacted at 25° C. for 3 hours, and then prepared by prep-HPLC (column: C18 100×40 mm; mobile phase: [water (trifluoroacetic acid)-acetonitrile], gradient: acetonitrile proportion was increased from 16% to 46% in 8 minutes) and purified to obtain Compound 5A. LCMS: m/z=873.9 $[M+1]^+$. 1 H NMR ($CD_3OD$, 400 MHz) δ 8.5-8.6 (m, 1H), 8.2-8.3 (m, 1H), 7.7-7.7 (m, 1H), 7.61 (br d, J=2.3 Hz, 1H), 7.4-7.5 (m, 2H), 5.5-5.6 (m, 3H), 5.3-5.4 (m, 3H), 4.0-4.3 (m, 6H), 3.8-3.9 (m, 2H), 3.4-3.6 (m, 5H), 3.0-3.1 (m, 5H), 2.2-2.3 (m, 3H), 2.1-2.2 (m, 2H), 2.0-2.1 (m, 6H), 1.6-1.7 (m, 3H), 1.4-1.5 (m, 3H), 1.0-1.1 (m, 3H), 0.8-1.0 (m, 6H).

Example 6

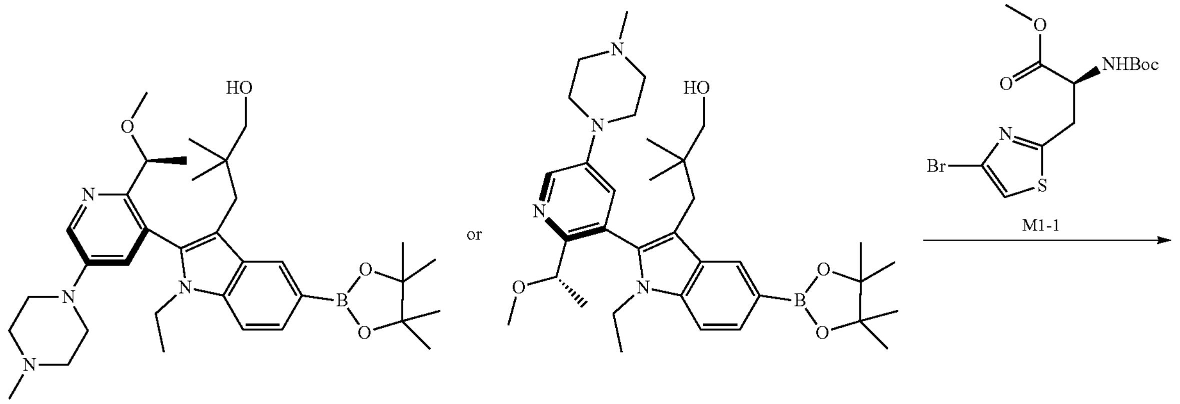

M8

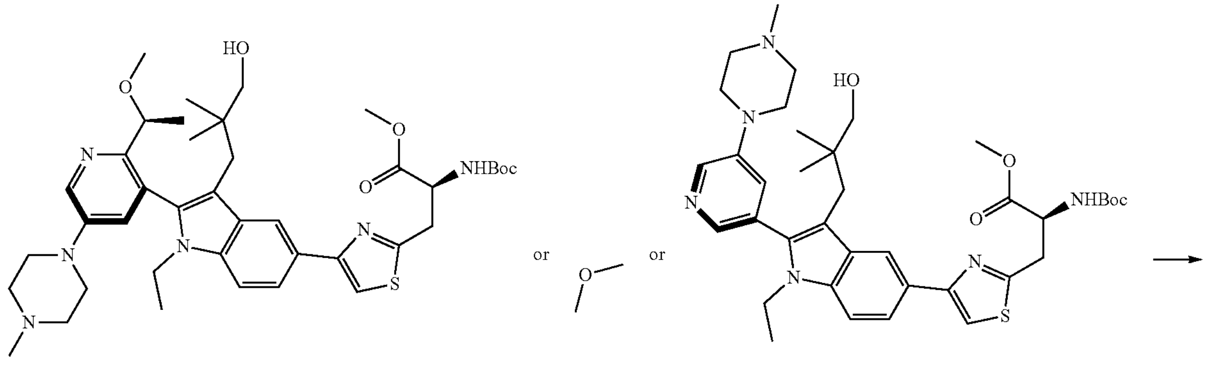

6-1A

-continued
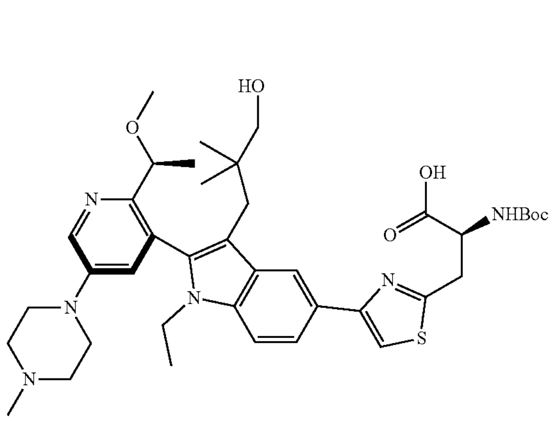
or
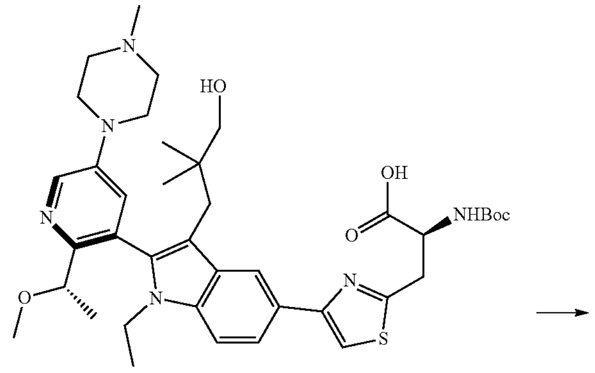
6-2A
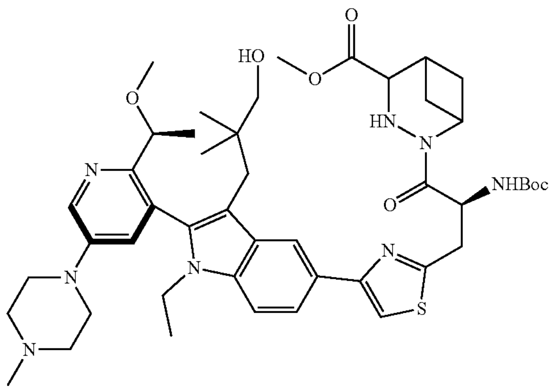
or
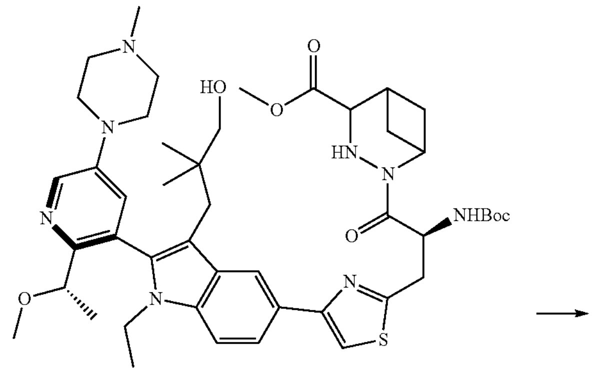
6-3A
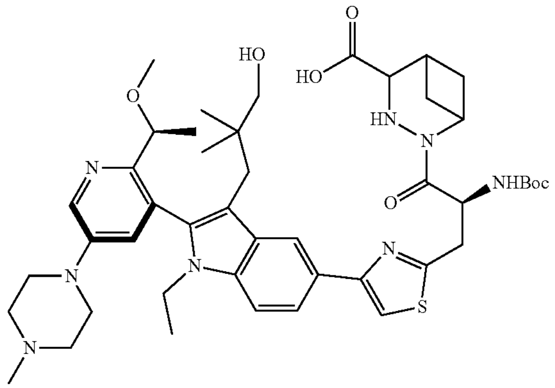
or
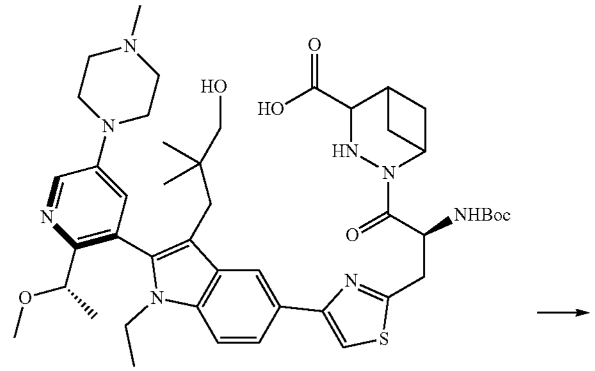
6-4A -continued
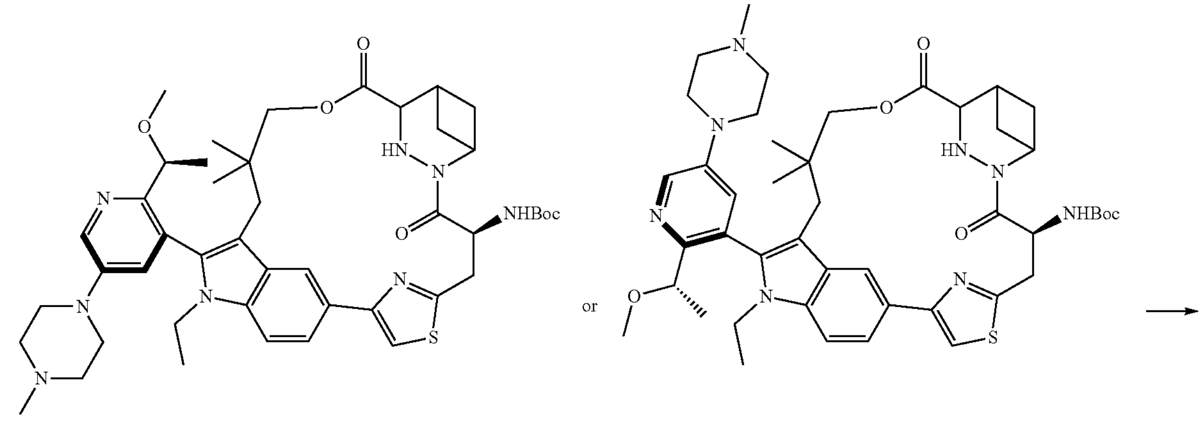
6-5A
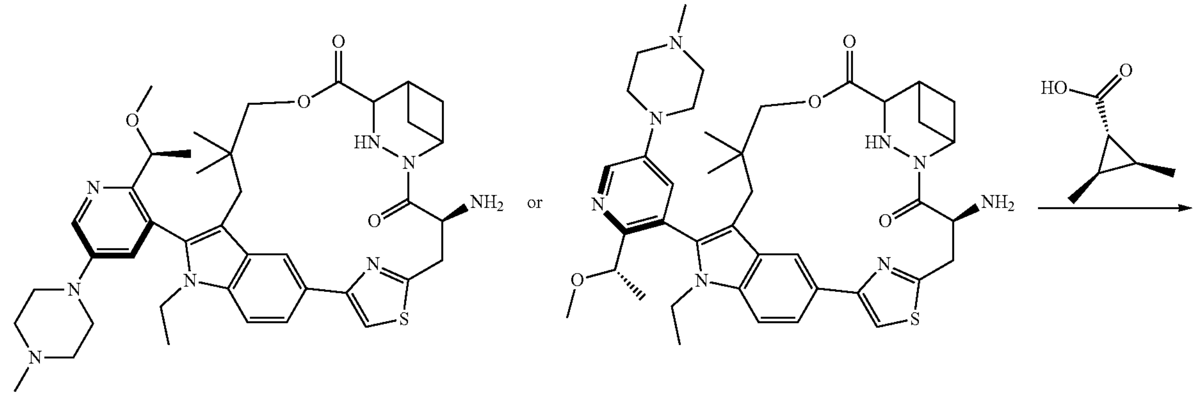
6-6A
6A + 6B
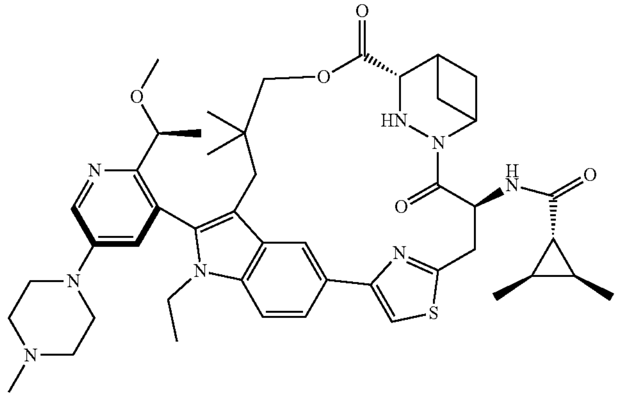
or
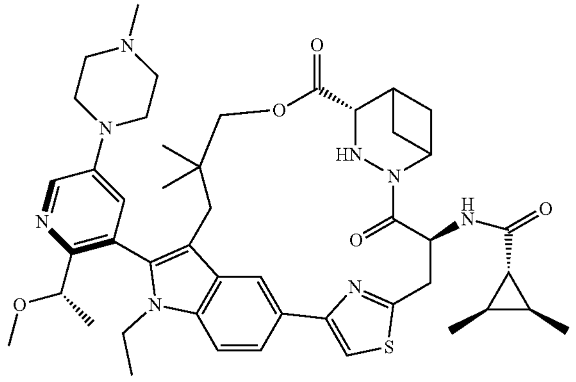
or -continued

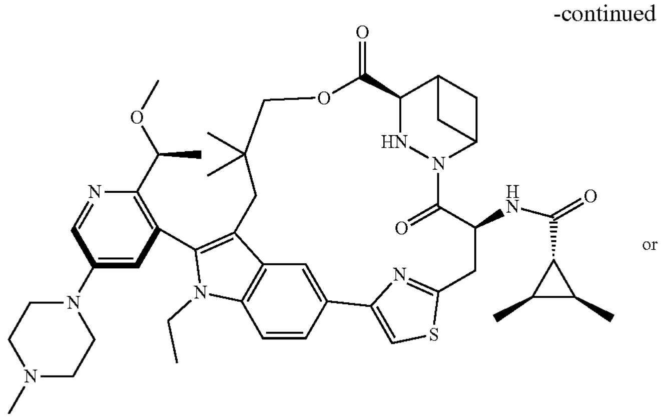

or

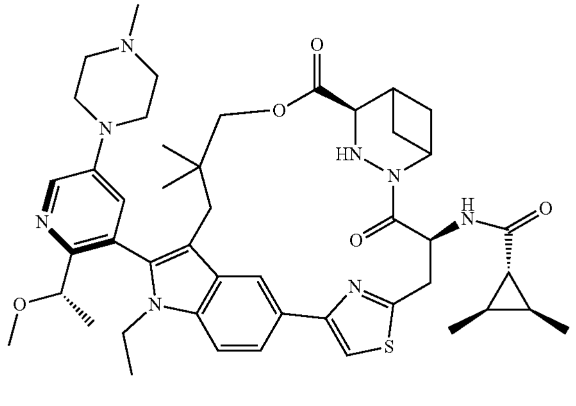

Step 1

Compounds M8 (120 mg, 203.18 μmol) and M1-1 (89.05 mg, 243.82 μmol) were dissolved in toluene (9 mL), 1,4-dioxane (3 mL), and water (3 mL), and potassium phosphate (129.39 mg, 609.55 μmol) and [1,1'-bis(diphenylphosphino) ferrocene]dichloropalladium(II)(26.48 mg, 40.64 μmol) were added under nitrogen protection and stirred at 70° C. for 12 h. After the reaction solution was cooled, it was directly concentrated and then purified by column chromatography (eluent: ethyl acetate/petroleum ether 3% to 7%) to obtain Compound 6-1A. LCMS: m/z=749.6 $[M+1]^+$.

Step 2

Compound 6-1A (130 mg, 173.57 μmol) was dissolved in tetrahydrofuran (3 mL), methanol (1 mL) and water (3 mL), lithium hydroxide monohydrate (36.42 mg, 867.86 μmol) was added and stirred at 25° C. for half an hour. The pH of the system was adjusted to 7.0 with 1 M hydrochloric acid, then diluted with saturated brine (50 mL) and extracted twice with ethyl acetate (30 mL) and tetrahydrofuran (30 mL). The combined organic phases were dried with anhydrous sodium sulfate filtered, and the filtrate was concentrated to obtain Compound 6-2A, which was directly used in the next step. LCMS: m/z=735.6 $[M+1]^+$.

Step 3

Compound M6 (21.82 mg, 95.25 μmol) and Compound 6-2A (70 mg, 95.25 μmol) were dissolved in DMF (2 mL), and N,N-diisopropylethylamine (952.45 μmol, 165.90 μL) and 2-(7-azabenzotriazol-1-yl)-N,N,N',N'-tetramethyluronium hexafluorophosphate (HATU)(43.46 mg, 114.29 μmol) were added and stirred at 25° C. for half an hour. After the reaction was completed, saturated brine (30 mL) was added and extracted with ethyl acetate (30 mL) and tetrahydrofuran (30 mL). The organic phases were dried with anhydrous sodium sulfate, filtered, and the filtrate was concentrated to obtain Compound 6-3A, which was directly used in the next step. LCMS: m/z=874.0 $[M+1]^+$.

Step 4

Compound 6-3A (130 mg, 173.57 μmol) was dissolved in tetrahydrofuran (3 mL), methanol (1 mL) and water (3 mL), lithium hydroxide monohydrate (36.42 mg, 867.86 μmol) was added and stirred at 25° C. for half an hour. The pH of the system was adjusted to 7.0 with 1 M hydrochloric acid, then diluted with saturated brine (50 mL) and extracted twice with ethyl acetate (30 mL) and tetrahydrofuran (30 mL). The combined organic phases were dried with anhydrous sodium sulfate, filtered, and the filtrate was concentrated to obtain Compound 6-4A, which was directly used in the next step. LCMS: m/z=860.0 $[M+1]^+$.

Step 5

Compound 6-4A (61 mg, 71.01 μmol) was dissolved in acetonitrile (20 mL), and N,N,N',N-tetramethylchloroformamidinium-hexafluorophosphate (TCFH) (597.68 mg, 2.13 mmol) and N-methylimidazole (174.89 mg, 2.13 mmol, 169.80 μL) were added and stirred at 25° C. for 1 hour under nitrogen protection. The reaction solution was concentrated and then prepared by pre-TLC (DCM/MeOH=10:1) and separated to obtain Compound 6-5A. LCMS: m/z=842.0 $[M+1]^+$.

Step 6

Compound 6-5A (52 mg, 61.83 μmol) was dissolved in dichloromethane (2 mL), trifluoroacetic acid (798.20 mg, 7.0) mmol, 520.00 μL) was added, and stirred at 25° C. for 1 hour. The reaction solution was concentrated to obtain the crude trifluoroacetate of Compound 6-6A, which was directly used in the next step.

Step 7

Compounds 6-6A (35 mg, 40.9 μmol) and (1r,2R,3S)-2,3-dimethylcyclopropyl-1-carboxylic acid (9.35 mg, 81.8

μmol) were dissolved in DMF (2 mL), and HATU (31.13 mg, 81.87 μmol) and N,N-diisopropylethylamine (409.37 μmol, 71.30 μL) were added and stirred at 25° C. for 1 hour. The solution was diluted with saturated brine (50 mL) and extracted twice with ethyl acetate (30 mL) and tetrahydrofuran (30 mL). The combined organic phases were dried with anhydrous sodium sulfate filtered, and the filtrate was concentrated to obtain the crude product, which was purified by pre-TLC (developing solvent:dichloromethane/methanol=10:1), and then separated and purified by SFC (column: DAICEL CHIRALCEL OD (250 mm*30 mm, 10 μm); mobile phases: phase A was supercritical carbon dioxide, phase B was ethanol (0.1% ammonia), gradient (B %): 50%, isobaric elution) to obtain Compounds 6A and 6B.

Analysis was performed by SFC (column: Chiralcel OD-3 50*4.6 mm I.D., 3 um, mobile phases: A: supercritical carbon dioxide B: ethanol (containing 0.05% diethylamine), gradient elution: mobile phase B was increased from 5% to 40% in 2 minutes, then held at 40% for 1.2 minutes, then held at 5% for 0.8 minutes), the RT of Compound 6A was 1.896 min, ee=96.98%; the RT of Compound 6B was 2.201 min, ee=98.82%. Compound 6A: LCMS: m/z=837.5 $[M+1]^+$; 1H NMR (400 MHz, $CD_3OD$) δ=8.33 (br d, J=10.5 Hz, 2H), 7.59 (br d, J=8.3 Hz, 1H), 7.45 (s, 1H), 7.39 (br d, J=8.5 Hz, 1H), 7.25 (br s, 1H), 5.48 (br s, 1H), 4.61-4.50 (m, 2H), 4.24-4.05 (m, 2H), 3.64-3.50 (m, 2H), 3.28 (br s, 3H), 3.21 (br s, 6H), 2.97 (br d, J=13.3 Hz, 1H), 2.63 (br s, 4H), 2.58-2.44 (m, 2H), 233 (br s, 4H), 2.10 (br t, J=9.0 Hz, 1H), 1.46 (br s, 1H), 1.38-1.16 (m, 8H), 1.05 (br dd, J=6.0, 13.3 Hz, 6H), 0.93-0.85 (m, 3H), 0.81 (br s, 3H), 0.38 (br s, 3H).

Compound 6B LCMS: m/z=837.5 $[M+1]^+$; $^1H$ NMR (400 MHz, $CD_3OD$) δ=8.57 (d, J=28 Hz, 1H), 8.53 (s, 1H), 8.28 (d, J=3.0 Hz, 1H), 7.76 (d, J=9.8 Hz, 1H), 7.60-7.52 (m, 2H), 6.05 (dd, J=3.6, 7.9 Hz, 1H), 4.64 (br d, J=5.0 Hz, 1H), 4.49 (s, 1H), 4.32-4.08 (m, 5H), 3.97-3.86 (m, 2H), 3.79-3.61 (m, 3H), 3.41-3.35 (m, 4H), 3.24 (s, 3H), 3.01 (s, 3H), 2.70 (br d, J=5.8 Hz, 1H), 257-2.49 (m, 1H), 2.48-2.41 (m, 1H), 2.38-2.28 (m, 1H), 2.17 (br d, J=13.8 Hz, 1H), 1.80 (t, J=9.3 Hz, 1H), 1.43 (d, J=6.3 Hz, 3H), 1.37-1.25 (m, 6H), 1.09 (dd, J=5.6, 9.7 Hz, 8H) 0.90 (s, 3H), 0.8) (s, 3H).

Example 7

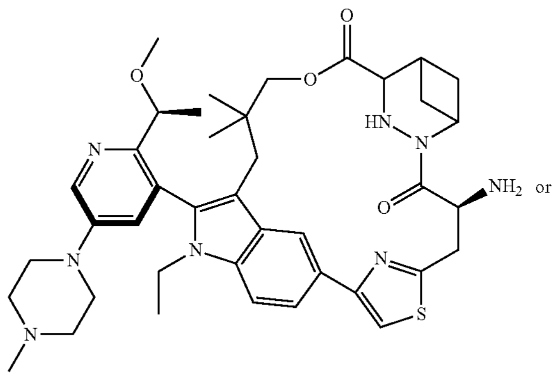

or

-continued

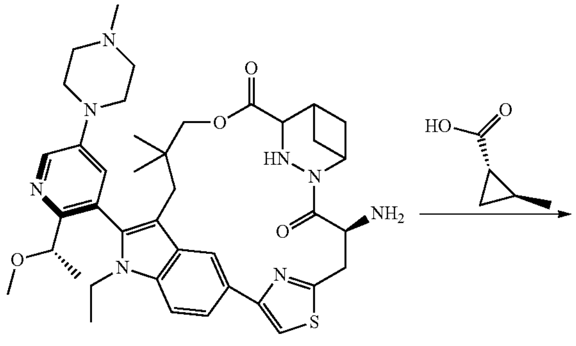

6-6A

7A + 7B

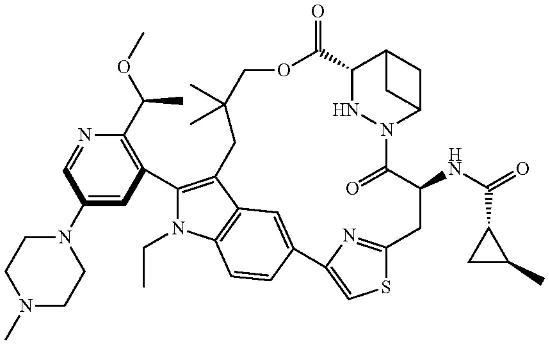

or

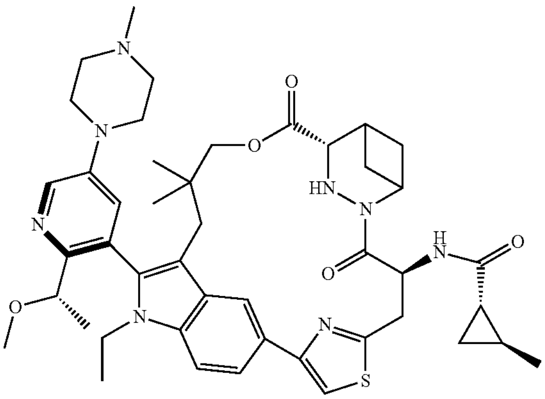

or

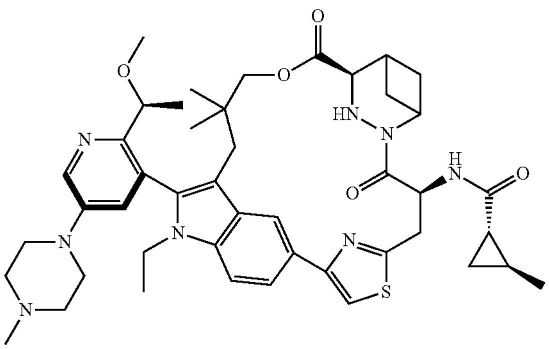

or

-continued

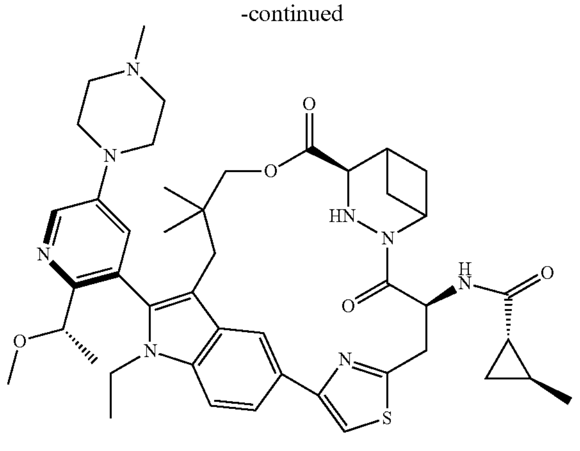

Compound 6-6A (60 mg, 70.18 μmol) and (1S,2S)-2-methylcyclopropyl-1-carboxylic aid (14.05 mg, 81.8 μmol) were dissolved in DMF (10 mL), and HATU (53.37 mg, 140.35 μmol) and N,N-diisopropylethylamine (72.56 mg, 561.42 μmol) were added and stirred at 25° C. for 1 hour. The solution was diluted with saturated brine (50 mL) and extracted twice with ethyl acetate (30 mL) and tetrahydrofuran (30 mL). The combined organic phases were dried with anhydrous sodium sulfate filtered, and the filtrate was concentrated to obtain the crude product, which was purified with a flash silica gel column (mobile phase: dichloromethane/methanol=100:1), and then separated and purified by SFC (column: DAICEL CHIRALCEL OD (250 mm*30 mm, 10 μm); mobile phases: phase A was supercritical carbon dioxide, phase B was ethanol (0.1% ammonia), gradient (B %): 50%) to obtain Compounds 7A and 7B. Analysis was performed by SFC (method: column: chiral OD-3 100*4.6*m I. D., 3 μm, mobile phases: A: supercritical carbon dioxide, B: ethanol (containing 0.05% diethylamine), gradient (B %): 40%), the RT of Compound 7A was 1.365 min, ee=100%; the RT of Compound 7B was 2.325 min, ee=88.2%. Compound 7A LCMS: m/z=823.7 $[M+1]^+$; $^1$H NMR (400 MHz, $CD_3OD$) δ=8.34 (s, 1H), 8.31 (d, J=2.8 Hz, 1H), 7.58 (dd, J=1.5, 8.8 Hz, 1H), 7.44 (s, 1H), 7.38 (d, J=8.5 Hz, 1H), 7.24 (d, J=3.0 Hz, 1H), 5.47 (br s, 1H), 4.60-4.44 (m, 3H), 4.22-4.03 (m, 3H), 3.64-3.50 (m, 2H), 3.31-3.26 (m, 4H), 3.25 (s, 2H), 3.02-2.91 (m, 1H), 2.61 (br t, J=4.9 Hz, 5H), 2.53-246 (m, 1H), 2.38-2.32 (m, 1H), 2.31 (s, 3H), 2.09 (t, J=9.9 Hz, 1H), 1.50-1.36 (m, 2H), 1.32 (d, J=6.3 Hz, 3H), 1.21-1.11 (m, 3H), 1.08 (t, J=7.0 Hz, 1H), 1.04-0.98 (m, 4H), 0.88 (br t, J=7.0 Hz, 3H), 0.81 (s, 3H), 0.60-0.52 (m, 1H), 0.37 (s, 3H).

Compound 7B LCMS: m/z=823.7 $[M+1]^+$; $^1$H NMR (400 MHz, $CD_3OD$) δ=8.38 (s, 1H), 8.33 (d, J=2.8 Hz, 1H), 7.60-7.54 (m, 1H), 7.39-7.34 (m, 2H), 7.31 (d, J=3.0 Hz, 1H), 5.98-5.88 (m, 1H), 4.57-4.50 (m, 1H), 4.37 (s, 1H), 4.07-3.98 (m, 1H), 3.96-3.88 (m, 2H), 3.86-3.74 (m, 2H), 3.55-3.46 (m, 1H), 3.36-3.26 (m, 4H), 2.97 (br d, J=14.3 Hz, 1H), 2.90 (s, 3H), 2.62 (br s, 5H), 2.46-2.38 (m, 1H), 2.32 (s, 3H) 2.26-2.11 (m, 2H), 1.70 (t, J=9.5 Hz, 1H), 1.36-1.28 (m, 4H), 1.20-1.11 (m, 1H), 1.23-1.10 (m, 5H), 0.98-0.98 (m, 1H), 0.99 (d, J=6.0 Hz, 2H) 0.91 (td, J=4.3, 8.5 Hz, 1H), 0.69 (s, 3H), 0.63-0.57 (m, 3H), 0.50-0.41 (m, 1H).

Example 8

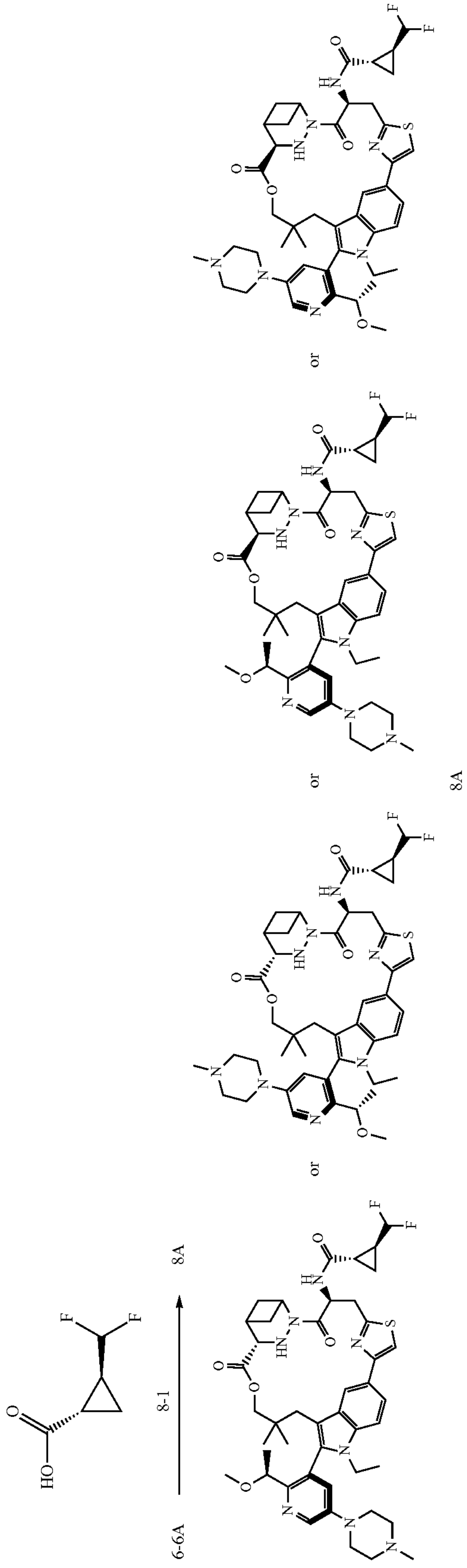
6-6A
8-1
8A
or
or
or
8A

Using Compound 8-1 and Compound 6-6A as the raw materials, referring to the synthesis method of Example 7, the reaction solution obtained was directly prepared by HPLC (column: C18 100×40 mm; mobile phase: [water (trifluoroacetic acid)-acetonitrile]:gradient:acetonitrile was increased from 16% to 46% in 8 minutes) and purified to obtain the trifluoroacetate of Compound 8A. LCMS: m/z=859.5 $[M+1]^+$. $^1$H NMR (400 MHz, DMSO-d6) δ=8.88 (br d, J=9.0 Hz, 1H), 8.51-8.47 (m, 1H), 8.41 (s, 1H), 7.84-7.80 (m, 1H), 7.76-7.71 (m, 1H), 7.59-7.55 (m, 1H), 7.44-7.39 (m, 1H), 6.01 (br d, J=11.3 Hz, 1H), 5.46-5.37 (m, 1H), 5.34-5.30 (m, 1H), 4.68-4.61 (m, 1H), 4.53-4.47 (m, 1H), 4.37-4.23 (m, 1H), 4.20-4.09 (m, 2H), 4.06-3.99 (m, 2H), 3.20 (s, 3H) 3.05 (br s, 2H), 2.95-2.89 (m, 1H), 2.86 (s, 3H), 2.65-2.58 (m, 1H), 2.33 (br d, J=1.5 Hz, 1H), 2.20-2.13 (m, 1H), 2.11-2.05 (m, 1H), 2.04-1.94 (m, 3H), 1.70-1.63 (m, 1H), 1.62-1.54 (m, 1H), 1.48-1.43 (m, 1H), 1.34 (br d, J=6.3 Hz, 4H), 1.05 (br t, J=6.9 Hz, 3H), 0.94-0.83 (m, 10H), 0.39-0.28 (m, 3H).

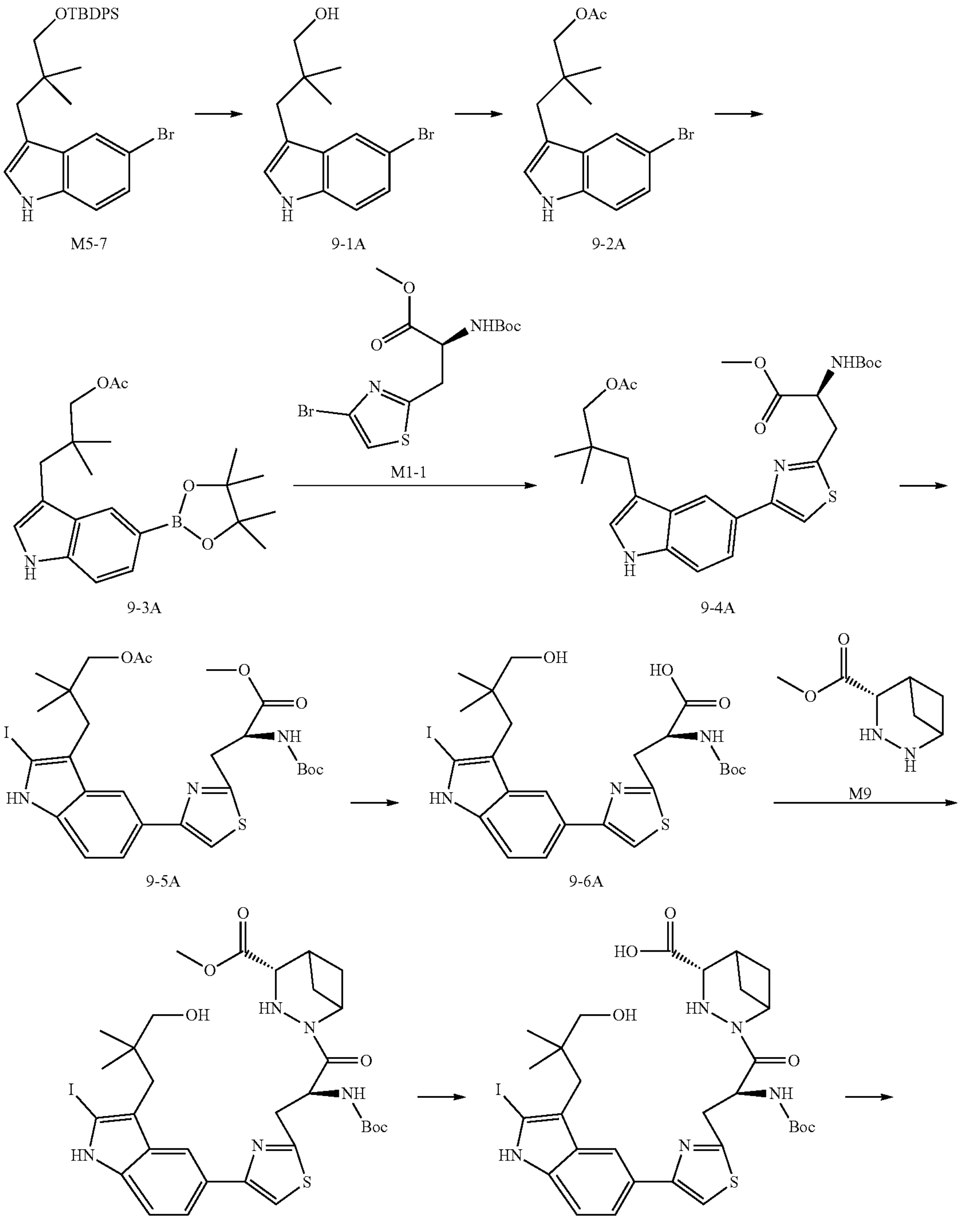

M5-7, 9-1A, 9-2A, 9-3A, 9-4A, 9-5A, 9-6A, 9-7A, 9-8A

-continued
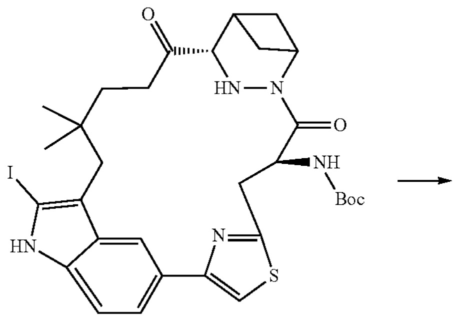
9-9A
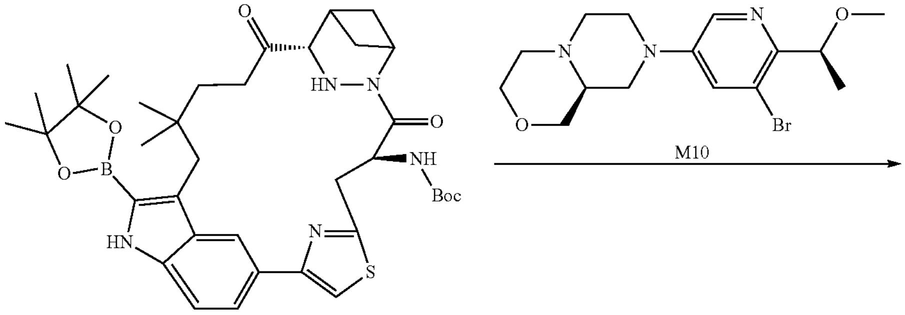
9-10A
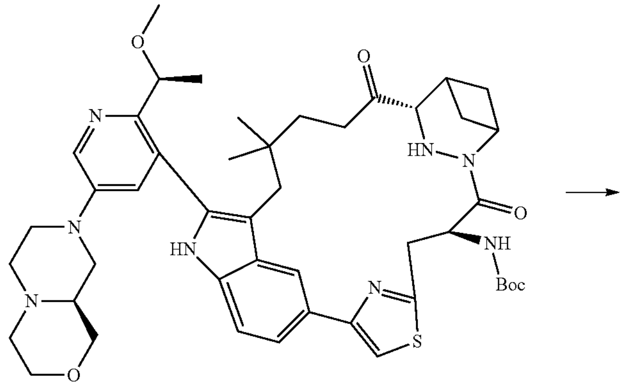
9-11A
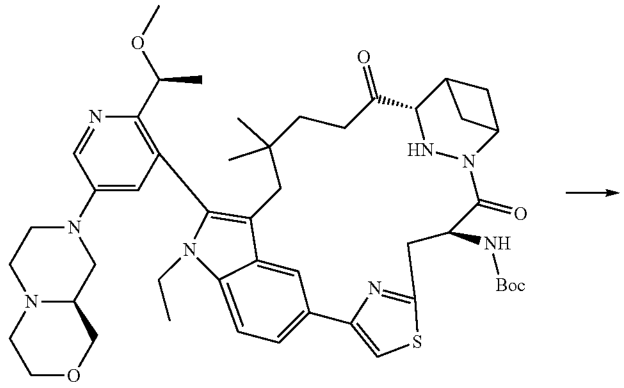
9-12A -continued

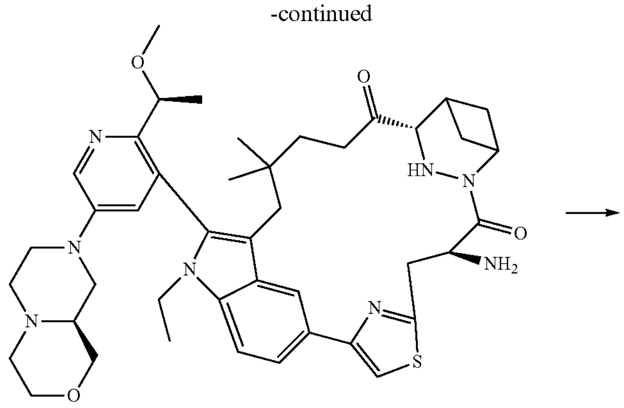

9-13A

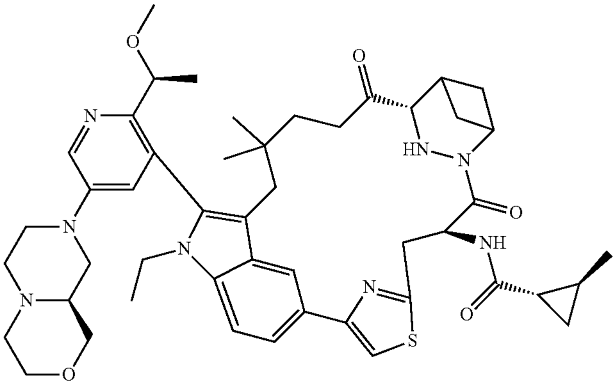

9A

Step 1

Compound M5-7 (6.83 g, 13.12 mmol) was dissolved in tetrahydrofuran (50 mL) and tetrabutylammonium fluoride (1 M solution in tetrahydrofuran, 65.60 mL) was added. The reaction solution was stirred at 50° C. for 16 hours. After the reaction was completed, the reaction solution was concentrated directly. The crude product was diluted with water (100 mL) and the solution was extracted with ethyl acetate (50 mL*3). The organic phases were combined and washed once with saturated brine (50 mL), dried with anhydrous sodium sulfate, filtered, and the filtrate was directly concentrated. The crude product was purified with a flash chromatography column (silica gel, eluent: ethyl acetate/petroleum ether, ethyl acetate proportion: 0-55%) to obtain Compound 9-1A. LCMS: m/z=281.9 $[M+1]^+$.

Step 2

Compound 9-1A (3.31 g, 11.73 mmol) was dissolved in dichloromethane (30 mL), then triethylamine (3.56 g, 35.19 mmol) and 4-dimethylaminopyridine (72 mg, 596.51 μmol) were added, the solution was cooled to 0° C., and acetic anhydride (1.16 g, 11.38 mmol,) was added dropwise. The reaction solution was stirred at 0° C. for 10 minutes. After the reaction was completed, the reaction solution was diluted with water (50 mL), and the solution was extracted with dichloromethane (50 mL*3). The organic phases were combined and washed once with saturated brine (50 mL), dried with anhydrous sodium sulfate, filtered, and the filtrate was directly concentrated. The crude product was purified with a flash chromatography column (silica gel, eluent: ethyl acetate/petroleum ether, ethyl acetate proportion: 0-30%) to obtain Compound 9-2A. LCMS: m/z=323.9 $[M+1]^+$.

Step 3

Compound 9-2A (3.4 g, 10.49 mmol), bis(pinacolato) diboron (6.66 g, 26.22 mmol), potassium acetate (2.57 g, 26.22 mmol), and 1,1-bis(diphenylphosphino)ferrocene]palladium(II) dichloride (0.768 g, 1.05 mmol) were dissolved in toluene (40 mL), nitrogen was replaced three times, and the reaction solution was stirred at 90° C. for 3 hours. After the reaction was completed, the reaction solution was concentrated directly. The crude product was purified with a flash chromatography column (silica gel, eluent: ethyl acetate/petroleum ether, ethyl acetate proportion 0-30%) to obtain Compound 9-3A. LCMS: m/z=372.1 $[M+1]^+$.

Step 4

Compound 9-3A (3.8 g, 10.23 mmol), M1-1 (5.61 g, 15.35 mmol), potassium phosphate (5.43 g, 25.59 mmol), and 1,1-bis(diphenylphosphino)ferrocene]palladium(II) dichloride (750 mg, 1.12 mmol) were dissolved in toluene (30 mL), dioxane (10 mL) and water (10 mL), nitrogen was replaced three times, and the reaction solution was stirred at 70° C. for 12 hours. After the reaction was completed, the reaction solution was concentrated directly. The crude product was purified with a flash chromatography column (silica gel, eluent: ethyl acetate/petroleum ether, ethyl acetate proportion: 0-50%) to obtain Compound 9-4A. LCMS: m/z=530.2 [M+1]=.

Step 5

Compound 9-4A (5.4 g, 10.20 mmol) was dissolved in tetrahydrofuran (50 mL), cooled to 0° C., then sodium bicarbonate (1.03 g, 12.28 mmol) and silver trifluoromethanesulfonate (3.15 g, 12.25 mmol) were added, then iodine (2.33 g, 9.18 mmol) in tetrahydrofuran solution (5 mL) was added dropwise. The reaction solution was stirred at 0° C. for 15 minutes. After the reaction was completed, the reaction solution was quenched by adding saturated sodium sulfite solution (100 mL) at 0° C., and the obtained solution was extracted with ethyl acetate (100 mL*3). The organic phases were combined, washed with saturated brine (100 mL), dried with anhydrous sodium sulfate, filtered, and the filtrate was directly concentrated. The obtained crude product was purified with a flash chromatography column (silica gel, eluent: ethyl acetate/petroleum ether, ethyl acetate proportion 0-40%) to obtain Compound 9-5A. LCMS: m/z=656.1 $[M+1]^+$.

Step 6

Compound 9-5A (3.2 g, 4.88 mmol) was dissolved in tetrahydrofuran (3 mL) and water (1 mL), and lithium hydroxide monohydrate (615 mg, 15.64 mmol) was added at 0° C. The reaction solution was stirred at 25° C. for 12 hours. After the reaction was completed, the reaction solution was added with saturated citric acid solution to adjust the pH to about 6, and the obtained solution was extracted with ethyl acetate (100 mL*3). The organic phases were combined and washed once with saturated brine (100 mL), dried with anhydrous sodium sulfate, filtered, and the crude product was directly concentrated by HPLC (column: C18 100×40 mm; mobile phase: [water (trifluoroacetic acid)-acetonitrile]; gradient: acetonitrile was increased from 30% to 60% in 8 minutes) and purified. The target separation solution was concentrated under reduced pressure, adjusted to pH 7-8 with dilute ammonia solution, and extracted with ethyl acetate (30 mL*3). The organic phases were combined and concentrated to obtain Compound 9-6A. LCMS: m/z=600.1 $[M+1]^+$.

Step 7

Compound 9-6A (0.32 g, 1.18 mmol) was dissolved in DMF (7 mL), then N,N-diisopropylethylamine (1.44 g, 11.18 mmol), Compound M9 (0.67 g, 1.12 mmol), and HATU (510 mg, 1.44 mmol) were added. The reaction solution was stirred at 25° C. for 2 hours. After the reaction was completed, the reaction solution was diluted with water (50 mL), and the solution was extracted with ethyl acetate (50 mL*3). The organic phases were combined and washed once with saturated brine (50 mL), dried with anhydrous sodium sulfate, filtered, and the filtrate was directly concentrated. The obtained crude product was purified with a flash chromatography column (silica gel, eluent: ethyl acetate/petroleum ether, ethyl acetate proportion: 0-60%) to obtain Compound 9-7A. LCMS: m/z=738.2 $[M+1]^+$.

Step 8

9-7A (0.63 g, 854.07 μmol) was dissolved in tetrahydrofuran (6 mL) and methanol (6 mL), and a solution of lithium hydroxide monohydrate (0.18 g, 4.29 mmol) in water (6 mL) was added dropwise at 0° C. The reaction solution was stirred at 0° C. for 1 hour. After the reaction was completed, the reaction solution was added with saturated citric acid solution to adjust the pH to about 6, and the solution was extracted with ethyl acetate (50 mL*3). The organic phases were combined and washed once with saturated brine (50 mL), dried with anhydrous sodium sulfate, filtered, and the filtrate was directly concentrated. The obtained crude product was purified with a flash chromatography column (silica gel, eluent: ethyl acetate/petroleum ether, ethyl acetate proportion: 0-100%) to obtain Compound 9-8A. LCMS: m/z=724.1 $[M+1]^+$.

Step 9

Compound 9-8A (0.2 g, 276.39 μmol) was dissolved in acetonitrile (20 mL) and DMF (2 mL), then N-methylimidazole (1.13 g, 13.82 mmol,) and TCFH (388 mg, 1.48 mmol) were added. The reaction solution was stirred at 80° C. for 2 hours. After the reaction was completed, the reaction solution was directly concentrated to remove acetonitrile, diluted with water (30 mL), and extracted with ethyl acetate (30 mL*3). The organic phases were combined and washed once with saturated brine (30 mL), dried with anhydrous sodium sulfate, filtered, and the filtrate was directly concentrated. The obtained crude product was purified with a flash chromatography column (silica gel, eluent: ethyl acetate/petroleum ether, ethyl acetate proportion; 0-40° %) to obtain Compound 9-9A. LCMS: m/z=706.1 $[M+1]+^+$.

Step 10

Compound 9-9A (0.1 g, 141.72 μmol), potassium acetate (48.68 mg, 496.03 μmol), 2-dicyclohexylphosphino-2',6'-dimethoxy-1,1'-biphenyl (30 mg, 71.86 μmol), and tris (dibenzylideneacetone)dipalladium(0) (26 mg, 28.54 μmol) were dissolved in toluene (5 mL), and pinacolborane (145.10 mg, 1.13 mmol) was added dropwise at 0° C. under nitrogen protection. The reaction solution was stirred at 60° C. under nitrogen protection for 3 hours. After the reaction was completed, saturated ammonium chloride (10 mL) was added dropwise to the reaction solution for quenching, and the solution was extracted with ethyl acetate (50 mL*3). The organic phases were combined and washed once with saturated brine (50 mL), dried with anhydrous sodium sulfate, filtered, and the filtrate was directly concentrated. The obtained crude product was purified with a flash chromatography column (silica gel, eluent: ethyl acetate/petroleum ether, ethyl acetate proportion: 0-40%) to obtain Compound 9-10A. LCMS: m/z=706.4 $[M+1]^+$.

Step 11

Compounds 9-10A (0.1 g, 141.71 μmol), M10 (76 mg, 212.76 μmol), potassium carbonate (58.76 mg, 425.13 μmol) and 1,1-bis(diphenylphosphino)ferrocene]palladium(II) dichloride (21 mg, 28.54 μmol) were dissolved in toluene (3 mL), dioxane (1 mL), and water (1 mL), nitrogen was replaced three times, and the reaction solution was stirred at 65° C. for 12 hours. After the reaction was completed, the reaction solution was directly concentrated, and crude 9-11A was directly used in the next step. LCMS: m/z=855.6 $[M+1]^+$.

Step 12

Compound 9-11A (0.1 g, 116.95 μmol) and cesium carbonate (115 mg, 351.85 μmol) were dissolved in DMF (3 mL), and ethyl iodide (28 mg, 176.43 μmol) was added dropwise at 0° C. The reaction solution was stirred at 25° C. for 12 hours. After the reaction was completed, the reaction solution was filtered, and the filtrate was prepared by HPLC (column: C18 100×40 mm; mobile phase: [water (trifluoroacetic acid)–acetonitrile]; gradient:acetonitrile was increased from 22% to 52% in 8 minutes), separated and purified to obtain the trifluoro acetate of Compound 9-12A. LCMS: m/z=883.4 $[M+1]^+$.

Step 13

Compound 9-12A (30 mg, 33.97 μmol) was dissolved in hydrochloric acid/dioxane (2 M, 2 mL), and the reaction solution was stirred at 25° C. for 1 hour. After the reaction was completed, the reaction solution was directly concentrated, and crude 9-13A was directly used in the next step. LCMS: m/z=783.3 $[M+1]^+$.

Step 14

Compound 9-13A (0.03 g, 38.31 μmol) and (1S,2S)-2-methylcyclopropane-1-carboxylic acid (8 mg, 79.91 μmol) were dissolved in DMF (2 mL), then N,N-diisopropylethylamine (50 mg, 386.87 μmol) and HATU (30 mg, 78.90 μmol) were added. The reaction solution was stirred at 25° C. for 12 hours. After the reaction was completed, the reaction solution was filtered, and the filtrate was prepared by HPLC (column: C18 100×40 mm; mobile phase: [water (trifluoroacetic acid)-acetonitrile]; gradient acetonitrile was increased from 17% to 47% in 8 minutes), separated, and purified to obtain the trifluoroacetate of Compound 9A. LCMS: m/z=865.3 $[M+1]^+$. $^1H$ NMR (400 MHz, $CD_3OD$) δ ppm 8.88 (s, 1H) 8.57 (s, 1H) 8.20 (s, 1H) 7.74 (s, 1H) 7.54 (s, 2H) 6.8-6.41 (m, 2H) 4.54-4.45 (m, 1H) 4.29-4.11 (m, 9H) 4.03-3.89 (s, 3H) 3.77-3.57 (m, 6H) 3.06-2.97 (m, 1H) 2.44-2.35 (m, 1H), 2.27-2.15 (m, 5H), 2.09-1.95 (m, 10H), 1.66-1.57 (m, 5H), 1.13-1.06 (m, 3H), 0.92-0.% (m, 6H).
Example 10
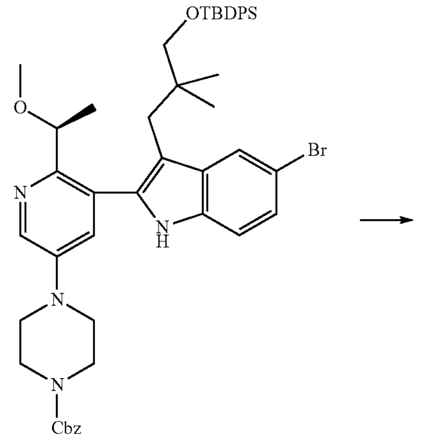
3-4
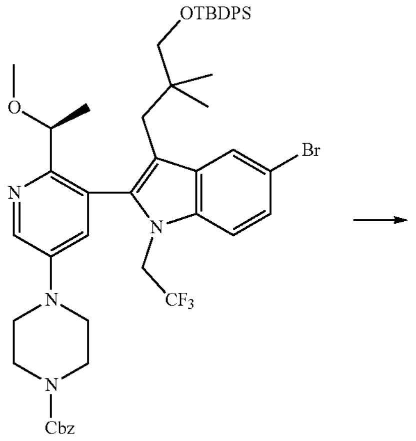
10-1A
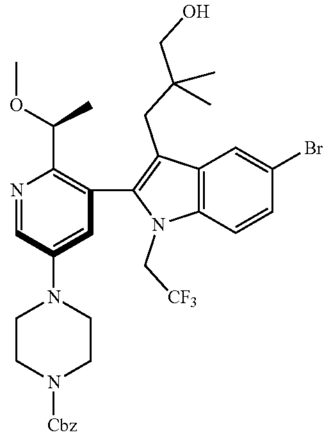
or
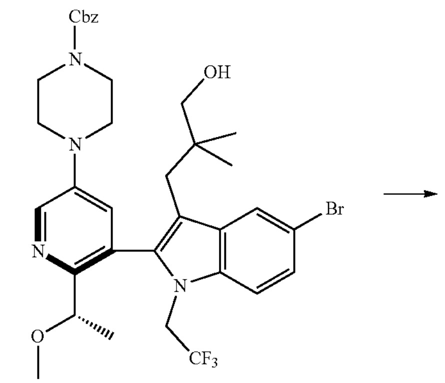
10-2A
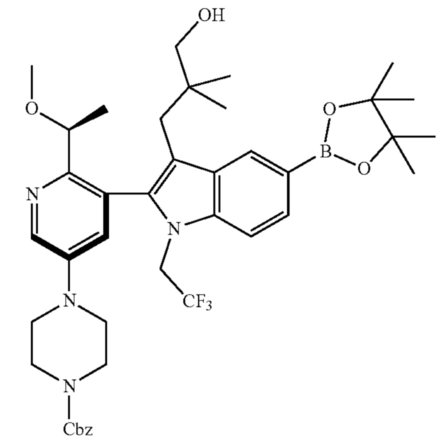
or
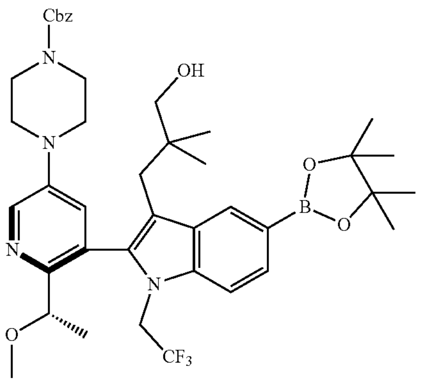
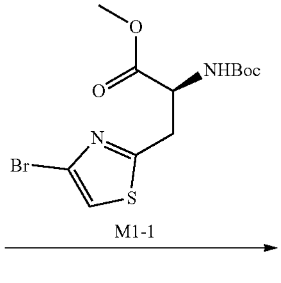
10-3A -continued
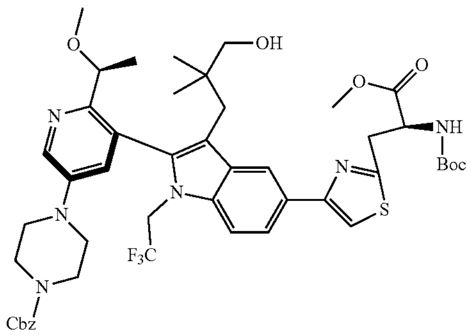
or
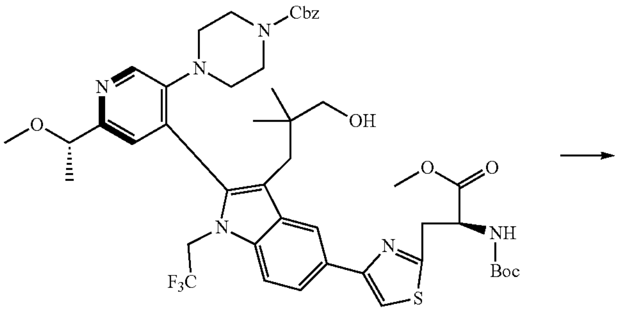
10-4A
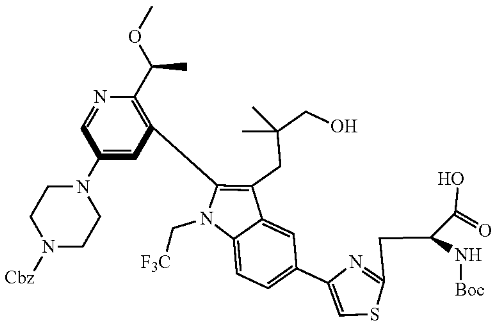
or
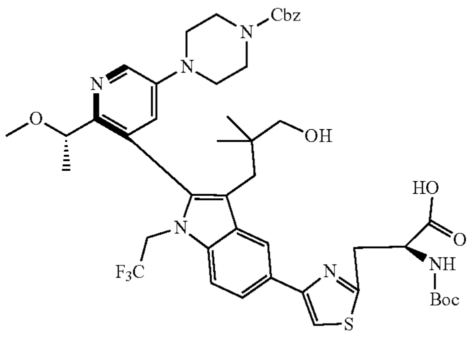
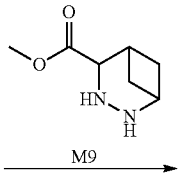
10-5A
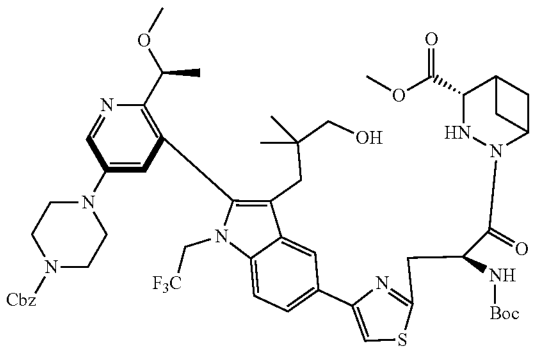
or
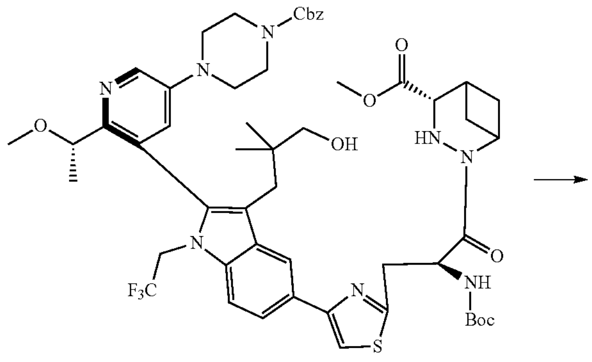
10-6A
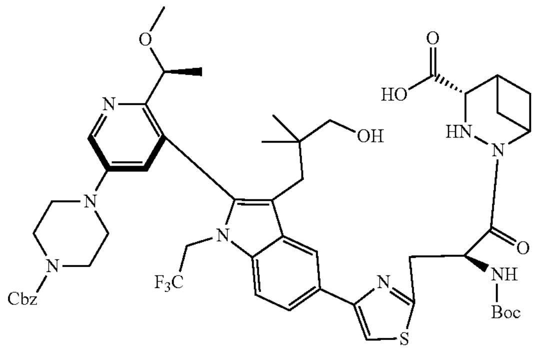
or
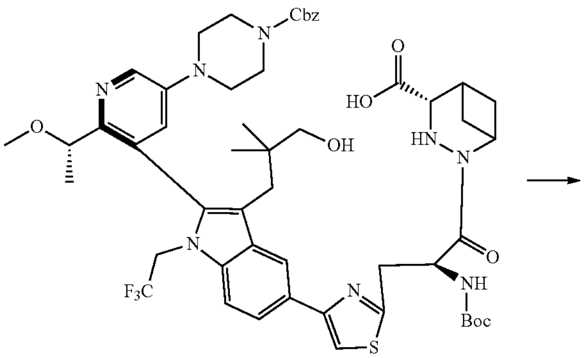
10-7A -continued

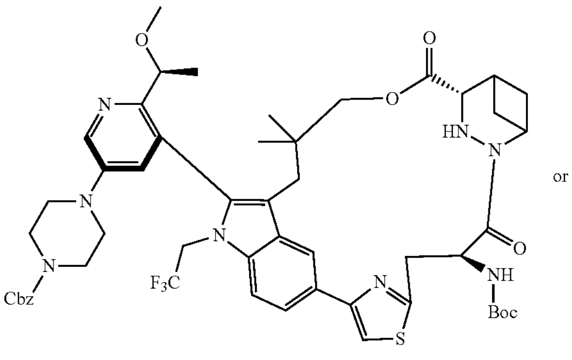

or

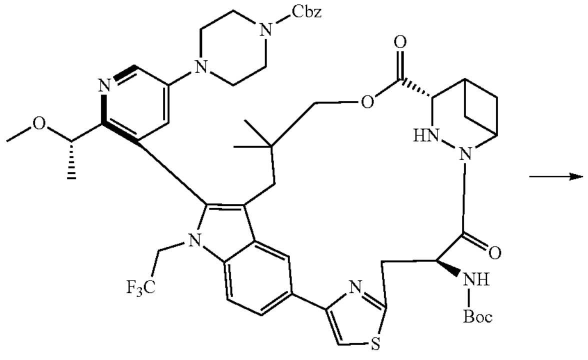

10-8A

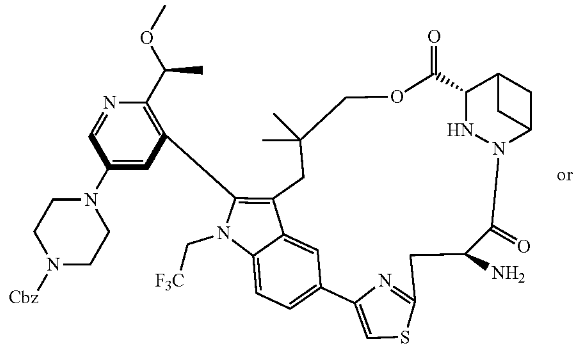

or

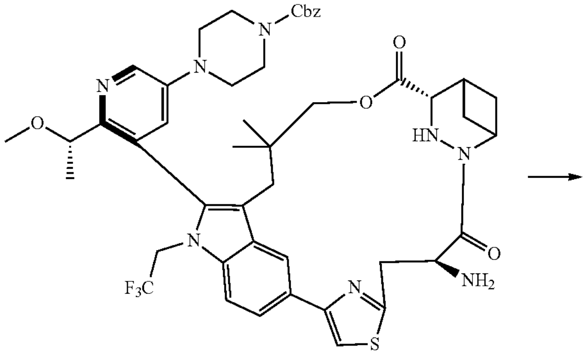

10-9A

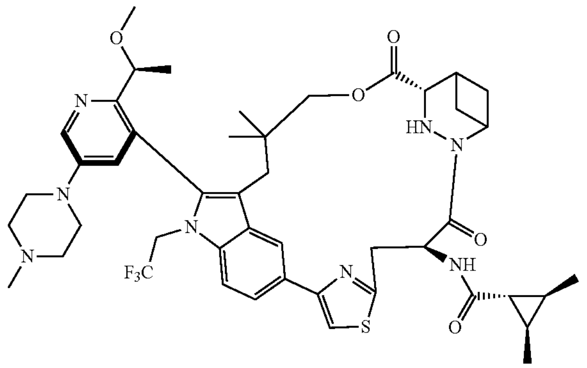

or

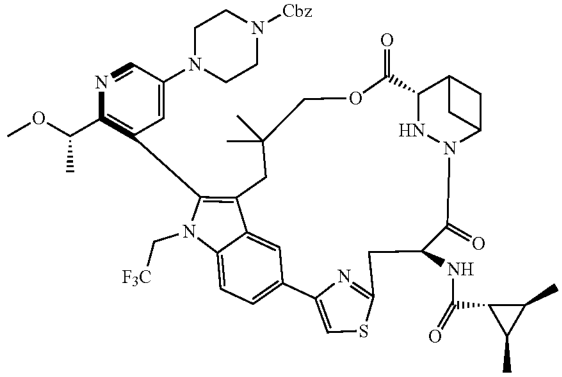

10A

Step 1

Compound 3-4 (1 g, 1.14 mmol) and cesium carbonate (2.61 g, 8.01 mmol) were dissolved in 1-methyl-2-pyrrolidinone (10 mL), cooled to 0° C., then 2,2,2-trifluoroethyl trifluoromethanesulfonate (2.66 g, 11.44 mmol) was added dropwise. The reaction solution was stirred at 25° C. for 48 hours. After the reaction was completed, water (100 mL) was added to the reaction, and the solution was extracted with ethyl acetate (50 mL*3). The organic phases were combined and washed once with saturated brine (50 mL), dried with anhydrous sodium sulfate, filtered, and the filtrate was directly concentrated. The crude product was purified with a flash chromatography column (silica gel, eluent: ethyl acetate/petroleum ether, ethyl acetate proportion: 0-50%) to obtain Compound 10-1A. LCMS: m/z=955.3 $[M+1]^+$.

Step 2

Tetrabutylammonium fluoride (1 M solution in tetrahydrofuran, 5 mL) was added to Compound 10-1A (0.5 g, 523.01 μmol) at 0° C. The reaction solution was stirred at 40° C. for 12 hours After the reaction was completed, water (50 mL) was added to the reaction, and the solution was extracted with ethyl acetate (50 mL*3). The organic phases were combined and washed once with saturated brine (50 mL), dried with anhydrous sodium sulfate, filtered, and the filtrate was directly concentrated. The crude product was purified with a flash chromatography column (silica gel, eluent: ethyl acetate/petroleum ether, ethyl acetate proportion: 0-80%) to obtain Compound 10-2A (LC-MS analysis method: 5-95AB_1.5 min, the retention time of Compound 10-2A was 1.009 min, and the retention time of the isomer thereof was 0.981 min). LCMS: m/z=717.1 [M+1].

Steps 3-11

The reaction solution of Compound 10A was obtained with reference to the synthesis methods of Examples 6-9, the reaction solution was filtered, and the filtrate was prepared by HPLC (column-C18 100×40 mm; mobile phase: [water (trifluoroacetic acid)-acetonitrile]; gradient:acetonitrile was increased from 20% to 50% in 8 minutes), separated and purified to obtain the trifluoroacetate of Example 10A. LCMS: m/z=891.5[M+1]$^+$. $^1$H NMR (400 MHz, $CD_3OD$) δ ppm 8.57-8.43 (m, 2H) 7.80-7.71 (m, 1H) 7.64 (s, 1H) 7.59-7.48 (m, 2H) 5.54-5.49 (m, 1H) 5.38-5.34 (m, 2H) 4.12-4.00 (m, 1H) 3.70-3.68 (m, 1H) 3.62 (s, 1H) 3.37-3.35 (m, 3H) 3.05-2.99 (m, 4H), 2.25-2.18 (m, 4H), 2.11-2.01 (m, 4H), 1.71-1.56 (m, 5H), 1.49-1.42 (m, 5H), 1.41-1.36 (m, 10H), 1.22-1.13 (m, 5H), 1.12-1.04 (m, 3H).

Example 11

11A

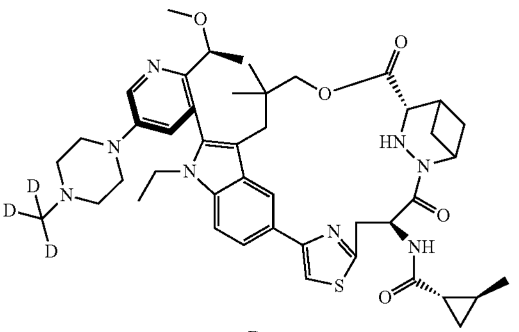

or

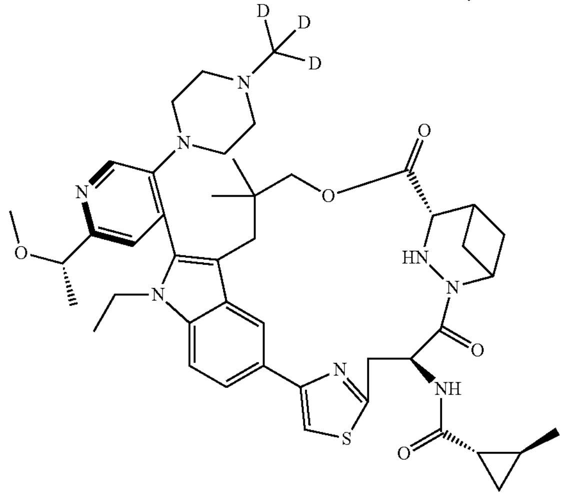

The reaction solution of Compound 11A was obtained with reference to the synthesis methods of Examples 6-9. The reaction solution was added with water until no more solids precipitated, vacuum filtered, the solid was collected, then prepared by HPLC (column: C18 100-40 mm; mobile phase: [water (trifluoroacetic acid)-acetonitrile]; gradient: acetonitrile was increased from 15% to 45% in 8 minutes) and purified to obtain the trifluoroacetate of Compound 11A. LCMS: m/z=825.4 [M+1]$^+$. 1H NMR (400 MHz, $CDCl_3$) δ=8.92-8.78 (m, 1H), 8.28-8.21 (m, 1H), 7.62-7.56 (m, 1H), 7.44-7.37 (m, 2H), 7.36-7.31 (m, 1H), 7.11-7.04 (m, 1H), 5.43-5.31 (m, 1H), 4.97-4.86 (m, 1H), 4.80-4.71 (m, 1H), 4.41-4.32 (m, 1H), 4.23-4.13 (m, 2H), 3.73-3.66 (m, 5H), 3.59-3.55 (m, 2H), 3.41 (br s, 4H), 3.21 (br dd, J=11.8, 12.8 Hz, 3H), 2.96-2.87 (m, 1H), 2.81-2.72 (m, 1H), 2.65-2.56 (m, 1H), 2.47-2.34 (m, 2H), 2.13-2.02 (m, 1H), 1.78-1.67 (m, 1H), 1.48 (br d, J=5.5 Hz, 3H) 1.44-1.36 (m, 1H), 1.31-1.19 (m, 3H), 1.13 (br d, J=5.8 Hz, 3H), 1.02-0.93 (m, 6H), 0.73-0.64 (m, 1H), 0.49-0.34 (m, 3H).

Example 12

12A

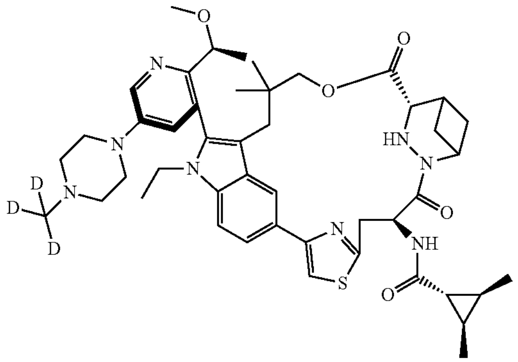

or

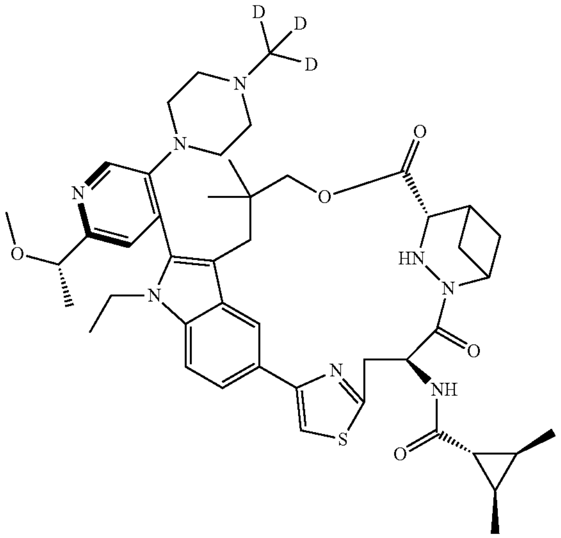

The reaction solution of Compound 12A was obtained with reference to the synthesis methods of Examples 6-9. The reaction solution was added with water until no more solids precipitated, the solid was vacuum filtered and collected, and then prepared by HPLC (column: C18 100×40 mm; mobile phase: [water (trifluoroacetic acid)-acetonitrile]; gradient: acetonitrile was increased from 17% to 47% within 8 minutes) and purified to obtain the trifluoroacetate of target Compound 12A. LCMS: m/z=862.2 [M+23]$^+$. $^1$H NMR (400 MHz, $CDCl_3$) δ=8.64-8.48 (m, 1H), 8.32-8.19 (m, 1H), 7.52 (br d, J=8.8 Hz, 1H), 7.29 (br d, J=8.5 Hz, 1H), 7.25-7.22 (m, 1H), 7.17-7.13 (m, 1H), 6.81-6.73 (m) 1H), 5.45-5.35 (m, 1H), 4.78 (br s, 1H), 4.70-4.63 (m, 1H), 4.24 (br d, J=6.0 Hz, 1H), 4.15-4.08 (m, 2H), 3.62 (br d, J=10.8 Hz, 3H), 3.51 (br d, J=11.3 Hz, 3H), 3.46 (br d, J=5.8 Hz, 1H), 3.31 (s, 3H), 3.16-3.05 (m, 3H), 2.84-2.77 (m, 1H), 2.71-2.63 (m, 1H), 2.55-2.47 (m, 1H), 2.36-229 (m, 2H), 2.22-2.11 (m, 2H), 2.04-1.91 (m, 3H), 1.67-1.53 (m, 3H), 1.51-1.41 (m, 2H), 1.37 (br d, J=5.8 Hz, 4H), 1.07 (br d, J=6.0 Hz, 3H), 1.03 (br d, J=6.0 Hz, 3H), 0.85 to 0.79 (m, 3H), 0.33 (br s, 3H).

Example 13

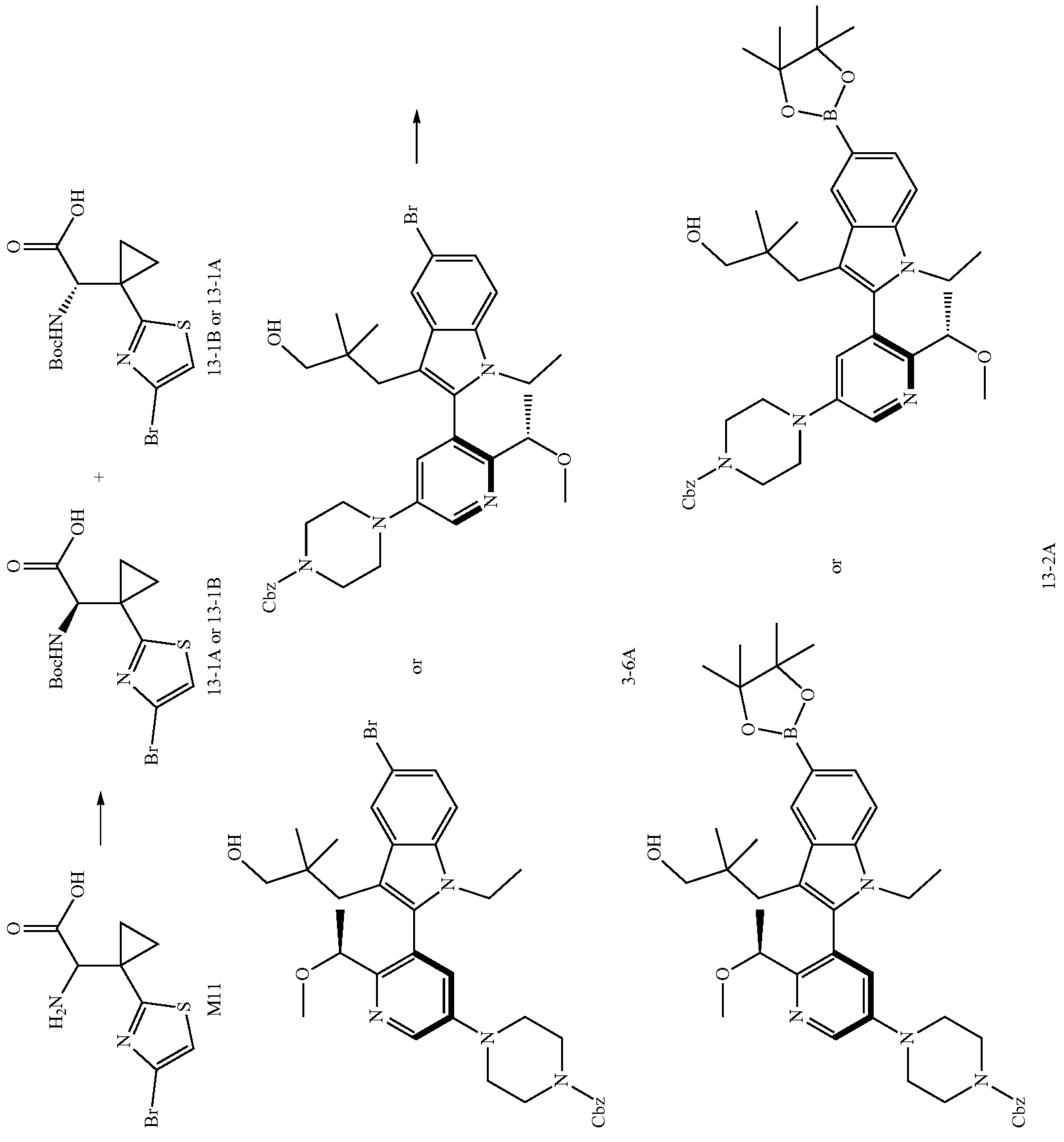
M11
13-1A or 13-1B
+
13-1B or 13-1A
or
3-6A
or
13-2A

-continued
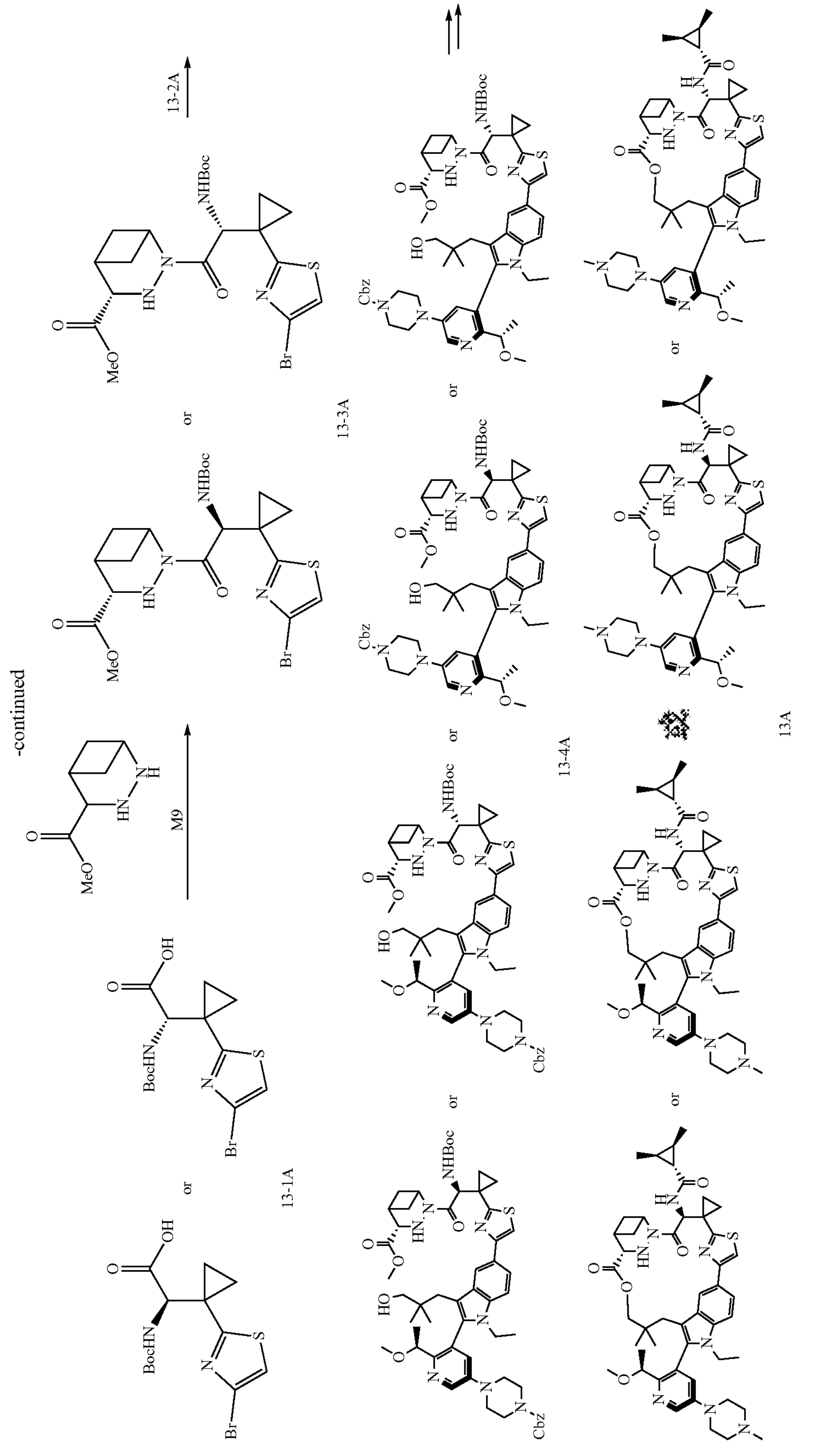
or
13-1A
or
13-3A
or
or
or
13-4A
or
or
or
13A

Step 1

Compound M11 (1.36 g, 4.90 mmol) was dissolved in tetrahydrofuran (40 mL) and water (10 mL), and sodium bicarbonate (1.44 g, 17.14 mmol) and $Boc_2O$ (1.17 g, 5.34 mmol) were added and stirred at 25° C. for 12 hours. After the reaction was completed, water (50 mL) and ethyl acetate (50 mL*3) were extracted. After the organic phases were dried and concentrated, it was prepared by SFC (column: DAICEL CHIRALPAK IG (250 mm*30 mm, 10 um); mobile phases: [phase A: supercritical carbon dioxide fluid, phase B: isopropanol containing 0.1% ammonia]; phase B was purified by 30% isocratic elution) and purified to obtain Compound 13-1A (Rt=3.625; SFC analysis method: column: DAICEL CHIRALPAK IG (100*4.6 mm I.D., 3 um); mobile phases: [phase A: supercritical carbon dioxide fluid, phase B: isopropanol containing 0.05% ammonia solution]; phase B was increased from 5% to 40% in 4.5 minutes, then held at 5% for 1.5 minutes, flow rate 2.5 mL/min, column temperature: 40° C.) and 13-1B (Rt=4.200; SFC analysis method: column: DAICEL CHIRALPAK IG (100*4.6 mm I.D., 3 μm); mobile phases: [phase A: supercritical carbon dioxide fluid, phase B: isopropanol containing 0.05% ammonia solution]; phase B was increased from 5% to 40% in 4.5 minutes, then held at 5% for 1.5 minutes, flow rate 2.5 mL % min, column temperature: 40° C.). LCMS: m/z=321.1, 323.1 $[M+1-56]^+$.

Step 2

Compound 3-6A (1.2 g, 1.81 mmol) and bis(pinacolato) diboron (688.76 mg, 2.71 mmol) we added to toluene (10 mL), then potassium acetate (354.91 mg, 3.62 mmol) was added, nitrogen was replaced, and 1,1-bis(diphenylphosphino)ferrocene]palladium(II)dichloride (1,32.31 mg, 180.82 μmol) was added. The reaction solution was stirred under nitrogen and 70° C. for 12 hours. The reaction solution was filtered and the filtrate was concentrated. The crude product was purified by column chromatography (0-15% methanol/dichloromethane) to obtain Compound 13-2A. LCMS: m/z=711.4 $[M+1]^+$.

Step 3

Compound 13-1A (0.05 g, 132.54 μmol) was dissolved in dichloromethane (2 mL), then 1-ethyl-3-(3-dimethylaminopropyl)carbodiimide (30.49 mg, 159.04 μmol), 1-hydroxybenzotriazole (21.49 mg, 159.04 μmol), and N-methylmorpholine (26.81 mg, 265.07 μmol) were added, stirred at 0° C. for 0.5 hours, then trifluoroacetate of Compound M9 (35.81 mg, 132.54 μmol) was added at 0° C., and stirred at 25° C. for 1 hour. After the reaction, the solution was extracted with water (50 mL) (ethyl acetate (50 mL*3), and the organic phases were dried and concentrated to obtain Compound 13-3A LCMS: m/z=515.0, 517.0 $[M+1]^+$.

Step 4

Compound 13-3A (52.00 mg, 100.89 μmol) and Compound 13-2A (89.63 mg, 126.11 μmol) were dissolved in dioxane (1 mL), water (1 mL) and toluene (3 mL), then potassium phosphate (64.25 mg, 302.67 μmol) and 1,1-di (tert-butylphosphino)ferrocenepalladium chloride (13.15 mg, 20.18 μmol) were added, stirred at 70° C. for 12 hours under nitrogen protection, water (10 mL) was added after the reaction was completed, and the solution was extracted with ethyl acetate (10 mL*3). After the organic phases were dried and concentrated, the crude product was separated with a thin-layer chromatography preparation plate (petroleum ester:ethyl acetate=1:1) to obtain Compound 13-4A. LCMS: m/z=510.0 $[M/2+1]^+$.

Step 5

The reaction solution of Compound 13A was obtained with reference to the synthesis methods of Examples 6-9.

Water (10 mL) was added to the reaction solution and the solution was extracted with ethyl acetate (10 mL*3). After the organic phases were dried and concentrated, the crude product was separated with a thin-layer chromatography preparation plate (dichloromethane:methanol=10-1) to obtain Compound 13A. LCMS: m/z=850.0 $[M+1]^+$. $^1H$ NMR (400 MHz, $CD_3OD$) δ ppm 0.59 (s, 3H) 0.67 (s, 3H) 0.99 (s, 3H) 1.06 (br t, J=7.15 Hz, 6H) 1.50 (br s, 2H) 1.59 (br d, J=9.29 Hz, 1H) 1.94 (s, 2H) 2.10 (t, J=7.53 Hz, 1H) 2.19-2.28 (m, 1H) 2.40 (br d, J=5.02 Hz, 2H) 2.59-2.64 (m, 1H), 2.73-2.77 (m, 3H) 2.80 (s, 1H) 2.95 (d, J=7.28 Hz, 1H), 3.03 (s, 3H), 3.09-3.17 (m, 8H) 3.43 (br d, J=9.03 Hz, 3H) 3.58-3.67 (m, 7H) 3.87 (s, 1H) 7.36 (s, 1H) 7.38-7.42 (m, 2H) 7.59 (d, J=8.78 Hz, 1H) 8.34-8.38 (m, 2H).

Example 14

14A

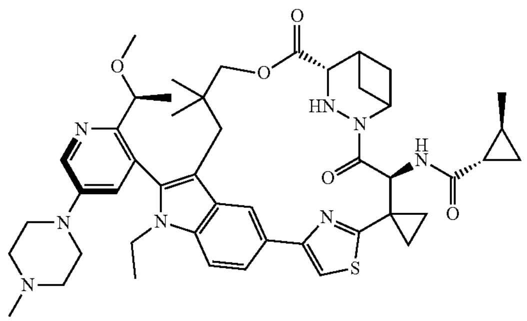

or

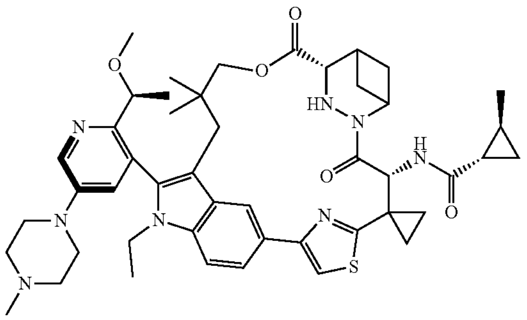

or

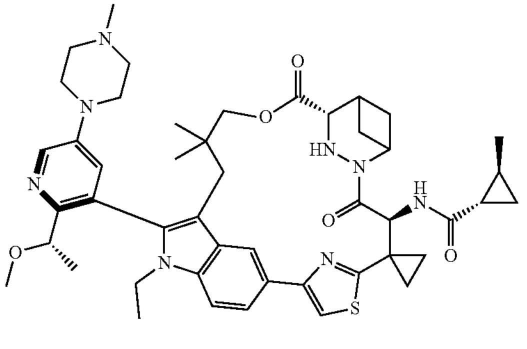

or

-continued
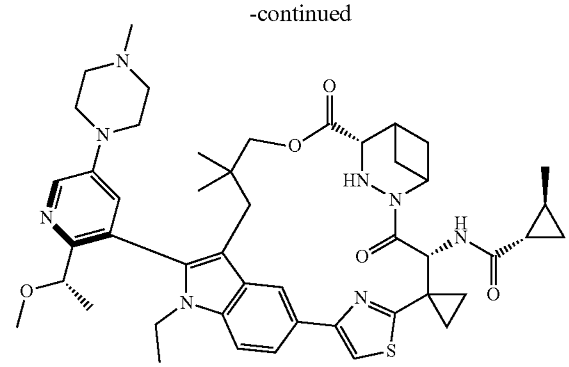
Using Compound 13-1B as the raw material. Compound 14A was prepared with reference to the synthesis method of Example 13.
LCMS: m/z=850.0 $[M+1]^+$. $^1H$ NMR (400 MHz, $CD_3OD$) δ ppm 0.56 (br s, 3H) 0.66 (br s, 1H) 0.90 (s, 3H) 1.04 (br s, 3H) 1.13 (br d, J=5.77 Hz, 4H) 1.24-1.29 (m, 1H) 1.31 (br s, 2H) 1.33-1.38 (m, 2H) 1.44 (br d, J=6.02 Hz, 3H) 1.61 (br s, 1H) 1.73-1.79 (m, 1H) 2.23 (s, 1H) 2.38 (s, 3H) 2.47 (br d, J=10.04 Hz, 1H) 2.60 (br s, 1H) 2.67 (br s, 4H) 2.74 (br s, 1H) 2.97 (s, 1H) 3.27 (s, 3H) 3.37 (br s, 4H) 3.60 (br d, J=10.79 Hz, 1H) 3.74 (br d, J=12.55 Hz, 1H) 4.24 (br d, J=6.53 Hz, 1H) 4.58 (br s, 5H) 4.68 (br s, 1H) 7.37 (s, 1H) 7.46-7.50 (m, 2H) 7.66 (brd, J=8.53 Hz, 1H) 8.43 (s, 2H).
Example 15
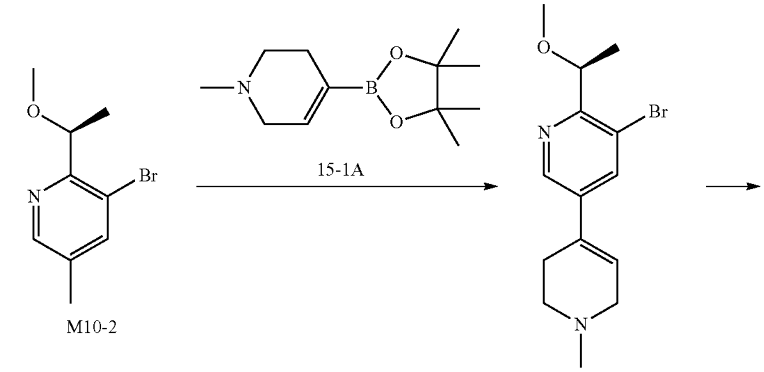
M10-2 15-1A 15-2A
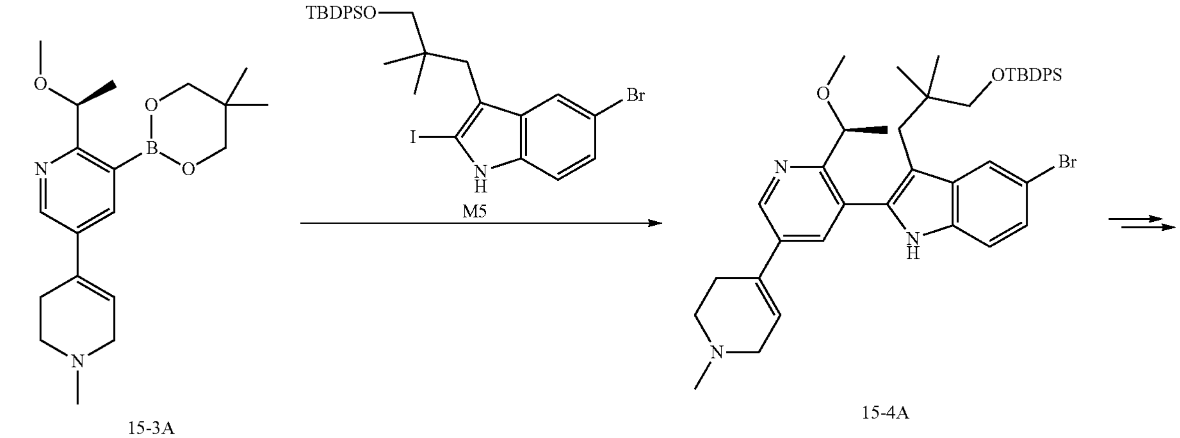
15-3A M5 15-4A -continued

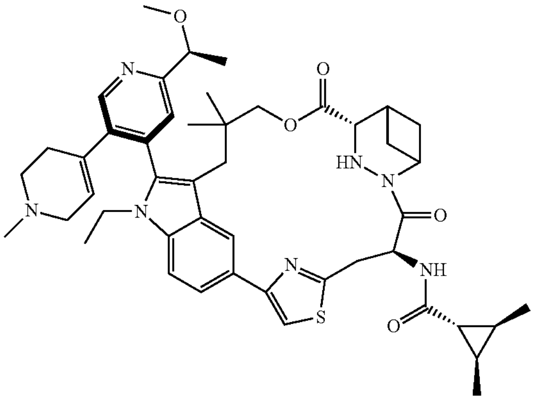

or

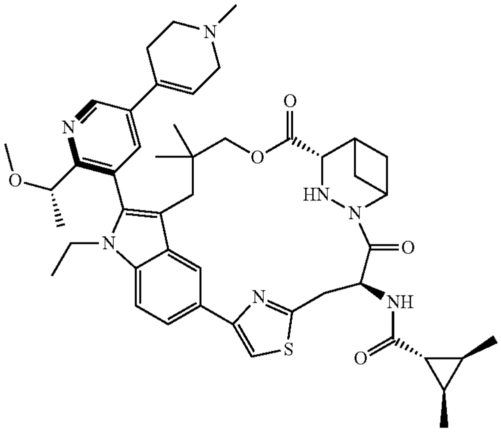

15A

Step 1

Compound M10-2 (728.03 mg, 2.13 mmol) and Compound 15-1A (570 mg, 2.55 mmol) we dissolved in 1,4-dioxane (10 mL), water (2 mL), then potassium carbonate (735.57 mg, 5.32 mmol) and 1,1-bis(diphenylphosphino) ferrocene-palladium(II) (155.77 mg, 212.89 μmol) were added, and the reaction solution was stirred under nitrogen at 50° C. for 2 hours. Then, the reaction solution was filtered to remove insoluble impurities, and the filtrate was concentrated and dried to obtain the crude product. The crude product was purified by column chromatography (0-5% methanol/dichloromethane) to obtain Compound 15-2A. L CMS: m/z=312.9 [M+1]$^+$.

Step 2

Compound 15-2A (580 mg, 1.86 mmol) and bis(neopentyl glycolato)diboron (505.16 mg, 2.24 mmol) were dissolved in toluene (10 mL), then potassium acetate (457.26 mg, 4.66 mmol) and 1,1-bis(diphenylphosphino)ferrocene-palladium(I) (136.37 mg, 186.37 μmol) were added, and the reaction solution was stirred under nitrogen at 80° C. for 2 hours. Then, the reaction solution was filtered to remove insoluble impurities, and the filtrate was concentrated and dried to obtain Compound 15-3A. LCMS: m/z=345.1 [M+1]$^+$.

Step 3

Compound 15-3A (640 mg, 1.86 mmol, 1 eq) and Compound M5 (1.20 g, 1.86 mmol, 1 eq) were dissolved in 1,4-dioxane (20 mL), water (4 mL), potassium carbonate (770.83 mg, 5.58 mmol) was added, nitrogen was replaced three times, 1,1-bis(diphenylphosphino)ferrocene-palladium (II) (136.03 mg, 185.91 μmol) was added, and the reaction solution was stirred under nitrogen and 7 (PC for 3 hr. After the reaction, the reaction solution was filtered to remove insoluble impurities, and the organic solvent was removed by vacuum distillation to obtain the crude product, which was purified by column chromatography (0-10% methanol/dichloromethane) to obtain Compound 15-4A. LCMS: m/z=750.2 [M+1]$^+$.

Step 4

Compound 15A was obtained with reference to the synthesis methods of Examples 6-9. LCMS: m/z=834.5 [M+H]$^+$.

Example 16

16A

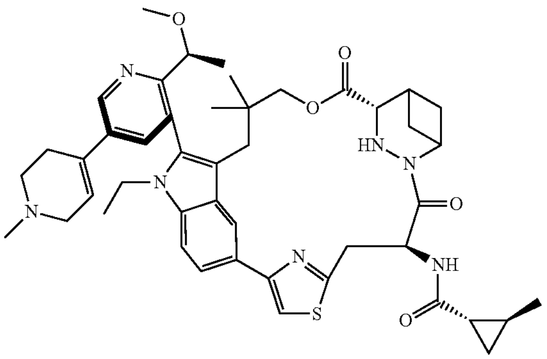

or

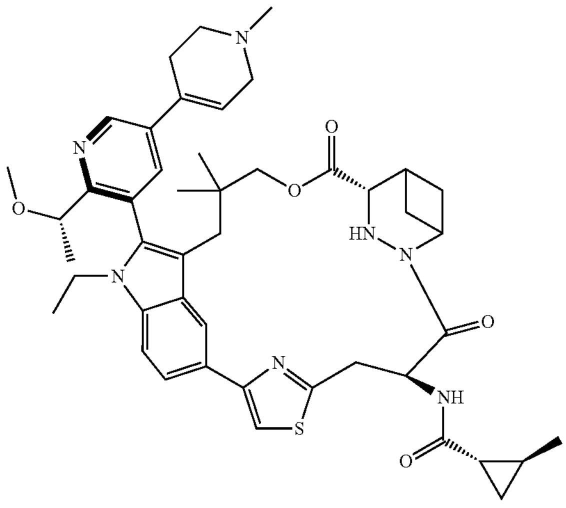

-continued
17A
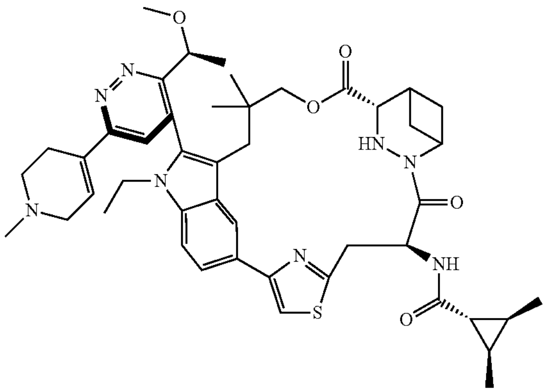
or
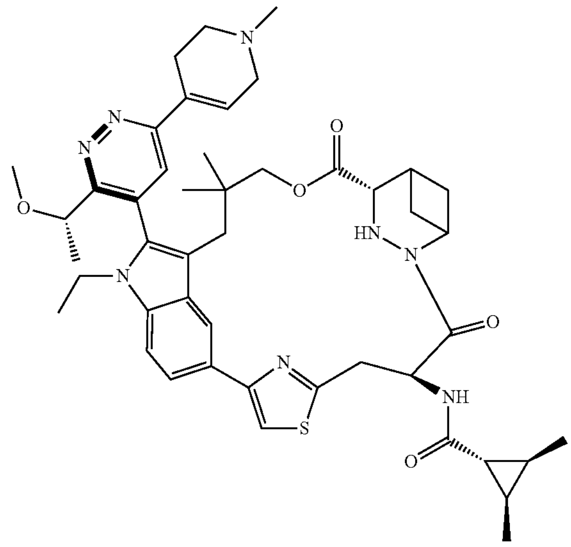
18A
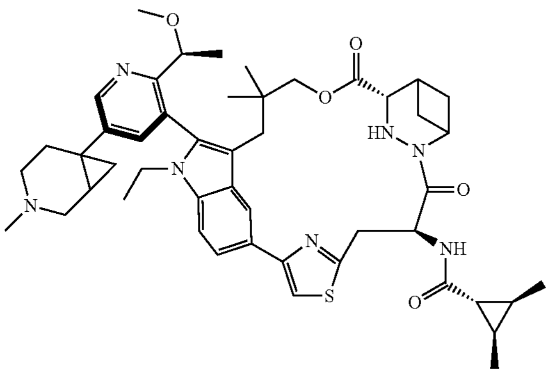
or
-continued
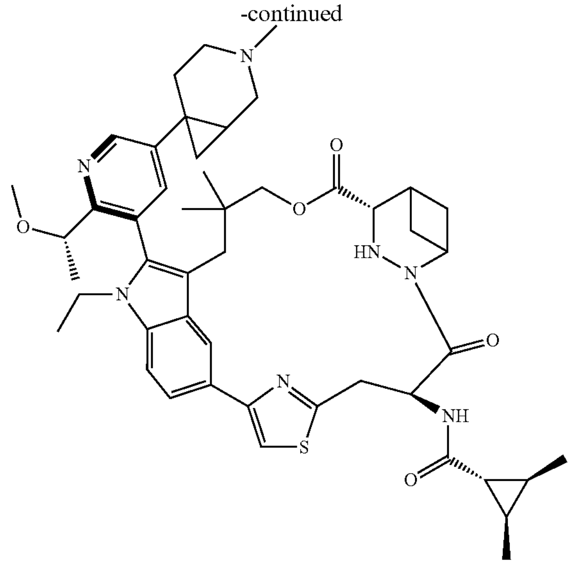
19A
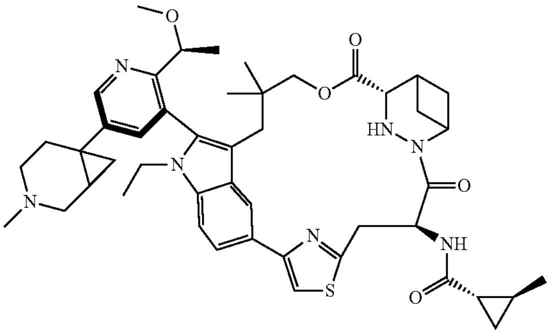
or
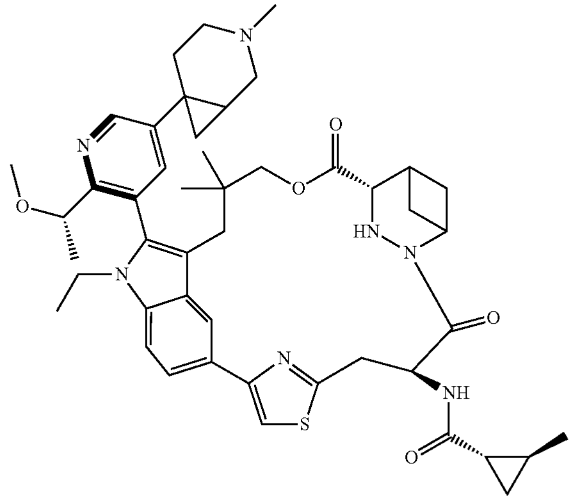
Compound 16A (LCMS: m/z=820.5 $[M+H]^+$), Compound 17A (LCMS: m/z=836.0 $[M+H]^+$), Compound 18A (LCMS: m/z=848.5 $[M+H]^+$), and Compound 19A (LCMS: m/z=834.5 $[M+H]^+$) were prepared with reference to the synthesis methods of Examples 6-9.

Biological Test Data

Experimental Example 1: In Vitro AsPC-1 Cell Proliferation Experiment

Experimental Materials

RPMI1640 medium, penicillin/streptomycin antibiotics were purchased from Gibco, and fetal bovine serum was purchased from Hyclone. 3D CellTiter-Glo (cell viability chemiluminescent detection reagent) reagent was purchased from Promega. The AsPC-1 cell line was purchased from ATCC, Envision multilabel plate reader (PerkinElmer).

Experimental Method

AsPC-1 cells were seeded in an ultra-low adsorption 96-well U-shaped plate, with 80 μL of cell suspension per well, containing 1,000 AsPC-1 cells. The plate was incubated overnight in a carbon dioxide incubator.

The test compound was diluted by 5-fold to 8 concentrations with a pipette, i.e., from 2 mM to 25.6 nM and replicate wells were set up for the experiment. 78 μL of culture medium was added to the intermediate plate, then 2 μL of the gradient diluted compound was transferred into each well of the intermediate plate according to the corresponding position. After mixing well, 20 μL of each well was transferred to the cell plate. The compound concentration transferred to the cell plate ranged from 10 μM to 0.128 nM. The cell plate was cultured in a carbon dioxide incubator for 10 days. Another cell plate was prepared, and the signal value was read as the maximum value (the maximum value in the following equation) on the day of dosing for data analysis.

100 μL of cell viability chemiluminescent detection reagent was added to the cell plate and incubated at room temperature for 30 minutes to stabilize the luminescence signal. A multilabel plate reader was used for reading.

Data Analysis:

The raw data were converted to the inhibition rate using the equation (Sample−Mn 1 Max−Min)*100%, and the $IC_{50}$ value could be obtained by four-parameter curve fitting (obtained from the "log(inhibitor) vs. response—Variable slope" mode in GraphPad Prism). Table 1 provides the inhibitory activity of a compound of the present disclosure on AsPC-1 cell proliferation.

TABLE 1

| | Results of in vitro screening test of a compound of the present disclosure |
|---|---|
| Compound No. | AsPC-1 $IC_{50}$ (nM) |
| Compound 6A | 1 |

Conclusion: The compound of the present disclosure has significant inhibitory activity on AsPC-1 cell proliferation.

Experimental Example 2: In Vitro Cell Proliferation Experiment

Experimental Materials

RPMI 1640 medium, DMEM, Ham's F12 medium, F12K medium, IMDM and penicillin/streptomycin antibiotics were purchased from Gibco, fetal bovine serum was purchased from Hyclone, Envision multilabel plate reader (PerkinElmer).

3D CellTiter-Glo (cell viability chemiluminescence detection reagent) reagent was purchased from Promega; GP2D cell line (DMEM+10% FBS+1% penicillin/streptomycin) was purchased from ECACC; PK-59 cell line (DMEM+10% FBS+1% penicillin/streptomycin), LOVO cells (RPMI1640+10% FBS+1% penicillin/streptomycin), NCI—H727 cells (RPMI1640+10% FBS+1% penicillin/streptomycin), A427 cell line (RPMI1640+10% FBS+1% penicillin/streptomycin), Capan-1 cells (IMDM+20% FBS+1% penicillin/streptomycin) were purchased from Nanjing Cobioer Biosciences Co., Ltd.; A375 cell line (DMEM+10% FBS+1% penicillin/streptomycin), AsPC-1 cells (RPMI1640+10% FBS+1% penicillin/streptomycin), PSN-1 cell line (RPMI1640+10% FBS+1% penicillin/streptomycin), SW620 cells (RPMI1640+10% FBS+1% penicillin/streptomycin), HCT116 cells (RPMI1640+10% FBS+1% penicillin/streptomycin), A549 cells (F12K+10% FBS+1% penicillin/streptomycin), NCI—H441 cells (RPMI1640+10% FBS+1% penicillin/streptomycin) we purchased from ATCC; RKN cell line (Ham's F12+10% FBS+1% penicillin/streptomycin), LU99 cell line (RPMI1640+10% FBS+1% penicillin/streptomycin) were purchased from JCRB.

Experimental Method

The cells were seeded in a ultra-low adsorption 96-well U-shaped plate, with 80 μL of cell suspension per well, containing 1,000 cells. The plate was incubated overnight in a carbon dioxide incubator.

The test compound was diluted by 5-fold to 8 concentrations with a pipette, i.e., from 2 mM to 25.6 nM, and replicate wells were set up for the experiment. 78 μL of culture medium was added to the intermediate plate, then 2 μL of the gradient diluted compound was transferred into each well of the intermediate plate according to the corresponding position. After mixing well, 20 μL of each well was transferred to the cell plate. The compound concentration transferred to the cell plate ranged from 10 μM to 0.128 nM. The cell plate was cultured in a carbon dioxide incubator for 5 days. Another cell plate was prepared, and the signal value was read as the maximum value (the maximum value in the following equation) on the day of dosing for data analysis.

50 μL of cell viability chemiluminescent detection reagent was added to the cell plate and incubated at room temperature for 30 minutes to stabilize the luminescence signal. A multilabel plate reader was used for reading.

Data Analysis:

The raw data were converted to inhibition rate using the equation (Sample−Min/Max−Min)*100%, and the $IC_{50}$ value could be obtained by four-parameter curve fitting (derived from the "log(inhibitor) vs. response—Variable slope" mode in GraphPad Prism). Table 2 provides the experimental results of the inhibitory activity of the compounds of the present disclosure on cell proliferation.

TABLE 2

| Results of in vitro cell proliferation inhibition activity of the compounds of the present disclosure | | |
|---|---|---|
| Inhibitory Activity $IC_{50}$ (nM) | Compound 6A | Compound 7A |
| GP2D | 0.9 | / |
| PK-59 | 2.3 | / |
| AsPC-1 | 2.1 | 6.6 |
| PSN-1 | 5.3 | 10.5 |
| RKN | 4.5 | 7.5 |
| SW620 | 0.2 | / |
| HCT116 | 5.5 | / |
| LOVO | 2.8 | 5.9 |
| A549 | 4.1 | / |
| H441 | 1.4 | / |
| H727 | 0.4 | / |
| LU99 | 8.7 | / |
| A427 | 13.3 | / |
| Capan-1 | 2.5 | / |
| A375 | >6000 | / |

Conclusion: The compounds of the present disclosure has significant inhibitory activity on cell proliferation of RAS mutant cell lines (such as GP2D, PK-59, AsPC-1, PSN-1, RKN, Capan-1, SW620, HCT116. LOVO, A549, H441, H727. LU99 and A427), but they do not demonstrate significant inhibitory effect on wild-type independent cell lines (such as A375), and they have good selectivity.

Experimental Example 3: Detection of p-ERK Level in AsPC-1 Cells

Experimental Materials

AsPC-1 cells were purchased from ATCC: RPMI-1640 medium was purchased from Gibco; fetal bovine serum was purchased from Hyclone; Advanced Phospho-ERK1/2 (THR202/TYR204) KIT was purchased from Bioauxilium-Advanced Phospho; ERK1/2(THR202/TYR204) KIT components were: Advanced PhosphoERK1/2 Eu Cryptate antibody, Advanced PhosphoERK1/2 d2 antibody, Blocking reagent (stock solution 100×), Lysis buffer #1 (stock solution 4×). Detection buffer (ready-to-use), with a storage temperature of ≤−16° C. for all.

Experimental Method (1) The cells were seeded in a white-bottomed 384-well cell culture plate, 8 μL of cell suspension per well, each well containing 7,500 cells. The cell plate was placed in a carbon dioxide incubator and incubated overnight at 37° C.;

(2) The test compound was diluted with 100% DMSO to 3 mM as the first concentration, and then diluted with a pipette to 10 concentrations of 3,000, 1,000, 300, 100, 30, 10, 3, 1, 0.3 and 0.1 μM. 2 μL of the compound was taken and added to 198 μL of cell starvation medium, mixed well, 15 μl, of compound solution was taken and added to 35 μL of cell starvation medium and mixed well. Then, the compound solution of the last step was added to the corresponding cell plate well with 4 μL per well, and the cell plate was placed back into the carbon dioxide incubator to continue incubation for 3 hours, at which time the compound concentration was 3,000, 1,000, 300, 100, 30, 10, 3, 1, 0.3, 0.1 nM;

(3) After incubation, 3 μL of 5× cell lysate was added to each well, and shaken at room temperature for 30 minutes;

(4) The detection buffer was used to dilute the Phospho-ERK1/2 Eu Cryptate antibody and Phospho-ERK1/2 d2 antibody 20 folds, they were mixed at a ratio of 1:1, 5 μL per well was added to the cell culture plate, and incubated at room temperature for 2 h;

(5) After incubation, a multilabel plate reader was used to read the HTRF excitation: 320 nm, emission: 615 nm, and 665 nm.

Data Analysis:

The raw data were converted to inhibition rate using the equation (Sample−Min/Max−Min)*100%, and the IC50 value could be obtained by four-parameter curve fitting (log(inhibitor) vs response—Variable slope mode in GraphPad Prism). Table 4 provides the inhibitory effect of a compound of the present disclosure on p-ERK. Max well: The reading of the positive control well was 1× lysate; Min well: The reading of the negative control well was 0.5% DMSO cell well cell lysate See Table 3 for the experimental results.

TABLE 3

| Results of in vitro pERK inhibition screening test of a compound of the present disclosure | |
|---|---|
| Compound No. | AsPC-1 pERK $IC_{50}$ (nM) |
| Compound 6A | 0.3 |

Conclusion: The compound of the present disclosure has significant inhibitory activity on pERK levels in AsPC-1 cells.

Experimental Example 4: Detection of p-ERK Level in GP2D Cells

Experimental Materials

GP2D cell line (DMEM+10% FBS+1% penicillin/streptomycin) was purchased from ECACC; RPMI-1640 medium was purchased from Gibco; fetal bovine serum was purchased from Hyclone; Advanced Phospho-ERK1/2 (THR202/TYR204) KIT was purchased from Bioauxilium-Advanced Phospho; ERK1/2(THR202/TYR204) KIT was composed of: Advanced PhosphoERK1/2Eu Cryptate antibody, Advanced PhosphoERK1/2 d2 antibody. Blocking reagent (stock solution 100×), Lysis buffer #1 (stock solution 4×), Detection buffer (ready-to-use), with a storage temperature of ≤−16° C. for all.

Experimental Method (1) The cells were seeded in a white-bottomed 384-well cell culture plate, 8 μL of cell suspension per well, each well containing 7,500 cells. The cell plate was placed in a carbon dioxide incubator and incubated overnight at 37° C.;

(2) The test compound was diluted with 100% DMSO to 3 mM as the first concentration, and then diluted with a pipette to 10 concentrations of 3,000, 1,000, 300, 100, 30, 10, 3, 1, 0.3 and 0.1 μM 2 μL of the compound was taken and added to 198 μL of cell starvation medium, mixed well, 15 μL of compound solution was taken and added to 35 μL of cell starvation medium and mixed well. Then, the compound solution of the last step was added to the corresponding cell plate well with 4 μL per well, and the cell plate was placed back into the carbon dioxide incubator to continue incubation for 3 hours, at which time the compound concentration was 3,000, 1.000, 300, 100, 30, 10, 3, 1, 0.3, 0.1 nM:

(3) After incubation, 3 μL of 5× cell lysate was added to each well, and shaken at room temperature for 30 minutes:

(4) The detection buffer was used to dilute the Phospho-ERK1/2 Eu Cryptate antibody and Phospho-ERK1/2 d2 antibody 20 folds, they were mixed at a ratio of 1:1, 5 μL per well was added to the cell culture plate, and incubated at room temperature for 2 h;

(5) After incubation, a multilabel plate reader was used to read the HTRF excitation: 320 nm, emission: 615 nm, and 665 nm.

Data Analysis:

The raw data were converted to inhibition rate using the equation (Sample−Min/Max−Min)*100%, and the IC50 value could be obtained by four-parameter curve fitting (log(inhibitor) vs. response—Variable slope mode in GraphPad Prism). Table 4 provides the inhibitory effect of a compound of the present disclosure on p-ERK. Max well: The reading of the positive control well was 1× lysate; Min well: The reading of the negative control well was 0.5% DMSO cell well cell lysate See Table 4 for the experimental results.

TABLE 4

Results of in vitro pERK inhibition screening test of a compound of the present disclosure

| Compound No. | GP2D pERK $IC_{50}$ (nM) |
|---|---|
| Trifluoroacetate of Compound 8A | 0.8 |
| Trifluoroacetate of Compound 10A | 0.5 |
| Trifluoroacetate of Compound 11A | 0.6 |
| Trifluoroacetate of Compound 12A | 0.2 |
| Trifluoroacetate of Compound 13A | 1.8 |

Conclusion: The compounds of the present disclosure has significant inhibitory activity on pERK levels in GP2D cells.

Experimental Example 5: In Vivo Pharmacodynamic Studies

Experimental Objective

To study the in vivo efficacy of a compound of the present disclosure on human lung bronchial benign NCI—H727 cells in a subcutaneous xenograft tumor model in BALB/c nude mice.

Experimental Methods and Steps

Laboratory animals: Female BALB/c nude mice, 6-8 weeks old, weighing 18-22 g; supplier Beijing Vital River Laboratory Animal Technology Co., Ltd.

(1) Cell culture: Human lung bronchial benign tumor cells were cultured in vitro in a monolayer, and the culture conditions were 10% fetal bovine serum added to Gibco RMPI1640 medium, incubated at 37° C. in a 5% $CO_2$ incubator. Routine passage was performed twice a week with trypsin-EDTA for digestion. When the cell saturation was 80%-90% and the required number was reached, the cells were collected, counted, and inoculated.

(2) Tumour cell inoculation and grouping: 0.2 mL ($2\times10^6$) of NCI—H727 cells (Matrigel was added in a volume ratio of 1:1) were inoculated subcutaneously into the right back of each mouse, and dosing was initiated when the mean tumor volume reached approximately 134 $mm^3$, with 6 animals in each group.

The vehicle was 5% DMSO/10% solutol/85% water. Control group: The vehicle was administered twice daily by gavage at a dose of 10 μL/g; treatment group: After dissolving the test compound in the vehicle, the compound was administered by gavage once daily. See Table 4 for the dose.

(3) The tumor diameter was measured with a vernier caliper twice weekly, and the tumor volume(V) was calculated. The formula is: $V=0.5a\times b^2$, where a and b are the long and short diameters of the tumor, respectively. The tumor inhibitory efficacy of the test compound was evaluated by the tumor growth inhibition rate (TGI). The calculation formula is: TGI %=1−(Mean tumor volume at the end of dosing in a treatment group−Mean tumor volume at the start of dosing in this treatment group)/(Mean tumor volume at the end of treatment in the vehicle control group−Mean tumor volume at the start of treatment in the vehicle control group)×100%.

Experimental Results

The body weight of mice in each treatment group was maintained well after dosing, and TGI was calculated based on the mean tumor volume on Day 21 after dosing. See Table 5 for the specific experimental results.

TABLE 5

Evaluation of the tumor inhibitory efficacy of a compound of the present disclosure in human lung bronchial benign tumor NCI-H727 model

| | Tumour Volume ($mm^3$) | | | | TGI |
|---|---|---|---|---|---|
| Group | Day 1 | Day 7 | Day 14 | Day 21 | (%) |
| Control group | 134.6 | 326.8 | 876.9 | 1982.0 | / |
| Treatment group (Compound 6A, at a dose of 25 mg/kg on Days 1-6 and 1 mg/kg on Days 7-21) | 134.5 | 76.8 | 71.1 | 75.1 | 103.2 |
| Treatment group (Compound 6A at a dose of 5 mg/kg) | 134.6 | 86.5 | 78.5 | 51.6 | 104.4 |

Conclusion: The compound of the present disclosure has demonstrated excellent tumor inhibitory effects in the NCI—H727 tumor model.

Experimental Example 6: In Vivo Pharmacodynamic Studies

Experimental Objective

To study the in vivo efficacy of a compound of the present disclosure in BALB/c nude mice subcutaneous xenograft tumor model of human pancreatic cancer PK59 cells.

Experimental Methods and Steps

Laboratory animals: Female BALB/c nude mice, 6-8 weeks old, weighing 18-22 g; supplier. Beijing Vital River Laboratory Animal Technology Co., Ltd.

(1) Cell culture. Human pancreatic cancer PK59 cells were cultured in vitro in a monolayer, and the culture conditions were 10% fetal bovine serum added to Gibco RMPI1640 medium, incubated at 37° C. in a 5% $CO_2$ incubator. Routine passage was performed twice a week with trypsin-EDTA for digestion. When the cell saturation was 80%-90% and the required number was reached, the cells were collected, counted, and inoculated.

(2) Tumour cell inoculation and grouping: 0.2 mL ($2\times10^6$) of PK59 cells (Matrigel was added in a volume ratio of 1:1)

was subcutaneously inoculated into the right back of each mouse, and dosing was started when the mean tumor volume reached about 104.4 $mm^3$, with 6 animals in each group.

The vehicle was 5% DMSO/10% solutol/85% water. Control group: The vehicle was administered via gavage once daily at a dose of 10 μL/g; treatment group: After dissolving the test compound in the vehicle, the compound was administered by gavage once daily. See Table 5 for the dose.

(3) The tumor diameter was measured with a vernier caliper twice weekly, and the tumor volume (V) was calculated. The formula is: $V=0.5a\times b^2$, where a and b are the long and short diameters of the tumor, respectively. The tumor inhibitory efficacy of the test compound was evaluated by the tumor growth inhibition rate (TGI). The calculation formula is: TGI %=[1−(Mean tumor volume at the end of dosing in a treatment group−Mean tumor volume at the start of dosing in this treatment group)/(Mean tumor volume at the end of treatment in the vehicle control group−Mean tumor volume at the start of treatment in the vehicle control group)×100%.

Experimental Results

The body weight of mice in each treatment group was maintained well after dosing, and TG was calculated based on the mean tumor volume on Day 22 after dosing. See Table 6 for the specific experimental results.

TABLE 6

Tumour inhibitory efficacy experimental results of a compound of the present disclosure in human pancreatic cancer PK59 model

| | Tumour Volume ($mm^3$) | | | | TGI (%) |
|---|---|---|---|---|---|
| Group | Day 1 | Day 7 | Day 14 | Day 22 | Day 22 |
| Control group | 103.8 | 329.0 | 547.2 | 943.1 | / |
| Treatment group (Compound 6A, 5 mpk) | 103.8 | 65.0 | 35.7 | 34.3 | 108 |
| Treatment group (Compound 6A, 2 mpk) | 103.5 | 64.3 | 45.5 | 43.3 | 107 |
| Treatment group (Compound 6A, 0.5 mpk) | 103.6 | 111.0 | 112.4 | 96.4 | 101 |

Conclusion: The compound of the present disclosure has demonstrated excellent tumor inhibitory effect in the PK59 tumor model.

Experimental Example 7: In Vitro Determination of Whole Blood to Plasma Concentration Ratios

Experimental Steps (1) Fresh mouse and human whole blood (n≥3 for number of individual animals and n≥2 for number of individual humans) were collected in blood collection tubes containing EDTAK2 anticoagulant. Whole blood samples had to be mixed well and stored at 2-8° C. or on wet ice before use. They were used within 36 hours of whole blood collection. Blank whole blood was centrifuged at 2,000×g for 15 minutes at room temperature to obtain blank plasma. The plasma status was checked and hemolyzed plasma samples could not be used.

(2) The hematocrit (the percentage content of red blood cells in whole blood) was determined by centrifugation of whole blood samples in microhematocrit centrifuge tubes.

(3) Diclofenac (all species), chlorthalidone (mouse) or chloroquine (human) were used as control compounds.

(4) ACN solution containing 2% DMSO with a final concentration of 1 μM of the test compound was added to blank whole blood samples, and three parallel treatments were performed. The final content of the organic phase in the system should not exceed 0.5% (the content of DMSO should not exceed 0.1%). A certain volume of the drug-containing whole blood sample was pipetted to the sample receiving plate (three replicates), an equal volume of blank plasma was added, and mixed well to obtain the $T_0$ sample.

(5) The whole blood sample containing the test compound was incubated at 37° C. with shaking for 60 minutes.

(6) After the end of incubation, a certain volume of whole blood samples containing the drug was pipetted to the sample receiving plate (three replicates) as $T_{60}$-whole blood samples.

(7) The remaining whole blood samples were centrifuged at 2,000×g for 15 minutes in a 37° C. centrifuge to obtain plasma samples. A certain volume of plasma was pipetted to the sample receiving plate (three replicates) as $T_{60}$-plasma samples.

(8) During sample treatment, all samples were equilibrated with the matrix (i.e., blank whole blood or blank plasma of the same volume was added) and mixed well.

(9) 1-fold volume of pure water was added to the equilibrated sample, and then a certain volume of stop solution containing internal standard compound was added to terminate the reaction.

(10) The analytes and control compounds in the samples were determined by liquid chromatography-tandem mass spectrometry (LC-MS/MS) method. The ratio of analyte peak area to internal standard peak area was used to represent the concentration in the sample.

Experimental Results

See Table 7 for the experimental results. Wherein $K_{B/P}$ represents the concentration ratio of the compound in whole blood and plasma. $K_{E/P}$ represents the concentration ratio of the compound in red blood cells and plasma, and recovery (%) represents the recovery of the compound in whole blood.

TABLE 7

Distribution results of the compounds of the present disclosure in whole blood and plasma

| Compound | Species | $K_{B/P}$ | $K_{E/P}$ | Recovery (%) |
|---|---|---|---|---|
| Compound 6A | Human | 3.5 | 6.5 | 96.4 |
| Compound 6A | CD-1 mouse | 5.3 | 9.4 | 101.5 |
| Compound 7A | Human | 2.6 | 5.2 | 102.6 |
| Compound 7A | CD-1 mouse | 5.1 | 8.1 | 97.3 |

Conclusion: The compounds of the present disclosure has a high distribution in whole blood and red blood cells as compared to human and mouse plasma.

Experimental Example 8: Pharmacokinetics Test in Mice

Experimental Objective

The pharmacokinetic behavior of the compounds of the present disclosure was evaluated in male CD-1 (ICR) mice.

Experimental Method

The compounds to be tested were dissolved in the vehicle (5% DMSO/10% solutol/85% water). Four male CD-1 mice were divided into 2 groups of 2 mice each. Group 1 mice were administered a single intravenous bolus injection of the compound at a dose of 1 mg/kg. Group 2 mice were administered a single dose of the compound by gavage at a dose of 10 mg/kg. Whole blood samples were collected at 0.083 (intravenous bolus group only), 0.25, 0.5, 1, 2, 4, 8 and 24 hours after dosing. The LC-MS/MS method was used to determine the concentration of the test compound in whole blood samples.

Experimental Results

In the test, all animals had good tolerance, and no abnormalities were observed. After intravenous bolus injection of Compound 7A, the whole blood clearance (C1) was 6.29 mL/min/kg, the apparent volume of distribution at steady state (Vd) was 2.18 L/kg, the elimination half-life ($T_{1/2}$) was 4.29 h, and the value of the area under the whole blood concentration-time curve from time 0 to the last quantifiable time point ($AUC_{0\text{-}last}$) was 3.160 h·nmol/mL. After administration of Compound 7A by gavage, the time to maximum concentration ($\tau_{max}$ occurred at 3.0 h after dosing, the maximum concentration (Cmax) was 2,000 nmol/mL, the $AUC_{0\text{-}last}$ was 17,119 h·nmol/mL, and the bioavailability (F) was 54.3%.

Conclusion: The compounds of the present disclosure have high exposure, long half-life, and good pharmacokinetic properties.

Experimental Example 9: Pharmacokinetic Study in Rats

Experimental Objective

To evaluate the pharmacokinetic behavior of the compounds of the present disclosure in male SD rats.

Experimental Method

The compounds to be tested were dissolved in the vehicle (5% DMSO/10% solutol/85% water). Four male SD rats were divided into 2 groups, with 2 rats in each group. Group 1 rats were administered a single intravenous bolus injection (i.v.) of the compounds at a dose of 1 mg/kg. Group 2 rats were administered a single dose of the compounds by gavage (p.o.) at a dose of 10 mg/kg. Whole blood samples were collected at 0.083 (intravenous bolus group only), 0.25, 0.5, 1, 2, 4, 8 and 24 hours after dosing. The LC-MS/MS method was used to determine the concentration of the test compound in whole blood samples.

Experimental Results

In the test, all animals had good tolerance, and no abnormalities were observed. See Table 8 for the specific experimental results.

TABLE 8

Pharmacokinetic test results of the compounds of the present disclosure in rats

| | Parameters | Compound 6A | Compound 7A |
|---|---|---|---|
| i.v. | $T_{1/2}$ (h) | 5.7 | 8.5 |
| | Vd (L/kg) | 1.9 | 2.5 |
| | Cl (mL/Kg/min) | 4.6 | 3.6 |
| | $AUC_{0\text{-}last}$ (nM · h) | 4125 | 4950 |
| p.o. | $C_{max}$ (nmol/L) | 1620 | 1455 |
| | $T_{Max}$ (h) | 1.5 | 4.0 |
| | $T_{1/2}$ (h) | 6.1 | 7.3 |
| | $AUC_{0\text{-}last}$ (nM · h) | 15213 | 17069 |
| | F(%) | 38 | 34.2 |

Conclusion: The compounds of the present disclosure have high exposure, long half-life, aid good pharmacokinetic properties.

Experimental Example 10: Pharmacokinetic Study in Beagle Dogs

Experimental Objective

To evaluate the pharmacokinetic behavior of the compounds of the present disclosure in male Beagle dogs.

Experimental Method

The compounds to be tested were dissolved in the vehicle (5% DMSO/10% solutol/85% water). Four male beagle dogs were divided into 2 groups of 2. Group 1 animals were administered a single intravenous bolus injection (i.v.) of the compounds at a dose of 1 mg/kg. Group 2 animals were administered a single dose of the compounds by gavage (p.o.) at a dose of 5 mg/kg. Whole blood samples were collected at 0.083 (intravenous bolus group only), 0.25, 0.5, 1, 2, 4, 8 and 24 hours after dosing. The LC-MS/MS method was used to determine the concentration of the test compound in whole blood samples.

Experimental Results

The compounds were well tolerated in all animals and no abnormalities were observed in the test. See Table 9 for the specific experimental results.

TABLE 9

Pharmacokinetic test results of the compounds of the present disclosure in Beagle dogs

| | Parameters | Compound 6A | Compound 7A |
|---|---|---|---|
| i.v. | $T_{1/2}$ (h) | 24.5 | 10.3 |
| | Vd (L/kg) | 3.8 | 3.0 |
| | Cl (mL/Kg/min) | 1.9 | 4.2 |
| | $AUC_{0\text{-}last}$ (nM · h) | 7910 | 4712 |
| p.o. | $C_{max}$ (nmol/L) | 472 | 618 |
| | $T_{Max}$ (h) | 1.5 | 1.0 |
| | $T_{1/2}$ (h) | 22.4 | 12.0 |
| | $AUC_{0\text{-}last}$ (nM · h) | 8720 | 7632 |
| | F(%) | 22 | 33.2 |

Conclusion: The compounds of the present disclosure have high exposure, long half-life, aid good pharmacokinetic properties.

What is claimed is:
1. A compound, a stereoisomer thereof, or a pharmaceutically acceptable salt thereof, selected from the group consisting of:
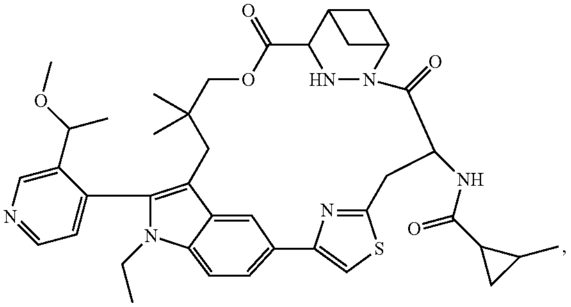
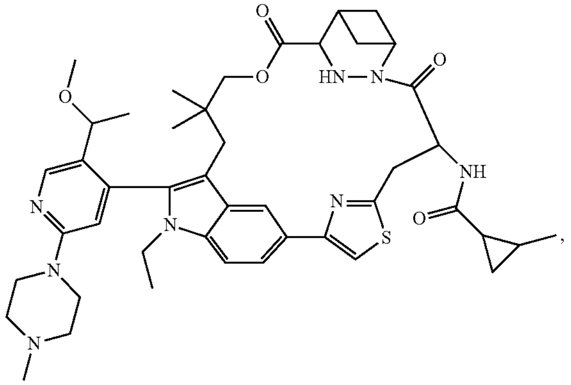
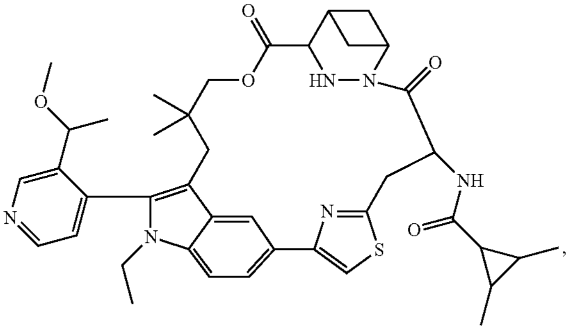
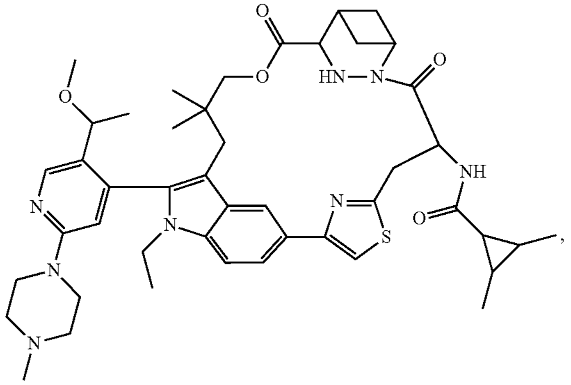
-continued
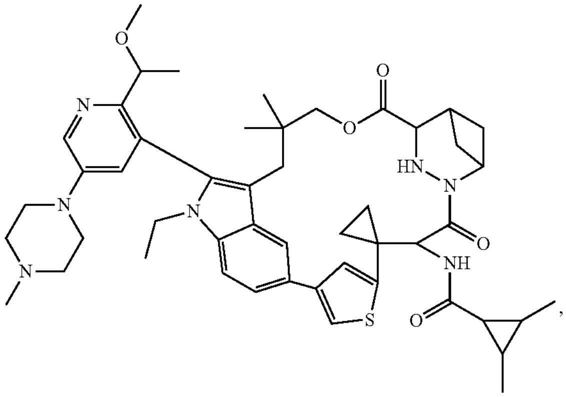
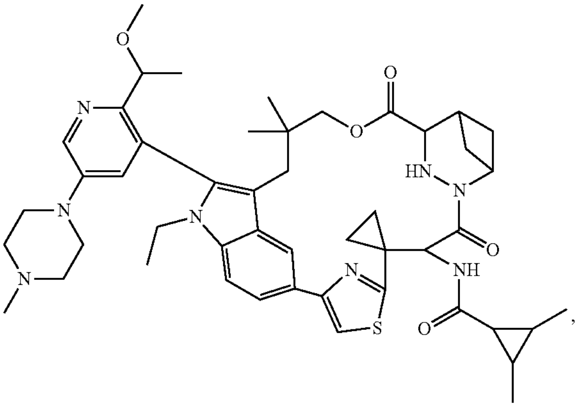
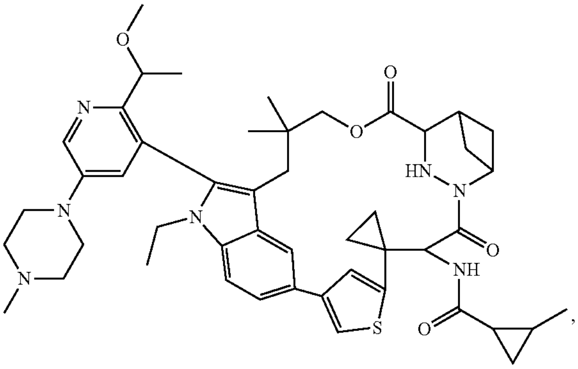
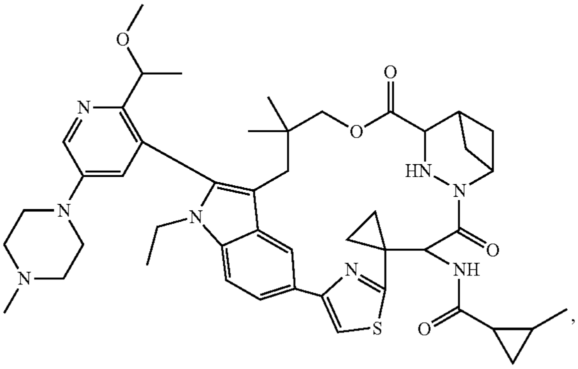

-continued
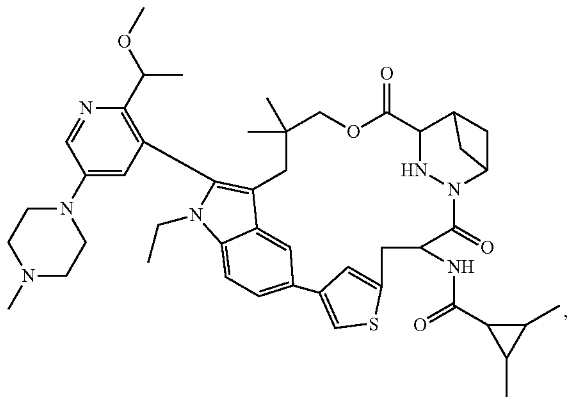
,
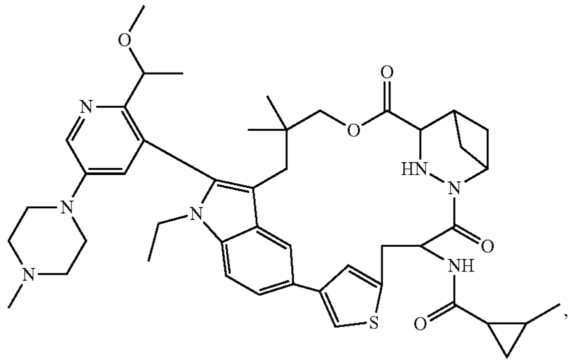
,
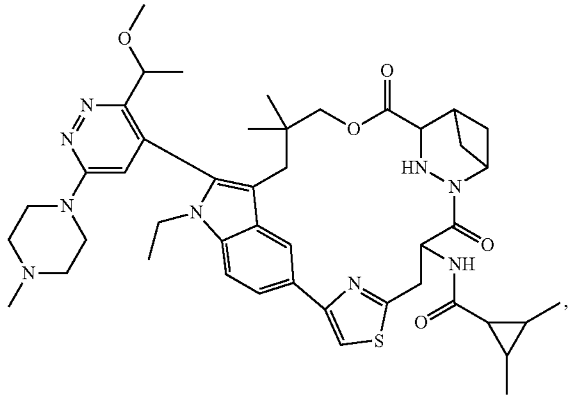
,
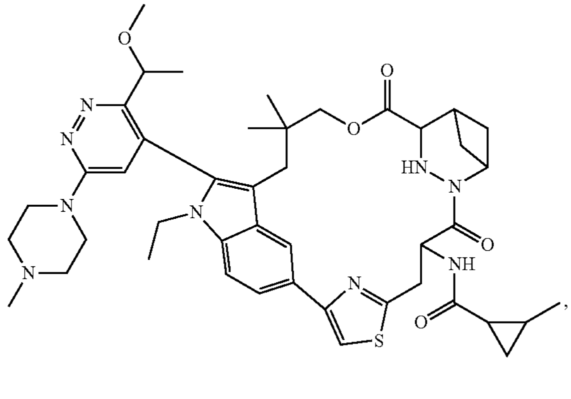
,
-continued
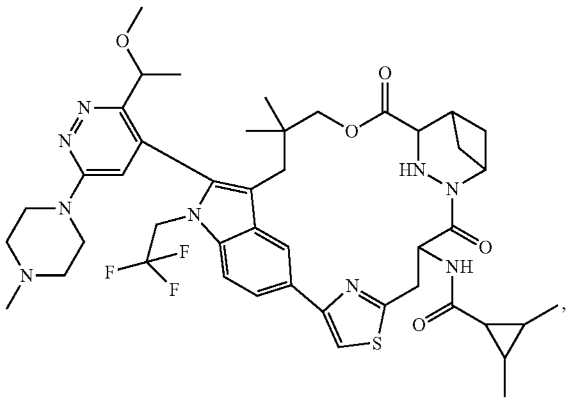
,
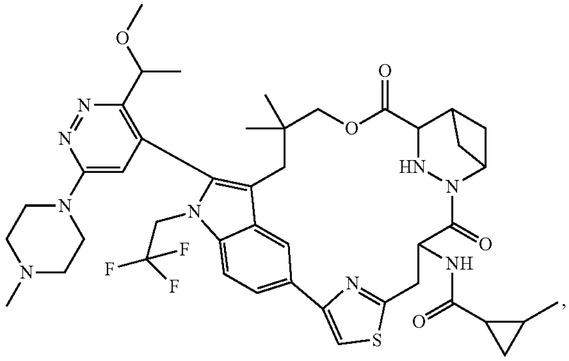
,
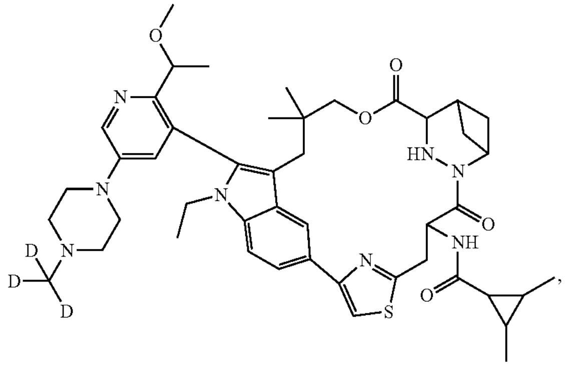
,
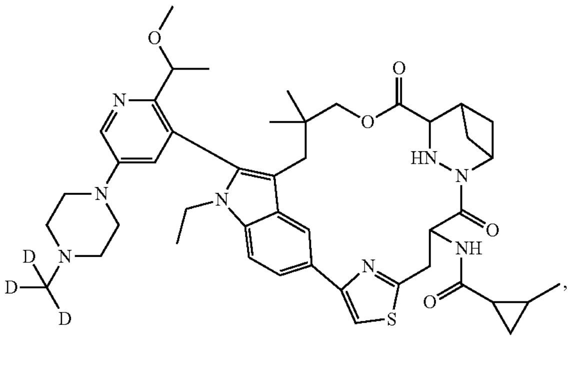
, -continued
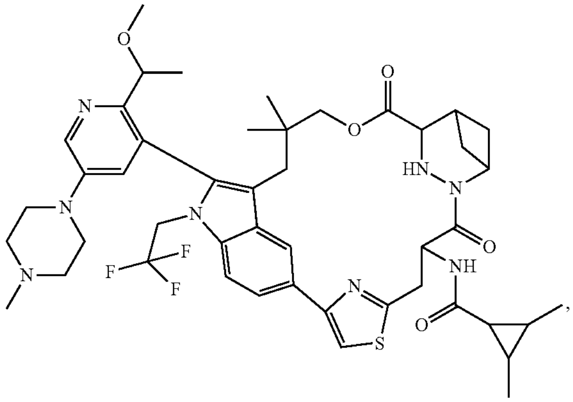,
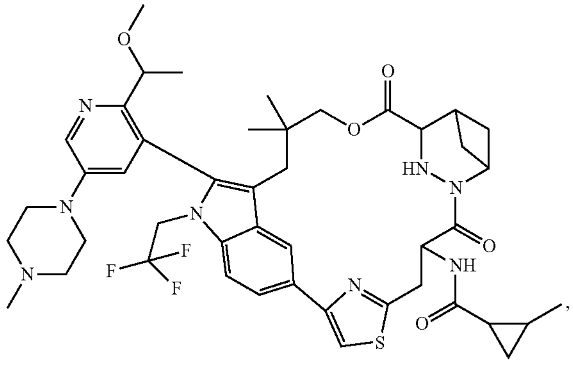,
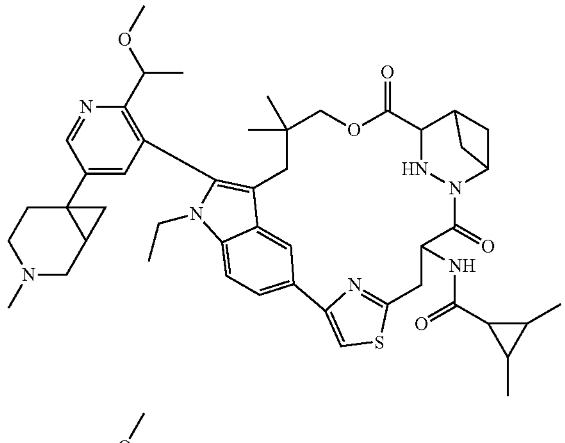,
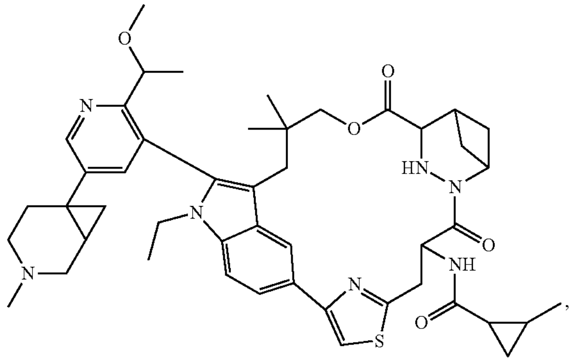,
-continued
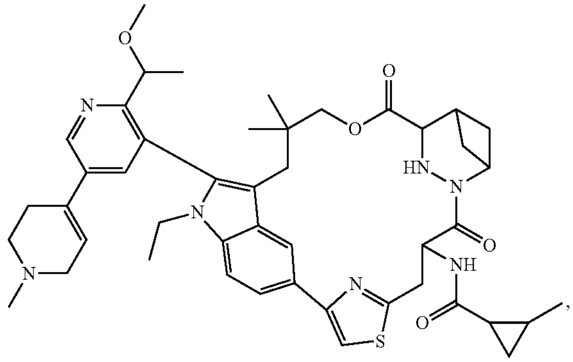,
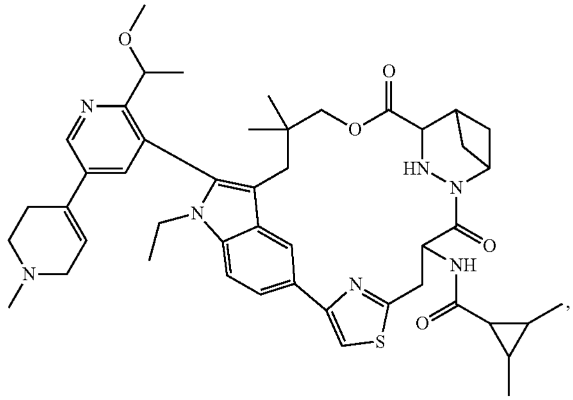,
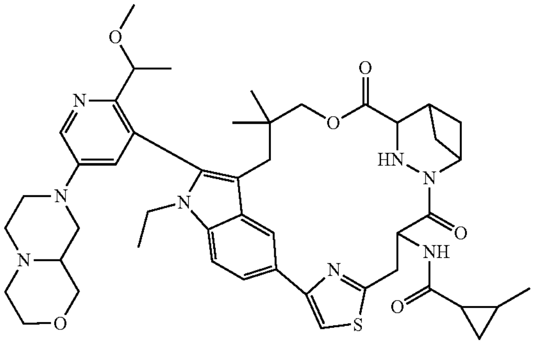
and
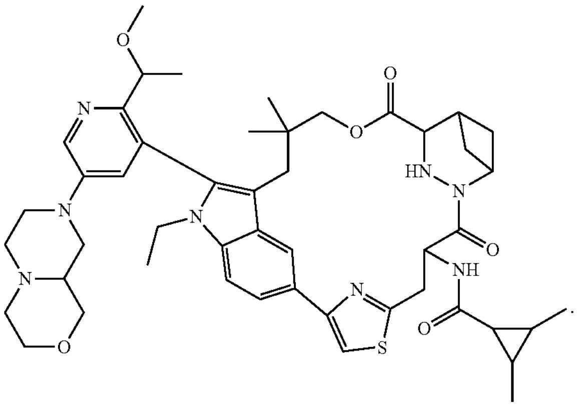.
2. The compound or the pharmaceutically acceptable salt thereof according to claim 1 selected from the group consisting of:

-continued
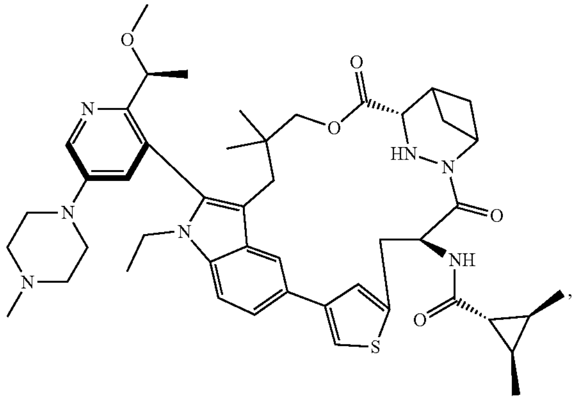
,
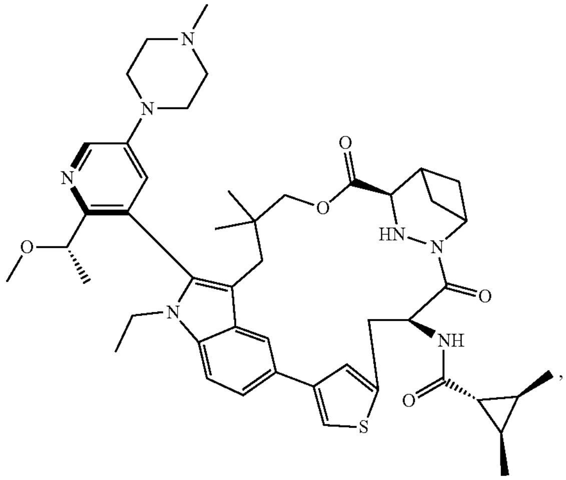
,
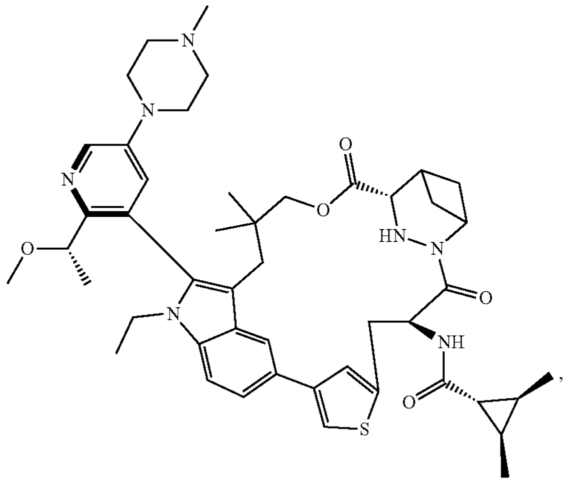
,
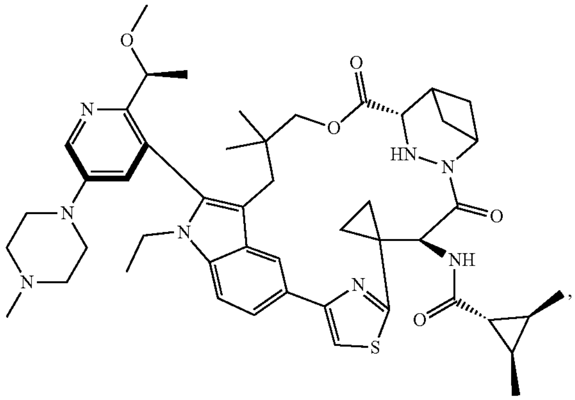
,
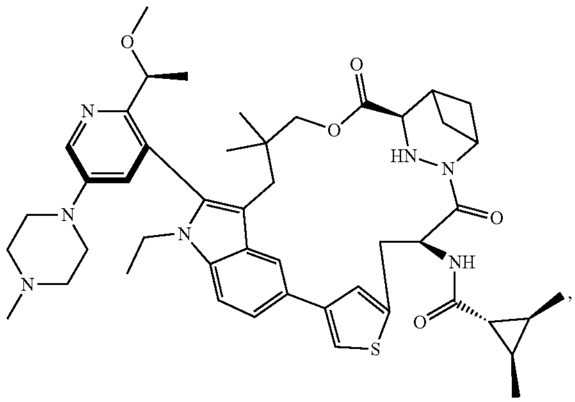
,
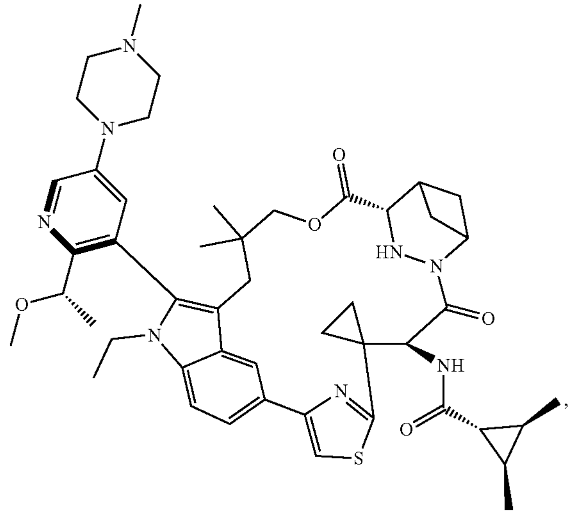
, -continued
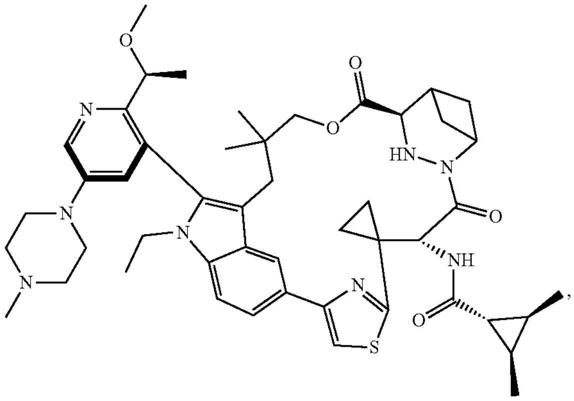,
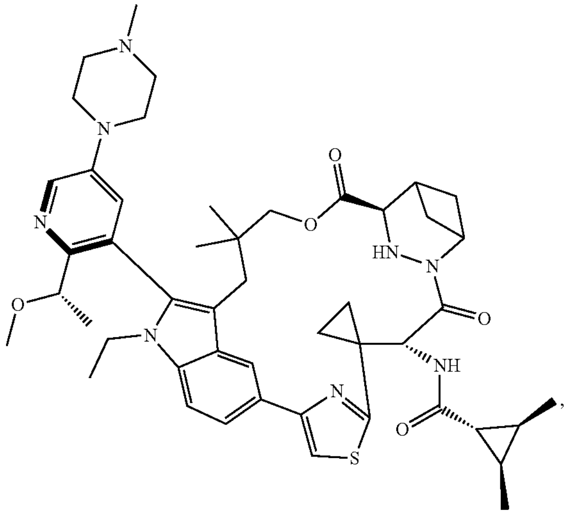,
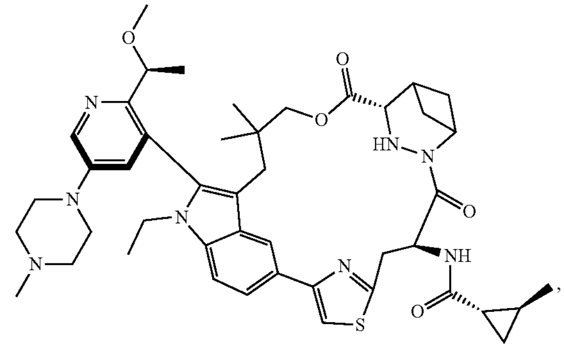,
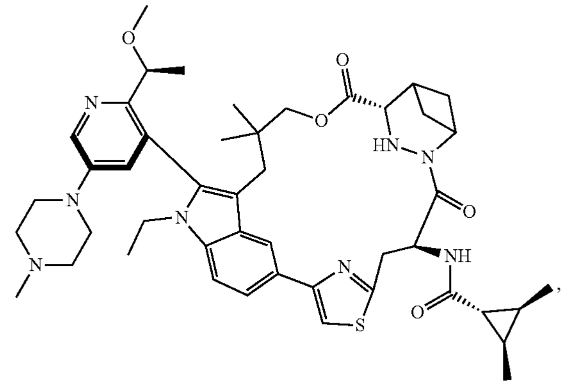,
-continued
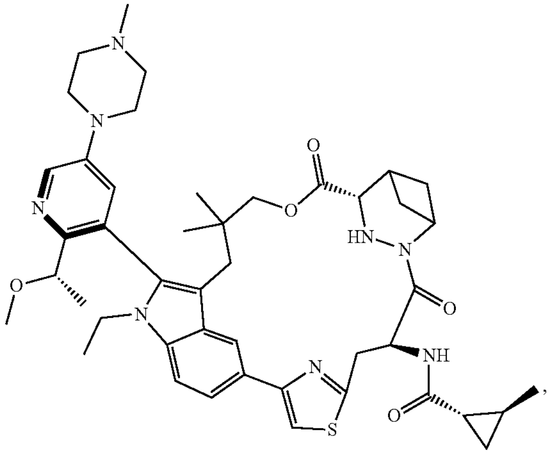,
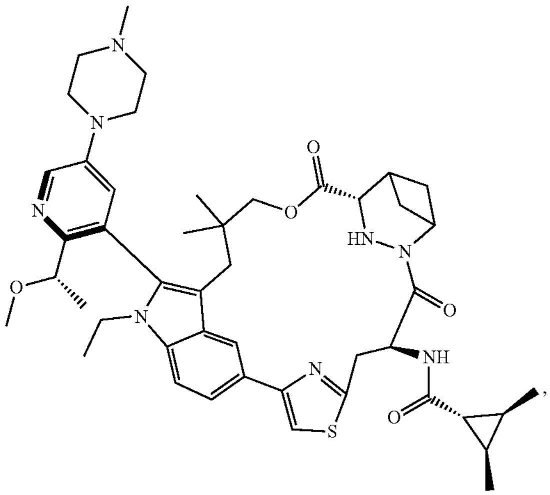,
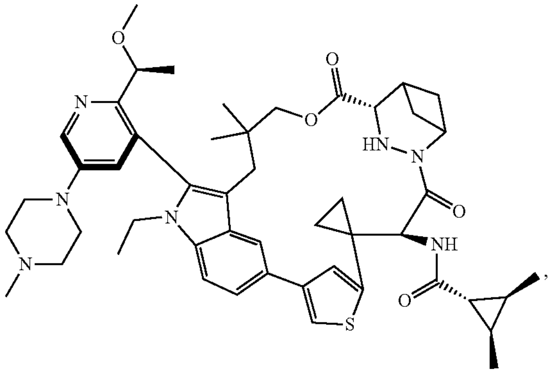, -continued
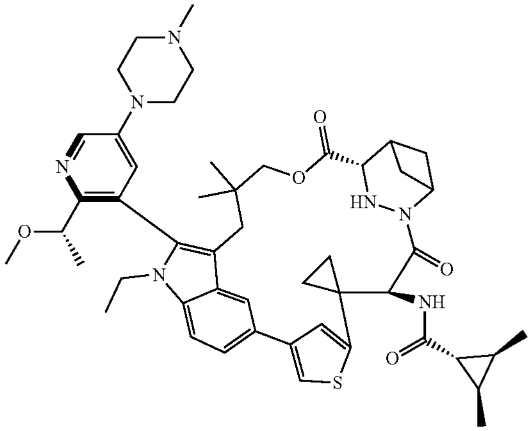
,
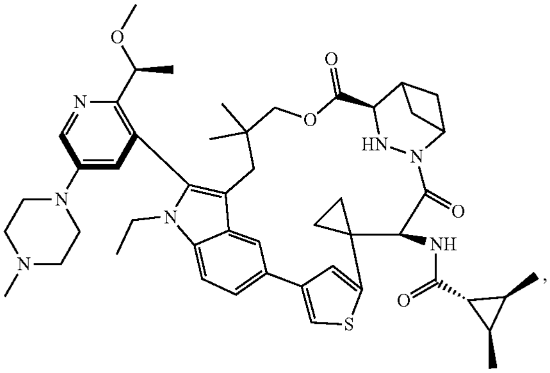
,
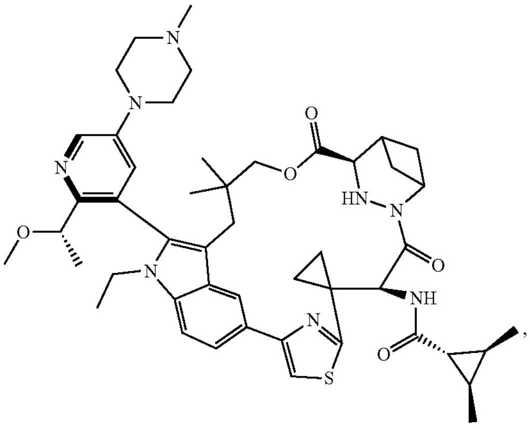
,
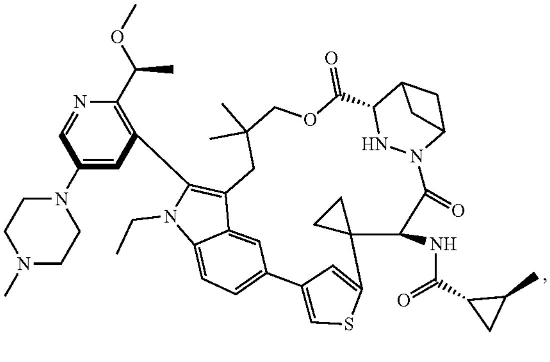
,
-continued
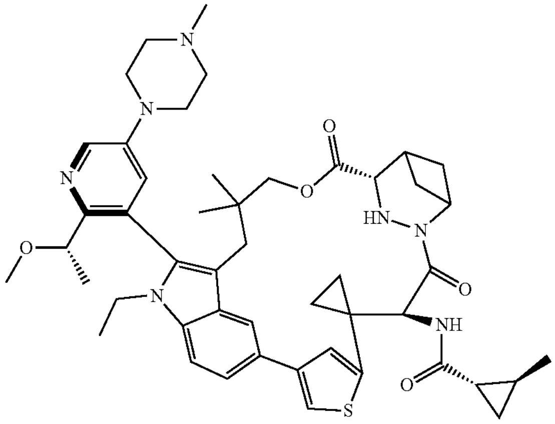
,
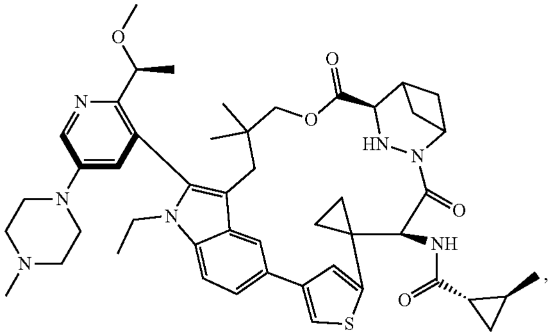
,
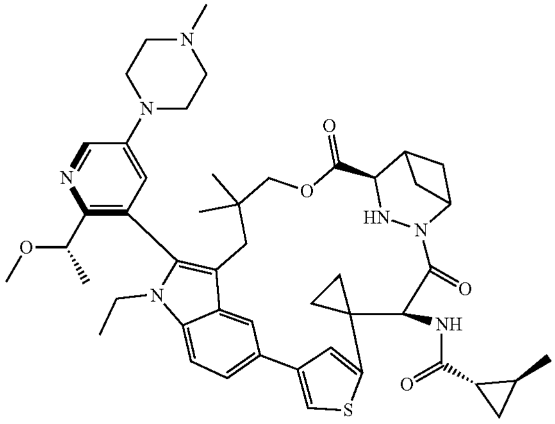
,
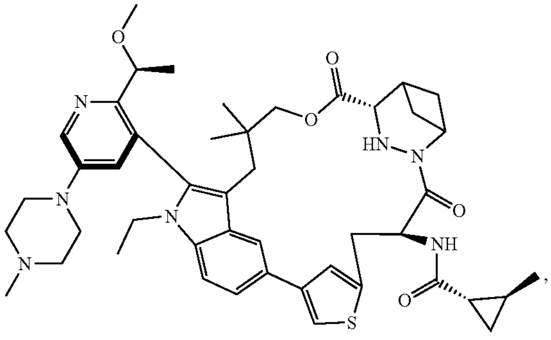
, -continued
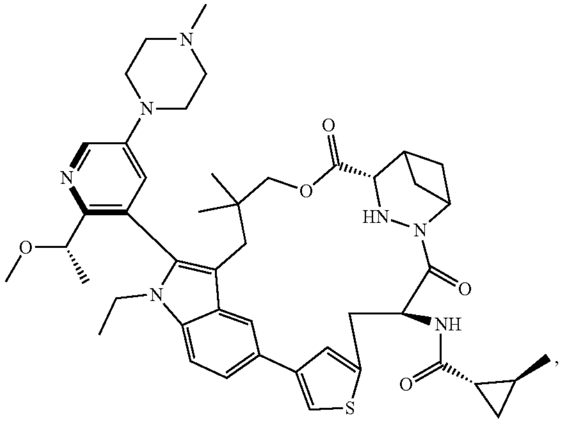
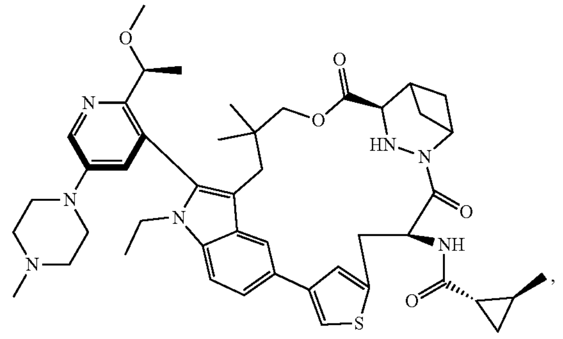
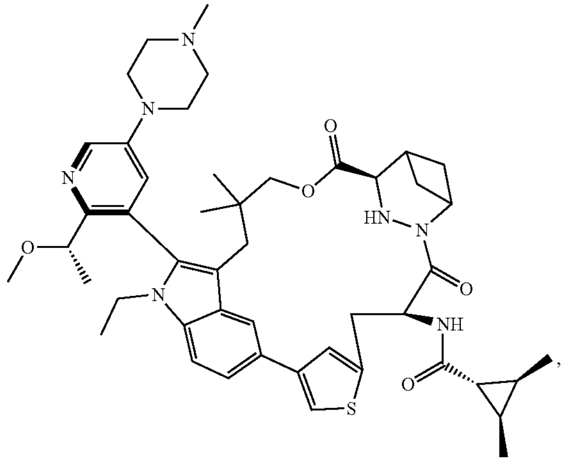
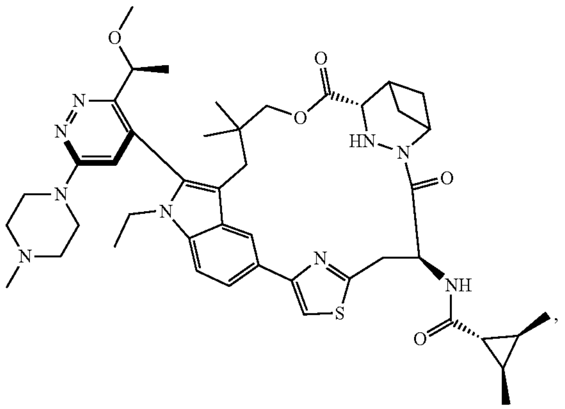
-continued
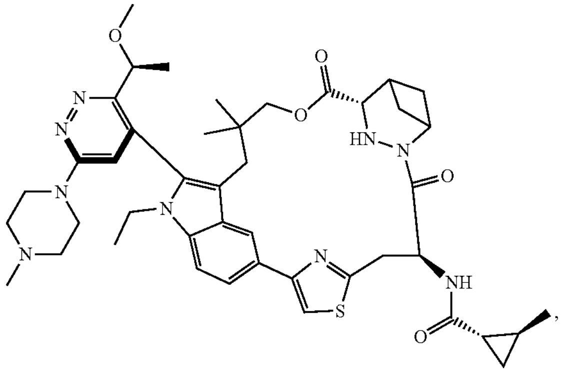
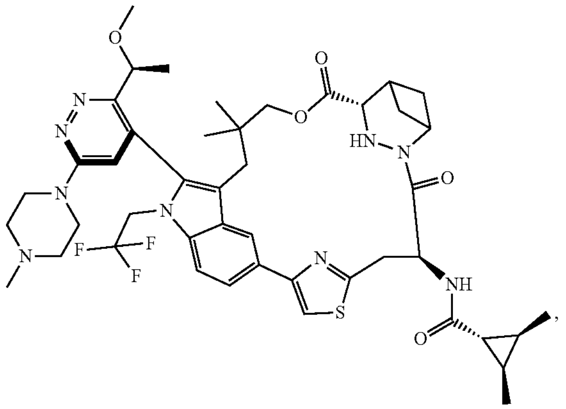
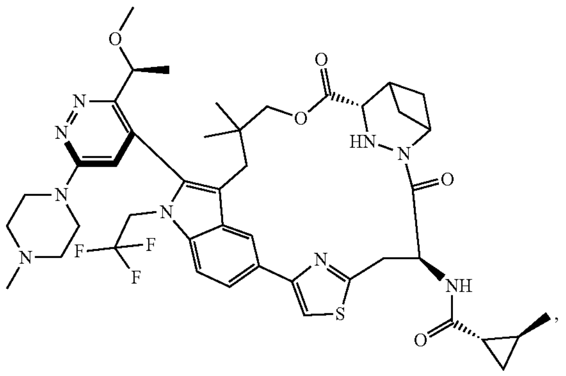
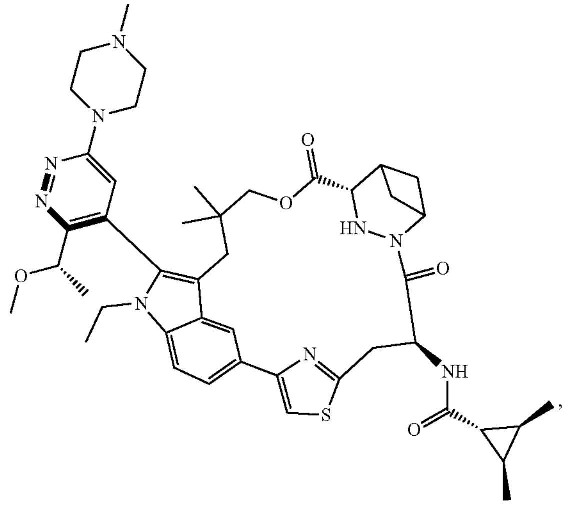

-continued
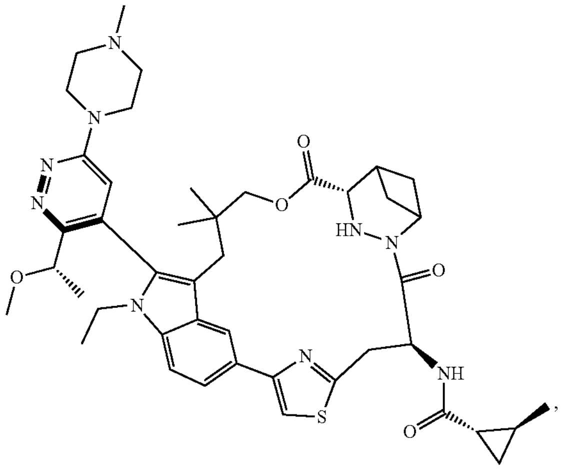,
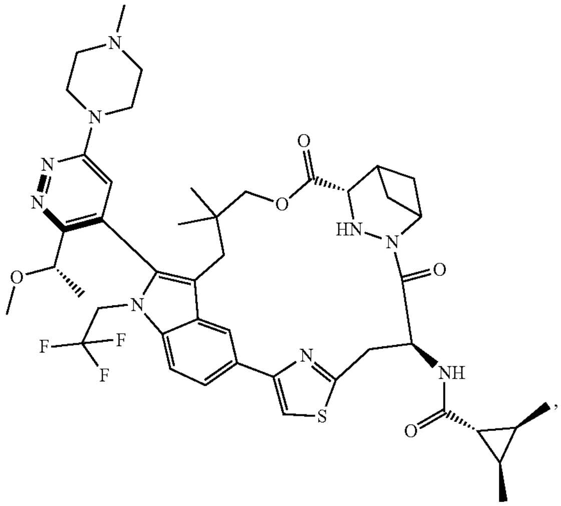,
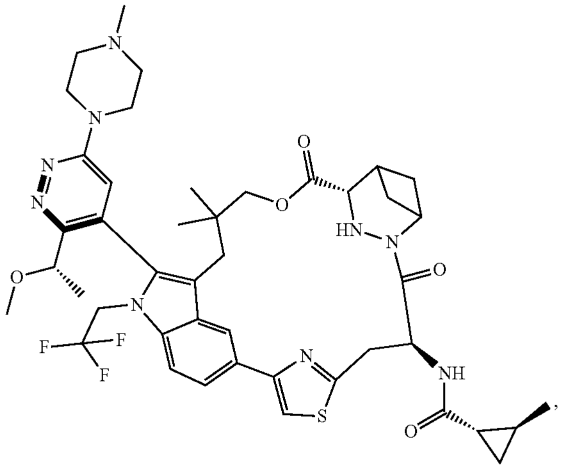,
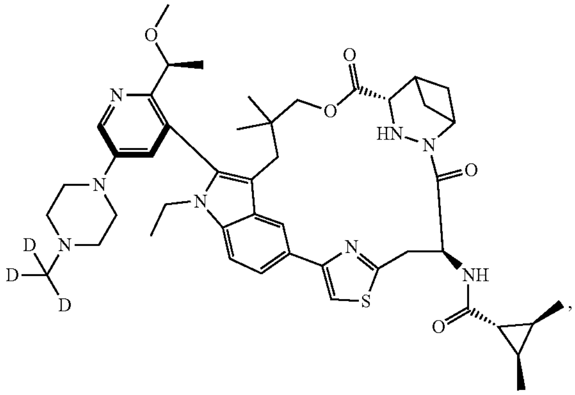,
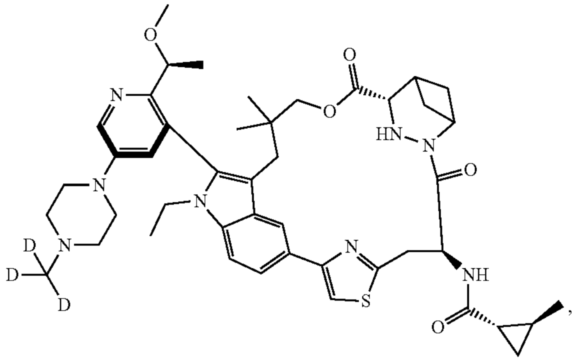,
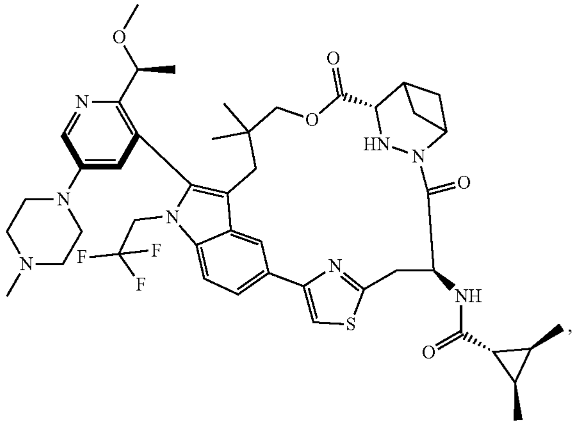,
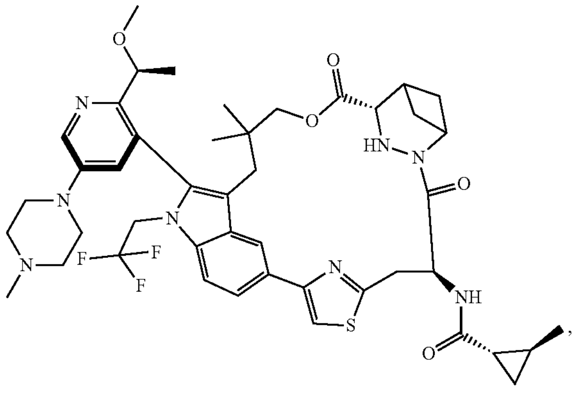, -continued
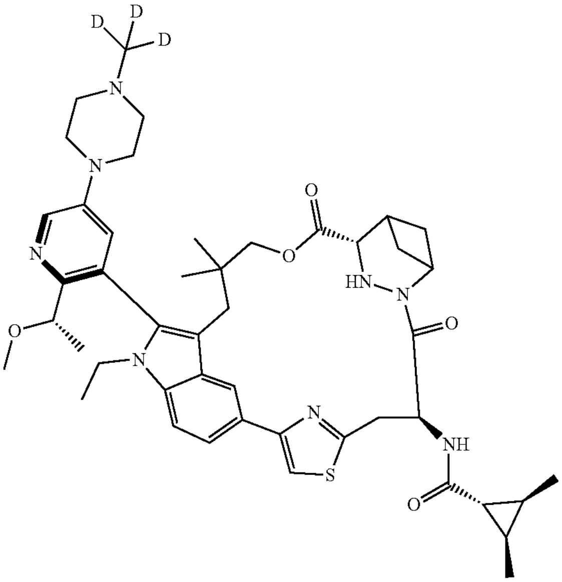
,
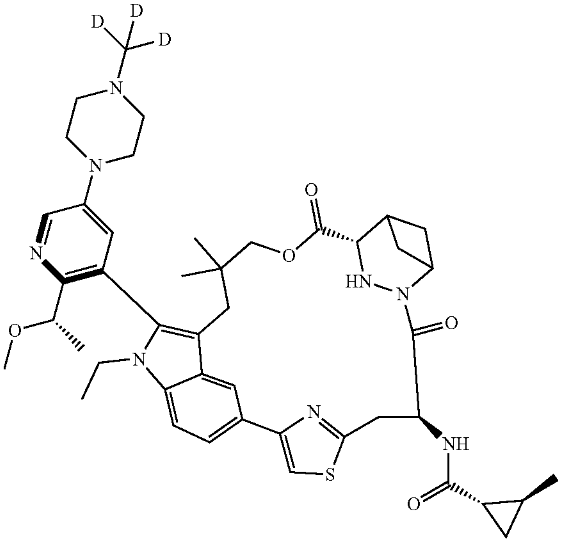
,
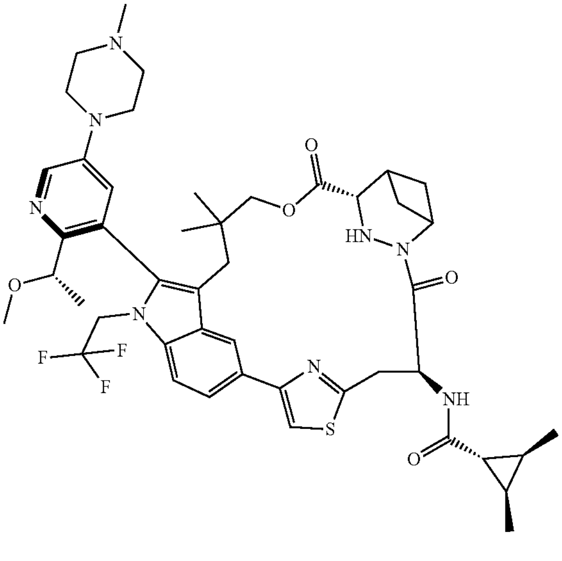
,
-continued
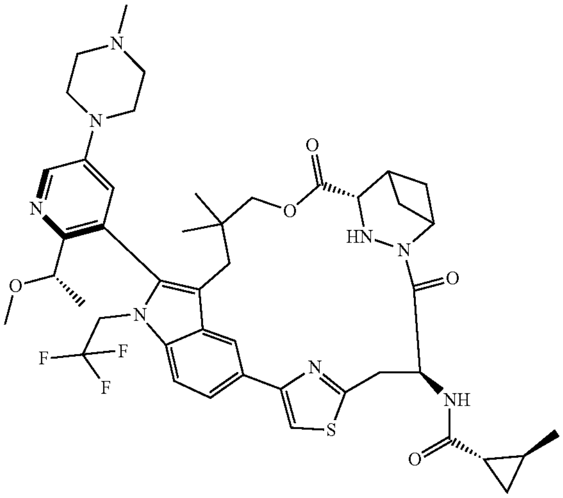
,
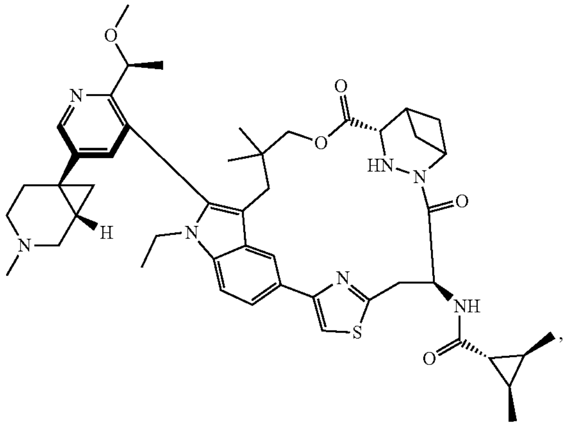
,
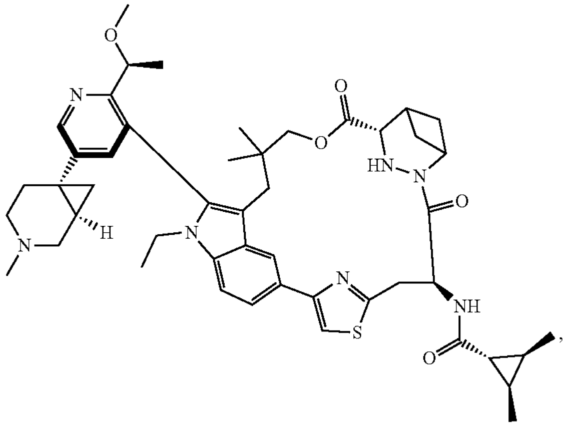
, -continued
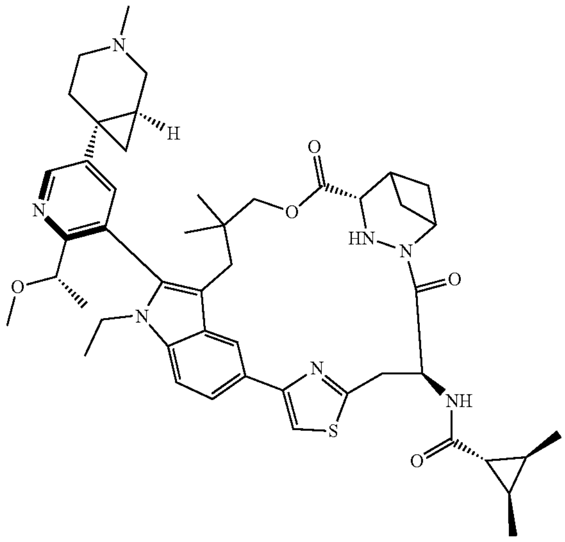
,
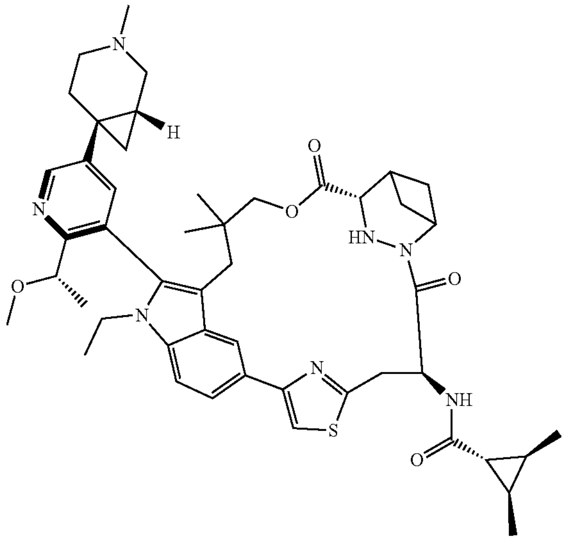
,
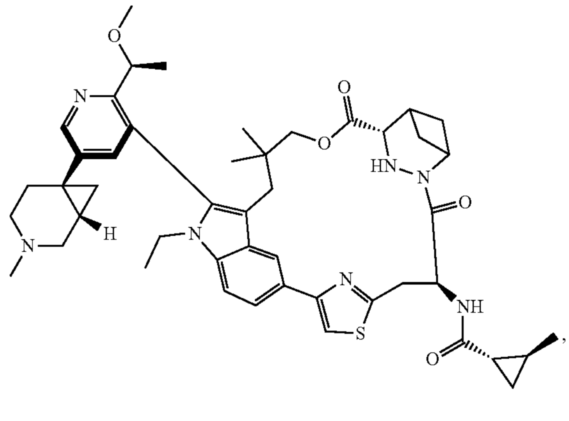
,
-continued
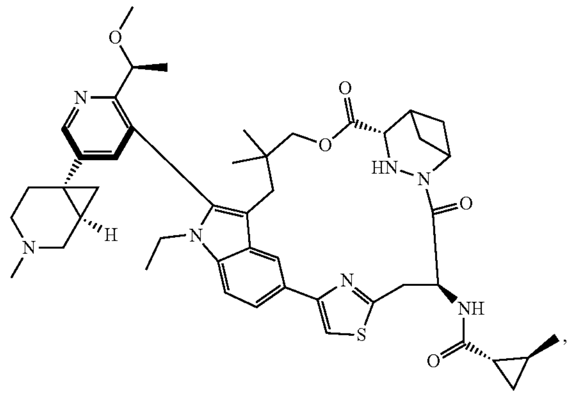
,
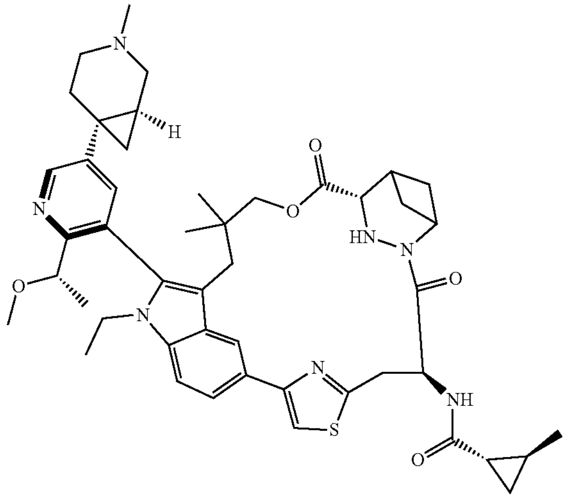
,
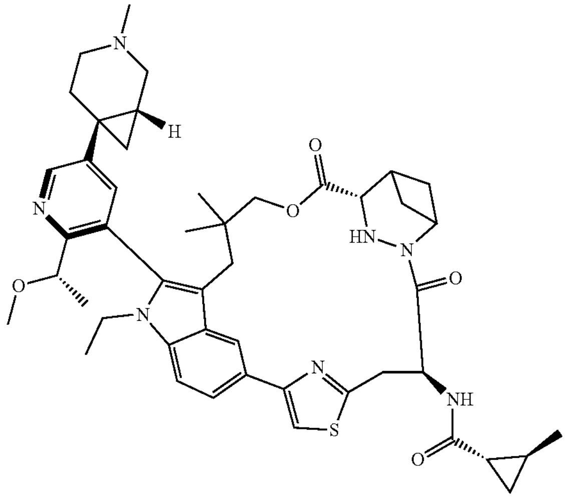
, -continued
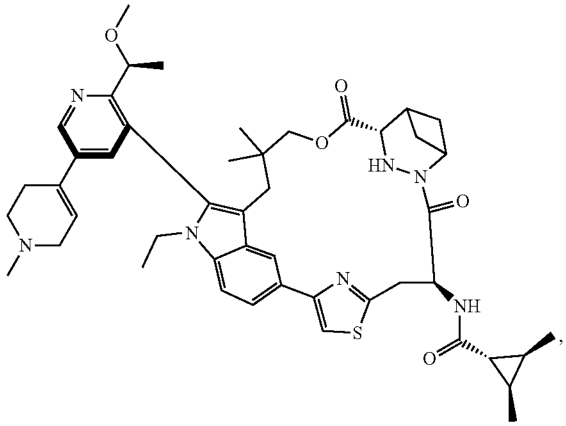
,
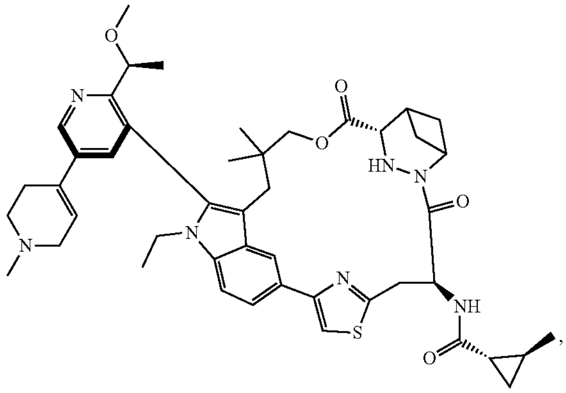
,
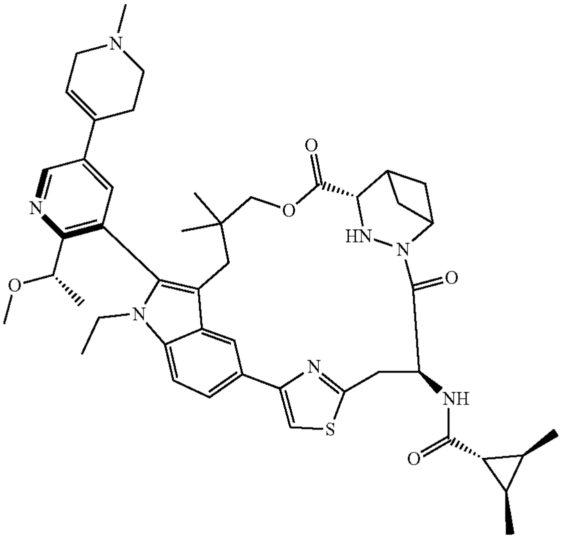
,
-continued
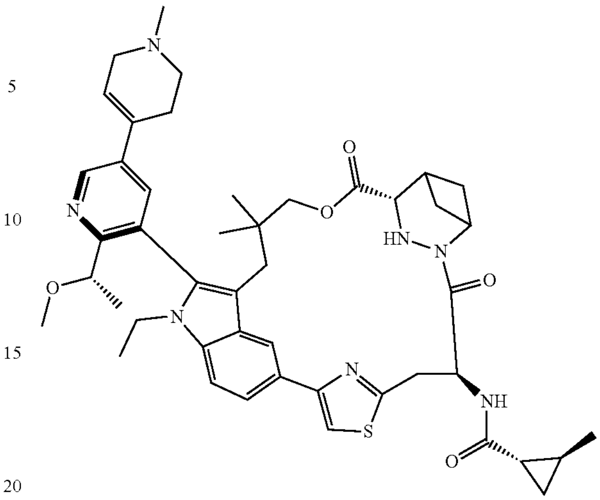
,
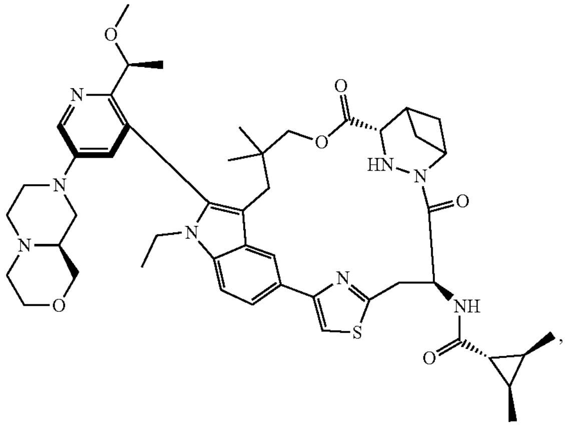
,
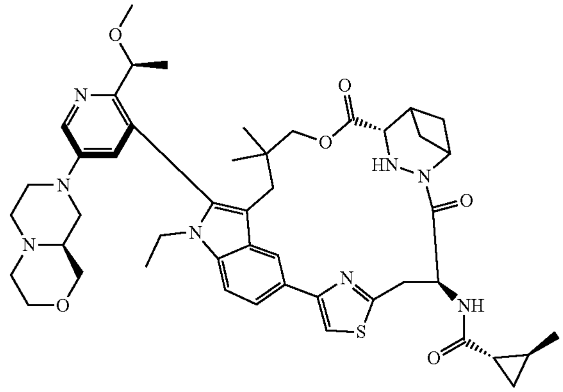

-continued

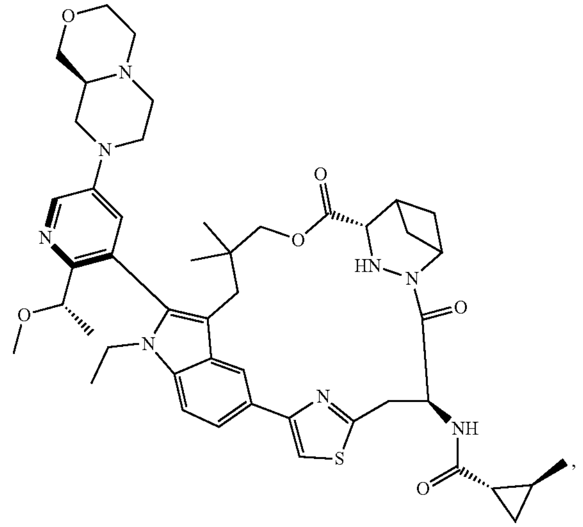

and

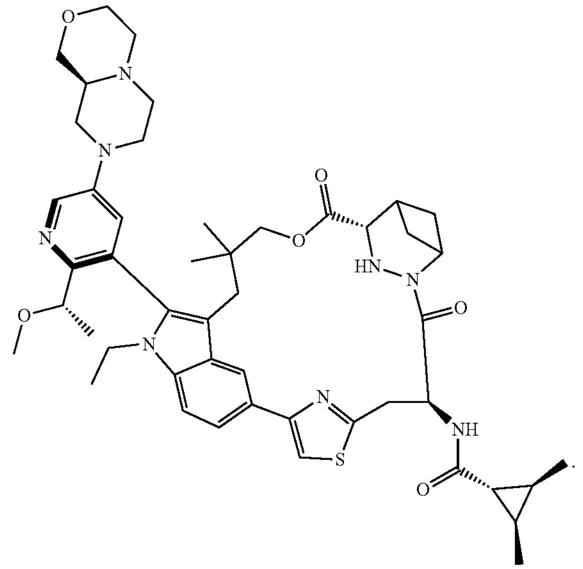

3. The compound or the pharmaceutically acceptable salt thereof of claim 1, wherein the compound is:

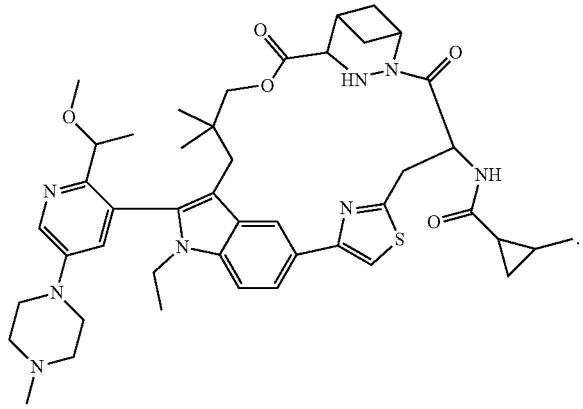 [SMILES: CCn1c(-c2cc(N3CCN(C)CC3)cnc2C(C)OC)c2c3cc(ccc31)-c1csc(n1)CC(NC(=O)C1CC1C)C(=O)N1NC(C(=O)OCC(C)(C)C2)C2CC1C2]

4. The compound or the pharmaceutically acceptable salt thereof of claim 1, wherein the compound is:

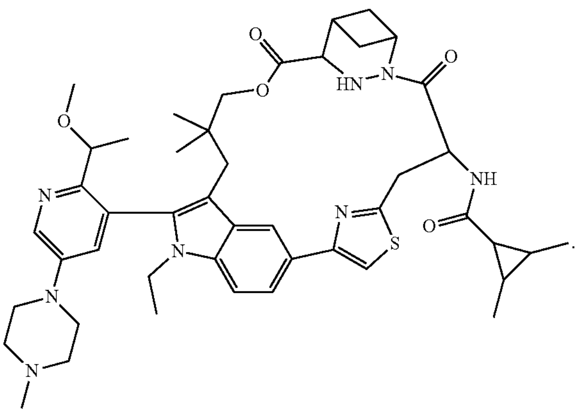 [SMILES: CCn1c(-c2cc(N3CCN(C)CC3)cnc2C(C)OC)c2c3cc(ccc31)-c1csc(n1)CC(NC(=O)C1C(C)C1C)C(=O)N1NC(C(=O)OCC(C)(C)C2)C2CC1C2]

5. The compound or the pharmaceutically acceptable salt thereof of claim 1, wherein the compound is:

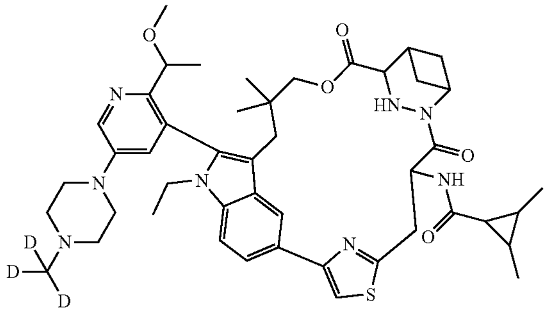

or

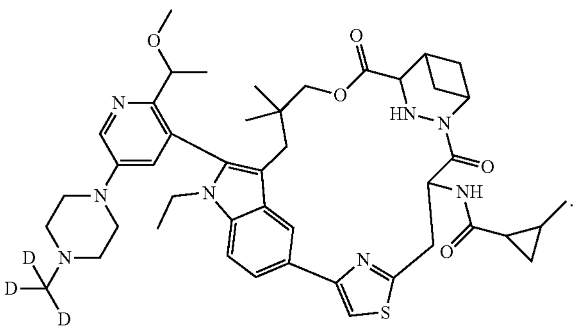

6. The compound or the pharmaceutically acceptable salt thereof of claim 2, wherein the compound is:

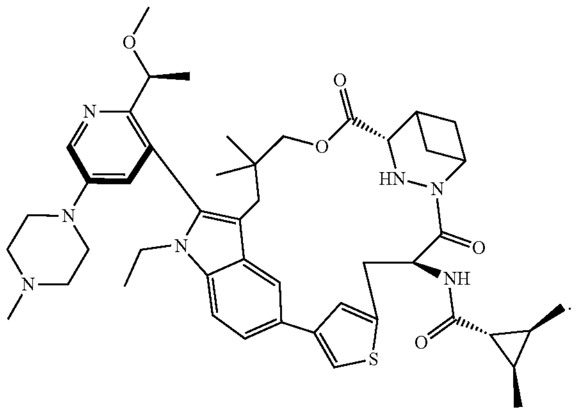

7. The compound or the pharmaceutically acceptable salt thereof of claim 2, wherein the compound is:

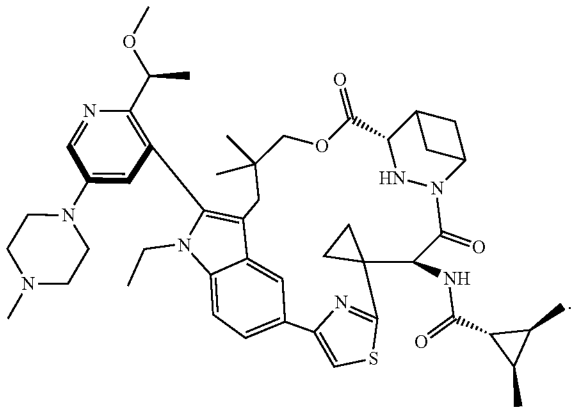

8. The compound or the pharmaceutically acceptable salt thereof of claim 2, wherein the compound is:

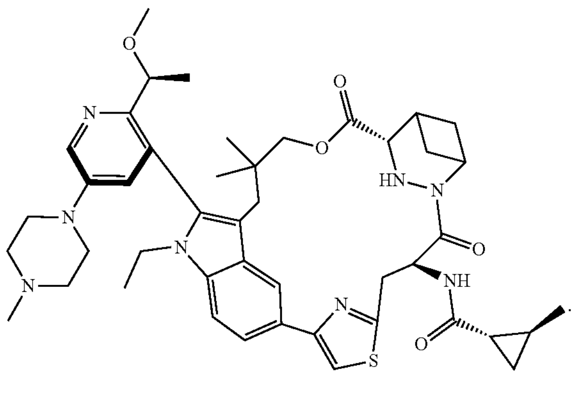

9. The compound or the pharmaceutically acceptable salt thereof of claim 2, wherein the compound is:

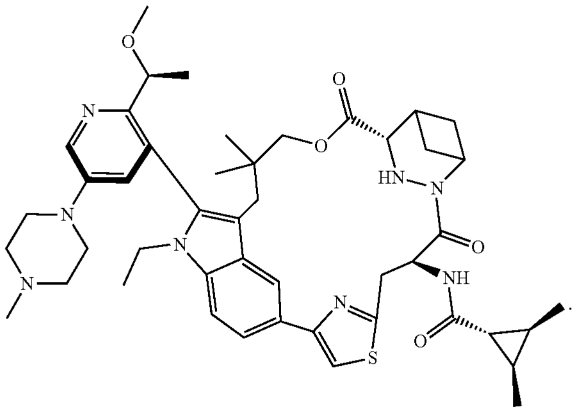

10. The compound or the pharmaceutically acceptable salt thereof of claim 2, wherein the compound is:

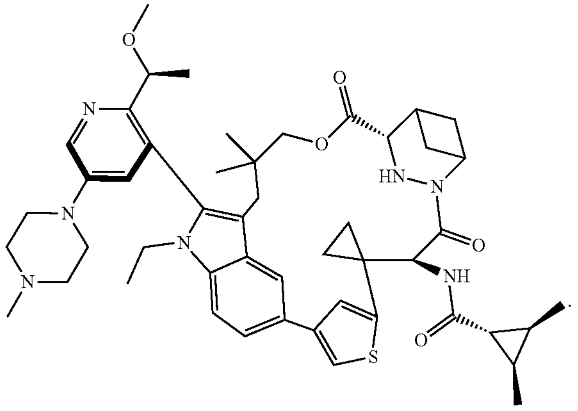

11. The compound or the pharmaceutically acceptable salt thereof of claim 2, wherein the compound is:

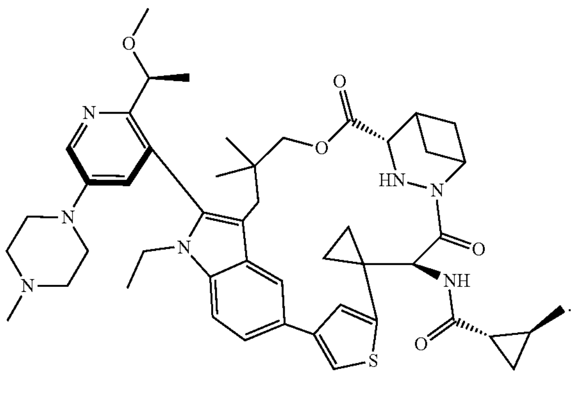

12. The compound or the pharmaceutically acceptable salt thereof of claim 2, wherein the compound is:

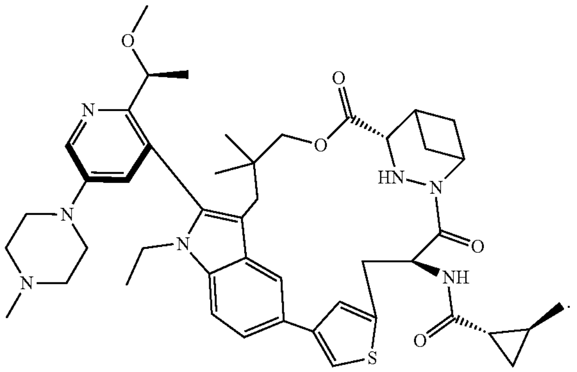

13. The compound or the pharmaceutically acceptable salt thereof of claim 2, wherein the compound is:

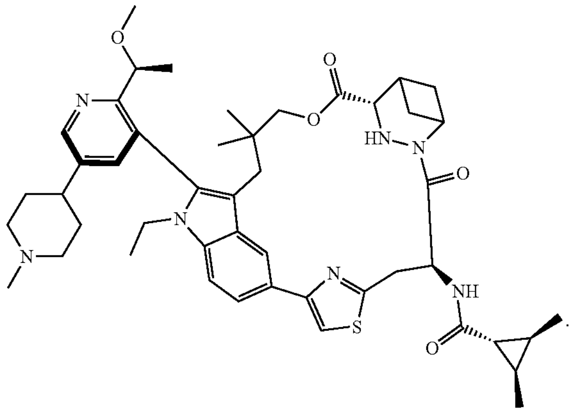

14. The compound or the pharmaceutically acceptable salt thereof of claim 2, wherein the compound is:

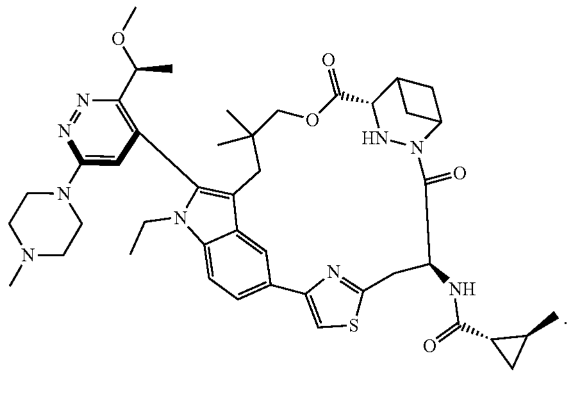

15. The compound or the pharmaceutically acceptable salt thereof of claim 2, wherein the compound is:

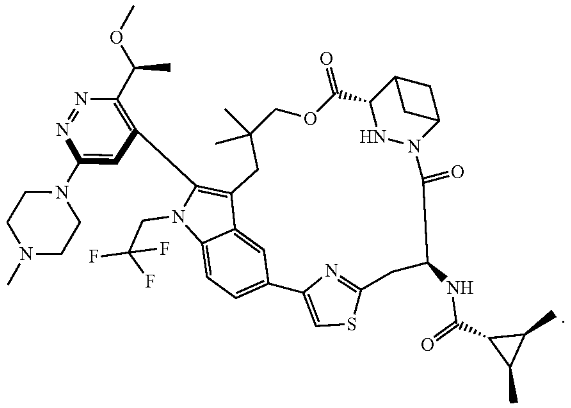

16. The compound or the pharmaceutically acceptable salt thereof of claim 2, wherein the compound is:

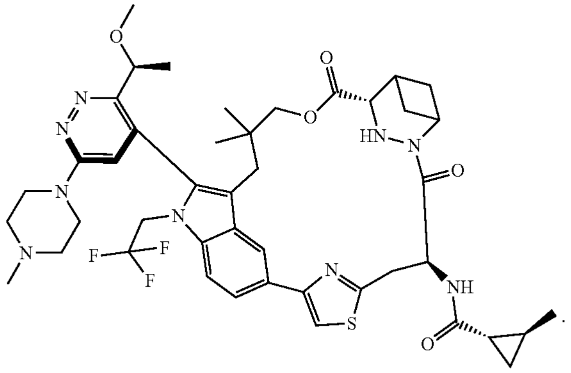

17. The compound or the pharmaceutically acceptable salt thereof of claim 2, wherein the compound is:

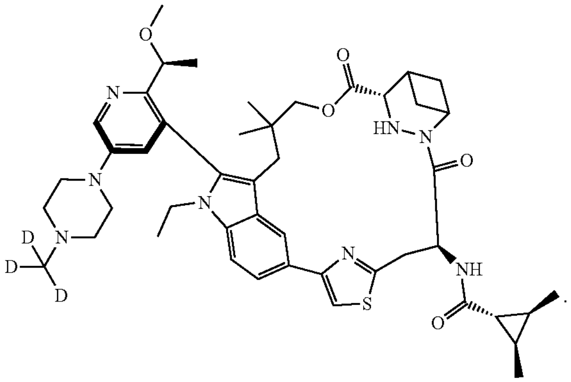

18. The compound or the pharmaceutically acceptable salt thereof of claim 2, wherein the compound is:

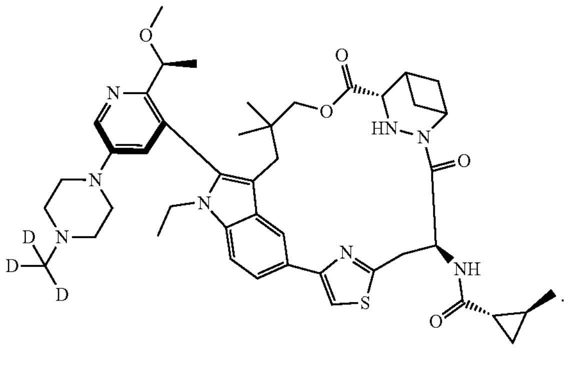

19. The compound or the pharmaceutically acceptable salt thereof of claim 2, wherein the compound is:

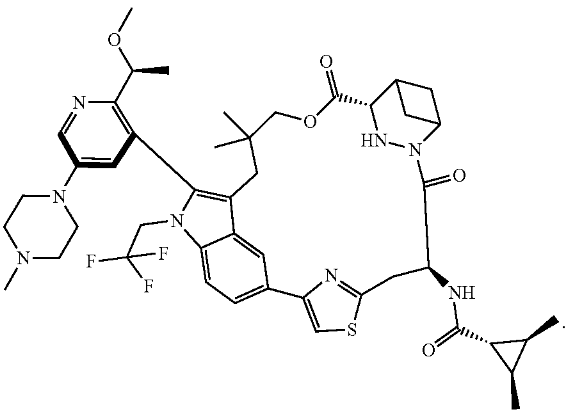

20. The compound or the pharmaceutically acceptable salt thereof of claim 2, wherein the compound is:

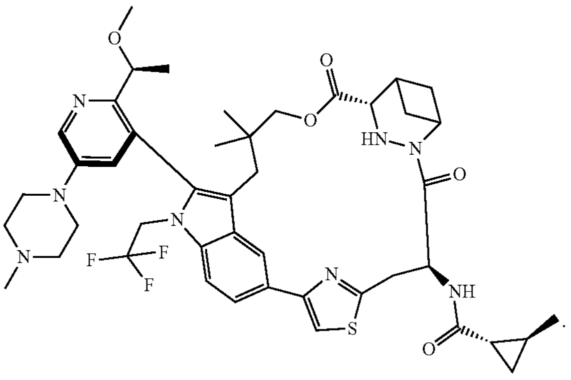

21. The compound or the pharmaceutically acceptable salt thereof of claim 2, wherein the compound is:

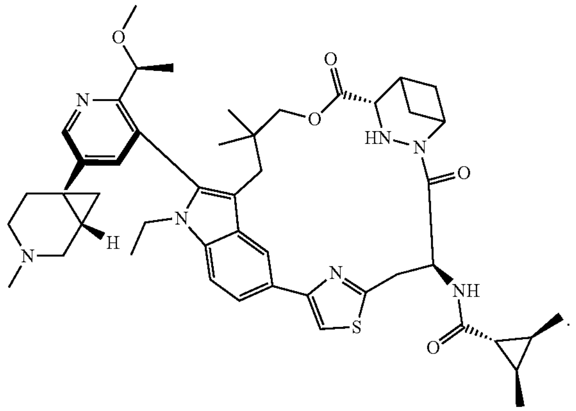

22. The compound or the pharmaceutically acceptable salt thereof of claim 2, wherein the compound is:

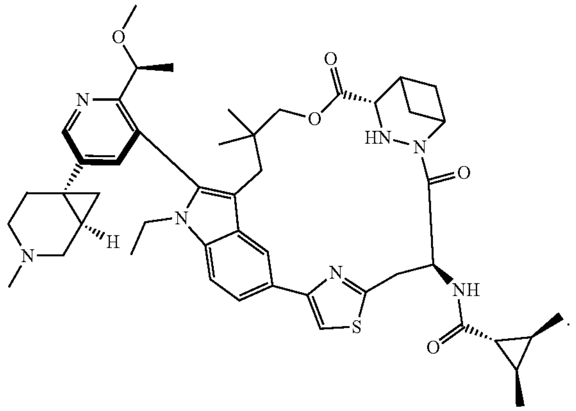

23. The compound or the pharmaceutically acceptable salt thereof of claim 2, wherein the compound is:

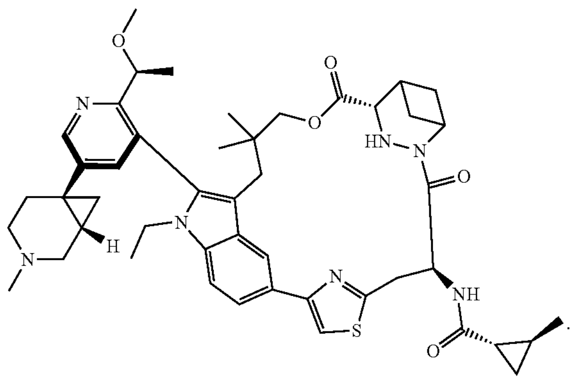

24. The compound or the pharmaceutically acceptable salt thereof of claim 2, wherein the compound is:

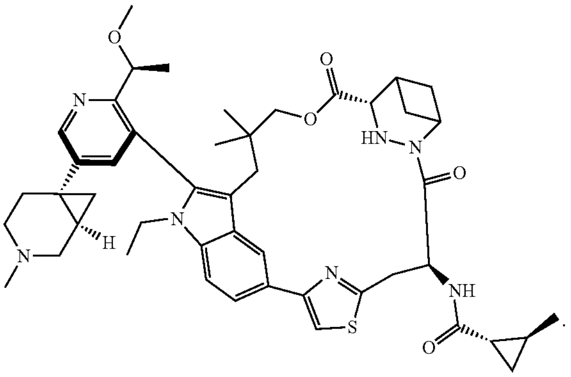

25. The compound or the pharmaceutically acceptable salt thereof of claim 2, wherein the compound is:

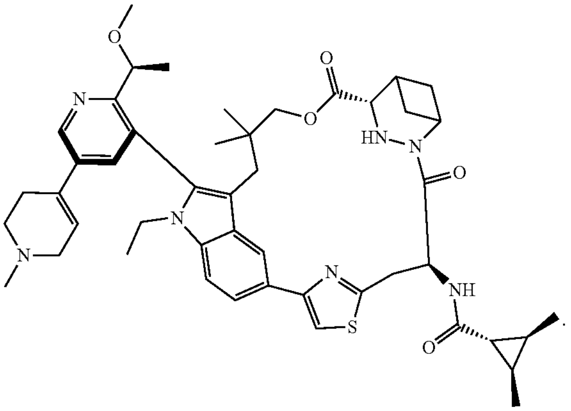

26. The compound or the pharmaceutically acceptable salt thereof of claim 2, wherein the compound is:

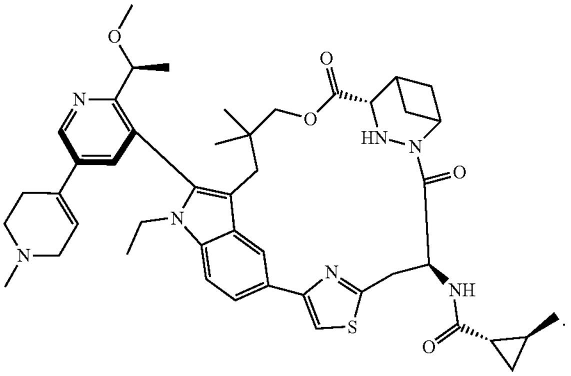

27. The compound or the pharmaceutically acceptable salt thereof of claim 2, wherein the compound is:

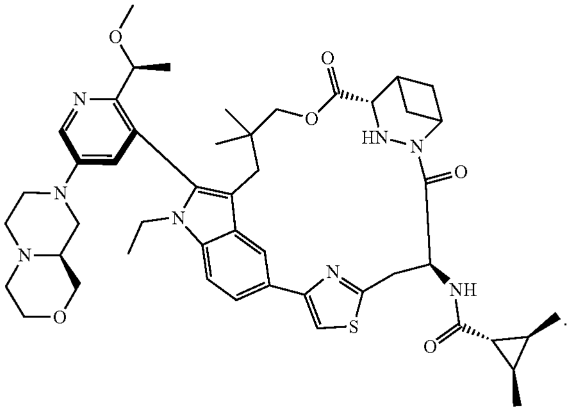

28. The compound or the pharmaceutically acceptable salt thereof of claim 2, wherein the compound is:

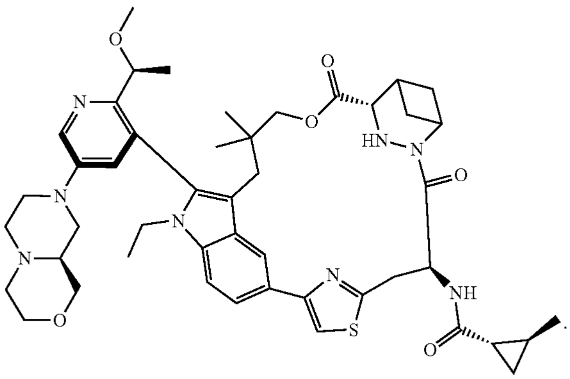

29. A pharmaceutical composition comprising a compound, or pharmaceutically acceptable salt thereof, of claim 1 and a pharmaceutically acceptable excipient.

30. A pharmaceutical composition comprising a compound, or pharmaceutically acceptable salt thereof, of claim 2 and a pharmaceutically acceptable excipient.

* * * * *